(12) United States Patent
Ashwell et al.

(10) Patent No.: US 7,960,134 B1
(45) Date of Patent: Jun. 14, 2011

(54) KINASE INHIBITION MODELS AND THEIR USES

(75) Inventors: Mark A. Ashwell, Carlisle, MA (US); Rocio Palma, North Andover, MA (US); Sudharshan Eathiraj, North Andover, MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 12/221,440

(22) Filed: Jul. 31, 2008

Related U.S. Application Data

(60) Provisional application No. 60/962,881, filed on Aug. 1, 2007.

(51) Int. Cl.
*C12Q 1/48* (2006.01)
*G06F 19/00* (2011.01)

(52) U.S. Cl. ............................................. 435/15; 702/27

(58) Field of Classification Search ........................ None
See application file for complete search history.

(56) References Cited

FOREIGN PATENT DOCUMENTS

EP 1243596 A2 9/2002
WO 2006/086484 A1 8/2006

OTHER PUBLICATIONS

Wiencek, J. M. New Strategies for Protein Growth. Ann. Rev. Biomed. Eng. 1999, 1, 505-534.*
Albrecht et al., "Discovery and Optimization of Triazolopyridazines as Potent and Selective Inhibitors of the c-Met Kinase", *J. Med. Chem.*, 51(10):2879-2882 (2008).
Appelt, K., "Crystal structures of HIV-1 protease-inhibitor complexes", *Persp. Drug Disc. Des.*, 1(1):23-48 (1993).
Bellon et al., "c-Met Inhibitors with Novel Binding Mode Show Activity against Several Hereditary Papillary Renal Cell Carcinoma-related Mutations", *J. Biol. Chem.*, 283(5):2675-2683 (2008).
Cowan-Jacob et al., "Structural biology contributions to the discovery of drugs to treat chronic myelogenous leukaemia", *Acta Crystal,*. D63:80-93 (2007).
Erickson, J.W., "Design and structure of symmetry-based inhibitors of HIV-1 protease", *Persp. Drug Disc. Des.*, 1(1):109-128 (1993).
Griffith et al., "The Structural Basis for Autoinhibition of FLT3 by the Juxtamembrane Domain", *Mol. Cell*, 13:169-178 (2004).
Hubbard et al., "Crystal structure of the tyrosine kinase domain of the human insulin receptor", *Nature*, 372(6508):746-754 (1994).
Huse et al., "The Conformational Plasticity of Protein Kinases", *Cell*, 109:275-282 (2002).
Johnson et al., "Active and Inactive Protein Kinases: Structural Basis for Regulation", *Cell*, 85:149-158 (1996).
Jones et al., "Improved Methods for Building Protein Models in Electron Density Maps and the Location of Errors in these Models", *Acta. Crystal.*, A47:110-119 (1991).
Kissinger et al., "Rapid automated molecular replacement by evolutionary search", *Acta Cryst.*, D55:484-491 (1999).
La Fortelle et al., "Maximum-Likelihood Heavy-Atom Parameter Refinement for Multiple Isomorphous Replacement and Multiwavelength Anomalous Diffraction Methods", *Meth. Enzymol.*, 276:472-494 (1997).

(Continued)

*Primary Examiner* — Nashaat T Nashed
(74) *Attorney, Agent, or Firm* — Mintz Levin Cohn Ferris Glovsky and Popeo, P.C.; Ivor R. Elrifi; Matthew Pavao

(57) ABSTRACT

The present invention provides a c-Met inhibition model. The invention further provides a method to derive inhibition models for other kinases. The kinase inhibition models of the present invention can be used to design or screen for inhibitors for kinases.

2 Claims, 4 Drawing Sheets

OTHER PUBLICATIONS

Lam et al., "Rational Design of Potent, Bioavailable, Nonpeptide Cyclic Ureas as HIV Protease Inhibitors", *Science*, 263:380-384 (1994).

Mohammadi et al.,"Structure of the FGF Receptor Tyrosine Kinase Domain Reveals a Novel Autoinhibitory Mechanism", *Cell*, 86:577-587 (1996).

Mol et al, "Structural Basis for the Autoinhibition and STI-571 Inhibition of c-Kit Tyrosine Kinase", *J. Biol. Chem.*, 279(30):31655-31663 (2004).

Nagar et al., "Crystal Structures of the Kinase Domain of c-Abl in Complex with the Small Molecule Inhibitors PD173955 and Imatinib (STI-571)", *Cancer Res.*, 62:4236-4243 (2002).

Navaza, J., "Research Papers. AMoRe: an Automated Package for Molecular Replacement", *Acta Cryst.*, A5O:157-163 (1994).

Otwinowski et al., "Processing of X-Ray Diffraction Data Collected in Oscillation Mode", *Meth. Enymol.*, 276:307-326 (1997).

Schiering et al., "Crystal structure of the tyrosine kinase domain of the hepatocyte growth factor receptor c-Met and its complex with the microbial alkaloid K-252a", *Proc. Nat'l. Acad. Sci. U.S.A.*, 100(22):112654-12659 (2003).

Schindler et al., "Structural Mechanism for STI-571 Inhibition of Abelson Tyrosine Kinase", *Science*, 289:1938-1942 (2000).

Schindler et al., "Crystal Structure of Hck in Complex with a Src Family-Selective Tyrosine Kinase Inhibitor", *Mol. Cell*, 3:639-648 (1999).

Schubert et al., "Crystal Structure of the Tyrosine Kinase Domain of Colony-stimulating Factor-1 Receptor (cFMS) in Complex with Two Inhibitors", *J. Biol. Chem.*, 282(6):4094-4101 (2007).

Wang et al., "Structural characterization of autoinhibited c-Met kinase produced by coexpression in bacteria with phosphatase", *Proc. Natl. Sci. U.S.A.*, 103(10):3563-3568 (2006).

Wlodawer et al., "Structure-Based Inhibitors of HIV-1 Protease", *Ann. Rev. Biochem.*, 62:543-585 (1993).

Xu et al., "Crystal Structures of c-Src Reveal Features of its Autoinhibitory Mechanism", *Mol. Cell*, 3:629-638 (1999).

\* cited by examiner

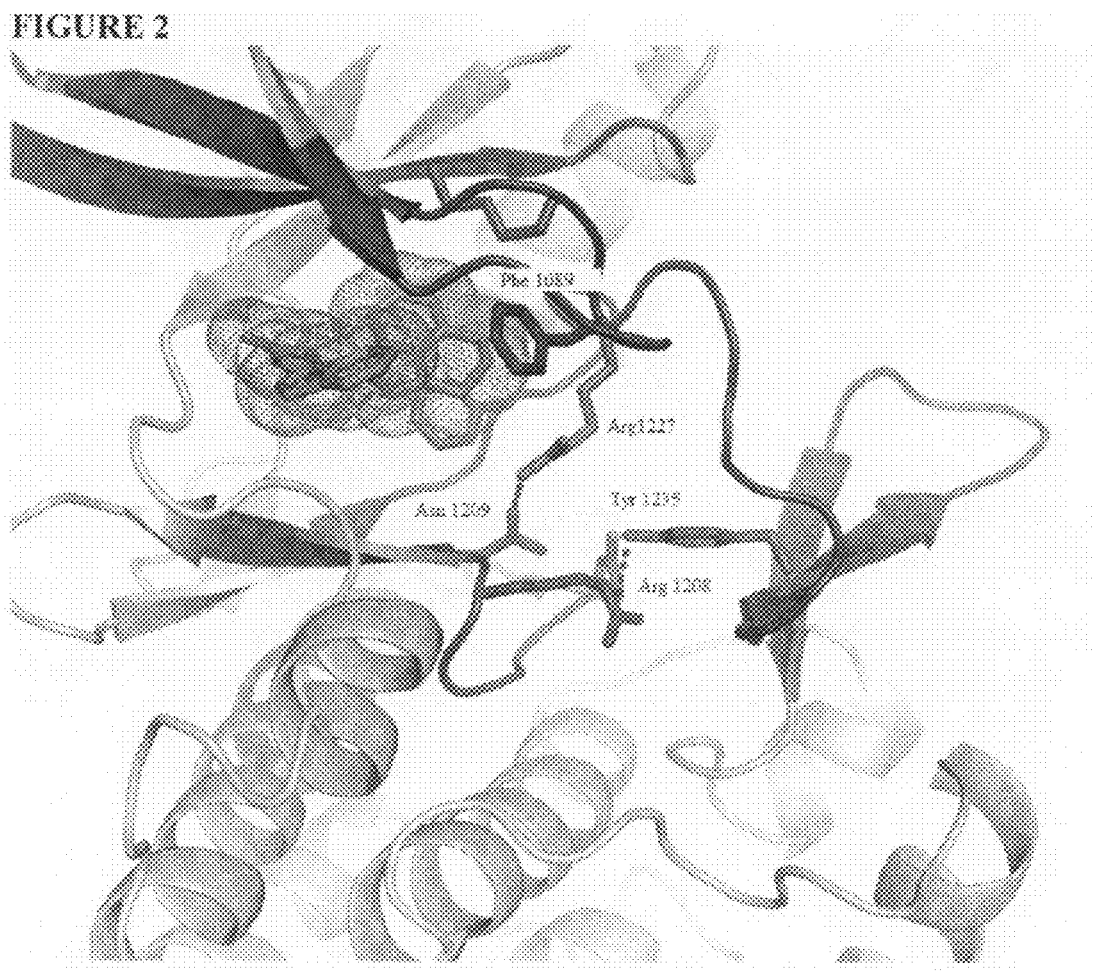

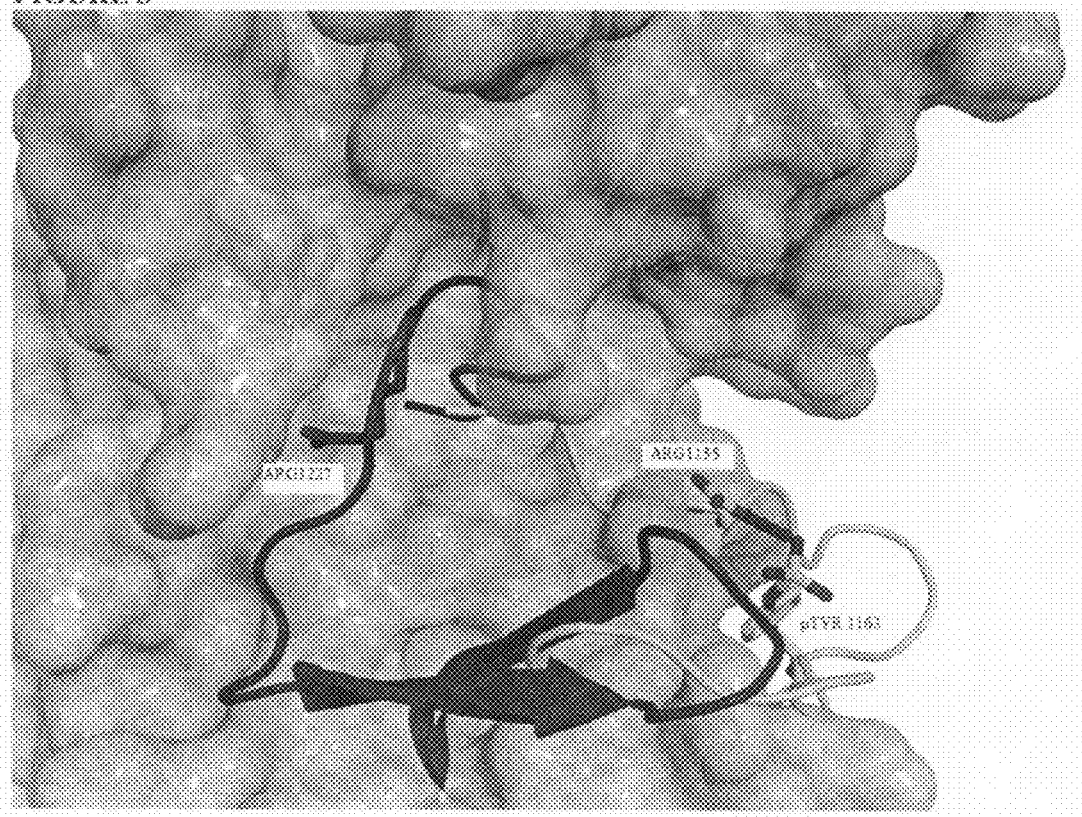

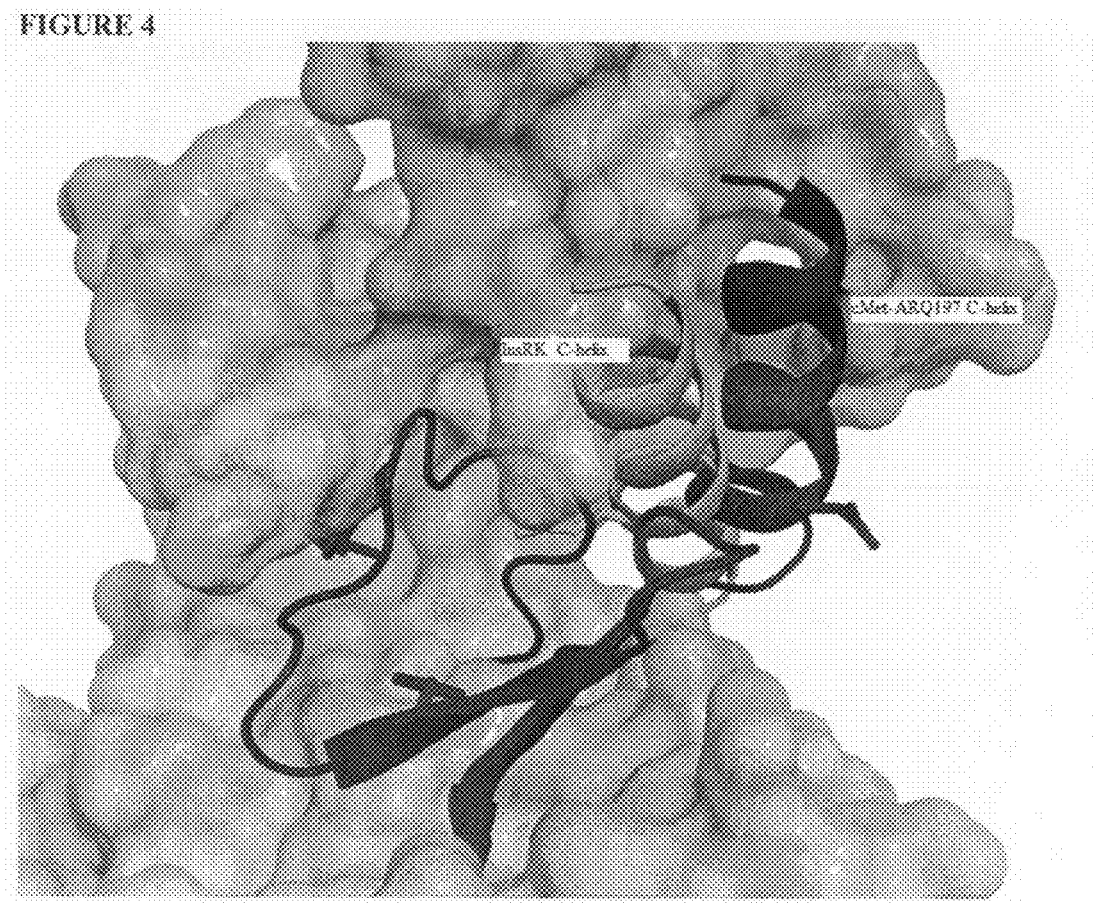

SEQUENCE LISTING

```
<160> NUMBER OF SEQ ID NOS: 14

<210> SEQ ID NO 1
<211> LENGTH: 602
<212> TYPE: PRT
<213> ORGANISM: Homo sapiens

<400> SEQUENCE: 1

Leu Leu Gln Ala Thr Val His Ile Asp Leu Ser Ala Leu Asn Pro Glu
1               5                   10                  15

Leu Val Gln Ala Val Gln His Val Val Ile Gly Pro Ser Ser Leu Ile
            20                  25                  30

Val His Phe Asn Glu Val Ile Gly Arg Gly His Phe Gly Cys Val Tyr
        35                  40                  45
```

-continued

His Gly Thr Leu Leu Asp Asn Asp Gly Lys Lys Ile His Cys Ala Val
         50                  55                  60

Lys Ser Leu Asn Arg Ile Thr Asp Ile Gly Glu Val Ser Gln Phe Leu
 65              70                  75                  80

Thr Glu Gly Ile Ile Met Lys Asp Phe Ser His Pro Asn Val Leu Ser
                 85                  90                  95

Leu Leu Gly Ile Cys Leu Arg Ser Glu Gly Ser Pro Leu Val Val Leu
                100                 105                 110

Pro Tyr Met Lys His Gly Asp Leu Gln Asn Phe Ile Arg Asn Glu Thr
            115                 120                 125

His Asn Pro Thr Val Lys Asp Leu Ile Gly Phe Gly Leu Gln Val Ala
            130                 135                 140

Lys Gly Met Lys Tyr Leu Ala Ser Lys Lys Phe Val His Arg Asp Leu
145                 150                 155                 160

Ala Ala Arg Asn Cys Met Leu Asp Glu Lys Phe Thr Val Lys Val Ala
                165                 170                 175

Asp Phe Gly Leu Ala Arg Asp Met Tyr Asp Lys Glu Tyr Tyr Ser Val
            180                 185                 190

His Asn Lys Thr Gly Ala Lys Leu Pro Val Lys Trp Met Ala Leu Glu
            195                 200                 205

Ser Leu Gln Thr Gln Lys Phe Thr Thr Lys Ser Asp Val Trp Ser Phe
210                 215                 220

Gly Val Leu Leu Trp Glu Leu Met Thr Arg Gly Ala Pro Pro Tyr Pro
225                 230                 235                 240

Asp Val Asn Thr Phe Asp Ile Thr Val Tyr Leu Leu Gln Gly Arg Arg
                245                 250                 255

Leu Leu Gln Pro Glu Tyr Cys Pro Asp Pro Leu Tyr Glu Val Met Leu
            260                 265                 270

Lys Cys Trp His Pro Lys Ala Glu Met Arg Pro Ser Phe Ser Glu Leu
            275                 280                 285

Val Ser Arg Ile Ser Ala Ile Phe Ser Thr Phe Ile Gly Leu Leu Gln
290                 295                 300

Asn Thr Val His Ile Asp Leu Ser Ala Ile Asp Pro Glu Leu Val Gln
305                 310                 315                 320

Ala Val Gln His Val Ile Gly Pro Ser Ser Leu Ile Val His Phe
                325                 330                 335

Asn Glu Val Ile Gly Arg Gly His Phe Gly Cys Val Tyr His Gly Thr
            340                 345                 350

Leu Leu Asp Asn Asp Gly Lys Lys Ile His Cys Ala Val Lys Ser Leu
            355                 360                 365

Asn Arg Ile Thr Asp Ile Gly Glu Val Ser Gln Phe Leu Thr Glu Gly
            370                 375                 380

Ile Ile Met Lys Asp Phe Ser His Pro Asn Val Leu Ser Leu Leu Gly
385                 390                 395                 400

Ile Cys Leu Arg Ser Glu Gly Ser Pro Leu Val Val Leu Pro Tyr Met
            405                 410                 415

Lys His Gly Asp Leu Gln Asn Phe Ile Arg Asn Glu Thr His Asn Pro
            420                 425                 430

Thr Val Lys Asp Leu Ile Gly Phe Gly Leu Gln Val Ala Lys Gly Met
            435                 440                 445

Lys Tyr Leu Ala Ser Lys Lys Phe Val His Arg Asp Leu Ala Ala Arg
450                 455                 460

Asn Cys Met Leu Asp Glu Lys Phe Thr Val Lys Val Ala Asp Phe Gly

```
                465                 470                 475                 480
Leu Ala Arg Asp Met Tyr Asp Lys Glu Tyr Tyr Ser Val His Asn Lys
                    485                 490                 495
Thr Gly Ala Lys Leu Pro Val Lys Trp Met Ala Leu Glu Ser Leu Gln
                500                 505                 510
Thr Gln Lys Phe Thr Thr Lys Ser Asp Val Trp Ser Phe Gly Val Leu
            515                 520                 525
Leu Trp Glu Leu Met Thr Arg Gly Ala Pro Tyr Pro Asp Val Asn
        530                 535                 540
Thr Phe Asp Ile Thr Val Tyr Leu Leu Gln Gly Arg Arg Leu Leu Gln
545                 550                 555                 560
Pro Glu Tyr Cys Pro Asp Pro Leu Tyr Glu Val Met Leu Lys Cys Trp
                565                 570                 575
His Pro Lys Ala Glu Met Arg Pro Ser Phe Ser Glu Leu Val Ser Arg
                580                 585                 590
Ile Ser Ala Ile Phe Ser Thr Phe Ile Gly
                595                 600

<210> SEQ ID NO 2
<211> LENGTH: 301
<212> TYPE: PRT
<213> ORGANISM: Homo sapiens

<400> SEQUENCE: 2

Leu Leu Gln Asn Thr Val His Ile Asp Leu Ser Ala Ile Asp Pro Glu
1               5                   10                  15
Leu Val Gln Ala Val Gln His Val Val Ile Gly Pro Ser Ser Leu Ile
                20                  25                  30
Val His Pro Asn Glu Val Ile Gly Arg Gly His Phe Gly Cys Val Trp
            35                  40                  45
His Gly Thr Leu Leu Asp Asn Asp Gly Lys Lys Ile His Cys Ala Val
        50                  55                  60
Lys Ser Leu Asn Arg Ile Thr Asp Ile Gly Glu Val Ser Gln Phe Leu
65                  70                  75                  80
Thr Glu Gly Ile Ile Met Lys Asp Phe Ser His Pro Asn Val Leu Ser
                85                  90                  95
Leu Leu Gly Ile Cys Leu Arg Ser Glu Gly Ser Pro Leu Val Val Leu
                100                 105                 110
Pro Tyr Met Lys His Gly Asp Leu Arg Asn Phe Ile Arg Asn Glu Thr
            115                 120                 125
His Asn Pro Thr Val Lys Asp Leu Ile Gly Phe Gly Leu Gln Val Ala
        130                 135                 140
Lys Gly Met Lys Tyr Leu Ala Ser Lys Lys Phe Val His Arg Asp Leu
145                 150                 155                 160
Ala Ala Arg Asn Cys Met Leu Asp Glu Lys Phe Thr Val Lys Val Ala
                165                 170                 175
Asp Phe Gly Leu Ala Arg Asp Met Tyr Asp Lys Glu Tyr Tyr Ser Val
            180                 185                 190
His Asn Lys Thr Gly Ala Lys Leu Pro Val Lys Trp Met Ala Leu Glu
        195                 200                 205
Ser Leu Gln Thr Gln Lys Phe Thr Thr Lys Ser Asp Val Trp Ser Phe
    210                 215                 220
Gly Val Leu Leu Trp Glu Leu Met Thr Arg Gly Ala Pro Pro Tyr Pro
225                 230                 235                 240
Asp Val Asn Thr Phe Asp Ile Thr Val Tyr Leu Leu Gln Gly Arg Arg
```

```
                   245                 250                 255
Leu Leu Gln Pro Glu Tyr Cys Pro Asp Pro Leu Tyr Glu Val Met Leu
                260                 265                 270

Lys Cys Trp His Pro Lys Ala Glu Met Arg Pro Ser Phe Ser Glu Leu
            275                 280                 285

Val Ser Arg Ile Ser Ala Ile Phe Ser Thr Phe Ile Gly
        290                 295                 300

<210> SEQ ID NO 3
<211> LENGTH: 894
<212> TYPE: PRT
<213> ORGANISM: Homo sapiens

<400> SEQUENCE: 3

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
```

```
                        325                 330                 335
Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750
```

```
Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
            835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 4
<211> LENGTH: 993
<212> TYPE: PRT
<213> ORGANISM: Homo sapiens

<400> SEQUENCE: 4

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
        130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240
```

-continued

```
Cys Thr Arg Leu Phe Thr Ile Asp Leu Asn Gln Thr Pro Gln Thr Thr
            245                 250                 255

Leu Pro Gln Leu Phe Leu Lys Val Gly Glu Pro Leu Trp Ile Arg Cys
        260                 265                 270

Lys Ala Val His Val Asn His Gly Phe Gly Leu Thr Trp Glu Leu Glu
    275                 280                 285

Asn Lys Ala Leu Glu Glu Gly Asn Tyr Phe Glu Met Ser Thr Tyr Ser
290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670
```

```
Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
        850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
        930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 5
<211> LENGTH: 972
<212> TYPE: PRT
<213> ORGANISM: Homo sapiens

<400> SEQUENCE: 5

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45
```

-continued

```
Arg Val Gly Asp Glu Ile Arg Leu Leu Cys Thr Asp Pro Gly Phe Val
 50                  55                  60

Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                 85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480
```

```
Ser Ala Phe Lys His Asn Gly Thr Val Glu Cys Lys Ala Tyr Asn Asp
            485                 490                 495
Val Gly Lys Thr Ser Ala Tyr Phe Asn Phe Ala Phe Lys Glu Gln Ile
            500                 505                 510
His Pro His Thr Leu Phe Thr Pro Leu Leu Ile Gly Phe Val Ile Val
            515                 520                 525
Ala Gly Met Met Cys Ile Ile Val Met Ile Leu Thr Tyr Lys Tyr Leu
            530                 535                 540
Gln Lys Pro Met Tyr Glu Val Gln Trp Lys Val Val Glu Glu Ile Asn
545                 550                 555                 560
Gly Asn Asn Tyr Val Tyr Ile Asp Pro Thr Gln Leu Pro Tyr Asp His
                565                 570                 575
Lys Trp Glu Phe Pro Arg Asn Arg Leu Ser Phe Gly Lys Thr Leu Gly
            580                 585                 590
Ala Gly Ala Phe Gly Lys Val Val Glu Ala Thr Ala Tyr Gly Leu Ile
            595                 600                 605
Lys Ser Asp Ala Ala Met Thr Val Ala Val Lys Met Leu Lys Pro Ser
            610                 615                 620
Ala His Leu Thr Glu Arg Glu Ala Leu Met Ser Glu Leu Lys Val Leu
625                 630                 635                 640
Ser Tyr Leu Gly Asn His Met Asn Ile Val Asn Leu Leu Gly Ala Cys
                645                 650                 655
Thr Ile Gly Gly Pro Thr Leu Val Ile Thr Glu Tyr Cys Cys Tyr Gly
            660                 665                 670
Asp Leu Leu Asn Phe Leu Arg Arg Lys Arg Asp Ser Phe Ile Cys Ser
            675                 680                 685
Lys Gln Glu Asp His Ala Glu Ala Ala Leu Tyr Lys Asn Leu Leu His
            690                 695                 700
Ser Lys Glu Ser Ser Cys Ser Asp Ser Thr Asn Glu Tyr Met Asp Met
705                 710                 715                 720
Lys Pro Gly Val Ser Tyr Val Val Pro Thr Lys Ala Asp Lys Arg Arg
                725                 730                 735
Ser Val Arg Ile Gly Ser Tyr Ile Glu Arg Asp Val Thr Pro Ala Ile
            740                 745                 750
Met Glu Asp Asp Glu Leu Ala Leu Asp Leu Glu Asp Leu Leu Ser Phe
            755                 760                 765
Ser Tyr Gln Val Ala Lys Gly Met Ala Phe Leu Ala Ser Lys Asn Cys
            770                 775                 780
Ile His Arg Asp Leu Ala Ala Arg Asn Ile Leu Leu Thr His Gly Arg
785                 790                 795                 800
Ile Thr Lys Ile Cys Asp Phe Gly Leu Ala Arg Asp Ile Lys Asn Asp
                805                 810                 815
Ser Asn Tyr Val Val Lys Gly Asn Ala Arg Leu Pro Val Lys Trp Met
                820                 825                 830
Ala Pro Glu Ser Ile Phe Asn Cys Val Tyr Thr Phe Glu Ser Asp Val
            835                 840                 845
Trp Ser Tyr Gly Ile Phe Leu Trp Glu Leu Phe Ser Leu Gly Ser Ser
            850                 855                 860
Pro Tyr Pro Gly Met Pro Val Asp Ser Lys Phe Tyr Lys Met Ile Lys
865                 870                 875                 880
Glu Gly Phe Arg Met Leu Ser Pro Glu His Ala Pro Ala Glu Met Tyr
                885                 890                 895
Asp Ile Met Lys Thr Cys Trp Asp Ala Asp Pro Leu Lys Arg Pro Thr
```

```
                        900                 905                 910
Phe Lys Gln Ile Val Gln Leu Ile Glu Lys Gln Ile Ser Glu Ser Thr
            915                 920                 925

Asn His Ile Tyr Ser Asn Leu Ala Asn Cys Ser Pro Asn Arg Gln Lys
        930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Asp Val
                965                 970

<210> SEQ ID NO 6
<211> LENGTH: 1382
<212> TYPE: PRT
<213> ORGANISM: Homo sapiens

<400> SEQUENCE: 6

Met Gly Thr Gly Gly Arg Arg Gly Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
    50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
    290                 295                 300

Val Ile His Asn Asn Lys Cys Ile Pro Glu Cys Pro Ser Gly Tyr Thr
```

```
                305                 310                 315                 320
Met Asn Ser Ser Asn Leu Leu Cys Thr Pro Cys Leu Gly Pro Cys Pro
                    325                 330                 335

Lys Val Cys His Leu Leu Glu Gly Glu Lys Thr Ile Asp Ser Val Thr
                    340                 345                 350

Ser Ala Gln Glu Leu Arg Gly Cys Thr Val Ile Asn Gly Ser Leu Ile
                    355                 360                 365

Ile Asn Ile Arg Gly Gly Asn Asn Leu Ala Ala Glu Leu Glu Ala Asn
                370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                    405                 410                 415

Gly Glu Thr Leu Glu Ile Gly Asn Tyr Ser Phe Tyr Ala Leu Asp Asn
                    420                 425                 430

Gln Asn Leu Arg Gln Leu Trp Asp Trp Ser Lys His Asn Leu Thr Ile
                    435                 440                 445

Thr Gln Gly Lys Leu Phe Phe His Tyr Asn Pro Lys Leu Cys Leu Ser
                450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Gln Ala Ser Cys Glu
                    485                 490                 495

Asn Glu Leu Leu Lys Phe Ser Tyr Ile Arg Thr Ser Phe Asp Lys Ile
                    500                 505                 510

Leu Leu Arg Trp Glu Pro Tyr Trp Pro Pro Asp Phe Arg Asp Leu Leu
                    515                 520                 525

Gly Phe Met Leu Phe Tyr Lys Glu Ala Pro Tyr Gln Asn Val Thr Glu
                    530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                    565                 570                 575

Gly Trp Leu Met Arg Gly Leu Lys Pro Trp Thr Gln Tyr Ala Ile Phe
                    580                 585                 590

Val Lys Thr Leu Val Thr Phe Ser Asp Glu Arg Arg Thr Tyr Gly Ala
                    595                 600                 605

Lys Ser Asp Ile Ile Tyr Val Gln Thr Asp Ala Thr Asn Pro Ser Val
                610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                    645                 650                 655

Val Phe Trp Glu Arg Gln Ala Glu Asp Ser Glu Leu Phe Glu Leu Asp
                    660                 665                 670

Tyr Cys Leu Lys Gly Leu Lys Leu Pro Ser Arg Thr Trp Ser Pro Pro
                    675                 680                 685

Phe Glu Ser Glu Asp Ser Gln Lys His Asn Gln Ser Glu Tyr Glu Asp
                    690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                    725                 730                 735
```

-continued

His Asn Val Val Phe Val Pro Arg Lys Thr Ser Ser Gly Thr Gly Ala
                740                 745                 750

Glu Asp Pro Arg Pro Ser Arg Lys Arg Arg Ser Leu Gly Asp Val Gly
                755                 760                 765

Asn Val Thr Val Ala Val Pro Thr Val Ala Ala Phe Pro Asn Thr Ser
770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
                820                 825                 830

Arg Cys Ser Val Ala Ala Tyr Val Ser Ala Arg Thr Met Pro Glu Ala
                835                 840                 845

Lys Ala Asp Asp Ile Val Gly Pro Val Thr His Glu Ile Phe Glu Asn
                850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
                900                 905                 910

Leu Arg Gly Leu Ser Pro Gly Asn Tyr Ser Val Arg Ile Arg Ala Thr
                915                 920                 925

Ser Leu Ala Gly Asn Gly Ser Trp Thr Glu Pro Thr Tyr Phe Tyr Val
                930                 935                 940

Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
                965                 970                 975

Leu Phe Leu Arg Lys Arg Gln Pro Asp Gly Pro Leu Gly Pro Leu Tyr
                980                 985                 990

Ala Ser Ser Asn Pro Glu Tyr Leu Ser Ala Ser Asp Val Phe Pro Cys
                995                 1000                1005

Ser Val Tyr Val Pro Asp Glu Trp Glu Val Ser Arg Glu Lys Ile
    1010                1015                1020

Thr Leu Leu Arg Glu Leu Gly Gln Gly Ser Phe Gly Met Val Tyr
    1025                1030                1035

Glu Gly Asn Ala Arg Asp Ile Ile Lys Gly Glu Ala Glu Thr Arg
    1040                1045                1050

Val Ala Val Lys Thr Val Asn Glu Ser Ala Ser Leu Arg Glu Arg
    1055                1060                1065

Ile Glu Phe Leu Asn Glu Ala Ser Val Met Lys Gly Phe Thr Cys
    1070                1075                1080

His His Val Val Arg Leu Leu Gly Val Val Ser Lys Gly Gln Pro
    1085                1090                1095

Thr Leu Val Val Met Glu Leu Met Ala His Gly Asp Leu Lys Ser
    1100                1105                1110

Tyr Leu Arg Ser Leu Arg Pro Glu Ala Glu Asn Asn Pro Gly Arg
    1115                1120                1125

Pro Pro Pro Thr Leu Gln Glu Met Ile Gln Met Ala Ala Glu Ile
    1130                1135                1140

Ala Asp Gly Met Ala Tyr Leu Asn Ala Lys Lys Phe Val His Arg
    1145                1150                1155

```
Asp Leu Ala Ala Arg Asn Cys Met Val Ala His Asp Phe Thr Val
    1160                1165                1170

Lys Ile Gly Asp Phe Gly Met Thr Arg Asp Ile Tyr Glu Thr Asp
    1175                1180                1185

Tyr Tyr Arg Lys Gly Lys Gly Leu Leu Pro Val Arg Trp Met
    1190                1195                1200

Ala Pro Glu Ser Leu Lys Asp Gly Val Phe Thr Thr Ser Ser Asp
    1205                1210                1215

Met Trp Ser Phe Gly Val Val Leu Trp Glu Ile Thr Ser Leu Ala
    1220                1225                1230

Glu Gln Pro Tyr Gln Gly Leu Ser Asn Glu Gln Val Leu Lys Phe
    1235                1240                1245

Val Met Asp Gly Gly Tyr Leu Asp Gln Pro Asp Asn Cys Pro Glu
    1250                1255                1260

Arg Val Thr Asp Leu Met Arg Met Cys Trp Gln Phe Asn Pro Lys
    1265                1270                1275

Met Arg Pro Thr Phe Leu Glu Ile Val Asn Leu Leu Lys Asp Asp
    1280                1285                1290

Leu His Pro Ser Phe Pro Glu Val Ser Phe Phe His Ser Glu Glu
    1295                1300                1305

Asn Lys Ala Pro Glu Ser Glu Glu Leu Glu Met Glu Phe Glu Asp
    1310                1315                1320

Met Glu Asn Val Pro Leu Asp Arg Ser Ser His Cys Gln Arg Glu
    1325                1330                1335

Glu Ala Gly Gly Arg Asp Gly Gly Ser Ser Leu Gly Phe Lys Arg
    1340                1345                1350

Ser Tyr Glu Glu His Ile Pro Tyr Thr His Met Asn Gly Gly Lys
    1355                1360                1365

Lys Asn Gly Arg Ile Leu Thr Leu Pro Arg Ser Asn Pro Ser
    1370                1375                1380

<210> SEQ ID NO 7
<211> LENGTH: 972
<212> TYPE: PRT
<213> ORGANISM: Homo sapiens

<400> SEQUENCE: 7

Met Gly Pro Gly Val Leu Leu Leu Leu Val Ala Thr Ala Trp His
1                   5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140
```

```
Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
    435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
    515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
```

```
                565                 570                 575
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
    610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
    690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
        755                 760                 765
Leu Ala Ser Lys Asn Cys Ile His Arg Asp Val Ala Ala Arg Asn Val
    770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
    850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Glu Leu Glu Glu
    930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
                965                 970

<210> SEQ ID NO 8
<211> LENGTH: 1149
```

```
<212> TYPE: PRT
<213> ORGANISM: Homo sapiens

<400> SEQUENCE: 8

Met Gly Gln Gln Pro Gly Lys Val Leu Gly Asp Gln Arg Pro Ser
1               5                   10                  15

Leu Pro Ala Leu His Phe Ile Lys Gly Ala Gly Lys Glu Ser Ser
            20                  25                  30

Arg His Gly Gly Pro His Cys Asn Val Phe Val Glu His Glu Ala Leu
        35                  40                  45

Gln Arg Pro Val Ala Ser Asp Phe Glu Pro Gln Gly Leu Ser Glu Ala
    50                  55                  60

Ala Arg Trp Asn Ser Lys Glu Asn Leu Leu Ala Gly Pro Ser Glu Asn
65                  70                  75                  80

Asp Pro Asn Leu Phe Val Ala Leu Tyr Asp Phe Val Ala Ser Gly Asp
                85                  90                  95

Asn Thr Leu Ser Ile Thr Lys Gly Glu Lys Leu Arg Val Leu Gly Tyr
            100                 105                 110

Asn His Asn Gly Glu Trp Cys Glu Ala Gln Thr Lys Asn Gly Gln Gly
        115                 120                 125

Trp Val Pro Ser Asn Tyr Ile Thr Pro Val Asn Ser Leu Glu Lys His
130                 135                 140

Ser Trp Tyr His Gly Pro Val Ser Arg Asn Ala Ala Glu Tyr Leu Leu
145                 150                 155                 160

Ser Ser Gly Ile Asn Gly Ser Phe Leu Val Arg Glu Ser Glu Ser Ser
                165                 170                 175

Pro Gly Gln Arg Ser Ile Ser Leu Arg Tyr Glu Gly Arg Val Tyr His
            180                 185                 190

Tyr Arg Ile Asn Thr Ala Ser Asp Gly Lys Leu Tyr Val Ser Ser Glu
        195                 200                 205

Ser Arg Phe Asn Thr Leu Ala Glu Leu Val His His Ser Thr Val
210                 215                 220

Ala Asp Gly Leu Ile Thr Thr Leu His Tyr Pro Ala Pro Lys Arg Asn
225                 230                 235                 240

Lys Pro Thr Val Tyr Gly Val Ser Pro Asn Tyr Asp Lys Trp Glu Met
                245                 250                 255

Glu Arg Thr Asp Ile Thr Met Lys His Lys Leu Gly Gly Gly Gln Tyr
            260                 265                 270

Gly Glu Val Tyr Glu Gly Val Trp Lys Lys Tyr Ser Leu Thr Val Ala
        275                 280                 285

Val Lys Thr Leu Lys Glu Asp Thr Met Glu Val Glu Glu Phe Leu Lys
    290                 295                 300

Glu Ala Ala Val Met Lys Glu Ile Lys His Pro Asn Leu Val Gln Leu
305                 310                 315                 320

Leu Gly Val Cys Thr Arg Glu Pro Pro Phe Tyr Ile Ile Thr Glu Phe
                325                 330                 335

Met Thr Tyr Gly Asn Leu Leu Asp Tyr Leu Arg Glu Cys Asn Arg Gln
            340                 345                 350

Glu Val Asn Ala Val Val Leu Leu Tyr Met Ala Thr Gln Ile Ser Ser
        355                 360                 365

Ala Met Glu Tyr Leu Glu Lys Lys Asn Phe Ile His Arg Asp Leu Ala
    370                 375                 380

Ala Arg Asn Cys Leu Val Gly Glu Asn His Leu Val Lys Val Ala Asp
385                 390                 395                 400
```

```
Phe Gly Leu Ser Arg Leu Met Thr Gly Asp Thr Tyr Thr Ala His Ala
                405                 410                 415

Gly Ala Lys Phe Pro Ile Lys Trp Thr Ala Pro Glu Ser Leu Ala Tyr
            420                 425                 430

Asn Lys Phe Ser Ile Lys Ser Asp Val Trp Ala Phe Gly Val Leu Leu
        435                 440                 445

Trp Glu Ile Ala Thr Tyr Gly Met Ser Pro Tyr Pro Gly Ile Asp Leu
    450                 455                 460

Ser Gln Val Tyr Glu Leu Leu Glu Lys Asp Tyr Arg Met Glu Arg Pro
465                 470                 475                 480

Glu Gly Cys Pro Glu Lys Val Tyr Glu Leu Met Arg Ala Cys Trp Gln
            485                 490                 495

Trp Asn Pro Ser Asp Arg Pro Ser Phe Ala Glu Ile His Gln Ala Phe
        500                 505                 510

Glu Thr Met Phe Gln Glu Ser Ile Ser Asp Glu Val Glu Lys Glu
    515                 520                 525

Leu Gly Lys Gln Gly Val Arg Gly Ala Val Ser Thr Leu Leu Gln Ala
    530                 535                 540

Pro Glu Leu Pro Thr Lys Thr Arg Thr Ser Arg Arg Ala Ala Glu His
545                 550                 555                 560

Arg Asp Thr Thr Asp Val Pro Glu Met Pro His Ser Lys Gly Gln Gly
            565                 570                 575

Glu Ser Asp Pro Leu Asp His Glu Pro Ala Val Ser Pro Leu Leu Pro
        580                 585                 590

Arg Lys Glu Arg Gly Pro Pro Glu Gly Gly Leu Asn Gly Asp Glu Arg
    595                 600                 605

Leu Leu Pro Lys Asp Lys Lys Thr Asn Leu Phe Ser Ala Leu Ile Lys
    610                 615                 620

Lys Lys Lys Lys Thr Ala Pro Thr Pro Pro Lys Arg Ser Ser Ser Phe
625                 630                 635                 640

Arg Glu Met Asp Gly Gln Pro Glu Arg Arg Gly Ala Gly Glu Glu Glu
            645                 650                 655

Gly Arg Asp Ile Ser Asn Gly Ala Leu Ala Phe Thr Pro Leu Asp Thr
        660                 665                 670

Ala Asp Pro Ala Lys Ser Pro Lys Pro Ser Asn Gly Ala Gly Val Pro
    675                 680                 685

Asn Gly Ala Leu Arg Glu Ser Gly Gly Ser Gly Phe Arg Ser Pro His
    690                 695                 700

Leu Trp Lys Lys Ser Ser Thr Leu Thr Ser Ser Arg Leu Ala Thr Gly
705                 710                 715                 720

Glu Glu Glu Gly Gly Gly Ser Ser Ser Lys Arg Phe Leu Arg Ser Cys
            725                 730                 735

Ser Ala Ser Cys Val Pro His Gly Ala Lys Asp Thr Glu Trp Arg Ser
        740                 745                 750

Val Thr Leu Pro Arg Asp Leu Gln Ser Thr Gly Arg Gln Phe Asp Ser
    755                 760                 765

Ser Thr Phe Gly Gly His Lys Ser Glu Lys Pro Ala Leu Pro Arg Lys
    770                 775                 780

Arg Ala Gly Glu Asn Arg Ser Asp Gln Val Thr Arg Gly Thr Val Thr
785                 790                 795                 800

Pro Pro Pro Arg Leu Val Lys Lys Asn Glu Glu Ala Ala Asp Glu Val
            805                 810                 815

Phe Lys Asp Ile Met Glu Ser Ser Pro Gly Ser Ser Pro Pro Asn Leu
        820                 825                 830
```

```
Thr Pro Lys Pro Leu Arg Arg Gln Val Thr Val Ala Pro Ala Ser Gly
            835                 840                 845

Leu Pro His Lys Glu Glu Ala Gly Lys Gly Ser Ala Leu Gly Thr Pro
850                 855                 860

Ala Ala Ala Glu Pro Val Thr Pro Thr Ser Lys Ala Gly Ser Gly Ala
865                 870                 875                 880

Pro Gly Gly Thr Ser Lys Gly Pro Ala Glu Glu Ser Arg Val Arg Arg
                885                 890                 895

His Lys His Ser Ser Glu Ser Pro Gly Arg Asp Lys Gly Lys Leu Ser
            900                 905                 910

Arg Leu Lys Pro Ala Pro Pro Pro Pro Ala Ala Ser Ala Gly Lys
        915                 920                 925

Ala Gly Gly Lys Pro Ser Gln Ser Pro Ser Gln Glu Ala Ala Gly Glu
930                 935                 940

Ala Val Leu Gly Ala Lys Thr Lys Ala Thr Ser Leu Val Asp Ala Val
945                 950                 955                 960

Asn Ser Asp Ala Ala Lys Pro Ser Gln Pro Gly Glu Gly Leu Lys Lys
                965                 970                 975

Pro Val Leu Pro Ala Thr Pro Lys Pro Gln Ser Ala Lys Pro Ser Gly
            980                 985                 990

Thr Pro Ile Ser Pro Ala Pro Val Pro Ser Thr Leu Pro Ser Ala Ser
        995                 1000                1005

Ser Ala Leu Ala Gly Asp Gln Pro Ser Ser Thr Ala Phe Ile Pro
    1010                1015                1020

Leu Ile Ser Thr Arg Val Ser Leu Arg Lys Thr Arg Gln Pro Pro
    1025                1030                1035

Glu Arg Ile Ala Ser Gly Ala Ile Thr Lys Gly Val Val Leu Asp
    1040                1045                1050

Ser Thr Glu Ala Leu Cys Leu Ala Ile Ser Arg Asn Ser Glu Gln
    1055                1060                1065

Met Ala Ser His Ser Ala Val Leu Glu Ala Gly Lys Asn Leu Tyr
    1070                1075                1080

Thr Phe Cys Val Ser Tyr Val Asp Ser Ile Gln Gln Met Arg Asn
    1085                1090                1095

Lys Phe Ala Phe Arg Glu Ala Ile Asn Lys Leu Glu Asn Asn Leu
    1100                1105                1110

Arg Glu Leu Gln Ile Cys Pro Ala Thr Ala Gly Ser Gly Pro Ala
    1115                1120                1125

Ala Thr Gln Asp Phe Ser Lys Leu Leu Ser Ser Val Lys Glu Ile
    1130                1135                1140

Ser Asp Ile Val Gln Arg
    1145

<210> SEQ ID NO 9
<211> LENGTH: 313
<212> TYPE: PRT
<213> ORGANISM: Homo sapiens

<400> SEQUENCE: 9

Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
            20                  25                  30

Pro Leu Glu Ser Gln Tyr Gln Val Gly Pro Leu Leu Gly Ser Gly Gly
        35                  40                  45
```

```
Phe Gly Ser Val Tyr Ser Gly Ile Arg Val Ser Asp Asn Leu Pro Val
 50                  55                  60

Ala Ile Lys His Val Glu Lys Asp Arg Ile Ser Asp Trp Gly Glu Leu
65                  70                  75                  80

Pro Asn Gly Thr Arg Val Pro Met Glu Val Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
290                 295                 300

His Ser Leu Ser Pro Gly Pro Ser Lys
305                 310

<210> SEQ ID NO 10
<211> LENGTH: 821
<212> TYPE: PRT
<213> ORGANISM: Homo sapiens

<400> SEQUENCE: 10

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110
```

Val Asp Ser Glu Thr Trp Tyr Phe Met Val Asn Val Thr Asp Ala Ile
115                 120                 125

Ser Ser Gly Asp Asp Glu Asp Thr Asp Gly Ala Glu Asp Phe Val
130             135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
            165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
            325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
            370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His

-continued

```
                530                 535                 540
Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
                675                 680                 685

Phe Gly Val Leu Met Trp Glu Ile Phe Thr Leu Gly Gly Ser Pro Tyr
            690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 11
<211> LENGTH: 23
<212> TYPE: PRT
<213> ORGANISM: Homo sapiens

<400> SEQUENCE: 11

Ile Gly Phe Val Ala Val Lys Leu Val Leu Pro Tyr Met Lys His Gly
1               5                   10                  15

Asp Met Ala Asp Phe Ala Arg
            20

<210> SEQ ID NO 12
<211> LENGTH: 1389
<212> TYPE: PRT
<213> ORGANISM: Homo sapiens

<400> SEQUENCE: 12

Met Lys Ala Pro Ala Val Leu Ala Pro Gly Ile Leu Val Leu Leu Phe
1               5                   10                  15
```

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
    275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
    420                 425                 430

Gln Phe Ser Glu Val Leu Leu Thr Ser Ile Ser Thr Phe Ile Lys Gly

-continued

```
            435                 440                 445
Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Glu Ile Lys Gly Asn Asp Ile
    850                 855                 860
```

```
Asp Pro Glu Ala Val Lys Gly Glu Val Leu Lys Val Gly Asn Lys Ser
865                 870                 875                 880

Cys Glu Asn Ile His Leu His Ser Glu Ala Val Leu Cys Thr Val Pro
                885                 890                 895

Asn Asp Leu Leu Lys Leu Asn Ser Glu Leu Asn Ile Glu Trp Lys Gln
            900                 905                 910

Ala Ile Ser Ser Thr Val Leu Gly Lys Val Ile Val Gln Pro Asp Gln
        915                 920                 925

Asn Phe Thr Gly Leu Ile Ala Gly Val Val Ser Ile Ser Thr Ala Leu
    930                 935                 940

Leu Leu Leu Leu Gly Phe Phe Leu Trp Leu Lys Lys Arg Lys Gln Ile
945                 950                 955                 960

Lys Asp Leu Gly Ser Glu Leu Val Arg Tyr Asp Ala Arg Val His Thr
                965                 970                 975

Pro His Leu Asp Arg Leu Val Ser Ala Arg Ser Val Ser Pro Thr Thr
            980                 985                 990

Glu Met Val Ser Asn Glu Ser Val Asp Tyr Arg Ala Thr Phe Pro Glu
        995                 1000                1005

Asp Gln Phe Pro Asn Ser Ser Gln Asn Gly Ser Cys Arg Gln Val
    1010                1015                1020

Gln Tyr Pro Leu Thr Asp Met Ser Pro Ile Leu Thr Ser Gly Asp
    1025                1030                1035

Ser Asp Ile Ser Ser Pro Leu Leu Gln Asn Thr Val His Ile Asp
    1040                1045                1050

Leu Ser Ala Leu Asn Pro Glu Leu Val Gln Ala Val Gln His Val
    1055                1060                1065

Val Ile Gly Pro Ser Ser Leu Ile Val His Phe Asn Glu Val Ile
    1070                1075                1080

Gly Arg Gly His Phe Gly Cys Val Tyr His Gly Thr Leu Leu Asp
    1085                1090                1095

Asn Asp Gly Lys Lys Ile His Cys Ala Val Lys Ser Leu Asn Arg
    1100                1105                1110

Ile Thr Asp Ile Gly Glu Val Ser Gln Phe Leu Thr Glu Gly Ile
    1115                1120                1125

Ile Met Lys Asp Phe Ser His Pro Asn Val Leu Ser Leu Leu Gly
    1130                1135                1140

Ile Cys Leu Arg Ser Glu Gly Ser Pro Leu Val Val Leu Pro Tyr
    1145                1150                1155

Met Lys His Gly Asp Leu Arg Asn Phe Ile Arg Asn Glu Thr His
    1160                1165                1170

Asn Pro Thr Val Lys Asp Leu Ile Gly Phe Gly Leu Gln Val Ala
    1175                1180                1185

Lys Gly Met Lys Tyr Leu Ala Ser Lys Lys Phe Val His Arg Asp
    1190                1195                1200

Leu Ala Ala Arg Asn Cys Met Leu Asp Glu Lys Phe Thr Val Lys
    1205                1210                1215

Val Ala Asp Phe Gly Leu Ala Arg Asp Met Tyr Asp Lys Glu Tyr
    1220                1225                1230

Tyr Ser Val His Asn Lys Thr Gly Ala Lys Leu Pro Val Lys Trp
    1235                1240                1245

Met Ala Leu Glu Ser Leu Gln Thr Gln Lys Phe Thr Thr Lys Ser
    1250                1255                1260

Asp Val Trp Ser Phe Gly Val Val Leu Trp Glu Leu Met Thr Arg
    1265                1270                1275
```

```
Gly Ala Pro Pro Tyr Pro Asp Val Asn Thr Phe Asp Ile Thr Val
    1280            1285                1290

Tyr Leu Leu Gln Gly Arg Arg Leu Leu Gln Pro Glu Tyr Cys Pro
    1295            1300                1305

Asp Pro Leu Tyr Glu Val Met Leu Lys Cys Trp His Pro Lys Ala
    1310            1315                1320

Glu Met Arg Pro Ser Phe Ser Glu Leu Val Ser Arg Ile Ser Ala
    1325            1330                1335

Ile Phe Ser Thr Phe Ile Gly Glu His Tyr Val His Val Asn Ala
    1340            1345                1350

Thr Tyr Val Asn Val Lys Cys Val Ala Pro Tyr Pro Ser Leu Leu
    1355            1360                1365

Ser Ser Glu Asp Asn Ala Asp Asp Glu Val Asp Thr Arg Pro Ala
    1370            1375                1380

Ser Phe Trp Glu Thr Ser
    1385

<210> SEQ ID NO 13
<211> LENGTH: 23
<212> TYPE: PRT
<213> ORGANISM: Homo sapiens

<400> SEQUENCE: 13

Leu Gly Phe Val Ala Val Lys Ile Val Val Glu Tyr Ala Ser Lys Gly
1               5                   10                  15

Asn Leu Ala Asp Phe Ala Arg
            20

<210> SEQ ID NO 14
<211> LENGTH: 26
<212> TYPE: PRT
<213> ORGANISM: Homo sapiens

<400> SEQUENCE: 14

Leu Gly Phe Gly Gln Val Ala Val Lys Ile Val Val Glu Tyr Ala Ser
1               5                   10                  15

Lys Gly Asn Leu Ala Asp Phe Gly Ala Arg
            20                  25
```

KINASE INHIBITION MODELS AND THEIR USES

RELATED APPLICATIONS

This application is related to provisional application U.S. Ser. No. 60/962,881, filed Aug. 1, 2007, the contents which are herein incorporated by reference in their entirety.

BACKGROUND OF THE INVENTION

Protein tyrosine kinases perform diverse functions ranging from stimulation of cell growth and differentiation to arrest of cell proliferation. They are either receptor tyrosine kinases (RTK) or intracellular tyrosine kinases. Inhibition of kinase activity is recognized as an effective way to control disease in humans.

The activation loop (A-loop) plays a key role in the activation of kinases. Many kinases switch on and off depending on the conformational state of the A-loop. The structural nature of these changes involves the phosphorylation of 1-3 residues in the A-loop, which, in turn, leads to the formation of salt bridges in the catalytic loop (C-loop) and the N-lobe. The N-lobe comprises residues from N1049 to M1160. Three important motifs are located in this lobe; the P-loop, the αC-helix and the Lys-Glu ionic pair. The precise alignment of which plays a critical role in the kinase catalytic activity. Other kinases do not require the phosphorylation of these A-loop residues to become active. It is thought that these kinases adopt a unique conformation and, as a result acidic residues in the A-loop, form a salt bridge with a conserved arginine residue in the C-loop. This allows access to the ATP binding pocket.

Upon tyrosine residue phosphorylation, the A-loop adopts a configuration optimized for substrate binding and catalysis. In many kinase structures resolved to date, the A-loop, in the phosphorylated form, adopts similar conformations to satisfy catalytic constraints and to provide a platform for substrate binding.

The activation loops in the unphosphorylated kinases exhibit a wide range of different conformations, which may explain their role in kinase activity regulation. In this unphosphorylated state, the A-loop can assume conformations ranging from fully open to completely closed (Huse, M. and Kuriyan, J. 2002. Cell 109:275-282). The open, autoinhibited, conformation has been observed in the crystal structures of fibroblast growth factor receptor (Mohammadi, M. et al. 1996. Cell, 86, 577-587) and c-Met (Wang, W. et al. 2006. Proc. Natl. Acad. Sci. USA 103:3563-3568). In this conformation of the fibroblast growth factor receptor, the A-loop is not suitable for substrate binding but does not obstruct the ATP binding site. In the closed, canonical, autoinhibited conformation, the activation loop folds as a pseudosubstrate, obstructing binding of both ATP and the peptide substrate.

The canonical, autoinhibited conformation has been detected in the unbound insulin receptor tyrosine kinase IRK, one of the most studied receptor tyrosine kinases (Hubbard, S. R. et al. 1994. Nature 372:746-754), c-Src kinase bound to the ATP analog AMP-PNP (Xu, W. et al. 1999. Molecular Cell 3:629-638), Hck bound to a small molecule inhibitor (Schindler, T. et al. 1999. *Mol. Cell.* 3: 639-648), FLT3 receptor tyrosine kinase (Griffith, J. et al. 2004. Molecular Cell 13:69-178), c-Abl bound to Imatinib (Schindler, T. et al. 2000. Science 289, 1938-1942; Nagar, B. et al. 2002. Cancer Research 62:4236-4243), c-Kit tyrosine kinase receptor unbound and bound to Gleevec (Mol, C. D. et al. 2004. The Journal of Biological Chemistry 279:31655-31663), and more recently cFMS (colony stimulating factor receptor-1) bound to small molecule inhibitors (Schubert, C. et al. 2007. J. Biol. Chem. 282:4094-4101).

The majority of kinase inhibitors is believed to be interacting with the protein in a region which binds ATP. The conformation of the kinase, when bound by the inhibitors, is frequently very similar to the one in which ATP is bound, i.e., the active conformation of the kinase.

Typically, kinase inhibitors binding to the ATP pocket take advantage of limited sequence variations in the nucleotide binding site as well as conformational differences between phosphorylated and unphosphorylated forms of kinases. While phosphorylated forms may adopt similar conformations in different kinases, unphosphorylated, inactive conformations of kinases show great variability. Knowledge of these distinct kinase conformations allow rational drug design of high affinity, specific compounds.

A body of knowledge has given rise to the concept of ATP-competitive ligands and the use of X-ray crystallography to aid in their design. In such approaches it has become established that the ligand is required to at least in part to mimic the binding of ATP in the active site. The notion of these ligands competing for access to this site and on binding place the A-loop in a catalytically inactive conformation has been demonstrated by X-ray studies for the insulin-like receptor IGF1, IRK, cFMS, c-Abl, c-Kit, Flt3, MusK, etc.

More recently, a different type of kinase inhibitor has become known in the field. These new inhibitors appear to interact with an inactive form of the kinase in the ATP binding site. Stabilization of unphosphorylated inactive forms of RTKs provides a different approach to modulate signaling through kinases. It provides another mechanism to control over expression and non-ligand activation.

Controlling the position of the activation loop by use of small molecule inhibitors has been documented and shown by the use of X-ray crystallography. This technique provides a detailed structural insight into the mechanism by which the A-loop is prevented from achieving a catalytically active conformation. It is this technique which provides important and valuable information for the use of the design of more efficacious and selective kinase inhibitors.

In the case of the ATP-competitive ligand STI-571 binding to the inactive form of c-Abl, X-ray studies show that DFG is in the out conformation, and that the A-loop is held in an inactive conformation (Nagar, B. et al. 2002. Cancer Research 62:4236-4243).

Despite the identification of many agents which have been described to affect such control there remains a need for additional, novel and selective agents which offer the benefits of increased specificity and reduced side effects. Despite many reports, there remains a need to identify methods to inhibit the signaling through this important class of proteins.

The references cited herein are not admitted to be prior art to the claimed invention.

SUMMARY OF THE INVENTION

The invention provides a crystal structure including c-Met or c-Met kinase domain, and a ligand complexed thereto. In one aspect of the invention, the c-Met kinase domain comprises the amino acid sequence of cMet1 (SEQ ID NO: 1) from Table 1A or cMet2 (SEQ ID NO: 2) from Table 1B.

In certain embodiments of the invention, the ligand is a selective small molecule inhibitor of c-Met. In other embodiments of the invention, the inhibitor is (−)-trans-3-(5,6-dihydro-4H-pyrrolo[3,2,1-ij]quinolin-1-yl)-4(1H-indol-3-yl)pyrrolidine-2,5-dione, also known as "the selective c-Met inhibitor."

The invention provides a process for constructing a c-Met inhibition model including the steps of crystallizing c-Met kinase domain bound to (−)-trans-3-(5,6-dihydro-4H-pyrrolo[3,2,1-ij]quinolin-1-yl)-4(1H-indol-3-yl)pyrrolidine-2,5-dione, resolving the x-ray crystallography of the c-Met kinase domain, applying the data generated from resolving the x-ray crystallography of the c-Met kinase domain to a computer algorithm, and generating from the computer algorithm a c-Met inhibition model suitable for screening or designing c-Met inhibitors. In one aspect of the invention, resolving the x-ray crystallography includes obtaining crystallographic coordinates for the c-Met kinase domain. The invention further provides a process for screening or designing c-Met inhibitors including using the c-Met inhibition model to screen or design c-Met inhibitors.

The invention provides a c-Met inhibition model including the crystallography coordinates of c-Met amino acids I_1084, G_1085, F_1089, V_1092, A_1108, V_1109, K_1110, L_1140, V_1155, L_1157, P_1158, Y_1159, M_1160, K_1161, H_1162, G_1163, D_1164, M_1211, A_1221, D_1222, F_1223, A_1226, and R_1227 (SEQ ID NO: 11) which are within about a root mean square deviation of not more than about 1.5 Å from the backbone atoms of the amino acids according to Table 4. In one aspect of the invention, the crystallography coordinates contain coordinates of all the amino acids of c-Met that are within about a root mean square deviation of not more than about 1.5 Å from the backbone atoms of the amino acids according to Table 1A or Table 1B.

The invention provides a method for making an inhibition model for a kinase including the steps of performing sequence alignment between the amino acid sequences of the kinase and c-Met using four motifs: P-loop, salt-bridge, DFG-motif and the A-loop; identifying non-conserved residues between c-Met and the kinase, replacing the crystallography coordinates of the non-conserved residues in the c-Met inhibition model with those of the corresponding residues from the kinase, and refining the c-Met inhibition model with replaced crystallography coordinates to generate the inhibition model for the kinase. In one aspect of the invention, the method for making an inhibition model for a kinase further contains the step of evaluating the inhibition model for the kinase. In certain embodiments of the invention, the kinase is a tyrosine kinase. Alternatively, or in addition, the tyrosine kinase is a receptor tyrosine kinase. An exemplary receptor tyrosine kinase is selected from the group consisting of EGFR, VEGFR, FGFR, PDGFR, HER2, Kit, IRK, RET, AXL, FLT-3, EphB4, c-Met homologs, and c-Met mutants. In one embodiment of the invention, the receptor tyrosine kinase is FGFR-2. In another embodiment of the invention, the tyrosine kinase is a non-receptor tyrosine kinase. An exemplary non-receptor tyrosine kinase is selected from the group consisting of c-Abl, Src, Fyn, Lyn, and Yes. In one embodiment of the invention, the non-receptor tyrosine kinase is c-Abl. In one aspect of the invention, the kinase is a serine/threonine kinase. An exemplary serine/threonine kinase is selected from the group consisting of B-Raf, PIM, PAK, MEK, MAPK, AKT, and Aurora kinase.

The invention provides a c-Abl inhibition model including the crystallography coordinates of c-Abl amino acids L_266, G_267, Y_271, V_274, A_287, V_288, K_289, V_317, I_331, T_333, E_334, F_335, M_336, T_337, Y_338, G_339, N_340, L_388, A_398, D_399, F_400, S_403, and R_404 (SEQ ID NO: 8) which are within about a root mean square deviation of not more than about 1.5 Å from the backbone atoms of the amino acids according to Table 5.

The invention also provides a method of similarity assessment including comparing the inhibition models of various kinases derived from the c-Met inhibition model. In one aspect of the invention, the models are compared applying a weighting system. In another aspect of the invention, the weighting system includes positive scores for residues critical for ligand binding, residues with side chain lining the inhibition model, and residues which are part of backbone of the inhibition model; and negative scores for additions, deletions and changes in backbone flexibility, or lack of residue alignment, and dramatic changes in size and/or polarity inside the inhibition model, lack of alignment of critical residues. In a further aspect of the invention, the positive score for residues critical for ligand binding is 2, for residues with side chain lining the inhibition model is 1, and for residues which are part of backbone of the inhibition model is 1; and the negative score for additions, deletions and changes in backbone flexibility, or lack of residue alignment is −1, and that for dramatic changes in size and/or polarity inside the inhibition model, lack of alignment of critical residues is −2. Alternatively, or in addition, conserved residue substitutions are assigned 1.

The invention provides a kinase inhibition model obtained by the method of making an inhibition model for a kinase as described above.

Finally, the invention provides a FGFR-2 inhibition model including the crystallography coordinates of FGFR-2 amino acids L_487, G_488, F_492, V_495, A_515, V_516, K_517, I_548, V 562, V 564, E_565, Y 566, A 567, S 568, K 569, G_570, N_571, L_633, A_643, D_644, F_645, A 648, and R_649 (SEQ ID NO: 10) which are within about a root mean square deviation of not more than about 1.5 Å from the backbone atoms of the amino acids according to Table 7.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 2 is a schematic representation of the c-Met kinase domain, in which the activation loop is shown in the canonical, autoinhibitory, conformation forming a typical short antiparallel strand.

FIG. 3 is a schematic representation of unphosphorylated c-Met bound to the selective c-Met inhibitor, in which Arg 1227 forms part of the inhibitor's binding site (dark grey).

FIG. 4 is a schematic representation of unphosphorylated c-Met bound to the selective c-Met inhibitor, in which a salt bridge, usually formed by the strictly conserved Lys (β3) and Glu (αC) residues that stabilize the phosphate group transfer, is disrupted as a result of the conformational changes of the A-loop and the helix αC.

DETAILED DESCRIPTION OF THE INVENTION

Figure 1:
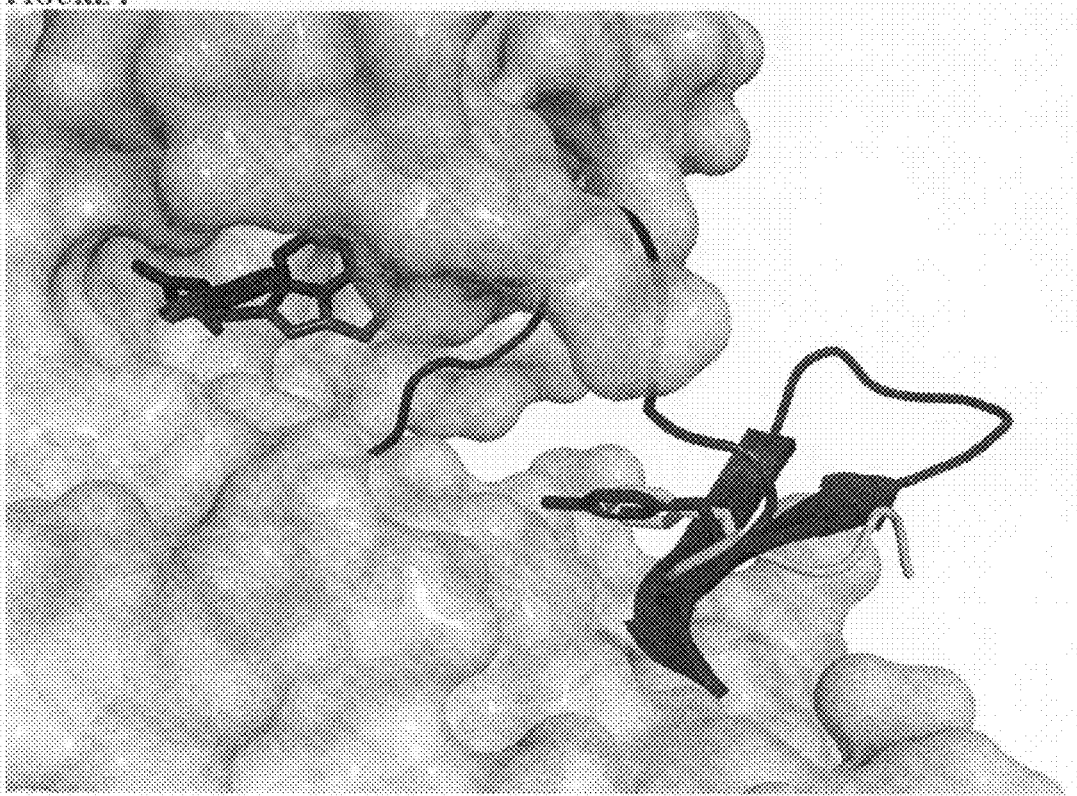
FIG. 1 is a schematic representation of the activation loop of unphosphorylated c-Met bound to the selective c-Met inhibitor (dark grey) superimposed with the peptide substrate (light grey) as seen in the phosphorylated insulin receptor IRK in complex with ATP and a peptide (Tyr residues are shown as sticks).

The present invention relates to methods of designing and screening for kinase inhibitors. The present invention provides a c-Met inhibition model. The present invention further provides a method to derive an inhibition model for another kinase from the c-Met inhibition model. The present invention also provides a method to compare inhibition models derived from multiple kinases in order to determine the degree of similarity between inhibition models.

The receptor tyrosine kinase (RTK) c-Met belongs to the HGF receptor family, which includes tyrosine kinases encoded by three oncogenes: MET (mesenchymal-epithelial transition factor), RON (also known as MST1R, macrophage stimulating 1 receptor (c-met-related tyrosine kinase)), and SEA (S13 erythroblastosis oncogene homolog (avian)).

These RTKs share specific structural features: a heterodimeric α-β subunits, two neighboring tyrosine residues in the kinase domain responsible for the activation upon phosphorylation and two tyrosine docking sites in the C-terminal domain tail.

The extracellular α- and transmembrane-β chains are present after receptor proteolitic cleavage and linked together by disulfide bonds. The intracellular β-subunit (residues 956-1390) can be further divided into juxtamembrane (residues 956-1093), catalytic and C-terminal domains. The C-terminal docking sites mediate high affinity interactions with multiple SH2-containing transducers of several key signaling pathways, including Ras, MAPK, PI3K, Src and Stat3 which contribute to the malignant features of Met.

Ligand binding to the extracellular domain of the RTKs leads to dimerization of monomeric receptors resulting in autophosphorylation of specific tyrosine residues in the cytoplasmic domain. RTKs are subject to several auto regulatory mechanisms to limit ligand-independent activation. One of these mechanisms is the phosphorylation of the kinase activation loop. The tyrosine doublet is present at homologous locations in the A-loop in RON and SEA.

The structure of the unphosphorylated kinase domain of c-Met bound to the selective c-Met inhibitor is an example of how a small molecule can achieve specificity by recognizing and binding the canonical, autoinhibited form of the kinase. Herein we describe a novel mechanism of inhibition of the receptor tyrosine kinase (RTK) c-Met and its use to define an inhibition model of general application in the identification of novel kinase inhibitors.

1. The Structure of the c-Met Bound to the Selective c-Met Inhibitor (−)-trans-3-(5,6-dihydro-4H-pyrrolo[3,2,1-ij]quinolin-1-yl)-4(1H-indol-3-yl)pyrrolidine-2,5-dione is a selective c-Met inhibitor (WO 2006/086484 A1).

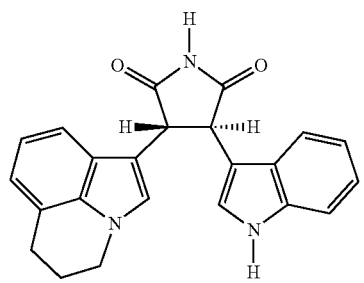

A 2-Å resolution X-ray crystallographic shows that this compound binds to the unphosphorylated kinase domain of c-Met. This compound is referred to herein as "the selective c-Met inhibitor."

The selective c-Met inhibitor is a single enantiomer that binds unphosphorylated c-Met at the highly conserved nucleotide-binding pocket. Overall the c-Met structure resembles the structures resolved for other tyrosine kinases in the presence of inhibitors such as Gleevec bound to c-Abl kinase and small molecules bound to cFMS. Structures of other receptor tyrosine kinases such as insulin receptor, cKit, Flt-3 in the absence of ligands also share a similar fold. In all these structures the activation loop is in the canonical, autoinhibitory conformation, blocking the access of ATP and the peptide substrate to the active site. In this particular conformation a tyrosine residue is in a pseudosubstrate conformation, buried deeply into the protein, making hydrogen bonds with important residues in the catalytic loop.

The structure of the c-Met bound to the selective c-Met inhibitor was compared with the inactive structure of c-Met in the public domain (PDB entry 2G15). In this structure, Tyr 1234 is not available for phosphorylation. The A-loop is in a different, open conformation. It is possible that the selective c-Met inhibitor recognizes and binds this particular, autoinhibitory conformation of c-Met, as it has been suggested for Gleevec bound to c-Abl and c-Kit kinases.

1.1. P-Loop Contains a Phenylalanine or a Similar Residue Able to Form Stacking Interaction with the Ligand Another important structural motif of a kinase is the phosphate binding loop (P-loop). This loop contains a conserved glycine residue rich sequence (GXGXΦG), where Φ is usually a tyrosine or phenylalanine. The glycine residues allow the coordination of the ATP by well defined backbone interactions. In the absence of ATP, the P-loop is very flexible allowing the binding of small molecules. Some inhibitors stabilize this loop by interacting with the conserved aromatic residue, as is the case of crystal structures of Abl, FGFR in complex with inhibitors STI-571 (PDB entry 2HYY), SU-5402 (PDB entry 1 FGI), and unphosphorylated c-Met bound to the selective c-Met inhibitor.

The nucleotide binding loop, the P-loop is well ordered in the structure of c-Met bound to the selective c-Met inhibitor, where residues I1084 to G1087 form part of the β1 strand. F1089 stabilizes the downfold of the loop by van de Waals contacts with the selective c-Met inhibitor.

1.2. A Tyrosine Residue in the A-Loop is Able to Interfere with the Peptide Substrate Binding Autophosphorylation of key tyrosine residues in the catalytic core of the RTK enhances kinase activity. In the case of c-Met, Y1235 has been described as being the site of autophosphorylation and playing this regulatory role.

In the structure of c-Met bound to the selective c-Met inhibitor, the activation loop is in the canonical, autoinhibitory conformation with a short anti-parallel strand. Two tyrosine residues Y1234 and Y1235 located in the A-loop of the kinase domain are responsible for c-Met catalytic activity and in the structure of c-Met bound to the selective c-Met inhibitor, Y1234 is exposed. However, Y1235 is sequestered into the active site occupying the site of the substrate tyrosine. Un-phosphorylated Y1235 is held by a hydrogen bond network formed by catalytic loop (C-loop) D1204 and R1208. The arginine residue engages in hydrogen bonding interactions that orient asparagine ensuring the inaccessibility of Y1235.

1.3. Phenylalanine (of the DFG Motif which Consists of Residues D1222, F1223 and G1224 in the Activation Loop) Prevents the ATP Binding.

Most of our knowledge about RTK comes from structural and biochemical studies on the insulin receptor kinase IRK. Structures of IRK show that sequestration of the tyrosine residue in the active site is correlated with the movement away from the active site of a number of critical important residues. When the apo structure (DFG-out) is superposed with the phosphorylated IRK (DFG-in) in complex with ATP analog and a peptide substrate (PDB entry 1RK3) the side chain of F1151 occupies the pocket of the adenine ring and the activation loop intersects the β- and γ-phosphate groups.

The positioning of phenylalanine from the DFG motif is critical for the proper orientation of the aspartic acid (DFG) which coordinates an essential $Mg^{2+}$ and the ATP. Conformational changes of the DFG-motif are often linked to the conformation of the αC-helix, the only conserved helix in the β sheet-rich N terminal domain. An absolute conserved glutamic acid residue located in αC-helix forms an ion pair with another conserved lysine residue from the β3 sheet. This ion pair coordinates the α- and β-phosphates of the ATP.

In the structure of c-Met bound to the selective c-Met inhibitor, a 'DFG-out' conformation is present. The aspartic acid (of the DFG) points away from where the ATP would bind and phenylalanine is situated in the approximated position of the ATP adenine moiety. Stabilization of this portion of the A-loop is provided, in part, by the tricyclic group of the selective c-Met inhibitor, which makes van der Waals interactions with the phenylalanine residue from the DFG motif. In this way, although the hydroxyl group of Y1234 is in position for phospho-transfer, the DFG-out motif occludes the ATP binding site from interfering with phopho-transfer.

1.4. The Salt Bridge Between Lysine (N-Terminus) and Glutamic Acid (αC Helix) is Disrupted The αC helix is a key regulatory element of protein kinases. Due to its proximity to the active site and its interactions with many conserved and essential kinase elements, the orientation of this helix is critical for catalytic activity. This helix contains a conserved glutamic acid residue that forms an ion pair with a lysine residue from the N-lobe. Glutamic acid is a strictly conserved feature in the kinase family and lysine is part of the protein kinase ATP binding region signature (PROSITE rule PS00107). The lysine residue coordinates the α- and the β-phosphates of ATP and is required for kinase activity. Moreover, the αC helix often interacts with the DFG motif of the activation loop.

In the structure of c-Met bound to the selective c-Met inhibitor, the alignment of the lysine-glutamic acid ion pair is disrupted, K1110 and E1127 are 16 Å apart, accentuating the inactive nature of the c-Met kinase conformation in the presence of the selective c-Met inhibitor.

When the αC helix of the complex formed by c-Met bound to the selective c-Met inhibitor is compared to the fully activated IRK structure bound to ATP and a peptide substrate, it is clear that the αC helix is partially disrupted and shifted away from the N-lobe. This movement, which is a combination of rotation and translation, results from the insertion of the activation loop deep between the P-loop and the αC helix.

In the structure formed by the complex formed when c-Met is bound to the selective c-Met inhibitor, the β3-αC loop has several contacts with the activation loop that are not observed in apo c-Met. R1114 from the β3-αC loop makes two contacts with the activation loop: R1114 forms salt bridges with G1224 from the DFG motif and with the carbonyl oxygen of R1227. In the structure of the apo c-Met kinase domain, the β3-αC loop adopts a more open conformation because the side chain of R1114 extends in the opposite direction towards the solvent.

An additional important feature of the activation loop is the conformation of R1227. It is hypothesized that R1227 plays a critical role in the stabilization of the activation loop by hydrogen bonding to the activated tyrosine upon phosphorylation (Johnson, L. M. and Noble, M. E. M. 1996. Cell, 85: 149-158). Three structures are often used to illustrate this interaction. First, the fully activated, triple phosphorylated insulin receptor kinase when bound to ATP and a peptide (1IR3). In this instance, the equivalent residue to R1227 in c-Met, residue R1155, makes hydrogen bonds with the phosphate group of Y1163. Second, a similar role has been described for R387 in the active form of the Hck tyrosine kinase (3LCK). With respect to Hck, R387 is making a hydrogen bond with the phosphorylated Y394. Finally, residue K189 of the serine/threonine kinase PKA bound to balanol (1BX6) fulfills a similar role. Using the foregoing examples as evidence, it is assumed that a critical role for R1227 is providing stabilization to the activation loop upon phosphorylation of c-Met.

The structures provided herein are contrary to published structures. For instance, in recently published structures of c-Met bound to small molecule inhibitors, the side chain of R1227 is missing (Bellon, S. F. ET AL. 2008. J. Biol. Chem. 283: 2675-2683; Albrecht, B. K. ET AL. 2008. J. Med. Chem. 51: 2879-2882). Similarly, in the structure of human Abl bound to Gleevec, the corresponding residue R386 is also missing (Cowan-Jacob, S. W. et al. 2007. ACTA CRYSTALLOGR., SECT. D 63: 80-93).

However, in the structure of the complex of c-Met bound to the selective c-Met inhibitor provided herein, R1227 is locked away from Y1234 and Y1235 through a direct hydrogen bond with N1209 and a water-mediated hydrogen bond to R1208, presenting the hydrophobic chain to the inhibitor. This van der Waals contact with the selective c-Met inhibitor restricts the movement of R1227 and prevents phosphate stabilization upon activation. Such a conformational change of this part of the activation loop, brought about by the selective c-Met inhibitor, is similar to that described for the activation loop containing R801 and a small molecule inhibitor of the auto-inhibited cFMS (Schubert, C. ET AL. 2007. J. Biol. Chem. 282:4094-4101), the R815 residue of apo c-Kit bound to Gleevec (Mol, C. D. ET AL. 2004. The Journal of Biological Chemistry 279:31655-31663), and the R834 residue of apo Flt-3 (Griffith, J. ET AL. 2004. Molecular Cell 13:69-178).

1.5. A Small Molecule is Stabilizing 1-4, Preventing ATP and Peptide Binding

In the structure of c-Met bound to the selective c-Met inhibitor, the small molecule is placed in the interdomain cleft between the N (residues 1049-1160)- and C-lobes (residues 1161-1346). The carbonyl group from the succinamide ring forms hydrogen bond with the backbone amide of M1160 and the N—H group forms hydrogen bonds with the backbone carbonyl of P1158. The indole ring is close to the ATP binding site opening while the tricyclic ring is bound deep inside the hydrophobic pocket. The tricyclic moiety of the selective c-Met inhibitor forms van der Waals interactions with phenylalanine residues F1089 from the P-loop and F1223 from the DFG motif. European Patent Application No. EP1243596A2 (the contents of which are incorporated herein in their entirety) describes a small molecule bound to the kinase domain of c-Met. The structure of c-Met bound to the selective c-Met inhibitor differs significantly. Of particular note are differences in the P-loop and the A-loops. The selective c-Met inhibitor makes a van de Waals contact with the residue F1089 at the apex of the P-loop, F1089 of cMet (described in EP1243596A2, the contents of which are incorporated by reference in their entirety) is inserted towards the αC helix. Also of note are differences between the residue F1223. This residue is in the -out conformation while in the above mentioned patent it is in the -in conformation. The selective c-Met inhibitor prevents this residue from occupying a region close to the triphosphate binding site found when ATP binds the catalytic site.

European Patent Application No. EP1243596A2 provides the wild-type sequence of the c-Met kinase (SEQ ID NO: 12) shown below:

```
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSLQQLNLQLPLKTKAFFMLDGILSKYFDLIYVHNPVFKPFEKPVMI

SMGNENVEIKGNDIDPEAVKGEVLKVGNKSCENIHLHSEAVLCTVPNDLL

KLNSELNIEWKQAISSTVLGKVIVQPDQNFTGLIAGVVSISTALLLLLGF

FLWLKKRKQIKDLGSELVRYDARVHTPHLDRLVSARSVSPTTEMVSNESV

DYRATFPEDQFPNSSQNGSCRQVQYPLTDMSPILTSGDSDISSPLLQNTV

HIDLSALNPELVQAVQHVVIGPSSLIVHFNEVIGRGHFGCVYHGTLLDND

GKKIHCAVKSLNRITDIGEVSQFLTEGIIMKDFSHPNVLSLLGICLRSEG

SPLVVLPYMKHGDLRNFIRNETHNPTVKDLIGFGLQVAKGMKYLASKKFV

HRDLAARNCMLDEKFTVKVADFGLARDMYDKEYYSVHNKTGAKLPVKWMA

LESLQTQKFTTKSDVWSFGVVLWELMTRGAPPYPDVNTFDITVYLLQGRR

LLQPEYCPDPLYEVMLKCWHPKAEMRPSFSELVSRISAIFSTFIGEHYVH

VNATYVNVKCVAPYPSLLSSEDNADDEVDTRPASFWETS
```

1.6. Computers, Computer Software, Computer Modeling

Computers are known in the art and may include a central processing unit (CPU), a working memory, which can be random-access memory, core memory, mass-storage memory, or combinations of all of the aforementioned.

The CPU may encode one or more programs. Computers may also include display, and input and output devices, such as one or more cathode-ray tube display terminals, keyboards, modems, input lines and output lines. Persons skilled in the computer art will understand that many variations of a computer exist in the art and all such variations are applicable to the present invention. Further, said computers may be networked to computer servers (the machine on which large calculations can be run in batch), and file servers (the main machine for all the centralized databases). Machine-readable media containing data, such as the crystal structure coordinates of the polypeptides of the invention may be inputted using various hardware, including modems, CD-ROM drives, disk drives, or keyboards.

Output hardware, such as a CRT display terminal may be used for displaying a graphical representation of the HGFR polypeptide of the invention or the c-Met substrate-binding domain of these polypeptides using programs such as QUANTA. Output hardware may also include a printer, and disk drives.

The CPU coordinates the use of the various input and output devices, coordinates data accesses from storage and accesses to and from working memory, and determines the sequence of data processing steps. A number of programs may be used to process the machine-readable data of this invention. Such programs are discussed in reference to the computational methods of drug discovery as described herein.

Thus, one embodiment of the present invention includes X-ray coordinate data capable of being processed into a three dimensional graphical display of a molecule or molecular complex that comprises an c-Met-like substrate-binding pocket stored in a machine-readable storage medium. The three-dimensional structure of a molecule or molecular complex comprising an c-Met-like substrate-binding pocket may be used for a variety of purposes, including, but not limited to, drug discovery.

For example, the three-dimensional structure derived from the structure coordinate data may be computationally evaluated for its ability to associate with chemical entities. Such entities would be potential drug candidates and would be evaluated for their ability to inhibit or modulate the activity of c-Met.

As used herein, the term "three dimensional representation" refers to converting the lists of structure coordinates into structural models or graphical representation in three-dimensional space. The three dimensional structure may be displayed or used to perform computer modeling or fitting operations.

"Inhibition model", refers to a region or regions of proteins that can associate with another chemical entity or compound. Such regions are of significant utility in fields such as drug discovery. These regions are formed by amino acid residues key for ligand binding or may be residues that are spatially related and define a three-dimensional shape of the binding pocket. The amino acid residues may be contiguous or non-contiguous in primary sequence. The region or regions may be embodied as a dataset (e.g. an array) recorded on computer readable media.

The term "motif" refers to a group of amino acid residues in proteins that defines a structural compartment or carries out a function in the protein, for example, catalysis, structural stabilization or phosphorylation. The motif may be conserved in sequence, structure and function. The motif can be contiguous in primary sequence or three-dimensional space. Examples of a motif include, but are not limited to, a binding pocket; activation loop, the glycine-rich or P-loop, and the DFG loop.

The term "homology model" refers to a set of coordinates derived from known three-dimensional structure used as a template. Generation of the homology model, termed "homology modeling", involves sequence alignment, residue replacement, residue conformation adjustment through energy minimization.

The term "part of the inhibition model" also referred as "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. Part of the inhibition model has at least five amino acid residues, preferably at least, ten to fourteen amino acid residues.

The term "chemical entity" refers to chemical compounds, complexes of at least two chemical compounds, and fragments of such compounds or complexes.

The "Chemical structure" term is applied to any atom or group of atoms that constitute a part of a molecule. Normally, chemical structures of a scaffold or ligand have a role in binding to a target molecule.

The term "associating with" or "binds to" or "binding affinity" refers to a condition of proximity between a chemical entity or compound, or portions thereof, and the inhibition model, or binding pocket or binding site on a protein. The association may be non-covalent, for example, wherein the juxtaposition is energetically favored by hydrogen bonding, van der Waals and/or electrostatic interactions.

The term "interaction energy" refers to the energy determined for the interaction of a chemical entity and a binding pocket, domain, molecule or molecular complex or portion thereof, Interactions include but are not limited to one or more of covalent interactions, non-covalent interactions such as hydrogen bond, electrostatic, hydrophobic, aromatic, van der Waals interactions, and non-complementary electrostatic interactions such as repulsive charge-charge, dipole-dipole and charge-dipole interactions. As interaction energies are measured in negative values, the lower the value the more favorable the interaction.

For the purposes of this description and the following claims, the term "crystal structure" of a composition shall mean a computer readable medium in which is stored a representation of three dimensional positional information for atoms of the composition.

2.1 Construction of c-Met Inhibition Model

The model for the inhibition of c-Met kinase is constructed by the preparation of the 3-dimensional representation of the c-Met protein based on crystallographic structure of c-Met bound to the selective c-Met inhibitor complex.

An electronic representation of c-Met-ligand kinase domain structure was obtained from X-ray crystallographic data. Crystals of the ligand complexes of c-Met kinase can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used.

Once a crystal of the present invention is grown, X-ray diffraction data can be collected. X-ray diffraction data collection can be obtained using, for example, a MAR imaging plate detector. Crystals can be characterized by using X-rays produced in a conventional source (such as a sealed tube or a rotating anode) or using a synchrotron source.

Data processing and reduction can be carried out using programs such as HKL, DENZO, and SCALEPACK (Otwinowski and Minor, 1997, Meth. Enymol. 276:307-326 (1997)). In addition, X-PLOR, (Bruger, X-PLOR v. 3.1 Manual, New Haven: Yale University, (1993)) or Heavy (T. Terwilliger, Los Alamos National Laboratory) may be utilized for bulk solvent correction and B-factor scaling. Electron density maps can be calculated using SHARP (La Fortelle, E. D. and Bricogne G., Meth. Enzymol. 276:472-494 (1997)) and SOLOMON. Molecular models can be built into this map using O (Jones, T. et al., ACTA Crystallogr. A47: 110-119 (1991)), XTALVIEW (Scripps Research) or QUANTA96 (Accelrys, Inc. San Diego). Refinement can be done using XPLOR (Brunger, "X-PLOR:A System for X-ray Crystallography and NMR," Yale University Press, New Haven, Conn.), using the free R-value to monitor the course of refinement. Molecular replacement involves using a known three-dimensional structure as a search model to determine the structure of an identical or closely related molecule or protein-ligand complex in a new crystal form. The measured X-ray diffraction properties of the new crystal are compared with those calculated from a search model structure to compute the position and orientation of the protein in the new crystal. Computer programs that can be used for this purpose include: X-PLOR, EPMR (Kissinger et al. Acta Cryst. D55:484-491 (1999)), ProLSQ and AMORE (J. Navaza, Acta Crystallographics ASO, 157-163 (1994)). Once the position and orientation are known an electron density map can be calculated using the search model to provide X-ray phases. Thereafter, the electron density is inspected for structural differences and the search model is modified to conform to the new structure. Other computer programs that can be used to solve the structures of kinase crystals include X-site, QUANTA, INSIGHT, ARP/wARP, and ICM.

The amino acids of the kinase domain of c-Met1 bound to the selective c-Met inhibitor are described herein and are defined by a set of structure coordinates set forth in Table 1A. The amino acids of the kinase domain of c-Met2 bound to the selective c-Met inhibitor are described herein and are defined by a set of structure coordinates set forth in Table 1B. The terms "structure coordinates" or "atomic coordinates" refer to Cartesian coordinates derived from mathematical equations related to the patterns obtained on diffraction of a monochromatic beam of X-rays by the atoms (scattering centers) of a protein or protein-ligand complex in crystal form. The diffraction data are used to calculate an electron density map of the repeating unit of the crystal. The electron density maps are then used to establish the positions of the individual atoms of the enzyme or enzyme complex.

TABLE 1A

| ATOM | 1 | CB | LEU | A1046 | −12.128 | 23.172 | 12.578 | 56.91 | C |
|---|---|---|---|---|---|---|---|---|---|
| ATOM | 2 | CG | LEU | A1046 | −10.61 | 22.897 | 12.417 | 57.12 | C |
| ATOM | 3 | CD1 | LEU | A1046 | −10.172 | 21.715 | 13.29 | 57.11 | C |
| ATOM | 4 | CD2 | LEU | A1046 | −10.196 | 22.666 | 10.944 | 56.48 | C |
| ATOM | 5 | C | LEU | A1046 | −11.878 | 25.227 | 14.012 | 55.44 | C |
| ATOM | 6 | O | LEU | A1046 | −11.778 | 26.019 | 13.032 | 55.74 | O |
| ATOM | 7 | N | LEU | A1046 | −14.148 | 24.094 | 13.796 | 56.63 | N |
| ATOM | 8 | CA | LEU | A1046 | −12.645 | 23.903 | 13.852 | 56.54 | C |
| ATOM | 9 | N | LEU | A1047 | −11.331 | 25.48 | 15.21 | 53.3 | N |
| ATOM | 10 | CA | LEU | A1047 | −10.406 | 26.598 | 15.301 | 50.4 | C |
| ATOM | 11 | CB | LEU | A1047 | −10.5 | 27.402 | 16.574 | 51.71 | C |
| ATOM | 12 | CG | LEU | A1047 | −10.362 | 28.806 | 15.979 | 51.83 | C |
| ATOM | 13 | CD1 | LEU | A1047 | −11.47 | 28.957 | 14.891 | 53.47 | C |

TABLE 1A-continued

| | | | | | | | | |
|---|---|---|---|---|---|---|---|---|
| ATOM | 14 | CD2 | LEU | A1047 | −10.363 | 29.918 | 17.042 | 52 | C |
| ATOM | 15 | C | LEU | A1047 | −8.96 | 26.289 | 14.95 | 48.45 | C |
| ATOM | 16 | O | LEU | A1047 | −8.275 | 25.497 | 15.594 | 48.01 | O |
| ATOM | 17 | N | GLN | A1048 | −8.562 | 26.995 | 13.891 | 44.96 | N |
| ATOM | 18 | CA | GLN | A1048 | −7.335 | 26.9 | 13.179 | 40.88 | C |
| ATOM | 19 | CB | GLN | A1048 | −7.455 | 25.718 | 12.207 | 42.63 | C |
| ATOM | 20 | CG | GLN | A1048 | −7.818 | 25.972 | 10.72 | 41.6 | C |
| ATOM | 21 | CD | GLN | A1048 | −6.669 | 25.468 | 9.808 | 44.09 | C |
| ATOM | 22 | OE1 | GLN | A1048 | −5.912 | 26.261 | 9.217 | 39.73 | O |
| ATOM | 23 | NE2 | GLN | A1048 | −6.52 | 24.143 | 9.728 | 46.71 | N |
| ATOM | 24 | C | GLN | A1048 | −7.28 | 28.319 | 12.517 | 38.85 | C |
| ATOM | 25 | O | GLN | A1048 | −6.273 | 28.777 | 11.876 | 36.37 | O |
| ATOM | 26 | N | ALA | A1049 | −8.408 | 29.017 | 12.748 | 35.35 | N |
| ATOM | 27 | CA | ALA | A1049 | −8.506 | 30.471 | 12.686 | 31.97 | C |
| ATOM | 28 | CB | ALA | A1049 | −9.981 | 30.902 | 12.748 | 31.67 | C |
| ATOM | 29 | C | ALA | A1049 | −7.691 | 30.943 | 13.89 | 29.81 | C |
| ATOM | 30 | O | ALA | A1049 | −7.868 | 32.004 | 14.431 | 29.2 | O |
| ATOM | 31 | N | THR | A1050 | −6.732 | 30.11 | 14.251 | 27.92 | N |
| ATOM | 32 | CA | THR | A1050 | −5.889 | 30.248 | 15.41 | 26.75 | C |
| ATOM | 33 | CB | THR | A1050 | −6.401 | 29.283 | 16.498 | 27.8 | C |
| ATOM | 34 | OG1 | THR | A1050 | −5.967 | 29.726 | 17.75 | 29.58 | O |
| ATOM | 35 | CG2 | THR | A1050 | −5.908 | 27.822 | 16.32 | 31.14 | C |
| ATOM | 36 | C | THR | A1050 | −4.448 | 29.924 | 15.044 | 24.25 | C |
| ATOM | 37 | O | THR | A1050 | −3.59 | 30.157 | 15.797 | 24.4 | O |
| ATOM | 38 | N | VAL | A1051 | −4.212 | 29.439 | 13.836 | 23.39 | N |
| ATOM | 39 | CA | VAL | A1051 | −2.877 | 28.99 | 13.358 | 22.24 | C |
| ATOM | 40 | CB | VAL | A1051 | −2.947 | 27.788 | 12.359 | 20.45 | C |
| ATOM | 41 | CG1 | VAL | A1051 | −1.579 | 27.485 | 11.875 | 18.55 | C |
| ATOM | 42 | CG2 | VAL | A1051 | −3.595 | 26.532 | 13.011 | 19.38 | C |
| ATOM | 43 | C | VAL | A1051 | −2.1 | 30.118 | 12.657 | 22.8 | C |
| ATOM | 44 | O | VAL | A1051 | −2.522 | 30.662 | 11.621 | 22.92 | O |
| ATOM | 45 | N | HIS | A1052 | −0.978 | 30.488 | 13.223 | 22.7 | N |
| ATOM | 46 | CA | HIS | A1052 | −0.228 | 31.494 | 12.584 | 23.68 | C |
| ATOM | 47 | CB | HIS | A1052 | −0.265 | 32.834 | 13.364 | 22.38 | C |
| ATOM | 48 | CG | HIS | A1052 | 0.836 | 33.742 | 12.975 | 22.43 | C |
| ATOM | 49 | CD2 | HIS | A1052 | 2.061 | 33.943 | 13.536 | 27.19 | C |
| ATOM | 50 | ND1 | HIS | A1052 | 0.821 | 34.463 | 11.794 | 19.13 | N |
| ATOM | 51 | CE1 | HIS | A1052 | 1.969 | 35.092 | 11.658 | 24.7 | C |
| ATOM | 52 | NE2 | HIS | A1052 | 2.74 | 34.811 | 12.711 | 28.02 | N |
| ATOM | 53 | C | HIS | A1052 | 1.174 | 30.932 | 12.455 | 24.4 | C |
| ATOM | 54 | O | HIS | A1052 | 1.745 | 30.455 | 13.427 | 24.15 | O |
| ATOM | 55 | N | ILE | A1053 | 1.716 | 30.972 | 11.242 | 26.45 | N |
| ATOM | 56 | CA | ILE | A1053 | 3.121 | 30.613 | 11.024 | 27.16 | C |
| ATOM | 57 | CB | ILE | A1053 | 3.251 | 29.516 | 9.914 | 28.26 | C |
| ATOM | 58 | CG2 | ILE | A1053 | 4.734 | 29.093 | 9.685 | 26.49 | C |
| ATOM | 59 | CG1 | ILE | A1053 | 2.359 | 28.302 | 10.239 | 29.2 | C |
| ATOM | 60 | CD1 | ILE | A1053 | 2.763 | 27.523 | 11.503 | 29.05 | C |
| ATOM | 61 | C | ILE | A1053 | 3.87 | 31.843 | 10.573 | 27.98 | C |
| ATOM | 62 | O | ILE | A1053 | 3.477 | 32.505 | 9.609 | 28.95 | O |
| ATOM | 63 | N | ASP | A1054 | 4.961 | 32.165 | 11.241 | 29.63 | N |
| ATOM | 64 | CA | ASP | A1054 | 5.824 | 33.221 | 10.723 | 31.12 | C |
| ATOM | 65 | CB | ASP | A1054 | 6.616 | 33.903 | 11.853 | 31.79 | C |
| ATOM | 66 | CG | ASP | A1054 | 7.232 | 35.248 | 11.435 | 33.67 | C |
| ATOM | 67 | OD1 | ASP | A1054 | 7.123 | 35.707 | 10.245 | 31.69 | O |
| ATOM | 68 | OD2 | ASP | A1054 | 7.858 | 35.842 | 12.343 | 36.33 | O |
| ATOM | 69 | C | ASP | A1054 | 6.716 | 32.541 | 9.714 | 31.2 | C |
| ATOM | 70 | O | ASP | A1054 | 7.551 | 31.707 | 10.089 | 30.57 | O |
| ATOM | 71 | N | LEU | A1055 | 6.476 | 32.851 | 8.443 | 33.07 | N |
| ATOM | 72 | CA | LEU | A1055 | 7.198 | 32.223 | 7.316 | 35.79 | C |
| ATOM | 73 | CB | LEU | A1055 | 6.468 | 32.463 | 5.965 | 35.66 | C |
| ATOM | 74 | CG | LEU | A1055 | 5.094 | 31.724 | 5.872 | 35.17 | C |
| ATOM | 75 | CD1 | LEU | A1055 | 4.42 | 31.654 | 4.439 | 30.21 | C |
| ATOM | 76 | CD2 | LEU | A1055 | 5.19 | 30.345 | 6.57 | 30.42 | C |
| ATOM | 77 | C | LEU | A1055 | 8.702 | 32.622 | 7.259 | 37.77 | C |
| ATOM | 78 | O | LEU | A1055 | 9.593 | 31.826 | 6.823 | 38.16 | O |
| ATOM | 79 | N | SER | A1056 | 8.996 | 33.842 | 7.712 | 38.44 | N |
| ATOM | 80 | CA | SER | A1056 | 10.361 | 34.138 | 8.058 | 39.83 | C |
| ATOM | 81 | CB | SER | A1056 | 10.53 | 35.611 | 8.209 | 39.82 | C |
| ATOM | 82 | OG | SER | A1056 | 11.807 | 35.884 | 7.633 | 46.45 | O |
| ATOM | 83 | C | SER | A1056 | 10.692 | 33.399 | 9.366 | 39.54 | C |
| ATOM | 84 | O | SER | A1056 | 9.778 | 32.908 | 10.012 | 40.79 | O |
| ATOM | 85 | N | ALA | A1057 | 11.954 | 33.251 | 9.762 | 38.82 | N |
| ATOM | 86 | CA | ALA | A1057 | 12.222 | 32.456 | 10.987 | 38.37 | C |
| ATOM | 87 | CB | ALA | A1057 | 11.15 | 32.739 | 12.058 | 38.35 | C |
| ATOM | 88 | C | ALA | A1057 | 12.288 | 30.949 | 10.736 | 38.3 | C |
| ATOM | 89 | O | ALA | A1057 | 12.676 | 30.15 | 11.618 | 37.56 | O |
| ATOM | 90 | N | LEU | A1058 | 11.81 | 30.567 | 9.554 | 38.37 | N |
| ATOM | 91 | CA | LEU | A1058 | 11.986 | 29.242 | 9.036 | 38.18 | C |
| ATOM | 92 | CB | LEU | A1058 | 11.113 | 29.053 | 7.79 | 38.51 | C |
| ATOM | 93 | CG | LEU | A1058 | 9.756 | 28.341 | 7.928 | 37.27 | C |

TABLE 1A-continued

| ATOM | 94 | CD1 | LEU | A1058 | 9.136 | 28.263 | 6.541 | 35.77 | C |
|---|---|---|---|---|---|---|---|---|---|
| ATOM | 95 | CD2 | LEU | A1058 | 9.864 | 26.954 | 8.632 | 34.79 | C |
| ATOM | 96 | C | LEU | A1058 | 13.445 | 29.182 | 8.652 | 38.37 | C |
| ATOM | 97 | O | LEU | A1058 | 13.942 | 30.156 | 8.091 | 36.78 | O |
| ATOM | 98 | N | ASN | A1059 | 14.11 | 28.051 | 8.952 | 39.31 | N |
| ATOM | 99 | CA | ASN | A1059 | 15.505 | 27.793 | 8.556 | 40.53 | C |
| ATOM | 100 | CB | ASN | A1059 | 15.835 | 26.343 | 8.802 | 41.11 | C |
| ATOM | 101 | CG | ASN | A1059 | 17.226 | 25.977 | 8.342 | 45.43 | C |
| ATOM | 102 | OD1 | ASN | A1059 | 17.992 | 25.369 | 9.092 | 51.44 | O |
| ATOM | 103 | ND2 | ASN | A1059 | 17.569 | 26.327 | 7.112 | 49.14 | N |
| ATOM | 104 | C | ASN | A1059 | 15.768 | 28.158 | 7.071 | 41.05 | C |
| ATOM | 105 | O | ASN | A1059 | 15.198 | 27.542 | 6.158 | 40.67 | O |
| ATOM | 106 | N | PRO | A1060 | 16.577 | 29.206 | 6.827 | 41.31 | N |
| ATOM | 107 | CD | PRO | A1060 | 17.241 | 30.03 | 7.84 | 41.79 | C |
| ATOM | 108 | CA | PRO | A1060 | 16.835 | 29.7 | 5.483 | 41.66 | C |
| ATOM | 109 | CB | PRO | A1060 | 17.753 | 30.888 | 5.721 | 42.18 | C |
| ATOM | 110 | CG | PRO | A1060 | 17.385 | 31.301 | 7.127 | 43.84 | C |
| ATOM | 111 | C | PRO | A1060 | 17.483 | 28.659 | 4.578 | 41.37 | C |
| ATOM | 112 | O | PRO | A1060 | 17.289 | 28.689 | 3.372 | 40.14 | O |
| ATOM | 113 | N | GLU | A1061 | 18.217 | 27.727 | 5.17 | 41.83 | N |
| ATOM | 114 | CA | GLU | A1061 | 18.738 | 26.625 | 4.399 | 42.84 | C |
| ATOM | 115 | CB | GLU | A1061 | 19.811 | 25.863 | 5.194 | 44.84 | C |
| ATOM | 116 | CG | GLU | A1061 | 21.075 | 25.53 | 4.347 | 48.59 | C |
| ATOM | 117 | CD | GLU | A1061 | 21.714 | 26.811 | 3.785 | 53.07 | C |
| ATOM | 118 | OE1 | GLU | A1061 | 21.973 | 27.726 | 4.605 | 55.39 | O |
| ATOM | 119 | OE2 | GLU | A1061 | 21.919 | 26.916 | 2.539 | 55.02 | O |
| ATOM | 120 | C | GLU | A1061 | 17.627 | 25.663 | 3.957 | 41.97 | C |
| ATOM | 121 | O | GLU | A1061 | 17.714 | 25.019 | 2.895 | 42.05 | O |
| ATOM | 122 | N | LEU | A1062 | 16.596 | 25.539 | 4.785 | 39.78 | N |
| ATOM | 123 | CA | LEU | A1062 | 15.602 | 24.545 | 4.529 | 37.71 | C |
| ATOM | 124 | CB | LEU | A1062 | 14.842 | 24.154 | 5.797 | 37.57 | C |
| ATOM | 125 | CG | LEU | A1062 | 13.492 | 23.442 | 5.605 | 38.39 | C |
| ATOM | 126 | CD1 | LEU | A1062 | 13.118 | 22.609 | 6.804 | 41.69 | C |
| ATOM | 127 | CD2 | LEU | A1062 | 12.386 | 24.433 | 5.387 | 38.42 | C |
| ATOM | 128 | C | LEU | A1062 | 14.701 | 25.111 | 3.449 | 36.6 | C |
| ATOM | 129 | O | LEU | A1062 | 14.26 | 24.355 | 2.556 | 35.41 | O |
| ATOM | 130 | N | VAL | A1063 | 14.492 | 26.43 | 3.493 | 34.92 | N |
| ATOM | 131 | CA | VAL | A1063 | 13.566 | 27.111 | 2.567 | 34.29 | C |
| ATOM | 132 | CB | VAL | A1063 | 13.244 | 28.526 | 3.087 | 34.3 | C |
| ATOM | 133 | CG1 | VAL | A1063 | 12.661 | 28.432 | 4.463 | 34.16 | C |
| ATOM | 134 | CG2 | VAL | A1063 | 14.486 | 29.41 | 3.087 | 33.47 | C |
| ATOM | 135 | C | VAL | A1063 | 14.005 | 27.153 | 1.079 | 34.81 | C |
| ATOM | 136 | O | VAL | A1063 | 13.196 | 27.221 | 0.151 | 33.36 | O |
| ATOM | 137 | N | GLN | A1064 | 15.317 | 27.136 | 0.839 | 36.44 | N |
| ATOM | 138 | CA | GLN | A1064 | 15.766 | 27.189 | −0.531 | 36.8 | C |
| ATOM | 139 | CB | GLN | A1064 | 17.107 | 27.891 | −0.714 | 37.34 | C |
| ATOM | 140 | CG | GLN | A1064 | 18.298 | 26.933 | −0.903 | 42.24 | C |
| ATOM | 141 | CD | GLN | A1064 | 18.941 | 26.556 | 0.423 | 48.21 | C |
| ATOM | 142 | OE1 | GLN | A1064 | 19.424 | 25.401 | 0.631 | 46.84 | O |
| ATOM | 143 | NE2 | GLN | A1064 | 18.93 | 27.533 | 1.361 | 49.57 | N |
| ATOM | 144 | C | GLN | A1064 | 15.785 | 25.789 | −1.019 | 35.4 | C |
| ATOM | 145 | O | GLN | A1064 | 15.745 | 25.572 | −2.223 | 36.53 | O |
| ATOM | 146 | N | ALA | A1065 | 15.822 | 24.836 | −0.102 | 34.9 | N |
| ATOM | 147 | CA | ALA | A1065 | 15.734 | 23.427 | −0.484 | 34.71 | C |
| ATOM | 148 | CB | ALA | A1065 | 16.265 | 22.522 | 0.617 | 33.98 | C |
| ATOM | 149 | C | ALA | A1065 | 14.294 | 23.02 | −0.867 | 35.39 | C |
| ATOM | 150 | O | ALA | A1065 | 14.084 | 21.938 | −1.404 | 37.15 | O |
| ATOM | 151 | N | VAL | A1066 | 13.299 | 23.857 | −0.567 | 34.68 | N |
| ATOM | 152 | CA | VAL | A1066 | 11.925 | 23.526 | −0.857 | 33.72 | C |
| ATOM | 153 | CB | VAL | A1066 | 11.105 | 23.259 | 0.451 | 33.44 | C |
| ATOM | 154 | CG1 | VAL | A1066 | 11.819 | 22.214 | 1.276 | 35.84 | C |
| ATOM | 155 | CG2 | VAL | A1066 | 10.853 | 24.515 | 1.308 | 31.99 | C |
| ATOM | 156 | C | VAL | A1066 | 11.255 | 24.559 | −1.73 | 34.18 | C |
| ATOM | 157 | O | VAL | A1066 | 10.05 | 24.555 | −1.852 | 34.26 | O |
| ATOM | 158 | N | GLN | A1067 | 12.006 | 25.457 | −2.355 | 34.69 | N |
| ATOM | 159 | CA | GLN | A1067 | 11.311 | 26.561 | −3.041 | 35.45 | C |
| ATOM | 160 | CB | GLN | A1067 | 12.234 | 27.745 | −3.342 | 35.7 | C |
| ATOM | 161 | CG | GLN | A1067 | 13.58 | 27.38 | −4.01 | 39.46 | C |
| ATOM | 162 | CD | GLN | A1067 | 13.902 | 28.27 | −5.218 | 41.67 | C |
| ATOM | 163 | OE1 | GLN | A1067 | 15.065 | 28.643 | −5.421 | 40.43 | O |
| ATOM | 164 | NE2 | GLN | A1067 | 12.864 | 28.609 | −6.03 | 41.3 | N |
| ATOM | 165 | C | GLN | A1067 | 10.592 | 26.046 | −4.298 | 34.39 | C |
| ATOM | 166 | O | GLN | A1067 | 9.513 | 26.551 | −4.704 | 33.28 | O |
| ATOM | 167 | N | HIS | A1068 | 11.184 | 24.999 | −4.874 | 33.52 | N |
| ATOM | 168 | CA | HIS | A1068 | 10.604 | 24.326 | −6.044 | 32.41 | C |
| ATOM | 169 | CB | HIS | A1068 | 11.598 | 23.345 | −6.731 | 31.19 | C |
| ATOM | 170 | CG | HIS | A1068 | 11.982 | 22.16 | −5.912 | 30.41 | C |
| ATOM | 171 | CD2 | HIS | A1068 | 11.716 | 20.828 | −6.08 | 32.9 | C |
| ATOM | 172 | ND1 | HIS | A1068 | 12.762 | 22.256 | −4.775 | 30.19 | N |
| ATOM | 173 | CE1 | HIS | A1068 | 12.951 | 21.041 | −4.273 | 27.55 | C |

TABLE 1A-continued

| | | | | | | | | |
|---|---|---|---|---|---|---|---|---|
| ATOM | 174 | NE2 | HIS | A1068 | 12.318 | 20.159 | −5.038 | 30.41 | N |
| ATOM | 175 | C | HIS | A1068 | 9.28 | 23.677 | −5.688 | 31.32 | C |
| ATOM | 176 | O | HIS | A1068 | 8.382 | 23.674 | −6.484 | 33.73 | O |
| ATOM | 177 | N | VAL | A1069 | 9.13 | 23.197 | −4.467 | 30.56 | N |
| ATOM | 178 | CA | VAL | A1069 | 7.856 | 22.582 | −3.983 | 29.15 | C |
| ATOM | 179 | CB | VAL | A1069 | 8.163 | 21.81 | −2.733 | 29.55 | C |
| ATOM | 180 | CG1 | VAL | A1069 | 7.234 | 20.651 | −2.639 | 31.08 | C |
| ATOM | 181 | CG2 | VAL | A1069 | 9.625 | 21.383 | −2.751 | 30.94 | C |
| ATOM | 182 | C | VAL | A1069 | 6.711 | 23.542 | −3.57 | 26.86 | C |
| ATOM | 183 | O | VAL | A1069 | 5.518 | 23.206 | −3.653 | 25.45 | O |
| ATOM | 184 | N | VAL | A1070 | 7.105 | 24.72 | −3.111 | 24.89 | N |
| ATOM | 185 | CA | VAL | A1070 | 6.187 | 25.716 | −2.632 | 25.08 | C |
| ATOM | 186 | CB | VAL | A1070 | 6.875 | 26.794 | −1.768 | 24.76 | C |
| ATOM | 187 | CG1 | VAL | A1070 | 5.823 | 27.937 | −1.397 | 27.38 | C |
| ATOM | 188 | CG2 | VAL | A1070 | 7.398 | 26.161 | −0.518 | 22.87 | C |
| ATOM | 189 | C | VAL | A1070 | 5.335 | 26.363 | −3.725 | 24.92 | C |
| ATOM | 190 | O | VAL | A1070 | 5.866 | 26.883 | −4.671 | 25.57 | O |
| ATOM | 191 | N | ILE | A1071 | 4.017 | 26.331 | −3.539 | 24.9 | N |
| ATOM | 192 | CA | ILE | A1071 | 3.066 | 26.947 | −4.426 | 25.41 | C |
| ATOM | 193 | CB | ILE | A1071 | 1.841 | 25.984 | −4.658 | 26.26 | C |
| ATOM | 194 | CG2 | ILE | A1071 | 0.936 | 26.512 | −5.742 | 25.59 | C |
| ATOM | 195 | CG1 | ILE | A1071 | 2.322 | 24.56 | −5.002 | 27.15 | C |
| ATOM | 196 | CD1 | ILE | A1071 | 1.219 | 23.495 | −5.119 | 24.77 | C |
| ATOM | 197 | C | ILE | A1071 | 2.552 | 28.291 | −3.916 | 25.98 | C |
| ATOM | 198 | O | ILE | A1071 | 2.139 | 28.459 | −2.744 | 25.3 | O |
| ATOM | 199 | N | GLY | A1072 | 2.475 | 29.24 | −4.825 | 26.18 | N |
| ATOM | 200 | CA | GLY | A1072 | 1.98 | 30.52 | −4.46 | 26.79 | C |
| ATOM | 201 | C | GLY | A1072 | 0.488 | 30.535 | −4.409 | 27.83 | C |
| ATOM | 202 | O | GLY | A1072 | −0.147 | 29.872 | −5.205 | 26.82 | O |
| ATOM | 203 | N | PRO | A1073 | −0.085 | 31.374 | −3.509 | 29.78 | N |
| ATOM | 204 | CD | PRO | A1073 | 0.556 | 32.418 | −2.675 | 30.6 | C |
| ATOM | 205 | CA | PRO | A1073 | −1.515 | 31.335 | −3.283 | 30.69 | C |
| ATOM | 206 | CB | PRO | A1073 | −1.744 | 32.379 | −2.15 | 31.44 | C |
| ATOM | 207 | CG | PRO | A1073 | −0.627 | 33.301 | −2.24 | 30.55 | C |
| ATOM | 208 | C | PRO | A1073 | −2.233 | 31.821 | −4.49 | 31.3 | C |
| ATOM | 209 | O | PRO | A1073 | −3.436 | 31.784 | −4.49 | 33.38 | O |
| ATOM | 210 | N | SER | A1074 | −1.532 | 32.348 | −5.49 | 30.64 | N |
| ATOM | 211 | CA | SER | A1074 | −2.259 | 32.82 | −6.665 | 29 | C |
| ATOM | 212 | CB | SER | A1074 | −1.796 | 34.218 | −7.058 | 28.51 | C |
| ATOM | 213 | OG | SER | A1074 | −2.372 | 35.183 | −6.185 | 26.91 | O |
| ATOM | 214 | C | SER | A1074 | −2.124 | 31.81 | −7.79 | 28.72 | C |
| ATOM | 215 | O | SER | A1074 | −2.763 | 31.956 | −8.833 | 28.82 | O |
| ATOM | 216 | N | SER | A1075 | −1.311 | 30.771 | −7.522 | 27.32 | N |
| ATOM | 217 | CA | SER | A1075 | −1.055 | 29.665 | −8.421 | 25.33 | C |
| ATOM | 218 | CB | SER | A1075 | 0.381 | 29.215 | −8.266 | 25.63 | C |
| ATOM | 219 | OG | SER | A1075 | 1.239 | 30.134 | −8.912 | 26.14 | O |
| ATOM | 220 | C | SER | A1075 | −1.978 | 28.476 | −8.173 | 25.13 | C |
| ATOM | 221 | O | SER | A1075 | −1.868 | 27.453 | −8.857 | 25.41 | O |
| ATOM | 222 | N | LEU | A1076 | −2.879 | 28.615 | −7.2 | 23.73 | N |
| ATOM | 223 | CA | LEU | A1076 | −3.72 | 27.546 | −6.762 | 21.91 | C |
| ATOM | 224 | CB | LEU | A1076 | −3.187 | 26.898 | −5.467 | 20.79 | C |
| ATOM | 225 | CG | LEU | A1076 | −4.03 | 25.669 | −5.036 | 20.11 | C |
| ATOM | 226 | CD1 | LEU | A1076 | −3.951 | 24.503 | −6.038 | 15.91 | C |
| ATOM | 227 | CD2 | LEU | A1076 | −3.717 | 25.152 | −3.646 | 19.98 | C |
| ATOM | 228 | C | LEU | A1076 | −5.131 | 28.047 | −6.533 | 22.97 | C |
| ATOM | 229 | O | LEU | A1076 | −5.408 | 28.796 | −5.548 | 24.03 | O |
| ATOM | 230 | N | ILE | A1077 | −6.029 | 27.628 | −7.42 | 22.57 | N |
| ATOM | 231 | CA | ILE | A1077 | −7.439 | 27.868 | −7.216 | 23.08 | C |
| ATOM | 232 | CB | ILE | A1077 | −8.261 | 27.904 | −8.53 | 24.06 | C |
| ATOM | 233 | CG2 | ILE | A1077 | −9.65 | 28.526 | −8.221 | 20.11 | C |
| ATOM | 234 | CG1 | ILE | A1077 | −7.464 | 28.606 | −9.652 | 22.13 | C |
| ATOM | 235 | CD1 | ILE | A1077 | −7.14 | 30.062 | −9.29 | 25.62 | C |
| ATOM | 236 | C | ILE | A1077 | −8.061 | 26.798 | −6.385 | 23.17 | C |
| ATOM | 237 | O | ILE | A1077 | −7.874 | 25.639 | −6.679 | 24.09 | O |
| ATOM | 238 | N | VAL | A1078 | −8.804 | 27.195 | −5.351 | 23.26 | N |
| ATOM | 239 | CA | VAL | A1078 | −9.607 | 26.28 | −4.572 | 23.02 | C |
| ATOM | 240 | CB | VAL | A1078 | −8.916 | 25.876 | −3.223 | 22.97 | C |
| ATOM | 241 | CG1 | VAL | A1078 | −9.859 | 25.009 | −2.365 | 22.11 | C |
| ATOM | 242 | CG2 | VAL | A1078 | −7.658 | 25.173 | −3.466 | 23.96 | C |
| ATOM | 243 | C | VAL | A1078 | −10.893 | 26.989 | −4.227 | 23.24 | C |
| ATOM | 244 | O | VAL | A1078 | −10.877 | 27.922 | −3.464 | 23.89 | O |
| ATOM | 245 | N | HIS | A1079 | −12.003 | 26.51 | −4.758 | 24.26 | N |
| ATOM | 246 | CA | HIS | A1079 | −13.337 | 26.941 | −4.381 | 24.97 | C |
| ATOM | 247 | CB | HIS | A1079 | −14.21 | 26.807 | −5.596 | 24.57 | C |
| ATOM | 248 | CG | HIS | A1079 | −13.671 | 27.5 | −6.804 | 24.97 | C |
| ATOM | 249 | CD2 | HIS | A1079 | −13.2 | 27.014 | −7.974 | 26.02 | C |
| ATOM | 250 | ND1 | HIS | A1079 | −13.61 | 28.875 | −6.909 | 24.64 | N |
| ATOM | 251 | CE1 | HIS | A1079 | −13.12 | 29.202 | −8.093 | 25.68 | C |
| ATOM | 252 | NE2 | HIS | A1079 | −12.871 | 28.09 | −8.763 | 25.4 | N |
| ATOM | 253 | C | HIS | A1079 | −13.875 | 26.039 | −3.251 | 27.07 | C |

TABLE 1A-continued

| ATOM | 254 | O | HIS | A1079 | −13.889 | 24.8 | −3.387 | 26.98 | O |
|---|---|---|---|---|---|---|---|---|---|
| ATOM | 255 | N | PHE | A1080 | −14.317 | 26.624 | −2.137 | 28.58 | N |
| ATOM | 256 | CA | PHE | A1080 | −14.61 | 25.778 | −0.968 | 31.3 | C |
| ATOM | 257 | CB | PHE | A1080 | −14.449 | 26.52 | 0.389 | 33.68 | C |
| ATOM | 258 | CG | PHE | A1080 | −13.052 | 26.915 | 0.647 | 35.21 | C |
| ATOM | 259 | CD1 | PHE | A1080 | −12.68 | 28.264 | 0.595 | 40.09 | C |
| ATOM | 260 | CD2 | PHE | A1080 | −12.079 | 25.927 | 0.826 | 32.59 | C |
| ATOM | 261 | CE1 | PHE | A1080 | −11.294 | 28.615 | 0.751 | 42.72 | C |
| ATOM | 262 | CE2 | PHE | A1080 | −10.769 | 26.232 | 1 | 35.14 | C |
| ATOM | 263 | CZ | PHE | A1080 | −10.341 | 27.577 | 0.966 | 40.38 | C |
| ATOM | 264 | C | PHE | A1080 | −15.91 | 25.034 | −0.977 | 30.93 | C |
| ATOM | 265 | O | PHE | A1080 | −16.144 | 24.233 | −0.073 | 31.9 | O |
| ATOM | 266 | N | ASN | A1081 | −16.749 | 25.261 | −1.98 | 29.99 | N |
| ATOM | 267 | CA | ASN | A1081 | −17.951 | 24.477 | −2.052 | 28.6 | C |
| ATOM | 268 | CB | ASN | A1081 | −19.041 | 25.218 | −2.808 | 29.48 | C |
| ATOM | 269 | CG | ASN | A1081 | −18.671 | 25.483 | −4.236 | 31.25 | C |
| ATOM | 270 | OD1 | ASN | A1081 | −17.865 | 26.382 | −4.541 | 29.24 | O |
| ATOM | 271 | ND2 | ASN | A1081 | −19.204 | 24.643 | −5.131 | 31.12 | N |
| ATOM | 272 | C | ASN | A1081 | −17.608 | 23.185 | −2.732 | 27.52 | C |
| ATOM | 273 | O | ASN | A1081 | −18.403 | 22.229 | −2.665 | 29.53 | O |
| ATOM | 274 | N | GLU | A1082 | −16.414 | 23.124 | −3.333 | 24.89 | N |
| ATOM | 275 | CA | GLU | A1082 | −16.04 | 22.01 | −4.213 | 22.44 | C |
| ATOM | 276 | CB | GLU | A1082 | −15.32 | 22.481 | −5.481 | 22.29 | C |
| ATOM | 277 | CG | GLU | A1082 | −16.068 | 23.386 | −6.341 | 22.97 | C |
| ATOM | 278 | CD | GLU | A1082 | −15.26 | 23.767 | −7.575 | 27.8 | C |
| ATOM | 279 | OE1 | GLU | A1082 | −15.742 | 24.562 | −8.432 | 28.49 | O |
| ATOM | 280 | OE2 | GLU | A1082 | −14.136 | 23.253 | −7.713 | 29.66 | O |
| ATOM | 281 | C | GLU | A1082 | −15.21 | 20.951 | −3.497 | 20.44 | C |
| ATOM | 282 | O | GLU | A1082 | −14.018 | 21.015 | −3.435 | 20.29 | O |
| ATOM | 283 | N | VAL | A1083 | −15.888 | 19.932 | −3.019 | 19.69 | N |
| ATOM | 284 | CA | VAL | A1083 | −15.309 | 18.879 | −2.201 | 16.58 | C |
| ATOM | 285 | CB | VAL | A1083 | −16.098 | 18.697 | −0.886 | 15.58 | C |
| ATOM | 286 | CG1 | VAL | A1083 | −15.45 | 17.604 | −0.042 | 12.74 | C |
| ATOM | 287 | CG2 | VAL | A1083 | −16.132 | 20.05 | −0.121 | 12.18 | C |
| ATOM | 288 | C | VAL | A1083 | −15.236 | 17.566 | −2.955 | 16.73 | C |
| ATOM | 289 | O | VAL | A1083 | −16.201 | 17.105 | −3.555 | 16.56 | O |
| ATOM | 290 | N | ILE | A1084 | −14.054 | 16.977 | −2.913 | 16.19 | N |
| ATOM | 291 | CA | ILE | A1084 | −13.822 | 15.663 | −3.494 | 15.78 | C |
| ATOM | 292 | CB | ILE | A1084 | −12.32 | 15.465 | −3.831 | 14.2 | C |
| ATOM | 293 | CG2 | ILE | A1084 | −12.057 | 14.095 | −4.192 | 12.01 | C |
| ATOM | 294 | CG1 | ILE | A1084 | −11.939 | 16.363 | −5.007 | 14.72 | C |
| ATOM | 295 | CD1 | ILE | A1084 | −10.462 | 16.58 | −5.098 | 12.82 | C |
| ATOM | 296 | C | ILE | A1084 | −14.343 | 14.608 | −2.533 | 15.45 | C |
| ATOM | 297 | O | ILE | A1084 | −15.065 | 13.716 | −2.937 | 15.82 | O |
| ATOM | 298 | N | GLY | A1085 | −13.969 | 14.733 | −1.273 | 14.58 | N |
| ATOM | 299 | CA | GLY | A1085 | −14.324 | 13.76 | −0.272 | 15.49 | C |
| ATOM | 300 | C | GLY | A1085 | −14.158 | 14.328 | 1.144 | 16.4 | C |
| ATOM | 301 | O | GLY | A1085 | −13.28 | 15.137 | 1.41 | 14.09 | O |
| ATOM | 302 | N | ARG | A1086 | −15.036 | 13.887 | 2.039 | 18.79 | N |
| ATOM | 303 | CA | ARG | A1086 | −14.945 | 14.135 | 3.466 | 20.86 | C |
| ATOM | 304 | CB | ARG | A1086 | −16.251 | 14.676 | 3.989 | 21.21 | C |
| ATOM | 305 | CG | ARG | A1086 | −16.373 | 16.172 | 3.885 | 23.45 | C |
| ATOM | 306 | CD | ARG | A1086 | −17.9 | 16.646 | 3.969 | 26.42 | C |
| ATOM | 307 | NE | ARG | A1086 | −18.001 | 18.021 | 3.466 | 27.6 | N |
| ATOM | 308 | CZ | ARG | A1086 | −17.48 | 19.093 | 4.091 | 32.33 | C |
| ATOM | 309 | NH1 | ARG | A1086 | −16.816 | 18.961 | 5.242 | 35.28 | N |
| ATOM | 310 | NH2 | ARG | A1086 | −17.595 | 20.32 | 3.569 | 32.16 | N |
| ATOM | 311 | C | ARG | A1086 | −14.682 | 12.807 | 4.096 | 20.17 | C |
| ATOM | 312 | O | ARG | A1086 | −14.958 | 11.754 | 3.495 | 20.3 | O |
| ATOM | 313 | N | GLY | A1087 | −14.079 | 12.823 | 5.28 | 20.64 | N |
| ATOM | 314 | CA | GLY | A1087 | −13.973 | 11.578 | 6.063 | 20.22 | C |
| ATOM | 315 | C | GLY | A1087 | −13.277 | 11.809 | 7.358 | 19.8 | C |
| ATOM | 316 | O | GLY | A1087 | −13.267 | 12.898 | 7.864 | 20.95 | O |
| ATOM | 317 | N | HIS | A1088 | −12.638 | 10.785 | 7.88 | 19.64 | N |
| ATOM | 318 | CA | HIS | A1088 | −11.928 | 10.907 | 9.153 | 18.07 | C |
| ATOM | 319 | CB | HIS | A1088 | −11.39 | 9.532 | 9.544 | 18.11 | C |
| ATOM | 320 | CG | HIS | A1088 | −12.414 | 8.645 | 10.11 | 18.13 | C |
| ATOM | 321 | CD2 | HIS | A1088 | −12.848 | 7.416 | 9.726 | 19.99 | C |
| ATOM | 322 | ND1 | HIS | A1088 | −13.147 | 8.999 | 11.226 | 19.52 | N |
| ATOM | 323 | CE1 | HIS | A1088 | −13.989 | 8.018 | 11.518 | 20.66 | C |
| ATOM | 324 | NE2 | HIS | A1088 | −13.831 | 7.051 | 10.622 | 21.93 | N |
| ATOM | 325 | C | HIS | A1088 | −10.732 | 11.749 | 8.888 | 16.52 | C |
| ATOM | 326 | O | HIS | A1088 | −10.263 | 12.502 | 9.743 | 16.94 | O |
| ATOM | 327 | N | PHE | A1089 | −10.193 | 11.522 | 7.698 | 14.83 | N |
| ATOM | 328 | CA | PHE | A1089 | −9.003 | 12.234 | 7.244 | 13.7 | C |
| ATOM | 329 | CB | PHE | A1089 | −8.494 | 11.675 | 5.925 | 11.64 | C |
| ATOM | 330 | CG | PHE | A1089 | −9.525 | 11.593 | 4.91 | 10.95 | C |
| ATOM | 331 | CD1 | PHE | A1089 | −9.965 | 12.794 | 4.219 | 13.52 | C |
| ATOM | 332 | CD2 | PHE | A1089 | −10.09 | 10.376 | 4.612 | 8.32 | C |
| ATOM | 333 | CE1 | PHE | A1089 | −10.956 | 12.734 | 3.249 | 10.64 | C |

TABLE 1A-continued

| ATOM | 334 | CE2 | PHE | A1089 | −11.079 | 10.261 | 3.648 | 10.05 | C |
|---|---|---|---|---|---|---|---|---|---|
| ATOM | 335 | CZ | PHE | A1089 | −11.543 | 11.452 | 2.966 | 15.19 | C |
| ATOM | 336 | C | PHE | A1089 | −9.287 | 13.746 | 7.164 | 12.68 | C |
| ATOM | 337 | O | PHE | A1089 | −8.348 | 14.505 | 7.187 | 11.45 | O |
| ATOM | 338 | N | GLY | A1090 | −10.577 | 14.126 | 7.178 | 11.98 | N |
| ATOM | 339 | CA | GLY | A1090 | −11.019 | 15.513 | 7.028 | 13.34 | C |
| ATOM | 340 | C | GLY | A1090 | −11.674 | 15.859 | 5.68 | 14 | C |
| ATOM | 341 | O | GLY | A1090 | −12.487 | 15.12 | 5.127 | 14.32 | O |
| ATOM | 342 | N | CYS | A1091 | −11.346 | 17.001 | 5.142 | 14.77 | N |
| ATOM | 343 | CA | CYS | A1091 | −12.027 | 17.454 | 3.959 | 14.05 | C |
| ATOM | 344 | CB | CYS | A1091 | −12.905 | 18.65 | 4.304 | 14.11 | C |
| ATOM | 345 | SG | CYS | A1091 | −13.959 | 19.211 | 2.883 | 19.49 | S |
| ATOM | 346 | C | CYS | A1091 | −11.019 | 17.769 | 2.824 | 13.5 | C |
| ATOM | 347 | O | CYS | A1091 | −10.098 | 18.585 | 2.975 | 11.93 | O |
| ATOM | 348 | N | VAL | A1092 | −11.215 | 17.09 | 1.711 | 12.32 | N |
| ATOM | 349 | CA | VAL | A1092 | −10.36 | 17.217 | 0.573 | 12.75 | C |
| ATOM | 350 | CB | VAL | A1092 | −9.928 | 15.823 | 0.058 | 12.83 | C |
| ATOM | 351 | CG1 | VAL | A1092 | −9.089 | 15.986 | −1.186 | 13.1 | C |
| ATOM | 352 | CG2 | VAL | A1092 | −9.154 | 15.079 | 1.144 | 10.11 | C |
| ATOM | 353 | C | VAL | A1092 | −11.092 | 17.993 | −0.543 | 13.41 | C |
| ATOM | 354 | O | VAL | A1092 | −12.196 | 17.644 | −0.947 | 11.1 | O |
| ATOM | 355 | N | TYR | A1093 | −10.405 | 19.012 | −1.084 | 14.21 | N |
| ATOM | 356 | CA | TYR | A1093 | −10.987 | 19.843 | −2.087 | 13.01 | C |
| ATOM | 357 | CB | TYR | A1093 | −10.838 | 21.298 | −1.671 | 15.58 | C |
| ATOM | 358 | CG | TYR | A1093 | −11.421 | 21.639 | −0.338 | 16.74 | C |
| ATOM | 359 | CD1 | TYR | A1093 | −10.62 | 21.582 | 0.8 | 20.27 | C |
| ATOM | 360 | CE1 | TYR | A1093 | −11.131 | 21.931 | 2.072 | 24.42 | C |
| ATOM | 361 | CD2 | TYR | A1093 | −12.767 | 22.025 | −0.212 | 15.71 | C |
| ATOM | 362 | CE2 | TYR | A1093 | −13.326 | 22.363 | 1.026 | 19.23 | C |
| ATOM | 363 | CZ | TYR | A1093 | −12.491 | 22.327 | 2.2 | 24.72 | C |
| ATOM | 364 | OH | TYR | A1093 | −12.946 | 22.676 | 3.505 | 25.2 | O |
| ATOM | 365 | C | TYR | A1093 | −10.429 | 19.689 | −3.461 | 13.15 | C |
| ATOM | 366 | O | TYR | A1093 | −9.223 | 19.373 | −3.67 | 10.61 | O |
| ATOM | 367 | N | HIS | A1094 | −11.288 | 20.032 | −4.413 | 13.11 | N |
| ATOM | 368 | CA | HIS | A1094 | −10.809 | 20.226 | −5.759 | 14.03 | C |
| ATOM | 369 | CB | HIS | A1094 | −11.964 | 20.459 | −6.695 | 13.93 | C |
| ATOM | 370 | CG | HIS | A1094 | −12.696 | 19.219 | −7.059 | 13.98 | C |
| ATOM | 371 | CD2 | HIS | A1094 | −13.885 | 18.736 | −6.647 | 15.38 | C |
| ATOM | 372 | ND1 | HIS | A1094 | −12.217 | 18.329 | −7.988 | 16.1 | N |
| ATOM | 373 | CE1 | HIS | A1094 | −13.102 | 17.372 | −8.161 | 19.29 | C |
| ATOM | 374 | NE2 | HIS | A1094 | −14.106 | 17.58 | −7.337 | 18.15 | N |
| ATOM | 375 | C | HIS | A1094 | −9.891 | 21.425 | −5.84 | 14.5 | C |
| ATOM | 376 | O | HIS | A1094 | −10.192 | 22.432 | −5.262 | 14.97 | O |
| ATOM | 377 | N | GLY | A1095 | −8.78 | 21.306 | −6.553 | 15.67 | N |
| ATOM | 378 | CA | GLY | A1095 | −7.939 | 22.453 | −6.806 | 17.79 | C |
| ATOM | 379 | C | GLY | A1095 | −7.533 | 22.565 | −8.27 | 18.77 | C |
| ATOM | 380 | O | GLY | A1095 | −7.707 | 21.662 | −9.049 | 17.49 | O |
| ATOM | 381 | N | THR | A1096 | −7.015 | 23.715 | −8.636 | 21.94 | N |
| ATOM | 382 | CA | THR | A1096 | −6.45 | 23.941 | −9.964 | 24.75 | C |
| ATOM | 383 | CB | THR | A1096 | −7.362 | 24.783 | −10.89 | 24.55 | C |
| ATOM | 384 | OG1 | THR | A1096 | −8.54 | 24.038 | −11.201 | 25.91 | O |
| ATOM | 385 | CG2 | THR | A1096 | −6.679 | 25.036 | −12.2 | 24.08 | C |
| ATOM | 386 | C | THR | A1096 | −5.135 | 24.63 | −9.743 | 26.07 | C |
| ATOM | 387 | O | THR | A1096 | −5.071 | 25.709 | −9.187 | 26.93 | O |
| ATOM | 388 | N | LEU | A1097 | −4.081 | 23.94 | −10.117 | 28.65 | N |
| ATOM | 389 | CA | LEU | A1097 | −2.772 | 24.458 | −10.032 | 31.8 | C |
| ATOM | 390 | CB | LEU | A1097 | −1.85 | 23.345 | −9.609 | 30.83 | C |
| ATOM | 391 | CG | LEU | A1097 | −0.375 | 23.607 | −9.399 | 32.94 | C |
| ATOM | 392 | CD1 | LEU | A1097 | −0.234 | 24.57 | −8.252 | 32.31 | C |
| ATOM | 393 | CD2 | LEU | A1097 | 0.493 | 22.298 | −9.219 | 30.24 | C |
| ATOM | 394 | C | LEU | A1097 | −2.449 | 25.09 | −11.421 | 35.83 | C |
| ATOM | 395 | O | LEU | A1097 | −2.405 | 24.415 | −12.477 | 35.53 | O |
| ATOM | 396 | N | LEU | A1098 | −2.31 | 26.421 | −11.415 | 39.47 | N |
| ATOM | 397 | CA | LEU | A1098 | −1.987 | 27.14 | −12.619 | 43.37 | C |
| ATOM | 398 | CB | LEU | A1098 | −2.541 | 28.54 | −12.571 | 41.93 | C |
| ATOM | 399 | CG | LEU | A1098 | −3.928 | 28.572 | −11.927 | 43.36 | C |
| ATOM | 400 | CD1 | LEU | A1098 | −4.141 | 29.836 | −11.071 | 41.52 | C |
| ATOM | 401 | CD2 | LEU | A1098 | −5.056 | 28.35 | −12.955 | 42.76 | C |
| ATOM | 402 | C | LEU | A1098 | −0.512 | 27.166 | −12.525 | 47.12 | C |
| ATOM | 403 | O | LEU | A1098 | 0.04 | 27.78 | −11.624 | 48.42 | O |
| ATOM | 404 | N | ASP | A1099 | 0.157 | 26.422 | −13.379 | 51.62 | N |
| ATOM | 405 | CA | ASP | A1099 | 1.604 | 26.58 | −13.384 | 56.85 | C |
| ATOM | 406 | CB | ASP | A1099 | 2.383 | 25.931 | −12.186 | 57.68 | C |
| ATOM | 407 | CG | ASP | A1099 | 2.043 | 24.437 | −11.941 | 63.37 | C |
| ATOM | 408 | OD1 | ASP | A1099 | 0.976 | 23.902 | −12.415 | 70.78 | O |
| ATOM | 409 | OD2 | ASP | A1099 | 2.863 | 23.795 | −11.226 | 65.81 | O |
| ATOM | 410 | C | ASP | A1099 | 2.297 | 26.411 | −14.726 | 58.47 | C |
| ATOM | 411 | O | ASP | A1099 | 2.446 | 25.303 | −15.282 | 59.18 | O |
| ATOM | 412 | N | ASN | A1100 | 2.591 | 27.597 | −15.241 | 60.14 | N |
| ATOM | 413 | CA | ASN | A1100 | 3.733 | 27.913 | −16.05 | 61.85 | C |

TABLE 1A-continued

| | | | | | | | | |
|---|---|---|---|---|---|---|---|---|
| ATOM | 414 | CB | ASN | A1100 | 5.058 | 27.881 | −15.346 | 62.48 | C |
| ATOM | 415 | CG | ASN | A1100 | 5.207 | 29.074 | −14.421 | 64.67 | C |
| ATOM | 416 | OD1 | ASN | A1100 | 4.493 | 30.084 | −14.6 | 66.33 | O |
| ATOM | 417 | ND2 | ASN | A1100 | 6.098 | 28.973 | −13.414 | 65.49 | N |
| ATOM | 418 | C | ASN | A1100 | 3.704 | 28.415 | −17.45 | 61.64 | C |
| ATOM | 419 | O | ASN | A1100 | 3.76 | 27.649 | −18.43 | 61.43 | O |
| ATOM | 420 | N | ASP | A1101 | 3.616 | 29.729 | −17.532 | 61.13 | N |
| ATOM | 421 | CA | ASP | A1101 | 2.785 | 30.288 | −18.571 | 61.44 | C |
| ATOM | 422 | CB | ASP | A1101 | 3.612 | 30.958 | −19.687 | 62.05 | C |
| ATOM | 423 | CG | ASP | A1101 | 2.907 | 32.203 | −20.251 | 63.68 | C |
| ATOM | 424 | OD1 | ASP | A1101 | 2.526 | 32.22 | −21.452 | 62.73 | O |
| ATOM | 425 | OD2 | ASP | A1101 | 2.702 | 33.157 | −19.455 | 66.21 | O |
| ATOM | 426 | C | ASP | A1101 | 1.805 | 29.22 | −19.135 | 60.4 | C |
| ATOM | 427 | O | ASP | A1101 | 2.226 | 28.267 | −19.83 | 60.81 | O |
| ATOM | 428 | N | GLY | A1102 | 0.516 | 29.356 | −18.804 | 58.95 | N |
| ATOM | 429 | CA | GLY | A1102 | −0.534 | 28.677 | −19.573 | 56.58 | C |
| ATOM | 430 | C | GLY | A1102 | −1.253 | 27.537 | −18.885 | 54.7 | C |
| ATOM | 431 | O | GLY | A1102 | −2.465 | 27.587 | −18.683 | 53.95 | O |
| ATOM | 432 | N | LYS | A1103 | −0.534 | 26.476 | −18.542 | 53.24 | N |
| ATOM | 433 | CA | LYS | A1103 | −1.278 | 25.235 | −18.237 | 51.22 | C |
| ATOM | 434 | CB | LYS | A1103 | −0.65 | 23.93 | −18.814 | 51.58 | C |
| ATOM | 435 | CG | LYS | A1103 | 0.762 | 23.585 | −18.409 | 54.34 | C |
| ATOM | 436 | CD | LYS | A1103 | 1.789 | 24.509 | −19.112 | 57.47 | C |
| ATOM | 437 | CE | LYS | A1103 | 2.423 | 25.478 | −18.11 | 55.46 | C |
| ATOM | 438 | NZ | LYS | A1103 | 3.733 | 24.994 | −17.598 | 53.32 | N |
| ATOM | 439 | C | LYS | A1103 | −1.924 | 25.068 | −16.843 | 48.72 | C |
| ATOM | 440 | O | LYS | A1103 | −1.492 | 25.647 | −15.82 | 48.06 | O |
| ATOM | 441 | N | LYS | A1104 | −3.032 | 24.329 | −16.899 | 45.99 | N |
| ATOM | 442 | CA | LYS | A1104 | −3.879 | 24.011 | −15.771 | 43.3 | C |
| ATOM | 443 | CB | LYS | A1104 | −5.317 | 24.45 | −16.004 | 42.65 | C |
| ATOM | 444 | CG | LYS | A1104 | −5.508 | 25.939 | −15.923 | 41.8 | C |
| ATOM | 445 | CD | LYS | A1104 | −6.917 | 26.243 | −16.354 | 40.69 | C |
| ATOM | 446 | CE | LYS | A1104 | −6.952 | 27.394 | −17.336 | 40.81 | C |
| ATOM | 447 | NZ | LYS | A1104 | −8.305 | 28.012 | −17.239 | 41.64 | N |
| ATOM | 448 | C | LYS | A1104 | −3.825 | 22.516 | −15.436 | 41.44 | C |
| ATOM | 449 | O | LYS | A1104 | −3.898 | 21.605 | −16.313 | 40.97 | O |
| ATOM | 450 | N | ILE | A1105 | −3.657 | 22.291 | −14.142 | 37.97 | N |
| ATOM | 451 | CA | ILE | A1105 | −3.705 | 20.976 | −13.612 | 34.91 | C |
| ATOM | 452 | CB | ILE | A1105 | −2.301 | 20.361 | −13.454 | 35.61 | C |
| ATOM | 453 | CG2 | ILE | A1105 | −1.135 | 21.401 | −13.762 | 37.19 | C |
| ATOM | 454 | CG1 | ILE | A1105 | −2.155 | 19.599 | −12.139 | 36.65 | C |
| ATOM | 455 | CD1 | ILE | A1105 | −0.883 | 18.749 | −12.072 | 36.89 | C |
| ATOM | 456 | C | ILE | A1105 | −4.701 | 20.852 | −12.444 | 31.98 | C |
| ATOM | 457 | O | ILE | A1105 | −4.608 | 21.565 | −11.427 | 27.87 | O |
| ATOM | 458 | N | HIS | A1106 | −5.686 | 19.967 | −12.693 | 28.84 | N |
| ATOM | 459 | CA | HIS | A1106 | −6.645 | 19.518 | −11.728 | 26.8 | C |
| ATOM | 460 | CB | HIS | A1106 | −7.622 | 18.551 | −12.383 | 28.08 | C |
| ATOM | 461 | CG | HIS | A1106 | −8.818 | 18.218 | −11.543 | 30.25 | C |
| ATOM | 462 | CD2 | HIS | A1106 | −9.146 | 18.556 | −10.269 | 31.62 | C |
| ATOM | 463 | ND1 | HIS | A1106 | −9.881 | 17.478 | −12.03 | 33.44 | N |
| ATOM | 464 | CE1 | HIS | A1106 | −10.804 | 17.357 | −11.087 | 33.23 | C |
| ATOM | 465 | NE2 | HIS | A1106 | −10.375 | 17.991 | −10.003 | 35.32 | N |
| ATOM | 466 | C | HIS | A1106 | −5.886 | 18.793 | −10.631 | 24.68 | C |
| ATOM | 467 | O | HIS | A1106 | −4.955 | 18.018 | −10.904 | 25.45 | O |
| ATOM | 468 | N | CYS | A1107 | −6.243 | 19.048 | −9.386 | 21.07 | N |
| ATOM | 469 | CA | CYS | A1107 | −5.523 | 18.458 | −8.31 | 19.54 | C |
| ATOM | 470 | CB | CYS | A1107 | −4.265 | 19.297 | −8 | 20.32 | C |
| ATOM | 471 | SG | CYS | A1107 | −4.67 | 21.059 | −7.642 | 21.01 | S |
| ATOM | 472 | C | CYS | A1107 | −6.454 | 18.368 | −7.115 | 18.93 | C |
| ATOM | 473 | O | CYS | A1107 | −7.648 | 18.819 | −7.131 | 17.53 | O |
| ATOM | 474 | N | ALA | A1108 | −5.915 | 17.78 | −6.063 | 17.24 | N |
| ATOM | 475 | CA | ALA | A1108 | −6.65 | 17.696 | −4.829 | 15.77 | C |
| ATOM | 476 | CB | ALA | A1108 | −6.865 | 16.206 | −4.395 | 15.49 | C |
| ATOM | 477 | C | ALA | A1108 | −5.856 | 18.437 | −3.791 | 14.69 | C |
| ATOM | 478 | O | ALA | A1108 | −4.645 | 18.317 | −3.75 | 14.65 | O |
| ATOM | 479 | N | VAL | A1109 | −6.559 | 19.158 | −2.927 | 13.84 | N |
| ATOM | 480 | CA | VAL | A1109 | −5.932 | 20.008 | −1.939 | 12.57 | C |
| ATOM | 481 | CB | VAL | A1109 | −6.094 | 21.513 | −2.247 | 12.13 | C |
| ATOM | 482 | CG1 | VAL | A1109 | −5.136 | 22.321 | −1.227 | 11.45 | C |
| ATOM | 483 | CG2 | VAL | A1109 | −5.762 | 21.768 | −3.729 | 8.23 | C |
| ATOM | 484 | C | VAL | A1109 | −6.49 | 19.734 | −0.554 | 12.99 | C |
| ATOM | 485 | O | VAL | A1109 | −7.719 | 19.469 | −0.365 | 12.53 | O |
| ATOM | 486 | N | LYS | A1110 | −5.587 | 19.781 | 0.41 | 12.17 | N |
| ATOM | 487 | CA | LYS | A1110 | −5.977 | 19.552 | 1.81 | 14.24 | C |
| ATOM | 488 | CB | LYS | A1110 | −5.985 | 18.063 | 2.167 | 13.99 | C |
| ATOM | 489 | CG | LYS | A1110 | −6.46 | 17.861 | 3.594 | 21.03 | C |
| ATOM | 490 | CD | LYS | A1110 | −6.867 | 16.451 | 3.838 | 23.19 | C |
| ATOM | 491 | CE | LYS | A1110 | −7.619 | 16.316 | 5.141 | 25.85 | C |
| ATOM | 492 | NZ | LYS | A1110 | −7.133 | 17.189 | 6.257 | 25.05 | N |
| ATOM | 493 | C | LYS | A1110 | −5.123 | 20.326 | 2.802 | 13.07 | C |

TABLE 1A-continued

| | | | | | | | | | |
|---|---|---|---|---|---|---|---|---|---|
| ATOM | 494 | O | LYS | A1110 | −3.911 | 20.547 | 2.592 | 11.93 | O |
| ATOM | 495 | N | SER | A1111 | −5.803 | 20.812 | 3.831 | 13.22 | N |
| ATOM | 496 | CA | SER | A1111 | −5.157 | 21.588 | 4.925 | 13.91 | C |
| ATOM | 497 | CB | SER | A1111 | −6.208 | 22.486 | 5.632 | 13.19 | C |
| ATOM | 498 | OG | SER | A1111 | −5.588 | 23.295 | 6.645 | 16.46 | O |
| ATOM | 499 | C | SER | A1111 | −4.531 | 20.633 | 5.894 | 12.91 | C |
| ATOM | 500 | O | SER | A1111 | −5.173 | 19.691 | 6.345 | 13.35 | O |
| ATOM | 501 | N | LEU | A1112 | −3.251 | 20.769 | 6.16 | 13.27 | N |
| ATOM | 502 | CA | LEU | A1112 | −2.67 | 19.886 | 7.215 | 12.16 | C |
| ATOM | 503 | CB | LEU | A1112 | −1.183 | 19.77 | 6.984 | 12.71 | C |
| ATOM | 504 | CG | LEU | A1112 | −0.892 | 19.329 | 5.545 | 13.33 | C |
| ATOM | 505 | CD1 | LEU | A1112 | 0.556 | 19.371 | 5.272 | 10.72 | C |
| ATOM | 506 | CD2 | LEU | A1112 | −1.401 | 17.897 | 5.255 | 16.22 | C |
| ATOM | 507 | C | LEU | A1112 | −2.964 | 20.401 | 8.632 | 12.03 | C |
| ATOM | 508 | O | LEU | A1112 | −2.145 | 21.009 | 9.264 | 11.5 | O |
| ATOM | 509 | N | ASN | A1113 | −4.201 | 20.228 | 9.091 | 13.41 | N |
| ATOM | 510 | CA | ASN | A1113 | −4.652 | 20.809 | 10.366 | 12.87 | C |
| ATOM | 511 | CB | ASN | A1113 | −6.092 | 20.435 | 10.644 | 13.74 | C |
| ATOM | 512 | CG | ASN | A1113 | −6.994 | 20.782 | 9.52 | 11.65 | C |
| ATOM | 513 | OD1 | ASN | A1113 | −6.819 | 21.773 | 8.853 | 17.02 | O |
| ATOM | 514 | ND2 | ASN | A1113 | −7.919 | 19.946 | 9.271 | 13.53 | N |
| ATOM | 515 | C | ASN | A1113 | −3.822 | 20.364 | 11.556 | 12.79 | C |
| ATOM | 516 | O | ASN | A1113 | −3.905 | 20.982 | 12.625 | 11.81 | O |
| ATOM | 517 | N | ARG | A1114 | −2.993 | 19.335 | 11.362 | 11.67 | N |
| ATOM | 518 | CA | ARG | A1114 | −2.192 | 18.838 | 12.447 | 11.69 | C |
| ATOM | 519 | CB | ARG | A1114 | −1.872 | 17.402 | 12.26 | 12.4 | C |
| ATOM | 520 | CG | ARG | A1114 | −3.031 | 16.474 | 12.672 | 15.55 | C |
| ATOM | 521 | CD | ARG | A1114 | −2.856 | 15.116 | 12.074 | 19.31 | C |
| ATOM | 522 | NE | ARG | A1114 | −1.941 | 14.212 | 12.787 | 25.78 | N |
| ATOM | 523 | CZ | ARG | A1114 | −1.491 | 13.059 | 12.246 | 29.79 | C |
| ATOM | 524 | NH1 | ARG | A1114 | −1.851 | 12.685 | 10.979 | 24.36 | N |
| ATOM | 525 | NH2 | ARG | A1114 | −0.693 | 12.264 | 12.964 | 26.37 | N |
| ATOM | 526 | C | ARG | A1114 | −0.933 | 19.587 | 12.57 | 12.08 | C |
| ATOM | 527 | O | ARG | A1114 | −0.203 | 19.386 | 13.495 | 12.99 | O |
| ATOM | 528 | N | ILE | A1115 | −0.645 | 20.425 | 11.59 | 13.44 | N |
| ATOM | 529 | CA | ILE | A1115 | 0.508 | 21.284 | 11.629 | 14.59 | C |
| ATOM | 530 | CB | ILE | A1115 | 1.202 | 21.342 | 10.297 | 14.68 | C |
| ATOM | 531 | CG2 | ILE | A1115 | 2.221 | 22.495 | 10.326 | 12.88 | C |
| ATOM | 532 | CG1 | ILE | A1115 | 1.808 | 19.959 | 9.988 | 12.83 | C |
| ATOM | 533 | CD1 | ILE | A1115 | 2.105 | 19.742 | 8.559 | 15.91 | C |
| ATOM | 534 | C | ILE | A1115 | 0.012 | 22.649 | 12.063 | 16.19 | C |
| ATOM | 535 | O | ILE | A1115 | −0.616 | 23.356 | 11.311 | 15.61 | O |
| ATOM | 536 | N | THR | A1116 | 0.255 | 22.94 | 13.329 | 18.45 | N |
| ATOM | 537 | CA | THR | A1116 | −0.373 | 24.035 | 14.047 | 20.84 | C |
| ATOM | 538 | CB | THR | A1116 | −0.99 | 23.595 | 15.441 | 20 | C |
| ATOM | 539 | OG1 | THR | A1116 | 0.063 | 23.267 | 16.354 | 22.88 | O |
| ATOM | 540 | CG2 | THR | A1116 | −1.914 | 22.399 | 15.325 | 19.02 | C |
| ATOM | 541 | C | THR | A1116 | 0.647 | 25.161 | 14.281 | 22.42 | C |
| ATOM | 542 | O | THR | A1116 | 0.262 | 26.269 | 14.657 | 24.01 | O |
| ATOM | 543 | N | ASP | A1117 | 1.925 | 24.884 | 14.072 | 24.01 | N |
| ATOM | 544 | CA | ASP | A1117 | 2.966 | 25.857 | 14.387 | 27.46 | C |
| ATOM | 545 | CB | ASP | A1117 | 3.215 | 25.998 | 15.919 | 28.91 | C |
| ATOM | 546 | CG | ASP | A1117 | 4.169 | 24.937 | 16.472 | 33.12 | C |
| ATOM | 547 | OD1 | ASP | A1117 | 5.406 | 25.172 | 16.513 | 42.43 | O |
| ATOM | 548 | OD2 | ASP | A1117 | 3.693 | 23.861 | 16.88 | 39.9 | O |
| ATOM | 549 | C | ASP | A1117 | 4.283 | 25.595 | 13.691 | 27.09 | C |
| ATOM | 550 | O | ASP | A1117 | 4.521 | 24.504 | 13.158 | 27.63 | O |
| ATOM | 551 | N | ILE | A1118 | 5.154 | 26.598 | 13.782 | 27.49 | N |
| ATOM | 552 | CA | ILE | A1118 | 6.42 | 26.628 | 13.014 | 28.72 | C |
| ATOM | 553 | CB | ILE | A1118 | 7.229 | 27.969 | 13.169 | 28.25 | C |
| ATOM | 554 | CG2 | ILE | A1118 | 7.455 | 28.31 | 14.587 | 28.16 | C |
| ATOM | 555 | CG1 | ILE | A1118 | 8.569 | 27.892 | 12.419 | 29.89 | C |
| ATOM | 556 | CD1 | ILE | A1118 | 8.654 | 28.76 | 11.192 | 26.9 | C |
| ATOM | 557 | C | ILE | A1118 | 7.296 | 25.38 | 13.127 | 28.67 | C |
| ATOM | 558 | O | ILE | A1118 | 7.848 | 24.949 | 12.137 | 29.24 | O |
| ATOM | 559 | N | GLY | A1119 | 7.361 | 24.755 | 14.293 | 28.57 | N |
| ATOM | 560 | CA | GLY | A1119 | 8.258 | 23.631 | 14.422 | 28.01 | C |
| ATOM | 561 | C | GLY | A1119 | 7.757 | 22.432 | 13.65 | 28.19 | C |
| ATOM | 562 | O | GLY | A1119 | 8.574 | 21.626 | 13.154 | 28.46 | O |
| ATOM | 563 | N | GLU | A1120 | 6.428 | 22.287 | 13.578 | 26.88 | N |
| ATOM | 564 | CA | GLU | A1120 | 5.838 | 21.15 | 12.906 | 26.64 | C |
| ATOM | 565 | CB | GLU | A1120 | 4.42 | 20.865 | 13.421 | 27.07 | C |
| ATOM | 566 | CG | GLU | A1120 | 4.269 | 20.751 | 14.884 | 27.63 | C |
| ATOM | 567 | CD | GLU | A1120 | 2.846 | 21.044 | 15.39 | 28.22 | C |
| ATOM | 568 | OE1 | GLU | A1120 | 2.099 | 21.807 | 14.783 | 28.44 | O |
| ATOM | 569 | OE2 | GLU | A1120 | 2.46 | 20.487 | 16.42 | 29.07 | O |
| ATOM | 570 | C | GLU | A1120 | 5.81 | 21.407 | 11.383 | 26.7 | C |
| ATOM | 571 | O | GLU | A1120 | 5.802 | 20.462 | 10.573 | 25.57 | O |
| ATOM | 572 | N | VAL | A1121 | 5.748 | 22.693 | 11.022 | 27.37 | N |
| ATOM | 573 | CA | VAL | A1121 | 5.922 | 23.13 | 9.647 | 27.71 | C |

TABLE 1A-continued

| | | | | | | | | | |
|---|---|---|---|---|---|---|---|---|---|
| ATOM | 574 | CB | VAL | A1121 | 5.683 | 24.628 | 9.497 | 27.27 | C |
| ATOM | 575 | CG1 | VAL | A1121 | 6.097 | 25.15 | 8.094 | 23.83 | C |
| ATOM | 576 | CG2 | VAL | A1121 | 4.232 | 24.897 | 9.771 | 27.4 | C |
| ATOM | 577 | C | VAL | A1121 | 7.325 | 22.81 | 9.246 | 28.92 | C |
| ATOM | 578 | O | VAL | A1121 | 7.574 | 22.155 | 8.242 | 29.26 | O |
| ATOM | 579 | N | SER | A1122 | 8.239 | 23.273 | 10.055 | 29.93 | N |
| ATOM | 580 | CA | SER | A1122 | 9.619 | 23.092 | 9.773 | 32.48 | C |
| ATOM | 581 | CB | SER | A1122 | 10.424 | 23.719 | 10.877 | 32.29 | C |
| ATOM | 582 | OG | SER | A1122 | 11.749 | 23.285 | 10.758 | 38.18 | O |
| ATOM | 583 | C | SER | A1122 | 9.979 | 21.618 | 9.585 | 32.67 | C |
| ATOM | 584 | O | SER | A1122 | 10.711 | 21.274 | 8.654 | 32.69 | O |
| ATOM | 585 | N | GLN | A1123 | 9.433 | 20.778 | 10.459 | 33.88 | N |
| ATOM | 586 | CA | GLN | A1123 | 9.694 | 19.352 | 10.488 | 35.82 | C |
| ATOM | 587 | CB | GLN | A1123 | 9.422 | 18.731 | 11.856 | 36.63 | C |
| ATOM | 588 | CG | GLN | A1123 | 10.061 | 17.303 | 11.912 | 43.42 | C |
| ATOM | 589 | CD | GLN | A1123 | 9.12 | 16.204 | 12.492 | 51.27 | C |
| ATOM | 590 | OE1 | GLN | A1123 | 8.588 | 16.34 | 13.639 | 52.06 | O |
| ATOM | 591 | NE2 | GLN | A1123 | 8.934 | 15.093 | 11.713 | 49.85 | N |
| ATOM | 592 | C | GLN | A1123 | 8.86 | 18.583 | 9.502 | 35.76 | C |
| ATOM | 593 | O | GLN | A1123 | 9.02 | 17.389 | 9.395 | 36.26 | O |
| ATOM | 594 | N | PHE | A1124 | 7.937 | 19.267 | 8.837 | 35.73 | N |
| ATOM | 595 | CA | PHE | A1124 | 7.195 | 18.716 | 7.759 | 35.08 | C |
| ATOM | 596 | CB | PHE | A1124 | 5.78 | 19.251 | 7.763 | 34.12 | C |
| ATOM | 597 | CG | PHE | A1124 | 5.026 | 18.881 | 6.552 | 33.72 | C |
| ATOM | 598 | CD1 | PHE | A1124 | 4.905 | 17.538 | 6.189 | 33.01 | C |
| ATOM | 599 | CD2 | PHE | A1124 | 4.467 | 19.855 | 5.735 | 34.39 | C |
| ATOM | 600 | CE1 | PHE | A1124 | 4.217 | 17.146 | 5.019 | 35.69 | C |
| ATOM | 601 | CE2 | PHE | A1124 | 3.769 | 19.486 | 4.546 | 37.38 | C |
| ATOM | 602 | CZ | PHE | A1124 | 3.623 | 18.098 | 4.198 | 33.44 | C |
| ATOM | 603 | C | PHE | A1124 | 7.856 | 19.11 | 6.465 | 36.22 | C |
| ATOM | 604 | O | PHE | A1124 | 7.758 | 18.418 | 5.471 | 36.62 | O |
| ATOM | 605 | N | LEU | A1125 | 8.515 | 20.253 | 6.458 | 37.74 | N |
| ATOM | 606 | CA | LEU | A1125 | 9.041 | 20.818 | 5.213 | 38.87 | C |
| ATOM | 607 | CB | LEU | A1125 | 9.55 | 22.25 | 5.41 | 37.31 | C |
| ATOM | 608 | CG | LEU | A1125 | 8.45 | 23.306 | 5.26 | 31.73 | C |
| ATOM | 609 | CD1 | LEU | A1125 | 9.085 | 24.585 | 5.245 | 27.34 | C |
| ATOM | 610 | CD2 | LEU | A1125 | 7.633 | 23.113 | 4.006 | 29.13 | C |
| ATOM | 611 | C | LEU | A1125 | 10.118 | 19.936 | 4.675 | 41.71 | C |
| ATOM | 612 | O | LEU | A1125 | 10.5 | 20.024 | 3.508 | 43.58 | O |
| ATOM | 613 | N | THR | A1126 | 10.569 | 19.051 | 5.536 | 44.24 | N |
| ATOM | 614 | CA | THR | A1126 | 11.528 | 18.045 | 5.199 | 47.41 | C |
| ATOM | 615 | CB | THR | A1126 | 12.226 | 17.613 | 6.523 | 46.64 | C |
| ATOM | 616 | OG1 | THR | A1126 | 12.818 | 18.766 | 7.167 | 44.19 | O |
| ATOM | 617 | CG2 | THR | A1126 | 13.246 | 16.566 | 6.262 | 44.87 | C |
| ATOM | 618 | C | THR | A1126 | 10.862 | 16.834 | 4.43 | 49.62 | C |
| ATOM | 619 | O | THR | A1126 | 11.561 | 15.942 | 3.935 | 50.03 | O |
| ATOM | 620 | N | GLU | A1127 | 9.516 | 16.791 | 4.341 | 52.19 | N |
| ATOM | 621 | CA | GLU | A1127 | 8.783 | 15.674 | 3.645 | 52.2 | C |
| ATOM | 622 | CB | GLU | A1127 | 7.449 | 15.293 | 4.324 | 52.31 | C |
| ATOM | 623 | CG | GLU | A1127 | 7.501 | 15.199 | 5.841 | 53.81 | C |
| ATOM | 624 | CD | GLU | A1127 | 8.832 | 14.692 | 6.389 | 55.9 | C |
| ATOM | 625 | OE1 | GLU | A1127 | 9.174 | 15.026 | 7.545 | 57.21 | O |
| ATOM | 626 | OE2 | GLU | A1127 | 9.547 | 13.971 | 5.665 | 57.62 | O |
| ATOM | 627 | C | GLU | A1127 | 8.545 | 15.969 | 2.176 | 53.81 | C |
| ATOM | 628 | O | GLU | A1127 | 8.112 | 15.1 | 1.439 | 55.01 | O |
| ATOM | 629 | N | GLY | A1128 | 8.782 | 17.202 | 1.749 | 54.61 | N |
| ATOM | 630 | CA | GLY | A1128 | 9.106 | 17.403 | 0.357 | 55.06 | C |
| ATOM | 631 | C | GLY | A1128 | 10.488 | 16.749 | 0.176 | 55.64 | C |
| ATOM | 632 | O | GLY | A1128 | 10.614 | 15.726 | −0.532 | 55.14 | O |
| ATOM | 633 | N | ILE | A1129 | 11.511 | 17.316 | 0.845 | 55.99 | N |
| ATOM | 634 | CA | ILE | A1129 | 12.95 | 16.959 | 0.641 | 56.67 | C |
| ATOM | 635 | CB | ILE | A1129 | 13.908 | 17.691 | 1.668 | 56.95 | C |
| ATOM | 636 | CG2 | ILE | A1129 | 13.492 | 19.182 | 1.83 | 55.72 | C |
| ATOM | 637 | CG1 | ILE | A1129 | 14.077 | 16.912 | 3.024 | 56.78 | C |
| ATOM | 638 | CD1 | ILE | A1129 | 15.422 | 16.113 | 3.3 | 53.37 | C |
| ATOM | 639 | C | ILE | A1129 | 13.277 | 15.432 | 0.541 | 57.46 | C |
| ATOM | 640 | O | ILE | A1129 | 14.386 | 15.035 | 0.094 | 58.01 | O |
| ATOM | 641 | N | ILE | A1130 | 12.309 | 14.597 | 0.965 | 57.33 | N |
| ATOM | 642 | CA | ILE | A1130 | 12.338 | 13.139 | 0.758 | 55.98 | C |
| ATOM | 643 | CB | ILE | A1130 | 12.578 | 12.337 | 2.059 | 55.97 | C |
| ATOM | 644 | CG2 | ILE | A1130 | 13.335 | 11.008 | 1.723 | 56.77 | C |
| ATOM | 645 | CG1 | ILE | A1130 | 13.265 | 13.188 | 3.132 | 55.59 | C |
| ATOM | 646 | CD1 | ILE | A1130 | 13.016 | 12.698 | 4.536 | 57.13 | C |
| ATOM | 647 | C | ILE | A1130 | 11.017 | 12.641 | 0.192 | 54.95 | C |
| ATOM | 648 | O | ILE | A1130 | 10.363 | 11.849 | 0.881 | 54.45 | O |
| ATOM | 649 | N | MET | A1131 | 10.628 | 13.064 | −1.032 | 53.3 | N |
| ATOM | 650 | CA | MET | A1131 | 9.326 | 12.664 | −1.518 | 52.51 | C |
| ATOM | 651 | CB | MET | A1131 | 8.386 | 12.568 | −0.315 | 52.76 | C |
| ATOM | 652 | CG | MET | A1131 | 6.879 | 12.691 | −0.612 | 55.76 | C |
| ATOM | 653 | SD | MET | A1131 | 5.963 | 12.687 | 0.939 | 55.65 | S |

TABLE 1A-continued

| | | | | | | | | |
|---|---|---|---|---|---|---|---|---|
| ATOM | 654 | CE | MET | A1131 | 6.21 | 10.987 | 1.559 | 53.64 | C |
| ATOM | 655 | C | MET | A1131 | 8.643 | 13.474 | −2.611 | 51.28 | C |
| ATOM | 656 | O | MET | A1131 | 8.018 | 12.882 | −3.51 | 51.1 | O |
| ATOM | 657 | N | LYS | A1132 | 8.644 | 14.809 | −2.476 | 49.59 | N |
| ATOM | 658 | CA | LYS | A1132 | 8.324 | 15.729 | −3.595 | 47.3 | C |
| ATOM | 659 | CB | LYS | A1132 | 8.789 | 17.164 | −3.285 | 48.03 | C |
| ATOM | 660 | CG | LYS | A1132 | 10.293 | 17.164 | −2.812 | 50.92 | C |
| ATOM | 661 | CD | LYS | A1132 | 11.15 | 18.336 | −3.247 | 55.23 | C |
| ATOM | 662 | CE | LYS | A1132 | 12.093 | 18.78 | −2.115 | 59.29 | C |
| ATOM | 663 | NZ | LYS | A1132 | 11.331 | 19.555 | −1.032 | 62.84 | N |
| ATOM | 664 | C | LYS | A1132 | 9.143 | 15.254 | −4.799 | 44.44 | C |
| ATOM | 665 | O | LYS | A1132 | 8.7 | 15.357 | −5.954 | 44.56 | O |
| ATOM | 666 | N | ASP | A1133 | 10.318 | 14.71 | −4.467 | 40.34 | N |
| ATOM | 667 | CA | ASP | A1133 | 11.375 | 14.342 | −5.376 | 36.85 | C |
| ATOM | 668 | CB | ASP | A1133 | 12.709 | 14.419 | −4.644 | 38.1 | C |
| ATOM | 669 | CG | ASP | A1133 | 13.169 | 15.86 | −4.393 | 39.25 | C |
| ATOM | 670 | OD1 | ASP | A1133 | 12.747 | 16.789 | −5.118 | 41.64 | O |
| ATOM | 671 | OD2 | ASP | A1133 | 13.953 | 16.054 | −3.429 | 43.78 | O |
| ATOM | 672 | C | ASP | A1133 | 11.207 | 12.94 | −5.944 | 34.05 | C |
| ATOM | 673 | O | ASP | A1133 | 11.739 | 12.66 | −7.041 | 34.56 | O |
| ATOM | 674 | N | PHE | A1134 | 10.49 | 12.067 | −5.218 | 28.41 | N |
| ATOM | 675 | CA | PHE | A1134 | 10.146 | 10.735 | −5.744 | 24.7 | C |
| ATOM | 676 | CB | PHE | A1134 | 9.28 | 9.939 | −4.749 | 23.35 | C |
| ATOM | 677 | CG | PHE | A1134 | 10.06 | 9.444 | −3.583 | 22.72 | C |
| ATOM | 678 | CD1 | PHE | A1134 | 9.434 | 8.928 | −2.485 | 22.8 | C |
| ATOM | 679 | CD2 | PHE | A1134 | 11.454 | 9.545 | −3.574 | 22.21 | C |
| ATOM | 680 | CE1 | PHE | A1134 | 10.225 | 8.477 | −1.407 | 26.8 | C |
| ATOM | 681 | CE2 | PHE | A1134 | 12.231 | 9.132 | −2.522 | 23.45 | C |
| ATOM | 682 | CZ | PHE | A1134 | 11.652 | 8.565 | −1.446 | 22.5 | C |
| ATOM | 683 | C | PHE | A1134 | 9.473 | 10.818 | −7.109 | 22.06 | C |
| ATOM | 684 | O | PHE | A1134 | 8.578 | 11.597 | −7.275 | 21.7 | O |
| ATOM | 685 | N | SER | A1135 | 9.928 | 10.048 | −8.079 | 19.56 | N |
| ATOM | 686 | CA | SER | A1135 | 9.24 | 10.001 | −9.339 | 18.42 | C |
| ATOM | 687 | CB | SER | A1135 | 10.033 | 10.836 | −10.349 | 19.51 | C |
| ATOM | 688 | OG | SER | A1135 | 9.252 | 11.189 | −11.487 | 19.35 | O |
| ATOM | 689 | C | SER | A1135 | 9.127 | 8.538 | −9.816 | 17.14 | C |
| ATOM | 690 | O | SER | A1135 | 10.052 | 7.971 | −10.389 | 16.98 | O |
| ATOM | 691 | N | HIS | A1136 | 8.002 | 7.906 | −9.564 | 15.18 | N |
| ATOM | 692 | CA | HIS | A1136 | 7.775 | 6.589 | −10.15 | 12.41 | C |
| ATOM | 693 | CB | HIS | A1136 | 8.12 | 5.487 | −9.143 | 11.98 | C |
| ATOM | 694 | CG | HIS | A1136 | 8.054 | 4.111 | −9.726 | 12.38 | C |
| ATOM | 695 | CD2 | HIS | A1136 | 9.014 | 3.342 | −10.296 | 12.91 | C |
| ATOM | 696 | ND1 | HIS | A1136 | 6.887 | 3.402 | −9.823 | 10.71 | N |
| ATOM | 697 | CE1 | HIS | A1136 | 7.124 | 2.27 | −10.449 | 14.23 | C |
| ATOM | 698 | NE2 | HIS | A1136 | 8.415 | 2.198 | −10.725 | 8.48 | N |
| ATOM | 699 | C | HIS | A1136 | 6.306 | 6.582 | −10.556 | 11.29 | C |
| ATOM | 700 | O | HIS | A1136 | 5.478 | 7.238 | −9.9 | 10.24 | O |
| ATOM | 701 | N | PRO | A1137 | 5.981 | 5.977 | −11.708 | 10.16 | N |
| ATOM | 702 | CD | PRO | A1137 | 6.95 | 5.593 | −12.754 | 10.83 | C |
| ATOM | 703 | CA | PRO | A1137 | 4.582 | 5.808 | −12.11 | 9.53 | C |
| ATOM | 704 | CB | PRO | A1137 | 4.65 | 5.004 | −13.437 | 10.43 | C |
| ATOM | 705 | CG | PRO | A1137 | 6.114 | 4.696 | −13.672 | 11.57 | C |
| ATOM | 706 | C | PRO | A1137 | 3.648 | 5.099 | −11.124 | 9.5 | C |
| ATOM | 707 | O | PRO | A1137 | 2.46 | 5.254 | −11.205 | 11.49 | O |
| ATOM | 708 | N | ASN | A1138 | 4.153 | 4.305 | −10.205 | 9.85 | N |
| ATOM | 709 | CA | ASN | A1138 | 3.317 | 3.68 | −9.221 | 9.77 | C |
| ATOM | 710 | CB | ASN | A1138 | 3.543 | 2.164 | −9.193 | 9.54 | C |
| ATOM | 711 | CG | ASN | A1138 | 3.25 | 1.539 | −10.487 | 9.02 | C |
| ATOM | 712 | OD1 | ASN | A1138 | 4.175 | 0.982 | −11.148 | 10.24 | O |
| ATOM | 713 | ND2 | ASN | A1138 | 1.987 | 1.653 | −10.932 | 9.34 | N |
| ATOM | 714 | C | ASN | A1138 | 3.502 | 4.246 | −7.809 | 10.27 | C |
| ATOM | 715 | O | ASN | A1138 | 3.104 | 3.638 | −6.837 | 9.17 | O |
| ATOM | 716 | N | VAL | A1139 | 4.045 | 5.448 | −7.727 | 11.2 | N |
| ATOM | 717 | CA | VAL | A1139 | 4.147 | 6.196 | −6.473 | 11.12 | C |
| ATOM | 718 | CB | VAL | A1139 | 5.614 | 6.467 | −6.114 | 10.21 | C |
| ATOM | 719 | CG1 | VAL | A1139 | 5.682 | 7.242 | −4.755 | 9.07 | C |
| ATOM | 720 | CG2 | VAL | A1139 | 6.356 | 5.132 | −6.068 | 5.79 | C |
| ATOM | 721 | C | VAL | A1139 | 3.411 | 7.492 | −6.689 | 11.77 | C |
| ATOM | 722 | O | VAL | A1139 | 3.647 | 8.158 | −7.713 | 10.94 | O |
| ATOM | 723 | N | LEU | A1140 | 2.522 | 7.823 | −5.745 | 13.02 | N |
| ATOM | 724 | CA | LEU | A1140 | 1.71 | 9.03 | −5.83 | 15.05 | C |
| ATOM | 725 | CB | LEU | A1140 | 0.503 | 8.927 | −4.925 | 15.32 | C |
| ATOM | 726 | CG | LEU | A1140 | −0.733 | 9.865 | −4.978 | 14.43 | C |
| ATOM | 727 | CD1 | LEU | A1140 | −0.669 | 10.86 | −3.921 | 17.59 | C |
| ATOM | 728 | CD2 | LEU | A1140 | −0.925 | 10.507 | −6.316 | 12.71 | C |
| ATOM | 729 | C | LEU | A1140 | 2.641 | 10.14 | −5.355 | 17.56 | C |
| ATOM | 730 | O | LEU | A1140 | 3.161 | 10.068 | −4.248 | 18.36 | O |
| ATOM | 731 | N | SER | A1141 | 2.944 | 11.121 | −6.193 | 18.73 | N |
| ATOM | 732 | CA | SER | A1141 | 3.834 | 12.13 | −5.697 | 21.1 | C |
| ATOM | 733 | CB | SER | A1141 | 5.055 | 12.328 | −6.649 | 24.1 | C |

TABLE 1A-continued

| ATOM | 734 | OG | SER | A1141 | 6.3 | 11.941 | −6.014 | 26.54 | O |
|---|---|---|---|---|---|---|---|---|---|
| ATOM | 735 | C | SER | A1141 | 3.144 | 13.464 | −5.374 | 20.71 | C |
| ATOM | 736 | O | SER | A1141 | 2.13 | 13.815 | −5.93 | 19.98 | O |
| ATOM | 737 | N | LEU | A1142 | 3.752 | 14.182 | −4.45 | 20.91 | N |
| ATOM | 738 | CA | LEU | A1142 | 3.323 | 15.505 | −4.03 | 22.16 | C |
| ATOM | 739 | CB | LEU | A1142 | 4.34 | 15.894 | −2.937 | 23.71 | C |
| ATOM | 740 | CG | LEU | A1142 | 4.041 | 16.699 | −1.689 | 23.78 | C |
| ATOM | 741 | CD1 | LEU | A1142 | 3.912 | 18.061 | −2.193 | 27.43 | C |
| ATOM | 742 | CD2 | LEU | A1142 | 2.719 | 16.18 | −1.182 | 26.21 | C |
| ATOM | 743 | C | LEU | A1142 | 3.373 | 16.496 | −5.235 | 21.52 | C |
| ATOM | 744 | O | LEU | A1142 | 4.395 | 16.47 | −5.96 | 19.46 | O |
| ATOM | 745 | N | LEU | A1143 | 2.31 | 17.314 | −5.498 | 19.99 | N |
| ATOM | 746 | CA | LEU | A1143 | 2.485 | 18.436 | −6.495 | 19.13 | C |
| ATOM | 747 | CB | LEU | A1143 | 1.204 | 18.79 | −7.251 | 18.43 | C |
| ATOM | 748 | CG | LEU | A1143 | 0.689 | 17.786 | −8.297 | 18.69 | C |
| ATOM | 749 | CD1 | LEU | A1143 | −0.597 | 18.167 | −8.903 | 12.55 | C |
| ATOM | 750 | CD2 | LEU | A1143 | 1.731 | 17.452 | −9.369 | 14.52 | C |
| ATOM | 751 | C | LEU | A1143 | 3.082 | 19.719 | −5.899 | 18.63 | C |
| ATOM | 752 | O | LEU | A1143 | 3.836 | 20.444 | −6.547 | 17.14 | O |
| ATOM | 753 | N | GLY | A1144 | 2.692 | 20.033 | −4.675 | 18.45 | N |
| ATOM | 754 | CA | GLY | A1144 | 3.367 | 21.071 | −3.916 | 18.59 | C |
| ATOM | 755 | C | GLY | A1144 | 2.707 | 21.3 | −2.586 | 19.82 | C |
| ATOM | 756 | O | GLY | A1144 | 1.828 | 20.563 | −2.135 | 19.78 | O |
| ATOM | 757 | N | ILE | A1145 | 3.144 | 22.371 | −1.964 | 22.33 | N |
| ATOM | 758 | CA | ILE | A1145 | 2.663 | 22.855 | −0.703 | 22.29 | C |
| ATOM | 759 | CB | ILE | A1145 | 3.805 | 22.853 | 0.339 | 23.4 | C |
| ATOM | 760 | CG2 | ILE | A1145 | 3.223 | 22.796 | 1.739 | 22.81 | C |
| ATOM | 761 | CG1 | ILE | A1145 | 4.753 | 21.695 | 0.117 | 23.81 | C |
| ATOM | 762 | CD1 | ILE | A1145 | 4.176 | 20.356 | 0.659 | 27.04 | C |
| ATOM | 763 | C | ILE | A1145 | 2.325 | 24.302 | −0.914 | 22.87 | C |
| ATOM | 764 | O | ILE | A1145 | 3.085 | 24.998 | −1.56 | 22.95 | O |
| ATOM | 765 | N | CYS | A1146 | 1.213 | 24.758 | −0.345 | 24.26 | N |
| ATOM | 766 | CA | CYS | A1146 | 1.049 | 26.164 | −0.048 | 27.33 | C |
| ATOM | 767 | CB | CYS | A1146 | −0.335 | 26.706 | −0.453 | 27.93 | C |
| ATOM | 768 | SG | CYS | A1146 | −0.799 | 25.936 | −2.042 | 40.01 | S |
| ATOM | 769 | C | CYS | A1146 | 1.314 | 26.435 | 1.413 | 26.36 | C |
| ATOM | 770 | O | CYS | A1146 | 0.576 | 26.017 | 2.263 | 26.54 | O |
| ATOM | 771 | N | LEU | A1147 | 2.381 | 27.169 | 1.681 | 26.97 | N |
| ATOM | 772 | CA | LEU | A1147 | 2.702 | 27.677 | 3.028 | 26.84 | C |
| ATOM | 773 | CB | LEU | A1147 | 4.215 | 27.96 | 3.13 | 25.24 | C |
| ATOM | 774 | CG | LEU | A1147 | 5.124 | 26.744 | 3.04 | 23.65 | C |
| ATOM | 775 | CD1 | LEU | A1147 | 6.564 | 27.203 | 3.331 | 22.66 | C |
| ATOM | 776 | CD2 | LEU | A1147 | 4.686 | 25.628 | 4.009 | 22.26 | C |
| ATOM | 777 | C | LEU | A1147 | 1.92 | 28.956 | 3.281 | 27.19 | C |
| ATOM | 778 | O | LEU | A1147 | 2.092 | 29.949 | 2.592 | 27.3 | O |
| ATOM | 779 | N | ARG | A1148 | 1.034 | 28.926 | 4.254 | 29.23 | N |
| ATOM | 780 | CA | ARG | A1148 | 0.26 | 30.107 | 4.572 | 30.63 | C |
| ATOM | 781 | CB | ARG | A1148 | −1.216 | 29.77 | 4.627 | 29.46 | C |
| ATOM | 782 | CG | ARG | A1148 | −1.673 | 29.076 | 3.423 | 29.26 | C |
| ATOM | 783 | CD | ARG | A1148 | −3.153 | 29.009 | 3.391 | 24.3 | C |
| ATOM | 784 | NE | ARG | A1148 | −3.536 | 28.04 | 4.382 | 23.08 | N |
| ATOM | 785 | CZ | ARG | A1148 | −4.774 | 27.756 | 4.699 | 22.68 | C |
| ATOM | 786 | NH1 | ARG | A1148 | −5.728 | 28.404 | 4.05 | 25.32 | N |
| ATOM | 787 | NH2 | ARG | A1148 | −5.034 | 26.805 | 5.596 | 19.48 | N |
| ATOM | 788 | C | ARG | A1148 | 0.772 | 30.687 | 5.885 | 32.3 | C |
| ATOM | 789 | O | ARG | A1148 | 1.33 | 29.934 | 6.749 | 32.98 | O |
| ATOM | 790 | N | SER | A1149 | 0.656 | 32.013 | 6.005 | 33.88 | N |
| ATOM | 791 | CA | SER | A1149 | 0.938 | 32.721 | 7.301 | 35.81 | C |
| ATOM | 792 | CB | SER | A1149 | 1.614 | 34.074 | 7.063 | 36.19 | C |
| ATOM | 793 | OG | SER | A1149 | 3.02 | 34.017 | 7.166 | 40.64 | O |
| ATOM | 794 | C | SER | A1149 | −0.398 | 33.008 | 7.919 | 35.4 | C |
| ATOM | 795 | O | SER | A1149 | −0.839 | 34.149 | 7.871 | 38.1 | O |
| ATOM | 796 | N | GLU | A1150 | −1.06 | 31.972 | 8.401 | 33.94 | N |
| ATOM | 797 | CA | GLU | A1150 | −2.447 | 31.964 | 8.87 | 33.33 | C |
| ATOM | 798 | CB | GLU | A1150 | −3.232 | 33.244 | 8.587 | 33.3 | C |
| ATOM | 799 | CG | GLU | A1150 | −2.992 | 34.371 | 9.613 | 35.05 | C |
| ATOM | 800 | CD | GLU | A1150 | −3.965 | 35.531 | 9.472 | 36.72 | C |
| ATOM | 801 | OE1 | GLU | A1150 | −3.696 | 36.603 | 10.093 | 41.98 | O |
| ATOM | 802 | OE2 | GLU | A1150 | −5.026 | 35.391 | 8.789 | 41.29 | O |
| ATOM | 803 | C | GLU | A1150 | −3.119 | 30.737 | 8.235 | 30.98 | C |
| ATOM | 804 | O | GLU | A1150 | −3.349 | 30.674 | 7.024 | 29.7 | O |
| ATOM | 805 | N | GLY | A1151 | −3.385 | 29.744 | 9.066 | 28.12 | N |
| ATOM | 806 | CA | GLY | A1151 | −3.827 | 28.45 | 8.559 | 24.41 | C |
| ATOM | 807 | C | GLY | A1151 | −2.653 | 27.52 | 8.348 | 21.21 | C |
| ATOM | 808 | O | GLY | A1151 | −1.513 | 27.918 | 8.1 | 20.6 | O |
| ATOM | 809 | N | SER | A1152 | −2.965 | 26.243 | 8.455 | 19.89 | N |
| ATOM | 810 | CA | SER | A1152 | −2.038 | 25.175 | 8.252 | 16.36 | C |
| ATOM | 811 | CB | SER | A1152 | −2.709 | 23.894 | 8.687 | 16.61 | C |
| ATOM | 812 | OG | SER | A1152 | −2.738 | 23.798 | 10.107 | 17.18 | O |
| ATOM | 813 | C | SER | A1152 | −1.604 | 25.15 | 6.792 | 15.1 | C |

TABLE 1A-continued

| ATOM | 814 | O | SER | A1152 | −2.313 | 25.628 | 5.915 | 16.63 | O |
|---|---|---|---|---|---|---|---|---|---|
| ATOM | 815 | N | PRO | A1153 | −0.426 | 24.621 | 6.515 | 13.76 | N |
| ATOM | 816 | CD | PRO | A1153 | 0.58 | 24.139 | 7.483 | 13.56 | C |
| ATOM | 817 | CA | PRO | A1153 | −0.015 | 24.444 | 5.132 | 13.75 | C |
| ATOM | 818 | CB | PRO | A1153 | 1.3 | 23.722 | 5.273 | 13.97 | C |
| ATOM | 819 | CG | PRO | A1153 | 1.807 | 24.225 | 6.721 | 13.45 | C |
| ATOM | 820 | C | PRO | A1153 | −0.982 | 23.58 | 4.363 | 14.15 | C |
| ATOM | 821 | O | PRO | A1153 | −1.705 | 22.739 | 4.935 | 15.18 | O |
| ATOM | 822 | N | LEU | A1154 | −1.04 | 23.84 | 3.079 | 14.16 | N |
| ATOM | 823 | CA | LEU | A1154 | −1.901 | 23.118 | 2.192 | 15.42 | C |
| ATOM | 824 | CB | LEU | A1154 | −2.525 | 24.029 | 1.175 | 14.91 | C |
| ATOM | 825 | CG | LEU | A1154 | −3.898 | 24.572 | 1.467 | 19.4 | C |
| ATOM | 826 | CD1 | LEU | A1154 | −4.454 | 24.434 | 2.886 | 17.68 | C |
| ATOM | 827 | CD2 | LEU | A1154 | −3.97 | 25.964 | 0.981 | 16.05 | C |
| ATOM | 828 | C | LEU | A1154 | −0.996 | 22.156 | 1.485 | 14.7 | C |
| ATOM | 829 | O | LEU | A1154 | 0.175 | 22.461 | 1.248 | 15.04 | O |
| ATOM | 830 | N | VAL | A1155 | −1.527 | 20.973 | 1.215 | 13.24 | N |
| ATOM | 831 | CA | VAL | A1155 | −0.806 | 20.022 | 0.444 | 12.27 | C |
| ATOM | 832 | CB | VAL | A1155 | −0.535 | 18.73 | 1.26 | 12.93 | C |
| ATOM | 833 | CG1 | VAL | A1155 | −1.88 | 17.94 | 1.51 | 11.63 | C |
| ATOM | 834 | CG2 | VAL | A1155 | 0.462 | 17.886 | 0.543 | 13.81 | C |
| ATOM | 835 | C | VAL | A1155 | −1.622 | 19.8 | −0.827 | 10.87 | C |
| ATOM | 836 | O | VAL | A1155 | −2.762 | 19.527 | −0.794 | 12.07 | O |
| ATOM | 837 | N | VAL | A1156 | −0.977 | 19.902 | −1.962 | 12.01 | N |
| ATOM | 838 | CA | VAL | A1156 | −1.583 | 19.681 | −3.277 | 11.31 | C |
| ATOM | 839 | CB | VAL | A1156 | −1.229 | 20.937 | −4.185 | 10.29 | C |
| ATOM | 840 | CG1 | VAL | A1156 | −1.952 | 20.883 | −5.456 | 11.18 | C |
| ATOM | 841 | CG2 | VAL | A1156 | −1.469 | 22.212 | −3.418 | 6.3 | C |
| ATOM | 842 | C | VAL | A1156 | −1.103 | 18.318 | −3.926 | 11.26 | C |
| ATOM | 843 | O | VAL | A1156 | 0.103 | 18.047 | −4.127 | 11.04 | O |
| ATOM | 844 | N | LEU | A1157 | −2.064 | 17.505 | −4.295 | 11.75 | N |
| ATOM | 845 | CA | LEU | A1157 | −1.796 | 16.193 | −4.836 | 13.19 | C |
| ATOM | 846 | CB | LEU | A1157 | −2.393 | 15.103 | −3.892 | 14.39 | C |
| ATOM | 847 | CG | LEU | A1157 | −1.414 | 14.668 | −2.797 | 14.11 | C |
| ATOM | 848 | CD1 | LEU | A1157 | −1.38 | 15.742 | −1.819 | 18.43 | C |
| ATOM | 849 | CD2 | LEU | A1157 | −1.93 | 13.478 | −2.133 | 20.54 | C |
| ATOM | 850 | C | LEU | A1157 | −2.435 | 16.028 | −6.195 | 14 | C |
| ATOM | 851 | O | LEU | A1157 | −3.476 | 16.716 | −6.456 | 14.03 | O |
| ATOM | 852 | N | PRO | A1158 | −1.868 | 15.084 | −7.043 | 13.2 | N |
| ATOM | 853 | CD | PRO | A1158 | −0.643 | 14.268 | −6.906 | 11.65 | C |
| ATOM | 854 | CA | PRO | A1158 | −2.582 | 14.75 | −8.303 | 13.36 | C |
| ATOM | 855 | CB | PRO | A1158 | −1.725 | 13.611 | −8.951 | 11.42 | C |
| ATOM | 856 | CG | PRO | A1158 | −0.418 | 13.751 | −8.253 | 10.64 | C |
| ATOM | 857 | C | PRO | A1158 | −4.015 | 14.35 | −8.05 | 12.86 | C |
| ATOM | 858 | O | PRO | A1158 | −4.261 | 13.651 | −7.092 | 14.24 | O |
| ATOM | 859 | N | TYR | A1159 | −4.932 | 14.859 | −8.858 | 13.23 | N |
| ATOM | 860 | CA | TYR | A1159 | −6.252 | 14.393 | −8.865 | 13.78 | C |
| ATOM | 861 | CB | TYR | A1159 | −7.058 | 15.142 | −9.93 | 15.01 | C |
| ATOM | 862 | CG | TYR | A1159 | −8.481 | 14.649 | −9.961 | 12.86 | C |
| ATOM | 863 | CD1 | TYR | A1159 | −9.297 | 14.773 | −8.806 | 12.4 | C |
| ATOM | 864 | CE1 | TYR | A1159 | −10.556 | 14.308 | −8.758 | 11.04 | C |
| ATOM | 865 | CD2 | TYR | A1159 | −8.985 | 13.989 | −11.08 | 13.73 | C |
| ATOM | 866 | CE2 | TYR | A1159 | −10.307 | 13.454 | −11.037 | 13.1 | C |
| ATOM | 867 | CZ | TYR | A1159 | −11.07 | 13.657 | −9.875 | 13.4 | C |
| ATOM | 868 | OH | TYR | A1159 | −12.355 | 13.191 | −9.804 | 16.89 | O |
| ATOM | 869 | C | TYR | A1159 | −6.2 | 12.948 | −9.211 | 15.49 | C |
| ATOM | 870 | O | TYR | A1159 | −5.444 | 12.519 | −10.099 | 16.43 | O |
| ATOM | 871 | N | MET | A1160 | −6.991 | 12.165 | −8.506 | 16.74 | N |
| ATOM | 872 | CA | MET | A1160 | −6.931 | 10.714 | −8.614 | 16.11 | C |
| ATOM | 873 | CB | MET | A1160 | −6.311 | 10.119 | −7.325 | 17.37 | C |
| ATOM | 874 | CG | MET | A1160 | −5.161 | 9.13 | −7.551 | 19.28 | C |
| ATOM | 875 | SD | MET | A1160 | −3.813 | 9.522 | −8.699 | 23.59 | S |
| ATOM | 876 | CE | MET | A1160 | −3.543 | 7.869 | −9.241 | 22.32 | C |
| ATOM | 877 | C | MET | A1160 | −8.355 | 10.257 | −8.795 | 16.51 | C |
| ATOM | 878 | O | MET | A1160 | −9.082 | 9.992 | −7.822 | 14.78 | O |
| ATOM | 879 | N | LYS | A1161 | −8.752 | 10.184 | −10.066 | 16.45 | N |
| ATOM | 880 | CA | LYS | A1161 | −10.146 | 9.947 | −10.418 | 17.31 | C |
| ATOM | 881 | CB | LYS | A1161 | −10.245 | 9.711 | −11.902 | 17.73 | C |
| ATOM | 882 | CG | LYS | A1161 | −11.664 | 9.683 | −12.341 | 20.77 | C |
| ATOM | 883 | CD | LYS | A1161 | −11.705 | 9.365 | −13.814 | 24.83 | C |
| ATOM | 884 | CE | LYS | A1161 | −13.144 | 9.363 | −14.295 | 25.08 | C |
| ATOM | 885 | NZ | LYS | A1161 | −13.025 | 9.002 | −15.7 | 26.92 | N |
| ATOM | 886 | C | LYS | A1161 | −10.867 | 8.77 | −9.707 | 16.89 | C |
| ATOM | 887 | O | LYS | A1161 | −12.07 | 8.888 | −9.275 | 17.09 | O |
| ATOM | 888 | N | HIS | A1162 | −10.193 | 7.624 | −9.613 | 15.69 | N |
| ATOM | 889 | CA | HIS | A1162 | −10.88 | 6.482 | −8.989 | 15.59 | C |
| ATOM | 890 | CB | HIS | A1162 | −10.72 | 5.207 | −9.789 | 14.21 | C |
| ATOM | 891 | CG | HIS | A1162 | −11.262 | 5.341 | −11.169 | 13.81 | C |
| ATOM | 892 | CD2 | HIS | A1162 | −10.65 | 5.378 | −12.376 | 15.14 | C |
| ATOM | 893 | ND1 | HIS | A1162 | −12.602 | 5.556 | −11.41 | 14.06 | N |

TABLE 1A-continued

| | | | | | | | | | |
|---|---|---|---|---|---|---|---|---|---|
| ATOM | 894 | CE1 | HIS | A1162 | −12.797 | 5.689 | −12.713 | 16.19 | C |
| ATOM | 895 | NE2 | HIS | A1162 | −11.631 | 5.557 | −13.328 | 16.34 | N |
| ATOM | 896 | C | HIS | A1162 | −10.631 | 6.293 | −7.505 | 15.76 | C |
| ATOM | 897 | O | HIS | A1162 | −11.07 | 5.273 | −6.918 | 17.54 | O |
| ATOM | 898 | N | GLY | A1163 | −9.981 | 7.281 | −6.891 | 14.54 | N |
| ATOM | 899 | CA | GLY | A1163 | −9.797 | 7.311 | −5.446 | 13.69 | C |
| ATOM | 900 | C | GLY | A1163 | −8.933 | 6.175 | −4.992 | 13.15 | C |
| ATOM | 901 | O | GLY | A1163 | −8.07 | 5.685 | −5.752 | 12.3 | O |
| ATOM | 902 | N | ASP | A1164 | −9.204 | 5.721 | −3.784 | 13.21 | N |
| ATOM | 903 | CA | ASP | A1164 | −8.424 | 4.633 | −3.228 | 15.24 | C |
| ATOM | 904 | CB | ASP | A1164 | −8.358 | 4.621 | −1.67 | 15.61 | C |
| ATOM | 905 | CG | ASP | A1164 | −9.602 | 3.98 | −0.995 | 20.21 | C |
| ATOM | 906 | OD1 | ASP | A1164 | −10.69 | 4.556 | −0.969 | 25.32 | O |
| ATOM | 907 | OD2 | ASP | A1164 | −9.498 | 2.888 | −0.421 | 27.01 | O |
| ATOM | 908 | C | ASP | A1164 | −8.831 | 3.266 | −3.739 | 15.25 | C |
| ATOM | 909 | O | ASP | A1164 | −9.991 | 2.932 | −3.954 | 14.63 | O |
| ATOM | 910 | N | LEU | A1165 | −7.802 | 2.456 | −3.823 | 16.8 | N |
| ATOM | 911 | CA | LEU | A1165 | −7.867 | 1.131 | −4.346 | 18.15 | C |
| ATOM | 912 | CB | LEU | A1165 | −6.471 | 0.555 | −4.155 | 18.15 | C |
| ATOM | 913 | CG | LEU | A1165 | −6.254 | −0.82 | −4.745 | 18.98 | C |
| ATOM | 914 | CD1 | LEU | A1165 | −6.799 | −0.956 | −6.187 | 19.58 | C |
| ATOM | 915 | CD2 | LEU | A1165 | −4.782 | −0.942 | −4.773 | 23.5 | C |
| ATOM | 916 | C | LEU | A1165 | −8.88 | 0.262 | −3.617 | 18.36 | C |
| ATOM | 917 | O | LEU | A1165 | −9.566 | −0.575 | −4.2 | 17.43 | O |
| ATOM | 918 | O | GLN | A1166 | −11.809 | −1.243 | −1.678 | 23.09 | O |
| ATOM | 919 | N | GLN | A1166 | −8.781 | 0.307 | −2.284 | 20 | |
| ATOM | 920 | CA | GLN | A1166 | −9.693 | −0.321 | −1.354 | 20 | |
| ATOM | 921 | C | GLN | A1166 | −11.177 | −0.243 | −1.617 | 20 | |
| ATOM | 922 | CB | GLN | A1166 | −9.303 | −0.104 | 0.131 | 20 | |
| ATOM | 923 | CG | GLN | A1166 | −9.599 | −1.201 | 1.163 | 20 | |
| ATOM | 924 | CD | GLN | A1166 | −11.008 | −1.183 | 1.711 | 20 | |
| ATOM | 925 | OE1 | GLN | A1166 | −11.667 | −0.191 | 1.668 | 20 | |
| ATOM | 926 | NE2 | GLN | A1166 | −11.455 | −2.294 | 2.208 | 20 | |
| ATOM | 927 | N | ASN | A1167 | −11.721 | 0.971 | −1.76 | 22.82 | N |
| ATOM | 928 | CA | ASN | A1167 | −13.142 | 1.243 | −2.091 | 22.98 | C |
| ATOM | 929 | CB | ASN | A1167 | −13.482 | 2.739 | −1.849 | 23.61 | C |
| ATOM | 930 | CG | ASN | A1167 | −13.721 | 3.05 | −0.404 | 24.86 | C |
| ATOM | 931 | OD1 | ASN | A1167 | −14.747 | 2.681 | 0.17 | 29.97 | O |
| ATOM | 932 | ND2 | ASN | A1167 | −12.777 | 3.729 | 0.201 | 24.59 | N |
| ATOM | 933 | C | ASN | A1167 | −13.365 | 0.97 | −3.554 | 22.09 | C |
| ATOM | 934 | O | ASN | A1167 | −14.472 | 0.568 | −3.972 | 22.42 | O |
| ATOM | 935 | N | PHE | A1168 | −12.336 | 1.214 | −4.352 | 20.93 | N |
| ATOM | 936 | CA | PHE | A1168 | −12.444 | 0.801 | −5.741 | 21.8 | C |
| ATOM | 937 | CB | PHE | A1168 | −11.238 | 1.267 | −6.545 | 22.22 | C |
| ATOM | 938 | CG | PHE | A1168 | −11.36 | 1.012 | −7.966 | 23.93 | C |
| ATOM | 939 | CD1 | PHE | A1168 | −12.022 | 1.922 | −8.777 | 28.08 | C |
| ATOM | 940 | CD2 | PHE | A1168 | −10.854 | −0.18 | −8.513 | 28.78 | C |
| ATOM | 941 | CE1 | PHE | A1168 | −12.208 | 1.659 | −10.153 | 31.38 | C |
| ATOM | 942 | CE2 | PHE | A1168 | −11.014 | −0.482 | −9.875 | 30.49 | C |
| ATOM | 943 | CZ | PHE | A1168 | −11.688 | 0.438 | −10.709 | 29.96 | C |
| ATOM | 944 | C | PHE | A1168 | −12.742 | −0.711 | −5.906 | 20.84 | C |
| ATOM | 945 | O | PHE | A1168 | −13.71 | −1.104 | −6.509 | 21.8 | O |
| ATOM | 946 | N | ILE | A1169 | −11.932 | −1.557 | −5.318 | 21.69 | N |
| ATOM | 947 | CA | ILE | A1169 | −12.101 | −3.02 | −5.434 | 21.21 | C |
| ATOM | 948 | CB | ILE | A1169 | −10.79 | −3.818 | −4.97 | 20.88 | C |
| ATOM | 949 | CG2 | ILE | A1169 | −9.584 | −3.379 | −5.84 | 16.89 | C |
| ATOM | 950 | CG1 | ILE | A1169 | −10.53 | −3.655 | −3.444 | 20.13 | C |
| ATOM | 951 | CD1 | ILE | A1169 | −9.219 | −4.284 | −2.912 | 17.66 | C |
| ATOM | 952 | C | ILE | A1169 | −13.327 | −3.475 | −4.699 | 22.65 | C |
| ATOM | 953 | O | ILE | A1169 | −13.956 | −4.433 | −5.044 | 24.92 | O |
| ATOM | 954 | N | ARG | A1170 | −13.696 | −2.769 | −3.675 | 24.78 | N |
| ATOM | 955 | CA | ARG | A1170 | −14.841 | −3.173 | −2.895 | 27.45 | C |
| ATOM | 956 | CB | ARG | A1170 | −14.573 | −2.797 | −1.471 | 26.7 | C |
| ATOM | 957 | CG | ARG | A1170 | −15.698 | −2.707 | −0.613 | 29.73 | C |
| ATOM | 958 | CD | ARG | A1170 | −15.338 | −1.544 | 0.225 | 36.17 | C |
| ATOM | 959 | NE | ARG | A1170 | −15.115 | −1.902 | 1.627 | 43.74 | N |
| ATOM | 960 | CZ | ARG | A1170 | −14.896 | −0.989 | 2.59 | 45.61 | C |
| ATOM | 961 | NH1 | ARG | A1170 | −14.837 | 0.324 | 2.25 | 37.76 | N |
| ATOM | 962 | NH2 | ARG | A1170 | −14.718 | −1.399 | 3.877 | 43.16 | N |
| ATOM | 963 | C | ARG | A1170 | −16.198 | −2.692 | −3.43 | 29.47 | C |
| ATOM | 964 | O | ARG | A1170 | −17.234 | −3.059 | −2.907 | 31.36 | O |
| ATOM | 965 | N | ASN | A1171 | −16.217 | −1.936 | −4.522 | 32.08 | N |
| ATOM | 966 | CA | ASN | A1171 | −17.475 | −1.556 | −5.177 | 33.39 | C |
| ATOM | 967 | CB | ASN | A1171 | −17.367 | −0.142 | −5.702 | 34.28 | C |
| ATOM | 968 | CG | ASN | A1171 | −18.728 | 0.484 | −5.977 | 34.85 | C |
| ATOM | 969 | OD1 | ASN | A1171 | −18.83 | 1.706 | −6.129 | 32.84 | O |
| ATOM | 970 | ND2 | ASN | A1171 | −19.779 | −0.34 | −6.017 | 34.99 | N |
| ATOM | 971 | C | ASN | A1171 | −17.889 | −2.476 | −6.327 | 33.85 | C |
| ATOM | 972 | O | ASN | A1171 | −17.171 | −2.562 | −7.326 | 32.39 | O |
| ATOM | 973 | N | GLU | A1172 | −19.046 | −3.143 | −6.172 | 35.59 | N |

TABLE 1A-continued

| | | | | | | | | |
|---|---|---|---|---|---|---|---|---|
| ATOM | 974 | CA | GLU | A1172 | −19.548 | −4.089 | −7.207 | 37.83 | C |
| ATOM | 975 | CB | GLU | A1172 | −20.558 | −5.143 | −6.681 | 38.24 | C |
| ATOM | 976 | CG | GLU | A1172 | −20.166 | −5.831 | −5.304 | 42.55 | C |
| ATOM | 977 | CD | GLU | A1172 | −18.806 | −6.659 | −5.293 | 48.09 | C |
| ATOM | 978 | OE1 | GLU | A1172 | −18.827 | −7.858 | −5.695 | 49.77 | O |
| ATOM | 979 | OE2 | GLU | A1172 | −17.727 | −6.153 | −4.82 | 48.47 | O |
| ATOM | 980 | C | GLU | A1172 | −20.001 | −3.393 | −8.499 | 37.62 | C |
| ATOM | 981 | O | GLU | A1172 | −20.113 | −4.038 | −9.537 | 38.48 | O |
| ATOM | 982 | N | THR | A1173 | −20.151 | −2.072 | −8.448 | 37.81 | N |
| ATOM | 983 | CA | THR | A1173 | −20.229 | −1.225 | −9.646 | 38.22 | C |
| ATOM | 984 | CB | THR | A1173 | −20.255 | 0.238 | −9.247 | 38.54 | C |
| ATOM | 985 | OG1 | THR | A1173 | −21.41 | 0.471 | −8.421 | 42.46 | O |
| ATOM | 986 | CG2 | THR | A1173 | −20.294 | 1.169 | −10.489 | 39.4 | C |
| ATOM | 987 | C | THR | A1173 | −19.051 | −1.353 | −10.595 | 37.94 | C |
| ATOM | 988 | O | THR | A1173 | −19.151 | −0.997 | −11.783 | 39.05 | O |
| ATOM | 989 | N | HIS | A1174 | −17.913 | −1.768 | −10.058 | 36.95 | N |
| ATOM | 990 | CA | HIS | A1174 | −16.674 | −1.912 | −10.826 | 36.02 | C |
| ATOM | 991 | CB | HIS | A1174 | −15.462 | −1.363 | −10.036 | 37.52 | C |
| ATOM | 992 | CG | HIS | A1174 | −15.661 | −0.004 | −9.393 | 41.68 | C |
| ATOM | 993 | CD2 | HIS | A1174 | −14.856 | 1.087 | −9.375 | 42.46 | C |
| ATOM | 994 | ND1 | HIS | A1174 | −16.769 | 0.337 | −8.635 | 47.13 | N |
| ATOM | 995 | CE1 | HIS | A1174 | −16.646 | 1.581 | −8.205 | 44.27 | C |
| ATOM | 996 | NE2 | HIS | A1174 | −15.493 | 2.056 | −8.641 | 44.18 | N |
| ATOM | 997 | C | HIS | A1174 | −16.519 | −3.437 | −11 | 33.97 | C |
| ATOM | 998 | O | HIS | A1174 | −17.201 | −4.25 | −10.316 | 33.49 | O |
| ATOM | 999 | N | ASN | A1175 | −15.63 | −3.856 | −11.89 | 31.33 | N |
| ATOM | 1000 | CA | ASN | A1175 | −15.406 | −5.303 | −12.013 | 28.29 | C |
| ATOM | 1001 | CB | ASN | A1175 | −16.401 | −5.944 | −13.003 | 26.81 | C |
| ATOM | 1002 | CG | ASN | A1175 | −16.56 | −7.457 | −12.797 | 27.33 | C |
| ATOM | 1003 | OD1 | ASN | A1175 | −16.965 | −7.914 | −11.714 | 25.48 | O |
| ATOM | 1004 | ND2 | ASN | A1175 | −16.234 | −8.25 | −13.846 | 23.69 | N |
| ATOM | 1005 | C | ASN | A1175 | −13.967 | −5.677 | −12.35 | 26.55 | C |
| ATOM | 1006 | O | ASN | A1175 | −13.708 | −6.266 | −13.408 | 26.61 | O |
| ATOM | 1007 | N | PRO | A1176 | −13.036 | −5.42 | −11.418 | 25.23 | N |
| ATOM | 1008 | CD | PRO | A1176 | −13.117 | −4.731 | −10.105 | 24.47 | C |
| ATOM | 1009 | CA | PRO | A1176 | −11.683 | −5.913 | −11.71 | 24.16 | C |
| ATOM | 1010 | CB | PRO | A1176 | −10.826 | −5.27 | −10.581 | 24.13 | C |
| ATOM | 1011 | CG | PRO | A1176 | −11.784 | −5.014 | −9.455 | 23.25 | C |
| ATOM | 1012 | C | PRO | A1176 | −11.63 | −7.463 | −11.712 | 22.75 | C |
| ATOM | 1013 | O | PRO | A1176 | −12.121 | −8.118 | −10.79 | 23.37 | O |
| ATOM | 1014 | N | THR | A1177 | −11.114 | −8.04 | −12.784 | 21.08 | N |
| ATOM | 1015 | CA | THR | A1177 | −10.898 | −9.469 | −12.874 | 18.85 | C |
| ATOM | 1016 | CB | THR | A1177 | −10.494 | −9.914 | −14.3 | 18.88 | C |
| ATOM | 1017 | OG1 | THR | A1177 | −9.242 | −9.28 | −14.634 | 19.84 | O |
| ATOM | 1018 | CG2 | THR | A1177 | −11.598 | −9.527 | −15.347 | 18.87 | C |
| ATOM | 1019 | C | THR | A1177 | −9.757 | −9.846 | −11.899 | 17.26 | C |
| ATOM | 1020 | O | THR | A1177 | −9.065 | −9.003 | −11.348 | 15.8 | O |
| ATOM | 1021 | N | VAL | A1178 | −9.607 | −11.133 | −11.684 | 15.8 | N |
| ATOM | 1022 | CA | VAL | A1178 | −8.509 | −11.651 | −10.904 | 16.14 | C |
| ATOM | 1023 | CB | VAL | A1178 | −8.5 | −13.223 | −10.915 | 15.53 | C |
| ATOM | 1024 | CG1 | VAL | A1178 | −7.309 | −13.705 | −10.261 | 15.69 | C |
| ATOM | 1025 | CG2 | VAL | A1178 | −9.747 | −13.793 | −10.221 | 15.73 | C |
| ATOM | 1026 | C | VAL | A1178 | −7.219 | −11.17 | −11.532 | 14.86 | C |
| ATOM | 1027 | O | VAL | A1178 | −6.359 | −10.704 | −10.845 | 15.18 | O |
| ATOM | 1028 | N | LYS | A1179 | −7.085 | −11.347 | −12.847 | 15.44 | N |
| ATOM | 1029 | CA | LYS | A1179 | −5.966 | −10.765 | −13.584 | 16.04 | C |
| ATOM | 1030 | CB | LYS | A1179 | −6.177 | −10.988 | −15.109 | 16.98 | C |
| ATOM | 1031 | CG | LYS | A1179 | −5.079 | −10.35 | −16.015 | 18.66 | C |
| ATOM | 1032 | CD | LYS | A1179 | −4.147 | −11.355 | −16.683 | 18.04 | C |
| ATOM | 1033 | CE | LYS | A1179 | −3.388 | −10.723 | −17.929 | 20.93 | C |
| ATOM | 1034 | NZ | LYS | A1179 | −2.56 | −11.797 | −18.707 | 22.94 | N |
| ATOM | 1035 | C | LYS | A1179 | −5.727 | −9.246 | −13.248 | 14.25 | C |
| ATOM | 1036 | O | LYS | A1179 | −4.607 | −8.793 | −13.141 | 11.31 | O |
| ATOM | 1037 | N | ASP | A1180 | −6.812 | −8.495 | −13.133 | 14.79 | N |
| ATOM | 1038 | CA | ASP | A1180 | −6.788 | −7.03 | −12.867 | 15.14 | C |
| ATOM | 1039 | CB | ASP | A1180 | −8.224 | −6.451 | −13.001 | 15.66 | C |
| ATOM | 1040 | CG | ASP | A1180 | −8.624 | −6.138 | −14.446 | 21.29 | C |
| ATOM | 1041 | OD1 | ASP | A1180 | −9.866 | −5.915 | −14.763 | 24.01 | O |
| ATOM | 1042 | OD2 | ASP | A1180 | −7.679 | −6.095 | −15.281 | 27.62 | O |
| ATOM | 1043 | C | ASP | A1180 | −6.25 | −6.82 | −11.46 | 13.2 | C |
| ATOM | 1044 | O | ASP | A1180 | −5.379 | −5.979 | −11.212 | 13.36 | O |
| ATOM | 1045 | N | LEU | A1181 | −6.756 | −7.615 | −10.527 | 11.47 | N |
| ATOM | 1046 | CA | LEU | A1181 | −6.303 | −7.517 | −9.13 | 9.77 | C |
| ATOM | 1047 | CB | LEU | A1181 | −7.187 | −8.413 | −8.305 | 9.68 | C |
| ATOM | 1048 | CG | LEU | A1181 | −8.476 | −7.975 | −7.638 | 7.92 | C |
| ATOM | 1049 | CD1 | LEU | A1181 | −8.865 | −6.576 | −7.944 | 8.74 | C |
| ATOM | 1050 | CD2 | LEU | A1181 | −9.58 | −9 | −7.905 | 3.42 | C |
| ATOM | 1051 | C | LEU | A1181 | −4.848 | −7.876 | −8.912 | 8.81 | C |
| ATOM | 1052 | O | LEU | A1181 | −4.104 | −7.223 | −8.163 | 8.69 | O |
| ATOM | 1053 | N | ILE | A1182 | −4.408 | −8.927 | −9.57 | 8.8 | N |

TABLE 1A-continued

| ATOM | 1054 | CA | ILE | A1182 | −2.986 | −9.267 | −9.562 | 8.84 | C |
|---|---|---|---|---|---|---|---|---|---|
| ATOM | 1055 | CB | ILE | A1182 | −2.76 | −10.613 | −10.313 | 10.68 | C |
| ATOM | 1056 | CG2 | ILE | A1182 | −1.247 | −11.036 | −10.247 | 7.66 | C |
| ATOM | 1057 | CG1 | ILE | A1182 | −3.664 | −11.715 | −9.681 | 10.62 | C |
| ATOM | 1058 | CD1 | ILE | A1182 | −3.664 | −13.062 | −10.422 | 12.08 | C |
| ATOM | 1059 | C | ILE | A1182 | −2.176 | −8.16 | −10.181 | 8.2 | C |
| ATOM | 1060 | O | ILE | A1182 | −1.12 | −7.817 | −9.686 | 8.72 | O |
| ATOM | 1061 | N | GLY | A1183 | −2.646 | −7.59 | −11.278 | 7.96 | N |
| ATOM | 1062 | CA | GLY | A1183 | −2.02 | −6.43 | −11.836 | 8.15 | C |
| ATOM | 1063 | C | GLY | A1183 | −1.877 | −5.284 | −10.854 | 9.46 | C |
| ATOM | 1064 | O | GLY | A1183 | −0.836 | −4.71 | −10.786 | 9.11 | O |
| ATOM | 1065 | N | PHE | A1184 | −2.966 | −4.912 | −10.133 | 11.34 | N |
| ATOM | 1066 | CA | PHE | A1184 | −2.919 | −3.923 | −9.065 | 10.26 | C |
| ATOM | 1067 | CB | PHE | A1184 | −4.239 | −3.763 | −8.316 | 9.89 | C |
| ATOM | 1068 | CG | PHE | A1184 | −5.4 | −3.275 | −9.179 | 11.92 | C |
| ATOM | 1069 | CD1 | PHE | A1184 | −5.194 | −2.497 | −10.285 | 14.53 | C |
| ATOM | 1070 | CD2 | PHE | A1184 | −6.724 | −3.591 | −8.847 | 14.63 | C |
| ATOM | 1071 | CE1 | PHE | A1184 | −6.273 | −2.09 | −11.091 | 15.48 | C |
| ATOM | 1072 | CE2 | PHE | A1184 | −7.779 | −3.188 | −9.636 | 14.52 | C |
| ATOM | 1073 | CZ | PHE | A1184 | −7.539 | −2.445 | −10.775 | 12.06 | C |
| ATOM | 1074 | C | PHE | A1184 | −1.799 | −4.254 | −8.124 | 10.46 | C |
| ATOM | 1075 | O | PHE | A1184 | −0.991 | −3.356 | −7.809 | 10.91 | O |
| ATOM | 1076 | N | GLY | A1185 | −1.732 | −5.534 | −7.687 | 10.44 | N |
| ATOM | 1077 | CA | GLY | A1185 | −0.685 | −6.022 | −6.776 | 7.06 | C |
| ATOM | 1078 | C | GLY | A1185 | 0.675 | −5.808 | −7.442 | 7.98 | C |
| ATOM | 1079 | O | GLY | A1185 | 1.649 | −5.263 | −6.834 | 8.85 | O |
| ATOM | 1080 | N | LEU | A1186 | 0.788 | −6.237 | −8.698 | 7.09 | N |
| ATOM | 1081 | CA | LEU | A1186 | 2.034 | −5.966 | −9.473 | 6.15 | C |
| ATOM | 1082 | CB | LEU | A1186 | 1.97 | −6.564 | −10.864 | 3.48 | C |
| ATOM | 1083 | CG | LEU | A1186 | 3.21 | −6.47 | −11.81 | 7.84 | C |
| ATOM | 1084 | CD1 | LEU | A1186 | 4.5 | −6.921 | −11.173 | 10.47 | C |
| ATOM | 1085 | CD2 | LEU | A1186 | 2.965 | −7.238 | −13.117 | 5.94 | C |
| ATOM | 1086 | C | LEU | A1186 | 2.456 | −4.469 | −9.46 | 6.45 | C |
| ATOM | 1087 | O | LEU | A1186 | 3.646 | −4.159 | −9.149 | 8.35 | O |
| ATOM | 1088 | N | GLN | A1187 | 1.518 | −3.556 | −9.706 | 4.69 | N |
| ATOM | 1089 | CA | GLN | A1187 | 1.827 | −2.119 | −9.774 | 7.07 | C |
| ATOM | 1090 | CB | GLN | A1187 | 0.559 | −1.336 | −10.225 | 7.15 | C |
| ATOM | 1091 | CG | GLN | A1187 | 0.145 | −1.578 | −11.706 | 9.39 | C |
| ATOM | 1092 | CD | GLN | A1187 | −1.053 | −0.767 | −12.136 | 9.26 | C |
| ATOM | 1093 | OE1 | GLN | A1187 | −1.039 | 0.462 | −12.092 | 11.28 | O |
| ATOM | 1094 | NE2 | GLN | A1187 | −2.08 | −1.441 | −12.595 | 10.28 | N |
| ATOM | 1095 | C | GLN | A1187 | 2.328 | −1.586 | −8.435 | 7.09 | C |
| ATOM | 1096 | O | GLN | A1187 | 3.262 | −0.835 | −8.35 | 8.11 | O |
| ATOM | 1097 | N | VAL | A1188 | 1.657 | −1.962 | −7.355 | 8.62 | N |
| ATOM | 1098 | CA | VAL | A1188 | 2.069 | −1.609 | −6.017 | 7.25 | C |
| ATOM | 1099 | CB | VAL | A1188 | 1.029 | −2.178 | −4.976 | 7.78 | C |
| ATOM | 1100 | CG1 | VAL | A1188 | 1.56 | −1.976 | −3.526 | 6.03 | C |
| ATOM | 1101 | CG2 | VAL | A1188 | −0.316 | −1.492 | −5.103 | 6.83 | C |
| ATOM | 1102 | C | VAL | A1188 | 3.452 | −2.217 | −5.683 | 7.86 | C |
| ATOM | 1103 | O | VAL | A1188 | 4.251 | −1.56 | −5.06 | 9.73 | O |
| ATOM | 1104 | N | ALA | A1189 | 3.692 | −3.491 | −5.993 | 6.51 | N |
| ATOM | 1105 | CA | ALA | A1189 | 5.007 | −4.053 | −5.813 | 6.67 | C |
| ATOM | 1106 | CB | ALA | A1189 | 5.075 | −5.504 | −6.374 | 5.44 | C |
| ATOM | 1107 | C | ALA | A1189 | 6.071 | −3.189 | −6.516 | 7.79 | C |
| ATOM | 1108 | O | ALA | A1189 | 7.194 | −3.024 | −5.945 | 7.89 | O |
| ATOM | 1109 | N | LYS | A1190 | 5.787 | −2.67 | −7.758 | 6.25 | N |
| ATOM | 1110 | CA | LYS | A1190 | 6.796 | −1.834 | −8.454 | 4.83 | C |
| ATOM | 1111 | CB | LYS | A1190 | 6.361 | −1.573 | −9.894 | 5.09 | C |
| ATOM | 1112 | CG | LYS | A1190 | 6.426 | −2.867 | −10.641 | 6.53 | C |
| ATOM | 1113 | CD | LYS | A1190 | 5.901 | −2.797 | −12.039 | 11.48 | C |
| ATOM | 1114 | CE | LYS | A1190 | 6.178 | −4.122 | −12.805 | 10.35 | C |
| ATOM | 1115 | NZ | LYS | A1190 | 5.376 | −4.012 | −14.119 | 5.13 | N |
| ATOM | 1116 | C | LYS | A1190 | 7.025 | −0.52 | −7.774 | 5.07 | C |
| ATOM | 1117 | O | LYS | A1190 | 8.171 | −0.069 | −7.643 | 6.03 | O |
| ATOM | 1118 | N | GLY | A1191 | 5.919 | 0.157 | −7.41 | 5.61 | N |
| ATOM | 1119 | CA | GLY | A1191 | 5.97 | 1.325 | −6.513 | 5.95 | C |
| ATOM | 1120 | C | GLY | A1191 | 6.781 | 1.045 | −5.299 | 6.41 | C |
| ATOM | 1121 | O | GLY | A1191 | 7.707 | 1.773 | −4.994 | 7.75 | O |
| ATOM | 1122 | N | MET | A1192 | 6.487 | −0.048 | −4.587 | 7.71 | N |
| ATOM | 1123 | CA | MET | A1192 | 7.236 | −0.323 | −3.339 | 8.41 | C |
| ATOM | 1124 | CB | MET | A1192 | 6.577 | −1.482 | −2.653 | 10.35 | C |
| ATOM | 1125 | CG | MET | A1192 | 5.282 | −1.115 | −1.963 | 9.89 | C |
| ATOM | 1126 | SD | MET | A1192 | 5.581 | 0.263 | −0.802 | 14.47 | S |
| ATOM | 1127 | CE | MET | A1192 | 6.863 | −0.345 | 0.254 | 11.37 | C |
| ATOM | 1128 | C | MET | A1192 | 8.718 | −0.659 | −3.568 | 9.94 | C |
| ATOM | 1129 | O | MET | A1192 | 9.61 | −0.216 | −2.828 | 9.3 | O |
| ATOM | 1130 | N | LYS | A1193 | 9.004 | −1.42 | −4.634 | 9.24 | N |
| ATOM | 1131 | CA | LYS | A1193 | 10.367 | −1.654 | −5.007 | 8.67 | C |
| ATOM | 1132 | CB | LYS | A1193 | 10.443 | −2.536 | −6.202 | 8.81 | C |
| ATOM | 1133 | CG | LYS | A1193 | 11.81 | −3.023 | −6.484 | 10.02 | C |

TABLE 1A-continued

| | | | | | | | | |
|---|---|---|---|---|---|---|---|---|
| ATOM | 1134 | CD | LYS | A1193 | 11.979 | −3.575 | −7.901 | 8.96 | C |
| ATOM | 1135 | CE | LYS | A1193 | 13.498 | −3.572 | −8.277 | 9.49 | C |
| ATOM | 1136 | NZ | LYS | A1193 | 13.743 | −4.27 | −9.513 | 15.27 | N |
| ATOM | 1137 | C | LYS | A1193 | 11.12 | −0.367 | −5.26 | 9.78 | C |
| ATOM | 1138 | O | LYS | A1193 | 12.272 | −0.228 | −4.873 | 9.11 | O |
| ATOM | 1139 | N | TYR | A1194 | 10.451 | 0.594 | −5.896 | 10.85 | N |
| ATOM | 1140 | CA | TYR | A1194 | 11.023 | 1.904 | −6.061 | 10.32 | C |
| ATOM | 1141 | CB | TYR | A1194 | 10.051 | 2.76 | −6.851 | 11.52 | C |
| ATOM | 1142 | CG | TYR | A1194 | 10.526 | 4.172 | −6.973 | 11.52 | C |
| ATOM | 1143 | CD1 | TYR | A1194 | 11.52 | 4.483 | −7.857 | 9.72 | C |
| ATOM | 1144 | CE1 | TYR | A1194 | 11.998 | 5.785 | −7.936 | 16.28 | C |
| ATOM | 1145 | CD2 | TYR | A1194 | 9.963 | 5.196 | −6.179 | 12.54 | C |
| ATOM | 1146 | CE2 | TYR | A1194 | 10.407 | 6.485 | −6.224 | 14.38 | C |
| ATOM | 1147 | CZ | TYR | A1194 | 11.42 | 6.793 | −7.129 | 18.51 | C |
| ATOM | 1148 | OH | TYR | A1194 | 11.878 | 8.103 | −7.25 | 19.47 | O |
| ATOM | 1149 | C | TYR | A1194 | 11.39 | 2.561 | −4.701 | 10.21 | C |
| ATOM | 1150 | O | TYR | A1194 | 12.564 | 2.975 | −4.43 | 9.3 | O |
| ATOM | 1151 | N | LEU | A1195 | 10.378 | 2.622 | −3.829 | 10.8 | N |
| ATOM | 1152 | CA | LEU | A1195 | 10.464 | 3.313 | −2.54 | 10.49 | C |
| ATOM | 1153 | CB | LEU | A1195 | 9.125 | 3.189 | −1.851 | 11.47 | C |
| ATOM | 1154 | CG | LEU | A1195 | 8.115 | 4.35 | −1.972 | 9.95 | C |
| ATOM | 1155 | CD1 | LEU | A1195 | 7.944 | 4.563 | −3.323 | 16.01 | C |
| ATOM | 1156 | CD2 | LEU | A1195 | 6.792 | 3.895 | −1.414 | 10.13 | C |
| ATOM | 1157 | C | LEU | A1195 | 11.53 | 2.694 | −1.692 | 10.23 | C |
| ATOM | 1158 | O | LEU | A1195 | 12.311 | 3.368 | −1.107 | 11.31 | O |
| ATOM | 1159 | N | ALA | A1196 | 11.587 | 1.377 | −1.681 | 11.66 | N |
| ATOM | 1160 | CA | ALA | A1196 | 12.606 | 0.636 | −0.935 | 12.04 | C |
| ATOM | 1161 | CB | ALA | A1196 | 12.259 | −0.832 | −0.918 | 14.25 | C |
| ATOM | 1162 | C | ALA | A1196 | 14.031 | 0.83 | −1.442 | 11.92 | C |
| ATOM | 1163 | O | ALA | A1196 | 14.956 | 0.679 | −0.685 | 10.62 | O |
| ATOM | 1164 | N | SER | A1197 | 14.196 | 1.198 | −2.704 | 12.53 | N |
| ATOM | 1165 | CA | SER | A1197 | 15.516 | 1.523 | −3.258 | 14.34 | C |
| ATOM | 1166 | CB | SER | A1197 | 15.512 | 1.502 | −4.809 | 12.95 | C |
| ATOM | 1167 | OG | SER | A1197 | 14.768 | 2.609 | −5.335 | 18.14 | O |
| ATOM | 1168 | C | SER | A1197 | 15.982 | 2.872 | −2.776 | 15.31 | C |
| ATOM | 1169 | O | SER | A1197 | 17.151 | 3.148 | −2.812 | 15.58 | O |
| ATOM | 1170 | N | LYS | A1198 | 15.038 | 3.733 | −2.368 | 17.2 | N |
| ATOM | 1171 | CA | LYS | A1198 | 15.335 | 5.058 | −1.872 | 17.87 | C |
| ATOM | 1172 | CB | LYS | A1198 | 14.182 | 5.996 | −2.238 | 18.38 | C |
| ATOM | 1173 | CG | LYS | A1198 | 13.869 | 6.115 | −3.698 | 20.26 | C |
| ATOM | 1174 | CD | LYS | A1198 | 15.011 | 6.846 | −4.464 | 25.11 | C |
| ATOM | 1175 | CE | LYS | A1198 | 14.913 | 6.593 | −6.028 | 30.26 | C |
| ATOM | 1176 | NZ | LYS | A1198 | 16.214 | 6.552 | −6.827 | 23.87 | N |
| ATOM | 1177 | C | LYS | A1198 | 15.376 | 4.861 | −0.383 | 19 | C |
| ATOM | 1178 | O | LYS | A1198 | 15.387 | 5.808 | 0.383 | 20.3 | O |
| ATOM | 1179 | N | LYS | A1199 | 15.344 | 3.605 | 0.022 | 18.71 | N |
| ATOM | 1180 | CA | LYS | A1199 | 15.19 | 3.22 | 1.411 | 20.01 | C |
| ATOM | 1181 | CB | LYS | A1199 | 16.523 | 3.188 | 2.164 | 20.74 | C |
| ATOM | 1182 | CG | LYS | A1199 | 17.471 | 4.222 | 1.788 | 21.64 | C |
| ATOM | 1183 | CD | LYS | A1199 | 18.294 | 3.84 | 0.543 | 31.5 | C |
| ATOM | 1184 | CE | LYS | A1199 | 19.039 | 2.467 | 0.574 | 29.62 | C |
| ATOM | 1185 | NZ | LYS | A1199 | 18.412 | 1.599 | 1.567 | 28.43 | N |
| ATOM | 1186 | C | LYS | A1199 | 14.135 | 4.038 | 2.147 | 19.36 | C |
| ATOM | 1187 | O | LYS | A1199 | 14.377 | 4.557 | 3.212 | 19.28 | O |
| ATOM | 1188 | N | PHE | A1200 | 12.961 | 4.151 | 1.547 | 18.79 | N |
| ATOM | 1189 | CA | PHE | A1200 | 11.834 | 4.788 | 2.197 | 17.86 | C |
| ATOM | 1190 | CB | PHE | A1200 | 11.029 | 5.568 | 1.14 | 17.17 | C |
| ATOM | 1191 | CG | PHE | A1200 | 9.743 | 6.111 | 1.664 | 18.38 | C |
| ATOM | 1192 | CD1 | PHE | A1200 | 8.571 | 5.39 | 1.535 | 12.53 | C |
| ATOM | 1193 | CD2 | PHE | A1200 | 9.718 | 7.361 | 2.338 | 17 | C |
| ATOM | 1194 | CE1 | PHE | A1200 | 7.385 | 5.872 | 2.071 | 15.8 | C |
| ATOM | 1195 | CE2 | PHE | A1200 | 8.535 | 7.851 | 2.811 | 14.97 | C |
| ATOM | 1196 | CZ | PHE | A1200 | 7.349 | 7.091 | 2.689 | 13.81 | C |
| ATOM | 1197 | C | PHE | A1200 | 11.01 | 3.658 | 2.786 | 16.62 | C |
| ATOM | 1198 | O | PHE | A1200 | 10.479 | 2.841 | 2.025 | 16.28 | O |
| ATOM | 1199 | N | VAL | A1201 | 10.893 | 3.612 | 4.107 | 16.06 | N |
| ATOM | 1200 | CA | VAL | A1201 | 9.965 | 2.684 | 4.803 | 14.92 | C |
| ATOM | 1201 | CB | VAL | A1201 | 10.506 | 2.167 | 6.16 | 14.85 | C |
| ATOM | 1202 | CG1 | VAL | A1201 | 9.448 | 1.315 | 6.839 | 14.19 | C |
| ATOM | 1203 | CG2 | VAL | A1201 | 11.84 | 1.313 | 5.982 | 12.79 | C |
| ATOM | 1204 | C | VAL | A1201 | 8.575 | 3.318 | 4.939 | 15.98 | C |
| ATOM | 1205 | O | VAL | A1201 | 8.428 | 4.412 | 5.475 | 18.87 | O |
| ATOM | 1206 | N | HIS | A1202 | 7.552 | 2.661 | 4.405 | 15.17 | N |
| ATOM | 1207 | CA | HIS | A1202 | 6.283 | 3.264 | 4.251 | 14.89 | C |
| ATOM | 1208 | CB | HIS | A1202 | 5.491 | 2.509 | 3.135 | 15.35 | C |
| ATOM | 1209 | CG | HIS | A1202 | 4.164 | 3.144 | 2.826 | 17.55 | C |
| ATOM | 1210 | CD2 | HIS | A1202 | 3.75 | 3.885 | 1.765 | 20.15 | C |
| ATOM | 1211 | ND1 | HIS | A1202 | 3.118 | 3.161 | 3.736 | 15.04 | N |
| ATOM | 1212 | CE1 | HIS | A1202 | 2.11 | 3.845 | 3.218 | 17.84 | C |
| ATOM | 1213 | NE2 | HIS | A1202 | 2.462 | 4.291 | 2.023 | 17.78 | N |

TABLE 1A-continued

| | | | | | | | | | |
|---|---|---|---|---|---|---|---|---|---|
| ATOM | 1214 | C | HIS | A1202 | 5.505 | 3.343 | 5.591 | 14.91 | C |
| ATOM | 1215 | O | HIS | A1202 | 4.95 | 4.386 | 5.964 | 12.58 | O |
| ATOM | 1216 | N | ARG | A1203 | 5.426 | 2.179 | 6.266 | 16.87 | N |
| ATOM | 1217 | CA | ARG | A1203 | 4.83 | 1.98 | 7.621 | 17.09 | C |
| ATOM | 1218 | CB | ARG | A1203 | 5.296 | 3.035 | 8.654 | 16.92 | C |
| ATOM | 1219 | CG | ARG | A1203 | 6.843 | 3.146 | 8.598 | 25.55 | C |
| ATOM | 1220 | CD | ARG | A1203 | 7.385 | 3.934 | 9.684 | 35.04 | C |
| ATOM | 1221 | NE | ARG | A1203 | 6.647 | 5.198 | 9.715 | 46.62 | N |
| ATOM | 1222 | CZ | ARG | A1203 | 7.231 | 6.397 | 9.8 | 50.6 | C |
| ATOM | 1223 | NH1 | ARG | A1203 | 6.485 | 7.493 | 9.835 | 51.11 | N |
| ATOM | 1224 | NH2 | ARG | A1203 | 8.569 | 6.492 | 9.91 | 52.32 | N |
| ATOM | 1225 | C | ARG | A1203 | 3.316 | 1.808 | 7.598 | 15.31 | C |
| ATOM | 1226 | O | ARG | A1203 | 2.804 | 1.194 | 8.459 | 16.7 | O |
| ATOM | 1227 | N | ASP | A1204 | 2.634 | 2.256 | 6.567 | 14.71 | N |
| ATOM | 1228 | CA | ASP | A1204 | 1.216 | 2.108 | 6.521 | 13.7 | C |
| ATOM | 1229 | CB | ASP | A1204 | 0.457 | 3.387 | 6.964 | 12.97 | C |
| ATOM | 1230 | CG | ASP | A1204 | −1.043 | 3.076 | 7.256 | 14.25 | C |
| ATOM | 1231 | OD1 | ASP | A1204 | −1.836 | 4.044 | 7.394 | 15.49 | O |
| ATOM | 1232 | OD2 | ASP | A1204 | −1.44 | 1.858 | 7.263 | 9.66 | O |
| ATOM | 1233 | C | ASP | A1204 | 0.774 | 1.643 | 5.141 | 12.88 | C |
| ATOM | 1234 | O | ASP | A1204 | −0.186 | 2.174 | 4.56 | 14.12 | O |
| ATOM | 1235 | N | LEU | A1205 | 1.478 | 0.646 | 4.609 | 11.34 | N |
| ATOM | 1236 | CA | LEU | A1205 | 1.112 | 0.108 | 3.321 | 8.79 | C |
| ATOM | 1237 | CB | LEU | A1205 | 2.258 | −0.744 | 2.749 | 8.43 | C |
| ATOM | 1238 | CG | LEU | A1205 | 1.935 | −1.463 | 1.458 | 10.04 | C |
| ATOM | 1239 | CD1 | LEU | A1205 | 1.684 | −0.398 | 0.27 | 13.53 | C |
| ATOM | 1240 | CD2 | LEU | A1205 | 3.076 | −2.419 | 1.125 | 13.6 | C |
| ATOM | 1241 | C | LEU | A1205 | −0.146 | −0.673 | 3.471 | 7.99 | C |
| ATOM | 1242 | O | LEU | A1205 | −0.17 | −1.624 | 4.263 | 8.8 | O |
| ATOM | 1243 | N | ALA | A1206 | −1.204 | −0.28 | 2.738 | 7.11 | N |
| ATOM | 1244 | CA | ALA | A1206 | −2.522 | −0.922 | 2.824 | 5.5 | C |
| ATOM | 1245 | CB | ALA | A1206 | −3.232 | −0.459 | 4.063 | 4.27 | C |
| ATOM | 1246 | C | ALA | A1206 | −3.265 | −0.446 | 1.584 | 6.81 | C |
| ATOM | 1247 | O | ALA | A1206 | −2.838 | 0.581 | 1.02 | 8.33 | O |
| ATOM | 1248 | N | ALA | A1207 | −4.313 | −1.167 | 1.132 | 5.92 | N |
| ATOM | 1249 | CA | ALA | A1207 | −5.061 | −0.819 | −0.065 | 6.86 | C |
| ATOM | 1250 | CB | ALA | A1207 | −6.198 | −1.931 | −0.465 | 6.56 | C |
| ATOM | 1251 | C | ALA | A1207 | −5.664 | 0.575 | −0.007 | 6.43 | C |
| ATOM | 1252 | O | ALA | A1207 | −5.717 | 1.282 | −0.997 | 7.31 | O |
| ATOM | 1253 | N | ARG | A1208 | −6.118 | 0.96 | 1.163 | 8.2 | N |
| ATOM | 1254 | CA | ARG | A1208 | −6.685 | 2.317 | 1.469 | 7.4 | C |
| ATOM | 1255 | CB | ARG | A1208 | −7.153 | 2.406 | 2.935 | 5.83 | C |
| ATOM | 1256 | CG | ARG | A1208 | −6.069 | 2.35 | 3.935 | 6.41 | C |
| ATOM | 1257 | CD | ARG | A1208 | −6.516 | 2.624 | 5.392 | 7.75 | C |
| ATOM | 1258 | NE | ARG | A1208 | −5.463 | 2.178 | 6.312 | 9.76 | N |
| ATOM | 1259 | CZ | ARG | A1208 | −5.268 | 0.92 | 6.703 | 10.11 | C |
| ATOM | 1260 | NH1 | ARG | A1208 | −6.079 | −0.022 | 6.275 | 11.92 | N |
| ATOM | 1261 | NH2 | ARG | A1208 | −4.249 | 0.595 | 7.505 | 10.73 | N |
| ATOM | 1262 | C | ARG | A1208 | −5.723 | 3.419 | 1.17 | 8.21 | C |
| ATOM | 1263 | O | ARG | A1208 | −6.139 | 4.544 | 0.915 | 9.68 | O |
| ATOM | 1264 | N | ASN | A1209 | −4.444 | 3.09 | 1.145 | 8.68 | N |
| ATOM | 1265 | CA | ASN | A1209 | −3.399 | 4.061 | 0.811 | 11.82 | C |
| ATOM | 1266 | CB | ASN | A1209 | −2.244 | 4.061 | 1.85 | 11.24 | C |
| ATOM | 1267 | CG | ASN | A1209 | −2.656 | 4.697 | 3.119 | 14.87 | C |
| ATOM | 1268 | OD1 | ASN | A1209 | −3.234 | 5.806 | 3.092 | 17.92 | O |
| ATOM | 1269 | ND2 | ASN | A1209 | −2.404 | 4.018 | 4.255 | 12.83 | N |
| ATOM | 1270 | C | ASN | A1209 | −2.83 | 3.996 | −0.638 | 11.91 | C |
| ATOM | 1271 | O | ASN | A1209 | −1.844 | 4.607 | −0.923 | 11.85 | O |
| ATOM | 1272 | N | CYS | A1210 | −3.491 | 3.295 | −1.537 | 12.5 | N |
| ATOM | 1273 | CA | CYS | A1210 | −3.014 | 3.254 | −2.893 | 12.98 | C |
| ATOM | 1274 | CB | CYS | A1210 | −2.797 | 1.789 | −3.34 | 14.54 | C |
| ATOM | 1275 | SG | CYS | A1210 | −1.63 | 0.848 | −2.296 | 12.02 | S |
| ATOM | 1276 | C | CYS | A1210 | −4.108 | 3.876 | −3.657 | 13.31 | C |
| ATOM | 1277 | O | CYS | A1210 | −5.28 | 3.55 | −3.418 | 13.93 | O |
| ATOM | 1278 | N | MET | A1211 | −3.749 | 4.745 | −4.594 | 13.69 | N |
| ATOM | 1279 | CA | MET | A1211 | −4.737 | 5.583 | −5.243 | 14.05 | C |
| ATOM | 1280 | CB | MET | A1211 | −4.318 | 7.044 | −5.221 | 13.18 | C |
| ATOM | 1281 | CG | MET | A1211 | −4.372 | 7.766 | −3.853 | 14.65 | C |
| ATOM | 1282 | SD | MET | A1211 | −6.007 | 7.72 | −3.108 | 19.96 | S |
| ATOM | 1283 | CE | MET | A1211 | −5.754 | 6.684 | −1.674 | 18.93 | C |
| ATOM | 1284 | C | MET | A1211 | −4.793 | 5.093 | −6.651 | 15.42 | C |
| ATOM | 1285 | O | MET | A1211 | −3.861 | 4.454 | −7.062 | 17.43 | O |
| ATOM | 1286 | N | LEU | A1212 | −5.844 | 5.432 | −7.405 | 15.97 | N |
| ATOM | 1287 | CA | LEU | A1212 | −6.055 | 4.901 | −8.741 | 16.16 | C |
| ATOM | 1288 | CB | LEU | A1212 | −7.151 | 3.801 | −8.617 | 16.56 | C |
| ATOM | 1289 | CG | LEU | A1212 | −7.139 | 2.614 | −9.573 | 17.65 | C |
| ATOM | 1290 | CD1 | LEU | A1212 | −5.859 | 1.949 | −9.639 | 23.51 | C |
| ATOM | 1291 | CD2 | LEU | A1212 | −8.148 | 1.645 | −9.272 | 19.13 | C |
| ATOM | 1292 | C | LEU | A1212 | −6.465 | 6.014 | −9.699 | 16.21 | C |
| ATOM | 1293 | O | LEU | A1212 | −7.471 | 6.687 | −9.487 | 14.42 | O |

TABLE 1A-continued

| | | | | | | | | |
|---|---|---|---|---|---|---|---|---|
| ATOM | 1294 | N | ASP | A1213 | −5.64 | 6.267 | −10.72 | 17.29 | N |
| ATOM | 1295 | CA | ASP | A1213 | −5.966 | 7.277 | −11.686 | 17.98 | C |
| ATOM | 1296 | CB | ASP | A1213 | −4.714 | 7.942 | −12.234 | 17.61 | C |
| ATOM | 1297 | CG | ASP | A1213 | −4.057 | 7.162 | −13.362 | 21.66 | C |
| ATOM | 1298 | OD1 | ASP | A1213 | −4.672 | 6.193 | −13.876 | 24.08 | O |
| ATOM | 1299 | OD2 | ASP | A1213 | −2.912 | 7.535 | −13.769 | 20.5 | O |
| ATOM | 1300 | C | ASP | A1213 | −6.965 | 6.79 | −12.774 | 20.22 | C |
| ATOM | 1301 | O | ASP | A1213 | −7.448 | 5.629 | −12.725 | 19.55 | O |
| ATOM | 1302 | N | GLU | A1214 | −7.314 | 7.705 | −13.703 | 21.62 | N |
| ATOM | 1303 | CA | GLU | A1214 | −8.236 | 7.449 | −14.83 | 23.37 | C |
| ATOM | 1304 | CB | GLU | A1214 | −8.604 | 8.755 | −15.616 | 23.66 | C |
| ATOM | 1305 | CG | GLU | A1214 | −7.572 | 9.41 | −16.542 | 26.65 | C |
| ATOM | 1306 | CD | GLU | A1214 | −6.209 | 9.664 | −15.865 | 35.32 | C |
| ATOM | 1307 | OE1 | GLU | A1214 | −5.163 | 9.62 | −16.55 | 34.94 | O |
| ATOM | 1308 | OE2 | GLU | A1214 | −6.161 | 9.901 | −14.619 | 42.76 | O |
| ATOM | 1309 | C | GLU | A1214 | −7.781 | 6.309 | −15.745 | 23.4 | C |
| ATOM | 1310 | O | GLU | A1214 | −8.61 | 5.643 | −16.379 | 24.55 | O |
| ATOM | 1311 | N | LYS | A1215 | −6.481 | 6.04 | −15.762 | 22.3 | N |
| ATOM | 1312 | CA | LYS | A1215 | −6.01 | 4.85 | −16.476 | 22.72 | C |
| ATOM | 1313 | CB | LYS | A1215 | −4.601 | 5.007 | −17.096 | 23.86 | C |
| ATOM | 1314 | CG | LYS | A1215 | −4.485 | 6.167 | −18.063 | 27.17 | C |
| ATOM | 1315 | CD | LYS | A1215 | −5.679 | 6.128 | −19.019 | 38.23 | C |
| ATOM | 1316 | CE | LYS | A1215 | −5.745 | 7.422 | −19.897 | 43.79 | C |
| ATOM | 1317 | NZ | LYS | A1215 | −7.201 | 7.763 | −20.262 | 43.62 | N |
| ATOM | 1318 | C | LYS | A1215 | −5.995 | 3.604 | −15.657 | 20.86 | C |
| ATOM | 1319 | O | LYS | A1215 | −5.58 | 2.607 | −16.183 | 20.64 | O |
| ATOM | 1320 | N | PHE | A1216 | −6.37 | 3.659 | −14.377 | 18.46 | N |
| ATOM | 1321 | CA | PHE | A1216 | −6.214 | 2.522 | −13.522 | 17.8 | C |
| ATOM | 1322 | CB | PHE | A1216 | −6.913 | 1.295 | −14.107 | 17.25 | C |
| ATOM | 1323 | CG | PHE | A1216 | −8.348 | 1.556 | −14.511 | 20.05 | C |
| ATOM | 1324 | CD1 | PHE | A1216 | −8.761 | 1.389 | −15.824 | 22.43 | C |
| ATOM | 1325 | CD2 | PHE | A1216 | −9.284 | 2.024 | −13.58 | 22.9 | C |
| ATOM | 1326 | CE1 | PHE | A1216 | −10.076 | 1.681 | −16.183 | 24.6 | C |
| ATOM | 1327 | CE2 | PHE | A1216 | −10.624 | 2.314 | −13.951 | 23.53 | C |
| ATOM | 1328 | CZ | PHE | A1216 | −11.008 | 2.147 | −15.237 | 22.85 | C |
| ATOM | 1329 | C | PHE | A1216 | −4.741 | 2.253 | −13.216 | 17.5 | C |
| ATOM | 1330 | O | PHE | A1216 | −4.304 | 1.15 | −13.082 | 18.14 | O |
| ATOM | 1331 | N | THR | A1217 | −3.957 | 3.298 | −13.18 | 17.79 | N |
| ATOM | 1332 | CA | THR | A1217 | −2.607 | 3.219 | −12.693 | 17.79 | C |
| ATOM | 1333 | CB | THR | A1217 | −1.804 | 4.287 | −13.327 | 18.38 | C |
| ATOM | 1334 | OG1 | THR | A1217 | −1.948 | 4.137 | −14.748 | 21.49 | O |
| ATOM | 1335 | CG2 | THR | A1217 | −0.354 | 4.224 | −12.873 | 13.71 | C |
| ATOM | 1336 | C | THR | A1217 | −2.699 | 3.462 | −11.183 | 17.99 | C |
| ATOM | 1337 | O | THR | A1217 | −3.245 | 4.477 | −10.67 | 16.42 | O |
| ATOM | 1338 | N | VAL | A1218 | −2.215 | 2.44 | −10.491 | 18.2 | N |
| ATOM | 1339 | CA | VAL | A1218 | −2.219 | 2.359 | −9.016 | 15.99 | C |
| ATOM | 1340 | CB | VAL | A1218 | −2.161 | 0.864 | −8.566 | 15.74 | C |
| ATOM | 1341 | CG1 | VAL | A1218 | −2.229 | 0.783 | −7.046 | 16.54 | C |
| ATOM | 1342 | CG2 | VAL | A1218 | −3.25 | 0.032 | −9.306 | 10.74 | C |
| ATOM | 1343 | C | VAL | A1218 | −0.991 | 3.132 | −8.554 | 14.73 | C |
| ATOM | 1344 | O | VAL | A1218 | 0.099 | 2.884 | −9.049 | 13.83 | O |
| ATOM | 1345 | N | LYS | A1219 | −1.17 | 4.075 | −7.639 | 14.58 | N |
| ATOM | 1346 | CA | LYS | A1219 | −0.015 | 4.811 | −7.058 | 13.67 | C |
| ATOM | 1347 | CB | LYS | A1219 | −0.099 | 6.274 | −7.451 | 15.2 | C |
| ATOM | 1348 | CG | LYS | A1219 | −0.59 | 6.535 | −8.83 | 12.87 | C |
| ATOM | 1349 | CD | LYS | A1219 | 0.553 | 7.063 | −9.626 | 17.61 | C |
| ATOM | 1350 | CE | LYS | A1219 | 0.129 | 8.243 | −10.531 | 17.38 | C |
| ATOM | 1351 | NZ | LYS | A1219 | 0.955 | 8.178 | −11.791 | 20.39 | N |
| ATOM | 1352 | C | LYS | A1219 | 0.04 | 4.726 | −5.535 | 12.93 | C |
| ATOM | 1353 | O | LYS | A1219 | −0.889 | 5.08 | −4.853 | 12.69 | O |
| ATOM | 1354 | N | VAL | A1220 | 1.133 | 4.22 | −5.006 | 13.18 | N |
| ATOM | 1355 | CA | VAL | A1220 | 1.295 | 4.11 | −3.584 | 14.16 | C |
| ATOM | 1356 | CB | VAL | A1220 | 2.612 | 3.296 | −3.195 | 15.1 | C |
| ATOM | 1357 | CG1 | VAL | A1220 | 2.647 | 2.973 | −1.626 | 10.24 | C |
| ATOM | 1358 | CG2 | VAL | A1220 | 2.803 | 2.046 | −4.12 | 13.42 | C |
| ATOM | 1359 | C | VAL | A1220 | 1.368 | 5.516 | −2.973 | 13.35 | C |
| ATOM | 1360 | O | VAL | A1220 | 2.135 | 6.359 | −3.443 | 12.9 | O |
| ATOM | 1361 | N | ALA | A1221 | 0.59 | 5.731 | −1.934 | 13.13 | N |
| ATOM | 1362 | CA | ALA | A1221 | 0.477 | 7.015 | −1.251 | 15.47 | C |
| ATOM | 1363 | CB | ALA | A1221 | −0.897 | 7.657 | −1.458 | 14.33 | C |
| ATOM | 1364 | C | ALA | A1221 | 0.767 | 6.868 | 0.204 | 17.59 | C |
| ATOM | 1365 | O | ALA | A1221 | 0.471 | 5.839 | 0.824 | 17.38 | O |
| ATOM | 1366 | N | ASP | A1222 | 1.379 | 7.919 | 0.731 | 22.48 | N |
| ATOM | 1367 | CA | ASP | A1222 | 1.684 | 8.106 | 2.149 | 25.6 | C |
| ATOM | 1368 | CB | ASP | A1222 | 3.192 | 8.125 | 2.428 | 27.07 | C |
| ATOM | 1369 | CG | ASP | A1222 | 3.493 | 8.453 | 3.94 | 32.14 | C |
| ATOM | 1370 | OD1 | ASP | A1222 | 2.699 | 7.951 | 4.822 | 33.77 | O |
| ATOM | 1371 | OD2 | ASP | A1222 | 4.486 | 9.212 | 4.217 | 33.87 | O |
| ATOM | 1372 | C | ASP | A1222 | 1.168 | 9.469 | 2.525 | 26.89 | C |
| ATOM | 1373 | O | ASP | A1222 | 1.8 | 10.507 | 2.234 | 27.25 | O |

TABLE 1A-continued

| | | | | | | | | |
|---|---|---|---|---|---|---|---|---|
| ATOM | 1374 | N | PHE | A1223 | 0.002 | 9.486 | 3.138 | 28.9 | N |
| ATOM | 1375 | CA | PHE | A1223 | −0.585 | 10.751 | 3.509 | 29.85 | C |
| ATOM | 1376 | CB | PHE | A1223 | −2.098 | 10.611 | 3.545 | 29.09 | C |
| ATOM | 1377 | CG | PHE | A1223 | −2.653 | 10.334 | 2.195 | 27.66 | C |
| ATOM | 1378 | CD1 | PHE | A1223 | −2.643 | 11.317 | 1.22 | 26.86 | C |
| ATOM | 1379 | CD2 | PHE | A1223 | −3.137 | 9.056 | 1.86 | 30.65 | C |
| ATOM | 1380 | CE1 | PHE | A1223 | −3.089 | 11.039 | −0.071 | 24.73 | C |
| ATOM | 1381 | CE2 | PHE | A1223 | −3.645 | 8.786 | 0.589 | 25.98 | C |
| ATOM | 1382 | CZ | PHE | A1223 | −3.582 | 9.774 | −0.378 | 26.39 | C |
| ATOM | 1383 | C | PHE | A1223 | 0.116 | 11.46 | 4.721 | 31.22 | C |
| ATOM | 1384 | O | PHE | A1223 | 0.264 | 12.703 | 4.723 | 29.93 | O |
| ATOM | 1385 | N | GLY | A1224 | 0.646 | 10.652 | 5.659 | 32.26 | N |
| ATOM | 1386 | CA | GLY | A1224 | 1.429 | 11.172 | 6.793 | 32.77 | C |
| ATOM | 1387 | C | GLY | A1224 | 1.115 | 12.632 | 7.186 | 32.9 | C |
| ATOM | 1388 | O | GLY | A1224 | 1.627 | 13.595 | 6.547 | 34.83 | O |
| ATOM | 1389 | N | LEU | A1225 | 0.298 | 12.814 | 8.224 | 30.34 | N |
| ATOM | 1390 | CA | LEU | A1225 | −0.024 | 14.15 | 8.732 | 28.57 | C |
| ATOM | 1391 | CB | LEU | A1225 | 1.211 | 15.102 | 8.77 | 29.79 | C |
| ATOM | 1392 | CG | LEU | A1225 | 1.929 | 15.448 | 10.104 | 30.95 | C |
| ATOM | 1393 | CD1 | LEU | A1225 | 3.437 | 15.355 | 10.005 | 34.31 | C |
| ATOM | 1394 | CD2 | LEU | A1225 | 1.597 | 16.811 | 10.571 | 30.73 | C |
| ATOM | 1395 | C | LEU | A1225 | −1.205 | 14.74 | 7.982 | 25.9 | C |
| ATOM | 1396 | O | LEU | A1225 | −1.955 | 15.535 | 8.544 | 24.79 | O |
| ATOM | 1397 | N | ALA | A1226 | −1.367 | 14.336 | 6.721 | 24.64 | N |
| ATOM | 1398 | CA | ALA | A1226 | −2.529 | 14.746 | 5.877 | 23.24 | C |
| ATOM | 1399 | CB | ALA | A1226 | −2.28 | 14.5 | 4.418 | 22.44 | C |
| ATOM | 1400 | C | ALA | A1226 | −3.874 | 14.179 | 6.293 | 22.93 | C |
| ATOM | 1401 | O | ALA | A1226 | −4.884 | 14.705 | 5.881 | 25.88 | O |
| ATOM | 1402 | N | ARG | A1227 | −3.899 | 13.13 | 7.111 | 21.9 | N |
| ATOM | 1403 | CA | ARG | A1227 | −5.103 | 12.644 | 7.801 | 20.66 | C |
| ATOM | 1404 | CB | ARG | A1227 | −5.072 | 11.105 | 8.016 | 20.71 | C |
| ATOM | 1405 | CG | ARG | A1227 | −4.785 | 10.271 | 6.78 | 21.21 | C |
| ATOM | 1406 | CD | ARG | A1227 | −4.87 | 8.73 | 7.056 | 25.36 | C |
| ATOM | 1407 | NE | ARG | A1227 | −4.892 | 7.917 | 5.827 | 26.96 | N |
| ATOM | 1408 | CZ | ARG | A1227 | −5.974 | 7.695 | 5.082 | 27.88 | C |
| ATOM | 1409 | NH1 | ARG | A1227 | −7.16 | 8.212 | 5.416 | 26.34 | N |
| ATOM | 1410 | NH2 | ARG | A1227 | −5.871 | 6.976 | 3.966 | 28.15 | N |
| ATOM | 1411 | C | ARG | A1227 | −5.291 | 13.342 | 9.152 | 18.83 | C |
| ATOM | 1412 | O | ARG | A1227 | −4.498 | 13.203 | 10.087 | 17.34 | O |
| ATOM | 1413 | N | ASP | A1228 | −6.334 | 14.138 | 9.243 | 18.68 | N |
| ATOM | 1414 | CA | ASP | A1228 | −6.686 | 14.721 | 10.519 | 18.91 | C |
| ATOM | 1415 | CB | ASP | A1228 | −7.921 | 15.575 | 10.374 | 17.57 | C |
| ATOM | 1416 | CG | ASP | A1228 | −7.668 | 16.824 | 9.579 | 19.31 | C |
| ATOM | 1417 | OD1 | ASP | A1228 | −6.496 | 17.218 | 9.34 | 19.72 | O |
| ATOM | 1418 | OD2 | ASP | A1228 | −8.671 | 17.429 | 9.178 | 20.69 | O |
| ATOM | 1419 | C | ASP | A1228 | −6.912 | 13.643 | 11.584 | 19.75 | C |
| ATOM | 1420 | O | ASP | A1228 | −6.289 | 13.678 | 12.62 | 19.14 | O |
| ATOM | 1421 | N | MET | A1229 | −7.813 | 12.698 | 11.298 | 21.88 | N |
| ATOM | 1422 | CA | MET | A1229 | −8.063 | 11.56 | 12.135 | 25.64 | C |
| ATOM | 1423 | CB | MET | A1229 | −9.439 | 11.661 | 12.693 | 24.99 | C |
| ATOM | 1424 | CG | MET | A1229 | −9.704 | 12.994 | 13.452 | 30.42 | C |
| ATOM | 1425 | SD | MET | A1229 | −11.278 | 12.878 | 14.395 | 36.16 | S |
| ATOM | 1426 | CE | MET | A1229 | −12.571 | 12.228 | 13.252 | 35.24 | C |
| ATOM | 1427 | C | MET | A1229 | −7.998 | 10.279 | 11.382 | 24.56 | C |
| ATOM | 1428 | O | MET | A1229 | −8.016 | 10.252 | 10.174 | 24.7 | O |
| ATOM | 1429 | N | TYR | A1230 | −7.966 | 9.201 | 12.145 | 26.77 | N |
| ATOM | 1430 | CA | TYR | A1230 | −7.921 | 7.806 | 11.669 | 26.42 | C |
| ATOM | 1431 | CB | TYR | A1230 | −6.702 | 7.141 | 12.275 | 27.51 | C |
| ATOM | 1432 | CG | TYR | A1230 | −5.446 | 7.784 | 11.808 | 28.23 | C |
| ATOM | 1433 | CD1 | TYR | A1230 | −5.082 | 9.065 | 12.25 | 29.43 | C |
| ATOM | 1434 | CE1 | TYR | A1230 | −3.974 | 9.693 | 11.788 | 28.12 | C |
| ATOM | 1435 | CD2 | TYR | A1230 | −4.679 | 7.176 | 10.867 | 28.14 | C |
| ATOM | 1436 | CE2 | TYR | A1230 | −3.527 | 7.772 | 10.422 | 32.14 | C |
| ATOM | 1437 | CZ | TYR | A1230 | −3.187 | 9.036 | 10.871 | 30.68 | C |
| ATOM | 1438 | OH | TYR | A1230 | −2.021 | 9.609 | 10.379 | 32.92 | O |
| ATOM | 1439 | C | TYR | A1230 | −9.133 | 7.062 | 12.158 | 27.27 | C |
| ATOM | 1440 | O | TYR | A1230 | −9.575 | 7.242 | 13.318 | 28.05 | O |
| ATOM | 1441 | N | ASP | A1231 | −9.672 | 6.224 | 11.281 | 27.51 | N |
| ATOM | 1442 | CA | ASP | A1231 | −10.722 | 5.291 | 11.618 | 27.33 | C |
| ATOM | 1443 | CB | ASP | A1231 | −11.113 | 4.53 | 10.355 | 28.35 | C |
| ATOM | 1444 | CG | ASP | A1231 | −12.533 | 3.939 | 10.428 | 30.8 | C |
| ATOM | 1445 | OD1 | ASP | A1231 | −12.904 | 3.368 | 11.506 | 27.15 | O |
| ATOM | 1446 | OD2 | ASP | A1231 | −13.254 | 4.051 | 9.374 | 32.11 | O |
| ATOM | 1447 | C | ASP | A1231 | −10.189 | 4.316 | 12.672 | 26.73 | C |
| ATOM | 1448 | O | ASP | A1231 | −9.124 | 3.73 | 12.492 | 26.31 | O |
| ATOM | 1449 | N | LYS | A1232 | −10.921 | 4.162 | 13.772 | 26.23 | N |
| ATOM | 1450 | CA | LYS | A1232 | −10.512 | 3.29 | 14.858 | 26.77 | C |
| ATOM | 1451 | CB | LYS | A1232 | −11.386 | 3.552 | 16.076 | 27.66 | C |
| ATOM | 1452 | CG | LYS | A1232 | −12.866 | 3.335 | 15.895 | 29.64 | C |
| ATOM | 1453 | CD | LYS | A1232 | −13.584 | 3.778 | 17.234 | 33.88 | C |

TABLE 1A-continued

| | | | | | | | | |
|---|---|---|---|---|---|---|---|---|
| ATOM | 1454 | CE | LYS | A1232 | −15.158 | 3.919 | 17.075 | 37.98 | C |
| ATOM | 1455 | NZ | LYS | A1232 | −15.727 | 5.229 | 17.684 | 37.47 | N |
| ATOM | 1456 | C | LYS | A1232 | −10.572 | 1.803 | 14.483 | 26.25 | C |
| ATOM | 1457 | O | LYS | A1232 | −10.143 | 0.931 | 15.234 | 25.01 | O |
| ATOM | 1458 | N | GLU | A1233 | −11.11 | 1.547 | 13.299 | 25.77 | N |
| ATOM | 1459 | CA | GLU | A1233 | −11.279 | 0.232 | 12.787 | 25.68 | C |
| ATOM | 1460 | CB | GLU | A1233 | −12.34 | 0.277 | 11.688 | 26.68 | C |
| ATOM | 1461 | CG | GLU | A1233 | −13.789 | −0.168 | 12.099 | 33.83 | C |
| ATOM | 1462 | CD | GLU | A1233 | −14.499 | 0.709 | 13.208 | 42.96 | C |
| ATOM | 1463 | OE1 | GLU | A1233 | −14.86 | 0.117 | 14.302 | 42.59 | O |
| ATOM | 1464 | OE2 | GLU | A1233 | −14.717 | 1.954 | 12.977 | 42.71 | O |
| ATOM | 1465 | C | GLU | A1233 | −9.963 | −0.242 | 12.227 | 24.54 | C |
| ATOM | 1466 | O | GLU | A1233 | −9.769 | −1.414 | 12.19 | 24.6 | O |
| ATOM | 1467 | N | TYR | A1234 | −9.048 | 0.655 | 11.801 | 23.56 | N |
| ATOM | 1468 | CA | TYR | A1234 | −7.777 | 0.205 | 11.19 | 22.08 | C |
| ATOM | 1469 | CB | TYR | A1234 | −7.554 | 0.688 | 9.75 | 24.83 | C |
| ATOM | 1470 | CG | TYR | A1234 | −8.779 | 0.596 | 8.908 | 27.05 | C |
| ATOM | 1471 | CD1 | TYR | A1234 | −9.405 | 1.764 | 8.447 | 32.67 | C |
| ATOM | 1472 | CE1 | TYR | A1234 | −10.59 | 1.71 | 7.702 | 34.74 | C |
| ATOM | 1473 | CD2 | TYR | A1234 | −9.363 | −0.637 | 8.628 | 28.02 | C |
| ATOM | 1474 | CE2 | TYR | A1234 | −10.562 | −0.729 | 7.895 | 30.43 | C |
| ATOM | 1475 | CZ | TYR | A1234 | −11.173 | 0.445 | 7.448 | 33.92 | C |
| ATOM | 1476 | OH | TYR | A1234 | −12.348 | 0.376 | 6.709 | 35.91 | O |
| ATOM | 1477 | C | TYR | A1234 | −6.604 | 0.532 | 12.054 | 19.79 | C |
| ATOM | 1478 | O | TYR | A1234 | −5.57 | −0.125 | 11.991 | 19.58 | O |
| ATOM | 1479 | N | TYR | A1235 | −6.787 | 1.532 | 12.906 | 17.81 | N |
| ATOM | 1480 | CA | TYR | A1235 | −5.682 | 1.997 | 13.724 | 14.18 | C |
| ATOM | 1481 | CB | TYR | A1235 | −5.331 | 3.388 | 13.366 | 13.99 | C |
| ATOM | 1482 | CG | TYR | A1235 | −5.008 | 3.583 | 11.916 | 12.91 | C |
| ATOM | 1483 | CD1 | TYR | A1235 | −3.681 | 3.405 | 11.449 | 8.54 | C |
| ATOM | 1484 | CE1 | TYR | A1235 | −3.357 | 3.532 | 10.153 | 6.16 | C |
| ATOM | 1485 | CD2 | TYR | A1235 | −6.053 | 3.895 | 10.984 | 12.53 | C |
| ATOM | 1486 | CE2 | TYR | A1235 | −5.743 | 4.111 | 9.651 | 14.2 | C |
| ATOM | 1487 | CZ | TYR | A1235 | −4.38 | 3.917 | 9.229 | 14.55 | C |
| ATOM | 1488 | OH | TYR | A1235 | −4.077 | 4.129 | 7.868 | 15.24 | O |
| ATOM | 1489 | C | TYR | A1235 | −5.972 | 1.952 | 15.171 | 13.04 | C |
| ATOM | 1490 | O | TYR | A1235 | −7.039 | 2.27 | 15.597 | 12.41 | O |
| ATOM | 1491 | N | SER | A1236 | −4.999 | 1.454 | 15.887 | 12.87 | N |
| ATOM | 1492 | CA | SER | A1236 | −4.921 | 1.538 | 17.288 | 13.9 | C |
| ATOM | 1493 | CB | SER | A1236 | −4.209 | 0.295 | 17.817 | 13.75 | C |
| ATOM | 1494 | OG | SER | A1236 | −5.074 | −0.828 | 17.649 | 14.05 | O |
| ATOM | 1495 | C | SER | A1236 | −4.083 | 2.768 | 17.579 | 15.02 | C |
| ATOM | 1496 | O | SER | A1236 | −3.273 | 3.238 | 16.72 | 13.02 | O |
| ATOM | 1497 | N | VAL | A1237 | −4.271 | 3.257 | 18.8 | 15.2 | N |
| ATOM | 1498 | CA | VAL | A1237 | −3.669 | 4.477 | 19.233 | 15.62 | C |
| ATOM | 1499 | CB | VAL | A1237 | −4.713 | 5.574 | 19.68 | 16.92 | C |
| ATOM | 1500 | CG1 | VAL | A1237 | −3.991 | 6.947 | 19.977 | 14.81 | C |
| ATOM | 1501 | CG2 | VAL | A1237 | −5.918 | 5.75 | 18.643 | 14.15 | C |
| ATOM | 1502 | C | VAL | A1237 | −2.757 | 4.186 | 20.391 | 17.2 | C |
| ATOM | 1503 | O | VAL | A1237 | −3.164 | 3.555 | 21.401 | 17.99 | O |
| ATOM | 1504 | N | HIS | A1238 | −1.532 | 4.675 | 20.285 | 16.58 | N |
| ATOM | 1505 | CA | HIS | A1238 | −0.63 | 4.538 | 21.372 | 16.6 | C |
| ATOM | 1506 | CB | HIS | A1238 | 0.79 | 4.641 | 20.897 | 14.86 | C |
| ATOM | 1507 | CG | HIS | A1238 | 1.781 | 4.197 | 21.91 | 18.5 | C |
| ATOM | 1508 | CD2 | HIS | A1238 | 2.607 | 3.122 | 21.943 | 22.35 | C |
| ATOM | 1509 | ND1 | HIS | A1238 | 2.023 | 4.899 | 23.075 | 21.05 | N |
| ATOM | 1510 | CE1 | HIS | A1238 | 2.961 | 4.28 | 23.78 | 23.43 | C |
| ATOM | 1511 | NE2 | HIS | A1238 | 3.336 | 3.197 | 23.116 | 23.63 | N |
| ATOM | 1512 | C | HIS | A1238 | −0.941 | 5.544 | 22.475 | 17.59 | C |
| ATOM | 1513 | O | HIS | A1238 | −0.965 | 6.753 | 22.219 | 16.29 | O |
| ATOM | 1514 | N | ASN | A1239 | −1.161 | 5.013 | 23.705 | 19.38 | N |
| ATOM | 1515 | CA | ASN | A1239 | −1.566 | 5.784 | 24.887 | 20.91 | C |
| ATOM | 1516 | CB | ASN | A1239 | −1.67 | 4.904 | 26.147 | 19.93 | C |
| ATOM | 1517 | CG | ASN | A1239 | −2.929 | 4.038 | 26.166 | 18.41 | C |
| ATOM | 1518 | OD1 | ASN | A1239 | −2.947 | 2.919 | 26.751 | 13.41 | O |
| ATOM | 1519 | ND2 | ASN | A1239 | −3.987 | 4.536 | 25.513 | 13.83 | N |
| ATOM | 1520 | C | ASN | A1239 | −0.63 | 6.964 | 25.164 | 23.6 | C |
| ATOM | 1521 | O | ASN | A1239 | −1.11 | 8.123 | 25.292 | 24.04 | O |
| ATOM | 1522 | N | LYS | A1240 | 0.679 | 6.679 | 25.225 | 25.19 | N |
| ATOM | 1523 | CA | LYS | A1240 | 1.674 | 7.662 | 25.602 | 27.16 | C |
| ATOM | 1524 | CB | LYS | A1240 | 2.949 | 6.948 | 25.947 | 27.24 | C |
| ATOM | 1525 | CG | LYS | A1240 | 2.753 | 5.852 | 27.025 | 31.39 | C |
| ATOM | 1526 | CD | LYS | A1240 | 2.092 | 6.44 | 28.311 | 33.31 | C |
| ATOM | 1527 | CE | LYS | A1240 | 1.02 | 5.512 | 28.908 | 35.74 | C |
| ATOM | 1528 | NZ | LYS | A1240 | 0.389 | 6.132 | 30.138 | 33.11 | N |
| ATOM | 1529 | C | LYS | A1240 | 1.924 | 8.663 | 24.477 | 29.32 | C |
| ATOM | 1530 | O | LYS | A1240 | 1.67 | 9.871 | 24.627 | 30.53 | O |
| ATOM | 1531 | N | THR | A1241 | 2.43 | 8.188 | 23.337 | 29.79 | N |
| ATOM | 1532 | CA | THR | A1241 | 2.509 | 9.073 | 22.222 | 29.89 | C |
| ATOM | 1533 | CB | THR | A1241 | 3.467 | 8.616 | 21.201 | 30.25 | C |

TABLE 1A-continued

| ATOM | 1534 | OG1 | THR | A1241 | 3.185 | 9.403 | 20.037 | 33.35 | O |
|---|---|---|---|---|---|---|---|---|---|
| ATOM | 1535 | CG2 | THR | A1241 | 3.344 | 7.112 | 20.901 | 28.34 | C |
| ATOM | 1536 | C | THR | A1241 | 1.096 | 9.212 | 21.643 | 30.22 | C |
| ATOM | 1537 | O | THR | A1241 | 0.134 | 9.339 | 22.39 | 32.12 | O |
| ATOM | 1538 | N | GLY | A1242 | 0.921 | 9.192 | 20.345 | 27.97 | N |
| ATOM | 1539 | CA | GLY | A1242 | −0.442 | 9.02 | 19.841 | 25.59 | C |
| ATOM | 1540 | C | GLY | A1242 | −0.261 | 8.357 | 18.492 | 23.61 | C |
| ATOM | 1541 | O | GLY | A1242 | −1.07 | 8.496 | 17.614 | 23.73 | O |
| ATOM | 1542 | N | ALA | A1243 | 0.859 | 7.673 | 18.364 | 22.33 | N |
| ATOM | 1543 | CA | ALA | A1243 | 1.246 | 6.956 | 17.18 | 21.48 | C |
| ATOM | 1544 | CB | ALA | A1243 | 2.497 | 6.121 | 17.461 | 19.16 | C |
| ATOM | 1545 | C | ALA | A1243 | 0.044 | 6.081 | 16.798 | 20.06 | C |
| ATOM | 1546 | O | ALA | A1243 | −0.532 | 5.452 | 17.648 | 18.79 | O |
| ATOM | 1547 | N | LYS | A1244 | −0.377 | 6.218 | 15.54 | 19.98 | N |
| ATOM | 1548 | CA | LYS | A1244 | −1.313 | 5.355 | 14.829 | 20.6 | C |
| ATOM | 1549 | CB | LYS | A1244 | −1.695 | 5.942 | 13.468 | 21.8 | C |
| ATOM | 1550 | CG | LYS | A1244 | −2.614 | 7.095 | 13.557 | 24.9 | C |
| ATOM | 1551 | CD | LYS | A1244 | −2.3 | 7.965 | 14.744 | 29.39 | C |
| ATOM | 1552 | CE | LYS | A1244 | −3.596 | 8.051 | 15.56 | 37.57 | C |
| ATOM | 1553 | NZ | LYS | A1244 | −4.284 | 6.676 | 15.714 | 36.7 | N |
| ATOM | 1554 | C | LYS | A1244 | −0.646 | 4.085 | 14.508 | 19.2 | C |
| ATOM | 1555 | O | LYS | A1244 | 0.49 | 4.124 | 14.123 | 19.11 | O |
| ATOM | 1556 | N | LEU | A1245 | −1.368 | 2.966 | 14.627 | 18.63 | N |
| ATOM | 1557 | CA | LEU | A1245 | −0.791 | 1.644 | 14.347 | 17.18 | C |
| ATOM | 1558 | CB | LEU | A1245 | −0.369 | 0.954 | 15.664 | 16.59 | C |
| ATOM | 1559 | CG | LEU | A1245 | 0.56 | 1.802 | 16.567 | 19.65 | C |
| ATOM | 1560 | CD1 | LEU | A1245 | 0.157 | 1.66 | 18.01 | 17.13 | C |
| ATOM | 1561 | CD2 | LEU | A1245 | 2.037 | 1.413 | 16.357 | 21.7 | C |
| ATOM | 1562 | C | LEU | A1245 | −1.757 | 0.774 | 13.587 | 14.78 | C |
| ATOM | 1563 | O | LEU | A1245 | −2.652 | 0.238 | 14.189 | 15 | O |
| ATOM | 1564 | N | PRO | A1246 | −1.545 | 0.587 | 12.279 | 13.51 | N |
| ATOM | 1565 | CD | PRO | A1246 | −0.403 | 1.159 | 11.572 | 14.89 | C |
| ATOM | 1566 | CA | PRO | A1246 | −2.353 | −0.239 | 11.366 | 13.3 | C |
| ATOM | 1567 | CB | PRO | A1246 | −1.767 | 0.072 | 9.956 | 12.09 | C |
| ATOM | 1568 | CG | PRO | A1246 | −0.694 | 0.867 | 10.104 | 11.81 | C |
| ATOM | 1569 | C | PRO | A1246 | −2.172 | −1.735 | 11.687 | 13.12 | C |
| ATOM | 1570 | O | PRO | A1246 | −1.721 | −2.584 | 10.83 | 12.05 | O |
| ATOM | 1571 | N | VAL | A1247 | −2.472 | −2.017 | 12.935 | 11.59 | N |
| ATOM | 1572 | CA | VAL | A1247 | −2.334 | −3.363 | 13.565 | 12.32 | C |
| ATOM | 1573 | CB | VAL | A1247 | −3.255 | −3.391 | 14.805 | 10.84 | C |
| ATOM | 1574 | CG1 | VAL | A1247 | −3.524 | −4.818 | 15.249 | 15.86 | C |
| ATOM | 1575 | CG2 | VAL | A1247 | −2.617 | −2.612 | 15.917 | 6.8 | C |
| ATOM | 1576 | C | VAL | A1247 | −2.446 | −4.663 | 12.667 | 11.2 | C |
| ATOM | 1577 | O | VAL | A1247 | −1.546 | −5.488 | 12.665 | 11.23 | O |
| ATOM | 1578 | N | LYS | A1248 | −3.525 | −4.804 | 11.918 | 10.8 | N |
| ATOM | 1579 | CA | LYS | A1248 | −3.743 | −5.957 | 11.027 | 12.03 | C |
| ATOM | 1580 | CB | LYS | A1248 | −5.177 | −5.964 | 10.572 | 13.05 | C |
| ATOM | 1581 | CG | LYS | A1248 | −6.152 | −5.331 | 11.58 | 19.76 | C |
| ATOM | 1582 | CD | LYS | A1248 | −7.062 | −6.387 | 12.249 | 23.58 | C |
| ATOM | 1583 | CE | LYS | A1248 | −8.534 | −5.932 | 12.134 | 30.55 | C |
| ATOM | 1584 | NZ | LYS | A1248 | −9.463 | −6.69 | 13.084 | 34.02 | N |
| ATOM | 1585 | C | LYS | A1248 | −2.883 | −6.023 | 9.745 | 10.65 | C |
| ATOM | 1586 | O | LYS | A1248 | −2.959 | −6.994 | 8.999 | 9.86 | O |
| ATOM | 1587 | N | TRP | A1249 | −2.086 | −4.981 | 9.491 | 10.31 | N |
| ATOM | 1588 | CA | TRP | A1249 | −1.18 | −4.913 | 8.351 | 8.47 | C |
| ATOM | 1589 | CB | TRP | A1249 | −1.359 | −3.605 | 7.607 | 8.12 | C |
| ATOM | 1590 | CG | TRP | A1249 | −2.504 | −3.633 | 6.747 | 7.42 | C |
| ATOM | 1591 | CD2 | TRP | A1249 | −3.871 | −3.47 | 7.156 | 5.46 | C |
| ATOM | 1592 | CE2 | TRP | A1249 | −4.665 | −3.607 | 5.983 | 5.77 | C |
| ATOM | 1593 | CE3 | TRP | A1249 | −4.494 | −3.162 | 8.381 | 6 | C |
| ATOM | 1594 | CD1 | TRP | A1249 | −2.526 | −3.943 | 5.372 | 4.82 | C |
| ATOM | 1595 | NE1 | TRP | A1249 | −3.811 | −3.91 | 4.929 | 5.43 | N |
| ATOM | 1596 | CZ2 | TRP | A1249 | −6.098 | −3.459 | 6.001 | 6.63 | C |
| ATOM | 1597 | CZ3 | TRP | A1249 | −5.928 | −2.947 | 8.392 | 4.82 | C |
| ATOM | 1598 | CH2 | TRP | A1249 | −6.698 | −3.109 | 7.2 | 7.88 | C |
| ATOM | 1599 | C | TRP | A1249 | 0.225 | −5.008 | 8.863 | 8.81 | C |
| ATOM | 1600 | O | TRP | A1249 | 1.186 | −5.191 | 8.069 | 8.2 | O |
| ATOM | 1601 | N | MET | A1250 | 0.346 | −4.956 | 10.201 | 9.07 | N |
| ATOM | 1602 | CA | MET | A1250 | 1.668 | −4.953 | 10.821 | 10.3 | C |
| ATOM | 1603 | CB | MET | A1250 | 1.62 | −4.238 | 12.155 | 8.96 | C |
| ATOM | 1604 | CG | MET | A1250 | 1.667 | −2.721 | 12.005 | 10.76 | C |
| ATOM | 1605 | SD | MET | A1250 | 1.131 | −1.902 | 13.583 | 11.56 | S |
| ATOM | 1606 | CE | MET | A1250 | 2.534 | −2.069 | 14.536 | 12.6 | C |
| ATOM | 1607 | C | MET | A1250 | 2.295 | −6.361 | 10.962 | 12.06 | C |
| ATOM | 1608 | O | MET | A1250 | 1.611 | −7.327 | 11.333 | 11.13 | O |
| ATOM | 1609 | N | ALA | A1251 | 3.614 | −6.434 | 10.703 | 13.83 | N |
| ATOM | 1610 | CA | ALA | A1251 | 4.46 | −7.603 | 11.026 | 14.52 | C |
| ATOM | 1611 | CB | ALA | A1251 | 5.94 | −7.409 | 10.539 | 11.9 | C |
| ATOM | 1612 | C | ALA | A1251 | 4.402 | −7.944 | 12.522 | 16.24 | C |
| ATOM | 1613 | O | ALA | A1251 | 4.346 | −7.052 | 13.376 | 16.66 | O |

TABLE 1A-continued

| | | | | | | | | |
|---|---|---|---|---|---|---|---|---|
| ATOM | 1614 | N | LEU | A1252 | 4.438 | −9.232 | 12.86 | 18.73 | N |
| ATOM | 1615 | CA | LEU | A1252 | 4.276 | −9.537 | 14.27 | 21.52 | C |
| ATOM | 1616 | CB | LEU | A1252 | 3.851 | −10.996 | 14.594 | 21.72 | C |
| ATOM | 1617 | CG | LEU | A1252 | 4.851 | −12.116 | 14.433 | 23.21 | C |
| ATOM | 1618 | CD1 | LEU | A1252 | 5.321 | −12.497 | 15.742 | 28.6 | C |
| ATOM | 1619 | CD2 | LEU | A1252 | 4.261 | −13.324 | 13.792 | 24.47 | C |
| ATOM | 1620 | C | LEU | A1252 | 5.478 | −9.077 | 15.042 | 21.57 | C |
| ATOM | 1621 | O | LEU | A1252 | 5.406 | −8.936 | 16.224 | 23.8 | O |
| ATOM | 1622 | N | GLU | A1253 | 6.569 | −8.764 | 14.386 | 22.36 | N |
| ATOM | 1623 | CA | GLU | A1253 | 7.621 | −8.143 | 15.118 | 23.04 | C |
| ATOM | 1624 | CB | GLU | A1253 | 9.001 | −8.442 | 14.545 | 22.64 | C |
| ATOM | 1625 | CG | GLU | A1253 | 9.349 | −7.787 | 13.254 | 25.77 | C |
| ATOM | 1626 | CD | GLU | A1253 | 8.924 | −8.608 | 12.003 | 31.65 | C |
| ATOM | 1627 | OE1 | GLU | A1253 | 8.158 | −9.631 | 12.111 | 30.46 | O |
| ATOM | 1628 | OE2 | GLU | A1253 | 9.38 | −8.206 | 10.895 | 34.18 | O |
| ATOM | 1629 | C | GLU | A1253 | 7.37 | −6.682 | 15.304 | 24.06 | C |
| ATOM | 1630 | O | GLU | A1253 | 7.937 | −6.101 | 16.209 | 25.96 | O |
| ATOM | 1631 | N | SER | A1254 | 6.544 | −6.048 | 14.464 | 25.72 | N |
| ATOM | 1632 | CA | SER | A1254 | 6.234 | −4.615 | 14.679 | 26.4 | C |
| ATOM | 1633 | CB | SER | A1254 | 5.766 | −3.88 | 13.427 | 25.25 | C |
| ATOM | 1634 | OG | SER | A1254 | 6.77 | −3.938 | 12.44 | 25.06 | O |
| ATOM | 1635 | C | SER | A1254 | 5.177 | −4.542 | 15.769 | 27.38 | C |
| ATOM | 1636 | O | SER | A1254 | 5.149 | −3.604 | 16.568 | 26.76 | O |
| ATOM | 1637 | N | LEU | A1255 | 4.311 | −5.555 | 15.81 | 28.96 | N |
| ATOM | 1638 | CA | LEU | A1255 | 3.313 | −5.671 | 16.904 | 30.09 | C |
| ATOM | 1639 | CB | LEU | A1255 | 2.445 | −6.892 | 16.682 | 28.19 | C |
| ATOM | 1640 | CG | LEU | A1255 | 1.457 | −6.67 | 15.571 | 25.9 | C |
| ATOM | 1641 | CD1 | LEU | A1255 | 0.648 | −7.916 | 15.545 | 21.2 | C |
| ATOM | 1642 | CD2 | LEU | A1255 | 0.623 | −5.462 | 15.862 | 22.34 | C |
| ATOM | 1643 | C | LEU | A1255 | 4.029 | −5.854 | 18.256 | 31.71 | C |
| ATOM | 1644 | O | LEU | A1255 | 3.438 | −5.765 | 19.341 | 32.56 | O |
| ATOM | 1645 | N | GLN | A1256 | 5.315 | −6.125 | 18.161 | 32.58 | N |
| ATOM | 1646 | CA | GLN | A1256 | 6.02 | −6.599 | 19.279 | 34.23 | C |
| ATOM | 1647 | CB | GLN | A1256 | 6.598 | −7.935 | 18.872 | 34.77 | C |
| ATOM | 1648 | CG | GLN | A1256 | 6.603 | −9.017 | 19.89 | 37.62 | C |
| ATOM | 1649 | CD | GLN | A1256 | 6.165 | −10.365 | 19.269 | 41.02 | C |
| ATOM | 1650 | OE1 | GLN | A1256 | 4.976 | −10.64 | 19.236 | 42.75 | O |
| ATOM | 1651 | NE2 | GLN | A1256 | 7.116 | −11.184 | 18.775 | 39.8 | N |
| ATOM | 1652 | C | GLN | A1256 | 7.164 | −5.65 | 19.573 | 33.79 | C |
| ATOM | 1653 | O | GLN | A1256 | 8.044 | −5.999 | 20.347 | 35.8 | O |
| ATOM | 1654 | N | THR | A1257 | 7.218 | −4.49 | 18.945 | 32.41 | N |
| ATOM | 1655 | CA | THR | A1257 | 8.397 | −3.635 | 19.143 | 31.17 | C |
| ATOM | 1656 | CB | THR | A1257 | 9.718 | −4.095 | 18.392 | 31.52 | C |
| ATOM | 1657 | OG1 | THR | A1257 | 9.638 | −3.809 | 16.969 | 30.13 | O |
| ATOM | 1658 | CG2 | THR | A1257 | 10.112 | −5.605 | 18.665 | 30.26 | C |
| ATOM | 1659 | C | THR | A1257 | 8.147 | −2.263 | 18.645 | 30.43 | C |
| ATOM | 1660 | O | THR | A1257 | 8.877 | −1.356 | 19.008 | 30.95 | O |
| ATOM | 1661 | N | GLN | A1258 | 7.193 | −2.138 | 17.734 | 29.57 | N |
| ATOM | 1662 | CA | GLN | A1258 | 6.735 | −0.853 | 17.219 | 30.28 | C |
| ATOM | 1663 | CB | GLN | A1258 | 6.459 | 0.13 | 18.384 | 31.08 | C |
| ATOM | 1664 | CG | GLN | A1258 | 5.144 | 0.893 | 18.275 | 33.11 | C |
| ATOM | 1665 | CD | GLN | A1258 | 5.061 | 2.095 | 19.274 | 33.27 | C |
| ATOM | 1666 | OE1 | GLN | A1258 | 5.397 | 1.939 | 20.463 | 39.41 | O |
| ATOM | 1667 | NE2 | GLN | A1258 | 4.584 | 3.27 | 18.798 | 29.74 | N |
| ATOM | 1668 | C | GLN | A1258 | 7.729 | −0.263 | 16.224 | 28.93 | C |
| ATOM | 1669 | O | GLN | A1258 | 7.637 | 0.916 | 15.872 | 29.28 | O |
| ATOM | 1670 | N | LYS | A1259 | 8.64 | −1.096 | 15.742 | 28.14 | N |
| ATOM | 1671 | CA | LYS | A1259 | 9.582 | −0.677 | 14.701 | 28.14 | C |
| ATOM | 1672 | CB | LYS | A1259 | 11.05 | −0.984 | 15.129 | 30.57 | C |
| ATOM | 1673 | CG | LYS | A1259 | 11.648 | 0.003 | 16.193 | 31.76 | C |
| ATOM | 1674 | CD | LYS | A1259 | 12.782 | −0.73 | 16.978 | 32.91 | C |
| ATOM | 1675 | CE | LYS | A1259 | 13.536 | 0.295 | 17.915 | 37.06 | C |
| ATOM | 1676 | NZ | LYS | A1259 | 14.494 | −0.291 | 18.924 | 32.88 | N |
| ATOM | 1677 | C | LYS | A1259 | 9.293 | −1.259 | 13.316 | 24.48 | C |
| ATOM | 1678 | O | LYS | A1259 | 8.873 | −2.411 | 13.2 | 21.83 | O |
| ATOM | 1679 | N | PHE | A1260 | 9.596 | −0.455 | 12.288 | 21.57 | N |
| ATOM | 1680 | CA | PHE | A1260 | 9.234 | −0.778 | 10.91 | 19.9 | C |
| ATOM | 1681 | CB | PHE | A1260 | 8.242 | 0.249 | 10.37 | 18.27 | C |
| ATOM | 1682 | CG | PHE | A1260 | 7 | 0.392 | 11.208 | 16.53 | C |
| ATOM | 1683 | CD1 | PHE | A1260 | 6.991 | 1.259 | 12.353 | 17.28 | C |
| ATOM | 1684 | CD2 | PHE | A1260 | 5.851 | −0.336 | 10.909 | 14.62 | C |
| ATOM | 1685 | CE1 | PHE | A1260 | 5.874 | 1.39 | 13.158 | 14.55 | C |
| ATOM | 1686 | CE2 | PHE | A1260 | 4.706 | −0.221 | 11.702 | 16.06 | C |
| ATOM | 1687 | CZ | PHE | A1260 | 4.698 | 0.646 | 12.807 | 18.96 | C |
| ATOM | 1688 | C | PHE | A1260 | 10.446 | −0.912 | 9.984 | 20.79 | C |
| ATOM | 1689 | O | PHE | A1260 | 11.497 | −0.282 | 10.19 | 22.74 | O |
| ATOM | 1690 | N | THR | A1261 | 10.319 | −1.739 | 8.958 | 19.25 | N |
| ATOM | 1691 | CA | THR | A1261 | 11.369 | −1.894 | 7.99 | 17.76 | C |
| ATOM | 1692 | CB | THR | A1261 | 12.358 | −3.043 | 8.369 | 18.7 | C |
| ATOM | 1693 | OG1 | THR | A1261 | 11.668 | −4.302 | 8.396 | 18.46 | O |

TABLE 1A-continued

| | | | | | | | | |
|---|---|---|---|---|---|---|---|---|
| ATOM | 1694 | CG2 | THR | A1261 | 13 | −2.793 | 9.746 | 19.38 | C |
| ATOM | 1695 | C | THR | A1261 | 10.726 | −2.181 | 6.637 | 16.24 | C |
| ATOM | 1696 | O | THR | A1261 | 9.519 | −2.344 | 6.549 | 15.68 | O |
| ATOM | 1697 | N | THR | A1262 | 11.542 | −2.225 | 5.581 | 13.6 | N |
| ATOM | 1698 | CA | THR | A1262 | 11.063 | −2.608 | 4.321 | 12.49 | C |
| ATOM | 1699 | CB | THR | A1262 | 12.175 | −2.541 | 3.221 | 14.06 | C |
| ATOM | 1700 | OG1 | THR | A1262 | 12.656 | −1.212 | 3.086 | 11.22 | O |
| ATOM | 1701 | CG2 | THR | A1262 | 11.636 | −2.914 | 1.843 | 14.36 | C |
| ATOM | 1702 | C | THR | A1262 | 10.525 | −3.996 | 4.475 | 11.49 | C |
| ATOM | 1703 | O | THR | A1262 | 9.629 | −4.349 | 3.817 | 11.81 | O |
| ATOM | 1704 | N | LYS | A1263 | 11.132 | −4.822 | 5.318 | 12.87 | N |
| ATOM | 1705 | CA | LYS | A1263 | 10.597 | −6.177 | 5.595 | 12.76 | C |
| ATOM | 1706 | CB | LYS | A1263 | 11.604 | −6.976 | 6.408 | 13.32 | C |
| ATOM | 1707 | CG | LYS | A1263 | 12.832 | −7.445 | 5.589 | 14.58 | C |
| ATOM | 1708 | CD | LYS | A1263 | 12.449 | −8.002 | 4.24 | 10.3 | C |
| ATOM | 1709 | CE | LYS | A1263 | 13.641 | −8.874 | 3.828 | 14.06 | C |
| ATOM | 1710 | NZ | LYS | A1263 | 13.635 | −9.233 | 2.408 | 10.78 | N |
| ATOM | 1711 | C | LYS | A1263 | 9.235 | −6.256 | 6.256 | 10.99 | C |
| ATOM | 1712 | O | LYS | A1263 | 8.509 | −7.228 | 6.056 | 10.11 | O |
| ATOM | 1713 | N | SER | A1264 | 8.925 | −5.263 | 7.076 | 10.36 | N |
| ATOM | 1714 | CA | SER | A1264 | 7.575 | −5.162 | 7.644 | 11.41 | C |
| ATOM | 1715 | CB | SER | A1264 | 7.54 | −4.346 | 8.93 | 11.47 | C |
| ATOM | 1716 | OG | SER | A1264 | 7.752 | −2.984 | 8.714 | 14.16 | O |
| ATOM | 1717 | C | SER | A1264 | 6.633 | −4.601 | 6.598 | 11.2 | C |
| ATOM | 1718 | O | SER | A1264 | 5.43 | −4.992 | 6.553 | 11.68 | O |
| ATOM | 1719 | N | ASP | A1265 | 7.204 | −3.819 | 5.679 | 9.67 | N |
| ATOM | 1720 | CA | ASP | A1265 | 6.45 | −3.364 | 4.538 | 11.37 | C |
| ATOM | 1721 | CB | ASP | A1265 | 7.171 | −2.28 | 3.753 | 10.45 | C |
| ATOM | 1722 | CG | ASP | A1265 | 6.956 | −0.879 | 4.332 | 14.18 | C |
| ATOM | 1723 | OD1 | ASP | A1265 | 7.593 | 0.032 | 3.753 | 14.77 | O |
| ATOM | 1724 | OD2 | ASP | A1265 | 6.163 | −0.667 | 5.331 | 16.48 | O |
| ATOM | 1725 | C | ASP | A1265 | 6.041 | −4.533 | 3.618 | 11.53 | C |
| ATOM | 1726 | O | ASP | A1265 | 4.944 | −4.545 | 3.046 | 14.2 | O |
| ATOM | 1727 | N | VAL | A1266 | 6.856 | −5.549 | 3.576 | 10.63 | N |
| ATOM | 1728 | CA | VAL | A1266 | 6.602 | −6.704 | 2.752 | 11.03 | C |
| ATOM | 1729 | CB | VAL | A1266 | 7.949 | −7.558 | 2.57 | 10.66 | C |
| ATOM | 1730 | CG1 | VAL | A1266 | 7.661 | −9.023 | 2.243 | 8.73 | C |
| ATOM | 1731 | CG2 | VAL | A1266 | 8.825 | −6.919 | 1.505 | 8.25 | C |
| ATOM | 1732 | C | VAL | A1266 | 5.475 | −7.515 | 3.393 | 10.47 | C |
| ATOM | 1733 | O | VAL | A1266 | 4.63 | −8.017 | 2.669 | 12.51 | O |
| ATOM | 1734 | N | TRP | A1267 | 5.455 | −7.602 | 4.728 | 9.37 | N |
| ATOM | 1735 | CA | TRP | A1267 | 4.375 | −8.239 | 5.466 | 8.82 | C |
| ATOM | 1736 | CB | TRP | A1267 | 4.633 | −8.156 | 7 | 8.16 | C |
| ATOM | 1737 | CG | TRP | A1267 | 3.559 | −8.824 | 7.849 | 10.92 | C |
| ATOM | 1738 | CD2 | TRP | A1267 | 3.665 | −10.046 | 8.612 | 9.89 | C |
| ATOM | 1739 | CE2 | TRP | A1267 | 2.394 | −10.3 | 9.176 | 9.5 | C |
| ATOM | 1740 | CE3 | TRP | A1267 | 4.712 | −10.904 | 8.911 | 8.75 | C |
| ATOM | 1741 | CD1 | TRP | A1267 | 2.232 | −8.433 | 7.972 | 10.68 | C |
| ATOM | 1742 | NE1 | TRP | A1267 | 1.552 | −9.29 | 8.779 | 6.35 | N |
| ATOM | 1743 | CZ2 | TRP | A1267 | 2.156 | −11.378 | 10.068 | 8.31 | C |
| ATOM | 1744 | CZ3 | TRP | A1267 | 4.465 | −11.994 | 9.747 | 10.23 | C |
| ATOM | 1745 | CH2 | TRP | A1267 | 3.187 | −12.215 | 10.325 | 8.98 | C |
| ATOM | 1746 | C | TRP | A1267 | 3.041 | −7.557 | 5.104 | 8.67 | C |
| ATOM | 1747 | O | TRP | A1267 | 2.055 | −8.236 | 4.836 | 9.65 | O |
| ATOM | 1748 | N | SER | A1268 | 3 | −6.206 | 5.109 | 9.54 | N |
| ATOM | 1749 | CA | SER | A1268 | 1.746 | −5.456 | 4.795 | 7.78 | C |
| ATOM | 1750 | CB | SER | A1268 | 1.913 | −3.967 | 5.045 | 7.03 | C |
| ATOM | 1751 | OG | SER | A1268 | 2.513 | −3.772 | 6.256 | 8.59 | O |
| ATOM | 1752 | C | SER | A1268 | 1.365 | −5.634 | 3.342 | 7.8 | C |
| ATOM | 1753 | O | SER | A1268 | 0.17 | −5.677 | 3.001 | 7.51 | O |
| ATOM | 1754 | N | PHE | A1269 | 2.387 | −5.73 | 2.479 | 8.59 | N |
| ATOM | 1755 | CA | PHE | A1269 | 2.169 | −5.956 | 1.088 | 9.1 | C |
| ATOM | 1756 | CB | PHE | A1269 | 3.473 | −5.888 | 0.338 | 8.27 | C |
| ATOM | 1757 | CG | PHE | A1269 | 3.314 | −6.245 | −1.096 | 8.45 | C |
| ATOM | 1758 | CD1 | PHE | A1269 | 2.619 | −5.363 | −1.972 | 9.17 | C |
| ATOM | 1759 | CD2 | PHE | A1269 | 3.719 | −7.495 | −1.559 | 8.51 | C |
| ATOM | 1760 | CE1 | PHE | A1269 | 2.369 | −5.68 | −3.271 | 7.04 | C |
| ATOM | 1761 | CE2 | PHE | A1269 | 3.495 | −7.836 | −2.88 | 8.56 | C |
| ATOM | 1762 | CZ | PHE | A1269 | 2.784 | −6.942 | −3.728 | 9.89 | C |
| ATOM | 1763 | C | PHE | A1269 | 1.442 | −7.323 | 0.919 | 10.64 | C |
| ATOM | 1764 | O | PHE | A1269 | 0.49 | −7.477 | 0.111 | 11.13 | O |
| ATOM | 1765 | N | GLY | A1270 | 1.857 | −8.317 | 1.702 | 11.64 | N |
| ATOM | 1766 | CA | GLY | A1270 | 1.14 | −9.587 | 1.648 | 11.42 | C |
| ATOM | 1767 | C | GLY | A1270 | −0.332 | −9.417 | 2.029 | 10.97 | C |
| ATOM | 1768 | O | GLY | A1270 | −1.199 | −10.04 | 1.413 | 11.25 | O |
| ATOM | 1769 | N | VAL | A1271 | −0.613 | −8.596 | 3.059 | 9.54 | N |
| ATOM | 1770 | CA | VAL | A1271 | −2.01 | −8.356 | 3.569 | 8.57 | C |
| ATOM | 1771 | CB | VAL | A1271 | −2.033 | −7.621 | 4.946 | 8.56 | C |
| ATOM | 1772 | CG1 | VAL | A1271 | −3.47 | −7.359 | 5.392 | 7 | C |
| ATOM | 1773 | CG2 | VAL | A1271 | −1.271 | −8.389 | 6.08 | 3.23 | C |

TABLE 1A-continued

| | | | | | | | | | |
|---|---|---|---|---|---|---|---|---|---|
| ATOM | 1774 | C | VAL | A1271 | −2.833 | −7.584 | 2.516 | 9.92 | C |
| ATOM | 1775 | O | VAL | A1271 | −4.001 | −7.95 | 2.211 | 10.22 | O |
| ATOM | 1776 | N | LEU | A1272 | −2.175 | −6.593 | 1.899 | 10.19 | N |
| ATOM | 1777 | CA | LEU | A1272 | −2.68 | −5.873 | 0.716 | 11.37 | C |
| ATOM | 1778 | CB | LEU | A1272 | −1.764 | −4.681 | 0.411 | 11.24 | C |
| ATOM | 1779 | CG | LEU | A1272 | −1.525 | −3.908 | −0.905 | 14.03 | C |
| ATOM | 1780 | CD1 | LEU | A1272 | −2.293 | −4.472 | −2.089 | 13.62 | C |
| ATOM | 1781 | CD2 | LEU | A1272 | −1.645 | −2.378 | −0.821 | 13.61 | C |
| ATOM | 1782 | C | LEU | A1272 | −3.038 | −6.764 | −0.501 | 11.35 | C |
| ATOM | 1783 | O | LEU | A1272 | −4.086 | −6.613 | −1.146 | 11.16 | O |
| ATOM | 1784 | N | LEU | A1273 | −2.208 | −7.748 | −0.75 | 10.97 | N |
| ATOM | 1785 | CA | LEU | A1273 | −2.507 | −8.766 | −1.748 | 10.03 | C |
| ATOM | 1786 | CB | LEU | A1273 | −1.341 | −9.755 | −1.83 | 19.71 | C |
| ATOM | 1787 | CG | LEU | A1273 | −0.17 | −9.307 | −2.652 | 12.95 | C |
| ATOM | 1788 | CD1 | LEU | A1273 | 0.852 | −10.401 | −2.848 | 13.19 | C |
| ATOM | 1789 | CD2 | LEU | A1273 | −0.706 | −8.847 | −3.99 | 16.74 | C |
| ATOM | 1790 | C | LEU | A1273 | −3.716 | −9.555 | −1.395 | 8.67 | C |
| ATOM | 1791 | O | LEU | A1273 | −4.436 | −9.945 | −2.273 | 7.96 | O |
| ATOM | 1792 | N | TRP | A1274 | −3.86 | −9.879 | −0.092 | 9.8 | N |
| ATOM | 1793 | CA | TRP | A1274 | −5.031 | −10.602 | 0.426 | 8.39 | C |
| ATOM | 1794 | CB | TRP | A1274 | −4.81 | −11.063 | 1.856 | 7.65 | C |
| ATOM | 1795 | CG | TRP | A1274 | −5.841 | −11.888 | 2.417 | 3.72 | C |
| ATOM | 1796 | CD2 | TRP | A1274 | −7.005 | −11.445 | 3.132 | 4.89 | C |
| ATOM | 1797 | CE2 | TRP | A1274 | −7.731 | −12.617 | 3.507 | 2 | C |
| ATOM | 1798 | CE3 | TRP | A1274 | −7.48 | −10.181 | 3.54 | 4.57 | C |
| ATOM | 1799 | CD1 | TRP | A1274 | −5.909 | −13.249 | 2.383 | 4.08 | C |
| ATOM | 1800 | NE1 | TRP | A1274 | −7.037 | −13.694 | 3.025 | 2.01 | N |
| ATOM | 1801 | CZ2 | TRP | A1274 | −8.903 | −12.574 | 4.242 | 2.67 | C |
| ATOM | 1802 | CZ3 | TRP | A1274 | −8.727 | −10.127 | 4.267 | 8.33 | C |
| ATOM | 1803 | CH2 | TRP | A1274 | −9.417 | −11.329 | 4.607 | 3.57 | C |
| ATOM | 1804 | C | TRP | A1274 | −6.228 | −9.715 | 0.277 | 9.2 | C |
| ATOM | 1805 | O | TRP | A1274 | −7.31 | −10.183 | −0.178 | 10.85 | O |
| ATOM | 1806 | N | GLU | A1275 | −6.053 | −8.426 | 0.596 | 9.74 | N |
| ATOM | 1807 | CA | GLU | A1275 | −7.159 | −7.458 | 0.406 | 10.36 | C |
| ATOM | 1808 | CB | GLU | A1275 | −6.761 | −6.009 | 0.771 | 9.95 | C |
| ATOM | 1809 | CG | GLU | A1275 | −6.544 | −5.683 | 2.246 | 11 | C |
| ATOM | 1810 | CD | GLU | A1275 | −6.205 | −4.183 | 2.392 | 12.14 | C |
| ATOM | 1811 | OE1 | GLU | A1275 | −5.043 | −3.754 | 2.104 | 12.7 | O |
| ATOM | 1812 | OE2 | GLU | A1275 | −7.131 | −3.392 | 2.7 | 11.37 | O |
| ATOM | 1813 | C | GLU | A1275 | −7.61 | −7.445 | −1.028 | 10.04 | C |
| ATOM | 1814 | O | GLU | A1275 | −8.794 | −7.315 | −1.306 | 10.34 | O |
| ATOM | 1815 | N | LEU | A1276 | −6.641 | −7.421 | −1.934 | 11.02 | N |
| ATOM | 1816 | CA | LEU | A1276 | −6.883 | −7.423 | −3.355 | 11.94 | C |
| ATOM | 1817 | CB | LEU | A1276 | −5.549 | −7.374 | −4.068 | 11.7 | C |
| ATOM | 1818 | CG | LEU | A1276 | −5.098 | −6.161 | −4.878 | 13.84 | C |
| ATOM | 1819 | CD1 | LEU | A1276 | −5.77 | −4.882 | −4.59 | 15.07 | C |
| ATOM | 1820 | CD2 | LEU | A1276 | −3.588 | −6.017 | −4.794 | 14.8 | C |
| ATOM | 1821 | C | LEU | A1276 | −7.649 | −8.691 | −3.79 | 12.76 | C |
| ATOM | 1822 | O | LEU | A1276 | −8.688 | −8.584 | −4.439 | 14.11 | O |
| ATOM | 1823 | N | MET | A1277 | −7.181 | −9.872 | −3.387 | 12.53 | N |
| ATOM | 1824 | CA | MET | A1277 | −7.783 | −11.114 | −3.844 | 13.7 | C |
| ATOM | 1825 | CB | MET | A1277 | −6.838 | −12.32 | −3.715 | 11.99 | C |
| ATOM | 1826 | CG | MET | A1277 | −5.573 | −12.151 | −4.52 | 16.79 | C |
| ATOM | 1827 | SD | MET | A1277 | −5.667 | −11.426 | −6.22 | 25.77 | S |
| ATOM | 1828 | CE | MET | A1277 | −6.432 | −12.816 | −7.071 | 17.04 | C |
| ATOM | 1829 | C | MET | A1277 | −9.1 | −11.424 | −3.185 | 14.22 | C |
| ATOM | 1830 | O | MET | A1277 | −9.877 | −12.227 | −3.727 | 15.37 | O |
| ATOM | 1831 | N | THR | A1278 | −9.345 | −10.845 | −2.007 | 14.32 | N |
| ATOM | 1832 | CA | THR | A1278 | −10.683 | −10.929 | −1.389 | 12.59 | C |
| ATOM | 1833 | CB | THR | A1278 | −10.597 | −10.94 | 0.12 | 13.16 | C |
| ATOM | 1834 | OG1 | THR | A1278 | −10.167 | −9.64 | 0.627 | 9.42 | O |
| ATOM | 1835 | CG2 | THR | A1278 | −9.611 | −12.04 | 0.543 | 8.23 | C |
| ATOM | 1836 | C | THR | A1278 | −11.582 | −9.779 | −1.809 | 13.58 | C |
| ATOM | 1837 | O | THR | A1278 | −12.71 | −9.661 | −1.286 | 14.22 | O |
| ATOM | 1838 | N | ARG | A1279 | −11.094 | −8.931 | −2.726 | 12.97 | N |
| ATOM | 1839 | CA | ARG | A1279 | −11.853 | −7.804 | −3.23 | 15.57 | C |
| ATOM | 1840 | CB | ARG | A1279 | −13.12 | −8.298 | −3.949 | 14.48 | C |
| ATOM | 1841 | CG | ARG | A1279 | −13.201 | −7.815 | −5.354 | 20.35 | C |
| ATOM | 1842 | CD | ARG | A1279 | −14.28 | −8.526 | −6.25 | 20.34 | C |
| ATOM | 1843 | NE | ARG | A1279 | −13.757 | −9.783 | −6.773 | 27.23 | N |
| ATOM | 1844 | CZ | ARG | A1279 | −13.268 | −10.03 | −8.019 | 29.48 | C |
| ATOM | 1845 | NH1 | ARG | A1279 | −13.237 | −9.082 | −8.967 | 19.95 | N |
| ATOM | 1846 | NH2 | ARG | A1279 | −12.773 | −11.281 | −8.296 | 29.36 | N |
| ATOM | 1847 | C | ARG | A1279 | −12.252 | −6.851 | −2.08 | 15.31 | C |
| ATOM | 1848 | O | ARG | A1279 | −13.412 | −6.454 | −1.997 | 16.43 | O |
| ATOM | 1849 | N | GLY | A1280 | −11.316 | −6.472 | −1.202 | 14.52 | N |
| ATOM | 1850 | CA | GLY | A1280 | −11.607 | −5.431 | −0.235 | 14.65 | C |
| ATOM | 1851 | C | GLY | A1280 | −12.149 | −5.991 | 1.088 | 15.17 | C |
| ATOM | 1852 | O | GLY | A1280 | −12.617 | −5.233 | 1.934 | 13.6 | O |
| ATOM | 1853 | N | ALA | A1281 | −12.066 | −7.311 | 1.31 | 14.02 | N |

TABLE 1A-continued

| ATOM | 1854 | CA | ALA | A1281 | −12.479 | −7.784 | 2.644 | 14.68 | C |
|---|---|---|---|---|---|---|---|---|---|
| ATOM | 1855 | CB | ALA | A1281 | −12.698 | −9.349 | 2.709 | 13.99 | C |
| ATOM | 1856 | C | ALA | A1281 | −11.512 | −7.29 | 3.732 | 14.17 | C |
| ATOM | 1857 | O | ALA | A1281 | −10.291 | −7.095 | 3.428 | 13.46 | O |
| ATOM | 1858 | N | PRO | A1282 | −12.025 | −7.152 | 4.989 | 13.83 | N |
| ATOM | 1859 | CD | PRO | A1282 | −13.426 | −7.463 | 5.268 | 15.14 | C |
| ATOM | 1860 | CA | PRO | A1282 | −11.327 | −6.761 | 6.233 | 15.61 | C |
| ATOM | 1861 | CB | PRO | A1282 | −12.477 | −6.518 | 7.241 | 16.49 | C |
| ATOM | 1862 | CG | PRO | A1282 | −13.805 | −6.384 | 6.27 | 16.92 | C |
| ATOM | 1863 | C | PRO | A1282 | −10.542 | −7.972 | 6.721 | 16.94 | C |
| ATOM | 1864 | O | PRO | A1282 | −11.135 | −9.035 | 6.958 | 17.36 | O |
| ATOM | 1865 | N | PRO | A1283 | −9.212 | −7.829 | 6.868 | 17.68 | N |
| ATOM | 1866 | CD | PRO | A1283 | −8.431 | −6.615 | 6.538 | 17.72 | C |
| ATOM | 1867 | CA | PRO | A1283 | −8.407 | −8.909 | 7.458 | 17.23 | C |
| ATOM | 1868 | CB | PRO | A1283 | −6.978 | −8.369 | 7.397 | 17.46 | C |
| ATOM | 1869 | CG | PRO | A1283 | −7.01 | −6.992 | 6.83 | 17.37 | C |
| ATOM | 1870 | C | PRO | A1283 | −8.809 | −9.139 | 8.924 | 17.48 | C |
| ATOM | 1871 | O | PRO | A1283 | −9.079 | −8.155 | 9.671 | 17.71 | O |
| ATOM | 1872 | N | TYR | A1284 | −8.86 | −10.402 | 9.336 | 16.72 | N |
| ATOM | 1873 | CA | TYR | A1284 | −9.106 | −10.759 | 10.742 | 17.3 | C |
| ATOM | 1874 | CB | TYR | A1284 | −7.938 | −10.382 | 11.624 | 16.01 | C |
| ATOM | 1875 | CG | TYR | A1284 | −6.551 | −10.698 | 11.111 | 17.42 | C |
| ATOM | 1876 | CD1 | TYR | A1284 | −5.946 | −11.957 | 11.312 | 15.84 | C |
| ATOM | 1877 | CE1 | TYR | A1284 | −4.631 | −12.201 | 10.876 | 14.8 | C |
| ATOM | 1878 | CD2 | TYR | A1284 | −5.809 | −9.724 | 10.468 | 16.16 | C |
| ATOM | 1879 | CE2 | TYR | A1284 | −4.539 | −9.98 | 10.008 | 16.45 | C |
| ATOM | 1880 | CZ | TYR | A1284 | −3.932 | −11.185 | 10.22 | 16.76 | C |
| ATOM | 1881 | OH | TYR | A1284 | −2.656 | −11.326 | 9.687 | 16.71 | O |
| ATOM | 1882 | C | TYR | A1284 | −10.342 | −10.136 | 11.365 | 18.43 | C |
| ATOM | 1883 | O | TYR | A1284 | −10.225 | −9.475 | 12.388 | 18.85 | O |
| ATOM | 1884 | N | PRO | A1285 | −11.519 | −10.319 | 10.758 | 20.37 | N |
| ATOM | 1885 | CD | PRO | A1285 | −11.84 | −11.196 | 9.635 | 20.13 | C |
| ATOM | 1886 | CA | PRO | A1285 | −12.689 | −9.555 | 11.184 | 23.29 | C |
| ATOM | 1887 | CB | PRO | A1285 | −13.739 | −9.907 | 10.135 | 22.39 | C |
| ATOM | 1888 | CG | PRO | A1285 | −13.326 | −11.24 | 9.66 | 21.13 | C |
| ATOM | 1889 | C | PRO | A1285 | −13.166 | −9.872 | 12.61 | 26.8 | C |
| ATOM | 1890 | O | PRO | A1285 | −13.433 | −8.936 | 13.408 | 25.99 | O |
| ATOM | 1891 | N | ASP | A1286 | −13.265 | −11.154 | 12.972 | 30.65 | N |
| ATOM | 1892 | CA | ASP | A1286 | −13.848 | −11.408 | 14.323 | 35.35 | C |
| ATOM | 1893 | CB | ASP | A1286 | −14.553 | −12.807 | 14.453 | 37.22 | C |
| ATOM | 1894 | CG | ASP | A1286 | −15.524 | −13.112 | 13.255 | 43.19 | C |
| ATOM | 1895 | OD1 | ASP | A1286 | −14.994 | −13.477 | 12.169 | 46.45 | O |
| ATOM | 1896 | OD2 | ASP | A1286 | −16.782 | −12.965 | 13.391 | 46.26 | O |
| ATOM | 1897 | C | ASP | A1286 | −12.895 | −11.155 | 15.535 | 35.1 | C |
| ATOM | 1898 | O | ASP | A1286 | −13.065 | −11.858 | 16.549 | 36.23 | O |
| ATOM | 1899 | N | VAL | A1287 | −11.959 | −10.172 | 15.481 | 32.52 | N |
| ATOM | 1900 | CA | VAL | A1287 | −10.802 | −10.275 | 16.39 | 29.97 | C |
| ATOM | 1901 | CB | VAL | A1287 | −9.744 | −11.371 | 15.935 | 29.53 | C |
| ATOM | 1902 | CG1 | VAL | A1287 | −9.59 | −11.36 | 14.514 | 30.14 | C |
| ATOM | 1903 | CG2 | VAL | A1287 | −8.408 | −11.176 | 16.544 | 30.07 | C |
| ATOM | 1904 | C | VAL | A1287 | −10.145 | −9.032 | 16.83 | 28.88 | C |
| ATOM | 1905 | O | VAL | A1287 | −9.891 | −8.145 | 16.02 | 29.31 | O |
| ATOM | 1906 | N | ASN | A1288 | −9.858 | −8.968 | 18.137 | 26.64 | N |
| ATOM | 1907 | CA | ASN | A1288 | −9.176 | −7.828 | 18.689 | 24.13 | C |
| ATOM | 1908 | CB | ASN | A1288 | −9.554 | −7.638 | 20.164 | 25 | C |
| ATOM | 1909 | CG | ASN | A1288 | −9.045 | −8.774 | 21.085 | 25.21 | C |
| ATOM | 1910 | OD1 | ASN | A1288 | −7.878 | −9.281 | 20.965 | 21.19 | O |
| ATOM | 1911 | ND2 | ASN | A1288 | −9.928 | −9.165 | 22.048 | 22.42 | N |
| ATOM | 1912 | C | ASN | A1288 | −7.678 | −7.882 | 18.51 | 23.31 | C |
| ATOM | 1913 | O | ASN | A1288 | −7.145 | −8.852 | 18.011 | 22.44 | O |
| ATOM | 1914 | N | THR | A1289 | −7.008 | −6.829 | 18.966 | 23.16 | N |
| ATOM | 1915 | CA | THR | A1289 | −5.58 | −6.648 | 18.82 | 22.72 | C |
| ATOM | 1916 | CB | THR | A1289 | −5.102 | −5.234 | 19.26 | 23.85 | C |
| ATOM | 1917 | OG1 | THR | A1289 | −5.823 | −4.741 | 20.416 | 26.46 | O |
| ATOM | 1918 | CG2 | THR | A1289 | −5.304 | −4.207 | 18.143 | 25.64 | C |
| ATOM | 1919 | C | THR | A1289 | −4.739 | −7.686 | 19.517 | 22.02 | C |
| ATOM | 1920 | O | THR | A1289 | −3.619 | −8.007 | 19.065 | 23 | O |
| ATOM | 1921 | N | PHE | A1290 | −5.251 | −8.222 | 20.614 | 20.54 | N |
| ATOM | 1922 | CA | PHE | A1290 | −4.486 | −9.215 | 21.359 | 19.45 | C |
| ATOM | 1923 | CB | PHE | A1290 | −4.935 | −9.309 | 22.861 | 19.8 | C |
| ATOM | 1924 | CG | PHE | A1290 | −4.062 | −10.269 | 23.708 | 18.62 | C |
| ATOM | 1925 | CD1 | PHE | A1290 | −2.808 | −9.855 | 24.201 | 16.3 | C |
| ATOM | 1926 | CD2 | PHE | A1290 | −4.466 | −11.598 | 23.931 | 20.15 | C |
| ATOM | 1927 | CE1 | PHE | A1290 | −1.999 | −10.702 | 24.984 | 19.55 | C |
| ATOM | 1928 | CE2 | PHE | A1290 | −3.661 | −12.486 | 24.692 | 18.86 | C |
| ATOM | 1929 | CZ | PHE | A1290 | −2.404 | −12.053 | 25.206 | 20.06 | C |
| ATOM | 1930 | C | PHE | A1290 | −4.587 | −10.609 | 20.684 | 18.03 | C |
| ATOM | 1931 | O | PHE | A1290 | −3.605 | −11.325 | 20.562 | 16.43 | O |
| ATOM | 1932 | N | ASP | A1291 | −5.793 | −10.996 | 20.303 | 17.58 | N |
| ATOM | 1933 | CA | ASP | A1291 | −5.964 | −12.302 | 19.726 | 19.32 | C |

TABLE 1A-continued

| | | | | | | | | |
|---|---|---|---|---|---|---|---|---|
| ATOM | 1934 | CB | ASP | A1291 | −7.414 | −12.688 | 19.644 | 18.53 | C |
| ATOM | 1935 | CG | ASP | A1291 | −8.056 | −12.83 | 20.984 | 21.78 | C |
| ATOM | 1936 | OD1 | ASP | A1291 | −7.39 | −13.29 | 21.98 | 19.49 | O |
| ATOM | 1937 | OD2 | ASP | A1291 | −9.277 | −12.483 | 21.039 | 24.79 | O |
| ATOM | 1938 | C | ASP | A1291 | −5.301 | −12.414 | 18.338 | 20.96 | C |
| ATOM | 1939 | O | ASP | A1291 | −4.776 | −13.486 | 17.993 | 21.73 | O |
| ATOM | 1940 | N | ILE | A1292 | −5.313 | −11.32 | 17.569 | 20.88 | N |
| ATOM | 1941 | CA | ILE | A1292 | −4.576 | −11.26 | 16.303 | 21.43 | C |
| ATOM | 1942 | CB | ILE | A1292 | −4.718 | −9.857 | 15.559 | 20.9 | C |
| ATOM | 1943 | CG2 | ILE | A1292 | −3.601 | −9.658 | 14.6 | 22.73 | C |
| ATOM | 1944 | CG1 | ILE | A1292 | −5.981 | −9.858 | 14.679 | 22.1 | C |
| ATOM | 1945 | CD1 | ILE | A1292 | −6.854 | −8.575 | 14.742 | 27.9 | C |
| ATOM | 1946 | C | ILE | A1292 | −3.153 | −11.697 | 16.529 | 20.67 | C |
| ATOM | 1947 | O | ILE | A1292 | −2.569 | −12.403 | 15.728 | 21.89 | O |
| ATOM | 1948 | N | THR | A1293 | −2.591 | −11.277 | 17.633 | 20.67 | N |
| ATOM | 1949 | CA | THR | A1293 | −1.187 | −11.53 | 17.92 | 21.87 | C |
| ATOM | 1950 | CB | THR | A1293 | −0.769 | −10.598 | 19.089 | 22.47 | C |
| ATOM | 1951 | OG1 | THR | A1293 | −0.81 | −9.23 | 18.606 | 25.62 | O |
| ATOM | 1952 | CG2 | THR | A1293 | 0.571 | −10.944 | 19.614 | 20.56 | C |
| ATOM | 1953 | C | THR | A1293 | −0.949 | −13.006 | 18.292 | 22.24 | C |
| ATOM | 1954 | O | THR | A1293 | 0.01 | −13.642 | 17.844 | 22.94 | O |
| ATOM | 1955 | N | VAL | A1294 | −1.844 | −13.548 | 19.105 | 22.43 | N |
| ATOM | 1956 | CA | VAL | A1294 | −1.887 | −14.965 | 19.401 | 22.79 | C |
| ATOM | 1957 | CB | VAL | A1294 | −3.039 | −15.316 | 20.484 | 24.33 | C |
| ATOM | 1958 | CG1 | VAL | A1294 | −2.905 | −16.703 | 20.93 | 21.06 | C |
| ATOM | 1959 | CG2 | VAL | A1294 | −3.012 | −14.34 | 21.698 | 22.9 | C |
| ATOM | 1960 | C | VAL | A1294 | −2.137 | −15.775 | 18.156 | 22.04 | C |
| ATOM | 1961 | O | VAL | A1294 | −1.472 | −16.737 | 17.979 | 23.52 | O |
| ATOM | 1962 | N | TYR | A1295 | −3.127 | −15.42 | 17.336 | 21.11 | N |
| ATOM | 1963 | CA | TYR | A1295 | −3.378 | −16.062 | 16.036 | 21.27 | C |
| ATOM | 1964 | CB | TYR | A1295 | −4.387 | −15.233 | 15.215 | 21.55 | C |
| ATOM | 1965 | CG | TYR | A1295 | −4.827 | −15.809 | 13.847 | 22.76 | C |
| ATOM | 1966 | CD1 | TYR | A1295 | −5.852 | −16.772 | 13.788 | 24.13 | C |
| ATOM | 1967 | CE1 | TYR | A1295 | −6.251 | −17.347 | 12.586 | 22.48 | C |
| ATOM | 1968 | CD2 | TYR | A1295 | −4.24 | −15.406 | 12.639 | 18.86 | C |
| ATOM | 1969 | CE2 | TYR | A1295 | −4.647 | −15.975 | 11.44 | 19.4 | C |
| ATOM | 1970 | CZ | TYR | A1295 | −5.662 | −16.957 | 11.412 | 22 | C |
| ATOM | 1971 | OH | TYR | A1295 | −6.157 | −17.572 | 10.245 | 15.34 | O |
| ATOM | 1972 | C | TYR | A1295 | −2.05 | −16.149 | 15.285 | 21.71 | C |
| ATOM | 1973 | O | TYR | A1295 | −1.72 | −17.214 | 14.76 | 23.7 | O |
| ATOM | 1974 | N | LEU | A1296 | −1.278 | −15.061 | 15.253 | 20.06 | N |
| ATOM | 1975 | CA | LEU | A1296 | −0.1 | −15.031 | 14.463 | 19.72 | C |
| ATOM | 1976 | CB | LEU | A1296 | 0.315 | −13.583 | 14.173 | 18.7 | C |
| ATOM | 1977 | CG | LEU | A1296 | −0.563 | −12.717 | 13.227 | 17.29 | C |
| ATOM | 1978 | CD1 | LEU | A1296 | −0.108 | −11.231 | 13.155 | 14.74 | C |
| ATOM | 1979 | CD2 | LEU | A1296 | −0.67 | −13.32 | 11.866 | 13.27 | C |
| ATOM | 1980 | C | LEU | A1296 | 1.069 | −15.809 | 15.034 | 21.48 | C |
| ATOM | 1981 | O | LEU | A1296 | 1.891 | −16.348 | 14.288 | 20.81 | O |
| ATOM | 1982 | N | LEU | A1297 | 1.202 | −15.8 | 16.367 | 23.54 | N |
| ATOM | 1983 | CA | LEU | A1297 | 2.303 | −16.527 | 17.031 | 23.91 | C |
| ATOM | 1984 | CB | LEU | A1297 | 2.543 | −16.042 | 18.472 | 23.89 | C |
| ATOM | 1985 | CG | LEU | A1297 | 3.38 | −14.752 | 18.474 | 27.22 | C |
| ATOM | 1986 | CD1 | LEU | A1297 | 3.407 | −13.97 | 19.768 | 28.81 | C |
| ATOM | 1987 | CD2 | LEU | A1297 | 4.763 | −15.022 | 18.017 | 31.47 | C |
| ATOM | 1988 | C | LEU | A1297 | 2.053 | −18.024 | 17.018 | 24.35 | C |
| ATOM | 1989 | O | LEU | A1297 | 2.956 | −18.785 | 17.371 | 26.26 | O |
| ATOM | 1990 | N | GLN | A1298 | 0.865 | −18.444 | 16.598 | 23.07 | N |
| ATOM | 1991 | CA | GLN | A1298 | 0.509 | −19.839 | 16.478 | 23.56 | C |
| ATOM | 1992 | CB | GLN | A1298 | −0.975 | −20.019 | 16.765 | 23.4 | C |
| ATOM | 1993 | CG | GLN | A1298 | −1.185 | −20.016 | 18.319 | 29.5 | C |
| ATOM | 1994 | CD | GLN | A1298 | −2.609 | −20.215 | 18.746 | 33.61 | C |
| ATOM | 1995 | OE1 | GLN | A1298 | −3.551 | −19.932 | 17.988 | 33.3 | O |
| ATOM | 1996 | NE2 | GLN | A1298 | −2.79 | −20.662 | 20.004 | 36.42 | N |
| ATOM | 1997 | C | GLN | A1298 | 0.813 | −20.336 | 15.092 | 23.28 | C |
| ATOM | 1998 | O | GLN | A1298 | 0.486 | −21.504 | 14.767 | 23.77 | O |
| ATOM | 1999 | N | GLY | A1299 | 1.427 | −19.453 | 14.293 | 21.11 | N |
| ATOM | 2000 | CA | GLY | A1299 | 1.761 | −19.705 | 12.913 | 19.57 | C |
| ATOM | 2001 | C | GLY | A1299 | 0.552 | −19.613 | 11.985 | 19.57 | C |
| ATOM | 2002 | O | GLY | A1299 | 0.69 | −19.848 | 10.779 | 19.65 | O |
| ATOM | 2003 | N | ARG | A1300 | −0.642 | −19.294 | 12.519 | 17.34 | N |
| ATOM | 2004 | CA | ARG | A1300 | −1.791 | −19.147 | 11.663 | 15.11 | C |
| ATOM | 2005 | CB | ARG | A1300 | −3.068 | −19.072 | 12.496 | 15.35 | C |
| ATOM | 2006 | CG | ARG | A1300 | −3.227 | −20.162 | 13.511 | 17.32 | C |
| ATOM | 2007 | CD | ARG | A1300 | −4.385 | −19.878 | 14.443 | 19 | C |
| ATOM | 2008 | NE | ARG | A1300 | −5.495 | −20.632 | 13.951 | 26.17 | N |
| ATOM | 2009 | CZ | ARG | A1300 | −5.943 | −21.75 | 14.51 | 26.18 | C |
| ATOM | 2010 | NH1 | ARG | A1300 | −5.407 | −22.226 | 15.639 | 26.4 | N |
| ATOM | 2011 | NH2 | ARG | A1300 | −6.947 | −22.383 | 13.935 | 28.78 | N |
| ATOM | 2012 | C | ARG | A1300 | −1.625 | −17.896 | 10.789 | 13.95 | C |
| ATOM | 2013 | O | ARG | A1300 | −0.906 | −16.952 | 11.167 | 11.48 | O |

TABLE 1A-continued

| | | | | | | | | |
|---|---|---|---|---|---|---|---|---|
| ATOM | 2014 | N | ARG | A1301 | −2.292 | −17.914 | 9.62 | 12.59 | N |
| ATOM | 2015 | CA | ARG | A1301 | −2.296 | −16.803 | 8.679 | 10.68 | C |
| ATOM | 2016 | CB | ARG | A1301 | −1.227 | −17.008 | 7.66 | 9.76 | C |
| ATOM | 2017 | CG | ARG | A1301 | 0.201 | −17.075 | 8.265 | 9.66 | C |
| ATOM | 2018 | CD | ARG | A1301 | 0.732 | −15.697 | 8.706 | 10.28 | C |
| ATOM | 2019 | NE | ARG | A1301 | 2.117 | −15.7 | 9.169 | 7.99 | N |
| ATOM | 2020 | CZ | ARG | A1301 | 2.433 | −16.002 | 10.423 | 11.74 | C |
| ATOM | 2021 | NH1 | ARG | A1301 | 1.466 | −16.398 | 11.307 | 6.97 | N |
| ATOM | 2022 | NH2 | ARG | A1301 | 3.713 | −15.986 | 10.777 | 11.06 | N |
| ATOM | 2023 | C | ARG | A1301 | −3.668 | −16.6 | 8.022 | 11.29 | C |
| ATOM | 2024 | O | ARG | A1301 | −4.596 | −17.417 | 8.188 | 10.02 | O |
| ATOM | 2025 | N | LEU | A1302 | −3.83 | −15.488 | 7.303 | 11.13 | N |
| ATOM | 2026 | CA | LEU | A1302 | −5.106 | −15.197 | 6.609 | 10.8 | C |
| ATOM | 2027 | CB | LEU | A1302 | −5.014 | −13.85 | 5.963 | 9.1 | C |
| ATOM | 2028 | CG | LEU | A1302 | −4.833 | −12.681 | 6.864 | 6.48 | C |
| ATOM | 2029 | CD1 | LEU | A1302 | −4.307 | −11.511 | 6.008 | 9.35 | C |
| ATOM | 2030 | CD2 | LEU | A1302 | −6.153 | −12.358 | 7.484 | 4.82 | C |
| ATOM | 2031 | C | LEU | A1302 | −5.312 | −16.286 | 5.57 | 12.1 | C |
| ATOM | 2032 | O | LEU | A1302 | −4.346 | −16.769 | 5.013 | 13.45 | O |
| ATOM | 2033 | N | LEU | A1303 | −6.537 | −16.737 | 5.331 | 14.81 | N |
| ATOM | 2034 | CA | LEU | A1303 | −6.711 | −18 | 4.542 | 15.67 | C |
| ATOM | 2035 | CB | LEU | A1303 | −8.023 | −18.684 | 4.826 | 14.95 | C |
| ATOM | 2036 | CG | LEU | A1303 | −8.178 | −19.581 | 6.054 | 18.31 | C |
| ATOM | 2037 | CD1 | LEU | A1303 | −6.996 | −19.498 | 6.984 | 20.03 | C |
| ATOM | 2038 | CD2 | LEU | A1303 | −9.492 | −19.163 | 6.791 | 15.76 | C |
| ATOM | 2039 | C | LEU | A1303 | −6.66 | −17.616 | 3.1 | 16.46 | C |
| ATOM | 2040 | O | LEU | A1303 | −6.816 | −16.433 | 2.806 | 17.16 | O |
| ATOM | 2041 | N | GLN | A1304 | −6.44 | −18.594 | 2.224 | 16.59 | N |
| ATOM | 2042 | CA | GLN | A1304 | −6.3 | −18.347 | 0.838 | 16.9 | C |
| ATOM | 2043 | CB | GLN | A1304 | −5.86 | −19.567 | 0.157 | 15.65 | C |
| ATOM | 2044 | CG | GLN | A1304 | −5.653 | −19.308 | −1.266 | 15.99 | C |
| ATOM | 2045 | CD | GLN | A1304 | −5.059 | −20.498 | −2.033 | 18.57 | C |
| ATOM | 2046 | OE1 | GLN | A1304 | −4.449 | −21.434 | −1.479 | 14.91 | O |
| ATOM | 2047 | NE2 | GLN | A1304 | −5.186 | −20.415 | −3.343 | 19.66 | N |
| ATOM | 2048 | C | GLN | A1304 | −7.665 | −17.96 | 0.305 | 20.07 | C |
| ATOM | 2049 | O | GLN | A1304 | −8.661 | −18.688 | 0.48 | 21.65 | O |
| ATOM | 2050 | N | PRO | A1305 | −7.758 | −16.779 | −0.303 | 20.86 | N |
| ATOM | 2051 | CD | PRO | A1305 | −6.779 | −15.677 | −0.48 | 21.62 | C |
| ATOM | 2052 | CA | PRO | A1305 | −9.075 | −16.464 | −0.792 | 21.48 | C |
| ATOM | 2053 | CB | PRO | A1305 | −8.959 | −14.995 | −1.167 | 20.75 | C |
| ATOM | 2054 | CG | PRO | A1305 | −7.643 | −14.505 | −0.558 | 21.05 | C |
| ATOM | 2055 | C | PRO | A1305 | −9.462 | −17.375 | −1.955 | 23.17 | C |
| ATOM | 2056 | O | PRO | A1305 | −8.602 | −18.053 | −2.505 | 22.48 | O |
| ATOM | 2057 | N | GLU | A1306 | −10.761 | −17.436 | −2.283 | 26 | N |
| ATOM | 2058 | CA | GLU | A1306 | −11.26 | −18.192 | −3.458 | 28.18 | C |
| ATOM | 2059 | CB | GLU | A1306 | −12.763 | −18.089 | −3.506 | 29.06 | C |
| ATOM | 2060 | CG | GLU | A1306 | −13.503 | −19.357 | −3.241 | 32.62 | C |
| ATOM | 2061 | CD | GLU | A1306 | −15.012 | −19.072 | −3.204 | 38.95 | C |
| ATOM | 2062 | OE1 | GLU | A1306 | −15.586 | −18.781 | −4.279 | 38.36 | O |
| ATOM | 2063 | OE2 | GLU | A1306 | −15.613 | −19.109 | −2.096 | 42.58 | O |
| ATOM | 2064 | C | GLU | A1306 | −10.727 | −17.481 | −4.699 | 29.17 | C |
| ATOM | 2065 | O | GLU | A1306 | −10.623 | −16.223 | −4.716 | 28.95 | O |
| ATOM | 2066 | N | TYR | A1307 | −10.373 | −18.239 | −5.733 | 29.22 | N |
| ATOM | 2067 | CA | TYR | A1307 | −9.876 | −17.566 | −6.982 | 29.91 | C |
| ATOM | 2068 | CB | TYR | A1307 | −10.817 | −16.438 | −7.467 | 31.22 | C |
| ATOM | 2069 | CG | TYR | A1307 | −12.238 | −16.847 | −7.415 | 34.72 | C |
| ATOM | 2070 | CD1 | TYR | A1307 | −12.651 | −17.996 | −8.093 | 37.5 | C |
| ATOM | 2071 | CE1 | TYR | A1307 | −13.982 | −18.423 | −8.057 | 37.34 | C |
| ATOM | 2072 | CD2 | TYR | A1307 | −13.183 | −16.105 | −6.674 | 37.26 | C |
| ATOM | 2073 | CE2 | TYR | A1307 | −14.515 | −16.517 | −6.635 | 38.36 | C |
| ATOM | 2074 | CZ | TYR | A1307 | −14.896 | −17.692 | −7.347 | 37.41 | C |
| ATOM | 2075 | OH | TYR | A1307 | −16.196 | −18.158 | −7.348 | 37.73 | O |
| ATOM | 2076 | C | TYR | A1307 | −8.469 | −16.946 | −6.918 | 27.27 | C |
| ATOM | 2077 | O | TYR | A1307 | −8.005 | −16.415 | −7.922 | 28.16 | O |
| ATOM | 2078 | N | CYS | A1308 | −7.836 | −16.986 | −5.76 | 24.33 | N |
| ATOM | 2079 | CA | CYS | A1308 | −6.448 | −16.581 | −5.609 | 22.31 | C |
| ATOM | 2080 | CB | CYS | A1308 | −6.179 | −16.264 | −4.155 | 21.21 | C |
| ATOM | 2081 | SG | CYS | A1308 | −4.524 | −15.866 | −3.835 | 21.98 | S |
| ATOM | 2082 | C | CYS | A1308 | −5.63 | −17.792 | −5.972 | 21.69 | C |
| ATOM | 2083 | O | CYS | A1308 | −5.657 | −18.776 | −5.197 | 21.71 | O |
| ATOM | 2084 | N | PRO | A1309 | −4.895 | −17.737 | −7.136 | 20.38 | N |
| ATOM | 2085 | CD | PRO | A1309 | −4.914 | −16.66 | −8.151 | 20.39 | C |
| ATOM | 2086 | CA | PRO | A1309 | −3.952 | −18.758 | −7.524 | 18.95 | C |
| ATOM | 2087 | CB | PRO | A1309 | −3.177 | −18.102 | −8.703 | 18.71 | C |
| ATOM | 2088 | CG | PRO | A1309 | −3.54 | −16.76 | −8.732 | 21.17 | C |
| ATOM | 2089 | C | PRO | A1309 | −2.999 | −19.167 | −6.393 | 17.95 | C |
| ATOM | 2090 | O | PRO | A1309 | −2.449 | −18.309 | −5.682 | 16.25 | O |
| ATOM | 2091 | N | ASP | A1310 | −2.831 | −20.485 | −6.258 | 17.69 | N |
| ATOM | 2092 | CA | ASP | A1310 | −1.936 | −21.129 | −5.289 | 18.08 | C |
| ATOM | 2093 | CB | ASP | A1310 | −1.805 | −22.64 | −5.628 | 17.94 | C |

TABLE 1A-continued

| ATOM | 2094 | CG  | ASP | A1310 | −3.062  | −23.451 | −5.251 | 26.79 | C |
|------|------|-----|-----|-------|---------|---------|--------|-------|---|
| ATOM | 2095 | OD1 | ASP | A1310 | −4.071  | −22.782 | −4.899 | 31.89 | O |
| ATOM | 2096 | OD2 | ASP | A1310 | −3.076  | −24.745 | −5.262 | 29.15 | O |
| ATOM | 2097 | C   | ASP | A1310 | −0.53   | −20.464 | −5.191 | 17.75 | C |
| ATOM | 2098 | O   | ASP | A1310 | −0.043  | −20.203 | −4.067 | 18.85 | O |
| ATOM | 2099 | N   | PRO | A1311 | 0.177   | −20.268 | −6.356 | 17.25 | N |
| ATOM | 2100 | CD  | PRO | A1311 | −0.102  | −20.803 | −7.725 | 16.88 | C |
| ATOM | 2101 | CA  | PRO | A1311 | 1.465   | −19.559 | −6.343 | 15.19 | C |
| ATOM | 2102 | CB  | PRO | A1311 | 1.82    | −19.434 | −7.84  | 13.7  | C |
| ATOM | 2103 | CG  | PRO | A1311 | 1.293   | −20.726 | −8.404 | 14.93 | C |
| ATOM | 2104 | C   | PRO | A1311 | 1.351   | −18.218 | −5.741 | 15.13 | C |
| ATOM | 2105 | O   | PRO | A1311 | 2.274   | −17.853 | −5.016 | 15.93 | O |
| ATOM | 2106 | N   | LEU | A1312 | 0.248   | −17.498 | −5.99  | 13.68 | N |
| ATOM | 2107 | CA  | LEU | A1312 | 0.124   | −16.184 | −5.399 | 14.9  | C |
| ATOM | 2108 | CB  | LEU | A1312 | −1.102  | −15.427 | −5.875 | 15.12 | C |
| ATOM | 2109 | CG  | LEU | A1312 | −1.007  | −13.901 | −6.065 | 16.16 | C |
| ATOM | 2110 | CD1 | LEU | A1312 | −2.415  | −13.27  | −6.038 | 17.09 | C |
| ATOM | 2111 | CD2 | LEU | A1312 | −0.203  | −13.323 | −5.007 | 22.34 | C |
| ATOM | 2112 | C   | LEU | A1312 | 0.05    | −16.301 | −3.88  | 15.48 | C |
| ATOM | 2113 | O   | LEU | A1312 | 0.695   | −15.523 | −3.154 | 14.57 | O |
| ATOM | 2114 | N   | TYR | A1313 | −0.724  | −17.288 | −3.406 | 15.42 | N |
| ATOM | 2115 | CA  | TYR | A1313 | −0.859  | −17.479 | −1.998 | 15.15 | C |
| ATOM | 2116 | CB  | TYR | A1313 | −1.893  | −18.528 | −1.643 | 15.52 | C |
| ATOM | 2117 | CG  | TYR | A1313 | −2.23   | −18.548 | −0.145 | 16.45 | C |
| ATOM | 2118 | CD1 | TYR | A1313 | −2.56   | −17.358 | 0.54   | 15.64 | C |
| ATOM | 2119 | CE1 | TYR | A1313 | −2.936  | −17.372 | 1.926  | 16.19 | C |
| ATOM | 2120 | CD2 | TYR | A1313 | −2.212  | −19.754 | 0.591  | 15.35 | C |
| ATOM | 2121 | CE2 | TYR | A1313 | −2.591  | −19.791 | 1.956  | 15.48 | C |
| ATOM | 2122 | CZ  | TYR | A1313 | −2.936  | −18.585 | 2.613  | 17.43 | C |
| ATOM | 2123 | OH  | TYR | A1313 | −3.289  | −18.608 | 3.927  | 14.53 | O |
| ATOM | 2124 | C   | TYR | A1313 | 0.474   | −17.838 | −1.447 | 15.35 | C |
| ATOM | 2125 | O   | TYR | A1313 | 0.814   | −17.353 | −0.375 | 14.4  | O |
| ATOM | 2126 | N   | GLU | A1314 | 1.256   | −18.633 | −2.188 | 15.71 | N |
| ATOM | 2127 | CA  | GLU | A1314 | 2.582   | −18.991 | −1.697 | 18.23 | C |
| ATOM | 2128 | CB  | GLU | A1314 | 3.388   | −19.844 | −2.715 | 18.61 | C |
| ATOM | 2129 | CG  | GLU | A1314 | 2.698   | −21.155 | −3.256 | 25.52 | C |
| ATOM | 2130 | CD  | GLU | A1314 | 3.287   | −21.719 | −4.675 | 29.14 | C |
| ATOM | 2131 | OE1 | GLU | A1314 | 4.453   | −21.269 | −5.127 | 32.9  | O |
| ATOM | 2132 | OE2 | GLU | A1314 | 2.545   | −22.601 | −5.337 | 34.86 | O |
| ATOM | 2133 | C   | GLU | A1314 | 3.328   | −17.677 | −1.454 | 15.23 | C |
| ATOM | 2134 | O   | GLU | A1314 | 4.172   | −17.576 | −0.566 | 14.59 | O |
| ATOM | 2135 | N   | VAL | A1315 | 3.088   | −16.69  | −2.301 | 13.92 | N |
| ATOM | 2136 | CA  | VAL | A1315 | 3.813   | −15.431 | −2.161 | 13.5  | C |
| ATOM | 2137 | CB  | VAL | A1315 | 3.785   | −14.546 | −3.475 | 14.69 | C |
| ATOM | 2138 | CG1 | VAL | A1315 | 4.069   | −13.078 | −3.177 | 14.19 | C |
| ATOM | 2139 | CG2 | VAL | A1315 | 4.77    | −15.107 | −4.591 | 12.06 | C |
| ATOM | 2140 | C   | VAL | A1315 | 3.327   | −14.682 | −0.917 | 12.08 | C |
| ATOM | 2141 | O   | VAL | A1315 | 4.137   | −14.155 | −0.228 | 10.73 | O |
| ATOM | 2142 | N   | MET | A1316 | 2.033   | −14.671 | −0.63  | 11.53 | N |
| ATOM | 2143 | CA  | MET | A1316 | 1.517   | −13.987 | 0.538  | 13.7  | C |
| ATOM | 2144 | CB  | MET | A1316 | −0.01   | −13.976 | 0.634  | 12.56 | C |
| ATOM | 2145 | CG  | MET | A1316 | −0.722  | −13.524 | −0.618 | 15.54 | C |
| ATOM | 2146 | SD  | MET | A1316 | −2.547  | −13.416 | −0.347 | 20.85 | S |
| ATOM | 2147 | CE  | MET | A1316 | −3.235  | −14.193 | −1.73  | 19.52 | C |
| ATOM | 2148 | C   | MET | A1316 | 2.079   | −14.643 | 1.748  | 13.01 | C |
| ATOM | 2149 | O   | MET | A1316 | 2.561   | −13.971 | 2.65   | 15.31 | O |
| ATOM | 2150 | N   | LEU | A1317 | 2.056   | −15.963 | 1.801  | 12.31 | N |
| ATOM | 2151 | CA  | LEU | A1317 | 2.673   | −16.625 | 2.935  | 11.49 | C |
| ATOM | 2152 | CB  | LEU | A1317 | 2.497   | −18.127 | 2.873  | 9.86  | C |
| ATOM | 2153 | CG  | LEU | A1317 | 1.111   | −18.695 | 2.882  | 7.48  | C |
| ATOM | 2154 | CD1 | LEU | A1317 | 1.176   | −20.143 | 2.433  | 7.53  | C |
| ATOM | 2155 | CD2 | LEU | A1317 | 0.443   | −18.515 | 4.217  | 3.61  | C |
| ATOM | 2156 | C   | LEU | A1317 | 4.115   | −16.342 | 3.052  | 11.01 | C |
| ATOM | 2157 | O   | LEU | A1317 | 4.637   | −16.294 | 4.137  | 14.42 | O |
| ATOM | 2158 | N   | LYS | A1318 | 4.837   | −16.313 | 1.961  | 12.75 | N |
| ATOM | 2159 | CA  | LYS | A1318 | 6.254   | −15.938 | 2.056  | 15.07 | C |
| ATOM | 2160 | CB  | LYS | A1318 | 6.876   | −15.918 | 0.675  | 15.17 | C |
| ATOM | 2161 | CG  | LYS | A1318 | 7.096   | −17.29  | 0.083  | 24.05 | C |
| ATOM | 2162 | CD  | LYS | A1318 | 8.157   | −18.097 | 0.911  | 34.28 | C |
| ATOM | 2163 | CE  | LYS | A1318 | 9.463   | −17.244 | 1.089  | 35.3  | C |
| ATOM | 2164 | NZ  | LYS | A1318 | 10.632  | −18.122 | 0.888  | 37.08 | N |
| ATOM | 2165 | C   | LYS | A1318 | 6.414   | −14.497 | 2.746  | 14.84 | C |
| ATOM | 2166 | O   | LYS | A1318 | 7.365   | −14.269 | 3.513  | 15.47 | O |
| ATOM | 2167 | N   | CYS | A1319 | 5.472   | −13.595 | 2.467  | 12.45 | N |
| ATOM | 2168 | CA  | CYS | A1319 | 5.395   | −12.258 | 3.016  | 13.65 | C |
| ATOM | 2169 | CB  | CYS | A1319 | 4.184   | −11.562 | 2.396  | 13.17 | C |
| ATOM | 2170 | SG  | CYS | A1319 | 4.626   | −11.089 | 0.668  | 17.23 | S |
| ATOM | 2171 | C   | CYS | A1319 | 5.242   | −12.206 | 4.498  | 11.7  | C |
| ATOM | 2172 | O   | CYS | A1319 | 5.657   | −11.255 | 5.129  | 11.48 | O |
| ATOM | 2173 | N   | TRP | A1320 | 4.674   | −13.272 | 5.038  | 11.74 | N |

TABLE 1A-continued

| ATOM | 2174 | CA | TRP | A1320 | 4.364 | −13.378 | 6.418 | 11.21 | C |
|---|---|---|---|---|---|---|---|---|---|
| ATOM | 2175 | CB | TRP | A1320 | 2.956 | −13.816 | 6.577 | 10.12 | C |
| ATOM | 2176 | CG | TRP | A1320 | 1.981 | −12.93 | 5.933 | 8.99 | C |
| ATOM | 2177 | CD2 | TRP | A1320 | 0.794 | −13.355 | 5.289 | 8.09 | C |
| ATOM | 2178 | CE2 | TRP | A1320 | 0.173 | −12.196 | 4.77 | 6.13 | C |
| ATOM | 2179 | CE3 | TRP | A1320 | 0.152 | −14.624 | 5.15 | 10.88 | C |
| ATOM | 2180 | CD1 | TRP | A1320 | 2.052 | −11.549 | 5.778 | 7.31 | C |
| ATOM | 2181 | NE1 | TRP | A1320 | 0.971 | −11.113 | 5.077 | 5.04 | N |
| ATOM | 2182 | CZ2 | TRP | A1320 | −1.05 | −12.246 | 4.139 | 5.59 | C |
| ATOM | 2183 | CZ3 | TRP | A1320 | −1.066 | −14.693 | 4.483 | 7.31 | C |
| ATOM | 2184 | CH2 | TRP | A1320 | −1.641 | −13.517 | 3.956 | 8.66 | C |
| ATOM | 2185 | C | TRP | A1320 | 5.244 | −14.353 | 7.147 | 13.67 | C |
| ATOM | 2186 | O | TRP | A1320 | 4.827 | −14.909 | 8.143 | 14.64 | O |
| ATOM | 2187 | N | HIS | A1321 | 6.471 | −14.547 | 6.666 | 15.52 | N |
| ATOM | 2188 | CA | HIS | A1321 | 7.441 | −15.283 | 7.387 | 15.52 | C |
| ATOM | 2189 | CB | HIS | A1321 | 8.71 | −15.494 | 6.566 | 15.45 | C |
| ATOM | 2190 | CG | HIS | A1321 | 9.52 | −16.676 | 7.019 | 19.13 | C |
| ATOM | 2191 | CD2 | HIS | A1321 | 9.627 | −17.924 | 6.509 | 18.26 | C |
| ATOM | 2192 | ND1 | HIS | A1321 | 10.327 | −16.649 | 8.147 | 17.94 | N |
| ATOM | 2193 | CE1 | HIS | A1321 | 10.873 | −17.836 | 8.318 | 19.05 | C |
| ATOM | 2194 | NE2 | HIS | A1321 | 10.487 | −18.617 | 7.323 | 21 | N |
| ATOM | 2195 | C | HIS | A1321 | 7.723 | −14.594 | 8.724 | 16.55 | C |
| ATOM | 2196 | O | HIS | A1321 | 7.91 | −13.367 | 8.798 | 14.69 | O |
| ATOM | 2197 | N | PRO | A1322 | 7.719 | −15.401 | 9.805 | 18.27 | N |
| ATOM | 2198 | CD | PRO | A1322 | 7.45 | −16.846 | 9.725 | 17.64 | C |
| ATOM | 2199 | CA | PRO | A1322 | 8.004 | −14.959 | 11.159 | 20.5 | C |
| ATOM | 2200 | CB | PRO | A1322 | 8.069 | −16.273 | 11.949 | 20.57 | C |
| ATOM | 2201 | CG | PRO | A1322 | 7.257 | −17.255 | 11.109 | 20.2 | C |
| ATOM | 2202 | C | PRO | A1322 | 9.373 | −14.272 | 11.183 | 22.28 | C |
| ATOM | 2203 | O | PRO | A1322 | 9.553 | −13.274 | 11.887 | 24.17 | O |
| ATOM | 2204 | N | LYS | A1323 | 10.32 | −14.818 | 10.441 | 23.53 | N |
| ATOM | 2205 | CA | LYS | A1323 | 11.644 | −14.265 | 10.317 | 26.14 | C |
| ATOM | 2206 | CB | LYS | A1323 | 12.676 | −15.384 | 10.057 | 26.85 | C |
| ATOM | 2207 | CG | LYS | A1323 | 13.098 | −16.183 | 11.289 | 32.8 | C |
| ATOM | 2208 | CD | LYS | A1323 | 14.653 | −16.203 | 11.372 | 40.5 | C |
| ATOM | 2209 | CE | LYS | A1323 | 15.207 | −14.739 | 11.543 | 40.83 | C |
| ATOM | 2210 | NZ | LYS | A1323 | 16.672 | −14.663 | 11.818 | 38.1 | N |
| ATOM | 2211 | C | LYS | A1323 | 11.736 | −13.231 | 9.224 | 26.02 | C |
| ATOM | 2212 | O | LYS | A1323 | 11.931 | −13.568 | 8.042 | 27.17 | O |
| ATOM | 2213 | N | ALA | A1324 | 11.669 | −11.973 | 9.63 | 27.03 | N |
| ATOM | 2214 | CA | ALA | A1324 | 11.753 | −10.83 | 8.711 | 27.52 | C |
| ATOM | 2215 | CB | ALA | A1324 | 12.013 | −9.546 | 9.448 | 27.19 | C |
| ATOM | 2216 | C | ALA | A1324 | 12.743 | −10.992 | 7.585 | 28.21 | C |
| ATOM | 2217 | O | ALA | A1324 | 12.55 | −10.353 | 6.541 | 29.23 | O |
| ATOM | 2218 | N | GLU | A1325 | 13.758 | −11.855 | 7.76 | 28.16 | N |
| ATOM | 2219 | CA | GLU | A1325 | 14.848 | −11.996 | 6.775 | 28.45 | C |
| ATOM | 2220 | CB | GLU | A1325 | 16.188 | −12.172 | 7.469 | 30.57 | C |
| ATOM | 2221 | CG | GLU | A1325 | 16.132 | −13.059 | 8.745 | 36.13 | C |
| ATOM | 2222 | CD | GLU | A1325 | 17.211 | −14.16 | 8.711 | 44.36 | C |
| ATOM | 2223 | OE1 | GLU | A1325 | 16.858 | −15.364 | 8.463 | 44.39 | O |
| ATOM | 2224 | OE2 | GLU | A1325 | 18.411 | −13.803 | 8.91 | 45.7 | O |
| ATOM | 2225 | C | GLU | A1325 | 14.615 | −13.104 | 5.73 | 26.67 | C |
| ATOM | 2226 | O | GLU | A1325 | 15.22 | −13.121 | 4.643 | 24.01 | O |
| ATOM | 2227 | N | MET | A1326 | 13.683 | −13.99 | 6.047 | 25.01 | N |
| ATOM | 2228 | CA | MET | A1326 | 13.262 | −14.975 | 5.077 | 24.44 | C |
| ATOM | 2229 | CB | MET | A1326 | 12.799 | −16.21 | 5.822 | 25.54 | C |
| ATOM | 2230 | CG | MET | A1326 | 13.81 | −16.689 | 6.838 | 30.66 | C |
| ATOM | 2231 | SD | MET | A1326 | 15.391 | −17.066 | 6.07 | 39.12 | S |
| ATOM | 2232 | CE | MET | A1326 | 15.057 | −18.795 | 5.656 | 38.1 | C |
| ATOM | 2233 | C | MET | A1326 | 12.146 | −14.455 | 4.17 | 22.62 | C |
| ATOM | 2234 | O | MET | A1326 | 11.629 | −15.161 | 3.301 | 22.3 | O |
| ATOM | 2235 | N | ARG | A1327 | 11.718 | −13.218 | 4.398 | 20.92 | N |
| ATOM | 2236 | CA | ARG | A1327 | 10.72 | −12.616 | 3.544 | 17.8 | C |
| ATOM | 2237 | CB | ARG | A1327 | 10.117 | −11.425 | 4.234 | 16.42 | C |
| ATOM | 2238 | CG | ARG | A1327 | 9.313 | −11.875 | 5.335 | 17.54 | C |
| ATOM | 2239 | CD | ARG | A1327 | 8.503 | −10.757 | 5.939 | 16.7 | C |
| ATOM | 2240 | NE | ARG | A1327 | 8.293 | −11.1 | 7.326 | 18.93 | N |
| ATOM | 2241 | CZ | ARG | A1327 | 8.294 | −10.232 | 8.337 | 12.34 | C |
| ATOM | 2242 | NH1 | ARG | A1327 | 8.497 | −8.965 | 8.137 | 8.64 | N |
| ATOM | 2243 | NH2 | ARG | A1327 | 8.151 | −10.678 | 9.537 | 12.79 | N |
| ATOM | 2244 | C | ARG | A1327 | 11.36 | −12.196 | 2.213 | 15.89 | C |
| ATOM | 2245 | O | ARG | A1327 | 12.484 | −11.73 | 2.175 | 14.94 | O |
| ATOM | 2246 | N | PRO | A1328 | 10.609 | −12.309 | 1.126 | 14.58 | N |
| ATOM | 2247 | CD | PRO | A1328 | 9.266 | −12.869 | 1.009 | 12.52 | C |
| ATOM | 2248 | CA | PRO | A1328 | 11.167 | −11.836 | −0.146 | 13.78 | C |
| ATOM | 2249 | CB | PRO | A1328 | 10.127 | −12.248 | −1.161 | 12.76 | C |
| ATOM | 2250 | CG | PRO | A1328 | 8.86 | −12.432 | −0.349 | 15.33 | C |
| ATOM | 2251 | C | PRO | A1328 | 11.328 | −10.322 | −0.181 | 14.39 | C |
| ATOM | 2252 | O | PRO | A1328 | 10.566 | −9.595 | 0.486 | 14.86 | O |
| ATOM | 2253 | N | SER | A1329 | 12.302 | −9.858 | −0.972 | 14.35 | N |

TABLE 1A-continued

| | | | | | | | | |
|---|---|---|---|---|---|---|---|---|
| ATOM | 2254 | CA | SER | A1329 | 12.494 | −8.429 | −1.282 | 14.19 | C |
| ATOM | 2255 | CB | SER | A1329 | 13.904 | −8.201 | −1.891 | 13.44 | C |
| ATOM | 2256 | OG | SER | A1329 | 13.89 | −8.853 | −3.18 | 15.17 | O |
| ATOM | 2257 | C | SER | A1329 | 11.481 | −8.011 | −2.31 | 11.85 | C |
| ATOM | 2258 | O | SER | A1329 | 11 | −8.862 | −3.097 | 14.08 | O |
| ATOM | 2259 | N | PHE | A1330 | 11.222 | −6.713 | −2.389 | 10.58 | N |
| ATOM | 2260 | CA | PHE | A1330 | 10.322 | −6.24 | −3.391 | 12.2 | C |
| ATOM | 2261 | CB | PHE | A1330 | 9.996 | −4.758 | −3.212 | 11.92 | C |
| ATOM | 2262 | CG | PHE | A1330 | 9.043 | −4.493 | −2.073 | 10.86 | C |
| ATOM | 2263 | CD1 | PHE | A1330 | 7.729 | −4.902 | −2.161 | 6 | C |
| ATOM | 2264 | CD2 | PHE | A1330 | 9.494 | −3.884 | −0.896 | 6.99 | C |
| ATOM | 2265 | CE1 | PHE | A1330 | 6.91 | −4.709 | −1.126 | 6.91 | C |
| ATOM | 2266 | CE2 | PHE | A1330 | 8.643 | −3.633 | 0.136 | 9.1 | C |
| ATOM | 2267 | CZ | PHE | A1330 | 7.349 | −4.088 | 0.049 | 8.01 | C |
| ATOM | 2268 | C | PHE | A1330 | 10.798 | −6.542 | −4.805 | 13.02 | C |
| ATOM | 2269 | O | PHE | A1330 | 10 | −6.6 | −5.692 | 14.88 | O |
| ATOM | 2270 | N | SER | A1331 | 12.086 | −6.71 | −5.022 | 14.67 | N |
| ATOM | 2271 | CA | SER | A1331 | 12.609 | −7.117 | −6.325 | 16.24 | C |
| ATOM | 2272 | CB | SER | A1331 | 14.109 | −7.298 | −6.207 | 17.17 | C |
| ATOM | 2273 | OG | SER | A1331 | 14.734 | −6.176 | −6.688 | 18.61 | O |
| ATOM | 2274 | C | SER | A1331 | 12.083 | −8.473 | −6.71 | 17.27 | C |
| ATOM | 2275 | O | SER | A1331 | 11.591 | −8.652 | −7.857 | 18.62 | O |
| ATOM | 2276 | N | GLU | A1332 | 12.201 | −9.432 | −5.777 | 17.22 | N |
| ATOM | 2277 | CA | GLU | A1332 | 11.72 | −10.756 | −6.074 | 18.79 | C |
| ATOM | 2278 | CB | GLU | A1332 | 12.302 | −11.826 | −5.205 | 19.77 | C |
| ATOM | 2279 | CG | GLU | A1332 | 11.983 | −13.29 | −5.763 | 28.13 | C |
| ATOM | 2280 | CD | GLU | A1332 | 12.543 | −13.635 | −7.25 | 32 | C |
| ATOM | 2281 | OE1 | GLU | A1332 | 12.099 | −14.666 | −7.872 | 28.88 | O |
| ATOM | 2282 | OE2 | GLU | A1332 | 13.401 | −12.879 | −7.778 | 32.58 | O |
| ATOM | 2283 | C | GLU | A1332 | 10.214 | −10.791 | −6.033 | 18.26 | C |
| ATOM | 2284 | O | GLU | A1332 | 9.584 | −11.529 | −6.828 | 18.92 | O |
| ATOM | 2285 | N | LEU | A1333 | 9.602 | −9.984 | −5.174 | 16.87 | N |
| ATOM | 2286 | CA | LEU | A1333 | 8.122 | −9.956 | −5.252 | 16.38 | C |
| ATOM | 2287 | CB | LEU | A1333 | 7.522 | −9.018 | −4.227 | 16.3 | C |
| ATOM | 2288 | CG | LEU | A1333 | 6.986 | −9.505 | −2.882 | 16.8 | C |
| ATOM | 2289 | CD1 | LEU | A1333 | 6.727 | −11.004 | −2.852 | 14.42 | C |
| ATOM | 2290 | CD2 | LEU | A1333 | 7.787 | −9.07 | −1.725 | 11.65 | C |
| ATOM | 2291 | C | LEU | A1333 | 7.685 | −9.55 | −6.66 | 16 | C |
| ATOM | 2292 | O | LEU | A1333 | 6.84 | −10.217 | −7.241 | 14.65 | O |
| ATOM | 2293 | N | VAL | A1334 | 8.31 | −8.508 | −7.243 | 15.24 | N |
| ATOM | 2294 | CA | VAL | A1334 | 7.993 | −8.138 | −8.648 | 14.36 | C |
| ATOM | 2295 | CB | VAL | A1334 | 8.677 | −6.82 | −9.026 | 14.96 | C |
| ATOM | 2296 | CG1 | VAL | A1334 | 8.585 | −6.5 | −10.556 | 10.22 | C |
| ATOM | 2297 | CG2 | VAL | A1334 | 8.057 | −5.675 | −8.214 | 14.56 | C |
| ATOM | 2298 | C | VAL | A1334 | 8.255 | −9.218 | −9.724 | 13.55 | C |
| ATOM | 2299 | O | VAL | A1334 | 7.422 | −9.446 | −10.626 | 12.74 | O |
| ATOM | 2300 | N | SER | A1335 | 9.399 | −9.865 | −9.634 | 13.77 | N |
| ATOM | 2301 | CA | SER | A1335 | 9.72 | −10.93 | −10.566 | 14.73 | C |
| ATOM | 2302 | CB | SER | A1335 | 11.063 | −11.566 | −10.217 | 14.19 | C |
| ATOM | 2303 | OG | SER | A1335 | 12.091 | −10.61 | −10.426 | 16.15 | O |
| ATOM | 2304 | C | SER | A1335 | 8.633 | −11.994 | −10.579 | 15.13 | C |
| ATOM | 2305 | O | SER | A1335 | 8.096 | −12.389 | −11.628 | 14.15 | O |
| ATOM | 2306 | N | ARG | A1336 | 8.282 | −12.397 | −9.376 | 15.11 | N |
| ATOM | 2307 | CA | ARG | A1336 | 7.33 | −13.462 | −9.19 | 16.04 | C |
| ATOM | 2308 | CB | ARG | A1336 | 7.326 | −13.919 | −7.745 | 15 | C |
| ATOM | 2309 | CG | ARG | A1336 | 8.714 | −14.435 | −7.37 | 18.51 | C |
| ATOM | 2310 | CD | ARG | A1336 | 8.656 | −14.946 | −5.887 | 31.61 | C |
| ATOM | 2311 | NE | ARG | A1336 | 8.945 | −16.391 | −5.826 | 37.59 | N |
| ATOM | 2312 | CZ | ARG | A1336 | 8.352 | −17.326 | −5.074 | 35.7 | C |
| ATOM | 2313 | NH1 | ARG | A1336 | 7.332 | −17.055 | −4.267 | 33.74 | N |
| ATOM | 2314 | NH2 | ARG | A1336 | 8.82 | −18.576 | −5.162 | 35.74 | N |
| ATOM | 2315 | C | ARG | A1336 | 5.961 | −13.09 | −9.649 | 14.98 | C |
| ATOM | 2316 | O | ARG | A1336 | 5.399 | −13.775 | −10.522 | 16.44 | O |
| ATOM | 2317 | N | ILE | A1337 | 5.422 | −12.005 | −9.104 | 14.66 | N |
| ATOM | 2318 | CA | ILE | A1337 | 4.113 | −11.611 | −9.481 | 16.19 | C |
| ATOM | 2319 | CB | ILE | A1337 | 3.342 | −10.739 | −8.46 | 16.11 | C |
| ATOM | 2320 | CG2 | ILE | A1337 | 4.17 | −9.721 | −7.791 | 20.81 | C |
| ATOM | 2321 | CG1 | ILE | A1337 | 2.252 | −9.97 | −9.195 | 20.46 | C |
| ATOM | 2322 | CD1 | ILE | A1337 | 1.345 | −9.167 | −8.18 | 23.81 | C |
| ATOM | 2323 | C | ILE | A1337 | 4.012 | −11.191 | −10.902 | 12.25 | C |
| ATOM | 2324 | O | ILE | A1337 | 3.022 | −11.435 | −11.54 | 14.02 | O |
| ATOM | 2325 | N | SER | A1338 | 5.028 | −10.58 | −11.446 | 11.38 | N |
| ATOM | 2326 | CA | SER | A1338 | 5.013 | −10.42 | −12.924 | 10.49 | C |
| ATOM | 2327 | CB | SER | A1338 | 6.354 | −9.854 | −13.388 | 10.85 | C |
| ATOM | 2328 | OG | SER | A1338 | 6.152 | −9.131 | −14.566 | 10.54 | O |
| ATOM | 2329 | C | SER | A1338 | 4.757 | −11.755 | −13.658 | 10 | C |
| ATOM | 2330 | O | SER | A1338 | 4.007 | −11.788 | −14.661 | 10.17 | O |
| ATOM | 2331 | N | ALA | A1339 | 5.416 | −12.836 | −13.207 | 8.72 | N |
| ATOM | 2332 | CA | ALA | A1339 | 5.326 | −14.152 | −13.868 | 7.99 | C |
| ATOM | 2333 | CB | ALA | A1339 | 6.29 | −15.077 | −13.294 | 5.14 | C |

TABLE 1A-continued

| | | | | | | | | |
|---|---|---|---|---|---|---|---|---|
| ATOM | 2334 | C | ALA | A1339 | 3.925 | −14.703 | −13.758 | 9.66 | C |
| ATOM | 2335 | O | ALA | A1339 | 3.353 | −15.213 | −14.736 | 9.27 | O |
| ATOM | 2336 | N | ILE | A1340 | 3.359 | −14.594 | −12.542 | 11.06 | N |
| ATOM | 2337 | CA | ILE | A1340 | 1.997 | −14.976 | −12.258 | 10.27 | C |
| ATOM | 2338 | CB | ILE | A1340 | 1.733 | −14.767 | −10.76 | 10.82 | C |
| ATOM | 2339 | CG2 | ILE | A1340 | 0.282 | −14.868 | −10.418 | 8.31 | C |
| ATOM | 2340 | CG1 | ILE | A1340 | 2.558 | −15.733 | −9.91 | 10.31 | C |
| ATOM | 2341 | CD1 | ILE | A1340 | 2.557 | −15.363 | −8.468 | 8.49 | C |
| ATOM | 2342 | C | ILE | A1340 | 1.016 | −14.125 | −13.086 | 11.55 | C |
| ATOM | 2343 | O | ILE | A1340 | 0.04 | −14.636 | −13.667 | 12.6 | O |
| ATOM | 2344 | N | PHE | A1341 | 1.239 | −12.82 | −13.094 | 11.83 | N |
| ATOM | 2345 | CA | PHE | A1341 | 0.472 | −11.93 | −13.942 | 12.83 | C |
| ATOM | 2346 | CB | PHE | A1341 | 0.933 | −10.462 | −13.794 | 11.93 | C |
| ATOM | 2347 | CG | PHE | A1341 | 0.097 | −9.488 | −14.628 | 10.99 | C |
| ATOM | 2348 | CD1 | PHE | A1341 | −1.227 | −9.222 | −14.264 | 7.52 | C |
| ATOM | 2349 | CD2 | PHE | A1341 | 0.627 | −8.868 | −15.775 | 8.04 | C |
| ATOM | 2350 | CE1 | PHE | A1341 | −2.058 | −8.307 | −15.048 | 11.01 | C |
| ATOM | 2351 | CE2 | PHE | A1341 | −0.177 | −7.999 | −16.562 | 11.88 | C |
| ATOM | 2352 | CZ | PHE | A1341 | −1.556 | −7.711 | −16.174 | 9.93 | C |
| ATOM | 2353 | C | PHE | A1341 | 0.463 | −12.325 | −15.397 | 12.79 | C |
| ATOM | 2354 | O | PHE | A1341 | −0.587 | −12.401 | −15.997 | 14.47 | O |
| ATOM | 2355 | N | SER | A1342 | 1.638 | −12.488 | −15.974 | 15.32 | N |
| ATOM | 2356 | CA | SER | A1342 | 1.824 | −12.793 | −17.415 | 17.78 | C |
| ATOM | 2357 | CB | SER | A1342 | 3.315 | −12.827 | −17.797 | 16.79 | C |
| ATOM | 2358 | OG | SER | A1342 | 3.831 | −11.526 | −17.777 | 21.88 | O |
| ATOM | 2359 | C | SER | A1342 | 1.264 | −14.123 | −17.826 | 18.08 | C |
| ATOM | 2360 | O | SER | A1342 | 0.703 | −14.274 | −18.9 | 17.24 | O |
| ATOM | 2361 | N | THR | A1343 | 1.455 | −15.104 | −16.971 | 19.94 | N |
| ATOM | 2362 | CA | THR | A1343 | 1.061 | −16.422 | −17.358 | 22.37 | C |
| ATOM | 2363 | CB | THR | A1343 | 2.005 | −17.478 | −16.806 | 21.44 | C |
| ATOM | 2364 | OG1 | THR | A1343 | 2.055 | −17.379 | −15.369 | 21.47 | O |
| ATOM | 2365 | CG2 | THR | A1343 | 3.42 | −17.315 | −17.408 | 20.58 | C |
| ATOM | 2366 | C | THR | A1343 | −0.371 | −16.659 | −16.921 | 25.51 | C |
| ATOM | 2367 | O | THR | A1343 | −0.857 | −17.769 | −17.004 | 26.88 | O |
| ATOM | 2368 | N | PHE | A1344 | −1.054 | −15.641 | −16.409 | 28.5 | N |
| ATOM | 2369 | CA | PHE | A1344 | −2.33 | −15.953 | −15.798 | 30.95 | C |
| ATOM | 2370 | CB | PHE | A1344 | −2.881 | −14.847 | −14.904 | 30.06 | C |
| ATOM | 2371 | CG | PHE | A1344 | −4.151 | −15.235 | −14.222 | 27 | C |
| ATOM | 2372 | CD1 | PHE | A1344 | −4.119 | −16.097 | −13.114 | 24.24 | C |
| ATOM | 2373 | CD2 | PHE | A1344 | −5.368 | −14.795 | −14.711 | 23.57 | C |
| ATOM | 2374 | CE1 | PHE | A1344 | −5.268 | −16.519 | −12.49 | 25.54 | C |
| ATOM | 2375 | CE2 | PHE | A1344 | −6.539 | −15.163 | −14.084 | 27.12 | C |
| ATOM | 2376 | CZ | PHE | A1344 | −6.52 | −16.033 | −12.955 | 27.52 | C |
| ATOM | 2377 | C | PHE | A1344 | −3.35 | −16.303 | −16.855 | 33.54 | C |
| ATOM | 2378 | O | PHE | A1344 | −3.642 | −15.49 | −17.717 | 34.12 | O |
| ATOM | 2379 | N | ILE | A1345 | −3.911 | −17.508 | −16.715 | 37.1 | N |
| ATOM | 2380 | CA | ILE | A1345 | −4.975 | −18.047 | −17.583 | 40.92 | C |
| ATOM | 2381 | CB | ILE | A1345 | −6.372 | −17.424 | −17.281 | 40.56 | C |
| ATOM | 2382 | CG2 | ILE | A1345 | −7.344 | −17.479 | −18.492 | 43.36 | C |
| ATOM | 2383 | CG1 | ILE | A1345 | −6.946 | −18.152 | −16.051 | 43.45 | C |
| ATOM | 2384 | CD1 | ILE | A1345 | −6.095 | −19.438 | −15.574 | 42.93 | C |
| ATOM | 2385 | C | ILE | A1345 | −4.582 | −18.074 | −19.053 | 42.84 | C |
| ATOM | 2386 | O | ILE | A1345 | −4.93 | −17.184 | −19.846 | 43.44 | O |
| ATOM | 2387 | N | GLY | A1346 | −3.853 | −19.135 | −19.387 | 44.61 | N |
| ATOM | 2388 | CA | GLY | A1346 | −3.191 | −19.289 | −20.675 | 47.27 | C |
| ATOM | 2389 | C | GLY | A1346 | −1.718 | −19.513 | −20.354 | 49.35 | C |
| ATOM | 2390 | O | GLY | A1346 | −0.836 | −18.874 | −20.993 | 50.37 | O |
| ATOM | 2391 | OXT | GLY | A1346 | −1.376 | −20.327 | −19.436 | 49.81 | O |
| ATOM | 2392 | CB | LEU | B1046 | −19.47 | −2.928 | −35.925 | 40.32 | C |
| ATOM | 2393 | CG | LEU | B1046 | −19.758 | −3.718 | −34.616 | 42.01 | C |
| ATOM | 2394 | CD1 | LEU | B1046 | −20.832 | −2.953 | −33.779 | 43.06 | C |
| ATOM | 2395 | CD2 | LEU | B1046 | −20.105 | −5.302 | −34.77 | 43.57 | C |
| ATOM | 2396 | C | LEU | B1046 | −21.81 | −3.071 | −37.017 | 38.8 | C |
| ATOM | 2397 | O | LEU | B1046 | −22.337 | −1.936 | −36.888 | 38.58 | O |
| ATOM | 2398 | N | LEU | B1046 | −19.683 | −2.665 | −38.453 | 39.51 | N |
| ATOM | 2399 | CA | LEU | B1046 | −20.269 | −3.271 | −37.199 | 39.72 | C |
| ATOM | 2400 | N | LEU | B1047 | −22.5 | −4.219 | −37.024 | 36.75 | N |
| ATOM | 2401 | CA | LEU | B1047 | −23.938 | −4.27 | −37.208 | 35 | C |
| ATOM | 2402 | CB | LEU | B1047 | −24.394 | −5.715 | −37.47 | 35.39 | C |
| ATOM | 2403 | CG | LEU | B1047 | −23.713 | −6.205 | −38.741 | 35.87 | C |
| ATOM | 2404 | CD1 | LEU | B1047 | −23.788 | −7.735 | −38.824 | 37.42 | C |
| ATOM | 2405 | CD2 | LEU | B1047 | −24.313 | −5.475 | −39.975 | 37.06 | C |
| ATOM | 2406 | C | LEU | B1047 | −24.768 | −3.645 | −36.094 | 34.09 | C |
| ATOM | 2407 | O | LEU | B1047 | −25.941 | −3.357 | −36.318 | 34.1 | O |
| ATOM | 2408 | N | GLN | B1048 | −24.173 | −3.443 | −34.92 | 32.01 | N |
| ATOM | 2409 | CA | GLN | B1048 | −24.918 | −2.908 | −33.804 | 31.29 | C |
| ATOM | 2410 | CB | GLN | B1048 | −24.251 | −3.227 | −32.485 | 32.27 | C |
| ATOM | 2411 | CG | GLN | B1048 | −25.255 | −3.176 | −31.342 | 33.61 | C |
| ATOM | 2412 | CD | GLN | B1048 | −26.259 | −4.273 | −31.386 | 32.27 | C |
| ATOM | 2413 | OE1 | GLN | B1048 | −27.227 | −4.221 | −30.635 | 33.78 | O |

TABLE 1A-continued

| | | | | | | | | |
|---|---|---|---|---|---|---|---|---|
| ATOM | 2414 | NE2 | GLN | B1048 | −26.062 | −5.279 | −32.267 | 31.81 | N |
| ATOM | 2415 | C | GLN | B1048 | −25.025 | −1.417 | −33.875 | 29.15 | C |
| ATOM | 2416 | O | GLN | B1048 | −25.992 | −0.848 | −33.361 | 27.54 | O |
| ATOM | 2417 | N | ASN | B1049 | −24.017 | −0.83 | −34.532 | 26.05 | N |
| ATOM | 2418 | CA | ASN | B1049 | −23.931 | 0.576 | −34.716 | 23.59 | C |
| ATOM | 2419 | CB | ASN | B1049 | −22.482 | 1.001 | −34.97 | 24.38 | C |
| ATOM | 2420 | CG | ASN | B1049 | −21.622 | 0.973 | −33.648 | 24.85 | C |
| ATOM | 2421 | OD1 | ASN | B1049 | −22.107 | 1.324 | −32.587 | 26.09 | O |
| ATOM | 2422 | ND2 | ASN | B1049 | −20.402 | 0.522 | −33.731 | 21.98 | N |
| ATOM | 2423 | C | ASN | B1049 | −24.868 | 1.003 | −35.796 | 22.45 | C |
| ATOM | 2424 | O | ASN | B1049 | −24.841 | 2.144 | −36.211 | 23.31 | O |
| ATOM | 2425 | N | THR | B1050 | −25.734 | 0.094 | −36.206 | 20.21 | N |
| ATOM | 2426 | CA | THR | B1050 | −26.721 | 0.383 | −37.195 | 20.27 | C |
| ATOM | 2427 | CB | THR | B1050 | −26.531 | −0.463 | −38.515 | 21.41 | C |
| ATOM | 2428 | OG1 | THR | B1050 | −26.525 | −1.886 | −38.239 | 19.46 | O |
| ATOM | 2429 | CG2 | THR | B1050 | −25.199 | −0.064 | −39.193 | 19.7 | C |
| ATOM | 2430 | C | THR | B1050 | −28.101 | 0.169 | −36.592 | 20.15 | C |
| ATOM | 2431 | O | THR | B1050 | −29.095 | 0.325 | −37.282 | 21.67 | O |
| ATOM | 2432 | N | VAL | B1051 | −28.179 | −0.187 | −35.313 | 18.2 | N |
| ATOM | 2433 | CA | VAL | B1051 | −29.469 | −0.378 | −34.68 | 16.02 | C |
| ATOM | 2434 | CB | VAL | B1051 | −29.476 | −1.635 | −33.802 | 15.07 | C |
| ATOM | 2435 | CG1 | VAL | B1051 | −30.907 | −1.929 | −33.219 | 13 | C |
| ATOM | 2436 | CG2 | VAL | B1051 | −28.978 | −2.812 | −34.622 | 14.4 | C |
| ATOM | 2437 | C | VAL | B1051 | −29.942 | 0.86 | −33.933 | 15.78 | C |
| ATOM | 2438 | O | VAL | B1051 | −29.384 | 1.279 | −32.964 | 16.31 | O |
| ATOM | 2439 | N | HIS | B1052 | −31.027 | 1.411 | −34.394 | 16.59 | N |
| ATOM | 2440 | CA | HIS | B1052 | −31.618 | 2.529 | −33.778 | 18.42 | C |
| ATOM | 2441 | CB | HIS | B1052 | −31.387 | 3.822 | −34.557 | 18.24 | C |
| ATOM | 2442 | CG | HIS | B1052 | −32.216 | 4.963 | −34.042 | 19.56 | C |
| ATOM | 2443 | CD2 | HIS | B1052 | −33.382 | 5.5 | −34.497 | 21.3 | C |
| ATOM | 2444 | ND1 | HIS | B1052 | −31.871 | 5.688 | −32.909 | 18.28 | N |
| ATOM | 2445 | CE1 | HIS | B1052 | −32.789 | 6.613 | −32.687 | 21.03 | C |
| ATOM | 2446 | NE2 | HIS | B1052 | −33.717 | 6.522 | −33.639 | 22.99 | N |
| ATOM | 2447 | C | HIS | B1052 | −33.121 | 2.309 | −33.659 | 19.7 | C |
| ATOM | 2448 | O | HIS | B1052 | −33.795 | 2.169 | −34.623 | 17.97 | O |
| ATOM | 2449 | N | ILE | B1053 | −33.613 | 2.326 | −32.421 | 22.55 | N |
| ATOM | 2450 | CA | ILE | B1053 | −35.034 | 2.208 | −32.114 | 23.12 | C |
| ATOM | 2451 | CB | ILE | B1053 | −35.285 | 0.984 | −31.134 | 23.12 | C |
| ATOM | 2452 | CG2 | ILE | B1053 | −36.733 | 0.925 | −30.644 | 24.87 | C |
| ATOM | 2453 | CG1 | ILE | B1053 | −35.093 | −0.36 | −31.88 | 25.79 | C |
| ATOM | 2454 | CD1 | ILE | B1053 | −33.685 | −0.82 | −31.891 | 25.97 | C |
| ATOM | 2455 | C | ILE | B1053 | −35.501 | 3.595 | −31.605 | 22.88 | C |
| ATOM | 2456 | O | ILE | B1053 | −34.884 | 4.229 | −30.723 | 21.71 | O |
| ATOM | 2457 | N | ASP | B1054 | −36.547 | 4.089 | −32.257 | 23.62 | N |
| ATOM | 2458 | CA | ASP | B1054 | −37.259 | 5.279 | −31.796 | 22.76 | C |
| ATOM | 2459 | CB | ASP | B1054 | −37.853 | 6.041 | −32.94 | 21.73 | C |
| ATOM | 2460 | CG | ASP | B1054 | −38.49 | 7.376 | −32.487 | 25.42 | C |
| ATOM | 2461 | OD1 | ASP | B1054 | −38.42 | 7.74 | −31.259 | 22.46 | O |
| ATOM | 2462 | OD2 | ASP | B1054 | −39.062 | 8.047 | −33.389 | 24.97 | O |
| ATOM | 2463 | C | ASP | B1054 | −38.321 | 4.895 | −30.767 | 22.65 | C |
| ATOM | 2464 | O | ASP | B1054 | −39.403 | 4.347 | −31.071 | 21.94 | O |
| ATOM | 2465 | N | LEU | B1055 | −37.966 | 5.172 | −29.529 | 22.61 | N |
| ATOM | 2466 | CA | LEU | B1055 | −38.7 | 4.625 | −28.442 | 22.29 | C |
| ATOM | 2467 | CB | LEU | B1055 | −37.762 | 4.498 | −27.224 | 22.09 | C |
| ATOM | 2468 | CG | LEU | B1055 | −36.525 | 3.601 | −27.266 | 18 | C |
| ATOM | 2469 | CD1 | LEU | B1055 | −35.705 | 4.088 | −26.122 | 12.81 | C |
| ATOM | 2470 | CD2 | LEU | B1055 | −36.869 | 2.13 | −27.07 | 13.43 | C |
| ATOM | 2471 | C | LEU | B1055 | −39.982 | 5.424 | −28.134 | 22.75 | C |
| ATOM | 2472 | O | LEU | B1055 | −40.843 | 4.978 | −27.358 | 23.67 | O |
| ATOM | 2473 | N | SER | B1056 | −40.102 | 6.61 | −28.713 | 22.3 | N |
| ATOM | 2474 | CA | SER | B1056 | −41.315 | 7.386 | −28.546 | 22.63 | C |
| ATOM | 2475 | CB | SER | B1056 | −41.038 | 8.903 | −28.703 | 22.8 | C |
| ATOM | 2476 | OG | SER | B1056 | −41.157 | 9.337 | −30.088 | 27.69 | O |
| ATOM | 2477 | C | SER | B1056 | −42.349 | 6.877 | −29.561 | 21.86 | C |
| ATOM | 2478 | O | SER | B1056 | −43.533 | 7.151 | −29.427 | 21.84 | O |
| ATOM | 2479 | N | ALA | B1057 | −41.879 | 6.157 | −30.584 | 20.99 | N |
| ATOM | 2480 | CA | ALA | B1057 | −42.734 | 5.647 | −31.616 | 20.22 | C |
| ATOM | 2481 | CB | ALA | B1057 | −41.99 | 5.632 | −32.978 | 18.95 | C |
| ATOM | 2482 | C | ALA | B1057 | −43.307 | 4.264 | −31.229 | 21.18 | C |
| ATOM | 2483 | O | ALA | B1057 | −44.219 | 3.778 | −31.926 | 20.6 | O |
| ATOM | 2484 | N | ILE | B1058 | −42.83 | 3.636 | −30.124 | 21.64 | N |
| ATOM | 2485 | CA | ILE | B1058 | −43.436 | 2.342 | −29.748 | 24.04 | C |
| ATOM | 2486 | CB | ILE | B1058 | −42.458 | 1.292 | −28.981 | 25.07 | C |
| ATOM | 2487 | CG2 | ILE | B1058 | −42.049 | 0.035 | −29.832 | 24.86 | C |
| ATOM | 2488 | CG1 | ILE | B1058 | −41.062 | 1.827 | −28.705 | 27.45 | C |
| ATOM | 2489 | CD1 | ILE | B1058 | −40.264 | 0.856 | −27.838 | 24.61 | C |
| ATOM | 2490 | C | ILE | B1058 | −44.831 | 2.573 | −29.065 | 24.88 | C |
| ATOM | 2491 | O | ILE | B1058 | −45.074 | 3.592 | −28.422 | 23.85 | O |
| ATOM | 2492 | N | ASP | B1059 | −45.751 | 1.635 | −29.243 | 25.65 | N |
| ATOM | 2493 | CA | ASP | B1059 | −47.12 | 1.761 | −28.726 | 27.02 | C |

TABLE 1A-continued

| | | | | | | | | |
|---|---|---|---|---|---|---|---|---|
| ATOM | 2494 | CB | ASP | B1059 | −47.874 | 0.466 | −29.066 | 27.56 | C |
| ATOM | 2495 | CG | ASP | B1059 | −49.325 | 0.485 | −28.635 | 30.75 | C |
| ATOM | 2496 | OD1 | ASP | B1059 | −49.705 | 1.293 | −27.785 | 40.3 | O |
| ATOM | 2497 | OD2 | ASP | B1059 | −50.123 | −0.314 | −29.14 | 31.86 | O |
| ATOM | 2498 | C | ASP | B1059 | −47.181 | 2.078 | −27.208 | 26.95 | C |
| ATOM | 2499 | O | ASP | B1059 | −46.646 | 1.356 | −26.4 | 26.36 | O |
| ATOM | 2500 | N | PRO | B1060 | −47.829 | 3.179 | −26.83 | 27.49 | N |
| ATOM | 2501 | CD | PRO | B1060 | −48.573 | 4.133 | −27.673 | 27.27 | C |
| ATOM | 2502 | CA | PRO | B1060 | −47.769 | 3.579 | −25.41 | 28.26 | C |
| ATOM | 2503 | CB | PRO | B1060 | −48.521 | 4.909 | −25.366 | 27.9 | C |
| ATOM | 2504 | CG | PRO | B1060 | −48.629 | 5.373 | −26.822 | 28.06 | C |
| ATOM | 2505 | C | PRO | B1060 | −48.32 | 2.587 | −24.385 | 29.45 | C |
| ATOM | 2506 | O | PRO | B1060 | −47.748 | 2.415 | −23.307 | 30.22 | O |
| ATOM | 2507 | N | GLU | B1061 | −49.408 | 1.942 | −24.706 | 30.74 | N |
| ATOM | 2508 | CA | GLU | B1061 | −49.959 | 0.958 | −23.839 | 33.13 | C |
| ATOM | 2509 | CB | GLU | B1061 | −51.478 | 0.826 | −24.17 | 34.78 | C |
| ATOM | 2510 | CG | GLU | B1061 | −51.864 | −0.178 | −25.282 | 40.8 | C |
| ATOM | 2511 | CD | GLU | B1061 | −52.775 | 0.432 | −26.428 | 49.08 | C |
| ATOM | 2512 | OE1 | GLU | B1061 | −52.827 | 1.704 | −26.613 | 48.2 | O |
| ATOM | 2513 | OE2 | GLU | B1061 | −53.38 | −0.394 | −27.2 | 48.8 | O |
| ATOM | 2514 | C | GLU | B1061 | −49.165 | −0.372 | −23.908 | 33.24 | C |
| ATOM | 2515 | O | GLU | B1061 | −49.181 | −1.18 | −22.979 | 34.27 | O |
| ATOM | 2516 | N | LEU | B1062 | −48.453 | −0.62 | −25.007 | 32.69 | N |
| ATOM | 2517 | CA | LEU | B1062 | −47.536 | −1.766 | −25.044 | 30.44 | C |
| ATOM | 2518 | CB | LEU | B1062 | −47.052 | −2.023 | −26.48 | 29.15 | C |
| ATOM | 2519 | CG | LEU | B1062 | −45.923 | −2.999 | −26.687 | 27.13 | C |
| ATOM | 2520 | CD1 | LEU | B1062 | −46.297 | −4.408 | −26.216 | 31.15 | C |
| ATOM | 2521 | CD2 | LEU | B1062 | −45.616 | −3.05 | −28.073 | 27.14 | C |
| ATOM | 2522 | C | LEU | B1062 | −46.37 | −1.497 | −24.1 | 30 | C |
| ATOM | 2523 | O | LEU | B1062 | −45.786 | −2.41 | −23.486 | 30.93 | O |
| ATOM | 2524 | N | VAL | B1063 | −46.038 | −0.227 | −23.992 | 29.06 | N |
| ATOM | 2525 | CA | VAL | B1063 | −44.925 | 0.206 | −23.206 | 29 | C |
| ATOM | 2526 | CB | VAL | B1063 | −44.365 | 1.581 | −23.717 | 29.34 | C |
| ATOM | 2527 | CG1 | VAL | B1063 | −43.551 | 2.311 | −22.617 | 29.44 | C |
| ATOM | 2528 | CG2 | VAL | B1063 | −43.511 | 1.386 | −24.988 | 28.58 | C |
| ATOM | 2529 | C | VAL | B1063 | −45.321 | 0.238 | −21.745 | 29.41 | C |
| ATOM | 2530 | O | VAL | B1063 | −44.469 | 0.028 | −20.86 | 30.22 | O |
| ATOM | 2531 | N | GLN | B1064 | −46.6 | 0.454 | −21.467 | 29.08 | N |
| ATOM | 2532 | CA | GLN | B1064 | −47.005 | 0.512 | −20.079 | 30.44 | C |
| ATOM | 2533 | CB | GLN | B1064 | −48.222 | 1.421 | −19.809 | 30.98 | C |
| ATOM | 2534 | CG | GLN | B1064 | −49.62 | 0.775 | −19.89 | 33.87 | C |
| ATOM | 2535 | CD | GLN | B1064 | −50.761 | 1.864 | −19.961 | 35.5 | C |
| ATOM | 2536 | OE1 | GLN | B1064 | −50.849 | 2.665 | −20.92 | 36.93 | O |
| ATOM | 2537 | NE2 | GLN | B1064 | −51.619 | 1.884 | −18.929 | 38.37 | N |
| ATOM | 2538 | C | GLN | B1064 | −47.189 | −0.853 | −19.531 | 28.49 | C |
| ATOM | 2539 | O | GLN | B1064 | −46.973 | −1.035 | −18.366 | 29.12 | O |
| ATOM | 2540 | N | ALA | B1065 | −47.533 | −1.823 | −20.37 | 27.57 | N |
| ATOM | 2541 | CA | ALA | B1065 | −47.577 | −3.233 | −19.945 | 26.74 | C |
| ATOM | 2542 | CB | ALA | B1065 | −48.221 | −4.172 | −21.041 | 25.84 | C |
| ATOM | 2543 | C | ALA | B1065 | −46.183 | −3.745 | −19.532 | 25.79 | C |
| ATOM | 2544 | O | ALA | B1065 | −46.007 | −4.275 | −18.419 | 27.1 | O |
| ATOM | 2545 | N | VAL | B1066 | −45.179 | −3.577 | −20.408 | 24.07 | N |
| ATOM | 2546 | CA | VAL | B1066 | −43.793 | −3.985 | −20.037 | 20.35 | C |
| ATOM | 2547 | CB | VAL | B1066 | −42.881 | −4.179 | −21.255 | 19.59 | C |
| ATOM | 2548 | CG1 | VAL | B1066 | −43.498 | −5.217 | −22.2 | 21.58 | C |
| ATOM | 2549 | CG2 | VAL | B1066 | −42.557 | −2.906 | −21.898 | 16.39 | C |
| ATOM | 2550 | C | VAL | B1066 | −43.041 | −3.122 | −19.037 | 18.35 | C |
| ATOM | 2551 | O | VAL | B1066 | −42.011 | −3.581 | −18.522 | 15.66 | O |
| ATOM | 2552 | N | GLN | B1067 | −43.518 | −1.892 | −18.781 | 17.6 | N |
| ATOM | 2553 | CA | GLN | B1067 | −42.692 | −0.943 | −18.001 | 18.58 | C |
| ATOM | 2554 | CB | GLN | B1067 | −43.438 | 0.308 | −17.614 | 19.35 | C |
| ATOM | 2555 | CG | GLN | B1067 | −42.496 | 1.426 | −17.248 | 21.19 | C |
| ATOM | 2556 | CD | GLN | B1067 | −42.009 | 2.22 | −18.529 | 28.66 | C |
| ATOM | 2557 | OE1 | GLN | B1067 | −42.801 | 2.91 | −19.19 | 34.61 | O |
| ATOM | 2558 | NE2 | GLN | B1067 | −40.715 | 2.116 | −18.857 | 29.45 | N |
| ATOM | 2559 | C | GLN | B1067 | −42.037 | −1.527 | −16.752 | 18.71 | C |
| ATOM | 2560 | O | GLN | B1067 | −40.856 | −1.297 | −16.503 | 18.11 | O |
| ATOM | 2561 | N | HIS | B1068 | −42.803 | −2.315 | −15.979 | 18.98 | N |
| ATOM | 2562 | CA | HIS | B1068 | −42.268 | −2.956 | −14.767 | 17.95 | C |
| ATOM | 2563 | CB | HIS | B1068 | −43.383 | −3.675 | −13.987 | 17.82 | C |
| ATOM | 2564 | CG | HIS | B1068 | −43.839 | −4.954 | −14.606 | 17.17 | C |
| ATOM | 2565 | CD2 | HIS | B1068 | −43.713 | −6.237 | −14.176 | 14.13 | C |
| ATOM | 2566 | ND1 | HIS | B1068 | −44.53 | −5.009 | −15.811 | 17.44 | N |
| ATOM | 2567 | CE1 | HIS | B1068 | −44.793 | −6.274 | −16.089 | 13.01 | C |
| ATOM | 2568 | NE2 | HIS | B1068 | −44.304 | −7.033 | −15.111 | 8.61 | N |
| ATOM | 2569 | C | HIS | B1068 | −41.102 | −3.933 | −15.002 | 18.08 | C |
| ATOM | 2570 | O | HIS | B1068 | −40.532 | −4.395 | −14.033 | 18.66 | O |
| ATOM | 2571 | N | VAL | B1069 | −40.726 | −4.255 | −16.243 | 16.48 | N |
| ATOM | 2572 | CA | VAL | B1069 | −39.549 | −5.075 | −16.433 | 16.15 | C |
| ATOM | 2573 | CB | VAL | B1069 | −39.863 | −6.453 | −17.109 | 16.83 | C |

TABLE 1A-continued

| | | | | | | | | |
|---|---|---|---|---|---|---|---|---|
| ATOM | 2574 | CG1 | VAL | B1069 | −41.014 | −7.1 | −16.412 | 19.33 | C |
| ATOM | 2575 | CG2 | VAL | B1069 | −40.229 | −6.338 | −18.559 | 14.34 | C |
| ATOM | 2576 | C | VAL | B1069 | −38.471 | −4.345 | −17.176 | 17.86 | C |
| ATOM | 2577 | O | VAL | B1069 | −37.419 | −4.952 | −17.516 | 16.09 | O |
| ATOM | 2578 | N | VAL | B1070 | −38.712 | −3.044 | −17.429 | 18.48 | N |
| ATOM | 2579 | CA | VAL | B1070 | −37.723 | −2.234 | −18.045 | 20.54 | C |
| ATOM | 2580 | CB | VAL | B1070 | −38.351 | −1.049 | −18.735 | 20.78 | C |
| ATOM | 2581 | CG1 | VAL | B1070 | −37.268 | 0.109 | −19.063 | 18.98 | C |
| ATOM | 2582 | CG2 | VAL | B1070 | −39.005 | −1.533 | −19.984 | 18.5 | C |
| ATOM | 2583 | C | VAL | B1070 | −36.728 | −1.82 | −16.945 | 24.51 | C |
| ATOM | 2584 | O | VAL | B1070 | −37.163 | −1.379 | −15.872 | 24.82 | O |
| ATOM | 2585 | N | ILE | B1071 | −35.412 | −1.965 | −17.193 | 26.55 | N |
| ATOM | 2586 | CA | ILE | B1071 | −34.446 | −1.77 | −16.119 | 30.01 | C |
| ATOM | 2587 | CB | ILE | B1071 | −33.245 | −2.653 | −16.216 | 30.69 | C |
| ATOM | 2588 | CG2 | ILE | B1071 | −32.383 | −2.125 | −17.338 | 33.43 | C |
| ATOM | 2589 | CG1 | ILE | B1071 | −32.445 | −2.495 | −14.932 | 33.59 | C |
| ATOM | 2590 | CD1 | ILE | B1071 | −31.103 | −3.292 | −14.886 | 40.65 | C |
| ATOM | 2591 | C | ILE | B1071 | −33.891 | −0.359 | −15.933 | 30.56 | C |
| ATOM | 2592 | O | ILE | B1071 | −33.696 | 0.101 | −14.761 | 34.27 | O |
| ATOM | 2593 | N | GLY | B1072 | −33.597 | 0.356 | −17.004 | 29.37 | N |
| ATOM | 2594 | CA | GLY | B1072 | −33.137 | 1.712 | −16.772 | 26.85 | C |
| ATOM | 2595 | C | GLY | B1072 | −31.662 | 1.57 | −16.679 | 26.99 | C |
| ATOM | 2596 | O | GLY | B1072 | −31.176 | 0.816 | −15.851 | 25.3 | O |
| ATOM | 2597 | N | PRO | B1073 | −30.927 | 2.277 | −17.567 | 27.71 | N |
| ATOM | 2598 | CD | PRO | B1073 | −31.427 | 3.359 | −18.434 | 27.61 | C |
| ATOM | 2599 | CA | PRO | B1073 | −29.496 | 2.058 | −17.766 | 27.02 | C |
| ATOM | 2600 | CB | PRO | B1073 | −29.153 | 3.005 | −18.892 | 27.25 | C |
| ATOM | 2601 | CG | PRO | B1073 | −30.131 | 4.068 | −18.823 | 28.49 | C |
| ATOM | 2602 | C | PRO | B1073 | −28.623 | 2.277 | −16.545 | 27.4 | C |
| ATOM | 2603 | O | PRO | B1073 | −27.721 | 1.477 | −16.282 | 29 | O |
| ATOM | 2604 | N | SER | B1074 | −28.896 | 3.3 | −15.759 | 26.53 | N |
| ATOM | 2605 | CA | SER | B1074 | −28.106 | 3.497 | −14.564 | 25.63 | C |
| ATOM | 2606 | CB | SER | B1074 | −28.601 | 4.769 | −13.836 | 27.59 | C |
| ATOM | 2607 | OG | SER | B1074 | −29.856 | 4.546 | −13.133 | 31.65 | O |
| ATOM | 2608 | C | SER | B1074 | −28.251 | 2.296 | −13.622 | 23.1 | C |
| ATOM | 2609 | O | SER | B1074 | −27.384 | 2.065 | −12.768 | 23.98 | O |
| ATOM | 2610 | N | SER | B1075 | −29.357 | 1.574 | −13.71 | 18.79 | N |
| ATOM | 2611 | CA | SER | B1075 | −29.571 | 0.456 | −12.794 | 18.39 | C |
| ATOM | 2612 | CB | SER | B1075 | −31.059 | 0.086 | −12.656 | 17.77 | C |
| ATOM | 2613 | OG | SER | B1075 | −31.839 | 1.212 | −12.351 | 19.47 | O |
| ATOM | 2614 | C | SER | B1075 | −28.779 | −0.81 | −13.213 | 17.24 | C |
| ATOM | 2615 | O | SER | B1075 | −28.733 | −1.788 | −12.462 | 16.14 | O |
| ATOM | 2616 | N | LEU | B1076 | −28.205 | −0.789 | −14.42 | 16.22 | N |
| ATOM | 2617 | CA | LEU | B1076 | −27.525 | −1.956 | −14.919 | 17.04 | C |
| ATOM | 2618 | CB | LEU | B1076 | −28.278 | −2.618 | −16.083 | 15.02 | C |
| ATOM | 2619 | CG | LEU | B1076 | −27.488 | −3.894 | −16.519 | 13.13 | C |
| ATOM | 2620 | CD1 | LEU | B1076 | −27.606 | −5.133 | −15.543 | 7.07 | C |
| ATOM | 2621 | CD2 | LEU | B1076 | −27.827 | −4.35 | −17.936 | 8.37 | C |
| ATOM | 2622 | C | LEU | B1076 | −26.094 | −1.653 | −15.374 | 18 | C |
| ATOM | 2623 | O | LEU | B1076 | −25.845 | −0.71 | −16.155 | 18.86 | O |
| ATOM | 2624 | N | ILE | B1077 | −25.169 | −2.464 | −14.871 | 18.31 | N |
| ATOM | 2625 | CA | ILE | B1077 | −23.807 | −2.441 | −15.319 | 18.16 | C |
| ATOM | 2626 | CB | ILE | B1077 | −22.839 | −2.115 | −14.189 | 19.53 | C |
| ATOM | 2627 | CG2 | ILE | B1077 | −22.56 | −3.33 | −13.34 | 22.33 | C |
| ATOM | 2628 | CG1 | ILE | B1077 | −21.569 | −1.492 | −14.799 | 21.29 | C |
| ATOM | 2629 | CD1 | ILE | B1077 | −21.712 | 0.173 | −14.883 | 24.57 | C |
| ATOM | 2630 | C | ILE | B1077 | −23.434 | −3.727 | −16.041 | 16.53 | C |
| ATOM | 2631 | O | ILE | B1077 | −23.573 | −4.818 | −15.513 | 15.15 | O |
| ATOM | 2632 | N | VAL | B1078 | −23.04 | −3.586 | −17.297 | 15.26 | N |
| ATOM | 2633 | CA | VAL | B1078 | −22.6 | −4.742 | −18.049 | 15.42 | C |
| ATOM | 2634 | CB | VAL | B1078 | −23.043 | −4.673 | −19.544 | 16.36 | C |
| ATOM | 2635 | CG1 | VAL | B1078 | −22.471 | −5.905 | −20.285 | 14.87 | C |
| ATOM | 2636 | CG2 | VAL | B1078 | −24.636 | −4.51 | −19.726 | 11.11 | C |
| ATOM | 2637 | C | VAL | B1078 | −21.104 | −4.807 | −17.967 | 15.76 | C |
| ATOM | 2638 | O | VAL | B1078 | −20.415 | −3.899 | −18.399 | 16.11 | O |
| ATOM | 2639 | N | HIS | B1079 | −20.585 | −5.882 | −17.405 | 17.22 | N |
| ATOM | 2640 | CA | HIS | B1079 | −19.151 | −6.04 | −17.273 | 17.57 | C |
| ATOM | 2641 | CB | HIS | B1079 | −18.811 | −6.974 | −16.077 | 16.84 | C |
| ATOM | 2642 | CG | HIS | B1079 | −19.364 | −6.485 | −14.776 | 17.03 | C |
| ATOM | 2643 | CD2 | HIS | B1079 | −20.056 | −7.12 | −13.793 | 21.02 | C |
| ATOM | 2644 | ND1 | HIS | B1079 | −19.275 | −5.165 | −14.389 | 16.77 | N |
| ATOM | 2645 | CE1 | HIS | B1079 | −19.92 | −5 | −13.24 | 19.8 | C |
| ATOM | 2646 | NE2 | HIS | B1079 | −20.386 | −6.173 | −12.847 | 20.06 | N |
| ATOM | 2647 | C | HIS | B1079 | −18.635 | −6.581 | −18.64 | 18.29 | C |
| ATOM | 2648 | O | HIS | B1079 | −18.643 | −7.789 | −18.891 | 19.18 | O |
| ATOM | 2649 | N | PHE | B1080 | −18.201 | −5.68 | −19.514 | 18.22 | N |
| ATOM | 2650 | CA | PHE | B1080 | −17.706 | −6.073 | −20.82 | 19.57 | C |
| ATOM | 2651 | CB | PHE | B1080 | −17.608 | −4.889 | −21.759 | 19.74 | C |
| ATOM | 2652 | CG | PHE | B1080 | −18.942 | −4.432 | −22.233 | 19.46 | C |
| ATOM | 2653 | CD1 | PHE | B1080 | −19.751 | −5.295 | −22.93 | 23.85 | C |

TABLE 1A-continued

| ATOM | 2654 | CD2 | PHE | B1080 | −19.403 | −3.179 | −21.925 | 22.05 | C |
|---|---|---|---|---|---|---|---|---|---|
| ATOM | 2655 | CE1 | PEE | B1080 | −21.015 | −4.902 | −23.356 | 26.81 | C |
| ATOM | 2656 | CE2 | PHE | B1080 | −20.663 | −2.732 | −22.313 | 21.69 | C |
| ATOM | 2657 | CZ | PHE | B1080 | −21.491 | −3.592 | −23.037 | 25.84 | C |
| ATOM | 2658 | C | PHE | B1080 | −16.419 | −6.756 | −20.781 | 20.12 | C |
| ATOM | 2659 | O | PHE | B1080 | −15.98 | −7.259 | −21.786 | 21.86 | O |
| ATOM | 2660 | N | ASN | B1081 | −15.811 | −6.815 | −19.61 | 20.99 | N |
| ATOM | 2661 | CA | ASN | B1081 | −14.49 | −7.401 | −19.465 | 21.84 | C |
| ATOM | 2662 | CB | ASN | B1081 | −13.673 | −6.529 | −18.514 | 21.63 | C |
| ATOM | 2663 | CG | ASN | B1081 | −14.274 | −6.49 | −17.069 | 20.2 | C |
| ATOM | 2664 | OD1 | ASN | B1081 | −15.501 | −6.616 | −16.867 | 16.99 | O |
| ATOM | 2665 | ND2 | ASN | B1081 | −13.405 | −6.322 | −16.085 | 15.89 | N |
| ATOM | 2666 | C | ASN | B1081 | −14.606 | −8.795 | −18.867 | 23.39 | C |
| ATOM | 2667 | O | ASN | B1081 | −13.604 | −9.426 | −18.54 | 24.79 | O |
| ATOM | 2668 | N | GLU | B1082 | −15.829 | −9.267 | −18.702 | 24.64 | N |
| ATOM | 2669 | CA | GLU | B1082 | −16.084 | −10.518 | −18.036 | 26.06 | C |
| ATOM | 2670 | CB | GLU | B1082 | −16.522 | −10.215 | −16.577 | 29.29 | C |
| ATOM | 2671 | CG | GLU | B1082 | −16.231 | −11.268 | −15.473 | 34.27 | C |
| ATOM | 2672 | CD | GLU | B1082 | −14.907 | −11.959 | −15.704 | 44.49 | C |
| ATOM | 2673 | OE1 | GLU | B1082 | −14.676 | −13.031 | −15.057 | 45.75 | O |
| ATOM | 2674 | OE2 | GLU | B1082 | −14.119 | −11.43 | −16.551 | 46.68 | O |
| ATOM | 2675 | C | GLU | B1082 | −17.217 | −11.233 | −18.766 | 24.39 | C |
| ATOM | 2676 | O | GLU | B1082 | −18.366 | −11.067 | −18.417 | 23.91 | O |
| ATOM | 2677 | N | VAL | B1083 | −16.87 | −12.048 | −19.745 | 22.94 | N |
| ATOM | 2678 | CA | VAL | B1083 | −17.822 | −12.922 | −20.483 | 21.14 | C |
| ATOM | 2679 | CB | VAL | B1083 | −17.234 | −13.339 | −21.91 | 20.22 | C |
| ATOM | 2680 | CG1 | VAL | B1083 | −18.168 | −14.113 | −22.678 | 20.65 | C |
| ATOM | 2681 | CG2 | VAL | B1083 | −16.972 | −12.155 | −22.701 | 20.7 | C |
| ATOM | 2682 | C | VAL | B1083 | −18.119 | −14.182 | −19.678 | 19.57 | C |
| ATOM | 2683 | O | VAL | B1083 | −17.216 | −14.89 | −19.278 | 20.67 | O |
| ATOM | 2684 | N | ILE | B1084 | −19.388 | −14.495 | −19.475 | 18.67 | N |
| ATOM | 2685 | CA | ILE | B1084 | −19.753 | −15.742 | −18.846 | 16.22 | C |
| ATOM | 2686 | CB | ILE | B1084 | −21.28 | −15.711 | −18.512 | 17.63 | C |
| ATOM | 2687 | CG2 | ILE | B1084 | −21.768 | −17.038 | −17.916 | 17.14 | C |
| ATOM | 2688 | CG1 | ILE | B1084 | −21.664 | −14.544 | −17.596 | 17.65 | C |
| ATOM | 2689 | CD1 | ILE | B1084 | −23.067 | −14.626 | −17.029 | 11.56 | C |
| ATOM | 2690 | C | ILE | B1084 | −19.458 | −16.902 | −19.867 | 16.46 | C |
| ATOM | 2691 | O | ILE | B1084 | −18.887 | −17.914 | −19.53 | 15.12 | O |
| ATOM | 2692 | N | GLY | B1085 | −19.893 | −16.739 | −21.118 | 16.34 | N |
| ATOM | 2693 | CA | GLY | B1085 | −19.514 | −17.614 | −22.216 | 16.79 | C |
| ATOM | 2694 | C | GLY | B1085 | −19.858 | −17.033 | −23.558 | 18.48 | C |
| ATOM | 2695 | O | GLY | B1085 | −20.736 | −16.182 | −23.688 | 17.84 | O |
| ATOM | 2696 | N | ARG | B1086 | −19.122 | −17.454 | −24.572 | 21.62 | N |
| ATOM | 2697 | CA | ARG | B1086 | −19.513 | −17.188 | −25.976 | 24.64 | C |
| ATOM | 2698 | CB | ARG | B1086 | −18.458 | −16.397 | −26.721 | 24.78 | C |
| ATOM | 2699 | CG | ARG | B1086 | −17.073 | −16.877 | −26.491 | 31.15 | C |
| ATOM | 2700 | CD | ARG | B1086 | −16.223 | −15.631 | −26.219 | 35.05 | C |
| ATOM | 2701 | NE | ARG | B1086 | −16.505 | −14.628 | −27.228 | 34.79 | N |
| ATOM | 2702 | CZ | ARG | B1086 | −16.196 | −13.337 | −27.146 | 39.83 | C |
| ATOM | 2703 | NH1 | ARG | B1086 | −15.603 | −12.816 | −26.057 | 37.31 | N |
| ATOM | 2704 | NH2 | ARG | B1086 | −16.52 | −12.555 | −28.176 | 42.02 | N |
| ATOM | 2705 | C | ARG | B1086 | −19.868 | −18.464 | −26.719 | 24.15 | C |
| ATOM | 2706 | O | ARG | B1086 | −19.849 | −19.536 | −26.129 | 25.44 | O |
| ATOM | 2707 | N | GLY | B1087 | −20.246 | −18.354 | −27.988 | 24.14 | N |
| ATOM | 2708 | CA | GLY | B1087 | −20.613 | −19.541 | −28.764 | 22.48 | C |
| ATOM | 2709 | C | GLY | B1087 | −21.557 | −19.128 | −29.866 | 22.96 | C |
| ATOM | 2710 | O | GLY | B1087 | −21.668 | −17.947 | −30.179 | 22.52 | O |
| ATOM | 2711 | N | HIS | B1088 | −22.276 | −20.087 | −30.435 | 22.87 | N |
| ATOM | 2712 | CA | HIS | B1088 | −23.123 | −19.797 | −31.547 | 23.11 | C |
| ATOM | 2713 | CB | HIS | B1088 | −23.739 | −21.099 | −32.06 | 23.86 | C |
| ATOM | 2714 | CG | HIS | B1088 | −22.764 | −22.012 | −32.747 | 29.02 | C |
| ATOM | 2715 | CD2 | HIS | B1088 | −21.826 | −21.771 | −33.703 | 33.46 | C |
| ATOM | 2716 | ND1 | HIS | B1088 | −22.688 | −23.375 | −32.471 | 31.16 | N |
| ATOM | 2717 | CE1 | HIS | B1088 | −21.741 | −23.927 | −33.216 | 31.77 | C |
| ATOM | 2718 | NE2 | HIS | B1088 | −21.198 | −22.979 | −33.969 | 35.52 | N |
| ATOM | 2719 | C | HIS | B1088 | −24.199 | −18.805 | −31.131 | 22.73 | C |
| ATOM | 2720 | O | HIS | B1088 | −24.67 | −18.004 | −31.946 | 23.01 | O |
| ATOM | 2721 | N | PHE | B1089 | −24.611 | −18.88 | −29.856 | 21.15 | N |
| ATOM | 2722 | CA | PHE | B1089 | −25.64 | −17.965 | −29.292 | 19.41 | C |
| ATOM | 2723 | CB | PHE | B1089 | −26.116 | −18.361 | −27.851 | 17.09 | C |
| ATOM | 2724 | CG | PHE | B1089 | −24.998 | −18.644 | −26.906 | 15.09 | C |
| ATOM | 2725 | CD1 | PHE | B1089 | −24.57 | −19.945 | −26.708 | 10.23 | C |
| ATOM | 2726 | CD2 | PHE | B1089 | −24.337 | −17.606 | −26.235 | 15.28 | C |
| ATOM | 2727 | CE1 | PHE | B1089 | −23.533 | −20.227 | −25.91 | 12.01 | C |
| ATOM | 2728 | CE2 | PHE | B1089 | −23.256 | −17.882 | −25.376 | 11.78 | C |
| ATOM | 2729 | CZ | PHE | B1089 | −22.833 | −19.17 | −25.219 | 12.66 | C |
| ATOM | 2730 | C | PHE | B1089 | −25.193 | −16.546 | −29.29 | 18.49 | C |
| ATOM | 2731 | O | PHE | B1089 | −26.008 | −15.624 | −29.268 | 19.76 | O |
| ATOM | 2732 | N | GLY | B1090 | −23.888 | −16.375 | −29.266 | 18.92 | N |
| ATOM | 2733 | CA | GLY | B1090 | −23.269 | −15.059 | −29.181 | 18.6 | C |

TABLE 1A-continued

| | | | | | | | | |
|---|---|---|---|---|---|---|---|---|
| ATOM | 2734 | C | GLY | B1090 | −22.421 | −14.958 | −27.952 | 19.37 | C |
| ATOM | 2735 | O | GLY | B1090 | −21.628 | −15.857 | −27.601 | 19.8 | O |
| ATOM | 2736 | N | CYS | B1091 | −22.632 | −13.863 | −27.246 | 20.89 | N |
| ATOM | 2737 | CA | CYS | B1091 | −21.784 | −13.532 | −26.131 | 18.73 | C |
| ATOM | 2738 | CB | CYS | B1091 | −20.765 | −12.491 | −26.582 | 17.69 | C |
| ATOM | 2739 | SG | CYS | B1091 | −19.599 | −12.191 | −25.292 | 25.76 | S |
| ATOM | 2740 | C | CYS | B1091 | −22.658 | −13.055 | −24.95 | 16.84 | C |
| ATOM | 2741 | O | CYS | B1091 | −23.368 | −12.093 | −25.073 | 16.87 | O |
| ATOM | 2742 | N | VAL | B1092 | −22.606 | −13.784 | −23.821 | 15.9 | N |
| ATOM | 2743 | CA | VAL | B1092 | −23.285 | −13.453 | −22.564 | 13.08 | C |
| ATOM | 2744 | CB | VAL | B1092 | −23.925 | −14.71 | −22.003 | 13.11 | C |
| ATOM | 2745 | CG1 | VAL | B1092 | −24.666 | −14.416 | −20.667 | 11.81 | C |
| ATOM | 2746 | CG2 | VAL | B1092 | −24.849 | −15.318 | −23.044 | 9.74 | C |
| ATOM | 2747 | C | VAL | B1092 | −22.28 | −12.846 | −21.558 | 13.31 | C |
| ATOM | 2748 | O | VAL | B1092 | −21.195 | −13.45 | −21.285 | 12.97 | O |
| ATOM | 2749 | N | TYR | B1093 | −22.614 | −11.675 | −21.01 | 12.17 | N |
| ATOM | 2750 | CA | TYR | B1093 | −21.69 | −11.008 | −20.081 | 12.63 | C |
| ATOM | 2751 | CB | TYR | B1093 | −21.487 | −9.535 | −20.455 | 15.65 | C |
| ATOM | 2752 | CG | TYR | B1093 | −20.841 | −9.296 | −21.779 | 19.09 | C |
| ATOM | 2753 | CD1 | TYR | B1093 | −21.625 | −9.162 | −22.952 | 23.98 | C |
| ATOM | 2754 | CE1 | TYR | B1093 | −21.015 | −8.929 | −24.224 | 24.21 | C |
| ATOM | 2755 | CD2 | TYR | B1093 | −19.438 | −9.231 | −21.89 | 23.44 | C |
| ATOM | 2756 | CE2 | TYR | B1093 | −18.811 | −9.033 | −23.136 | 22.72 | C |
| ATOM | 2757 | CZ | TYR | B1093 | −19.613 | −8.866 | −24.294 | 24.32 | C |
| ATOM | 2758 | OH | TYR | B1093 | −19.014 | −8.678 | −25.537 | 26.39 | O |
| ATOM | 2759 | C | TYR | B1093 | −22.208 | −11.057 | −18.669 | 11.68 | C |
| ATOM | 2760 | O | TYR | B1093 | −23.387 | −11.169 | −18.415 | 10.89 | O |
| ATOM | 2761 | N | HIS | B1094 | −21.299 | −10.925 | −17.749 | 12.3 | N |
| ATOM | 2762 | CA | HIS | B1094 | −21.586 | −10.755 | −16.356 | 13.94 | C |
| ATOM | 2763 | CB | HIS | B1094 | −20.262 | −10.865 | −15.54 | 14.31 | C |
| ATOM | 2764 | CG | HIS | B1094 | −19.78 | −12.281 | −15.292 | 17.39 | C |
| ATOM | 2765 | CD2 | HIS | B1094 | −18.702 | −12.953 | −15.769 | 16.61 | C |
| ATOM | 2766 | ND1 | HIS | B1094 | −20.423 | −13.158 | −14.434 | 19.34 | N |
| ATOM | 2767 | CE1 | HIS | B1094 | −19.751 | −14.297 | −14.387 | 17.95 | C |
| ATOM | 2768 | NE2 | HIS | B1094 | −18.701 | −14.196 | −15.185 | 16.9 | N |
| ATOM | 2769 | C | HIS | B1094 | −22.193 | −9.334 | −16.234 | 14.54 | C |
| ATOM | 2770 | O | HIS | B1094 | −21.766 | −8.464 | −16.954 | 14.33 | O |
| ATOM | 2771 | N | GLY | B1095 | −23.174 | −9.125 | −15.343 | 15.33 | N |
| ATOM | 2772 | CA | GLY | B1095 | −23.679 | −7.799 | −15.024 | 17.33 | C |
| ATOM | 2773 | C | GLY | B1095 | −24.024 | −7.644 | −13.537 | 19.43 | C |
| ATOM | 2774 | O | GLY | B1095 | −24.178 | −8.645 | −12.821 | 20.21 | O |
| ATOM | 2775 | N | THR | B1096 | −24.127 | −6.395 | −13.075 | 19.44 | N |
| ATOM | 2776 | CA | THR | B1096 | −24.62 | −6.053 | −11.77 | 20.54 | C |
| ATOM | 2777 | CB | THR | B1096 | −23.533 | −5.296 | −10.884 | 22.73 | C |
| ATOM | 2778 | OG1 | THR | B1096 | −22.325 | −6.063 | −10.81 | 24.87 | O |
| ATOM | 2779 | CG2 | THR | B1096 | −23.999 | −4.975 | −9.458 | 21.73 | C |
| ATOM | 2780 | C | THR | B1096 | −25.899 | −5.216 | −11.944 | 20.08 | C |
| ATOM | 2781 | O | THR | B1096 | −25.953 | −4.19 | −12.614 | 18.92 | O |
| ATOM | 2782 | N | LEU | B1097 | −26.939 | −5.68 | −11.29 | 20.8 | N |
| ATOM | 2783 | CA | LEU | B1097 | −28.208 | −5.019 | −11.339 | 21.12 | C |
| ATOM | 2784 | CB | LEU | B1097 | −29.271 | −6.052 | −11.687 | 20.87 | C |
| ATOM | 2785 | CG | LEU | B1097 | −30.728 | −5.667 | −11.808 | 20.41 | C |
| ATOM | 2786 | CD1 | LEU | B1097 | −30.878 | −4.58 | −12.837 | 16.06 | C |
| ATOM | 2787 | CD2 | LEU | B1097 | −31.543 | −6.919 | −12.214 | 21.59 | C |
| ATOM | 2788 | C | LEU | B1097 | −28.466 | −4.378 | −9.989 | 21.74 | C |
| ATOM | 2789 | O | LEU | B1097 | −28.114 | −4.932 | −8.956 | 21.45 | O |
| ATOM | 2790 | N | LEU | B1098 | −29.026 | −3.183 | −10.009 | 22.86 | N |
| ATOM | 2791 | CA | LEU | B1098 | −29.656 | −2.633 | −8.818 | 25.58 | C |
| ATOM | 2792 | CB | LEU | B1098 | −29.714 | −1.129 | −8.928 | 27.1 | C |
| ATOM | 2793 | CG | LEU | B1098 | −28.506 | −0.437 | −8.287 | 32.12 | C |
| ATOM | 2794 | CD1 | LEU | B1098 | −28.999 | 0.999 | −7.909 | 35.01 | C |
| ATOM | 2795 | CD2 | LEU | B1098 | −27.972 | −1.212 | −7.019 | 32.02 | C |
| ATOM | 2796 | C | LEU | B1098 | −31.076 | −3.162 | −8.549 | 26.01 | C |
| ATOM | 2797 | O | LEU | B1098 | −32.028 | −2.912 | −9.356 | 25.42 | O |
| ATOM | 2798 | N | ASP | B1099 | −31.232 | −3.895 | −7.445 | 25.81 | N |
| ATOM | 2799 | CA | ASP | B1099 | −32.545 | −4.391 | −7.105 | 27.24 | C |
| ATOM | 2800 | CB | ASP | B1099 | −32.484 | −5.6 | −6.116 | 28.47 | C |
| ATOM | 2801 | CG | ASP | B1099 | −32.237 | −5.18 | −4.638 | 30.23 | C |
| ATOM | 2802 | OD1 | ASP | B1099 | −32.055 | −6.081 | −3.819 | 34.88 | O |
| ATOM | 2803 | OD2 | ASP | B1099 | −32.207 | −3.984 | −4.275 | 32.44 | O |
| ATOM | 2804 | C | ASP | B1099 | −33.44 | −3.248 | −6.602 | 27.3 | C |
| ATOM | 2805 | O | ASP | B1099 | −32.963 | −2.101 | −6.454 | 25.57 | O |
| ATOM | 2806 | N | ASN | B1100 | −34.724 | −3.579 | −6.33 | 28.29 | N |
| ATOM | 2807 | CA | ASN | B1100 | −35.721 | −2.609 | −5.847 | 28.31 | C |
| ATOM | 2808 | CB | ASN | B1100 | −37.072 | −3.219 | −5.631 | 26.71 | C |
| ATOM | 2809 | CG | ASN | B1100 | −38.145 | −2.143 | −5.454 | 26.73 | C |
| ATOM | 2810 | OD1 | ASN | B1100 | −38.8 | −2.068 | −4.398 | 20.33 | O |
| ATOM | 2811 | ND2 | ASN | B1100 | −38.335 | −1.282 | −6.52 | 26.17 | N |
| ATOM | 2812 | C | ASN | B1100 | −35.348 | −1.864 | −4.576 | 29.84 | C |
| ATOM | 2813 | O | ASN | B1100 | −35.804 | −0.737 | −4.363 | 29.24 | O |

TABLE 1A-continued

| | | | | | | | | |
|---|---|---|---|---|---|---|---|---|
| ATOM | 2814 | N | ASP | B1101 | −34.554 | −2.538 | −3.74 | 31.72 | N |
| ATOM | 2815 | CA | ASP | B1101 | −33.82 | −1.927 | −2.64 | 34.59 | C |
| ATOM | 2816 | CB | ASP | B1101 | −33.808 | −2.889 | −1.481 | 33.48 | C |
| ATOM | 2817 | CG | ASP | B1101 | −35.207 | −2.991 | −0.827 | 39.38 | C |
| ATOM | 2818 | OD1 | ASP | B1101 | −35.775 | −1.921 | −0.349 | 45.14 | O |
| ATOM | 2819 | OD2 | ASP | B1101 | −35.761 | −4.108 | −0.813 | 36.72 | O |
| ATOM | 2820 | C | ASP | B1101 | −32.413 | −1.465 | −3.077 | 36.69 | C |
| ATOM | 2821 | O | ASP | B1101 | −32.127 | −1.237 | −4.265 | 36.88 | O |
| ATOM | 2822 | N | GLY | B1102 | −31.498 | −1.305 | −2.143 | 39.09 | N |
| ATOM | 2823 | CA | GLY | B1102 | −30.124 | −0.924 | −2.613 | 40.88 | C |
| ATOM | 2824 | C | GLY | B1102 | −29.297 | −2.014 | −3.32 | 39.37 | C |
| ATOM | 2825 | O | GLY | B1102 | −28.518 | −1.73 | −4.196 | 39.26 | O |
| ATOM | 2826 | N | LYS | B1103 | −29.521 | −3.246 | −2.908 | 38.65 | N |
| ATOM | 2827 | CA | LYS | B1103 | −28.754 | −4.403 | −3.272 | 38.51 | C |
| ATOM | 2828 | CB | LYS | B1103 | −29.56 | −5.646 | −2.852 | 39.63 | C |
| ATOM | 2829 | CG | LYS | B1103 | −28.778 | −6.767 | −2.134 | 44.66 | C |
| ATOM | 2830 | CD | LYS | B1103 | −29.167 | −6.92 | −0.629 | 52.43 | C |
| ATOM | 2831 | CE | LYS | B1103 | −30.716 | −6.764 | −0.3 | 54.14 | C |
| ATOM | 2832 | NZ | LYS | B1103 | −31.134 | −5.32 | 0.054 | 55.6 | N |
| ATOM | 2833 | C | LYS | B1103 | −28.243 | −4.509 | −4.736 | 36.26 | C |
| ATOM | 2834 | O | LYS | B1103 | −28.98 | −4.338 | −5.686 | 35.57 | O |
| ATOM | 2835 | N | LYS | B1104 | −26.964 | −4.828 | −4.861 | 34.09 | N |
| ATOM | 2836 | CA | LYS | B1104 | −26.323 | −5.12 | −6.123 | 34.17 | C |
| ATOM | 2837 | CB | LYS | B1104 | −24.868 | −4.601 | −6.109 | 34.35 | C |
| ATOM | 2838 | CG | LYS | B1104 | −24.593 | −3.486 | −5.057 | 36.56 | C |
| ATOM | 2839 | CD | LYS | B1104 | −23.171 | −2.909 | −5.185 | 38.62 | C |
| ATOM | 2840 | CE | LYS | B1104 | −23.128 | −1.452 | −5.724 | 43.22 | C |
| ATOM | 2841 | NZ | LYS | B1104 | −23.341 | −1.512 | −7.206 | 46.31 | N |
| ATOM | 2842 | C | LYS | B1104 | −26.402 | −6.652 | −6.38 | 31.81 | C |
| ATOM | 2843 | O | LYS | B1104 | −25.87 | −7.441 | −5.616 | 31.44 | O |
| ATOM | 2844 | N | ILE | B1105 | −27.149 | −7.033 | −7.414 | 29.56 | N |
| ATOM | 2845 | CA | ILE | B1105 | −27.428 | −8.426 | −7.813 | 27.18 | C |
| ATOM | 2846 | CB | ILE | B1105 | −28.907 | −8.58 | −8.179 | 27.2 | C |
| ATOM | 2847 | CG2 | ILE | B1105 | −29.283 | −9.993 | −8.613 | 26.76 | C |
| ATOM | 2848 | CG1 | ILE | B1105 | −29.777 | −8.168 | −6.994 | 29.84 | C |
| ATOM | 2849 | CD1 | ILE | B1105 | −29.216 | −8.504 | −5.573 | 31.01 | C |
| ATOM | 2850 | C | ILE | B1105 | −26.605 | −8.859 | −9.06 | 26.17 | C |
| ATOM | 2851 | O | ILE | B1105 | −26.553 | −8.178 | −10.122 | 24.06 | O |
| ATOM | 2852 | N | HIS | B1106 | −26.01 | −10.031 | −8.905 | 24.12 | N |
| ATOM | 2853 | CA | HIS | B1106 | −25.326 | −10.679 | −9.971 | 23.11 | C |
| ATOM | 2854 | CB | HIS | B1106 | −24.395 | −11.738 | −9.411 | 22.82 | C |
| ATOM | 2855 | CG | HIS | B1106 | −23.467 | −12.292 | −10.441 | 26.43 | C |
| ATOM | 2856 | CD2 | HIS | B1106 | −23.107 | −11.797 | −11.66 | 26.36 | C |
| ATOM | 2857 | ND1 | HIS | B1106 | −22.832 | −13.509 | −10.306 | 25.2 | N |
| ATOM | 2858 | CE1 | HIS | B1106 | −22.083 | −13.705 | −11.374 | 29.25 | C |
| ATOM | 2859 | NE2 | HIS | B1106 | −22.239 | −12.687 | −12.212 | 25.17 | N |
| ATOM | 2860 | C | HIS | B1106 | −26.274 | −11.204 | −11.077 | 21.62 | C |
| ATOM | 2861 | O | HIS | B1106 | −27.227 | −11.865 | −10.811 | 22.59 | O |
| ATOM | 2862 | N | CYS | B1107 | −26.007 | −10.883 | −12.33 | 19.48 | N |
| ATOM | 2863 | CA | CYS | B1107 | −26.835 | −11.388 | −13.385 | 17.55 | C |
| ATOM | 2864 | CB | CYS | B1107 | −27.965 | −10.384 | −13.666 | 18.07 | C |
| ATOM | 2865 | SG | CYS | B1107 | −27.227 | −8.718 | −14.16 | 18.42 | S |
| ATOM | 2866 | C | CYS | B1107 | −26 | −11.588 | −14.661 | 16.17 | C |
| ATOM | 2867 | O | CYS | B1107 | −24.815 | −11.264 | −14.744 | 15.08 | O |
| ATOM | 2868 | N | ALA | B1108 | −26.695 | −12.123 | −15.666 | 15.55 | N |
| ATOM | 2869 | CA | ALA | B1108 | −26.16 | −12.448 | −16.975 | 11.19 | C |
| ATOM | 2870 | CB | ALA | B1108 | −26.452 | −13.869 | −17.222 | 10.83 | C |
| ATOM | 2871 | C | ALA | B1108 | −26.894 | −11.561 | −17.972 | 9.92 | C |
| ATOM | 2872 | O | ALA | B1108 | −28.124 | −11.399 | −17.883 | 6.01 | O |
| ATOM | 2873 | N | VAL | B1109 | −26.136 | −10.926 | −18.872 | 8.97 | N |
| ATOM | 2874 | CA | VAL | B1109 | −26.774 | −10.01 | −19.843 | 9.33 | C |
| ATOM | 2875 | CB | VAL | B1109 | −26.807 | −8.391 | −19.481 | 9.45 | C |
| ATOM | 2876 | CG1 | VAL | B1109 | −26.032 | −8.005 | −18.3 | 8.25 | C |
| ATOM | 2877 | CG2 | VAL | B1109 | −26.452 | −7.547 | −20.668 | 8.77 | C |
| ATOM | 2878 | C | VAL | B1109 | −26.389 | −10.338 | −21.304 | 9.24 | C |
| ATOM | 2879 | O | VAL | B1109 | −25.3 | −10.815 | −21.579 | 7.3 | O |
| ATOM | 2880 | N | LYS | B1110 | −27.33 | −10.08 | −22.194 | 9.22 | N |
| ATOM | 2881 | CA | LYS | B1110 | −27.189 | −10.462 | −23.567 | 11.63 | C |
| ATOM | 2882 | CB | LYS | B1110 | −27.786 | −11.887 | −23.756 | 12.52 | C |
| ATOM | 2883 | CG | LYS | B1110 | −27.781 | −12.443 | −25.149 | 13.32 | C |
| ATOM | 2884 | CD | LYS | B1110 | −26.441 | −13.135 | −25.377 | 11.87 | C |
| ATOM | 2885 | CE | LYS | B1110 | −26.107 | −13.203 | −26.846 | 21 | C |
| ATOM | 2886 | NZ | LYS | B1110 | −27.201 | −13.071 | −27.897 | 14.68 | N |
| ATOM | 2887 | C | LYS | B1110 | −27.941 | −9.431 | −24.432 | 11.11 | C |
| ATOM | 2888 | O | LYS | B1110 | −29.071 | −9.075 | −24.095 | 8.61 | O |
| ATOM | 2889 | N | SER | B1111 | −27.245 | −8.907 | −25.467 | 11.93 | N |
| ATOM | 2890 | CA | SER | B1111 | −27.887 | −8.092 | −26.53 | 13.48 | C |
| ATOM | 2891 | CB | SER | B1111 | −26.851 | −7.147 | −27.199 | 14.94 | C |
| ATOM | 2892 | OG | SER | B1111 | −27.026 | −7.007 | −28.604 | 13.55 | O |
| ATOM | 2893 | C | SER | B1111 | −28.647 | −8.977 | −27.532 | 13.17 | C |

TABLE 1A-continued

| | | | | | | | | |
|---|---|---|---|---|---|---|---|---|
| ATOM | 2894 | O | SER | B1111 | −28.147 | −10.014 | −27.985 | 11.98 | O |
| ATOM | 2895 | N | LEU | B1112 | −29.896 | −8.608 | −27.816 | 14.3 | N |
| ATOM | 2896 | CA | LEU | B1112 | −30.675 | −9.407 | −28.783 | 14.87 | C |
| ATOM | 2897 | CB | LEU | B1112 | −32.192 | −9.38 | −28.546 | 15.11 | C |
| ATOM | 2898 | CG | LEU | B1112 | −32.469 | −9.532 | −27.068 | 12.54 | C |
| ATOM | 2899 | CD1 | LEU | B1112 | −33.858 | −9.321 | −26.935 | 11.61 | C |
| ATOM | 2900 | CD2 | LEU | B1112 | −32.111 | −10.95 | −26.66 | 12.26 | C |
| ATOM | 2901 | C | LEU | B1112 | −30.323 | −8.969 | −30.187 | 14.57 | C |
| ATOM | 2902 | O | LEU | B1112 | −31.054 | −8.269 | −30.824 | 13.73 | O |
| ATOM | 2903 | N | ASN | B1113 | −29.169 | −9.435 | −30.641 | 15.7 | N |
| ATOM | 2904 | CA | ASN | B1113 | −28.644 | −9.036 | −31.913 | 17.23 | C |
| ATOM | 2905 | CB | ASN | B1113 | −27.293 | −9.678 | −32.137 | 16.16 | C |
| ATOM | 2906 | CG | ASN | B1113 | −26.265 | −9.178 | −31.126 | 15.4 | C |
| ATOM | 2907 | OD1 | ASN | B1113 | −26.097 | −7.984 | −30.918 | 15.23 | O |
| ATOM | 2908 | ND2 | ASN | B1113 | −25.602 | −10.073 | −30.507 | 16.3 | N |
| ATOM | 2909 | C | ASN | B1113 | −29.569 | −9.245 | −33.104 | 18.32 | C |
| ATOM | 2910 | O | ASN | B1113 | −29.219 | −8.847 | −34.181 | 21.69 | O |
| ATOM | 2911 | N | ARG | B1114 | −30.765 | −9.776 | −32.907 | 16.84 | N |
| ATOM | 2912 | CA | ARG | B1114 | −31.561 | −10.105 | −34.016 | 16.33 | C |
| ATOM | 2913 | CB | ARG | B1114 | −32.027 | −11.553 | −33.914 | 17.05 | C |
| ATOM | 2914 | CG | ARG | B1114 | −30.88 | −12.544 | −34.163 | 19.42 | C |
| ATOM | 2915 | CD | ARG | B1114 | −31.261 | −13.954 | −33.837 | 22.69 | C |
| ATOM | 2916 | NE | ARG | B1114 | −32.327 | −14.399 | −34.716 | 29.67 | N |
| ATOM | 2917 | CZ | ARG | B1114 | −33.248 | −15.305 | −34.369 | 37.44 | C |
| ATOM | 2918 | NH1 | ARG | B1114 | −33.236 | −15.907 | −33.125 | 34.6 | N |
| ATOM | 2919 | NH2 | ARG | B1114 | −34.174 | −15.635 | −35.285 | 34.77 | N |
| ATOM | 2920 | C | ARG | B1114 | −32.719 | −9.186 | −34.121 | 16.57 | C |
| ATOM | 2921 | O | ARG | B1114 | −33.455 | −9.265 | −35.114 | 15.8 | O |
| ATOM | 2922 | N | ILE | B1115 | −32.923 | −8.377 | −33.064 | 16.18 | N |
| ATOM | 2923 | CA | ILE | B1115 | −33.885 | −7.318 | −33.061 | 15.66 | C |
| ATOM | 2924 | CB | ILE | B1115 | −34.432 | −6.958 | −31.659 | 16.8 | C |
| ATOM | 2925 | CG2 | ILE | B1115 | −35.521 | −5.899 | −31.741 | 14.64 | C |
| ATOM | 2926 | CG1 | ILE | B1115 | −34.762 | −8.167 | −30.74 | 19.85 | C |
| ATOM | 2927 | CD1 | ILE | B1115 | −35.743 | −9.11 | −31.195 | 21.64 | C |
| ATOM | 2928 | C | ILE | B1115 | −33.133 | −6.119 | −33.611 | 15.81 | C |
| ATOM | 2929 | O | ILE | B1115 | −32.31 | −5.46 | −32.89 | 15.75 | O |
| ATOM | 2930 | N | THR | B1116 | −33.362 | −5.856 | −34.901 | 15.82 | N |
| ATOM | 2931 | CA | THR | B1116 | −32.576 | −4.842 | −35.64 | 16.62 | C |
| ATOM | 2932 | CB | THR | B1116 | −32.017 | −5.435 | −36.928 | 15.6 | C |
| ATOM | 2933 | OG1 | THR | B1116 | −33.084 | −5.709 | −37.85 | 15.48 | O |
| ATOM | 2934 | CG2 | THR | B1116 | −31.311 | −6.728 | −36.622 | 14.81 | C |
| ATOM | 2935 | C | THR | B1116 | −33.361 | −3.528 | −35.902 | 18 | C |
| ATOM | 2936 | O | THR | B1116 | −32.808 | −2.563 | −36.384 | 19.97 | O |
| ATOM | 2937 | N | ASP | B1117 | −34.652 | −3.498 | −35.583 | 18.89 | N |
| ATOM | 2938 | CA | ASP | B1117 | −35.485 | −2.31 | −35.723 | 18.62 | C |
| ATOM | 2939 | CB | ASP | B1117 | −35.95 | −2.156 | −37.175 | 20.27 | C |
| ATOM | 2940 | CG | ASP | B1117 | −36.778 | −3.349 | −37.646 | 23.06 | C |
| ATOM | 2941 | OD1 | ASP | B1117 | −37.751 | −3.729 | −36.981 | 29.38 | O |
| ATOM | 2942 | OD2 | ASP | B1117 | −36.46 | −3.945 | −38.686 | 32.03 | O |
| ATOM | 2943 | C | ASP | B1117 | −36.701 | −2.351 | −34.8 | 17.98 | C |
| ATOM | 2944 | O | ASP | B1117 | −36.942 | −3.363 | −34.138 | 18.33 | O |
| ATOM | 2945 | N | ILE | B1118 | −37.435 | −1.232 | −34.758 | 17.89 | N |
| ATOM | 2946 | CA | ILE | B1118 | −38.546 | −1.012 | −33.845 | 18.34 | C |
| ATOM | 2947 | CB | ILE | B1118 | −39.083 | 0.396 | −33.961 | 19.06 | C |
| ATOM | 2948 | CG2 | ILE | B1118 | −39.857 | 0.592 | −35.276 | 18.01 | C |
| ATOM | 2949 | CG1 | ILE | B1118 | −39.932 | 0.715 | −32.733 | 20.21 | C |
| ATOM | 2950 | CD1 | ILE | B1118 | −40.595 | 2.106 | −32.764 | 20.59 | C |
| ATOM | 2951 | C | ILE | B1118 | −39.722 | −1.987 | −34.056 | 18.2 | C |
| ATOM | 2952 | O | ILE | B1118 | −40.434 | −2.352 | −33.116 | 16.36 | O |
| ATOM | 2953 | N | GLY | B1119 | −39.912 | −2.41 | −35.296 | 18.21 | N |
| ATOM | 2954 | CA | GLY | B1119 | −40.961 | −3.359 | −35.567 | 19.58 | C |
| ATOM | 2955 | C | GLY | B1119 | −40.705 | −4.683 | −34.836 | 20.43 | C |
| ATOM | 2956 | O | GLY | B1119 | −41.653 | −5.29 | −34.339 | 19.99 | O |
| ATOM | 2957 | N | GLU | B1120 | −39.423 | −5.094 | −34.794 | 19.5 | N |
| ATOM | 2958 | CA | GLU | B1120 | −38.965 | −6.307 | −34.155 | 20.69 | C |
| ATOM | 2959 | CB | GLU | B1120 | −37.588 | −6.722 | −34.711 | 20.04 | C |
| ATOM | 2960 | CG | GLU | B1120 | −37.682 | −6.969 | −36.176 | 23 | C |
| ATOM | 2961 | CD | GLU | B1120 | −36.343 | −7.215 | −36.859 | 26.75 | C |
| ATOM | 2962 | OE1 | GLU | B1120 | −35.262 | −6.975 | −36.243 | 25.12 | O |
| ATOM | 2963 | OE2 | GLU | B1120 | −36.4 | −7.619 | −38.049 | 28.35 | O |
| ATOM | 2964 | C | GLU | B1120 | −38.938 | −6.188 | −32.6 | 20.23 | C |
| ATOM | 2965 | O | GLU | B1120 | −39.085 | −7.197 | −31.923 | 18.33 | O |
| ATOM | 2966 | N | VAL | B1121 | −38.754 | −4.954 | −32.08 | 20.43 | N |
| ATOM | 2967 | CA | VAL | B1121 | −38.787 | −4.699 | −30.651 | 20.56 | C |
| ATOM | 2968 | CB | VAL | B1121 | −38.324 | −3.278 | −30.303 | 20.8 | C |
| ATOM | 2969 | CG1 | VAL | B1121 | −38.445 | −3.064 | −28.833 | 20.21 | C |
| ATOM | 2970 | CG2 | VAL | B1121 | −36.884 | −3.082 | −30.672 | 19.6 | C |
| ATOM | 2971 | C | VAL | B1121 | −40.217 | −4.911 | −30.185 | 21.33 | C |
| ATOM | 2972 | O | VAL | B1121 | −40.487 | −5.678 | −29.252 | 23.1 | O |
| ATOM | 2973 | N | SER | B1122 | −41.141 | −4.252 | −30.869 | 21.22 | N |

TABLE 1A-continued

| | | | | | | | | |
|---|---|---|---|---|---|---|---|---|
| ATOM | 2974 | CA | SER | B1122 | −42.512 | −4.24 | −30.503 | 20.16 | C |
| ATOM | 2975 | CB | SER | B1122 | −43.213 | −3.315 | −31.468 | 20.41 | C |
| ATOM | 2976 | OG | SER | B1122 | −44.646 | −3.36 | −31.284 | 27.62 | O |
| ATOM | 2977 | C | SER | B1122 | −43.054 | −5.679 | −30.533 | 20.02 | C |
| ATOM | 2978 | O | SER | B1122 | −43.856 | −6.091 | −29.659 | 16.24 | O |
| ATOM | 2979 | N | GLN | B1123 | −42.557 | −6.467 | −31.517 | 20.28 | N |
| ATOM | 2980 | CA | GLN | B1123 | −42.983 | −7.86 | −31.617 | 20.71 | C |
| ATOM | 2981 | CB | GLN | B1123 | −42.579 | −8.467 | −32.959 | 21.57 | C |
| ATOM | 2982 | CG | GLN | B1123 | −42.542 | −9.975 | −32.88 | 26.83 | C |
| ATOM | 2983 | CD | GLN | B1123 | −42.828 | −10.698 | −34.188 | 34.81 | C |
| ATOM | 2984 | OE1 | GLN | B1123 | −41.885 | −11.107 | −34.907 | 30.93 | O |
| ATOM | 2985 | NE2 | GLN | B1123 | −44.141 | −10.923 | −34.478 | 34.08 | N |
| ATOM | 2986 | C | GLN | B1123 | −42.472 | −8.71 | −30.43 | 19.33 | C |
| ATOM | 2987 | O | GLN | B1123 | −43.164 | −9.598 | −29.906 | 18.63 | O |
| ATOM | 2988 | N | PHE | B1124 | −41.245 | −8.416 | −30.046 | 18.92 | N |
| ATOM | 2989 | CA | PHE | B1124 | −40.593 | −8.976 | −28.889 | 19.21 | C |
| ATOM | 2990 | CB | PHE | B1124 | −39.17 | −8.464 | −28.855 | 19.71 | C |
| ATOM | 2991 | CG | PHE | B1124 | −38.487 | −8.783 | −27.6 | 20.88 | C |
| ATOM | 2992 | CD1 | PHE | B1124 | −38.26 | −10.104 | −27.248 | 23.63 | C |
| ATOM | 2993 | CD2 | PHE | B1124 | −38.134 | −7.77 | −26.724 | 20.85 | C |
| ATOM | 2994 | CE1 | PHE | B1124 | −37.659 | −10.407 | −26.031 | 24.95 | C |
| ATOM | 2995 | CE2 | PHE | B1124 | −37.538 | −8.052 | −25.524 | 20.74 | C |
| ATOM | 2996 | CZ | PHE | B1124 | −37.297 | −9.35 | −25.178 | 23.67 | C |
| ATOM | 2997 | C | PHE | B1124 | −41.296 | −8.611 | −27.564 | 18.85 | C |
| ATOM | 2998 | O | PHE | B1124 | −41.446 | −9.435 | −26.68 | 18.31 | O |
| ATOM | 2999 | N | LEU | B1125 | −41.75 | −7.369 | −27.439 | 18.95 | N |
| ATOM | 3000 | CA | LEU | B1125 | −42.379 | −6.957 | −26.208 | 19.31 | C |
| ATOM | 3001 | CB | LEU | B1125 | −42.611 | −5.444 | −26.14 | 18.61 | C |
| ATOM | 3002 | CG | LEU | B1125 | −41.395 | −4.544 | −26.055 | 17.81 | C |
| ATOM | 3003 | CD1 | LEU | B1125 | −41.888 | −3.154 | −25.953 | 13.16 | C |
| ATOM | 3004 | CD2 | LEU | B1125 | −40.476 | −4.981 | −24.911 | 14.76 | C |
| ATOM | 3005 | C | LEU | B1125 | −43.664 | −7.693 | −26.029 | 20.43 | C |
| ATOM | 3006 | O | LEU | B1125 | −43.999 | −8.102 | −24.885 | 19.8 | O |
| ATOM | 3007 | N | THR | B1126 | −44.346 | −7.892 | −27.165 | 21.81 | N |
| ATOM | 3008 | CA | THR | B1126 | −45.593 | −8.636 | −27.203 | 24.27 | C |
| ATOM | 3009 | CB | THR | B1126 | −46.294 | −8.457 | −28.491 | 25.04 | C |
| ATOM | 3010 | OG1 | THR | B1126 | −46.77 | −7.12 | −28.565 | 27.43 | O |
| ATOM | 3011 | CG2 | THR | B1126 | −47.491 | −9.396 | −28.593 | 27.15 | C |
| ATOM | 3012 | C | THR | B1126 | −45.397 | −10.114 | −26.995 | 25.94 | C |
| ATOM | 3013 | O | THR | B1126 | −45.977 | −10.651 | −26.074 | 25.49 | O |
| ATOM | 3014 | N | GLU | B1127 | −44.56 | −10.747 | −27.849 | 28.18 | N |
| ATOM | 3015 | CA | GLU | B1127 | −44.342 | −12.216 | −27.902 | 29.09 | C |
| ATOM | 3016 | CB | GLU | B1127 | −43.6 | −12.615 | −29.212 | 29.43 | C |
| ATOM | 3017 | CG | GLU | B1127 | −44.366 | −12.433 | −30.585 | 34.63 | C |
| ATOM | 3018 | CD | GLU | B1127 | −43.93 | −13.447 | −31.739 | 36.34 | C |
| ATOM | 3019 | OE1 | GLU | B1127 | −42.932 | −14.233 | −31.583 | 42.77 | O |
| ATOM | 3020 | OE2 | GLU | B1127 | −44.616 | −13.46 | −32.813 | 43.01 | O |
| ATOM | 3021 | C | GLU | B1127 | −43.509 | −12.73 | −26.759 | 27.06 | C |
| ATOM | 3022 | O | GLU | B1127 | −43.782 | −13.746 | −26.167 | 28.65 | O |
| ATOM | 3023 | N | GLY | B1128 | −42.419 | −12.061 | −26.507 | 25.65 | N |
| ATOM | 3024 | CA | GLY | B1128 | −41.409 | −12.606 | −25.676 | 23.56 | C |
| ATOM | 3025 | C | GLY | B1128 | −41.495 | −12.108 | −24.259 | 22.44 | C |
| ATOM | 3026 | O | GLY | B1128 | −40.861 | −12.688 | −23.385 | 23.01 | O |
| ATOM | 3027 | N | ILE | B1129 | −42.313 | −11.087 | −23.994 | 21.65 | N |
| ATOM | 3028 | CA | ILE | B1129 | −42.452 | −10.613 | −22.605 | 20.71 | C |
| ATOM | 3029 | CB | ILE | B1129 | −41.976 | −9.163 | −22.398 | 20.57 | C |
| ATOM | 3030 | CG2 | ILE | B1129 | −42.295 | −8.632 | −20.984 | 16.98 | C |
| ATOM | 3031 | CG1 | ILE | B1129 | −40.527 | −8.996 | −22.884 | 22.44 | C |
| ATOM | 3032 | CD1 | ILE | B1129 | −39.511 | −8.768 | −21.844 | 27.47 | C |
| ATOM | 3033 | C | ILE | B1129 | −43.868 | −10.773 | −22.116 | 21.37 | C |
| ATOM | 3034 | O | ILE | B1129 | −44.074 | −11.484 | −21.141 | 22.91 | O |
| ATOM | 3035 | N | ILE | B1130 | −44.83 | −10.116 | −22.768 | 21.42 | N |
| ATOM | 3036 | CA | ILE | B1130 | −46.225 | −10.12 | −22.373 | 21.54 | C |
| ATOM | 3037 | CB | ILE | B1130 | −46.963 | −8.979 | −23.165 | 23.73 | C |
| ATOM | 3038 | CG2 | ILE | B1130 | −48.557 | −9.195 | −23.349 | 23.9 | C |
| ATOM | 3039 | CG1 | ILE | B1130 | −46.652 | −7.612 | −22.528 | 22.28 | C |
| ATOM | 3040 | CD1 | ILE | B1130 | −46.984 | −6.542 | −23.431 | 29.63 | C |
| ATOM | 3041 | C | ILE | B1130 | −46.9 | −11.48 | −22.593 | 21.67 | C |
| ATOM | 3042 | O | ILE | B1130 | −47.808 | −11.858 | −21.875 | 20.59 | O |
| ATOM | 3043 | N | MET | B1131 | −46.453 | −12.211 | −23.587 | 21.62 | N |
| ATOM | 3044 | CA | MET | B1131 | −47.003 | −13.489 | −23.86 | 25.06 | C |
| ATOM | 3045 | CB | MET | B1131 | −46.974 | −13.796 | −25.365 | 25.52 | C |
| ATOM | 3046 | CG | MET | B1131 | −48.265 | −13.463 | −26.138 | 28.21 | C |
| ATOM | 3047 | SD | MET | B1131 | −47.881 | −13.85 | −27.932 | 37.9 | S |
| ATOM | 3048 | CE | MET | B1131 | −48.83 | −12.507 | −28.735 | 33.81 | C |
| ATOM | 3049 | C | MET | B1131 | −46.236 | −14.575 | −23.133 | 23.04 | C |
| ATOM | 3050 | O | MET | B1131 | −46.56 | −15.74 | −23.305 | 22.39 | O |
| ATOM | 3051 | N | LYS | B1132 | −45.22 | −14.212 | −22.347 | 22.43 | N |
| ATOM | 3052 | CA | LYS | B1132 | −44.486 | −15.183 | −21.513 | 21.49 | C |
| ATOM | 3053 | CB | LYS | B1132 | −43.145 | −15.617 | −22.13 | 21.65 | C |

TABLE 1A-continued

| ATOM | 3054 | CG | LYS | B1132 | −43.284 | −16.095 | −23.534 | 24.27 | C |
|---|---|---|---|---|---|---|---|---|---|
| ATOM | 3055 | CD | LYS | B1132 | −41.954 | −16.295 | −24.221 | 26.68 | C |
| ATOM | 3056 | CE | LYS | B1132 | −42.215 | −17.072 | −25.529 | 31.37 | C |
| ATOM | 3057 | NZ | LYS | B1132 | −40.981 | −17.343 | −26.409 | 30.29 | N |
| ATOM | 3058 | C | LYS | B1132 | −44.264 | −14.664 | −20.109 | 19.94 | C |
| ATOM | 3059 | O | LYS | B1132 | −43.142 | −14.619 | −19.637 | 18.91 | O |
| ATOM | 3060 | N | ASP | B1133 | −45.356 | −14.262 | −19.461 | 19.36 | N |
| ATOM | 3061 | CA | ASP | B1133 | −45.318 | −13.836 | −18.068 | 18.25 | C |
| ATOM | 3062 | CB | ASP | B1133 | −46.394 | −12.803 | −17.826 | 19.04 | C |
| ATOM | 3063 | CG | ASP | B1133 | −46.025 | −11.787 | −16.716 | 25.02 | C |
| ATOM | 3064 | OD1 | ASP | B1133 | −46.678 | −10.734 | −16.677 | 32.68 | O |
| ATOM | 3065 | OD2 | ASP | B1133 | −45.12 | −11.971 | −15.874 | 27.29 | O |
| ATOM | 3066 | C | ASP | B1133 | −45.459 | −15.042 | −17.07 | 16.25 | C |
| ATOM | 3067 | O | ASP | B1133 | −46.575 | −15.418 | −16.702 | 15.72 | O |
| ATOM | 3068 | N | PHE | B1134 | −44.334 | −15.661 | −16.703 | 13.2 | N |
| ATOM | 3069 | CA | PHE | B1134 | −44.371 | −16.847 | −15.908 | 13.49 | C |
| ATOM | 3070 | CB | PHE | B1134 | −43.749 | −18.062 | −16.681 | 13.84 | C |
| ATOM | 3071 | CG | PHE | B1134 | −44.392 | −18.326 | −17.977 | 12.66 | C |
| ATOM | 3072 | CD1 | PHE | B1134 | −43.665 | −18.247 | −19.149 | 8.62 | C |
| ATOM | 3073 | CD2 | PHE | B1134 | −45.74 | −18.598 | −18.038 | 13.15 | C |
| ATOM | 3074 | CE1 | PHE | B1134 | −44.24 | −18.472 | −20.344 | 9.63 | C |
| ATOM | 3075 | CE2 | PHE | B1134 | −46.381 | −18.775 | −19.284 | 11.64 | C |
| ATOM | 3076 | CZ | PHE | B1134 | −45.626 | −18.693 | −20.441 | 12.7 | C |
| ATOM | 3077 | C | PHE | B1134 | −43.658 | −16.664 | −14.532 | 12.63 | C |
| ATOM | 3078 | O | PHE | B1134 | −42.758 | −15.847 | −14.405 | 12.68 | O |
| ATOM | 3079 | N | SER | B1135 | −44.032 | −17.467 | −13.554 | 11.18 | N |
| ATOM | 3080 | CA | SER | B1135 | −43.437 | −17.455 | −12.292 | 12.48 | C |
| ATOM | 3081 | CB | SER | B1135 | −44.072 | −16.389 | −11.376 | 13.66 | C |
| ATOM | 3082 | OG | SER | B1135 | −43.358 | −16.274 | −10.114 | 19.22 | O |
| ATOM | 3083 | C | SER | B1135 | −43.606 | −18.843 | −11.714 | 11.96 | C |
| ATOM | 3084 | O | SER | B1135 | −44.722 | −19.284 | −11.4 | 10.34 | O |
| ATOM | 3085 | N | HIS | B1136 | −42.453 | −19.496 | −11.574 | 10.83 | N |
| ATOM | 3086 | CA | HIS | B1136 | −42.306 | −20.857 | −11.158 | 9.03 | C |
| ATOM | 3087 | CB | HIS | B1136 | −42.855 | −21.851 | −12.194 | 7.78 | C |
| ATOM | 3088 | CG | HIS | B1136 | −42.977 | −23.233 | −11.645 | 7.34 | C |
| ATOM | 3089 | CD2 | HIS | B1136 | −44.027 | −23.881 | −11.077 | 7.24 | C |
| ATOM | 3090 | ND1 | HIS | B1136 | −41.892 | −24.076 | −11.5 | 8.84 | N |
| ATOM | 3091 | CE1 | HIS | B1136 | −42.293 | −25.22 | −10.952 | 7.21 | C |
| ATOM | 3092 | NE2 | HIS | B1136 | −43.589 | −25.13 | −10.706 | 4.2 | N |
| ATOM | 3093 | C | HIS | B1136 | −40.833 | −21.147 | −10.873 | 9.44 | C |
| ATOM | 3094 | O | HIS | B1136 | −39.956 | −20.823 | −11.676 | 8.14 | O |
| ATOM | 3095 | N | PRO | B1137 | −40.546 | −21.776 | −9.716 | 9.87 | N |
| ATOM | 3096 | CD | PRO | B1137 | −41.499 | −22.126 | −8.63 | 10.69 | C |
| ATOM | 3097 | CA | PRO | B1137 | −39.187 | −22.146 | −9.357 | 10.54 | C |
| ATOM | 3098 | CB | PRO | B1137 | −39.406 | −23.019 | −8.096 | 11.7 | C |
| ATOM | 3099 | CG | PRO | B1137 | −40.94 | −23.414 | −8.112 | 11.22 | C |
| ATOM | 3100 | C | PRO | B1137 | −38.38 | −22.924 | −10.41 | 10.67 | C |
| ATOM | 3101 | O | PRO | B1137 | −37.14 | −22.846 | −10.452 | 11.71 | O |
| ATOM | 3102 | N | ASN | B1138 | −39.037 | −23.703 | −11.254 | 10.13 | N |
| ATOM | 3103 | CA | ASN | B1138 | −38.29 | −24.439 | −12.246 | 9.9 | C |
| ATOM | 3104 | CB | ASN | B1138 | −38.763 | −25.865 | −12.216 | 9.42 | C |
| ATOM | 3105 | CG | ASN | B1138 | −38.553 | −26.473 | −10.929 | 8.48 | C |
| ATOM | 3106 | OD1 | ASN | B1138 | −39.522 | −26.863 | −10.251 | 15.21 | O |
| ATOM | 3107 | ND2 | ASN | B1138 | −37.308 | −26.552 | −10.52 | 9.73 | N |
| ATOM | 3108 | C | ASN | B1138 | −38.452 | −23.889 | −13.678 | 10.14 | C |
| ATOM | 3109 | O | ASN | B1138 | −38.23 | −24.616 | −14.664 | 8.96 | O |
| ATOM | 3110 | N | VAL | B1139 | −38.924 | −22.657 | −13.754 | 9.25 | N |
| ATOM | 3111 | CA | VAL | B1139 | −39.065 | −21.923 | −15.004 | 10.14 | C |
| ATOM | 3112 | CB | VAL | B1139 | −40.54 | −21.427 | −15.265 | 8.36 | C |
| ATOM | 3113 | CG1 | VAL | B1139 | −40.555 | −20.35 | −16.371 | 8.76 | C |
| ATOM | 3114 | CG2 | VAL | B1139 | −41.434 | −22.588 | −15.597 | 5.54 | C |
| ATOM | 3115 | C | VAL | B1139 | −38.13 | −20.705 | −14.944 | 10.69 | C |
| ATOM | 3116 | O | VAL | B1139 | −38.19 | −19.885 | −14.027 | 10.15 | O |
| ATOM | 3117 | N | LEU | B1140 | −37.28 | −20.593 | −15.945 | 12.82 | N |
| ATOM | 3118 | CA | LEU | B1140 | −36.349 | −19.437 | −16.033 | 13.46 | C |
| ATOM | 3119 | CB | LEU | B1140 | −35.175 | −19.772 | −16.941 | 12.15 | C |
| ATOM | 3120 | CG | LEU | B1140 | −34.135 | −18.663 | −17.089 | 15.4 | C |
| ATOM | 3121 | CD1 | LEU | B1140 | −33.713 | −18.075 | −15.707 | 18.65 | C |
| ATOM | 3122 | CD2 | LEU | B1140 | −32.907 | −19.173 | −17.841 | 12.12 | C |
| ATOM | 3123 | C | LEU | B1140 | −37.037 | −18.175 | −16.586 | 13.98 | C |
| ATOM | 3124 | O | LEU | B1140 | −37.475 | −18.138 | −17.745 | 13.7 | O |
| ATOM | 3125 | N | SER | B1141 | −37.085 | −17.129 | −15.779 | 14.05 | N |
| ATOM | 3126 | CA | SER | B1141 | −37.655 | −15.877 | −16.224 | 14.32 | C |
| ATOM | 3127 | CB | SER | B1141 | −38.768 | −15.484 | −15.25 | 13.42 | C |
| ATOM | 3128 | OG | SER | B1141 | −39.906 | −16.321 | −15.411 | 13.02 | O |
| ATOM | 3129 | C | SER | B1141 | −36.596 | −14.766 | −16.233 | 15.85 | C |
| ATOM | 3130 | O | SER | B1141 | −35.669 | −14.739 | −15.377 | 15.5 | O |
| ATOM | 3131 | N | LEU | B1142 | −36.725 | −13.818 | −17.152 | 16.95 | N |
| ATOM | 3132 | CA | LEU | B1142 | −35.742 | −12.734 | −17.138 | 18.29 | C |
| ATOM | 3133 | CB | LEU | B1142 | −35.65 | −12.031 | −18.472 | 20.03 | C |

TABLE 1A-continued

| ATOM | 3134 | CG | LEU | B1142 | −36.683 | −11.192 | −19.185 | 24.65 | C |
|---|---|---|---|---|---|---|---|---|---|
| ATOM | 3135 | CD1 | LEU | B1142 | −36.465 | −11.506 | −20.665 | 29.86 | C |
| ATOM | 3136 | CD2 | LEU | B1142 | −38.054 | −11.563 | −18.827 | 32.52 | C |
| ATOM | 3137 | C | LEU | B1142 | −35.978 | −11.764 | −15.999 | 17.94 | C |
| ATOM | 3138 | O | LEU | B1142 | −37.135 | −11.543 | −15.618 | 17.46 | O |
| ATOM | 3139 | N | LEU | B1143 | −34.899 | −11.216 | −15.437 | 16.77 | N |
| ATOM | 3140 | CA | LEU | B1143 | −35.012 | −10.281 | −14.378 | 16.17 | C |
| ATOM | 3141 | CB | LEU | B1143 | −33.665 | −9.964 | −13.809 | 16.58 | C |
| ATOM | 3142 | CG | LEU | B1143 | −32.949 | −11.007 | −12.956 | 20.56 | C |
| ATOM | 3143 | CD1 | LEU | B1143 | −31.483 | −10.458 | −12.607 | 16.47 | C |
| ATOM | 3144 | CD2 | LEU | B1143 | −33.812 | −11.432 | −11.674 | 18.65 | C |
| ATOM | 3145 | C | LEU | B1143 | −35.629 | −9.006 | −14.915 | 17.22 | C |
| ATOM | 3146 | O | LEU | B1143 | −36.534 | −8.435 | −14.265 | 18.1 | O |
| ATOM | 3147 | N | GLY | B1144 | −35.191 | −8.583 | −16.1 | 15.71 | N |
| ATOM | 3148 | CA | GLY | B1144 | −35.812 | −7.492 | −16.747 | 17.55 | C |
| ATOM | 3149 | C | GLY | B1144 | −35.253 | −7.37 | −18.15 | 20.81 | C |
| ATOM | 3150 | O | GLY | B1144 | −34.589 | −8.28 | −18.639 | 19.87 | O |
| ATOM | 3151 | N | ILE | B1145 | −35.47 | −6.183 | −18.749 | 23.32 | N |
| ATOM | 3152 | CA | ILE | B1145 | −35.234 | −5.948 | −20.142 | 25.4 | C |
| ATOM | 3153 | CB | ILE | B1145 | −36.486 | −6.088 | −21.066 | 25.54 | C |
| ATOM | 3154 | CG2 | ILE | B1145 | −37.502 | −4.876 | −21.036 | 24.37 | C |
| ATOM | 3155 | CG1 | ILE | B1145 | −36.033 | −6.509 | −22.437 | 26.57 | C |
| ATOM | 3156 | CD1 | ILE | B1145 | −35.844 | −5.401 | −23.399 | 27.64 | C |
| ATOM | 3157 | C | ILE | B1145 | −34.341 | −4.823 | −20.522 | 26.94 | C |
| ATOM | 3158 | O | ILE | B1145 | −33.335 | −5.104 | −21.145 | 31.01 | O |
| ATOM | 3159 | N | CYS | B1146 | −34.585 | −3.572 | −20.255 | 26.18 | N |
| ATOM | 3160 | CA | CYS | B1146 | −33.589 | −2.676 | −20.911 | 27.81 | C |
| ATOM | 3161 | CB | CYS | B1146 | −32.206 | −3.307 | −20.8 | 28.25 | C |
| ATOM | 3162 | SG | CYS | B1146 | −30.968 | −2.29 | −20.084 | 39.86 | S |
| ATOM | 3163 | C | CYS | B1146 | −33.773 | −2.264 | −22.392 | 25.44 | C |
| ATOM | 3164 | O | CYS | B1146 | −33.198 | −2.858 | −23.32 | 23.13 | O |
| ATOM | 3165 | N | LEU | B1147 | −34.518 | −1.171 | −22.583 | 25.47 | N |
| ATOM | 3166 | CA | LEU | B1147 | −34.844 | −0.701 | −23.923 | 24.48 | C |
| ATOM | 3167 | CB | LEU | B1147 | −36.316 | −0.258 | −23.981 | 25.28 | C |
| ATOM | 3168 | CG | LEU | B1147 | −37.558 | −1.097 | −24.228 | 25.29 | C |
| ATOM | 3169 | CD1 | LEU | B1147 | −37.319 | −2.1 | −25.298 | 27.97 | C |
| ATOM | 3170 | CD2 | LEU | B1147 | −37.919 | −1.835 | −23.005 | 29.1 | C |
| ATOM | 3171 | C | LEU | B1147 | −33.936 | 0.474 | −24.325 | 24.42 | C |
| ATOM | 3172 | O | LEU | B1147 | −34.008 | 1.556 | −23.735 | 23.15 | O |
| ATOM | 3173 | N | ARG | B1148 | −33.121 | 0.273 | −25.353 | 23.32 | N |
| ATOM | 3174 | CA | ARG | B1148 | −32.146 | 1.268 | −25.796 | 21.75 | C |
| ATOM | 3175 | CB | ARG | B1148 | −30.787 | 0.593 | −25.999 | 20.87 | C |
| ATOM | 3176 | CG | ARG | B1148 | −30.383 | −0.248 | −24.849 | 19.8 | C |
| ATOM | 3177 | CD | ARG | B1148 | −28.89 | −0.531 | −24.978 | 18.29 | C |
| ATOM | 3178 | NE | ARG | B1148 | −28.626 | −1.545 | −25.976 | 13.37 | N |
| ATOM | 3179 | CZ | ARG | B1148 | −27.407 | −1.955 | −26.323 | 16.93 | C |
| ATOM | 3180 | NH1 | ARG | B1148 | −26.329 | −1.435 | −25.77 | 16.14 | N |
| ATOM | 3181 | NH2 | ARG | B1148 | −27.271 | −2.924 | −27.214 | 14.69 | N |
| ATOM | 3182 | C | ARG | B1148 | −32.559 | 1.823 | −27.148 | 21.36 | C |
| ATOM | 3183 | O | ARG | B1148 | −33.208 | 1.153 | −27.92 | 20.58 | O |
| ATOM | 3184 | N | SER | B1149 | −32.145 | 3.03 | −27.46 | 20.94 | N |
| ATOM | 3185 | CA | SER | B1149 | −32.415 | 3.529 | −28.803 | 23.03 | C |
| ATOM | 3186 | CB | SER | B1149 | −32.81 | 5 | −28.785 | 23.52 | C |
| ATOM | 3187 | OG | SER | B1149 | −32.164 | 5.688 | −27.735 | 27.64 | O |
| ATOM | 3188 | C | SER | B1149 | −31.197 | 3.354 | −29.678 | 22.72 | C |
| ATOM | 3189 | O | SER | B1149 | −31.312 | 3.299 | −30.88 | 24.19 | O |
| ATOM | 3190 | N | GLU | B1150 | −30.026 | 3.218 | −29.085 | 22.05 | N |
| ATOM | 3191 | CA | GLU | B1150 | −28.968 | 2.623 | −29.868 | 22.66 | C |
| ATOM | 3192 | CB | GLU | B1150 | −27.718 | 3.501 | −29.894 | 23.8 | C |
| ATOM | 3193 | CG | GLU | B1150 | −28.005 | 4.95 | −30.295 | 30 | C |
| ATOM | 3194 | CD | GLU | B1150 | −26.698 | 5.665 | −30.456 | 40.1 | C |
| ATOM | 3195 | OE1 | GLU | B1150 | −25.743 | 5.351 | −29.649 | 44.42 | O |
| ATOM | 3196 | OE2 | GLU | B1150 | −26.6 | 6.507 | −31.39 | 41.6 | O |
| ATOM | 3197 | C | GLU | B1150 | −28.647 | 1.196 | −29.458 | 20.41 | C |
| ATOM | 3198 | O | GLU | B1150 | −28.415 | 0.889 | −28.303 | 18.54 | O |
| ATOM | 3199 | N | GLY | B1151 | −28.638 | 0.337 | −30.449 | 18.5 | N |
| ATOM | 3200 | CA | GLY | B1151 | −28.221 | −1.006 | −30.23 | 17.16 | C |
| ATOM | 3201 | C | GLY | B1151 | −29.443 | −1.827 | −29.963 | 16.88 | C |
| ATOM | 3202 | O | GLY | B1151 | −30.511 | −1.283 | −29.731 | 17.89 | O |
| ATOM | 3203 | N | SER | B1152 | −29.291 | −3.138 | −30.001 | 16.38 | N |
| ATOM | 3204 | CA | SER | B1152 | −30.385 | −4.035 | −29.793 | 15.73 | C |
| ATOM | 3205 | CB | SER | B1152 | −29.973 | −5.418 | −30.296 | 16.22 | C |
| ATOM | 3206 | OG | SER | B1152 | −29.949 | −5.455 | −31.709 | 17.36 | O |
| ATOM | 3207 | C | SER | B1152 | −30.776 | −4.049 | −28.296 | 15.34 | C |
| ATOM | 3208 | O | SER | B1152 | −29.979 | −3.74 | −27.395 | 14.35 | O |
| ATOM | 3209 | N | PRO | B1153 | −32.021 | −4.399 | −28.026 | 15.04 | N |
| ATOM | 3210 | CD | PRO | B1153 | −33.116 | −4.774 | −28.945 | 13.23 | C |
| ATOM | 3211 | CA | PRO | B1153 | −32.397 | −4.431 | −26.604 | 15.68 | C |
| ATOM | 3212 | CB | PRO | B1153 | −33.902 | −4.764 | −26.616 | 14.25 | C |
| ATOM | 3213 | CG | PRO | B1153 | −34.335 | −4.63 | −28.038 | 14.42 | C |

TABLE 1A-continued

| | | | | | | | | |
|---|---|---|---|---|---|---|---|---|
| ATOM | 3214 | C | PRO | B1153 | −31.597 | −5.479 | −25.808 | 16.25 | C |
| ATOM | 3215 | O | PRO | B1153 | −31.076 | −6.412 | −26.374 | 18.1 | O |
| ATOM | 3216 | N | LEU | B1154 | −31.453 | −5.274 | −24.505 | 16.93 | N |
| ATOM | 3217 | CA | LEU | B1154 | −30.681 | −6.147 | −23.64 | 15.03 | C |
| ATOM | 3218 | CB | LEU | B1154 | −29.958 | −5.32 | −22.638 | 15.08 | C |
| ATOM | 3219 | CG | LEU | B1154 | −28.563 | −4.899 | −23.086 | 18.21 | C |
| ATOM | 3220 | CD1 | LEU | B1154 | −28.269 | −5.2 | −24.556 | 12.75 | C |
| ATOM | 3221 | CD2 | LEU | B1154 | −28.33 | −3.462 | −22.734 | 14.99 | C |
| ATOM | 3222 | C | LEU | B1154 | −31.623 | −7.012 | −22.876 | 14.73 | C |
| ATOM | 3223 | O | LEU | B1154 | −32.705 | −6.607 | −22.574 | 13.4 | O |
| ATOM | 3224 | N | VAL | B1155 | −31.199 | −8.227 | −22.585 | 13.87 | N |
| ATOM | 3225 | CA | VAL | B1155 | −32.019 | −9.147 | −21.863 | 13.52 | C |
| ATOM | 3226 | CB | VAL | B1155 | −32.349 | −10.322 | −22.832 | 14.55 | C |
| ATOM | 3227 | CG1 | VAL | B1155 | −31.496 | −11.534 | −22.58 | 14.03 | C |
| ATOM | 3228 | CG2 | VAL | B1155 | −33.823 | −10.609 | −22.785 | 18.15 | C |
| ATOM | 3229 | C | VAL | B1155 | −31.204 | −9.502 | −20.622 | 11.35 | C |
| ATOM | 3230 | O | VAL | B1155 | −30.018 | −9.713 | −20.715 | 11.04 | O |
| ATOM | 3231 | N | VAL | B1156 | −31.81 | −9.371 | −19.455 | 11.53 | N |
| ATOM | 3232 | CA | VAL | B1156 | −31.118 | −9.533 | −18.172 | 11.14 | C |
| ATOM | 3233 | CB | VAL | B1156 | −31.192 | −8.245 | −17.256 | 12.17 | C |
| ATOM | 3234 | CG1 | VAL | B1156 | −30.313 | −8.371 | −15.994 | 10.66 | C |
| ATOM | 3235 | CG2 | VAL | B1156 | −30.748 | −6.969 | −18.047 | 10.76 | C |
| ATOM | 3236 | C | VAL | B1156 | −31.722 | −10.771 | −17.483 | 12.56 | C |
| ATOM | 3237 | O | VAL | B1156 | −32.97 | −10.885 | −17.293 | 12.88 | O |
| ATOM | 3238 | N | LEU | B1157 | −30.847 | −11.733 | −17.187 | 11.87 | N |
| ATOM | 3239 | CA | LEU | B1157 | −31.252 | −12.933 | −16.52 | 10.49 | C |
| ATOM | 3240 | CB | LEU | B1157 | −31.067 | −14.103 | −17.467 | 11.83 | C |
| ATOM | 3241 | CG | LEU | B1157 | −32.163 | −14.083 | −18.539 | 10.1 | C |
| ATOM | 3242 | CD1 | LEU | B1157 | −31.622 | −13.381 | −19.796 | 10.35 | C |
| ATOM | 3243 | CD2 | LEU | B1157 | −32.674 | −15.419 | −18.81 | 8.6 | C |
| ATOM | 3244 | C | LEU | B1157 | −30.496 | −13.192 | −15.263 | 10.83 | C |
| ATOM | 3245 | O | LEU | B1157 | −29.321 | −12.728 | −15.103 | 11.75 | O |
| ATOM | 3246 | N | PRO | B1158 | −31.122 | −13.969 | −14.366 | 10.41 | N |
| ATOM | 3247 | CD | PRO | B1158 | −32.504 | −14.489 | −14.459 | 9.43 | C |
| ATOM | 3248 | CA | PRO | B1158 | −30.416 | −14.389 | −13.147 | 9.97 | C |
| ATOM | 3249 | CB | PRO | B1158 | −31.426 | −15.321 | −12.386 | 8.9 | C |
| ATOM | 3250 | CG | PRO | B1158 | −32.711 | −15.132 | −13.099 | 11.26 | C |
| ATOM | 3251 | C | PRO | B1158 | −29.15 | −15.139 | −13.487 | 10.1 | C |
| ATOM | 3252 | O | PRO | B1158 | −29.076 | −15.847 | −14.493 | 9.14 | O |
| ATOM | 3253 | N | TYR | B1159 | −28.138 | −14.912 | −12.675 | 11.58 | N |
| ATOM | 3254 | CA | TYR | B1159 | −26.951 | −15.703 | −12.742 | 13.59 | C |
| ATOM | 3255 | CB | TYR | B1159 | −25.849 | −15.174 | −11.787 | 13.68 | C |
| ATOM | 3256 | CG | TYR | B1159 | −24.551 | −15.855 | −12.053 | 11.81 | C |
| ATOM | 3257 | CD1 | TYR | B1159 | −24.019 | −15.89 | −13.372 | 10.98 | C |
| ATOM | 3258 | CE1 | TYR | B1159 | −22.863 | −16.554 | −13.655 | 13.01 | C |
| ATOM | 3259 | CD2 | TYR | B1159 | −23.877 | −16.487 | −11.057 | 9.14 | C |
| ATOM | 3260 | CE2 | TYR | B1159 | −22.661 | −17.182 | −11.319 | 13.66 | C |
| ATOM | 3261 | CZ | TYR | B1159 | −22.136 | −17.193 | −12.616 | 14.72 | C |
| ATOM | 3262 | OH | TYR | B1159 | −20.946 | −17.909 | −12.902 | 14.73 | O |
| ATOM | 3263 | C | TYR | B1159 | −27.242 | −17.175 | −12.476 | 15.39 | C |
| ATOM | 3264 | O | TYR | B1159 | −27.802 | −17.531 | −11.415 | 15.7 | O |
| ATOM | 3265 | N | MET | B1160 | −26.915 | −18.017 | −13.469 | 16.37 | N |
| ATOM | 3266 | CA | MET | B1160 | −27.146 | −19.454 | −13.38 | 17.49 | C |
| ATOM | 3267 | CB | MET | B1160 | −27.924 | −20.031 | −14.581 | 16.46 | C |
| ATOM | 3268 | CG | MET | B1160 | −29.345 | −19.722 | −14.506 | 18.94 | C |
| ATOM | 3269 | SD | MET | B1160 | −30.35 | −20.465 | −13.143 | 24.07 | S |
| ATOM | 3270 | CE | MET | B1160 | −30.719 | −19.019 | −12.29 | 18.12 | C |
| ATOM | 3271 | C | MET | B1160 | −25.792 | −20.045 | −13.308 | 17.29 | C |
| ATOM | 3272 | O | MET | B1160 | −25.206 | −20.378 | −14.31 | 18 | O |
| ATOM | 3273 | N | LYS | B1161 | −25.318 | −20.191 | −12.09 | 18.45 | N |
| ATOM | 3274 | CA | LYS | B1161 | −23.951 | −20.603 | −11.824 | 18.74 | C |
| ATOM | 3275 | CB | LYS | B1161 | −23.776 | −20.791 | −10.319 | 19.72 | C |
| ATOM | 3276 | CG | LYS | B1161 | −22.35 | −21.047 | −9.981 | 23.56 | C |
| ATOM | 3277 | CD | LYS | B1161 | −22.224 | −21.793 | −8.725 | 29.41 | C |
| ATOM | 3278 | CE | LYS | B1161 | −20.946 | −22.585 | −8.754 | 30.13 | C |
| ATOM | 3279 | NZ | LYS | B1161 | −20.265 | −22.285 | −7.519 | 27.21 | N |
| ATOM | 3280 | C | LYS | B1161 | −23.5 | −21.856 | −12.55 | 18.52 | C |
| ATOM | 3281 | O | LYS | B1161 | −22.321 | −21.926 | −12.981 | 18.11 | O |
| ATOM | 3282 | N | HIS | B1162 | −24.405 | −22.857 | −12.644 | 17.41 | N |
| ATOM | 3283 | CA | HIS | B1162 | −24.078 | −24.115 | −13.34 | 16.48 | C |
| ATOM | 3284 | CB | HIS | B1162 | −24.523 | −25.36 | −12.589 | 16.27 | C |
| ATOM | 3285 | CG | HIS | B1162 | −23.83 | −25.477 | −11.266 | 16.91 | C |
| ATOM | 3286 | CD2 | HIS | B1162 | −24.284 | −25.341 | −10.003 | 16.13 | C |
| ATOM | 3287 | ND1 | HIS | B1162 | −22.46 | −25.683 | −11.166 | 17.49 | N |
| ATOM | 3288 | CE1 | HIS | B1162 | −22.101 | −25.672 | −9.901 | 14.86 | C |
| ATOM | 3289 | NE2 | HIS | B1162 | −23.179 | −25.435 | −9.173 | 20.15 | N |
| ATOM | 3290 | C | HIS | B1162 | −24.306 | −24.198 | −14.829 | 15.43 | C |
| ATOM | 3291 | O | HIS | B1162 | −23.91 | −25.177 | −15.453 | 16.77 | O |
| ATOM | 3292 | N | GLY | B1163 | −24.847 | −23.142 | −15.4 | 14.23 | N |
| ATOM | 3293 | CA | GLY | B1163 | −25.038 | −23.084 | −16.822 | 14.76 | C |

TABLE 1A-continued

| | | | | | | | | |
|---|---|---|---|---|---|---|---|---|
| ATOM | 3294 | C | GLY | B1163 | −26.047 | −24.096 | −17.255 | 15.34 | C |
| ATOM | 3295 | O | GLY | B1163 | −26.976 | −24.428 | −16.501 | 16.36 | O |
| ATOM | 3296 | N | ASP | B1164 | −25.917 | −24.588 | −18.48 | 16.34 | N |
| ATOM | 3297 | CA | ASP | B1164 | −26.945 | −25.538 | −18.957 | 18.41 | C |
| ATOM | 3298 | CB | ASP | B1164 | −27.121 | −25.598 | −20.496 | 18.9 | C |
| ATOM | 3299 | CG | ASP | B1164 | −25.891 | −26.048 | −21.199 | 21.41 | C |
| ATOM | 3300 | OD1 | ASP | B1164 | −24.914 | −25.301 | −21.18 | 28.55 | O |
| ATOM | 3301 | OD2 | ASP | B1164 | −25.853 | −27.138 | −21.785 | 29.67 | O |
| ATOM | 3302 | C | ASP | B1164 | −26.682 | −26.928 | −18.37 | 17.3 | C |
| ATOM | 3303 | O | ASP | B1164 | −25.566 | −27.291 | −18.054 | 16 | O |
| ATOM | 3304 | N | LEU | B1165 | −27.774 | −27.648 | −18.211 | 17.7 | N |
| ATOM | 3305 | CA | LEU | B1165 | −27.81 | −28.965 | −17.592 | 18.17 | C |
| ATOM | 3306 | CB | LEU | B1165 | −29.266 | −29.359 | −17.491 | 17.68 | C |
| ATOM | 3307 | CG | LEU | B1165 | −29.707 | −30.465 | −16.606 | 19.62 | C |
| ATOM | 3308 | CD1 | LEU | B1165 | −29.32 | −30.147 | −15.204 | 16.24 | C |
| ATOM | 3309 | CD2 | LEU | B1165 | −31.247 | −30.479 | −16.754 | 18.87 | C |
| ATOM | 3310 | C | LEU | B1165 | −27.036 | −29.93 | −18.463 | 18.24 | C |
| ATOM | 3311 | O | LEU | B1165 | −26.37 | −30.857 | −17.984 | 19.49 | O |
| ATOM | 3312 | O | GLN | B1166 | −24.217 | −31.36 | −20.284 | 19.01 | O |
| ATOM | 3313 | N | GLN | B1166 | −27.018 | −29.582 | −19.74 | 20 | |
| ATOM | 3314 | CA | GLN | B1166 | −26.241 | −30.315 | −20.685 | 20 | |
| ATOM | 3315 | C | GLN | B1166 | −24.776 | −30.339 | −20.427 | 20 | |
| ATOM | 3316 | CB | GLN | B1166 | −26.63 | −30.114 | −22.143 | 20 | |
| ATOM | 3317 | CG | GLN | B1166 | −26.508 | −31.277 | −22.946 | 20 | |
| ATOM | 3318 | CD | GLN | B1166 | −25.18 | −31.389 | −23.537 | 20 | |
| ATOM | 3319 | OE1 | GLN | B1166 | −24.559 | −30.388 | −23.785 | 20 | |
| ATOM | 3320 | NE2 | GLN | B1166 | −24.739 | −32.604 | −23.846 | 20 | |
| ATOM | 3321 | N | ASN | B1167 | −24.187 | −29.18 | −20.32 | 17.24 | N |
| ATOM | 3322 | CA | ASN | B1167 | −22.791 | −29.026 | −20.108 | 16.95 | C |
| ATOM | 3323 | CB | ASN | B1167 | −22.376 | −27.567 | −20.263 | 20.74 | C |
| ATOM | 3324 | CG | ASN | B1167 | −22.142 | −27.188 | −21.735 | 27.08 | C |
| ATOM | 3325 | OD1 | ASN | B1167 | −22.25 | −26.022 | −22.133 | 31.53 | O |
| ATOM | 3326 | ND2 | ASN | B1167 | −21.845 | −28.203 | −22.554 | 33.46 | N |
| ATOM | 3327 | C | ASN | B1167 | −22.438 | −29.459 | −18.73 | 15.8 | C |
| ATOM | 3328 | O | ASN | B1167 | −21.324 | −29.908 | −18.491 | 15.55 | O |
| ATOM | 3329 | N | PHE | B1168 | −23.407 | −29.357 | −17.815 | 13.95 | N |
| ATOM | 3330 | CA | PHE | B1168 | −23.214 | −29.806 | −16.451 | 10.88 | C |
| ATOM | 3331 | CB | PHE | B1168 | −24.361 | −29.366 | −15.595 | 11.09 | C |
| ATOM | 3332 | CG | PHE | B1168 | −24.158 | −29.635 | −14.117 | 11.13 | C |
| ATOM | 3333 | CD1 | PHE | B1168 | −23.363 | −28.811 | −13.353 | 10.57 | C |
| ATOM | 3334 | CD2 | PHE | B1168 | −24.695 | −30.78 | −13.517 | 12.93 | C |
| ATOM | 3335 | CE1 | PHE | B1168 | −23.163 | −29.081 | −11.984 | 10.74 | C |
| ATOM | 3336 | CE2 | PHE | B1168 | −24.481 | −31.042 | −12.106 | 11.1 | C |
| ATOM | 3337 | CZ | PHE | B1168 | −23.755 | −30.167 | −11.369 | 8.04 | C |
| ATOM | 3338 | C | PHE | B1168 | −22.949 | −31.297 | −16.311 | 10.98 | C |
| ATOM | 3339 | O | PHE | B1168 | −21.953 | −31.673 | −15.737 | 11.29 | O |
| ATOM | 3340 | N | ILE | B1169 | −23.815 | −32.144 | −16.851 | 11.3 | N |
| ATOM | 3341 | CA | ILE | B1169 | −23.729 | −33.567 | −16.649 | 12.11 | C |
| ATOM | 3342 | CB | ILE | B1169 | −25.098 | −34.24 | −16.912 | 12.31 | C |
| ATOM | 3343 | CG2 | ILE | B1169 | −26.225 | −33.639 | −16.073 | 10.67 | C |
| ATOM | 3344 | CG1 | ILE | B1169 | −25.46 | −34.188 | −18.407 | 13.38 | C |
| ATOM | 3345 | CD1 | ILE | B1169 | −26.855 | −34.265 | −18.702 | 10.53 | C |
| ATOM | 3346 | C | ILE | B1169 | −22.594 | −34.162 | −17.527 | 15.08 | C |
| ATOM | 3347 | O | ILE | B1169 | −22.133 | −35.264 | −17.321 | 15.78 | O |
| ATOM | 3348 | N | ARG | B1170 | −22.087 | −33.403 | −18.478 | 18.02 | N |
| ATOM | 3349 | CA | ARG | B1170 | −20.955 | −33.871 | −19.3 | 20.11 | C |
| ATOM | 3350 | CB | ARG | B1170 | −20.93 | −33.178 | −20.633 | 20.14 | C |
| ATOM | 3351 | CG | ARG | B1170 | −21.93 | −33.631 | −21.507 | 25.59 | C |
| ATOM | 3352 | CD | ARG | B1170 | −21.717 | −32.821 | −22.713 | 37.19 | C |
| ATOM | 3353 | NE | ARG | B1170 | −20.989 | −33.521 | −23.777 | 45.62 | N |
| ATOM | 3354 | CZ | ARG | B1170 | −20.98 | −34.84 | −23.999 | 48.56 | C |
| ATOM | 3355 | NH1 | ARG | B1170 | −21.656 | −35.705 | −23.257 | 49.01 | N |
| ATOM | 3356 | NH2 | ARG | B1170 | −20.276 | −35.287 | −25.009 | 53.39 | N |
| ATOM | 3357 | C | ARG | B1170 | −19.646 | −33.526 | −18.713 | 19.84 | C |
| ATOM | 3358 | O | ARG | B1170 | −18.677 | −34.145 | −19.024 | 20.06 | O |
| ATOM | 3359 | N | ASN | B1171 | −19.618 | −32.485 | −17.907 | 21.49 | N |
| ATOM | 3360 | CA | ASN | B1171 | −18.43 | −32.106 | −17.182 | 22.67 | C |
| ATOM | 3361 | CB | ASN | B1171 | −18.795 | −30.932 | −16.286 | 23.22 | C |
| ATOM | 3362 | CG | ASN | B1171 | −17.572 | −30.201 | −15.733 | 23.88 | C |
| ATOM | 3363 | OD1 | ASN | B1171 | −16.55 | −30.813 | −15.4 | 20.38 | O |
| ATOM | 3364 | ND2 | ASN | B1171 | −17.694 | −28.874 | −15.624 | 20.34 | N |
| ATOM | 3365 | C | ASN | B1171 | −17.885 | −33.289 | −16.354 | 24.16 | C |
| ATOM | 3366 | O | ASN | B1171 | −18.536 | −33.819 | −15.452 | 22.97 | O |
| ATOM | 3367 | N | GLU | B1172 | −16.678 | −33.712 | −16.71 | 26.75 | N |
| ATOM | 3368 | CA | GLU | B1172 | −16.009 | −34.843 | −16.074 | 28.61 | C |
| ATOM | 3369 | CB | GLU | B1172 | −14.887 | −35.381 | −16.95 | 29.06 | C |
| ATOM | 3370 | CG | GLU | B1172 | −15.267 | −35.539 | −18.398 | 35.59 | C |
| ATOM | 3371 | CD | GLU | B1172 | −14.865 | −34.295 | −19.239 | 43.46 | C |
| ATOM | 3372 | OE1 | GLU | B1172 | −15.514 | −33.222 | −19.077 | 43.38 | O |
| ATOM | 3373 | OE2 | GLU | B1172 | −13.887 | −34.403 | −20.063 | 47.72 | O |

TABLE 1A-continued

| | | | | | | | | |
|---|---|---|---|---|---|---|---|---|
| ATOM | 3374 | C | GLU | B1172 | −15.483 | −34.444 | −14.708 | 27.92 | C |
| ATOM | 3375 | O | GLU | B1172 | −15.003 | −35.266 | −13.956 | 29.83 | O |
| ATOM | 3376 | N | THR | B1173 | −15.636 | −33.183 | −14.372 | 27.32 | N |
| ATOM | 3377 | CA | THR | B1173 | −15.43 | −32.68 | −13.012 | 26.3 | C |
| ATOM | 3378 | CB | THR | B1173 | −15.075 | −31.202 | −13.127 | 26.43 | C |
| ATOM | 3379 | OG1 | THR | B1173 | −13.63 | −31.125 | −13.229 | 30.48 | O |
| ATOM | 3380 | CG2 | THR | B1173 | −15.66 | −30.328 | −12.025 | 23.88 | C |
| ATOM | 3381 | C | THR | B1173 | −16.558 | −32.937 | −11.996 | 24.95 | C |
| ATOM | 3382 | O | THR | B1173 | −16.435 | −32.607 | −10.82 | 24.21 | O |
| ATOM | 3383 | N | HIS | B1174 | −17.62 | −33.571 | −12.472 | 24.38 | N |
| ATOM | 3384 | CA | HIS | B1174 | −18.893 | −33.624 | −11.786 | 25.17 | C |
| ATOM | 3385 | CB | HIS | B1174 | −20.018 | −32.862 | −12.503 | 25.48 | C |
| ATOM | 3386 | CG | HIS | B1174 | −19.887 | −31.375 | −12.444 | 29.5 | C |
| ATOM | 3387 | CD2 | HIS | B1174 | −19.494 | −30.546 | −11.44 | 31.51 | C |
| ATOM | 3388 | ND1 | HIS | B1174 | −20.152 | −30.563 | −13.535 | 33.78 | N |
| ATOM | 3389 | CE1 | HIS | B1174 | −19.929 | −29.297 | −13.204 | 33.6 | C |
| ATOM | 3390 | NE2 | HIS | B1174 | −19.518 | −29.261 | −11.942 | 33.57 | N |
| ATOM | 3391 | C | HIS | B1174 | −19.237 | −35.06 | −11.806 | 24.6 | C |
| ATOM | 3392 | O | HIS | B1174 | −19.048 | −35.739 | −12.822 | 25 | O |
| ATOM | 3393 | N | ASN | B1175 | −19.709 | −35.531 | −10.662 | 23.47 | N |
| ATOM | 3394 | CA | ASN | B1175 | −20.013 | −36.93 | −10.504 | 22.28 | C |
| ATOM | 3395 | CB | ASN | B1175 | −18.961 | −37.601 | −9.664 | 20.86 | C |
| ATOM | 3396 | CG | ASN | B1175 | −17.621 | −37.656 | −10.387 | 19.89 | C |
| ATOM | 3397 | OD1 | ASN | B1175 | −17.519 | −38.384 | −11.343 | 22.05 | O |
| ATOM | 3398 | ND2 | ASN | B1175 | −16.619 | −36.852 | −9.971 | 16.3 | N |
| ATOM | 3399 | C | ASN | B1175 | −21.423 | −37.021 | −9.946 | 23.32 | C |
| ATOM | 3400 | O | ASN | B1175 | −21.635 | −37.437 | −8.785 | 24.86 | O |
| ATOM | 3401 | N | PRO | B1176 | −22.414 | −36.616 | −10.773 | 22.41 | N |
| ATOM | 3402 | CD | PRO | B1176 | −22.338 | −36.215 | −12.177 | 22.32 | C |
| ATOM | 3403 | CA | PRO | B1176 | −23.771 | −36.663 | −10.305 | 23.02 | C |
| ATOM | 3404 | CB | PRO | B1176 | −24.534 | −35.94 | −11.415 | 22.38 | C |
| ATOM | 3405 | CG | PRO | B1176 | −23.765 | −36.251 | −12.623 | 22.63 | C |
| ATOM | 3406 | C | PRO | B1176 | −24.193 | −38.161 | −10.156 | 23.36 | C |
| ATOM | 3407 | O | PRO | B1176 | −23.874 | −38.971 | −11.045 | 23.72 | O |
| ATOM | 3408 | N | THR | B1177 | −24.891 | −38.522 | −9.066 | 22.41 | N |
| ATOM | 3409 | CA | THR | B1177 | −25.329 | −39.894 | −8.913 | 22.82 | C |
| ATOM | 3410 | CB | THR | B1177 | −25.906 | −40.189 | −7.496 | 23.27 | C |
| ATOM | 3411 | OG1 | THR | B1177 | −26.923 | −39.244 | −7.205 | 25.75 | O |
| ATOM | 3412 | CG2 | THR | B1177 | −24.846 | −40.122 | −6.402 | 24.8 | C |
| ATOM | 3413 | C | THR | B1177 | −26.445 | −40.103 | −9.907 | 21.38 | C |
| ATOM | 3414 | O | THR | B1177 | −27.015 | −39.122 | −10.377 | 22.43 | O |
| ATOM | 3415 | N | VAL | B1178 | −26.814 | −41.362 | −10.162 | 20.22 | N |
| ATOM | 3416 | CA | VAL | B1178 | −28.127 | −41.672 | −10.826 | 18.98 | C |
| ATOM | 3417 | CB | VAL | B1178 | −28.384 | −43.198 | −10.992 | 18.34 | C |
| ATOM | 3418 | CG1 | VAL | B1178 | −29.81 | −43.489 | −11.15 | 15.54 | C |
| ATOM | 3419 | CG2 | VAL | B1178 | −27.665 | −43.704 | −12.223 | 21.1 | C |
| ATOM | 3420 | C | VAL | B1178 | −29.339 | −40.965 | −10.181 | 17.51 | C |
| ATOM | 3421 | O | VAL | B1178 | −30.123 | −40.409 | −10.878 | 18.57 | O |
| ATOM | 3422 | N | LYS | B1179 | −29.475 | −40.98 | −8.856 | 17.04 | N |
| ATOM | 3423 | CA | LYS | B1179 | −30.533 | −40.228 | −8.217 | 16.95 | C |
| ATOM | 3424 | CB | LYS | B1179 | −30.434 | −40.373 | −6.733 | 17.15 | C |
| ATOM | 3425 | CG | LYS | B1179 | −31.75 | −40.037 | −6.122 | 20.25 | C |
| ATOM | 3426 | CD | LYS | B1179 | −31.633 | −39.315 | −4.835 | 21.96 | C |
| ATOM | 3427 | CE | LYS | B1179 | −32.453 | −40.04 | −3.77 | 20.85 | C |
| ATOM | 3428 | NZ | LYS | B1179 | −33.846 | −39.761 | −3.562 | 19.21 | N |
| ATOM | 3429 | C | LYS | B1179 | −30.573 | −38.71 | −8.511 | 16.1 | C |
| ATOM | 3430 | O | LYS | B1179 | −31.638 | −38.131 | −8.72 | 14.21 | O |
| ATOM | 3431 | N | ASP | B1180 | −29.418 | −38.055 | −8.42 | 16.12 | N |
| ATOM | 3432 | CA | ASP | B1180 | −29.33 | −36.644 | −8.707 | 16.31 | C |
| ATOM | 3433 | CB | ASP | B1180 | −27.843 | −36.248 | −8.692 | 19.77 | C |
| ATOM | 3434 | CG | ASP | B1180 | −27.216 | −36.236 | −7.291 | 22.65 | C |
| ATOM | 3435 | OD1 | ASP | B1180 | −25.969 | −36.124 | −7.281 | 24.69 | O |
| ATOM | 3436 | OD2 | ASP | B1180 | −27.935 | −36.383 | −6.262 | 27.87 | O |
| ATOM | 3437 | C | ASP | B1180 | −29.828 | −36.325 | −10.131 | 14.91 | C |
| ATOM | 3438 | O | ASP | B1180 | −30.496 | −35.363 | −10.344 | 13.63 | O |
| ATOM | 3439 | N | LEU | B1181 | −29.413 | −37.128 | −11.104 | 13.93 | N |
| ATOM | 3440 | CA | LEU | B1181 | −29.865 | −36.965 | −12.49 | 13.81 | C |
| ATOM | 3441 | CB | LEU | B1181 | −29.123 | −37.972 | −13.366 | 13.28 | C |
| ATOM | 3442 | CG | LEU | B1181 | −27.901 | −37.653 | −14.197 | 9.73 | C |
| ATOM | 3443 | CD1 | LEU | B1181 | −27.341 | −36.303 | −14.092 | 9.56 | C |
| ATOM | 3444 | CD2 | LEU | B1181 | −26.891 | −38.75 | −13.897 | 10.5 | C |
| ATOM | 3445 | C | LEU | B1181 | −31.377 | −37.123 | −12.681 | 13.36 | C |
| ATOM | 3446 | O | LEU | B1181 | −32.047 | −36.419 | −13.479 | 14.36 | O |
| ATOM | 3447 | N | ILE | B1182 | −31.922 | −38.037 | −11.915 | 13.26 | N |
| ATOM | 3448 | CA | ILE | B1182 | −33.364 | −38.243 | −11.922 | 14.38 | C |
| ATOM | 3449 | CB | ILE | B1182 | −33.811 | −39.543 | −11.232 | 14.16 | C |
| ATOM | 3450 | CG2 | ILE | B1182 | −35.3 | −39.644 | −11.367 | 14.28 | C |
| ATOM | 3451 | CG1 | ILE | B1182 | −33.124 | −40.796 | −11.852 | 16.35 | C |
| ATOM | 3452 | CD1 | ILE | B1182 | −33.51 | −42.162 | −11.15 | 13.84 | C |
| ATOM | 3453 | C | ILE | B1182 | −34.013 | −37.034 | −11.248 | 12.99 | C |

TABLE 1A-continued

| | | | | | | | | |
|---|---|---|---|---|---|---|---|---|
| ATOM | 3454 | O | ILE | B1182 | −35.112 | −36.592 | −11.651 | 13.57 | O |
| ATOM | 3455 | N | GLY | B1183 | −33.296 | −36.464 | −10.297 | 11.14 | N |
| ATOM | 3456 | CA | GLY | B1183 | −33.788 | −35.294 | −9.552 | 11.95 | C |
| ATOM | 3457 | C | GLY | B1183 | −33.881 | −34.082 | −10.45 | 11.52 | C |
| ATOM | 3458 | O | GLY | B1183 | −34.842 | −33.342 | −10.372 | 12.52 | O |
| ATOM | 3459 | N | PHE | B1184 | −32.878 | −33.895 | −11.321 | 11.73 | N |
| ATOM | 3460 | CA | PHE | B1184 | −32.913 | −32.822 | −12.365 | 11.3 | C |
| ATOM | 3461 | CB | PHE | B1184 | −31.571 | −32.746 | −13.138 | 10.96 | C |
| ATOM | 3462 | CG | PHE | B1184 | −30.39 | −32.459 | −12.273 | 11.49 | C |
| ATOM | 3463 | CD1 | PHE | B1184 | −30.525 | −31.643 | −11.109 | 13.87 | C |
| ATOM | 3464 | CD2 | PHE | B1184 | −29.157 | −32.957 | −12.595 | 11.09 | C |
| ATOM | 3465 | CE1 | PHE | B1184 | −29.436 | −31.36 | −10.293 | 9.36 | C |
| ATOM | 3466 | CE2 | PHE | B1184 | −28.055 | −32.649 | −11.827 | 13.76 | C |
| ATOM | 3467 | CZ | PHE | B1184 | −28.201 | −31.849 | −10.646 | 13.97 | C |
| ATOM | 3468 | C | PHE | B1184 | −34.078 | −33.017 | −13.34 | 10.31 | C |
| ATOM | 3469 | O | PHE | B1184 | −34.762 | −32.09 | −13.67 | 9.73 | O |
| ATOM | 3470 | N | GLY | B1185 | −34.284 | −34.259 | −13.786 | 11.17 | N |
| ATOM | 3471 | CA | GLY | B1185 | −35.405 | −34.585 | −14.702 | 10.09 | C |
| ATOM | 3472 | C | GLY | B1185 | −36.727 | −34.315 | −14.063 | 9.24 | C |
| ATOM | 3473 | O | GLY | B1185 | −37.591 | −33.763 | −14.709 | 10.87 | O |
| ATOM | 3474 | N | LEU | B1186 | −36.874 | −34.646 | −12.779 | 8.52 | N |
| ATOM | 3475 | CA | LEU | B1186 | −38.075 | −34.268 | −11.99 | 7.28 | C |
| ATOM | 3476 | CB | LEU | B1186 | −38.072 | −34.915 | −10.56 | 6.85 | C |
| ATOM | 3477 | CG | LEU | B1186 | −39.207 | −34.583 | −9.582 | 5.42 | C |
| ATOM | 3478 | CD1 | LEU | B1186 | −40.59 | −34.846 | −10.16 | 2 | C |
| ATOM | 3479 | CD2 | LEU | B1186 | −38.918 | −35.353 | −8.286 | 3.95 | C |
| ATOM | 3480 | C | LEU | B1186 | −38.308 | −32.767 | −11.899 | 8.57 | C |
| ATOM | 3481 | O | LEU | B1186 | −39.442 | −32.313 | −12.096 | 12.45 | O |
| ATOM | 3482 | N | GLN | B1187 | −37.292 | −31.971 | −11.62 | 18.71 | N |
| ATOM | 3483 | CA | GLN | B1187 | −37.472 | −30.518 | −11.66 | 10.1 | C |
| ATOM | 3484 | CB | GLN | B1187 | −36.18 | −29.843 | −11.25 | 11.08 | C |
| ATOM | 3485 | CG | GLN | B1187 | −35.743 | −30.165 | −9.871 | 11.17 | C |
| ATOM | 3486 | CD | GLN | B1187 | −34.601 | −29.239 | −9.455 | 13.84 | C |
| ATOM | 3487 | OE1 | GLN | B1187 | −34.721 | −28.008 | −9.538 | 14.08 | O |
| ATOM | 3488 | NE2 | GLN | B1187 | −33.476 | −29.829 | −9.045 | 15.84 | N |
| ATOM | 3489 | C | GLN | B1187 | −37.887 | −29.991 | −13.027 | 9.54 | C |
| ATOM | 3490 | O | GLN | B1187 | −38.666 | −29.035 | −13.151 | 11.12 | O |
| ATOM | 3491 | N | VAL | B1188 | −37.347 | −30.555 | −14.079 | 7.7 | N |
| ATOM | 3492 | CA | VAL | B1188 | −37.784 | −30.081 | −15.428 | 7.36 | C |
| ATOM | 3493 | CB | VAL | B1188 | −36.91 | −30.734 | −16.527 | 6.86 | C |
| ATOM | 3494 | CG1 | VAL | B1188 | −37.338 | −30.385 | −17.939 | 3.33 | C |
| ATOM | 3495 | CG2 | VAL | B1188 | −35.458 | −30.404 | −16.278 | 2 | C |
| ATOM | 3496 | C | VAL | B1188 | −39.245 | −30.414 | −15.687 | 8.4 | C |
| ATOM | 3497 | O | VAL | B1188 | −39.952 | −29.679 | −16.346 | 9.43 | O |
| ATOM | 3498 | N | ALA | B1189 | −39.704 | −31.547 | −15.173 | 9.65 | N |
| ATOM | 3499 | CA | ALA | B1189 | −41.041 | −31.997 | −15.446 | 9.84 | C |
| ATOM | 3500 | CB | ALA | B1189 | −41.181 | −33.479 | −15.04 | 9.75 | C |
| ATOM | 3501 | C | ALA | B1189 | −41.986 | −31.113 | −14.676 | 10.41 | C |
| ATOM | 3502 | O | ALA | B1189 | −43.117 | −30.837 | −15.14 | 11.55 | O |
| ATOM | 3503 | N | LYS | B1190 | −41.51 | −30.588 | −13.543 | 10.99 | N |
| ATOM | 3504 | CA | LYS | B1190 | −42.341 | −29.679 | −12.721 | 12.28 | C |
| ATOM | 3505 | CB | LYS | B1190 | −41.775 | −29.502 | −11.359 | 12.77 | C |
| ATOM | 3506 | CG | LYS | B1190 | −41.7 | −30.717 | −10.574 | 12.61 | C |
| ATOM | 3507 | CD | LYS | B1190 | −41.08 | −30.362 | −9.251 | 15.08 | C |
| ATOM | 3508 | CE | LYS | B1190 | −41.464 | −31.401 | −8.288 | 19.04 | C |
| ATOM | 3509 | NZ | LYS | B1190 | −40.942 | −30.924 | −6.946 | 25.19 | N |
| ATOM | 3510 | C | LYS | B1190 | −42.506 | −28.293 | −13.3 | 11.94 | C |
| ATOM | 3511 | O | LYS | B1190 | −43.611 | −27.659 | −13.176 | 14.36 | O |
| ATOM | 3512 | N | GLY | B1191 | −41.439 | −27.806 | −13.918 | 10.85 | N |
| ATOM | 3513 | CA | GLY | B1191 | −41.463 | −26.55 | −14.72 | 8.71 | C |
| ATOM | 3514 | C | GLY | B1191 | −42.34 | −26.777 | −15.935 | 8 | C |
| ATOM | 3515 | O | GLY | B1191 | −43.19 | −25.951 | −16.236 | 8.54 | O |
| ATOM | 3516 | N | MET | B1192 | −42.205 | −27.936 | −16.602 | 7.97 | N |
| ATOM | 3517 | CA | MET | B1192 | −42.971 | −28.222 | −17.854 | 8.25 | C |
| ATOM | 3518 | CB | MET | B1192 | −42.501 | −29.543 | −18.507 | 8.8 | C |
| ATOM | 3519 | CG | MET | B1192 | −41.361 | −29.451 | −19.436 | 11.12 | C |
| ATOM | 3520 | SD | MET | B1192 | −41.314 | −27.838 | −20.283 | 18 | S |
| ATOM | 3521 | CE | MET | B1192 | −42.181 | −27.995 | −21.823 | 11.46 | C |
| ATOM | 3522 | C | MET | B1192 | −44.437 | −28.371 | −17.563 | 7.29 | C |
| ATOM | 3523 | O | MET | B1192 | −45.335 | −27.941 | −18.337 | 7.17 | O |
| ATOM | 3524 | N | LYS | B1193 | −44.691 | −29.027 | −16.451 | 7.48 | N |
| ATOM | 3525 | CA | LYS | B1193 | −46.097 | −29.193 | −15.988 | 9.21 | C |
| ATOM | 3526 | CB | LYS | B1193 | −46.127 | −30.004 | −14.713 | 7.62 | C |
| ATOM | 3527 | CG | LYS | B1193 | −47.429 | −30.099 | −14.098 | 7.45 | C |
| ATOM | 3528 | CD | LYS | B1193 | −47.198 | −30.498 | −12.681 | 10.42 | C |
| ATOM | 3529 | CE | LYS | B1193 | −48.442 | −30.778 | −12.021 | 14.83 | C |
| ATOM | 3530 | NZ | LYS | B1193 | −48.088 | −30.966 | −10.58 | 22.35 | N |
| ATOM | 3531 | C | LYS | B1193 | −46.75 | −27.808 | −15.773 | 8.79 | C |
| ATOM | 3532 | O | LYS | B1193 | −47.911 | −27.589 | −16.18 | 9.23 | O |
| ATOM | 3533 | N | TYR | B1194 | −45.974 | −26.879 | −15.186 | 9.48 | N |

TABLE 1A-continued

| ATOM | 3534 | CA | TYR | B1194 | −46.435 | −25.503 | −15.04 | 10.02 | C |
|---|---|---|---|---|---|---|---|---|---|
| ATOM | 3535 | CB | TYR | B1194 | −45.485 | −24.704 | −14.143 | 10.13 | C |
| ATOM | 3536 | CG | TYR | B1194 | −45.798 | −23.213 | −14.084 | 9.08 | C |
| ATOM | 3537 | CD1 | TYR | B1194 | −46.675 | −22.706 | −13.116 | 7.43 | C |
| ATOM | 3538 | CE1 | TYR | B1194 | −46.958 | −21.357 | −13.076 | 9.59 | C |
| ATOM | 3539 | CD2 | TYR | B1194 | −45.186 | −22.323 | −14.971 | 5.88 | C |
| ATOM | 3540 | CE2 | TYR | B1194 | −45.424 | −20.998 | −14.942 | 7.13 | C |
| ATOM | 3541 | CZ | TYR | B1194 | −46.329 | −20.48 | −14.019 | 12.26 | C |
| ATOM | 3542 | OH | TYR | B1194 | −46.625 | −19.107 | −14.038 | 11.64 | O |
| ATOM | 3543 | C | TYR | B1194 | −46.645 | −24.811 | −16.41 | 10.44 | C |
| ATOM | 3544 | O | TYR | B1194 | −47.777 | −24.356 | −16.745 | 11.5 | O |
| ATOM | 3545 | N | LEU | B1195 | −45.606 | −24.771 | −17.235 | 9.91 | N |
| ATOM | 3546 | CA | LEU | B1195 | −45.724 | −24.136 | −18.545 | 10.18 | C |
| ATOM | 3547 | CB | LEU | B1195 | −44.469 | −24.386 | −19.357 | 11.31 | C |
| ATOM | 3548 | CG | LEU | B1195 | −43.235 | −23.478 | −19.274 | 8.14 | C |
| ATOM | 3549 | CD1 | LEU | B1195 | −43.559 | −22.302 | −18.412 | 11.05 | C |
| ATOM | 3550 | CD2 | LEU | B1195 | −42.091 | −24.231 | −18.759 | 11.77 | C |
| ATOM | 3551 | C | LEU | B1195 | −46.878 | −24.77 | −19.256 | 12.15 | C |
| ATOM | 3552 | O | LEU | B1195 | −47.733 | −24.094 | −19.829 | 12.53 | O |
| ATOM | 3553 | N | ALA | B1196 | −46.971 | −26.096 | −19.173 | 12.77 | N |
| ATOM | 3554 | CA | ALA | B1196 | −48.058 | −26.765 | −19.89 | 13.11 | C |
| ATOM | 3555 | CB | ALA | B1196 | −47.874 | −28.244 | −19.778 | 14.13 | C |
| ATOM | 3556 | C | ALA | B1196 | −49.452 | −26.395 | −19.441 | 13.63 | C |
| ATOM | 3557 | O | ALA | B1196 | −50.383 | −26.608 | −20.204 | 15.78 | O |
| ATOM | 3558 | N | SER | B1197 | −49.639 | −25.911 | −18.196 | 14.48 | N |
| ATOM | 3559 | CA | SER | B1197 | −50.99 | −25.572 | −17.664 | 12.95 | C |
| ATOM | 3560 | CB | SER | B1197 | −51.017 | −25.758 | −16.192 | 12.98 | C |
| ATOM | 3561 | OG | SER | B1197 | −50.055 | −24.902 | −15.565 | 17.5 | O |
| ATOM | 3562 | C | SER | B1197 | −51.308 | −24.121 | −18.035 | 12.58 | C |
| ATOM | 3563 | O | SER | B1197 | −52.442 | −23.652 | −17.985 | 12.68 | O |
| ATOM | 3564 | N | LYS | B1198 | −50.286 | −23.398 | −18.441 | 13.13 | N |
| ATOM | 3565 | CA | LYS | B1198 | −50.489 | −22.056 | −18.999 | 13.05 | C |
| ATOM | 3566 | CB | LYS | B1198 | −49.29 | −21.187 | −18.707 | 12.52 | C |
| ATOM | 3567 | CG | LYS | B1198 | −48.959 | −21.126 | −17.249 | 12.04 | C |
| ATOM | 3568 | CD | LYS | B1198 | −50.273 | −20.967 | −16.457 | 13.08 | C |
| ATOM | 3569 | CE | LYS | B1198 | −49.936 | −21.012 | −14.985 | 17.36 | C |
| ATOM | 3570 | NZ | LYS | B1198 | −51.129 | −20.589 | −14.245 | 21.98 | N |
| ATOM | 3571 | C | LYS | B1198 | −50.649 | −22.161 | −20.484 | 13.41 | C |
| ATOM | 3572 | O | LYS | B1198 | −50.651 | −21.132 | −21.155 | 13.33 | O |
| ATOM | 3573 | N | LYS | B1199 | −50.755 | −23.418 | −20.98 | 13.76 | N |
| ATOM | 3574 | CA | LYS | B1199 | −50.809 | −23.725 | −22.414 | 14.88 | C |
| ATOM | 3575 | CB | LYS | B1199 | −52.085 | −23.141 | −23.005 | 14.84 | C |
| ATOM | 3576 | CG | LYS | B1199 | −53.317 | −23.86 | −22.454 | 21.78 | C |
| ATOM | 3577 | CD | LYS | B1199 | −54.523 | −22.873 | −22.192 | 33.81 | C |
| ATOM | 3578 | CE | LYS | B1199 | −55.034 | −22.06 | −23.489 | 35.48 | C |
| ATOM | 3579 | NZ | LYS | B1199 | −55.173 | −22.933 | −24.757 | 39.92 | N |
| ATOM | 3580 | C | LYS | B1199 | −49.553 | −23.275 | −23.214 | 14.93 | C |
| ATOM | 3581 | O | LYS | B1199 | −49.62 | −22.835 | −24.357 | 14.95 | O |
| ATOM | 3582 | N | PHE | B1200 | −48.393 | −23.358 | −22.585 | 14.67 | N |
| ATOM | 3583 | CA | PHE | B1200 | −47.225 | −22.929 | −23.253 | 14.24 | C |
| ATOM | 3584 | CB | PHE | B1200 | −46.337 | −22.153 | −22.308 | 12.15 | C |
| ATOM | 3585 | CG | PHE | B1200 | −45.039 | −21.734 | −22.94 | 11.68 | C |
| ATOM | 3586 | CD1 | PHE | B1200 | −43.852 | −22.502 | −22.753 | 12.56 | C |
| ATOM | 3587 | CD2 | PHE | B1200 | −44.986 | −20.629 | −23.723 | 7.4 | C |
| ATOM | 3588 | CE1 | PHE | B1200 | −42.662 | −22.101 | −23.342 | 11.48 | C |
| ATOM | 3589 | CE2 | PHE | B1200 | −43.803 | −20.209 | −24.297 | 10.2 | C |
| ATOM | 3590 | CZ | PHE | B1200 | −42.657 | −20.938 | −24.138 | 10.48 | C |
| ATOM | 3591 | C | PHE | B1200 | −46.522 | −24.127 | −23.913 | 14.52 | C |
| ATOM | 3592 | O | PHE | B1200 | −46.239 | −25.117 | −23.274 | 14.04 | O |
| ATOM | 3593 | N | VAL | B1201 | −46.278 | −24.026 | −25.212 | 15.61 | N |
| ATOM | 3594 | CA | VAL | B1201 | −45.552 | −25.077 | −25.937 | 16.14 | C |
| ATOM | 3595 | CB | VAL | B1201 | −46.223 | −25.368 | −27.276 | 16.14 | C |
| ATOM | 3596 | CG1 | VAL | B1201 | −45.37 | −26.28 | −28.169 | 14.77 | C |
| ATOM | 3597 | CG2 | VAL | B1201 | −47.68 | −25.93 | −27.046 | 16.33 | C |
| ATOM | 3598 | C | VAL | B1201 | −44.093 | −24.6 | −26.108 | 16.79 | C |
| ATOM | 3599 | O | VAL | B1201 | −43.794 | −23.635 | −26.791 | 17.87 | O |
| ATOM | 3600 | N | HIS | B1202 | −43.185 | −25.274 | −25.451 | 15.99 | N |
| ATOM | 3601 | CA | HIS | B1202 | −41.85 | −24.848 | −25.49 | 17.06 | C |
| ATOM | 3602 | CB | HIS | B1202 | −41.108 | −25.639 | −24.44 | 16.49 | C |
| ATOM | 3603 | CG | HIS | B1202 | −39.733 | −25.142 | −24.188 | 15.87 | C |
| ATOM | 3604 | CD2 | HIS | B1202 | −39.216 | −24.479 | −23.131 | 13.61 | C |
| ATOM | 3605 | ND1 | HIS | B1202 | −38.697 | −25.338 | −25.084 | 16.33 | N |
| ATOM | 3606 | CE1 | HIS | B1202 | −37.596 | −24.822 | −24.575 | 15.98 | C |
| ATOM | 3607 | NE2 | HIS | B1202 | −37.887 | −24.287 | −23.392 | 16.78 | N |
| ATOM | 3608 | C | HIS | B1202 | −41.223 | −25.044 | −26.903 | 18.23 | C |
| ATOM | 3609 | O | HIS | B1202 | −40.688 | −24.086 | −27.441 | 18.63 | O |
| ATOM | 3610 | N | ARG | B1203 | −41.276 | −26.276 | −27.479 | 19.01 | N |
| ATOM | 3611 | CA | ARG | B1203 | −40.731 | −26.604 | −28.854 | 18.59 | C |
| ATOM | 3612 | CB | ARG | B1203 | −41.156 | −25.584 | −29.948 | 17.85 | C |
| ATOM | 3613 | CG | ARG | B1203 | −42.573 | −25.201 | −29.778 | 22.3 | C |

TABLE 1A-continued

| | | | | | | | | |
|---|---|---|---|---|---|---|---|---|
| ATOM | 3614 | CD | ARG | B1203 | −42.853 | −23.874 | −30.255 | 27.82 | C |
| ATOM | 3615 | NE | ARG | B1203 | −42.669 | −23.825 | −31.688 | 36.07 | N |
| ATOM | 3616 | CZ | ARG | B1203 | −43.656 | −23.621 | −32.572 | 35.92 | C |
| ATOM | 3617 | NH1 | ARG | B1203 | −44.903 | −23.457 | −32.111 | 34.73 | N |
| ATOM | 3618 | NH2 | ARG | B1203 | −43.375 | −23.574 | −33.901 | 31.08 | N |
| ATOM | 3619 | C | ARG | B1203 | −39.217 | −26.786 | −28.933 | 17.32 | C |
| ATOM | 3620 | O | ARG | B1203 | −38.669 | −26.981 | −30.009 | 16.84 | O |
| ATOM | 3621 | N | ASP | B1204 | −38.537 | −26.693 | −27.819 | 16.22 | N |
| ATOM | 3622 | CA | ASP | B1204 | −37.087 | −26.9 | −27.88 | 15.93 | C |
| ATOM | 3623 | CB | ASP | B1204 | −36.399 | −25.605 | −28.307 | 14.57 | C |
| ATOM | 3624 | CG | ASP | B1204 | −34.994 | −25.832 | −28.815 | 19.07 | C |
| ATOM | 3625 | OD1 | ASP | B1204 | −34.264 | −24.803 | −28.903 | 18.92 | O |
| ATOM | 3626 | OD2 | ASP | B1204 | −34.581 | −27.029 | −29.074 | 21.21 | O |
| ATOM | 3627 | C | ASP | B1204 | −36.575 | −27.412 | −26.517 | 14.81 | C |
| ATOM | 3628 | O | ASP | B1204 | −35.502 | −27.041 | −26.05 | 15.16 | O |
| ATOM | 3629 | N | LEU | B1205 | −37.383 | −28.239 | −25.875 | 13.6 | N |
| ATOM | 3630 | CA | LEU | B1205 | −37.041 | −28.817 | −24.611 | 13.38 | C |
| ATOM | 3631 | CB | LEU | B1205 | −38.261 | −29.547 | −24.046 | 11.84 | C |
| ATOM | 3632 | CG | LEU | B1205 | −38.072 | −30.052 | −22.634 | 10.06 | C |
| ATOM | 3633 | CD1 | LEU | B1205 | −37.692 | −28.865 | −21.634 | 7.06 | C |
| ATOM | 3634 | CD2 | LEU | B1205 | −39.28 | −30.784 | −22.242 | 7.43 | C |
| ATOM | 3635 | C | LEU | B1205 | −35.89 | −29.815 | −24.833 | 14.11 | C |
| ATOM | 3636 | O | LEU | B1205 | −36.033 | −30.718 | −25.665 | 15.58 | O |
| ATOM | 3637 | N | ALA | B1206 | −34.783 | −29.619 | −24.1 | 11.95 | N |
| ATOM | 3638 | CA | ALA | B1206 | −33.535 | −30.33 | −24.23 | 10.68 | C |
| ATOM | 3639 | CB | ALA | B1206 | −32.831 | −30.034 | −25.596 | 12.55 | C |
| ATOM | 3640 | C | ALA | B1206 | −32.67 | −29.834 | −23.122 | 8.83 | C |
| ATOM | 3641 | O | ALA | B1206 | −32.888 | −28.723 | −22.579 | 8.67 | O |
| ATOM | 3642 | N | ALA | B1207 | −31.68 | −30.636 | −22.748 | 7.74 | N |
| ATOM | 3643 | CA | ALA | B1207 | −30.893 | −30.32 | −21.534 | 6.84 | C |
| ATOM | 3644 | CB | ALA | B1207 | −29.986 | −31.448 | −21.186 | 7.04 | C |
| ATOM | 3645 | C | ALA | B1207 | −30.145 | −29.037 | −21.756 | 6.97 | C |
| ATOM | 3646 | O | ALA | B1207 | −29.853 | −28.316 | −20.814 | 7.07 | O |
| ATOM | 3647 | N | ARG | B1208 | −29.857 | −28.723 | −23.021 | 8.48 | N |
| ATOM | 3648 | CA | ARG | B1208 | −29.105 | −27.484 | −23.376 | 10.48 | C |
| ATOM | 3649 | CB | ARG | B1208 | −28.612 | −27.459 | −24.831 | 10.31 | C |
| ATOM | 3650 | CG | ARG | B1208 | −29.687 | −27.862 | −25.863 | 11.12 | C |
| ATOM | 3651 | CD | ARG | B1208 | −29.252 | −27.63 | −27.365 | 8.82 | C |
| ATOM | 3652 | NE | ARG | B1208 | −30.465 | −27.73 | −28.2 | 13.09 | N |
| ATOM | 3653 | CZ | ARG | B1208 | −31.072 | −28.876 | −28.53 | 11.69 | C |
| ATOM | 3654 | NH1 | ARG | B1208 | −30.58 | −30.006 | −28.144 | 16.97 | N |
| ATOM | 3655 | NH2 | ARG | B1208 | −32.179 | −28.902 | −29.258 | 16.72 | N |
| ATOM | 3656 | C | ARG | B1208 | −29.912 | −26.26 | −23.043 | 11.65 | C |
| ATOM | 3657 | O | ARG | B1208 | −29.374 | −25.15 | −22.889 | 12.53 | O |
| ATOM | 3658 | N | ASN | B1209 | −31.213 | −26.477 | −22.842 | 13.13 | N |
| ATOM | 3659 | CA | ASN | B1209 | −32.14 | −25.374 | −22.622 | 12.9 | C |
| ATOM | 3660 | CB | ASN | B1209 | −33.281 | −25.547 | −23.589 | 12.61 | C |
| ATOM | 3661 | CG | ASN | B1209 | −32.907 | −25.053 | −24.946 | 14.64 | C |
| ATOM | 3662 | OD1 | ASN | B1209 | −32.141 | −24.081 | −25.051 | 14.89 | O |
| ATOM | 3663 | ND2 | ASN | B1209 | −33.363 | −25.722 | −25.976 | 14.02 | N |
| ATOM | 3664 | C | ASN | B1209 | −32.641 | −25.213 | −21.198 | 13.91 | C |
| ATOM | 3665 | O | ASN | B1209 | −33.525 | −24.39 | −20.955 | 16.03 | O |
| ATOM | 3666 | N | CYS | B1210 | −32.125 | −26.041 | −20.284 | 13.09 | N |
| ATOM | 3667 | CA | CYS | B1210 | −32.375 | −25.967 | −18.881 | 11.8 | C |
| ATOM | 3668 | CB | CYS | B1210 | −32.63 | −27.335 | −18.338 | 12.69 | C |
| ATOM | 3669 | SG | CYS | B1210 | −34.022 | −28.189 | −19.054 | 17.53 | S |
| ATOM | 3670 | C | CYS | B1210 | −31.137 | −25.492 | −18.22 | 11.23 | C |
| ATOM | 3671 | O | CYS | B1210 | −30.016 | −26.019 | −18.489 | 11.67 | O |
| ATOM | 3672 | N | MET | B1211 | −31.34 | −24.527 | −17.333 | 10.14 | N |
| ATOM | 3673 | CA | MET | B1211 | −30.242 | −23.886 | −16.565 | 10.47 | C |
| ATOM | 3674 | CB | MET | B1211 | −30.323 | −22.352 | −16.588 | 9.5 | C |
| ATOM | 3675 | CG | MET | B1211 | −30.138 | −21.749 | −18.03 | 11.4 | C |
| ATOM | 3676 | SD | MET | B1211 | −28.622 | −22.258 | −18.911 | 15.66 | S |
| ATOM | 3677 | CE | MET | B1211 | −29.284 | −22.438 | −20.557 | 15.6 | C |
| ATOM | 3678 | C | MET | B1211 | −30.211 | −24.387 | −15.127 | 11.73 | C |
| ATOM | 3679 | O | MET | B1211 | −31.275 | −24.724 | −14.552 | 12.17 | O |
| ATOM | 3680 | N | LEU | B1212 | −29 | −24.496 | −14.577 | 12.21 | N |
| ATOM | 3681 | CA | LEU | B1212 | −28.819 | −24.898 | −13.23 | 13.72 | C |
| ATOM | 3682 | CB | LEU | B1212 | −27.911 | −26.104 | −13.209 | 15.2 | C |
| ATOM | 3683 | CG | LEU | B1212 | −28.199 | −27.458 | −12.58 | 14.9 | C |
| ATOM | 3684 | CD1 | LEU | B1212 | −26.877 | −27.911 | −12.068 | 19.56 | C |
| ATOM | 3685 | CD2 | LEU | B1212 | −29.154 | −27.446 | −11.458 | 18.72 | C |
| ATOM | 3686 | C | LEU | B1212 | −28.209 | −23.774 | −12.394 | 15.72 | C |
| ATOM | 3687 | O | LEU | B1212 | −27.178 | −23.229 | −12.73 | 14.42 | O |
| ATOM | 3688 | N | ASP | B1213 | −28.835 | −23.439 | −11.272 | 17.77 | N |
| ATOM | 3689 | CA | ASP | B1213 | −28.276 | −22.395 | −10.489 | 19.65 | C |
| ATOM | 3690 | CB | ASP | B1213 | −29.353 | −21.455 | −9.98 | 21.08 | C |
| ATOM | 3691 | CG | ASP | B1213 | −30.28 | −22.092 | −8.886 | 26.99 | C |
| ATOM | 3692 | OD1 | ASP | B1213 | −29.903 | −23.095 | −8.188 | 30.93 | O |
| ATOM | 3693 | OD2 | ASP | B1213 | −31.406 | −21.543 | −8.717 | 30.83 | O |

TABLE 1A-continued

| | | | | | | | | |
|---|---|---|---|---|---|---|---|---|
| ATOM | 3694 | C | ASP | B1213 | −27.46 | −22.962 | −9.377 | 20.76 | C |
| ATOM | 3695 | O | ASP | B1213 | −27.306 | −24.167 | −9.271 | 20.15 | O |
| ATOM | 3696 | N | GLU | B1214 | −26.976 | −22.073 | −8.511 | 23.75 | N |
| ATOM | 3697 | CA | GLU | B1214 | −25.965 | −22.404 | −7.491 | 25.83 | C |
| ATOM | 3698 | CB | GLU | B1214 | −25.358 | −21.152 | −6.856 | 25.58 | C |
| ATOM | 3699 | CG | GLU | B1214 | −25.832 | −20.942 | −5.458 | 33.06 | C |
| ATOM | 3700 | CD | GLU | B1214 | −26.949 | −19.858 | −5.364 | 42.46 | C |
| ATOM | 3701 | OE1 | GLU | B1214 | −27.904 | −19.886 | −6.208 | 40.39 | O |
| ATOM | 3702 | OE2 | GLU | B1214 | −26.834 | −18.969 | −4.437 | 46.68 | O |
| ATOM | 3703 | C | GLU | B1214 | −26.478 | −23.378 | −6.427 | 25.29 | C |
| ATOM | 3704 | O | GLU | B1214 | −25.668 | −24.107 | −5.833 | 26.69 | O |
| ATOM | 3705 | N | LYS | B1215 | −27.791 | −23.455 | −6.219 | 24.02 | N |
| ATOM | 3706 | CA | LYS | B1215 | −28.295 | −24.503 | −5.337 | 23.76 | C |
| ATOM | 3707 | CB | LYS | B1215 | −29.237 | −23.983 | −4.278 | 24.17 | C |
| ATOM | 3708 | CG | LYS | B1215 | −30.271 | −23.059 | −4.778 | 28.88 | C |
| ATOM | 3709 | CD | LYS | B1215 | −29.893 | −21.669 | −4.214 | 37.25 | C |
| ATOM | 3710 | CE | LYS | B1215 | −29.192 | −21.827 | −2.79 | 40.05 | C |
| ATOM | 3711 | NZ | LYS | B1215 | −30.165 | −22.103 | −1.649 | 40.23 | N |
| ATOM | 3712 | C | LYS | B1215 | −28.935 | −25.684 | −6.053 | 22.81 | C |
| ATOM | 3713 | O | LYS | B1215 | −29.587 | −26.555 | −5.397 | 21.67 | O |
| ATOM | 3714 | N | PHE | B1216 | −28.742 | −25.725 | −7.378 | 19.98 | N |
| ATOM | 3715 | CA | PHE | B1216 | −29.093 | −26.908 | −8.121 | 19.25 | C |
| ATOM | 3716 | CB | PHE | B1216 | −28.596 | −28.213 | −7.422 | 18.9 | C |
| ATOM | 3717 | CG | PHE | B1216 | −27.111 | −28.264 | −7.317 | 17.96 | C |
| ATOM | 3718 | CD1 | PHE | B1216 | −26.472 | −27.984 | −6.089 | 22.08 | C |
| ATOM | 3719 | CD2 | PHE | B1216 | −26.341 | −28.452 | −8.451 | 15.15 | C |
| ATOM | 3720 | CE1 | PHE | B1216 | −25.082 | −27.968 | −5.993 | 22.25 | C |
| ATOM | 3721 | CE2 | PHE | B1216 | −24.969 | −28.436 | −8.389 | 16.63 | C |
| ATOM | 3722 | CZ | PHE | B1216 | −24.317 | −28.182 | −7.178 | 20.9 | C |
| ATOM | 3723 | C | PHE | B1216 | −30.579 | −26.93 | −8.405 | 18.18 | C |
| ATOM | 3724 | O | PHE | B1216 | −31.197 | −28.017 | −8.558 | 17.35 | O |
| ATOM | 3725 | N | THR | B1217 | −31.133 | −25.72 | −8.503 | 16.24 | N |
| ATOM | 3726 | CA | THR | B1217 | −32.471 | −25.614 | −9.048 | 15.6 | C |
| ATOM | 3727 | CB | THR | B1217 | −33.189 | −24.352 | −8.566 | 15.47 | C |
| ATOM | 3728 | OG1 | THR | B1217 | −33.024 | −24.2 | −7.158 | 18.4 | O |
| ATOM | 3729 | CG2 | THR | B1217 | −34.651 | −24.371 | −8.888 | 13.83 | C |
| ATOM | 3730 | C | THR | B1217 | −32.262 | −25.557 | −10.554 | 14.84 | C |
| ATOM | 3731 | O | THR | B1217 | −31.423 | −24.774 | −11.038 | 14.57 | O |
| ATOM | 3732 | N | VAL | B1218 | −33.01 | −26.395 | −11.268 | 14.15 | N |
| ATOM | 3733 | CA | VAL | B1218 | −33.018 | −26.406 | −12.706 | 12.77 | C |
| ATOM | 3734 | CB | VAL | B1218 | −33.159 | −27.874 | −13.298 | 13.49 | C |
| ATOM | 3735 | CG1 | VAL | B1218 | −33.104 | −27.847 | −14.83 | 9.57 | C |
| ATOM | 3736 | CG2 | VAL | B1218 | −32.179 | −28.925 | −12.674 | 7.77 | C |
| ATOM | 3737 | C | VAL | B1218 | −34.221 | −25.557 | −13.152 | 13.52 | C |
| ATOM | 3738 | O | VAL | B1218 | −35.325 | −25.715 | −12.656 | 13.44 | O |
| ATOM | 3739 | N | LYS | B1219 | −34.008 | −24.668 | −14.112 | 13.6 | N |
| ATOM | 3740 | CA | LYS | B1219 | −35.076 | −23.906 | −14.656 | 13.99 | C |
| ATOM | 3741 | CB | LYS | B1219 | −34.912 | −22.43 | −14.337 | 13.77 | C |
| ATOM | 3742 | CG | LYS | B1219 | −34.736 | −22.145 | −12.842 | 15.83 | C |
| ATOM | 3743 | CD | LYS | B1219 | −34.667 | −20.645 | −12.534 | 17.05 | C |
| ATOM | 3744 | CE | LYS | B1219 | −34.331 | −20.44 | −11.093 | 19.12 | C |
| ATOM | 3745 | NZ | LYS | B1219 | −35.386 | −20.985 | −10.223 | 12.71 | N |
| ATOM | 3746 | C | LYS | B1219 | −35.093 | −24.089 | −16.135 | 13.43 | C |
| ATOM | 3747 | O | LYS | B1219 | −34.081 | −23.949 | −16.788 | 14.83 | O |
| ATOM | 3748 | N | VAL | B1220 | −36.266 | −24.392 | −16.652 | 13.41 | N |
| ATOM | 3749 | CA | VAL | B1220 | −36.505 | −24.466 | −18.075 | 14.22 | C |
| ATOM | 3750 | CB | VAL | B1220 | −37.875 | −25.175 | −18.41 | 13.64 | C |
| ATOM | 3751 | CG1 | VAL | B1220 | −38.048 | −25.272 | −19.877 | 8.54 | C |
| ATOM | 3752 | CG2 | VAL | B1220 | −37.865 | −26.569 | −17.79 | 14.53 | C |
| ATOM | 3753 | C | VAL | B1220 | −36.449 | −23.09 | −18.686 | 14.19 | C |
| ATOM | 3754 | O | VAL | B1220 | −37.167 | −22.162 | −18.266 | 14.96 | O |
| ATOM | 3755 | N | ALA | B1221 | −35.561 | −22.963 | −19.636 | 13.87 | N |
| ATOM | 3756 | CA | ALA | B1221 | −35.328 | −21.717 | −20.301 | 15.19 | C |
| ATOM | 3757 | CB | ALA | B1221 | −33.785 | −21.418 | −20.29 | 15.26 | C |
| ATOM | 3758 | C | ALA | B1221 | −35.897 | −21.712 | −21.722 | 16.2 | C |
| ATOM | 3759 | O | ALA | B1221 | −35.991 | −22.79 | −22.392 | 17.52 | O |
| ATOM | 3760 | O | ASP | B1222 | −36.185 | −18.2 | −23.979 | 22.75 | O |
| ATOM | 3761 | N | ASP | B1222 | −36.322 | −20.808 | −22.202 | 20 | |
| ATOM | 3762 | CA | ASP | B1222 | −36.839 | −20.404 | −23.504 | 20 | |
| ATOM | 3763 | C | ASP | B1222 | −35.94 | −19.354 | −24.15 | 20 | |
| ATOM | 3764 | CB | ASP | B1222 | −38.265 | −19.865 | −23.371 | 20 | |
| ATOM | 3765 | CG | ASP | B1222 | −38.851 | −19.436 | −24.701 | 20 | |
| ATOM | 3766 | OD1 | ASP | B1222 | −38.859 | −20.258 | −25.641 | 20 | |
| ATOM | 3767 | OD2 | ASP | B1222 | −39.327 | −18.297 | −24.9 | 20 | |
| ATOM | 3768 | N | PHE | B1223 | −34.78 | −19.366 | −24.725 | 23.53 | N |
| ATOM | 3769 | CA | PHE | B1223 | −33.976 | −18.324 | −25.306 | 24.64 | C |
| ATOM | 3770 | CB | PHE | B1223 | −32.475 | −18.638 | −25.161 | 24.08 | C |
| ATOM | 3771 | CG | PHE | B1223 | −31.998 | −18.609 | −23.729 | 21.07 | C |
| ATOM | 3772 | CD1 | PHE | B1223 | −31.895 | −17.386 | −23.043 | 18.95 | C |
| ATOM | 3773 | CD2 | PHE | B1223 | −31.693 | −19.817 | −23.064 | 21.87 | C |

TABLE 1A-continued

| ATOM | 3774 | CE1 | PHE | B1223 | −31.484 | −17.347 | −21.715 | 19.02 | C |
|---|---|---|---|---|---|---|---|---|---|
| ATOM | 3775 | CE2 | PHE | B1223 | −31.278 | −19.813 | −21.75 | 22.36 | C |
| ATOM | 3776 | CZ | PHE | B1223 | −31.168 | −18.553 | −21.058 | 20.58 | C |
| ATOM | 3777 | C | PHE | B1223 | −34.433 | −18.023 | −26.752 | 25.93 | C |
| ATOM | 3778 | O | PHE | B1223 | −35.098 | −17.003 | −26.979 | 28.12 | O |
| ATOM | 3779 | N | GLY | B1224 | −34.139 | −18.899 | −27.696 | 26.17 | N |
| ATOM | 3780 | CA | GLY | B1224 | −34.669 | −18.762 | −29.081 | 26.43 | C |
| ATOM | 3781 | C | GLY | B1224 | −34.263 | −17.432 | −29.737 | 25.34 | C |
| ATOM | 3782 | O | GLY | B1224 | −33.489 | −17.382 | −30.665 | 26.25 | O |
| ATOM | 3783 | N | LEU | B1225 | −34.786 | −16.339 | −29.259 | 24.71 | N |
| ATOM | 3784 | CA | LEU | B1225 | −34.479 | −15.087 | −29.874 | 24.72 | C |
| ATOM | 3785 | CB | LEU | B1225 | −35.596 | −14.08 | −29.58 | 26.46 | C |
| ATOM | 3786 | CG | LEU | B1225 | −35.598 | −12.769 | −30.422 | 27.12 | C |
| ATOM | 3787 | CD1 | LEU | B1225 | −35.356 | −12.934 | −31.951 | 23.65 | C |
| ATOM | 3788 | CD2 | LEU | B1225 | −36.986 | −12.146 | −30.112 | 29.78 | C |
| ATOM | 3789 | C | LEU | B1225 | −33.148 | −14.542 | −29.381 | 22.87 | C |
| ATOM | 3790 | O | LEU | B1225 | −32.485 | −13.767 | −30.09 | 22.83 | O |
| ATOM | 3791 | N | ALA | B1226 | −32.77 | −14.953 | −28.178 | 20.34 | N |
| ATOM | 3792 | CA | ALA | B1226 | −31.498 | −14.569 | −27.602 | 19.02 | C |
| ATOM | 3793 | CB | ALA | B1226 | −31.531 | −14.727 | −26.109 | 17.46 | C |
| ATOM | 3794 | C | ALA | B1226 | −30.378 | −15.378 | −28.218 | 19.07 | C |
| ATOM | 3795 | O | ALA | B1226 | −29.225 | −15.02 | −28.061 | 20.39 | O |
| ATOM | 3796 | N | ARG | B1227 | −30.703 | −16.45 | −28.964 | 18.81 | N |
| ATOM | 3797 | CA | ARG | B1227 | −29.694 | −17.22 | −29.655 | 18.06 | C |
| ATOM | 3798 | CB | ARG | B1227 | −30.088 | −18.681 | −29.784 | 18.31 | C |
| ATOM | 3799 | CG | ARG | B1227 | −29.835 | −19.543 | −28.561 | 17.06 | C |
| ATOM | 3800 | CD | ARG | B1227 | −30.517 | −20.942 | −28.639 | 18.88 | C |
| ATOM | 3801 | NE | ARG | B1227 | −30.674 | −21.617 | −27.318 | 20.95 | N |
| ATOM | 3802 | CZ | ARG | B1227 | −29.662 | −22.079 | −26.576 | 19.76 | C |
| ATOM | 3803 | NH1 | ARG | B1227 | −28.432 | −21.986 | −27.052 | 18.11 | N |
| ATOM | 3804 | NH2 | ARG | B1227 | −29.864 | −22.635 | −25.366 | 17.86 | N |
| ATOM | 3805 | C | ARG | B1227 | −29.386 | −16.612 | −31.009 | 18.92 | C |
| ATOM | 3806 | O | ARG | B1227 | −30.151 | −16.787 | −31.98 | 20.81 | O |
| ATOM | 3807 | N | ASP | B1228 | −28.265 | −15.897 | −31.089 | 18.42 | N |
| ATOM | 3808 | CA | ASP | B1228 | −27.778 | −15.365 | −32.373 | 19.28 | C |
| ATOM | 3809 | CB | ASP | B1228 | −26.42 | −14.667 | −32.241 | 19.39 | C |
| ATOM | 3810 | CG | ASP | B1228 | −26.49 | −13.339 | −31.488 | 19.96 | C |
| ATOM | 3811 | OD1 | ASP | B1228 | −27.59 | −12.824 | −31.102 | 21.82 | O |
| ATOM | 3812 | OD2 | ASP | B1228 | −25.385 | −12.84 | −31.234 | 19.46 | O |
| ATOM | 3813 | C | ASP | B1228 | −27.707 | −16.324 | −33.54 | 19.83 | C |
| ATOM | 3814 | O | ASP | B1228 | −28.274 | −16.027 | −34.579 | 19.82 | O |
| ATOM | 3815 | N | MET | B1229 | −26.956 | −17.419 | −33.38 | 22.04 | N |
| ATOM | 3816 | CA | MET | B1229 | −27.017 | −18.611 | −34.222 | 24.36 | C |
| ATOM | 3817 | CB | MET | B1229 | −25.71 | −18.746 | −34.988 | 23.85 | C |
| ATOM | 3818 | CG | MET | B1229 | −25.502 | −17.629 | −35.865 | 25.1 | C |
| ATOM | 3819 | SD | MET | B1229 | −23.917 | −17.588 | −36.672 | 29.2 | S |
| ATOM | 3820 | CE | MET | B1229 | −22.717 | −18.577 | −35.636 | 32.72 | C |
| ATOM | 3821 | C | MET | B1229 | −27.217 | −19.932 | −33.479 | 25.51 | C |
| ATOM | 3822 | O | MET | B1229 | −27.127 | −19.978 | −32.257 | 24 | O |
| ATOM | 3823 | N | TYR | B1230 | −27.46 | −21.001 | −34.261 | 29.08 | N |
| ATOM | 3824 | CA | TYR | B1230 | −27.471 | −22.413 | −33.826 | 34.08 | C |
| ATOM | 3825 | CB | TYR | B1230 | −28.893 | −22.891 | −33.966 | 34.58 | C |
| ATOM | 3826 | CG | TYR | B1230 | −29.933 | −21.946 | −33.4 | 35.75 | C |
| ATOM | 3827 | CD1 | TYR | B1230 | −30.167 | −20.688 | −33.993 | 40.7 | C |
| ATOM | 3828 | CE1 | TYR | B1230 | −31.112 | −19.783 | −33.488 | 37.49 | C |
| ATOM | 3829 | CD2 | TYR | B1230 | −30.716 | −22.305 | −32.318 | 35.53 | C |
| ATOM | 3830 | CE2 | TYR | B1230 | −31.691 | −21.421 | −31.826 | 36.77 | C |
| ATOM | 3831 | CZ | TYR | B1230 | −31.857 | −20.169 | −32.419 | 37.26 | C |
| ATOM | 3832 | OH | TYR | B1230 | −32.784 | −19.289 | −31.938 | 39.37 | O |
| ATOM | 3833 | C | TYR | B1230 | −26.584 | −23.265 | −34.755 | 35.95 | C |
| ATOM | 3834 | O | TYR | B1230 | −26.276 | −22.825 | −35.864 | 36.53 | O |
| ATOM | 3835 | N | ASP | B1231 | −26.162 | −24.491 | −34.382 | 39.69 | N |
| ATOM | 3836 | CA | ASP | B1231 | −25.538 | −25.425 | −35.463 | 41.03 | C |
| ATOM | 3837 | CB | ASP | B1231 | −23.995 | −25.454 | −35.35 | 42.61 | C |
| ATOM | 3838 | CG | ASP | B1231 | −23.553 | −26.179 | −34.024 | 46.08 | C |
| ATOM | 3839 | OD1 | ASP | B1231 | −22.866 | −27.237 | −34.085 | 44.26 | O |
| ATOM | 3840 | OD2 | ASP | B1231 | −23.991 | −25.72 | −32.92 | 48.62 | O |
| ATOM | 3841 | C | ASP | B1231 | −25.93 | −26.803 | −35.112 | 40.95 | C |
| ATOM | 3842 | O | ASP | B1231 | −26.455 | −26.898 | −34.011 | 41.5 | O |
| ATOM | 3843 | N | LYS | B1232 | −25.638 | −27.845 | −35.959 | 41.51 | N |
| ATOM | 3844 | CA | LYS | B1232 | −25.472 | −29.295 | −35.504 | 40.13 | C |
| ATOM | 3845 | CB | LYS | B1232 | −24.085 | −29.456 | −34.835 | 41.34 | C |
| ATOM | 3846 | CG | LYS | B1232 | −23.694 | −30.825 | −34.164 | 42.89 | C |
| ATOM | 3847 | CD | LYS | B1232 | −23.774 | −30.788 | −32.596 | 50.15 | C |
| ATOM | 3848 | CE | LYS | B1232 | −22.592 | −30.036 | −31.827 | 55.04 | C |
| ATOM | 3849 | NZ | LYS | B1232 | −21.62 | −30.864 | −30.923 | 57.08 | N |
| ATOM | 3850 | C | LYS | B1232 | −26.567 | −29.995 | −34.603 | 39.71 | C |
| ATOM | 3851 | O | LYS | B1232 | −26.902 | −31.182 | −34.778 | 41.39 | O |
| ATOM | 3852 | N | GLU | B1233 | −27.076 | −29.309 | −33.594 | 36.6 | N |
| ATOM | 3853 | CA | GLU | B1233 | −28.291 | −29.742 | −32.95 | 34.58 | C |

TABLE 1A-continued

| | | | | | | | | |
|---|---|---|---|---|---|---|---|---|
| ATOM | 3854 | CB | GLU | B1233 | −28.459 | −29.068 | −31.552 | 33.63 | C |
| ATOM | 3855 | CG | GLU | B1233 | −27.201 | −28.787 | −30.789 | 34.52 | C |
| ATOM | 3856 | CD | GLU | B1233 | −26.607 | −30.075 | −30.268 | 39.4 | C |
| ATOM | 3857 | OE1 | GLU | B1233 | −27.175 | −31.113 | −30.673 | 34.26 | O |
| ATOM | 3858 | OE2 | GLU | B1233 | −25.58 | −30.058 | −29.494 | 41.29 | O |
| ATOM | 3859 | C | GLU | B1233 | −29.512 | −29.434 | −33.859 | 32.39 | C |
| ATOM | 3860 | O | GLU | B1233 | −30.54 | −30.097 | −33.805 | 31.63 | O |
| ATOM | 3861 | N | TYR | B1234 | −29.388 | −28.4 | −34.664 | 31.28 | N |
| ATOM | 3862 | CA | TYR | B1234 | −30.539 | −27.798 | −35.324 | 30.52 | C |
| ATOM | 3863 | CB | TYR | B1234 | −30.68 | −26.355 | −34.903 | 28.19 | C |
| ATOM | 3864 | CG | TYR | B1234 | −31.041 | −26.123 | −33.508 | 25.71 | C |
| ATOM | 3865 | CD1 | TYR | B1234 | −30.067 | −26.048 | −32.545 | 23.54 | C |
| ATOM | 3866 | CE1 | TYR | B1234 | −30.372 | −25.814 | −31.211 | 26.06 | C |
| ATOM | 3867 | CD2 | TYR | B1234 | −32.361 | −25.907 | −33.142 | 25.16 | C |
| ATOM | 3868 | CE2 | TYR | B1234 | −32.692 | −25.663 | −31.797 | 27.03 | C |
| ATOM | 3869 | CZ | TYR | B1234 | −31.676 | −25.639 | −30.829 | 27.04 | C |
| ATOM | 3870 | OH | TYR | B1234 | −31.945 | −25.398 | −29.498 | 27 | O |
| ATOM | 3871 | C | TYR | B1234 | −30.413 | −27.788 | −36.846 | 32.17 | C |
| ATOM | 3872 | O | TYR | B1234 | −29.369 | −27.478 | −37.391 | 31.62 | O |
| ATOM | 3873 | N | TYR | B1235 | −31.509 | −28.08 | −37.519 | 33.9 | N |
| ATOM | 3874 | CA | TYR | B1235 | −31.561 | −28.031 | −38.973 | 35.7 | C |
| ATOM | 3875 | CB | TYR | B1235 | −32.229 | −29.329 | −39.529 | 38.55 | C |
| ATOM | 3876 | CG | TYR | B1235 | −31.255 | −30.498 | −39.286 | 44.18 | C |
| ATOM | 3877 | CD1 | TYR | B1235 | −30.527 | −31.097 | −40.361 | 48.85 | C |
| ATOM | 3878 | CE1 | TYR | B1235 | −29.571 | −32.17 | −40.097 | 50.41 | C |
| ATOM | 3879 | CD2 | TYR | B1235 | −30.956 | −30.943 | −37.925 | 48.72 | C |
| ATOM | 3880 | CE2 | TYR | B1235 | −30.005 | −31.974 | −37.619 | 48.36 | C |
| ATOM | 3881 | CZ | TYR | B1235 | −29.309 | −32.604 | −38.71 | 51.73 | C |
| ATOM | 3882 | OH | TYR | B1235 | −28.405 | −33.67 | −38.431 | 50.9 | O |
| ATOM | 3883 | C | TYR | B1235 | −32.282 | −26.749 | −39.291 | 33.92 | C |
| ATOM | 3884 | O | TYR | B1235 | −33.203 | −26.393 | −38.584 | 33.68 | O |
| ATOM | 3885 | N | SER | B1236 | −31.824 | −26.034 | −40.318 | 32.72 | N |
| ATOM | 3886 | CA | SER | B1236 | −32.467 | −24.785 | −40.759 | 31.62 | C |
| ATOM | 3887 | CB | SER | B1236 | −31.375 | −23.692 | −40.958 | 31.66 | C |
| ATOM | 3888 | OG | SER | B1236 | −31.925 | −22.409 | −41.29 | 26.78 | O |
| ATOM | 3889 | C | SER | B1236 | −33.328 | −25.04 | −42.009 | 30.87 | C |
| ATOM | 3890 | O | SER | B1236 | −32.823 | −25.681 | −42.919 | 31.06 | O |
| ATOM | 3891 | N | VAL | B1237 | −34.614 | −24.638 | −42.001 | 30.38 | N |
| ATOM | 3892 | CA | VAL | B1237 | −35.513 | −24.609 | −43.174 | 31.34 | C |
| ATOM | 3893 | CB | VAL | B1237 | −37.02 | −24.115 | −42.819 | 31.82 | C |
| ATOM | 3894 | CG1 | VAL | B1237 | −38.189 | −24.363 | −43.965 | 29.46 | C |
| ATOM | 3895 | CG2 | VAL | B1237 | −37.456 | −24.647 | −41.483 | 34.13 | C |
| ATOM | 3896 | C | VAL | B1237 | −34.947 | −23.539 | −44.081 | 32.51 | C |
| ATOM | 3897 | O | VAL | B1237 | −34.477 | −22.53 | −43.634 | 32.91 | O |
| ATOM | 3898 | N | HIS | B1238 | −35.049 | −23.735 | −45.373 | 34.9 | N |
| ATOM | 3899 | CA | HIS | B1238 | −34.462 | −22.809 | −46.339 | 37.53 | C |
| ATOM | 3900 | CB | HIS | B1238 | −34.445 | −23.514 | −47.653 | 36.06 | C |
| ATOM | 3901 | CG | HIS | B1238 | −33.489 | −24.626 | −47.685 | 32.65 | C |
| ATOM | 3902 | CD2 | HIS | B1238 | −33.56 | −25.853 | −48.262 | 30.91 | C |
| ATOM | 3903 | ND1 | HIS | B1238 | −32.268 | −24.532 | −47.074 | 28.37 | N |
| ATOM | 3904 | CE1 | HIS | B1238 | −31.615 | −25.658 | −47.287 | 35.6 | C |
| ATOM | 3905 | NE2 | HIS | B1238 | −32.378 | −26.476 | −48.01 | 31.54 | N |
| ATOM | 3906 | C | HIS | B1238 | −35.279 | −21.54 | −46.54 | 39.46 | C |
| ATOM | 3907 | O | HIS | B1238 | −34.9 | −20.463 | −46.144 | 41.81 | O |
| ATOM | 3908 | N | ASN | B1239 | −36.386 | −21.705 | −47.232 | 41.97 | N |
| ATOM | 3909 | CA | ASN | B1239 | −37.457 | −20.761 | −47.205 | 44.12 | C |
| ATOM | 3910 | CB | ASN | B1239 | −38.723 | −21.531 | −47.615 | 45.61 | C |
| ATOM | 3911 | CG | ASN | B1239 | −38.849 | −21.718 | −49.11 | 49.07 | C |
| ATOM | 3912 | OD1 | ASN | B1239 | −39.966 | −22.047 | −49.593 | 51.28 | O |
| ATOM | 3913 | ND2 | ASN | B1239 | −37.72 | −21.548 | −49.871 | 49.39 | N |
| ATOM | 3914 | C | ASN | B1239 | −37.732 | −20.193 | −45.825 | 44.34 | C |
| ATOM | 3915 | O | ASN | B1239 | −37.272 | −19.103 | −45.482 | 42.93 | O |
| ATOM | 3916 | N | LYS | B1240 | −38.44 | −21.031 | −45.039 | 46.24 | N |
| ATOM | 3917 | CA | LYS | B1240 | −39.575 | −20.652 | −44.125 | 46.09 | C |
| ATOM | 3918 | CB | LYS | B1240 | −40.686 | −21.755 | −44.078 | 47.2 | C |
| ATOM | 3919 | CG | LYS | B1240 | −41.403 | −22.078 | −42.682 | 48.07 | C |
| ATOM | 3920 | CD | LYS | B1240 | −42.986 | −22.34 | −42.824 | 48.07 | C |
| ATOM | 3921 | CE | LYS | B1240 | −43.353 | −23.625 | −43.614 | 47.33 | C |
| ATOM | 3922 | NZ | LYS | B1240 | −43.305 | −24.855 | −42.778 | 46.55 | N |
| ATOM | 3923 | C | LYS | B1240 | −39.042 | −20.3 | −42.796 | 44.7 | C |
| ATOM | 3924 | O | LYS | B1240 | −38.808 | −21.142 | −41.918 | 45.03 | O |
| ATOM | 3925 | N | THR | B1241 | −38.923 | −19 | −42.672 | 43.95 | N |
| ATOM | 3926 | CA | THR | B1241 | −37.75 | −18.379 | −42.113 | 43.68 | C |
| ATOM | 3927 | CB | THR | B1241 | −37.912 | −17.912 | −40.593 | 44.97 | C |
| ATOM | 3928 | OG1 | THR | B1241 | −36.612 | −17.659 | −40.012 | 48.88 | O |
| ATOM | 3929 | CG2 | THR | B1241 | −38.808 | −18.875 | −39.642 | 45.32 | C |
| ATOM | 3930 | C | THR | B1241 | −36.598 | −19.286 | −42.401 | 41.6 | C |
| ATOM | 3931 | O | THR | B1241 | −36.446 | −19.833 | −43.473 | 42.93 | O |
| ATOM | 3932 | N | GLY | B1242 | −35.739 | −19.421 | −41.448 | 39.81 | N |
| ATOM | 3933 | CA | GLY | B1242 | −34.996 | −20.61 | −41.362 | 36.11 | C |

TABLE 1A-continued

| | | | | | | | | | |
|---|---|---|---|---|---|---|---|---|---|
| ATOM | 3934 | C | GLY | B1242 | −35.436 | −20.956 | −39.967 | 33.19 | C |
| ATOM | 3935 | O | GLY | B1242 | −34.711 | −20.656 | −39.027 | 32.74 | O |
| ATOM | 3936 | N | ALA | B1243 | −36.661 | −21.472 | −39.836 | 29.81 | N |
| ATOM | 3937 | CA | ALA | B1243 | −37.037 | −22.105 | −38.585 | 27.88 | C |
| ATOM | 3938 | CB | ALA | B1243 | −38.491 | −22.775 | −38.648 | 27.63 | C |
| ATOM | 3939 | C | ALA | B1243 | −35.917 | −23.137 | −38.209 | 25.69 | C |
| ATOM | 3940 | O | ALA | B1243 | −35.434 | −23.861 | −39.04 | 23.82 | O |
| ATOM | 3941 | N | LYS | B1244 | −35.471 | −23.1 | −36.955 | 24.7 | N |
| ATOM | 3942 | CA | LYS | B1244 | −34.543 | −24.063 | −36.429 | 23.56 | C |
| ATOM | 3943 | CB | LYS | B1244 | −33.705 | −23.448 | −35.326 | 23.12 | C |
| ATOM | 3944 | CG | LYS | B1244 | −33.115 | −22.087 | −35.698 | 25.56 | C |
| ATOM | 3945 | CD | LYS | B1244 | −31.993 | −22.206 | −36.679 | 26.2 | C |
| ATOM | 3946 | CE | LYS | B1244 | −31.934 | −20.959 | −37.564 | 28.44 | C |
| ATOM | 3947 | NZ | LYS | B1244 | −32.549 | −19.815 | −36.856 | 27.98 | N |
| ATOM | 3948 | C | LYS | B1244 | −35.381 | −25.227 | −35.908 | 22.49 | C |
| ATOM | 3949 | O | LYS | B1244 | −36.427 | −25.057 | −35.33 | 22.76 | O |
| ATOM | 3950 | N | LEU | B1245 | −34.897 | −26.421 | −36.144 | 21.42 | N |
| ATOM | 3951 | CA | LEU | B1245 | −35.613 | −27.618 | −35.829 | 19.61 | C |
| ATOM | 3952 | CB | LEU | B1245 | −36.23 | −28.184 | −37.127 | 21.08 | C |
| ATOM | 3953 | CG | LEU | B1245 | −37.226 | −27.274 | −37.878 | 23.54 | C |
| ATOM | 3954 | CD1 | LEU | B1245 | −36.77 | −26.914 | −39.317 | 23.91 | C |
| ATOM | 3955 | CD2 | LEU | B1245 | −38.488 | −28.039 | −37.994 | 30.03 | C |
| ATOM | 3956 | C | LEU | B1245 | −34.584 | −28.554 | −35.206 | 17.53 | C |
| ATOM. | 3957 | O | LEU | B1245 | −33.66 | −29.055 | −35.916 | 14.78 | O |
| ATOM | 3958 | N | PRO | B1246 | −34.692 | −28.735 | −33.861 | 16.71 | N |
| ATOM | 3959 | CD | PRO | B1246 | −35.669 | −28.048 | −32.962 | 16.55 | C |
| ATOM | 3960 | CA | PRO | B1246 | −33.865 | −29.676 | −33.104 | 15.54 | C |
| ATOM | 3961 | CB | PRO | B1246 | −34.257 | −29.351 | −31.666 | 16.13 | C |
| ATOM | 3962 | CG | PRO | B1246 | −35.652 | −28.846 | −31.726 | 12.22 | C |
| ATOM | 3963 | C | PRO | B1246 | −34.36 | −31.108 | −33.453 | 15.49 | C |
| ATOM | 3964 | O | PRO | B1246 | −34.977 | −31.795 | −32.611 | 16.52 | O |
| ATOM | 3965 | N | VAL | B1247 | −34.123 | −31.535 | −34.689 | 13.12 | N |
| ATOM | 3966 | CA | VAL | B1247 | −34.584 | −32.798 | −35.143 | 13.03 | C |
| ATOM | 3967 | CB | VAL | B1247 | −34.022 | −33.173 | −36.545 | 13.66 | C |
| ATOM | 3968 | CG1 | VAL | B1247 | −33.97 | −32.026 | −37.403 | 16.62 | C |
| ATOM | 3969 | CG2 | VAL | B1247 | −32.671 | −33.871 | −36.495 | 16.62 | C |
| ATOM | 3970 | C | VAL | B1247 | −34.507 | −33.995 | −34.183 | 11.34 | C |
| ATOM | 3971 | O | VAL | B1247 | −35.466 | −34.721 | −34.083 | 11.5 | O |
| ATOM | 3972 | N | LYS | B1248 | −33.381 | −34.195 | −33.51 | 11.79 | N |
| ATOM | 3973 | CA | LYS | B1248 | −33.165 | −35.38 | −32.689 | 12.47 | C |
| ATOM | 3974 | CB | LYS | B1248 | −31.702 | −35.589 | −32.463 | 12.8 | C |
| ATOM | 3975 | CG | LYS | B1248 | −30.995 | −36.234 | −33.691 | 15.64 | C |
| ATOM | 3976 | CD | LYS | B1248 | −29.37 | −36.242 | −33.586 | 18.07 | C |
| ATOM | 3977 | CE | LYS | B1248 | −28.673 | −36.979 | −34.801 | 15.79 | C |
| ATOM | 3978 | NZ | LYS | B1248 | −29.745 | −37.139 | −35.892 | 23.64 | N |
| ATOM | 3979 | C | LYS | B1248 | −33.908 | −35.348 | −31.382 | 10.54 | C |
| ATOM | 3980 | O | LYS | B1248 | −33.981 | −36.36 | −30.728 | 10.31 | O |
| ATOM | 3981 | N | TRP | B1249 | −34.525 | −34.213 | −31.034 | 9.66 | N |
| ATOM | 3982 | CA | TRP | B1249 | −35.405 | −34.107 | −29.845 | 8.39 | C |
| ATOM | 3983 | CB | TRP | B1249 | −35.086 | −32.836 | −29.014 | 7.29 | C |
| ATOM | 3984 | CG | TRP | B1249 | −33.914 | −33.017 | −28.158 | 5.7 | C |
| ATOM | 3985 | CD2 | TRP | B1249 | −32.548 | −33.029 | −28.582 | 4.8 | C |
| ATOM | 3986 | CE2 | TRP | B1249 | −31.755 | −33.293 | −27.442 | 3.54 | C |
| ATOM | 3987 | CE3 | TRP | B1249 | −31.909 | −32.804 | −29.806 | 9.04 | C |
| ATOM | 3988 | CD1 | TRP | B1249 | −33.896 | −33.289 | −26.791 | 4.28 | C |
| ATOM | 3989 | NE1 | TRP | B1249 | −32.607 | −33.458 | −26.374 | 2.45 | N |
| ATOM | 3990 | CZ2 | TRP | B1249 | −30.337 | −33.352 | −27.5 | 2 | C |
| ATOM | 3991 | CZ3 | TRP | B1249 | −30.474 | −32.872 | −29.844 | 8.31 | C |
| ATOM | 3992 | CH2 | TRP | B1249 | −29.74 | −33.16 | −28.702 | 4.96 | C |
| ATOM | 3993 | C | TRP | B1249 | −36.828 | −33.99 | −30.325 | 9.48 | C |
| ATOM | 3994 | O | TRP | B1249 | −37.726 | −33.99 | −29.522 | 11.52 | O |
| ATOM | 3995 | N | MET | B1250 | −37.053 | −33.901 | −31.63 | 10.09 | N |
| ATOM | 3996 | CA | MET | B1250 | −38.384 | −33.689 | −32.159 | 11.64 | C |
| ATOM | 3997 | CB | MET | B1250 | −38.295 | −33.04 | −33.507 | 11.33 | C |
| ATOM | 3998 | CG | MET | B1250 | −38.313 | −31.485 | −33.482 | 12.69 | C |
| ATOM | 3999 | SD | MET | B1250 | −37.811 | −30.796 | −35.124 | 16.39 | S |
| ATOM | 4000 | CE | MET | B1250 | −39.348 | −30.884 | −36.046 | 17.08 | C |
| ATOM | 4001 | C | MET | B1250 | −39.178 | −34.974 | −32.272 | 13.02 | C |
| ATOM | 4002 | O | MET | B1250 | −38.606 | −36.105 | −32.53 | 12.68 | O |
| ATOM | 4003 | N | ALA | B1251 | −40.501 | −34.838 | −32.06 | 12.87 | N |
| ATOM | 4004 | CA | ALA | B1251 | −41.405 | −35.982 | −32.177 | 13.1 | C |
| ATOM | 4005 | CB | ALA | B1251 | −42.699 | −35.724 | −31.481 | 12.42 | C |
| ATOM | 4006 | C | ALA | B1251 | −41.62 | −36.363 | −33.651 | 15.54 | C |
| ATOM | 4007 | O | ALA | B1251 | −41.512 | −35.498 | −34.572 | 14.8 | O |
| ATOM | 4008 | N | LEU | B1252 | −41.903 | −37.662 | −33.866 | 17.95 | N |
| ATOM | 4009 | CA | LEU | B1252 | −42.248 | −38.215 | −35.18 | 19.26 | C |
| ATOM | 4010 | CB | LEU | B1252 | −42.867 | −39.609 | −35.016 | 20.92 | C |
| ATOM | 4011 | CG | LEU | B1252 | −43.079 | −40.544 | −36.227 | 21.26 | C |
| ATOM | 4012 | CD1 | LEU | B1252 | −41.988 | −40.407 | −37.34 | 19.45 | C |
| ATOM | 4013 | CD2 | LEU | B1252 | −43.292 | −42.011 | −35.699 | 19.03 | C |

TABLE 1A-continued

| ATOM | 4014 | C   | LEU | B1252 | −43.215 | −37.333 | −35.962 | 19.23 | C |
| ATOM | 4015 | O   | LEU | B1252 | −42.91  | −36.899 | −37.062 | 19.86 | O |
| ATOM | 4016 | N   | GLU | B1253 | −44.374 | −37.05  | −35.405 | 18.89 | N |
| ATOM | 4017 | CA  | GLU | B1253 | −45.26  | −36.124 | −36.066 | 20.29 | C |
| ATOM | 4018 | CB  | GLU | B1253 | −46.574 | −36.042 | −35.299 | 19.85 | C |
| ATOM | 4019 | CG  | GLU | B1253 | −46.507 | −35.19  | −33.996 | 22.81 | C |
| ATOM | 4020 | CD  | GLU | B1253 | −46.092 | −35.973 | −32.754 | 24.46 | C |
| ATOM | 4021 | OE1 | GLU | B1253 | −45.675 | −37.15  | −32.878 | 27.79 | O |
| ATOM | 4022 | OE2 | GLU | B1253 | −46.214 | −35.408 | −31.643 | 26.76 | O |
| ATOM | 4023 | C   | GLU | B1253 | −44.664 | −34.692 | −36.414 | 21.64 | C |
| ATOM | 4024 | O   | GLU | B1253 | −44.968 | −34.162 | −37.492 | 22.96 | O |
| ATOM | 4025 | N   | SER | B1254 | −43.818 | −34.079 | −35.567 | 21.49 | N |
| ATOM | 4026 | CA  | SER | B1254 | −43.302 | −32.735 | −35.855 | 21.38 | C |
| ATOM | 4027 | CB  | SER | B1254 | −42.609 | −32.116 | −34.647 | 21.56 | C |
| ATOM | 4028 | OG  | SER | B1254 | −43.485 | −32.087 | −33.503 | 25.03 | O |
| ATOM | 4029 | C   | SER | B1254 | −42.313 | −32.823 | −36.976 | 21.95 | C |
| ATOM | 4030 | O   | SER | B1254 | −42.22  | −31.926 | −37.784 | 22.06 | O |
| ATOM | 4031 | N   | LEU | B1255 | −41.534 | −33.896 | −37.031 | 22.64 | N |
| ATOM | 4032 | CA  | LEU | B1255 | −40.623 | −34.095 | −38.146 | 22.06 | C |
| ATOM | 4033 | CB  | LEU | B1255 | −39.865 | −35.409 | −37.985 | 20.16 | C |
| ATOM | 4034 | CG  | LEU | B1255 | −38.889 | −35.49  | −36.825 | 17.35 | C |
| ATOM | 4035 | CD1 | LEU | B1255 | −38.374 | −36.987 | −36.629 | 13.13 | C |
| ATOM | 4036 | CD2 | LEU | B1255 | −37.76  | −34.489 | −37.004 | 14.62 | C |
| ATOM | 4037 | C   | LEU | B1255 | −41.387 | −34.15  | −39.467 | 23.82 | C |
| ATOM | 4038 | O   | LEU | B1255 | −40.89  | −33.691 | −40.511 | 25.05 | O |
| ATOM | 4039 | N   | GLN | B1256 | −42.575 | −34.753 | −39.424 | 24.85 | N |
| ATOM | 4040 | CA  | GLN | B1256 | −43.34  | −35.01  | −40.605 | 26.22 | C |
| ATOM | 4041 | CB  | GLN | B1256 | −44.294 | −36.186 | −40.422 | 25.39 | C |
| ATOM | 4042 | CG  | GLN | B1256 | −43.687 | −37.577 | −40.193 | 26.12 | C |
| ATOM | 4043 | CD  | GLN | B1256 | −44.774 | −38.604 | −39.754 | 27.1  | C |
| ATOM | 4044 | OE1 | GLN | B1256 | −45.184 | −39.42  | −40.533 | 29.2  | O |
| ATOM | 4045 | NE2 | GLN | B1256 | −45.273 | −38.501 | −38.525 | 26.57 | N |
| ATOM | 4046 | C   | GLN | B1256 | −44.166 | −33.781 | −40.914 | 27.29 | C |
| ATOM | 4047 | O   | GLN | B1256 | −44.508 | −33.567 | −42.066 | 29.76 | O |
| ATOM | 4048 | N   | THR | B1257 | −44.5   | −32.968 | −39.926 | 27.03 | N |
| ATOM | 4049 | CA  | THR | B1257 | −45.449 | −31.874 | −40.149 | 26.26 | C |
| ATOM | 4050 | CB  | THR | B1257 | −46.737 | −32.13  | −39.348 | 27.06 | C |
| ATOM | 4051 | OG1 | THR | B1257 | −46.459 | −32.004 | −37.938 | 24.23 | O |
| ATOM | 4052 | CG2 | THR | B1257 | −47.303 | −33.527 | −39.645 | 25.82 | C |
| ATOM | 4053 | C   | THR | B1257 | −44.927 | −30.485 | −39.743 | 26.76 | C |
| ATOM | 4054 | O   | THR | B1257 | −45.495 | −29.455 | −40.084 | 26.46 | O |
| ATOM | 4055 | N   | GLN | B1258 | −43.854 | −30.465 | −38.979 | 27.16 | N |
| ATOM | 4056 | CA  | GLN | B1258 | −43.232 | −29.234 | −38.532 | 28.56 | C |
| ATOM | 4057 | CB  | GLN | B1258 | −42.773 | −28.422 | −39.75  | 28.63 | C |
| ATOM | 4058 | CG  | GLN | B1258 | −41.445 | −27.703 | −39.541 | 32.3  | C |
| ATOM | 4059 | CD  | GLN | B1258 | −41.202 | −26.525 | −40.556 | 33.04 | C |
| ATOM | 4060 | OE1 | GLN | B1258 | −40.718 | −25.425 | −40.163 | 35.92 | O |
| ATOM | 4061 | NE2 | GLN | B1258 | −41.511 | −26.766 | −41.852 | 31.94 | N |
| ATOM | 4062 | C   | GLN | B1258 | −44.152 | −28.424 | −37.578 | 27.21 | C |
| ATOM | 4063 | O   | GLN | B1258 | −43.982 | −27.187 | −37.391 | 27.96 | O |
| ATOM | 4064 | N   | LYS | B1259 | −45.122 | −29.117 | −36.987 | 25.61 | N |
| ATOM | 4065 | CA  | LYS | B1259 | −45.992 | −28.515 | −35.993 | 24.97 | C |
| ATOM | 4066 | CB  | LYS | B1259 | −47.448 | −28.482 | −36.486 | 26.14 | C |
| ATOM | 4067 | CG  | LYS | B1259 | −47.723 | −27.151 | −37.225 | 32.4  | C |
| ATOM | 4068 | CD  | LYS | B1259 | −48.102 | −27.291 | −38.71  | 40.86 | C |
| ATOM | 4069 | CE  | LYS | B1259 | −49.665 | −27.375 | −38.896 | 50.91 | C |
| ATOM | 4070 | NZ  | LYS | B1259 | −50.394 | −28.321 | −37.902 | 53.68 | N |
| ATOM | 4071 | C   | LYS | B1259 | −45.826 | −29.129 | −34.59  | 22.27 | C |
| ATOM | 4072 | O   | LYS | B1259 | −45.634 | −30.333 | −34.484 | 21.35 | O |
| ATOM | 4073 | N   | PHE | B1260 | −45.856 | −28.275 | −33.542 | 19.76 | N |
| ATOM | 4074 | CA  | PHE | B1260 | −45.587 | −28.652 | −32.148 | 17.39 | C |
| ATOM | 4075 | CB  | PHE | B1260 | −44.45  | −27.875 | −31.589 | 14.45 | C |
| ATOM | 4076 | CG  | PHE | B1260 | −43.248 | −27.866 | −32.479 | 16.95 | C |
| ATOM | 4077 | CD1 | PHE | B1260 | −43.232 | −27.143 | −33.676 | 12.95 | C |
| ATOM | 4078 | CD2 | PHE | B1260 | −42.1   | −28.615 | −32.149 | 18.21 | C |
| ATOM | 4079 | CE1 | PHE | B1260 | −42.09  | −27.176 | −34.51  | 14.99 | C |
| ATOM | 4080 | CE2 | PHE | B1260 | −40.962 | −28.61  | −33.022 | 15.9  | C |
| ATOM | 4081 | CZ  | PHE | B1260 | −40.981 | −27.874 | −34.185 | 11.08 | C |
| ATOM | 4082 | C   | PHE | B1260 | −46.778 | −28.545 | −31.202 | 18.09 | C |
| ATOM | 4083 | O   | PHE | B1260 | −47.724 | −27.776 | −31.422 | 18.72 | O |
| ATOM | 4084 | N   | THR | B1261 | −46.726 | −29.367 | −30.148 | 17.79 | N |
| ATOM | 4085 | CA  | THR | B1261 | −47.745 | −29.416 | −29.111 | 17.31 | C |
| ATOM | 4086 | CB  | THR | B1261 | −48.793 | −30.515 | −29.388 | 16.69 | C |
| ATOM | 4087 | OG1 | THR | B1261 | −48.125 | −31.755 | −29.671 | 17.09 | O |
| ATOM | 4088 | CG2 | THR | B1261 | −49.667 | −30.138 | −30.574 | 17.08 | C |
| ATOM | 4089 | C   | THR | B1261 | −47.083 | −29.751 | −27.801 | 16.71 | C |
| ATOM | 4090 | O   | THR | B1261 | −45.87  | −30.073 | −27.768 | 16.18 | O |
| ATOM | 4091 | N   | THR | B1262 | −47.886 | −29.729 | −26.728 | 15.26 | N |
| ATOM | 4092 | CA  | THR | B1262 | −47.439 | −30.274 | −25.427 | 14.24 | C |
| ATOM | 4093 | CB  | THR | B1262 | −48.509 | −29.994 | −24.355 | 12.83 | C |

TABLE 1A-continued

| | | | | | | | | |
|---|---|---|---|---|---|---|---|---|
| ATOM | 4094 | OG1 | THR | B1262 | −48.54 | −28.588 | −24.19 | 14.64 | O |
| ATOM | 4095 | CG2 | THR | B1262 | −48.162 | −30.554 | −23.009 | 12.65 | C |
| ATOM | 4096 | C | THR | B1262 | −47.08 | −31.73 | −25.49 | 13.76 | C |
| ATOM | 4097 | O | THR | B1262 | −46.206 | −32.128 | −24.782 | 16.54 | O |
| ATOM | 4098 | N | LYS | B1263 | −47.735 | −32.535 | −26.329 | 14.41 | N |
| ATOM | 4099 | CA | LYS | B1263 | −47.326 | −33.942 | −26.538 | 14.1 | C |
| ATOM | 4100 | CB | LYS | B1263 | −48.35 | −34.761 | −27.329 | 13.72 | C |
| ATOM | 4101 | CG | LYS | B1263 | −49.67 | −34.811 | −26.68 | 13.94 | C |
| ATOM | 4102 | CD | LYS | B1263 | −49.545 | −35.067 | −25.196 | 14.53 | C |
| ATOM | 4103 | CE | LYS | B1263 | −50.85 | −35.583 | −24.602 | 13.05 | C |
| ATOM | 4104 | NZ | LYS | B1263 | −50.49 | −36.259 | −23.363 | 17.05 | N |
| ATOM | 4105 | C | LYS | B1263 | −45.98 | −34.027 | −27.257 | 14.57 | C |
| ATOM | 4106 | O | LYS | B1263 | −45.2 | −34.932 | −26.975 | 15.41 | O |
| ATOM | 4107 | N | SER | B1264 | −45.698 | −33.099 | −28.16 | 11.65 | N |
| ATOM | 4108 | CA | SER | B1264 | −44.441 | −33.146 | −28.787 | 13.31 | C |
| ATOM | 4109 | CB | SER | B1264 | −44.492 | −32.375 | −30.104 | 12.51 | C |
| ATOM | 4110 | OG | SER | B1264 | −44.451 | −31.004 | −29.879 | 16.54 | O |
| ATOM | 4111 | C | SER | B1264 | −43.313 | −32.699 | −27.811 | 13 | C |
| ATOM | 4112 | O | SER | B1264 | −42.197 | −33.169 | −27.925 | 14.49 | O |
| ATOM | 4113 | N | ASP | B1265 | −43.639 | −31.859 | −26.829 | 13.66 | N |
| ATOM | 4114 | CA | ASP | B1265 | −42.758 | −31.435 | −25.724 | 13.49 | C |
| ATOM | 4115 | CB | ASP | B1265 | −43.434 | −30.31 | −24.857 | 14.45 | C |
| ATOM | 4116 | CG | ASP | B1265 | −43.277 | −28.836 | −25.42 | 15.31 | C |
| ATOM | 4117 | OD1 | ASP | B1265 | −42.551 | −28.551 | −26.437 | 11.54 | O |
| ATOM | 4118 | OD2 | ASP | B1265 | −43.948 | −27.93 | −24.789 | 14.05 | O |
| ATOM | 4119 | C | ASP | B1265 | −42.544 | −32.683 | −24.821 | 13.36 | C |
| ATOM | 4120 | O | ASP | B1265 | −41.438 | −32.905 | −24.309 | 12.68 | O |
| ATOM | 4121 | N | VAL | B1266 | −43.595 | −33.467 | −24.587 | 10.21 | N |
| ATOM | 4122 | CA | VAL | B1266 | −43.391 | −34.728 | −23.865 | 10.13 | C |
| ATOM | 4123 | CB | VAL | B1266 | −44.755 | −35.518 | −23.608 | 10.77 | C |
| ATOM | 4124 | CG1 | VAL | B1266 | −44.502 | −36.889 | −23.116 | 5.97 | C |
| ATOM | 4125 | CG2 | VAL | B1266 | −45.649 | −34.727 | −22.654 | 7.57 | C |
| ATOM | 4126 | C | VAL | B1266 | −42.382 | −35.637 | −24.548 | 8.48 | C |
| ATOM | 4127 | O | VAL | B1266 | −41.442 | −36.08 | −23.913 | 9.29 | O |
| ATOM | 4128 | N | TRP | B1267 | −42.506 | −35.856 | −25.849 | 8.05 | N |
| ATOM | 4129 | CA | TRP | B1267 | −41.517 | −36.661 | −26.578 | 8.38 | C |
| ATOM | 4130 | CB | TRP | B1267 | −41.77 | −36.609 | −28.027 | 9.04 | C |
| ATOM | 4131 | CG | TRP | B1267 | −40.748 | −37.362 | −28.859 | 13.03 | C |
| ATOM | 4132 | CD2 | TRP | B1267 | −41.036 | −38.518 | −29.698 | 11.67 | C |
| ATOM | 4133 | CE2 | TRP | B1267 | −39.819 | −38.935 | −30.278 | 9.47 | C |
| ATOM | 4134 | CE3 | TRP | B1267 | −42.215 | −39.227 | −29.994 | 10.04 | C |
| ATOM | 4135 | CD1 | TRP | B1267 | −39.388 | −37.129 | −28.96 | 18.94 | C |
| ATOM | 4136 | NE1 | TRP | B1267 | −38.826 | −38.097 | −29.82 | 12.78 | N |
| ATOM | 4137 | CZ2 | TRP | B1267 | −39.755 | −40.002 | −31.17 | 9.52 | C |
| ATOM | 4138 | CZ3 | TRP | B1267 | −42.168 | −40.258 | −30.893 | 10.1 | C |
| ATOM | 4139 | CH2 | TRP | B1267 | −40.934 | −40.653 | −31.466 | 11.36 | C |
| ATOM | 4140 | C | TRP | B1267 | −40.119 | −36.117 | −26.29 | 9.58 | C |
| ATOM | 4141 | O | TRP | B1267 | −39.173 | −36.924 | −25.943 | 11.1 | O |
| ATOM | 4142 | N | SER | B1268 | −39.984 | −34.779 | −26.408 | 7.45 | N |
| ATOM | 4143 | CA | SER | B1268 | −38.736 | −34.075 | −26.174 | 5.51 | C |
| ATOM | 4144 | CB | SER | B1268 | −38.926 | −32.562 | −26.31 | 7.41 | C |
| ATOM | 4145 | OG | SER | B1268 | −38.927 | −32.233 | −27.655 | 11.13 | O |
| ATOM | 4146 | C | SER | B1268 | −38.241 | −34.274 | −24.815 | 4.11 | C |
| ATOM | 4147 | O | SER | B1268 | −37.066 | −34.539 | −24.634 | 4.39 | O |
| ATOM | 4148 | N | PHE | B1269 | −39.125 | −34.142 | −23.834 | 3.73 | N |
| ATOM | 4149 | CA | PHE | B1269 | −38.794 | −34.445 | −22.45 | 4.56 | C |
| ATOM | 4150 | CB | PHE | B1269 | −40.038 | −34.29 | −21.58 | 5.96 | C |
| ATOM | 4151 | CG | PHE | B1269 | −39.81 | −34.636 | −20.125 | 6.7 | C |
| ATOM | 4152 | CD1 | PHE | B1269 | −39.078 | −33.763 | −19.287 | 9.71 | C |
| ATOM | 4153 | CD2 | PHE | B1269 | −40.265 | −35.832 | −19.623 | 4.42 | C |
| ATOM | 4154 | CE1 | PHE | B1269 | −38.847 | −34.07 | −17.953 | 8.28 | C |
| ATOM | 4155 | CE2 | PHE | B1269 | −40.061 | −36.155 | −18.32 | 8.23 | C |
| ATOM | 4156 | CZ | PHE | B1269 | −39.355 | −35.241 | −17.468 | 12.92 | C |
| ATOM | 4157 | C | PHE | B1269 | −38.181 | −35.834 | −22.267 | 5.12 | C |
| ATOM | 4158 | O | PHE | B1269 | −37.199 | −36.012 | −21.516 | 6.6 | O |
| ATOM | 4159 | N | GLY | B1270 | −38.728 | −36.828 | −22.949 | 4.58 | N |
| ATOM | 4160 | CA | GLY | B1270 | −38.154 | −38.129 | −22.823 | 5.87 | C |
| ATOM | 4161 | C | GLY | B1270 | −36.772 | −38.256 | −23.358 | 7.68 | C |
| ATOM | 4162 | O | GLY | B1270 | −35.909 | −38.968 | −22.753 | 8.82 | O |
| ATOM | 4163 | N | VAL | B1271 | −36.514 | −37.556 | −24.478 | 8.32 | N |
| ATOM | 4164 | CA | VAL | B1271 | −35.076 | −37.437 | −25.021 | 8.41 | C |
| ATOM | 4165 | CB | VAL | B1271 | −35.045 | −36.627 | −26.371 | 7.21 | C |
| ATOM | 4166 | CG1 | VAL | B1271 | −33.805 | −36.88 | −27.078 | 8.43 | C |
| ATOM | 4167 | CG2 | VAL | B1271 | −36.143 | −37.058 | −27.294 | 5.25 | C |
| ATOM | 4168 | C | VAL | B1271 | −34.114 | −36.804 | −24.012 | 8.67 | C |
| ATOM | 4169 | O | VAL | B1271 | −32.971 | −37.231 | −23.82 | 9.62 | O |
| ATOM | 4170 | N | LEU | B1272 | −34.621 | −35.749 | −23.379 | 10.91 | N |
| ATOM | 4171 | CA | LEU | B1272 | −33.95 | −35.009 | −22.261 | 11.66 | C |
| ATOM | 4172 | CB | LEU | B1272 | −34.818 | −33.81 | −21.792 | 11.01 | C |
| ATOM | 4173 | CG | LEU | B1272 | −34.161 | −32.875 | −20.766 | 13.19 | C |

TABLE 1A-continued

| ATOM | 4174 | CD1 | LEU | B1272 | −34.927 | −31.529 | −20.726 | 7.24 | C |
|---|---|---|---|---|---|---|---|---|---|
| ATOM | 4175 | CD2 | LEU | B1272 | −34.025 | −33.436 | −19.332 | 10.52 | C |
| ATOM | 4176 | C | LEU | B1272 | −33.668 | −35.96 | −21.094 | 10.21 | C |
| ATOM | 4177 | O | LEU | B1272 | −32.556 | −35.972 | −20.597 | 10.12 | O |
| ATOM | 4178 | N | LEU | B1273 | −34.65 | −36.774 | −20.685 | 9.18 | N |
| ATOM | 4179 | CA | LEU | B1273 | −34.331 | −37.803 | −19.659 | 11.07 | C |
| ATOM | 4180 | CB | LEU | B1273 | −35.542 | −38.655 | −19.303 | 10.87 | C |
| ATOM | 4181 | CG | LEU | B1273 | −36.725 | −37.912 | −18.694 | 16.19 | C |
| ATOM | 4182 | CD1 | LEU | B1273 | −37.954 | −38.84 | −18.631 | 16.15 | C |
| ATOM | 4183 | CD2 | LEU | B1273 | −36.396 | −37.352 | −17.34 | 14.22 | C |
| ATOM | 4184 | C | LEU | B1273 | −33.183 | −38.741 | −20.076 | 9.8 | C |
| ATOM | 4185 | O | LEU | B1273 | −32.389 | −39.109 | −19.277 | 9.52 | O |
| ATOM | 4186 | N | TRP | B1274 | −33.15 | −39.094 | −21.358 | 11.24 | N |
| ATOM | 4187 | CA | TRP | B1274 | −32.163 | −39.995 | −21.948 | 10.94 | C |
| ATOM | 4188 | CB | TRP | B1274 | −32.565 | −40.397 | −23.414 | 9.58 | C |
| ATOM | 4189 | CG | TRP | B1274 | −31.633 | −41.432 | −24.04 | 10.2 | C |
| ATOM | 4190 | CD2 | TRP | B1274 | −30.43 | −41.158 | −24.748 | 8.46 | C |
| ATOM | 4191 | CE2 | TRP | B1274 | −29.842 | −42.409 | −25.082 | 9.48 | C |
| ATOM | 4192 | CE3 | TRP | B1274 | −29.77 | −39.972 | −25.119 | 8.54 | C |
| ATOM | 4193 | CD1 | TRP | B1274 | −31.735 | −42.841 | −23.974 | 11.41 | C |
| ATOM | 4194 | NE1 | TRP | B1274 | −30.673 | −43.405 | −24.622 | 9.81 | N |
| ATOM | 4195 | CZ2 | TRP | B1274 | −28.617 | −42.499 | −25.784 | 6.65 | C |
| ATOM | 4196 | CZ3 | TRP | B1274 | −28.6 | −40.065 | −25.824 | 9.41 | C |
| ATOM | 4197 | CH2 | TRP | B1274 | −28.024 | −41.323 | −26.151 | 8.82 | C |
| ATOM | 4198 | C | TRP | B1274 | −30.795 | −39.344 | −21.861 | 10.81 | C |
| ATOM | 4199 | O | TRP | B1274 | −29.829 | −39.961 | −21.379 | 11.74 | O |
| ATOM | 4200 | N | GLU | B1275 | −30.715 | −38.082 | −22.242 | 10.72 | N |
| ATOM | 4201 | CA | GLU | B1275 | −29.426 | −37.332 | −22.148 | 10.68 | C |
| ATOM | 4202 | CB | GLU | B1275 | −29.639 | −35.857 | −22.527 | 10.88 | C |
| ATOM | 4203 | CG | GLU | B1275 | −30.153 | −35.543 | −23.903 | 11.46 | C |
| ATOM | 4204 | CD | GLU | B1275 | −30.4 | −34.021 | −24.049 | 14.34 | C |
| ATOM | 4205 | OE1 | GLU | B1275 | −31.524 | −33.501 | −23.805 | 15.39 | O |
| ATOM | 4206 | OE2 | GLU | B1275 | −29.401 | −33.309 | −24.396 | 22.77 | O |
| ATOM | 4207 | C | GLU | B1275 | −28.909 | −37.315 | −20.749 | 10.34 | C |
| ATOM | 4208 | O | GLU | B1275 | −27.707 | −37.337 | −20.528 | 10.71 | O |
| ATOM | 4209 | N | LEU | B1276 | −29.809 | −37.115 | −19.785 | 11.05 | N |
| ATOM | 4210 | CA | LEU | B1276 | −29.43 | −37.1 | −18.346 | 10.79 | C |
| ATOM | 4211 | CB | LEU | B1276 | −30.632 | −36.812 | −17.47 | 12.25 | C |
| ATOM | 4212 | CG | LEU | B1276 | −31.013 | −35.427 | −16.907 | 13.19 | C |
| ATOM | 4213 | CD1 | LEU | B1276 | −30.601 | −34.396 | −17.903 | 20.48 | C |
| ATOM | 4214 | CD2 | LEU | B1276 | −32.537 | −35.354 | −16.588 | 10.2 | C |
| ATOM | 4215 | C | LEU | B1276 | −28.834 | −38.412 | −17.94 | 10.65 | C |
| ATOM | 4216 | O | LEU | B1276 | −27.765 | −38.417 | −17.393 | 11.03 | O |
| ATOM | 4217 | N | MET | B1277 | −29.498 | −39.527 | −18.296 | 10.47 | N |
| ATOM | 4218 | CA | MET | B1277 | −29.091 | −40.868 | −17.899 | 10.55 | C |
| ATOM | 4219 | CB | MET | B1277 | −30.237 | −41.888 | −18.047 | 10.09 | C |
| ATOM | 4220 | CG | MET | B1277 | −31.411 | −41.644 | −17.096 | 14.97 | C |
| ATOM | 4221 | SD | MET | B1277 | −30.866 | −41.259 | −15.312 | 20.21 | S |
| ATOM | 4222 | CE | MET | B1277 | −31.078 | −42.892 | −14.719 | 17.84 | C |
| ATOM | 4223 | C | MET | B1277 | −27.823 | −41.309 | −18.596 | 10.99 | C |
| ATOM | 4224 | O | MET | B1277 | −27.194 | −42.218 | −18.136 | 12.08 | O |
| ATOM | 4225 | N | THR | B1278 | −27.456 | −40.657 | −19.701 | 12.51 | N |
| ATOM | 4226 | CA | THR | B1278 | −26.236 | −40.961 | −20.482 | 11.87 | C |
| ATOM | 4227 | CB | THR | B1278 | −26.515 | −41.002 | −21.99 | 12.63 | C |
| ATOM | 4228 | OG1 | THR | B1278 | −27.031 | −39.745 | −22.452 | 8.58 | O |
| ATOM | 4229 | CG2 | THR | B1278 | −27.547 | −42.16 | −22.375 | 10.3 | C |
| ATOM | 4230 | C | THR | B1278 | −25.239 | −39.865 | −20.205 | 13.76 | C |
| ATOM | 4231 | O | THR | B1278 | −24.179 | −39.799 | −20.812 | 14.83 | O |
| ATOM | 4232 | N | ARG | B1279 | −25.582 | −39.023 | −19.222 | 14.86 | N |
| ATOM | 4233 | CA | ARG | B1279 | −24.78 | −37.831 | −18.858 | 15.36 | C |
| ATOM | 4234 | CB | ARG | B1279 | −23.525 | −38.248 | −18.1 | 15.01 | C |
| ATOM | 4235 | CG | ARG | B1279 | −23.844 | −38.717 | −16.667 | 15.98 | C |
| ATOM | 4236 | CD | ARG | B1279 | −22.587 | −38.783 | −15.851 | 19.69 | C |
| ATOM | 4237 | NE | ARG | B1279 | −21.75 | −37.562 | −15.876 | 19.77 | N |
| ATOM | 4238 | CZ | ARG | B1279 | −20.576 | −37.432 | −15.229 | 19.3 | C |
| ATOM | 4239 | NH1 | ARG | B1279 | −20.15 | −38.439 | −14.507 | 19.24 | N |
| ATOM | 4240 | NH2 | ARG | B1279 | −19.831 | −36.31 | −15.296 | 18.68 | N |
| ATOM | 4241 | C | ARG | B1279 | −24.4 | −37.045 | −20.084 | 14.5 | C |
| ATOM | 4242 | O | ARG | B1279 | −23.215 | −36.816 | −20.333 | 13.92 | O |
| ATOM | 4243 | N | GLY | B1280 | −25.398 | −36.714 | −20.886 | 14.34 | N |
| ATOM | 4244 | CA | GLY | B1280 | −25.185 | −35.899 | −22.099 | 16.19 | C |
| ATOM | 4245 | C | GLY | B1280 | −24.691 | −36.567 | −23.394 | 17.54 | C |
| ATOM | 4246 | O | GLY | B1280 | −24.179 | −35.859 | −24.239 | 18.98 | O |
| ATOM | 4247 | N | ALA | B1281 | −24.788 | −37.899 | −23.583 | 17.6 | N |
| ATOM | 4248 | CA | ALA | B1281 | −24.37 | −38.477 | −24.854 | 17.07 | C |
| ATOM | 4249 | CB | ALA | B1281 | −24.456 | −39.91 | −24.849 | 17.2 | C |
| ATOM | 4250 | C | ALA | B1281 | −25.354 | −37.928 | −25.858 | 18.67 | C |
| ATOM | 4251 | O | ALA | B1281 | −26.479 | −37.691 | −25.487 | 18.23 | O |
| ATOM | 4252 | N | PRO | B1282 | −24.918 | −37.652 | −27.114 | 18.85 | N |
| ATOM | 4253 | CD | PRO | B1282 | −23.561 | −37.714 | −27.7 | 19.07 | C |

TABLE 1A-continued

| | | | | | | | | |
|---|---|---|---|---|---|---|---|---|
| ATOM | 4254 | CA | PRO | B1282 | −25.936 | −37.183 | −28.063 | 19.03 | C |
| ATOM | 4255 | CB | PRO | B1282 | −25.114 | −36.547 | −29.185 | 19.41 | C |
| ATOM | 4256 | CG | PRO | B1282 | −23.823 | −37.421 | −29.231 | 20.06 | C |
| ATOM | 4257 | C | PRO | B1282 | −26.794 | −38.329 | −28.631 | 18.75 | C |
| ATOM | 4258 | O | PRO | B1282 | −26.266 | −39.369 | −28.982 | 18.98 | O |
| ATOM | 4259 | N | PRO | B1283 | −28.118 | −38.108 | −28.775 | 19.17 | N |
| ATOM | 4260 | CD | PRO | B1283 | −28.853 | −36.859 | −28.437 | 18.86 | C |
| ATOM | 4261 | CA | PRO | B1283 | −29.024 | −39.124 | −29.297 | 19.02 | C |
| ATOM | 4262 | CB | PRO | B1283 | −30.43 | −38.501 | −29.009 | 18.56 | C |
| ATOM | 4263 | CG | PRO | B1283 | −30.258 | −37.142 | −28.879 | 17.23 | C |
| ATOM | 4264 | C | PRO | B1283 | −28.841 | −39.395 | −30.798 | 19.32 | C |
| ATOM | 4265 | O | PRO | B1283 | −28.662 | −38.429 | −31.591 | 21.46 | O |
| ATOM | 4266 | N | TYR | B1284 | −28.971 | −40.664 | −31.192 | 19.19 | N |
| ATOM | 4267 | CA | TYR | B1284 | −28.753 | −41.129 | −32.591 | 18.43 | C |
| ATOM | 4268 | CB | TYR | B1284 | −29.945 | −40.797 | −33.455 | 18.2 | C |
| ATOM | 4269 | CG | TYR | B1284 | −31.282 | −40.712 | −32.714 | 17.9 | C |
| ATOM | 4270 | CD1 | TYR | B1284 | −32.126 | −41.84 | −32.634 | 12.98 | C |
| ATOM | 4271 | CE1 | TYR | B1284 | −33.257 | −41.797 | −31.972 | 14.34 | C |
| ATOM | 4272 | CD2 | TYR | B1284 | −31.705 | −39.506 | −32.127 | 14.75 | C |
| ATOM | 4273 | CE2 | TYR | B1284 | −32.907 | −39.437 | −31.442 | 13.46 | C |
| ATOM | 4274 | CZ | TYR | B1284 | −33.697 | −40.579 | −31.388 | 16.98 | C |
| ATOM | 4275 | OH | TYR | B1284 | −34.93 | −40.54 | −30.755 | 16.26 | O |
| ATOM | 4276 | C | TYR | B1284 | −27.438 | −40.55 | −33.221 | 19.56 | C |
| ATOM | 4277 | O | TYR | B1284 | −27.451 | −39.885 | −34.266 | 17.04 | O |
| ATOM | 4278 | N | PRO | B1285 | −26.3 | −40.75 | −32.519 | 20.97 | N |
| ATOM | 4279 | CD | PRO | B1285 | −26.047 | −41.534 | −31.294 | 19.88 | C |
| ATOM | 4280 | CA | PRO | B1285 | −25.1 | −40.093 | −32.988 | 22.62 | C |
| ATOM | 4281 | CB | PRO | B1285 | −24.025 | −40.589 | −32 | 20.54 | C |
| ATOM | 4282 | CG | PRO | B1285 | −24.632 | −41.818 | −31.389 | 22.01 | C |
| ATOM | 4283 | C | PRO | B1285 | −24.786 | −40.524 | −34.415 | 24.49 | C |
| ATOM | 4284 | O | PRO | B1285 | −24.241 | −39.737 | −35.18 | 25.5 | O |
| ATOM | 4285 | N | ASP | B1286 | −25.164 | −41.749 | −34.766 | 27.37 | N |
| ATOM | 4286 | CA | ASP | B1286 | −24.704 | −42.331 | −36.018 | 31.08 | C |
| ATOM | 4287 | CB | ASP | B1286 | −24.187 | −43.772 | −35.778 | 32.37 | C |
| ATOM | 4288 | CG | ASP | B1286 | −22.72 | −43.794 | −35.198 | 37.41 | C |
| ATOM | 4289 | OD1 | ASP | B1286 | −22.403 | −44.628 | −34.255 | 38.84 | O |
| ATOM | 4290 | OD2 | ASP | B1286 | −21.907 | −42.938 | −35.687 | 38.04 | O |
| ATOM | 4291 | C | ASP | B1286 | −25.71 | −42.214 | −37.204 | 31.19 | C |
| ATOM | 4292 | O | ASP | B1286 | −25.473 | −42.825 | −38.251 | 31.88 | O |
| ATOM | 4293 | N | VAL | B1287 | −26.783 | −41.421 | −37.002 | 29.92 | N |
| ATOM | 4294 | CA | VAL | B1287 | −27.83 | −41.055 | −37.968 | 28.47 | C |
| ATOM | 4295 | CB | VAL | B1287 | −29.195 | −41.458 | −37.484 | 28.62 | C |
| ATOM | 4296 | CG1 | VAL | B1287 | −29.805 | −42.395 | −38.473 | 30.75 | C |
| ATOM | 4297 | CG2 | VAL | B1287 | −29.117 | −42.081 | −36.084 | 30.13 | C |
| ATOM | 4298 | C | VAL | B1287 | −28.018 | −39.58 | −38.409 | 27.43 | C |
| ATOM | 4299 | O | VAL | B1287 | −27.907 | −38.621 | −37.615 | 24.94 | O |
| ATOM | 4300 | N | ASN | B1288 | −28.357 | −39.439 | −39.7 | 25.37 | N |
| ATOM | 4301 | CA | ASN | B1288 | −28.695 | −38.162 | −40.252 | 23.52 | C |
| ATOM | 4302 | CB | ASN | B1288 | −28.217 | −38.016 | −41.715 | 24.34 | C |
| ATOM | 4303 | CG | ASN | B1288 | −29.032 | −38.899 | −42.718 | 22.8 | C |
| ATOM | 4304 | OD1 | ASN | B1288 | −30.22 | −39.086 | −42.568 | 23.33 | O |
| ATOM | 4305 | ND2 | ASN | B1288 | −28.376 | −39.421 | −43.706 | 18.01 | N |
| ATOM | 4306 | C | ASN | B1288 | −30.196 | −38.069 | −40.154 | 22.61 | C |
| ATOM | 4307 | O | ASN | B1288 | −30.911 | −39.051 | −39.908 | 21.14 | O |
| ATOM | 4308 | N | THR | B1289 | −30.686 | −36.882 | −40.389 | 21.92 | N |
| ATOM | 4309 | CA | THR | B1289 | −32.097 | −36.631 | −40.185 | 22.85 | C |
| ATOM | 4310 | CB | THR | B1289 | −32.339 | −35.133 | −40.101 | 22.97 | C |
| ATOM | 4311 | OG1 | THR | B1289 | −32.875 | −34.697 | −41.323 | 27.53 | O |
| ATOM | 4312 | CG2 | THR | B1289 | −31.049 | −34.441 | −39.957 | 21.76 | C |
| ATOM | 4313 | C | THR | B1289 | −33.046 | −37.19 | −41.219 | 22.8 | C |
| ATOM | 4314 | O | THR | B1289 | −34.233 | −37.072 | −41.045 | 23.92 | O |
| ATOM | 4315 | N | PHE | B1290 | −32.555 | −37.753 | −42.324 | 22.88 | N |
| ATOM | 4316 | CA | PHE | B1290 | −33.446 | −38.501 | −43.188 | 22.14 | C |
| ATOM | 4317 | CB | PHE | B1290 | −32.842 | −38.696 | −44.574 | 21.33 | C |
| ATOM | 4318 | CG | PHE | B1290 | −33.712 | −39.497 | −45.465 | 19.38 | C |
| ATOM | 4319 | CD1 | PHE | B1290 | −34.76 | −38.915 | −46.123 | 17.77 | C |
| ATOM | 4320 | CD2 | PHE | B1290 | −33.516 | −40.86 | −45.595 | 22.41 | C |
| ATOM | 4321 | CE1 | PHE | B1290 | −35.614 | −39.679 | −46.916 | 20.2 | C |
| ATOM | 4322 | CE2 | PHE | B1290 | −34.389 | −41.647 | −46.369 | 22.41 | C |
| ATOM | 4323 | CZ | PHE | B1290 | −35.419 | −41.053 | −47.042 | 20.49 | C |
| ATOM | 4324 | C | PHE | B1290 | −33.762 | −39.853 | −42.511 | 22.8 | C |
| ATOM | 4325 | O | PHE | B1290 | −34.938 | −40.28 | −42.341 | 23.53 | O |
| ATOM | 4326 | N | ASP | B1291 | −32.691 | −40.489 | −42.084 | 23.39 | N |
| ATOM | 4327 | CA | ASP | B1291 | −32.716 | −41.81 | −41.531 | 25.68 | C |
| ATOM | 4328 | CB | ASP | B1291 | −31.286 | −42.354 | −41.462 | 26.6 | C |
| ATOM | 4329 | CG | ASP | B1291 | −30.783 | −42.791 | −42.821 | 31.08 | C |
| ATOM | 4330 | OD1 | ASP | B1291 | −30.091 | −41.973 | −43.493 | 39.79 | O |
| ATOM | 4331 | OD2 | ASP | B1291 | −31.118 | −43.917 | −43.254 | 34.14 | O |
| ATOM | 4332 | C | ASP | B1291 | −33.404 | −41.887 | −40.173 | 25.96 | C |
| ATOM | 4333 | O | ASP | B1291 | −34.082 | −42.896 | −39.876 | 27.77 | O |

TABLE 1A-continued

| | | | | | | | | |
|---|---|---|---|---|---|---|---|---|
| ATOM | 4334 | N | ILE | B1292 | −33.219 | −40.865 | −39.354 | 24.64 | N |
| ATOM | 4335 | CA | ILE | B1292 | −33.978 | −40.718 | −38.086 | 24.06 | C |
| ATOM | 4336 | CB | ILE | B1292 | −33.717 | −39.333 | −37.395 | 23.91 | C |
| ATOM | 4337 | CG2 | ILE | B1292 | −34.52 | −38.228 | −38.039 | 22.83 | C |
| ATOM | 4338 | CG1 | ILE | B1292 | −34.137 | −39.381 | −35.934 | 25.2 | C |
| ATOM | 4339 | CD1 | ILE | B1292 | −33.285 | −40.209 | −35.142 | 29.16 | C |
| ATOM | 4340 | C | ILE | B1292 | −35.493 | −40.957 | −38.258 | 22.98 | C |
| ATOM | 4341 | O | ILE | B1292 | −36.167 | −41.598 | −37.392 | 22.39 | O |
| ATOM | 4342 | N | THR | B1293 | −36.038 | −40.498 | −39.379 | 20.83 | N |
| ATOM | 4343 | CA | THR | B1293 | −37.497 | −40.546 | −39.512 | 19.69 | C |
| ATOM | 4344 | CB | THR | B1293 | −37.956 | −39.539 | −40.585 | 19.99 | C |
| ATOM | 4345 | OG1 | THR | B1293 | −37.454 | −38.237 | −40.201 | 19.82 | O |
| ATOM | 4346 | CG2 | THR | B1293 | −39.542 | −39.516 | −40.79 | 18.66 | C |
| ATOM | 4347 | C | THR | B1293 | −37.916 | −41.972 | −39.768 | 18.48 | C |
| ATOM | 4348 | O | THR | B1293 | −38.92 | −42.457 | −39.319 | 18.06 | O |
| ATOM | 4349 | N | VAL | B1294 | −37.033 | −42.675 | −40.427 | 19.37 | N |
| ATOM | 4350 | CA | VAL | B1294 | −37.265 | −44.057 | −40.852 | 18.14 | C |
| ATOM | 4351 | CB | VAL | B1294 | −36.276 | −44.44 | −41.987 | 16.93 | C |
| ATOM | 4352 | CG1 | VAL | B1294 | −36.204 | −45.932 | −42.144 | 16.99 | C |
| ATOM | 4353 | CG2 | VAL | B1294 | −36.642 | −43.726 | −43.24 | 16.98 | C |
| ATOM | 4354 | C | VAL | B1294 | −37.007 | −44.934 | −39.68 | 18.45 | C |
| ATOM | 4355 | O | VAL | B1294 | −37.697 | −45.952 | −39.506 | 20.56 | O |
| ATOM | 4356 | N | TYR | B1295 | −35.997 | −44.564 | −38.899 | 16.67 | N |
| ATOM | 4357 | CA | TYR | B1295 | −35.638 | −45.276 | −37.722 | 16.51 | C |
| ATOM | 4358 | CB | TYR | B1295 | −34.492 | −44.495 | −37.098 | 18.46 | C |
| ATOM | 4359 | CG | TYR | B1295 | −33.946 | −45.014 | −35.785 | 22.08 | C |
| ATOM | 4360 | CD1 | TYR | B1295 | −32.897 | −45.936 | −35.786 | 18.65 | C |
| ATOM | 4361 | CE1 | TYR | B1295 | −32.39 | −46.441 | −34.598 | 21.13 | C |
| ATOM | 4362 | CD2 | TYR | B1295 | −34.508 | −44.595 | −34.522 | 20.64 | C |
| ATOM | 4363 | CE2 | TYR | B1295 | −33.997 | −45.107 | −33.318 | 22.26 | C |
| ATOM | 4364 | CZ | TYR | B1295 | −32.924 | −46.021 | −33.376 | 22.13 | C |
| ATOM | 4365 | OH | TYR | B1295 | −32.382 | −46.571 | −32.246 | 22.52 | O |
| ATOM | 4366 | C | TYR | B1295 | −36.854 | −45.256 | −36.846 | 16 | C |
| ATOM | 4367 | O | TYR | B1295 | −37.362 | −46.275 | −36.484 | 16.15 | O |
| ATOM | 4368 | N | LEU | B1296 | −37.335 | −44.069 | −36.518 | 17.4 | N |
| ATOM | 4369 | CA | LEU | B1296 | −38.569 | −43.871 | −35.695 | 18.14 | C |
| ATOM | 4370 | CB | LEU | B1296 | −38.857 | −42.369 | −35.415 | 16.41 | C |
| ATOM | 4371 | CG | LEU | B1296 | −37.827 | −41.579 | −34.591 | 17.12 | C |
| ATOM | 4372 | CD1 | LEU | B1296 | −38.248 | −40.118 | −34.316 | 17.69 | C |
| ATOM | 4373 | CD2 | LEU | B1296 | −37.568 | −42.248 | −33.297 | 19.55 | C |
| ATOM | 4374 | C | LEU | B1296 | −39.796 | −44.499 | −36.276 | 19.05 | C |
| ATOM | 4375 | O | LEU | B1296 | −40.678 | −45.011 | −35.565 | 19.99 | O |
| ATOM | 4376 | N | LEU | B1297 | −39.903 | −44.392 | −37.584 | 21.12 | N |
| ATOM | 4377 | CA | LEU | B1297 | −41.05 | −44.95 | −38.301 | 21.99 | C |
| ATOM | 4378 | CB | LEU | B1297 | −41.041 | −44.458 | −39.76 | 22.16 | C |
| ATOM | 4379 | CG | LEU | B1297 | −42.349 | −43.788 | −40.253 | 24.1 | C |
| ATOM | 4380 | CD1 | LEU | B1297 | −42.933 | −42.852 | −39.23 | 27.09 | C |
| ATOM | 4381 | CD2 | LEU | B1297 | −42.214 | −43.055 | −41.568 | 22.63 | C |
| ATOM | 4382 | C | LEU | B1297 | −40.944 | −46.474 | −38.189 | 22.27 | C |
| ATOM | 4383 | O | LEU | B1297 | −41.937 | −47.138 | −38.123 | 23.87 | O |
| ATOM | 4384 | N | GLN | B1298 | −39.745 | −47.049 | −38.124 | 22.59 | N |
| ATOM | 4385 | CA | GLN | B1298 | −39.64 | −48.519 | −37.939 | 22.65 | C |
| ATOM | 4386 | CB | GLN | B1298 | −38.239 | −49.031 | −38.273 | 22.35 | C |
| ATOM | 4387 | CG | GLN | B1298 | −37.925 | −48.986 | −39.772 | 22.45 | C |
| ATOM | 4388 | CD | GLN | B1298 | −36.406 | −48.945 | −40.084 | 25.99 | C |
| ATOM | 4389 | OE1 | GLN | B1298 | −35.576 | −48.486 | −39.278 | 28.63 | O |
| ATOM | 4390 | NE2 | GLN | B1298 | −36.052 | −49.376 | −41.283 | 28.14 | N |
| ATOM | 4391 | C | GLN | B1298 | −40.01 | −48.972 | −36.511 | 21.75 | C |
| ATOM | 4392 | O | GLN | B1298 | −39.95 | −50.191 | −36.19 | 21.69 | O |
| ATOM | 4393 | N | GLY | B1299 | −40.401 | −48.004 | −35.663 | 19.9 | N |
| ATOM | 4394 | CA | GLY | B1299 | −40.685 | −48.284 | −34.269 | 16.6 | C |
| ATOM | 4395 | C | GLY | B1299 | −39.444 | −48.332 | −33.427 | 15.5 | C |
| ATOM | 4396 | O | GLY | B1299 | −39.528 | −48.659 | −32.23 | 18.01 | O |
| ATOM | 4397 | N | ARG | B1300 | −38.279 | −48.013 | −33.986 | 13.06 | N |
| ATOM | 4398 | CA | ARG | B1300 | −37.018 | −48.036 | −33.185 | 11.49 | C |
| ATOM | 4399 | CB | ARG | B1300 | −35.761 | −48.001 | −34.1 | 10.35 | C |
| ATOM | 4400 | CG | ARG | B1300 | −35.596 | −49.253 | −34.881 | 8.8 | C |
| ATOM | 4401 | CD | ARG | B1300 | −34.804 | −49.057 | −36.208 | 11.14 | C |
| ATOM | 4402 | NE | ARG | B1300 | −35.001 | −50.267 | −37.006 | 14.02 | N |
| ATOM | 4403 | CZ | ARG | B1300 | −34.449 | −51.482 | −36.788 | 14.19 | C |
| ATOM | 4404 | NH1 | ARG | B1300 | −33.565 | −51.753 | −35.769 | 12.76 | N |
| ATOM | 4405 | NH2 | ARG | B1300 | −34.807 | −52.443 | −37.609 | 7.95 | N |
| ATOM | 4406 | C | ARG | B1300 | −36.982 | −46.825 | −32.278 | 12.12 | C |
| ATOM | 4407 | O | ARG | B1300 | −37.476 | −45.745 | −32.664 | 11.41 | O |
| ATOM | 4408 | N | ARG | B1301 | −36.379 | −47.001 | −31.085 | 12.18 | N |
| ATOM | 4409 | CA | ARG | B1301 | −36.242 | −45.941 | −30.083 | 10.47 | C |
| ATOM | 4410 | CB | ARG | B1301 | −37.226 | −46.167 | −28.949 | 10.51 | C |
| ATOM | 4411 | CG | ARG | B1301 | −38.659 | −45.805 | −29.248 | 10.7 | C |
| ATOM | 4412 | CD | ARG | B1301 | −38.823 | −44.561 | −30.173 | 12.65 | C |
| ATOM | 4413 | NE | ARG | B1301 | −40.219 | −44.305 | −30.478 | 10.61 | N |

TABLE 1A-continued

| | | | | | | | | |
|---|---|---|---|---|---|---|---|---|
| ATOM | 4414 | CZ | ARG | B1301 | −40.823 | −44.551 | −31.628 | 13.77 | C |
| ATOM | 4415 | NH1 | ARG | B1301 | −40.167 | −45.018 | −32.687 | 9.33 | N |
| ATOM | 4416 | NH2 | ARG | B1301 | −42.121 | −44.303 | −31.709 | 16.57 | N |
| ATOM | 4417 | C | ARG | B1301 | −34.833 | −45.866 | −29.54 | 10.44 | C |
| ATOM | 4418 | O | ARG | B1301 | −33.998 | −46.702 | −29.83 | 9.22 | O |
| ATOM | 4419 | N | LEU | B1302 | −34.55 | −44.825 | −28.783 | 9.97 | N |
| ATOM | 4420 | CA | LEU | B1302 | −33.246 | −44.705 | −28.137 | 9.91 | C |
| ATOM | 4421 | CB | LEU | B1302 | −33.199 | −43.365 | −27.393 | 8.2 | C |
| ATOM | 4422 | CG | LEU | B1302 | −33.005 | −42.134 | −28.25 | 7.77 | C |
| ATOM | 4423 | CD1 | LEU | B1302 | −33.264 | −40.843 | −27.548 | 2 | C |
| ATOM | 4424 | CD2 | LEU | B1302 | −31.622 | −42.163 | −28.913 | 7.03 | C |
| ATOM | 4425 | C | LEU | B1302 | −33.065 | −45.833 | −27.143 | 9.92 | C |
| ATOM | 4426 | O | LEU | B1302 | −33.97 | −46.117 | −26.398 | 11.67 | O |
| ATOM | 4427 | N | LEU | B1303 | −31.895 | −46.44 | −27.111 | 11.44 | N |
| ATOM | 4428 | CA | LEU | B1303 | −31.592 | −47.581 | −26.212 | 14.3 | C |
| ATOM | 4429 | CB | LEU | B1303 | −30.298 | −48.268 | −26.624 | 12.85 | C |
| ATOM | 4430 | CG | LEU | B1303 | −30.486 | −49.01 | −27.953 | 17.01 | C |
| ATOM | 4431 | CD1 | LEU | B1303 | −29.325 | −49.927 | −28.102 | 18.45 | C |
| ATOM | 4432 | CD2 | LEU | B1303 | −31.815 | −49.797 | −28.015 | 16.49 | C |
| ATOM | 4433 | C | LEU | B1303 | −31.546 | −47.25 | −24.715 | 14.72 | C |
| ATOM | 4434 | O | LEU | B1303 | −31.279 | −46.11 | −24.356 | 14.39 | O |
| ATOM | 4435 | N | GLN | B1304 | −31.854 | −48.245 | −23.865 | 15.16 | N |
| ATOM | 4436 | CA | GLN | B1304 | −31.831 | −47.99 | −22.453 | 15.6 | C |
| ATOM | 4437 | CB | GLN | B1304 | −32.393 | −49.143 | −21.651 | 14.32 | C |
| ATOM | 4438 | CG | GLN | B1304 | −32.316 | −48.821 | −20.17 | 16.69 | C |
| ATOM | 4439 | CD | GLN | B1304 | −33.193 | −49.657 | −19.327 | 17.17 | C |
| ATOM | 4440 | OE1 | GLN | B1304 | −33.604 | −49.242 | −18.239 | 20.26 | O |
| ATOM | 4441 | NE2 | GLN | B1304 | −33.452 | −50.876 | −19.778 | 19.03 | N |
| ATOM | 4442 | C | GLN | B1304 | −30.407 | −47.632 | −22.036 | 16.11 | C |
| ATOM | 4443 | O | GLN | B1304 | −29.497 | −48.327 | −22.357 | 18.26 | O |
| ATOM | 4444 | N | PRO | B1305 | −30.193 | −46.471 | −21.426 | 16.5 | N |
| ATOM | 4445 | CD | PRO | B1305 | −31.101 | −45.362 | −21.151 | 15.37 | C |
| ATOM | 4446 | CA | PRO | B1305 | −28.853 | −46.198 | −20.991 | 17.68 | C |
| ATOM | 4447 | CB | PRO | B1305 | −28.946 | −44.768 | −20.507 | 17.49 | C |
| ATOM | 4448 | CG | PRO | B1305 | −30.161 | −44.252 | −21.136 | 17.86 | C |
| ATOM | 4449 | C | PRO | B1305 | −28.443 | −47.116 | −19.839 | 20 | C |
| ATOM | 4450 | O | PRO | B1305 | −29.298 | −47.56 | −19.067 | 19.29 | O |
| ATOM | 4451 | N | GLU | B1306 | −27.158 | −47.439 | −19.757 | 22.81 | N |
| ATOM | 4452 | CA | GLU | B1306 | −26.626 | −48.241 | −18.644 | 26.21 | C |
| ATOM | 4453 | CB | GLU | B1306 | −25.118 | −48.456 | −18.828 | 25.64 | C |
| ATOM | 4454 | CG | GLU | B1306 | −24.533 | −49.314 | −17.738 | 27.34 | C |
| ATOM | 4455 | CD | GLU | B1306 | −23.03 | −49.575 | −17.862 | 30.37 | C |
| ATOM | 4456 | OE1 | GLU | B1306 | −22.589 | −50.618 | −17.295 | 36.66 | O |
| ATOM | 4457 | OE2 | GLU | B1306 | −22.289 | −48.75 | −18.461 | 32.22 | O |
| ATOM | 4458 | C | GLU | B1306 | −26.871 | −47.488 | −17.331 | 27.16 | C |
| ATOM | 4459 | O | GLU | B1306 | −26.692 | −46.268 | −17.269 | 29.39 | O |
| ATOM | 4460 | N | TYR | B1307 | −27.253 | −48.177 | −16.268 | 27.98 | N |
| ATOM | 4461 | CA | TYR | B1307 | −27.544 | −47.459 | −14.999 | 28.39 | C |
| ATOM | 4462 | CB | TYR | B1307 | −26.449 | −46.465 | −14.617 | 30.07 | C |
| ATOM | 4463 | CG | TYR | B1307 | −25.01 | −46.917 | −14.645 | 32.11 | C |
| ATOM | 4464 | CD1 | TYR | B1307 | −24.052 | −46.15 | −15.339 | 33.72 | C |
| ATOM | 4465 | CE1 | TYR | B1307 | −22.695 | −46.523 | −15.342 | 33.05 | C |
| ATOM | 4466 | CD2 | TYR | B1307 | −24.578 | −48.076 | −13.95 | 33.11 | C |
| ATOM | 4467 | CE2 | TYR | B1307 | −23.218 | −48.466 | −13.973 | 34.52 | C |
| ATOM | 4468 | CZ | TYR | B1307 | −22.305 | −47.662 | −14.672 | 33.21 | C |
| ATOM | 4469 | OH | TYR | B1307 | −20.998 | −47.985 | −14.726 | 35.57 | O |
| ATOM | 4470 | C | TYR | B1307 | −28.861 | −46.67 | −14.974 | 27.38 | C |
| ATOM | 4471 | O | TYR | B1307 | −29.237 | −46.121 | −13.927 | 27.77 | O |
| ATOM | 4472 | N | CYS | B1308 | −29.532 | −46.556 | −16.106 | 25.63 | N |
| ATOM | 4473 | CA | CYS | B1308 | −30.936 | −46.164 | −16.106 | 24.55 | C |
| ATOM | 4474 | CB | CYS | B1308 | −31.397 | −45.777 | −17.483 | 22.73 | C |
| ATOM | 4475 | SG | CYS | B1308 | −33.095 | −45.158 | −17.55 | 23.51 | S |
| ATOM | 4476 | C | CYS | B1308 | −31.832 | −47.271 | −15.538 | 24.84 | C |
| ATOM | 4477 | O | CYS | B1308 | −31.897 | −48.393 | −16.081 | 23.68 | O |
| ATOM | 4478 | N | PRO | B1309 | −32.6 | −46.935 | −14.466 | 25.41 | N |
| ATOM | 4479 | CD | PRO | B1309 | −32.656 | −45.647 | −13.763 | 24.46 | C |
| ATOM | 4480 | CA | PRO | B1309 | −33.584 | −47.895 | −13.88 | 24.77 | C |
| ATOM | 4481 | CB | PRO | B1309 | −34.204 | −47.104 | −12.715 | 23.63 | C |
| ATOM | 4482 | CG | PRO | B1309 | −33.172 | −46.086 | −12.433 | 25.74 | C |
| ATOM | 4483 | C | PRO | B1309 | −34.642 | −48.229 | −14.909 | 24.26 | C |
| ATOM | 4484 | O | PRO | B1309 | −34.95 | −47.377 | −15.795 | 23.66 | O |
| ATOM | 4485 | N | ASP | B1310 | −35.19 | −49.439 | −14.799 | 24.29 | N |
| ATOM | 4486 | CA | ASP | B1310 | −36.185 | −49.915 | −15.796 | 24.2 | C |
| ATOM | 4487 | CB | ASP | B1310 | −36.631 | −51.401 | −15.563 | 26.57 | C |
| ATOM | 4488 | CG | ASP | B1310 | −35.495 | −52.422 | −15.751 | 29.97 | C |
| ATOM | 4489 | OD1 | ASP | B1310 | −34.485 | −52.019 | −16.361 | 36.47 | O |
| ATOM | 4490 | OD2 | ASP | B1310 | −35.597 | −53.597 | −15.263 | 30.68 | O |
| ATOM | 4491 | C | ASP | B1310 | −37.418 | −49.003 | −15.83 | 21.98 | C |
| ATOM | 4492 | O | ASP | B1310 | −37.941 | −48.708 | −16.926 | 21.91 | O |
| ATOM | 4493 | N | PRO | B1311 | −37.923 | −48.602 | −14.646 | 19.96 | N |

TABLE 1A-continued

| ATOM | 4494 | CD | PRO | B1311 | −37.599 | −49.016 | −13.268 | 20.32 | C |
|---|---|---|---|---|---|---|---|---|---|
| ATOM | 4495 | CA | PRO | B1311 | −39.113 | −47.777 | −14.668 | 19.05 | C |
| ATOM | 4496 | CB | PRO | B1311 | −39.524 | −47.708 | −13.183 | 18.27 | C |
| ATOM | 4497 | CG | PRO | B1311 | −38.379 | −48.115 | −12.44 | 18.5 | C |
| ATOM | 4498 | C | PRO | B1311 | −38.918 | −46.399 | −15.249 | 17.86 | C |
| ATOM | 4499 | O | PRO | B1311 | −39.899 | −45.735 | −15.688 | 17.53 | O |
| ATOM | 4500 | N | LEU | B1312 | −37.67 | −45.965 | −15.271 | 16.14 | N |
| ATOM | 4501 | CA | LEU | B1312 | −37.465 | −44.677 | −15.858 | 16.38 | C |
| ATOM | 4502 | CB | LEU | B1312 | −36.183 | −43.984 | −15.37 | 16.29 | C |
| ATOM | 4503 | CG | LEU | B1312 | −36.067 | −42.524 | −15.792 | 16.08 | C |
| ATOM | 4504 | CD1 | LEU | B1312 | −37.295 | −41.659 | −15.348 | 11.99 | C |
| ATOM | 4505 | CD2 | LEU | B1312 | −34.769 | −41.986 | −15.207 | 17.66 | C |
| ATOM | 4506 | C | LEU | B1312 | −37.488 | −44.812 | −17.338 | 16.51 | C |
| ATOM | 4507 | O | LEU | B1312 | −38.021 | −43.942 | −17.987 | 18.01 | O |
| ATOM | 4508 | N | TYR | B1313 | −36.933 | −45.913 | −17.868 | 17.37 | N |
| ATOM | 4509 | CA | TYR | B1313 | −36.921 | −46.179 | −19.269 | 16.68 | C |
| ATOM | 4510 | CB | TYR | B1313 | −36.045 | −47.372 | −19.607 | 18.13 | C |
| ATOM | 4511 | CG | TYR | B1313 | −35.809 | −47.569 | −21.126 | 19.09 | C |
| ATOM | 4512 | CD1 | TYR | B1313 | −35.4 | −46.494 | −21.925 | 17.61 | C |
| ATOM | 4513 | CE1 | TYR | B1313 | −35.201 | −46.641 | −23.29 | 14.2 | C |
| ATOM | 4514 | CD2 | TYR | B1313 | −36.056 | −48.82 | −21.769 | 17.57 | C |
| ATOM | 4515 | CE2 | TYR | B1313 | −35.828 | −48.972 | −23.114 | 13.44 | C |
| ATOM | 4516 | CZ | TYR | B1313 | −35.396 | −47.877 | −23.866 | 15.63 | C |
| ATOM | 4517 | OH | TYR | B1313 | −35.189 | −47.951 | −25.217 | 17.24 | O |
| ATOM | 4518 | C | TYR | B1313 | −38.286 | −46.441 | −19.728 | 17.75 | C |
| ATOM | 4519 | O | TYR | B1313 | −38.61 | −46.123 | −20.875 | 18.79 | O |
| ATOM | 4520 | N | GLU | B1314 | −39.111 | −47.023 | −18.873 | 18.63 | N |
| ATOM | 4521 | CA | GLU | B1314 | −40.523 | −47.214 | −19.258 | 21.23 | C |
| ATOM | 4522 | CB | GLU | B1314 | −41.366 | −48.074 | −18.279 | 22.12 | C |
| ATOM | 4523 | CG | GLU | B1314 | −42.245 | −49.17 | −19.065 | 33.76 | C |
| ATOM | 4524 | CD | GLU | B1314 | −43.49 | −48.606 | −19.922 | 44.3 | C |
| ATOM | 4525 | OE1 | GLU | B1314 | −43.455 | −48.565 | −21.212 | 43.29 | O |
| ATOM | 4526 | OE2 | GLU | B1314 | −44.521 | −48.207 | −19.278 | 47.53 | O |
| ATOM | 4527 | C | GLU | B1314 | −41.229 | −45.89 | −19.486 | 19.2 | C |
| ATOM | 4528 | O | GLU | B1314 | −42.049 | −45.786 | −20.418 | 18.94 | O |
| ATOM | 4529 | N | VAL | B1315 | −40.898 | −44.905 | −18.64 | 16.5 | N |
| ATOM | 4530 | CA | VAL | B1315 | −41.316 | −43.504 | −18.813 | 15.13 | C |
| ATOM | 4531 | CB | VAL | B1315 | −40.713 | −42.501 | −17.729 | 15.61 | C |
| ATOM | 4532 | CG1 | VAL | B1315 | −41.278 | −41.055 | −17.932 | 14.24 | C |
| ATOM | 4533 | CG2 | VAL | B1315 | −40.98 | −43.034 | −16.234 | 13.55 | C |
| ATOM | 4534 | C | VAL | B1315 | −40.922 | −43.015 | −20.153 | 14.83 | C |
| ATOM | 4535 | O | VAL | B1315 | −41.775 | −42.65 | −20.949 | 15.7 | O |
| ATOM | 4536 | N | MET | B1316 | −39.633 | −43.05 | −20.434 | 15.52 | N |
| ATOM | 4537 | CA | MET | B1316 | −39.114 | −42.518 | −21.691 | 17.71 | C |
| ATOM | 4538 | CB | MET | B1316 | −37.623 | −42.804 | −21.81 | 18.78 | C |
| ATOM | 4539 | CG | MET | B1316 | −36.714 | −42.253 | −20.696 | 17.64 | C |
| ATOM | 4540 | SD | MET | B1316 | −35.014 | −42.678 | −21.236 | 22.89 | S |
| ATOM | 4541 | CE | MET | B1316 | −34.237 | −43.094 | −19.653 | 17.64 | C |
| ATOM | 4542 | C | MET | B1316 | −39.821 | −43.142 | −22.882 | 16.73 | C |
| ATOM | 4543 | O | MET | B1316 | −40.287 | −42.435 | −23.76 | 17.39 | O |
| ATOM | 4544 | N | LEU | B1317 | −39.934 | −44.469 | −22.886 | 16.32 | N |
| ATOM | 4545 | CA | LEU | B1317 | −40.676 | −45.179 | −23.93 | 15.32 | C |
| ATOM | 4546 | CB | LEU | B1317 | −40.662 | −46.667 | −23.706 | 15.3 | C |
| ATOM | 4547 | CG | LEU | B1317 | −39.334 | −47.379 | −23.955 | 14.27 | C |
| ATOM | 4548 | CD1 | LEU | B1317 | −39.561 | −48.82 | −23.47 | 8.02 | C |
| ATOM | 4549 | CD2 | LEU | B1317 | −38.892 | −47.248 | −25.466 | 9.83 | C |
| ATOM | 4550 | C | LEU | B1317 | −42.099 | −44.727 | −24.053 | 14.63 | C |
| ATOM | 4551 | O | LEU | B1317 | −42.565 | −44.533 | −25.151 | 15.33 | O |
| ATOM | 4552 | N | LYS | B1318 | −42.787 | −44.512 | −22.949 | 14.75 | N |
| ATOM | 4553 | CA | LYS | B1318 | −44.142 | −43.957 | −23.059 | 16.87 | C |
| ATOM | 4554 | CB | LYS | B1318 | −44.887 | −43.938 | −21.685 | 18.94 | C |
| ATOM | 4555 | CG | LYS | B1318 | −45.16 | −45.282 | −21.027 | 19.41 | C |
| ATOM | 4556 | CD | LYS | B1318 | −46.49 | −45.359 | −20.291 | 25.33 | C |
| ATOM | 4557 | CE | LYS | B1318 | −46.597 | −46.665 | −19.415 | 28.28 | C |
| ATOM | 4558 | NZ | LYS | B1318 | −45.911 | −46.56 | −18.01 | 30.63 | N |
| ATOM | 4559 | C | LYS | B1318 | −44.077 | −42.499 | −23.668 | 16.78 | C |
| ATOM | 4560 | O | LYS | B1318 | −45.021 | −42.028 | −24.327 | 18.11 | O |
| ATOM | 4561 | N | CYS | B1319 | −42.999 | −41.776 | −23.414 | 14.19 | N |
| ATOM | 4562 | CA | CYS | B1319 | −42.924 | −40.434 | −23.935 | 14.09 | C |
| ATOM | 4563 | CB | CYS | B1319 | −41.718 | −39.695 | −23.331 | 14.7 | C |
| ATOM | 4564 | SG | CYS | B1319 | −41.84 | −39.372 | −21.566 | 11.89 | S |
| ATOM | 4565 | C | CYS | B1319 | −42.792 | −40.447 | −25.456 | 13.72 | C |
| ATOM | 4566 | O | CYS | B1319 | −43.091 | −39.457 | −26.064 | 13.34 | O |
| ATOM | 4567 | N | TRP | B1320 | −42.324 | −41.566 | −26.028 | 13.62 | N |
| ATOM | 4568 | CA | TRP | B1320 | −41.978 | −41.687 | −27.437 | 14.07 | C |
| ATOM | 4569 | CB | TRP | B1320 | −40.553 | −42.252 | −27.636 | 11.41 | C |
| ATOM | 4570 | CG | TRP | B1320 | −39.484 | −41.481 | −26.985 | 11.53 | C |
| ATOM | 4571 | CD2 | TRP | B1320 | −38.262 | −42.01 | −26.378 | 15.7 | C |
| ATOM | 4572 | CE2 | TRP | B1320 | −37.53 | −40.897 | −25.884 | 13.52 | C |
| ATOM | 4573 | CE3 | TRP | B1320 | −37.735 | −43.317 | −26.194 | 8.48 | C |

TABLE 1A-continued

| | | | | | | | | |
|---|---|---|---|---|---|---|---|---|
| ATOM | 4574 | CD1 | TRP | B1320 | −39.384 | −40.132 | −26.883 | 10.51 | C |
| ATOM | 4575 | NE1 | TRP | B1320 | −38.257 | −39.769 | −26.169 | 9.79 | N |
| ATOM | 4576 | CZ2 | TRP | B1320 | −36.315 | −41.053 | −25.226 | 11.01 | C |
| ATOM | 4577 | CZ3 | TRP | B1320 | −36.609 | −43.469 | −25.541 | 8.17 | C |
| ATOM | 4578 | CH2 | TRP | B1320 | −35.888 | −42.337 | −25.043 | 12.57 | C |
| ATOM | 4579 | C | TRP | B1320 | −42.987 | −42.565 | −28.133 | 15.9 | C |
| ATOM | 4580 | O | TRP | B1320 | −42.714 | −43.143 | −29.198 | 16.2 | O |
| ATOM | 4581 | N | HIS | B1321 | −44.173 | −42.685 | −27.532 | 17.08 | N |
| ATOM | 4582 | CA | HIS | B1321 | −45.261 | −43.363 | −28.185 | 15.92 | C |
| ATOM | 4583 | CB | HIS | B1321 | −46.5 | −43.344 | −27.347 | 14.2 | C |
| ATOM | 4584 | CG | HIS | B1321 | −47.434 | −44.45 | −27.703 | 19.14 | C |
| ATOM | 4585 | CD2 | HIS | B1321 | −47.608 | −45.684 | −27.166 | 22.36 | C |
| ATOM | 4586 | ND1 | HIS | B1321 | −48.269 | −44.394 | −28.79 | 26.22 | N |
| ATOM | 4587 | CE1 | HIS | B1321 | −48.952 | −45.526 | −28.89 | 24.74 | C |
| ATOM | 4588 | NE2 | HIS | B1321 | −48.567 | −46.322 | −27.911 | 23.76 | N |
| ATOM | 4589 | C | HIS | B1321 | −45.551 | −42.714 | −29.528 | 16.58 | C |
| ATOM | 4590 | O | HIS | B1321 | −45.591 | −41.478 | −29.617 | 18.29 | O |
| ATOM | 4591 | N | PRO | B1322 | −45.786 | −43.53 | −30.577 | 16.64 | N |
| ATOM | 4592 | CD | PRO | B1322 | −45.701 | −45.007 | −30.548 | 16.05 | C |
| ATOM | 4593 | CA | PRO | B1322 | −46.182 | −43.061 | −31.892 | 16.76 | C |
| ATOM | 4594 | CB | PRO | B1322 | −46.609 | −44.369 | −32.58 | 17.01 | C |
| ATOM | 4595 | CG | PRO | B1322 | −45.74 | −45.372 | −31.976 | 14.36 | C |
| ATOM | 4596 | C | PRO | B1322 | −47.376 | −42.105 | −31.842 | 17.71 | C |
| ATOM | 4597 | O | PRO | B1322 | −47.397 | −41.119 | −32.583 | 16.57 | O |
| ATOM | 4598 | N | LYS | B1323 | −48.366 | −42.426 | −30.988 | 18.6 | N |
| ATOM | 4599 | CA | LYS | B1323 | −49.609 | −41.605 | −30.857 | 20.46 | C |
| ATOM | 4600 | CB | LYS | B1323 | −50.852 | −42.449 | −30.599 | 20.9 | C |
| ATOM | 4601 | CG | LYS | B1323 | −50.822 | −43.817 | −31.131 | 26.18 | C |
| ATOM | 4602 | CD | LYS | B1323 | −51.711 | −43.993 | −32.377 | 33.01 | C |
| ATOM | 4603 | CE | LYS | B1323 | −52.13 | −45.519 | −32.59 | 36.06 | C |
| ATOM | 4604 | NZ | LYS | B1323 | −52.282 | −45.886 | −34.085 | 37.09 | N |
| ATOM | 4605 | C | LYS | B1323 | −49.494 | −40.621 | −29.71 | 19 | C |
| ATOM | 4606 | O | LYS | B1323 | −49.409 | −41.013 | −28.554 | 17.22 | O |
| ATOM | 4607 | N | ALA | B1324 | −49.491 | −39.356 | −30.06 | 19.16 | N |
| ATOM | 4608 | CA | ALA | B1324 | −49.339 | −38.265 | −29.085 | 20.18 | C |
| ATOM | 4609 | CB | ALA | B1324 | −49.562 | −36.911 | −29.773 | 19.6 | C |
| ATOM | 4610 | C | ALA | B1324 | −50.25 | −38.408 | −27.868 | 20.98 | C |
| ATOM | 4611 | O | ALA | B1324 | −49.836 | −38.189 | −26.728 | 21.38 | O |
| ATOM | 4612 | N | GLU | B1325 | −51.495 | −38.801 | −28.113 | 22.65 | N |
| ATOM | 4613 | CA | GLU | B1325 | −52.46 | −38.931 | −27.031 | 24.7 | C |
| ATOM | 4614 | CB | GLU | B1325 | −53.939 | −38.946 | −27.489 | 25.28 | C |
| ATOM | 4615 | CG | GLU | B1325 | −54.193 | −38.902 | −28.924 | 30.62 | C |
| ATOM | 4616 | CD | GLU | B1325 | −53.75 | −40.2 | −29.585 | 36.79 | C |
| ATOM | 4617 | OE1 | GLU | B1325 | −53.291 | −40.133 | −30.771 | 36.59 | O |
| ATOM | 4618 | OE2 | GLU | B1325 | −53.846 | −41.257 | −28.888 | 38.64 | O |
| ATOM | 4619 | C | GLU | B1325 | −52.186 | −40.048 | −26.063 | 23.25 | C |
| ATOM | 4620 | O | GLU | B1325 | −52.792 | −40.066 | −24.997 | 24.62 | O |
| ATOM | 4621 | N | MET | B1326 | −51.276 | −40.945 | −26.409 | 22.92 | N |
| ATOM | 4622 | CA | MET | B1326 | −50.868 | −42.053 | −25.54 | 23.34 | C |
| ATOM | 4623 | CB | MET | B1326 | −50.321 | −43.185 | −26.382 | 24.62 | C |
| ATOM | 4624 | CG | MET | B1326 | −51.294 | −43.556 | −27.446 | 32.3 | C |
| ATOM | 4625 | SD | MET | B1326 | −52.808 | −44.354 | −26.742 | 38.17 | S |
| ATOM | 4626 | CE | MET | B1326 | −52.914 | −45.848 | −27.84 | 34.43 | C |
| ATOM | 4627 | C | MET | B1326 | −49.748 | −41.628 | −24.606 | 21.64 | C |
| ATOM | 4628 | O | MET | B1326 | −49.332 | −42.397 | −23.734 | 22.41 | O |
| ATOM | 4629 | N | ARG | B1327 | −49.245 | −40.425 | −24.821 | 18.28 | N |
| ATOM | 4630 | CA | ARG | B1327 | −48.081 | −39.982 | −24.146 | 16.16 | C |
| ATOM | 4631 | CB | ARG | B1327 | −47.379 | −38.925 | −24.998 | 14.09 | C |
| ATOM | 4632 | CG | ARG | B1327 | −46.835 | −39.546 | −26.213 | 13.42 | C |
| ATOM | 4633 | CD | ARG | B1327 | −45.957 | −38.589 | −26.997 | 13.18 | C |
| ATOM | 4634 | NE | ARG | B1327 | −45.905 | −39.079 | −28.352 | 11.83 | N |
| ATOM | 4635 | CZ | ARG | B1327 | −45.771 | −38.322 | −29.438 | 13.53 | C |
| ATOM | 4636 | NH1 | ARG | B1327 | −45.625 | −37.033 | −29.301 | 13.63 | N |
| ATOM | 4637 | NH2 | ARG | B1327 | −45.765 | −38.877 | −30.668 | 12.12 | N |
| ATOM | 4638 | C | ARG | B1327 | −48.55 | −39.447 | −22.818 | 15.22 | C |
| ATOM | 4639 | O | ARG | B1327 | −49.596 | −38.751 | −22.766 | 15.83 | O |
| ATOM | 4640 | N | PRO | B1328 | −47.788 | −39.734 | −21.739 | 14.57 | N |
| ATOM | 4641 | CD | PRO | B1328 | −46.543 | −40.522 | −21.631 | 15.56 | C |
| ATOM | 4642 | CA | PRO | B1328 | −48.155 | −39.17 | −20.447 | 14.81 | C |
| ATOM | 4643 | CB | PRO | B1328 | −47.009 | −39.646 | −19.526 | 14.49 | C |
| ATOM | 4644 | CG | PRO | B1328 | −45.89 | −39.938 | −20.437 | 14.09 | C |
| ATOM | 4645 | C | PRO | B1328 | −48.168 | −37.63 | −20.504 | 14.44 | C |
| ATOM | 4646 | O | PRO | B1328 | −47.362 | −37.037 | −21.186 | 14.21 | O |
| ATOM | 4647 | N | SER | B1329 | −49.061 | −37.013 | −19.76 | 15.23 | N |
| ATOM | 4648 | CA | SER | B1329 | −49.065 | −35.577 | −19.489 | 15.32 | C |
| ATOM | 4649 | CB | SER | B1329 | −50.377 | −35.136 | −18.769 | 16.24 | C |
| ATOM | 4650 | OG | SER | B1329 | −50.475 | −35.595 | −17.432 | 17.82 | O |
| ATOM | 4651 | C | SER | B1329 | −47.953 | −35.272 | −18.598 | 14.45 | C |
| ATOM | 4652 | O | SER | B1329 | −47.386 | −36.189 | −17.96 | 15.18 | O |
| ATOM | 4653 | N | PHE | B1330 | −47.618 | −33.985 | −18.5 | 15.11 | N |

TABLE 1A-continued

| | | | | | | | | |
|---|---|---|---|---|---|---|---|---|
| ATOM | 4654 | CA | PHE | B1330 | −46.528 | −33.582 | −17.536 | 13.94 | C |
| ATOM | 4655 | CB | PHE | B1330 | −46.061 | −32.16 | −17.801 | 12.57 | C |
| ATOM | 4656 | CG | PHE | B1330 | −45.132 | −32.059 | −18.976 | 7.65 | C |
| ATOM | 4657 | CD1 | PHE | B1330 | −43.828 | −32.576 | −18.882 | 5.76 | C |
| ATOM | 4658 | CD2 | PHE | B1330 | −45.551 | −31.446 | −20.148 | 3.23 | C |
| ATOM | 4659 | CE1 | PHE | B1330 | −42.976 | −32.543 | −19.978 | 9.3 | C |
| ATOM | 4660 | CE2 | PHE | B1330 | −44.681 | −31.378 | −21.294 | 5.74 | C |
| ATOM | 4661 | CZ | PHE | B1330 | −43.408 | −31.926 | −21.219 | 6.8 | C |
| ATOM | 4662 | C | PHE | B1330 | −46.793 | −33.884 | −16.06 | 14.54 | C |
| ATOM | 4663 | O | PHE | B1330 | −45.891 | −34.202 | −15.333 | 14.93 | O |
| ATOM | 4664 | N | SER | B1331 | −48.054 | −33.866 | −15.675 | 16.48 | N |
| ATOM | 4665 | CA | SER | B1331 | −48.5 | −34.249 | −14.339 | 18.67 | C |
| ATOM | 4666 | CB | SER | B1331 | −50.03 | −34.095 | −14.237 | 19.21 | C |
| ATOM | 4667 | OG | SER | B1331 | −50.368 | −32.723 | −14.292 | 22.71 | O |
| ATOM | 4668 | C | SER | B1331 | −48.175 | −35.696 | −14.026 | 19.57 | C |
| ATOM | 4669 | O | SER | B1331 | −47.687 | −35.99 | −12.934 | 20.05 | O |
| ATOM | 4670 | N | GLU | B1332 | −48.47 | −36.604 | −14.96 | 19.67 | N |
| ATOM | 4671 | CA | GLU | B1332 | −48.151 | −38.023 | −14.72 | 20.35 | C |
| ATOM | 4672 | CB | GLU | B1332 | −48.712 | −38.922 | −15.844 | 21.1 | C |
| ATOM | 4673 | CG | GLU | B1332 | −49.989 | −38.333 | −16.37 | 25.88 | C |
| ATOM | 4674 | CD | GLU | B1332 | −50.609 | −39.105 | −17.505 | 32.07 | C |
| ATOM | 4675 | OE1 | GLU | B1332 | −50.996 | −40.266 | −17.25 | 37.09 | O |
| ATOM | 4676 | OE2 | GLU | B1332 | −50.743 | −38.557 | −18.626 | 29.37 | O |
| ATOM | 4677 | C | GLU | B1332 | −46.666 | −38.179 | −14.629 | 17.39 | C |
| ATOM | 4678 | O | GLU | B1332 | −46.157 | −38.872 | −13.803 | 18.56 | O |
| ATOM | 4679 | N | LEU | B1333 | −45.962 | −37.512 | −15.49 | 17.55 | N |
| ATOM | 4680 | CA | LEU | B1333 | −44.492 | −37.546 | −15.487 | 17 | C |
| ATOM | 4681 | CB | LEU | B1333 | −43.952 | −36.584 | −16.542 | 16.13 | C |
| ATOM | 4682 | CG | LEU | B1333 | −43.485 | −37.135 | −17.893 | 16.66 | C |
| ATOM | 4683 | CD1 | LEU | B1333 | −43.469 | −38.652 | −18.04 | 11.84 | C |
| ATOM | 4684 | CD2 | LEU | B1333 | −44.25 | −36.425 | −18.993 | 15.31 | C |
| ATOM | 4685 | C | LEU | B1333 | −43.949 | −37.147 | −14.136 | 17.56 | C |
| ATOM | 4686 | O | LEU | B1333 | −43.079 | −37.842 | −13.573 | 17.14 | O |
| ATOM | 4687 | N | VAL | B1334 | −44.455 | −36.034 | −13.593 | 17.51 | N |
| ATOM | 4688 | CA | VAL | B1334 | −43.955 | −35.678 | −12.272 | 18.47 | C |
| ATOM | 4689 | CB | VAL | B1334 | −44.143 | −34.153 | −11.829 | 18.11 | C |
| ATOM | 4690 | CG1 | VAL | B1334 | −44.442 | −33.243 | −13.018 | 14.01 | C |
| ATOM | 4691 | CG2 | VAL | B1334 | −45.126 | −34.083 | −10.693 | 15.6 | C |
| ATOM | 4692 | C | VAL | B1334 | −44.396 | −36.63 | −11.139 | 19.77 | C |
| ATOM | 4693 | O | VAL | B1334 | −43.644 | −36.832 | −10.142 | 19.19 | O |
| ATOM | 4694 | N | SER | B1335 | −45.588 | −37.22 | −11.291 | 19.42 | N |
| ATOM | 4695 | CA | SER | B1335 | −45.993 | −38.174 | −10.308 | 20.01 | C |
| ATOM | 4696 | CB | SER | B1335 | −47.422 | −38.604 | −10.5 | 19.55 | C |
| ATOM | 4697 | OG | SER | B1335 | −48.127 | −37.893 | −9.525 | 24.31 | O |
| ATOM | 4698 | C | SER | B1335 | −45.084 | −39.35 | −10.397 | 20.57 | C |
| ATOM | 4699 | O | SER | B1335 | −44.477 | −39.799 | −9.382 | 22.6 | O |
| ATOM | 4700 | N | ARG | B1336 | −44.932 | −39.81 | −11.615 | 19.14 | N |
| ATOM | 4701 | CA | ARG | B1336 | −44.274 | −41.073 | −11.816 | 20.87 | C |
| ATOM | 4702 | CB | ARG | B1336 | −44.554 | −41.564 | −13.257 | 21.65 | C |
| ATOM | 4703 | CG | ARG | B1336 | −43.906 | −42.881 | −13.563 | 25.26 | C |
| ATOM | 4704 | CD | ARG | B1336 | −44.784 | −44.042 | −13.136 | 30.89 | C |
| ATOM | 4705 | NE | ARG | B1336 | −43.944 | −45.064 | −12.524 | 34.5 | N |
| ATOM | 4706 | CZ | ARG | B1336 | −44.048 | −45.462 | −11.251 | 37.83 | C |
| ATOM | 4707 | NH1 | ARG | B1336 | −43.176 | −46.392 | −10.831 | 34.4 | N |
| ATOM | 4708 | NH2 | ARG | B1336 | −45.001 | −44.926 | −10.416 | 33 | N |
| ATOM | 4709 | C | ARG | B1336 | −42.772 | −40.978 | −11.488 | 19.91 | C |
| ATOM | 4710 | O | ARG | B1336 | −42.178 | −41.918 | −10.906 | 20.62 | O |
| ATOM | 4711 | N | ILE | B1337 | −42.183 | −39.828 | −11.823 | 17.75 | N |
| ATOM | 4712 | CA | ILE | B1337 | −40.813 | −39.639 | −11.58 | 17.06 | C |
| ATOM | 4713 | CB | ILE | B1337 | −40.183 | −38.583 | −12.531 | 17.62 | C |
| ATOM | 4714 | CG2 | ILE | B1337 | −38.69 | −38.364 | −12.157 | 16.92 | C |
| ATOM | 4715 | CG1 | ILE | B1337 | −40.247 | −39.011 | −14.001 | 16.78 | C |
| ATOM | 4716 | CD1 | ILE | B1337 | −40.004 | −37.848 | −15.033 | 17.27 | C |
| ATOM | 4717 | C | ILE | B1337 | −40.514 | −39.39 | −10.072 | 17.05 | C |
| ATOM | 4718 | O | ILE | B1337 | −39.44 | −39.766 | −9.582 | 16.58 | O |
| ATOM | 4719 | N | SER | B1338 | −41.446 | −38.791 | −9.323 | 17.74 | N |
| ATOM | 4720 | CA | SER | B1338 | −41.214 | −38.622 | −7.839 | 19.11 | C |
| ATOM | 4721 | CB | SER | B1338 | −42.322 | −37.796 | −7.116 | 18.77 | C |
| ATOM | 4722 | OG | SER | B1338 | −42.68 | −36.632 | −7.87 | 21.59 | O |
| ATOM | 4723 | C | SER | B1338 | −41.086 | −39.958 | −7.155 | 17.75 | C |
| ATOM | 4724 | O | SER | B1338 | −40.175 | −40.172 | −6.406 | 18.2 | O |
| ATOM | 4725 | N | ALA | B1339 | −42.03 | −40.827 | −7.479 | 18.2 | N |
| ATOM | 4726 | CA | ALA | B1339 | −42.127 | −42.207 | −7.068 | 17.95 | C |
| ATOM | 4727 | CB | ALA | B1339 | −43.227 | −42.836 | −7.861 | 16.27 | C |
| ATOM | 4728 | C | ALA | B1339 | −40.84 | −42.941 | −7.32 | 19.39 | C |
| ATOM | 4729 | O | ALA | B1339 | −40.314 | −43.655 | −6.409 | 21.18 | O |
| ATOM | 4730 | N | ILE | B1340 | −40.301 | −42.781 | −8.552 | 20.07 | N |
| ATOM | 4731 | CA | ILE | B1340 | −39.065 | −43.48 | −8.95 | 17.93 | C |
| ATOM | 4732 | CB | ILE | B1340 | −38.853 | −43.383 | −10.432 | 17.93 | C |
| ATOM | 4733 | CG2 | ILE | B1340 | −37.443 | −43.926 | −10.849 | 16.49 | C |

TABLE 1A-continued

| ATOM | 4734 | CG1 | ILE | B1340 | −39.964 | −44.074 | −11.175 | 17.37 | C |
|---|---|---|---|---|---|---|---|---|---|
| ATOM | 4735 | CD1 | ILE | B1340 | −39.847 | −44.016 | −12.777 | 16.33 | C |
| ATOM | 4736 | C | ILE | B1340 | −37.884 | −42.87 | −8.179 | 18.75 | C |
| ATOM | 4737 | O | ILE | B1340 | −36.949 | −43.573 | −7.793 | 17.26 | O |
| ATOM | 4738 | N | PHE | B1341 | −37.965 | −41.545 | −7.969 | 20.47 | N |
| ATOM | 4739 | CA | PHE | B1341 | −36.935 | −40.757 | −7.283 | 20.98 | C |
| ATOM | 4740 | CB | PHE | B1341 | −37.206 | −39.264 | −7.419 | 19.62 | C |
| ATOM | 4741 | CG | PHE | B1341 | −36.215 | −38.396 | −6.69 | 17.4 | C |
| ATOM | 4742 | CD1 | PHE | B1341 | −34.924 | −38.216 | −7.209 | 18.52 | C |
| ATOM | 4743 | CD2 | PHE | B1341 | −36.562 | −37.789 | −5.463 | 15.18 | C |
| ATOM | 4744 | CE1 | PHE | B1341 | −33.962 | −37.381 | −6.529 | 22.53 | C |
| ATOM | 4745 | CE2 | PHE | B1341 | −35.657 | −36.973 | −4.732 | 19.9 | C |
| ATOM | 4746 | CZ | PHE | B1341 | −34.31 | −36.737 | −5.272 | 21.72 | C |
| ATOM | 4747 | C | PHE | B1341 | −36.898 | −41.127 | −5.827 | 23.05 | C |
| ATOM | 4748 | O | PHE | B1341 | −35.809 | −41.317 | −5.277 | 23.42 | O |
| ATOM | 4749 | N | SER | B1342 | −38.062 | −41.212 | −5.201 | 25.6 | N |
| ATOM | 4750 | CA | SER | B1342 | −38.149 | −41.713 | −3.819 | 31.43 | C |
| ATOM | 4751 | CB | SER | B1342 | −39.567 | −41.807 | −3.363 | 31.39 | C |
| ATOM | 4752 | OG | SER | B1342 | −39.717 | −40.757 | −2.434 | 36.05 | O |
| ATOM | 4753 | C | SER | B1342 | −37.516 | −43.06 | −3.501 | 34.23 | C |
| ATOM | 4754 | O | SER | B1342 | −36.693 | −43.154 | −2.57 | 35.16 | O |
| ATOM | 4755 | N | THR | B1343 | −37.901 | −44.101 | −4.257 | 36.83 | N |
| ATOM | 4756 | CA | THR | B1343 | −37.229 | −45.397 | −4.165 | 38.38 | C |
| ATOM | 4757 | CB | THR | B1343 | −37.554 | −46.287 | −5.308 | 38.54 | C |
| ATOM | 4758 | OG1 | THR | B1343 | −36.597 | −46.025 | −6.353 | 38.96 | O |
| ATOM | 4759 | CG2 | THR | B1343 | −38.995 | −46.003 | −5.763 | 37.89 | C |
| ATOM | 4760 | C | THR | B1343 | −35.742 | −45.266 | −4.224 | 39.74 | C |
| ATOM | 4761 | O | THR | B1343 | −35.032 | −46.224 | −3.938 | 41.03 | O |
| ATOM | 4762 | N | PHE | B1344 | −35.233 | −44.1 | −4.58 | 41.26 | N |
| ATOM | 4763 | CA | PHE | B1344 | −33.799 | −44.038 | −4.73 | 42.8 | C |
| ATOM | 4764 | CB | PHE | B1344 | −33.345 | −43.216 | −5.903 | 41.57 | C |
| ATOM | 4765 | CG | PHE | B1344 | −32.811 | −44.036 | −6.983 | 38.68 | C |
| ATOM | 4766 | CD1 | PHE | B1344 | −33.674 | −44.636 | −7.897 | 39.26 | C |
| ATOM | 4767 | CD2 | PHE | B1344 | −31.458 | −44.289 | −7.056 | 35.03 | C |
| ATOM | 4768 | CE1 | PHE | B1344 | −33.166 | −45.431 | −8.921 | 37.52 | C |
| ATOM | 4769 | CE2 | PHE | B1344 | −30.932 | −45.052 | −8.046 | 33.41 | C |
| ATOM | 4770 | CZ | PHE | B1344 | −31.769 | −45.642 | −8.984 | 38.56 | C |
| ATOM | 4771 | C | PHE | B1344 | −32.936 | −43.789 | −3.544 | 45.59 | C |
| ATOM | 4772 | O | PHE | B1344 | −33.206 | −42.962 | −2.646 | 45.42 | O |
| ATOM | 4773 | N | ILE | B1345 | −31.827 | −44.505 | −3.656 | 49.05 | N |
| ATOM | 4774 | CA | ILE | B1345 | −30.833 | −44.778 | −2.628 | 51.82 | C |
| ATOM | 4775 | CB | ILE | B1345 | −31.443 | −44.651 | −1.138 | 52.15 | C |
| ATOM | 4776 | CG2 | ILE | B1345 | −32.243 | −45.949 | −0.677 | 53.65 | C |
| ATOM | 4777 | CG1 | ILE | B1345 | −30.429 | −44.02 | −0.126 | 52.44 | C |
| ATOM | 4778 | CD1 | ILE | B1345 | −29.161 | −44.876 | 0.167 | 49.33 | C |
| ATOM | 4779 | C | ILE | B1345 | −30.383 | −46.197 | −3.124 | 53.09 | C |
| ATOM | 4780 | O | ILE | B1345 | −29.175 | −46.436 | −3.442 | 53.28 | O |
| ATOM | 4781 | N | GLY | B1346 | −31.38 | −47.09 | −3.271 | 53.8 | N |
| ATOM | 4782 | CA | GLY | B1346 | −31.227 | −48.359 | −3.998 | 54.24 | C |
| ATOM | 4783 | C | GLY | B1346 | −32.269 | −48.514 | −5.109 | 54.24 | C |
| ATOM | 4784 | O | GLY | B1346 | −32.572 | −47.603 | −5.915 | 53.17 | O |
| ATOM | 4785 | OXT | GLY | B1346 | −32.842 | −49.608 | −5.198 | 54.15 | O |
| ATOM | 4786 | C18 | M97 | C1 | −6.757 | 10.413 | 1.931 | 13.34 | C |
| ATOM | 4787 | C17 | M97 | C1 | −6.821 | 11.541 | 2.986 | 11.83 | C |
| ATOM | 4788 | C16 | M97 | C1 | −5.784 | 12.663 | 2.878 | 15.81 | C |
| ATOM | 4789 | C15 | M97 | C1 | −5.684 | 13.145 | 1.409 | 17.14 | C |
| ATOM | 4790 | C23 | M97 | C1 | −5.215 | 14.43 | 1.015 | 15.54 | C |
| ATOM | 4791 | C22 | M97 | C1 | −5.141 | 14.811 | −0.321 | 12.44 | C |
| ATOM | 4792 | C21 | M97 | C1 | −5.545 | 13.904 | −1.323 | 14.75 | C |
| ATOM | 4793 | C20 | M97 | C1 | −6.025 | 12.648 | −0.947 | 16.78 | C |
| ATOM | 4794 | C19 | M97 | C1 | −6.1 | 12.29 | 0.385 | 17.2 | C |
| ATOM | 4795 | N3 | M97 | C1 | −6.631 | 10.999 | 0.557 | 13.75 | N |
| ATOM | 4796 | C3 | M97 | C1 | −6.844 | 10.562 | −0.666 | 13.83 | C |
| ATOM | 4797 | C2 | M97 | C1 | −6.514 | 11.51 | −1.566 | 17.04 | C |
| ATOM | 4798 | C6 | M97 | C1 | −6.692 | 11.372 | −3.093 | 13.93 | C |
| ATOM | 4799 | C8 | M97 | C1 | −5.475 | 11.814 | −3.914 | 12.39 | C |
| ATOM | 4800 | O2 | M97 | C1 | −4.314 | 11.482 | −3.73 | 11.64 | O |
| ATOM | 4801 | N2 | M97 | C1 | −5.811 | 12.562 | −4.949 | 13.09 | N |
| ATOM | 4802 | C7 | M97 | C1 | −7.135 | 12.751 | −4.996 | 13.15 | C |
| ATOM | 4803 | O1 | M97 | C1 | −7.643 | 13.406 | −5.899 | 12.05 | O |
| ATOM | 4804 | C1 | M97 | C1 | −7.819 | 12.181 | −3.728 | 14.16 | C |
| ATOM | 4805 | C4 | M97 | C1 | −9.155 | 11.566 | −3.893 | 16.46 | C |
| ATOM | 4806 | C10 | M97 | C1 | −10.106 | 11.501 | −2.902 | 16.63 | C |
| ATOM | 4807 | C11 | M97 | C1 | −10.181 | 11.877 | −1.578 | 21.54 | C |
| ATOM | 4808 | C12 | M97 | C1 | −11.335 | 11.655 | −0.794 | 16.81 | C |
| ATOM | 4809 | C13 | M97 | C1 | −12.39 | 11.019 | −1.396 | 15.57 | C |
| ATOM | 4810 | C14 | M97 | C1 | −12.336 | 10.641 | −2.722 | 16.22 | C |
| ATOM | 4811 | C9 | M97 | C1 | −11.197 | 10.875 | −3.485 | 17.96 | C |
| ATOM | 4812 | N1 | M97 | C1 | −10.896 | 10.615 | −4.784 | 18.43 | N |
| ATOM | 4813 | C5 | M97 | C1 | −9.655 | 11.061 | −5.036 | 19.08 | C |

TABLE 1A-continued

| | | | | | | | | | |
|---|---|---|---|---|---|---|---|---|---|
| ATOM | 4814 | C18 | M97 | D1 | −27.796 | −19.375 | −23.523 | 24.48 | C |
| ATOM | 4815 | C17 | M97 | D1 | −27.404 | −18.301 | −24.565 | 25.28 | C |
| ATOM | 4816 | C16 | M97 | D1 | −28.222 | −17.006 | −24.512 | 22.55 | C |
| ATOM | 4817 | C15 | M97 | D1 | −28.24 | −16.516 | −23.076 | 22.61 | C |
| ATOM | 4818 | C23 | M97 | D1 | −28.488 | −15.163 | −22.754 | 23.09 | C |
| ATOM | 4819 | C22 | M97 | D1 | −28.498 | −14.791 | −21.391 | 24.77 | C |
| ATOM | 4820 | C21 | M97 | D1 | −28.295 | −15.729 | −20.363 | 22.55 | C |
| ATOM | 4821 | C20 | M97 | D1 | −28.099 | −17.062 | −20.721 | 19.7 | C |
| ATOM | 4822 | C19 | M97 | D1 | −28.082 | −17.41 | −22.029 | 19.61 | C |
| ATOM | 4823 | N3 | M97 | D1 | −27.855 | −18.769 | −22.162 | 22.53 | N |
| ATOM | 4824 | C3 | M97 | D1 | −27.736 | −19.275 | −20.961 | 22.1 | C |
| ATOM | 4825 | C2 | M97 | D1 | −27.884 | −18.269 | −20.099 | 21.74 | C |
| ATOM | 4826 | C6 | M97 | D1 | −27.783 | −18.535 | −18.611 | 22.97 | C |
| ATOM | 4827 | C8 | M97 | D1 | −28.6 | −17.631 | −17.729 | 21.97 | C |
| ATOM | 4828 | O2 | M97 | D1 | −29.818 | −17.491 | −17.8 | 24.31 | O |
| ATOM | 4829 | N2 | M97 | D1 | −27.842 | −17.074 | −16.78 | 24.76 | N |
| ATOM | 4830 | C7 | M97 | D1 | −26.556 | −17.369 | −16.9 | 22.86 | C |
| ATOM | 4831 | O1 | M97 | D1 | −25.701 | −16.934 | −16.141 | 24.63 | O |
| ATOM | 4832 | C1 | M97 | D1 | −26.415 | −18.195 | −18.118 | 26.09 | C |
| ATOM | 4833 | C4 | M97 | D1 | −25.204 | −18.618 | −18.914 | 28.08 | C |
| ATOM | 4834 | C10 | M97 | D1 | −24.147 | −19.415 | −18.721 | 27.23 | C |
| ATOM | 4835 | C11 | M97 | D1 | −23.744 | −20.094 | −17.651 | 29.15 | C |
| ATOM | 4836 | C12 | M97 | D1 | −22.572 | −20.813 | −17.843 | 30.82 | C |
| ATOM | 4837 | C13 | M97 | D1 | −21.838 | −20.791 | −19.03 | 29.97 | C |
| ATOM | 4838 | C14 | M97 | D1 | −22.247 | −20.076 | −20.127 | 28.69 | C |
| ATOM | 4839 | C9 | M97 | D1 | −23.408 | −19.39 | −19.928 | 30.21 | C |
| ATOM | 4840 | N1 | M97 | D1 | −24.007 | −18.618 | −20.831 | 32.6 | N |
| ATOM | 4841 | C5 | M97 | D1 | −25.078 | −18.18 | −20.181 | 33.7 | C |
| ATOM | 4842 | O | HOH | F1 | −29.32 | −45.647 | −32.002 | 16.53 | O |
| ATOM | 4843 | O | HOH | F5 | 6.241 | −1.313 | 7.848 | 9.44 | O |
| ATOM | 4844 | O | HOH | F6 | 9.31 | −0.294 | −12.45 | 10.96 | O |
| ATOM | 4845 | O | HOH | F8 | −0.518 | −17.255 | −13.443 | 12.19 | O |
| ATOM | 4846 | O | HOH | F11 | −41.781 | −18.635 | −8.479 | 18.73 | O |
| ATOM | 4847 | O | HOH | F13 | −7.464 | −2.012 | 15.403 | 16.58 | O |
| ATOM | 4848 | O | HOH | F15 | 14.609 | −0.995 | 6.201 | 11.01 | O |
| ATOM | 4849 | O | HOH | F16 | 8.312 | 34.844 | 14.609 | 21.07 | O |
| ATOM | 4850 | O | HOH | F17 | 3.508 | 8.749 | −10.788 | 15.51 | O |
| ATOM | 4851 | O | HOH | F18 | 14.725 | −4.454 | 5.272 | 30.25 | O |
| ATOM | 4852 | O | HOH | F19 | −13.905 | −9.795 | −22.444 | 15.68 | O |
| ATOM | 4853 | O | HOH | F21 | −42.866 | −29.624 | −28.883 | 28.13 | O |
| ATOM | 4854 | O | HOH | F22 | −26.774 | −0.392 | −19.528 | 11.42 | O |
| ATOM | 4855 | O | HOH | F23 | −11.848 | −12.69 | −13.164 | 37.75 | O |
| ATOM | 4856 | O | HOH | F24 | 4.702 | −18.668 | −5.903 | 19.11 | O |
| ATOM | 4857 | O | HOH | F25 | −33.344 | −32.268 | −6.818 | 31.15 | O |
| ATOM | 4858 | O | HOH | F26 | −25.708 | −43.353 | −8.875 | 20.32 | O |
| ATOM | 4859 | O | HOH | F29 | −45.908 | −39.581 | −34.22 | 19.74 | O |
| ATOM | 4860 | O | HOH | F30 | −30.706 | −12.15 | −30.792 | 11.84 | O |
| ATOM | 4861 | O | HOH | F31 | −33.571 | −22.557 | −28.722 | 29.36 | O |
| ATOM | 4862 | O | HOH | F33 | −50.609 | −28.235 | −27.266 | 30.52 | O |
| ATOM | 4863 | O | HOH | F34 | −27.54 | −39.356 | −4.277 | 23.05 | O |
| ATOM | 4864 | O | HOH | F38 | −16.68 | −38.138 | −14.134 | 19.08 | O |
| ATOM | 4865 | O | HOH | F41 | −8.258 | −22.143 | −2.471 | 21.09 | O |
| ATOM | 4866 | O | HOH | F42 | −6.61 | −0.884 | 3.132 | 4.31 | O |
| ATOM | 4867 | O | HOH | F43 | −37.744 | −19.121 | −10.97 | 9.19 | O |
| ATOM | 4868 | O | HOH | F44 | −13.126 | 9.645 | −6.048 | 28.15 | O |
| ATOM | 4869 | O | HOH | F47 | −20.145 | −18.005 | −8.987 | 50.58 | O |
| ATOM | 4870 | O | HOH | F48 | 10.711 | 2.092 | 12.972 | 21.72 | O |
| ATOM | 4871 | O | HOH | F49 | −36.132 | −38.07 | −31.151 | 6.14 | O |
| ATOM | 4872 | O | HOH | F51 | −35.488 | −29.638 | −28.278 | 11.04 | O |
| ATOM | 4873 | O | HOH | F52 | 14.842 | −11.981 | 10.718 | 30.87 | O |
| ATOM | 4874 | O | HOH | F55 | −35.382 | −49.541 | −30.387 | 26.91 | O |
| ATOM | 4875 | O | HOH | F56 | −11.404 | −13.613 | 12.021 | 10.79 | O |
| ATOM | 4876 | O | HOH | F59 | 0.123 | −4.338 | −14.067 | 16.42 | O |
| ATOM | 4877 | O | HOH | F61 | 2.695 | 29 | −0.436 | 14.27 | O |
| ATOM | 4878 | O | HOH | F63 | −17.953 | −3.003 | −15.671 | 12.17 | O |
| ATOM | 4879 | O | HOH | F65 | −36.272 | −14.628 | −12.624 | 12.14 | O |
| ATOM | 4880 | O | HOH | F66 | −37.039 | −52.238 | −39.018 | 10.87 | O |
| ATOM | 4881 | O | HOH | F68 | −1.256 | −13.25 | 7.793 | 7.61 | O |
| ATOM | 4882 | O | HOH | F69 | 13.93 | −6.17 | 1.302 | 7.23 | O |
| ATOM | 4883 | O | HOH | F74 | −21.281 | −26.8 | −15.829 | 36.75 | O |
| ATOM | 4884 | O | HOH | F75 | −8.945 | −12.697 | −14.696 | 15.11 | O |
| ATOM | 4885 | O | HOH | F78 | −41.02 | −15.364 | −18.372 | 32.16 | O |
| ATOM | 4886 | O | HOH | F79 | 2.29 | 10.714 | −1.259 | 16.47 | O |
| ATOM | 4887 | O | HOH | F80 | −48.619 | −49.393 | −27.169 | 27.17 | O |
| ATOM | 4888 | O | HOH | F81 | −49.904 | −38.791 | −33.25 | 27.2 | O |
| ATOM | 4889 | O | HOH | F82 | −13.586 | −12.029 | −4.742 | 30.12 | O |
| ATOM | 4890 | O | HOH | F84 | 15.912 | −6.318 | −3.476 | 24.03 | O |
| ATOM | 4891 | O | HOH | F86 | −8.824 | 20.746 | 3.879 | 17.29 | O |
| ATOM | 4892 | O | HOH | F87 | −0.697 | −8.031 | 11.805 | 9.36 | O |
| ATOM | 4893 | O | HOH | F89 | −48.633 | −6.161 | −17.326 | 10.19 | O |

TABLE 1A-continued

| ATOM | 4894 | O | HOH | F90 | −42.9 | −45.555 | −34.406 | 17.72 | O |
|---|---|---|---|---|---|---|---|---|---|
| ATOM | 4895 | O | HOH | F92 | 11.987 | −1.35 | 20.511 | 35.19 | O |
| ATOM | 4896 | O | HOH | F93 | −28.968 | −46.992 | −11.157 | 38.03 | O |
| ATOM | 4897 | O | HOH | F94 | 19.165 | 5.56 | −3.202 | 13.7 | O |
| ATOM | 4898 | O | HOH | F95 | −10.566 | −5.79 | −17.051 | 15.61 | O |
| ATOM | 4899 | O | HOH | F98 | −36.062 | −17.343 | −13.063 | 5.49 | O |
| ATOM | 4900 | O | HOH | F99 | −32.503 | −51.224 | −24.017 | 10.16 | O |
| ATOM | 4901 | O | HOH | F103 | 9.945 | 0.105 | 2.08 | 15.57 | O |
| ATOM | 4902 | O | HOH | F106 | 4.418 | −17.639 | 13.148 | 16.93 | O |
| ATOM | 4903 | O | HOH | F107 | −45.986 | −2.509 | −16.086 | 15.03 | O |
| ATOM | 4904 | O | HOH | F109 | −2.683 | −19.25 | −13.776 | 28.45 | O |
| ATOM | 4905 | O | HOH | F110 | −4.254 | −4.332 | −13.533 | 18.93 | O |
| ATOM | 4906 | O | HOH | F111 | −11.1 | 6.177 | −16.231 | 25.82 | O |
| ATOM | 4907 | O | HOH | F113 | −27.258 | −24.151 | −30.7 | 14.97 | O |
| ATOM | 4908 | O | HOH | F118 | −11.233 | 12.9 | −14.378 | 51.8 | O |
| ATOM | 4909 | O | HOH | F119 | −40.043 | −29.384 | −26.812 | 7.78 | O |
| ATOM | 4910 | O | HOH | F122 | −27.638 | −41.749 | −41.794 | 20.81 | O |
| ATOM | 4911 | O | HOH | F123 | −37.295 | −51.413 | −19.137 | 29.17 | O |
| ATOM | 4912 | O | HOH | F127 | 12.353 | 29.785 | 0.805 | 34.63 | O |
| ATOM | 4913 | O | HOH | F132 | −46.845 | −25.3 | −34.335 | 18.55 | O |
| ATOM | 4914 | O | HOH | F133 | −10.658 | 24.394 | −8.533 | 13.92 | O |
| ATOM | 4915 | O | HOH | F135 | −27.625 | −23.545 | −23.649 | 23.5 | O |
| ATOM | 4916 | O | HOH | F139 | −7.482 | −18.693 | −10.139 | 26.8 | O |
| ATOM | 4917 | O | HOH | F140 | −37.308 | 3.619 | −35.119 | 10.72 | O |
| ATOM | 4918 | O | HOH | F141 | −9.487 | −12.65 | 7.885 | 27.37 | O |
| ATOM | 4919 | O | HOH | F147 | −14.473 | −15.515 | −13.357 | 28.23 | O |
| ATOM | 4920 | O | HOH | F151 | −49.253 | −31.734 | −19.766 | 12.77 | O |
| ATOM | 4921 | O | HOH | F152 | −33.874 | −21.649 | −26.009 | 35.39 | O |
| ATOM | 4922 | O | HOH | F160 | −27.074 | −43.992 | −33.171 | 26.02 | O |
| ATOM | 4923 | O | HOH | F162 | −1.216 | −8.886 | 9.489 | 6.68 | O |
| ATOM | 4924 | O | HOH | F163 | −8.684 | −9.212 | −17.193 | 20.8 | O |
| ATOM | 4925 | O | HOH | F164 | −24.704 | −27.369 | −24.384 | 23.89 | O |
| ATOM | 4926 | O | HOH | F165 | 10.661 | −0.274 | −9.633 | 19.75 | O |
| ATOM | 4927 | O | HOH | F167 | −39.405 | −17 | −10.792 | 13.52 | O |
| ATOM | 4928 | O | HOH | F171 | −19.563 | −0.808 | −17.608 | 25.97 | O |
| ATOM | 4929 | O | HOH | F175 | −1.316 | 6.842 | 6.302 | 30.22 | O |
| ATOM | 4930 | O | HOH | F181 | −23.672 | −36.748 | −6.006 | 33.39 | O |
| ATOM | 4931 | O | HOH | F187 | −19.483 | 18.366 | 1.47 | 18.85 | O |
| ATOM | 4932 | O | HOH | F191 | −20.833 | −30.336 | −23.71 | 17.88 | O |
| ATOM | 4933 | O | HOH | F192 | −23.256 | −24.86 | −6.405 | 25.34 | O |
| ATOM | 4934 | O | HOH | F195 | −27.943 | −43.121 | −7.194 | 24.93 | O |
| ATOM | 4935 | O | HOH | F196 | −9.437 | −4.406 | 3.163 | 32.85 | O |
| ATOM | 4936 | O | HOH | F199 | −14.351 | −15.223 | −16.592 | 35.52 | O |
| ATOM | 4937 | O | HOH | F201 | −28.051 | −20.14 | −37.061 | 2.96 | O |
| ATOM | 4938 | O | HOH | F204 | 13.399 | −2.13 | 13.08 | 38.46 | O |
| ATOM | 4939 | O | HOH | F206 | −0.623 | 6.957 | −15.231 | 43.14 | O |
| ATOM | 4940 | O | HOH | F209 | 3.949 | 29.41 | −7.507 | 9.37 | O |
| ATOM | 4941 | O | HOH | F214 | −4.368 | 13.84 | −12.583 | 17.62 | O |
| ATOM | 4942 | O | HOH | F216 | −38.765 | −22.875 | −29.099 | 25.73 | O |
| ATOM | 4943 | O | HOH | F220 | 4.401 | 7.618 | −0.759 | 21.38 | O |
| ATOM | 4944 | O | HOH | F224 | −46.22 | −27.713 | −23.131 | 21.06 | O |
| ATOM | 4945 | O | HOH | F232 | −17.824 | −0.269 | 1.213 | 29.39 | O |
| ATOM | 4946 | O | HOH | F234 | −41.265 | −32.211 | −31.685 | 23.51 | O |
| ATOM | 4947 | O | HOH | F236 | 14.698 | −0.179 | 1.827 | 20.96 | O |
| ATOM | 4948 | O | HOH | F238 | −16.579 | 11.275 | −2.474 | 28.52 | O |
| ATOM | 4949 | O | HOH | F239 | −36.288 | −36.794 | −42.538 | 29.54 | O |
| ATOM | 4950 | O | HOH | F243 | −28.661 | −43.161 | −29.758 | 16.75 | O |
| ATOM | 4951 | O | HOH | F244 | −36.382 | −42.158 | −29.189 | 16.52 | O |
| ATOM | 4952 | O | HOH | F245 | −8.091 | −23.484 | 0.658 | 15.9 | O |
| ATOM | 4953 | O | HOH | F256 | −47.173 | −21.426 | −26.921 | 17.64 | O |
| ATOM | 4954 | O | HOH | F264 | 10.977 | −5.747 | 10.557 | 16.36 | O |
| ATOM | 4955 | O | HOH | F267 | −36.06 | 1.427 | −13.036 | 40.7 | O |
| ATOM | 4956 | O | HOH | F268 | 11.515 | 6.152 | 5.718 | 11.46 | O |
| ATOM | 4957 | O | HOH | F269 | −6.05 | 34.979 | 5.439 | 23.66 | O |
| ATOM | 4958 | O | HOH | F271 | −8.98 | −0.279 | 5.32 | 15.75 | O |
| ATOM | 4959 | O | HOH | F276 | 2.974 | 11.07 | 9.919 | 22.17 | O |
| ATOM | 4960 | O | HOH | F278 | −14.111 | −9.961 | 6.282 | 44.67 | O |
| ATOM | 4961 | O | HOH | F279 | −29.218 | −45.75 | −28.633 | 11.2 | O |
| ATOM | 4962 | O | HOH | F282 | −42.477 | −21.253 | −27.923 | 18.5 | O |
| ATOM | 4963 | O | HOH | F283 | −34.014 | −4.394 | 2.354 | 12.22 | O |
| ATOM | 4964 | O | HOH | F284 | 4.7 | 22.988 | −7.778 | 23.08 | O |
| ATOM | 4965 | O | HOH | F289 | −8.366 | −21.818 | 2.824 | 18.62 | O |
| ATOM | 4966 | O | HOH | F290 | 1.692 | 9.464 | 29.595 | 34.19 | O |
| ATOM | 4967 | O | HOH | F291 | −23.192 | −11.572 | −29.113 | 40.34 | O |
| ATOM | 4968 | O | HOH | F293 | −48.105 | −36.996 | −38.885 | 30.74 | O |
| ATOM | 4969 | O | HOH | F298 | −24.065 | −44.956 | −29.789 | 44.17 | O |
| ATOM | 4970 | O | HOH | F299 | −17.055 | −9.208 | 8.875 | 44.85 | O |
| ATOM | 4971 | O | HOH | F310 | −10.136 | 18.804 | 6.712 | 30.24 | O |
| ATOM | 4972 | O | HOH | F311 | −11.822 | 24.153 | −6.297 | 18.14 | O |
| ATOM | 4973 | O | HOH | F316 | 9.546 | 31.815 | −11.844 | 9.61 | O |

TABLE 1A-continued

| ATOM | 4974 | O | HOH | F317 | 11.95 | 30.507 | −11.564 | 11.26 | O |
|---|---|---|---|---|---|---|---|---|---|
| ATOM | 4975 | O | HOH | F321 | −6.987 | 10.303 | −12.194 | 12.61 | O |
| ATOM | 4976 | O | HOH | F323 | −8.229 | 12.163 | −14.579 | 17.55 | O |
| ATOM | 4977 | O | HOH | F324 | 3.683 | −0.89 | 5.686 | 18.78 | O |
| ATOM | 4978 | O | HOH | F325 | −11.488 | −14.186 | −3.45 | 20.66 | O |
| ATOM | 4979 | O | HOH | F327 | −11.968 | −13.195 | 7.446 | 33.2 | O |
| ATOM | 4980 | O | HOH | F328 | −16.3 | −13.463 | 9.956 | 22.62 | O |
| ATOM | 4981 | O | HOH | F329 | −9.272 | −14.428 | 11.275 | 15.93 | O |
| ATOM | 4982 | O | HOH | F330 | −1.857 | −22.856 | −1.675 | 31.54 | O |
| ATOM | 4983 | O | HOH | F331 | 11.811 | −10.851 | 12.466 | 27.69 | O |
| ATOM | 4984 | O | HOH | F332 | 15.961 | −8.575 | 7.8 | 18.32 | O |
| ATOM | 4985 | O | HOH | F333 | 18.235 | −17.932 | 8.891 | 22.9 | O |
| ATOM | 4986 | O | HOH | F340 | −24.46 | −9.744 | −25.665 | 12.78 | O |
| ATOM | 4987 | O | HOH | F342 | −27.314 | −21.134 | −29.776 | 13.86 | O |
| ATOM | 4988 | O | HOH | F348 | −40.626 | −30.693 | −29.559 | 28.67 | O |
| ATOM | 4989 | O | HOH | F351 | −9.41 | −15.753 | 7.013 | 14 | O |
| ATOM | 4990 | O | HOH | F352 | −32.049 | −50.283 | −33.663 | 35.95 | O |
| ATOM | 4991 | O | HOH | F356 | −18.866 | −15.309 | −30.177 | 24.26 | O |
| ATOM | 4992 | O | HOH | F358 | −33.287 | −55.033 | −37.052 | 9.53 | O |
| ATOM | 4993 | O | HOH | F359 | 4.652 | −3.504 | 10.226 | 33.1 | O |
| ATOM | 4994 | O | HOH | F360 | −31.099 | −32.445 | −33.508 | 5.43 | O |
| ATOM | 4995 | O | HOH | F361 | 5.952 | 9.627 | −8.466 | 18.68 | O |
| ATOM | 4996 | O | HOH | F362 | 12.851 | −5.168 | −0.578 | 11.64 | O |
| ATOM | 4997 | O | HOH | F363 | −31.321 | −33.548 | −8.199 | 25.88 | O |
| ATOM | 4998 | O | HOH | F365 | −14.509 | −15.416 | −24.15 | 28.59 | O |
| ATOM | 4999 | O | HOH | F368 | −12.027 | 4.182 | −4.641 | 5.68 | O |
| ATOM | 5000 | O | HOH | F372 | 2.882 | −3.106 | −13.774 | 28.16 | O |
| ATOM | 5001 | O | HOH | F373 | −38.023 | −25.397 | −32.152 | 17.02 | O |
| ATOM | 5002 | O | HOH | F374 | 11.155 | −20.718 | −4.4 | 29.01 | O |
| ATOM | 5003 | O | HOH | F376 | −10.556 | 7.527 | −1.55 | 18.42 | O |
| ATOM | 5004 | O | HOH | F377 | −48.85 | −18.397 | −12.457 | 12.98 | O |
| ATOM | 5005 | O | HOH | F380 | −36.569 | −37.246 | −33.524 | 11.2 | O |
| ATOM | 5006 | O | HOH | F381 | −24.863 | −41.265 | −28.065 | 25.79 | O |
| ATOM | 5007 | O | HOH | F383 | −45.552 | −0.183 | −14.246 | 21.66 | O |
| ATOM | 5008 | O | HOH | F384 | 4.701 | −21.598 | −7.352 | 26.64 | O |
| ATOM | 5009 | O | HOH | F386 | −0.6 | −0.52 | 6.816 | 31.53 | O |
| ATOM | 5010 | O | HOH | F387 | −10.111 | −2.953 | 5.26 | 17.96 | O |
| ATOM | 5011 | O | HOH | F388 | −25.049 | −17.468 | −7.969 | 32.9 | O |
| ATOM | 5012 | O | HOH | F389 | −26.332 | −11.606 | −6.498 | 36.6 | O |
| ATOM | 5013 | O | HOH | F391 | 14.913 | −6.481 | 8.487 | 36.2 | O |
| ATOM | 5014 | O | HOH | F394 | 16.259 | −15.826 | −6.447 | 37.58 | O |
| ATOM | 5015 | O | HOH | F395 | −9.203 | 4.244 | 6.795 | 17.76 | O |
| ATOM | 5016 | O | HOH | F396 | −40.086 | 0.372 | −8.964 | 21.08 | O |
| ATOM | 5017 | O | HOH | F398 | 16.994 | −6.858 | 0.059 | 42.45 | O |
| ATOM | 5018 | O | HOH | F402 | 2.118 | −1.406 | 8.674 | 16.11 | O |
| ATOM | 5019 | O | HOH | F405 | 0.837 | 9.273 | 11.254 | 24.81 | O |
| ATOM | 5020 | O | HOH | F407 | 3.045 | 12.282 | −8.946 | 33.67 | O |
| ATOM | 5021 | O | HOH | F410 | −51.076 | −26.098 | −29.893 | 35.22 | O |
| ATOM | 5022 | O | HOH | F413 | 5.628 | −20.263 | 13.119 | 19.98 | O |
| ATOM | 5023 | O | HOH | F414 | −3.942 | 17.588 | 8.986 | 20.79 | O |
| ATOM | 5024 | O | HOH | F415 | −4.646 | 12.122 | 15.494 | 35.45 | O |
| ATOM | 5025 | O | HOH | F420 | −21.567 | −21.045 | −15.42 | 45.94 | O |
| ATOM | 5026 | O | HOH | F421 | −33.27 | −1.351 | −28.007 | 16.96 | O |
| ATOM | 5027 | O | HOH | F422 | −33.732 | −14.336 | −37.208 | 18.79 | O |
| ATOM | 5028 | O | HOH | F423 | −24.498 | −22.642 | −29.114 | 26.48 | O |
| ATOM | 5029 | O | HOH | F427 | −42.526 | −46.274 | −14.79 | 18.27 | O |
| ATOM | 5030 | O | HOH | F430 | −14.75 | −31.131 | −19.055 | 48.87 | O |
| ATOM | 5031 | O | HOH | F431 | −34.878 | 6.53 | −28.368 | 19.91 | O |
| ATOM | 5032 | O | HOH | F432 | 10.549 | 29.362 | −2.166 | 24.44 | O |
| ATOM | 5033 | O | HOH | F433 | 8.3 | 29.965 | −3.709 | 42.01 | O |
| ATOM | 5034 | O | HOH | F434 | 4.93 | 35.082 | 7.767 | 27.24 | O |
| ATOM | 5035 | O | HOH | F435 | 7.01 | 38.01 | 9.004 | 21.31 | O |
| ATOM | 5036 | O | HOH | F436 | 18.755 | 27.791 | 9.77 | 46.05 | O |
| ATOM | 5037 | O | HOH | F438 | 0.35 | 28.842 | 15.624 | 13.72 | O |
| ATOM | 5038 | O | HOH | F439 | 6.557 | 22.735 | 17.683 | 31.05 | O |
| ATOM | 5039 | O | HOH | F440 | 3.297 | 0.092 | −13.573 | 29.27 | O |
| ATOM | 5040 | O | HOH | F441 | −7.94 | 23.432 | −18.434 | 28.66 | O |
| ATOM | 5041 | O | HOH | F442 | 1.802 | 29.841 | −11.164 | 42.98 | O |
| ATOM | 5042 | O | HOH | F443 | −50.163 | −32.075 | −16.975 | 13.52 | O |
| ATOM | 5043 | O | HOH | F444 | −50.324 | −33.207 | −22.394 | 34.24 | O |
| ATOM | 5044 | O | HOH | F445 | −30.405 | −27.894 | −41.835 | 20.26 | O |
| ATOM | 5045 | O | HOH | F446 | −42.528 | −50.128 | −39.155 | 34.7 | O |
| ATOM | 5046 | O | HOH | F447 | −6.122 | −20.519 | 10.241 | 31.88 | O |
| ATOM | 5047 | O | HOH | F448 | −9.471 | −17.911 | 15.198 | 29.11 | O |
| ATOM | 5048 | O | HOH | F449 | −10.256 | 8.058 | 1.039 | 22.58 | O |
| ATOM | 5049 | O | HOH | F450 | −10.084 | 8.041 | 6.965 | 35.26 | O |
| ATOM | 5050 | O | HOH | F451 | −8.258 | 10.019 | 15.224 | 14.39 | O |
| ATOM | 5051 | O | HOH | F452 | −3.132 | 9.777 | 17.396 | 43.71 | O |
| ATOM | 5052 | O | HOH | F453 | −7.844 | 6.196 | 15.354 | 25.77 | O |
| ATOM | 5053 | O | HOH | F454 | −33.488 | −47.929 | −40.055 | 17.2 | O |

TABLE 1A-continued

| ATOM | 5054 | O | HOH | F455 | −32.976 | −45.657 | −40.842 | 24.75 | O |
| ATOM | 5055 | O | HOH | F456 | −15.149 | 9.534 | 2.929 | 44.29 | O |
| ATOM | 5056 | O | HOH | F457 | −16.433 | 16.612 | −6.304 | 32 | O |
| ATOM | 5057 | O | HOH | F458 | −38.154 | −3.576 | −2.259 | 34.13 | O |
| ATOM | 5058 | O | HOH | F459 | −33.967 | 0.453 | −7.339 | 31.91 | O |

TABLE 1B

| ATOM | 1 | CB | LEU | 1046 | −19.713 | −2.925 | −36.938 | 37.65 | C |
| ATOM | 2 | CG | LEU | 1046 | −19.834 | −3.388 | −35.494 | 38.45 | C |
| ATOM | 3 | CD1 | LEU | 1046 | −20.915 | −2.586 | −34.807 | 37.79 | C |
| ATOM | 4 | CD2 | LEU | 1046 | −20.107 | −4.883 | −35.426 | 38.03 | C |
| ATOM | 5 | C | LEU | 1046 | −22.28 | −3.028 | −37.251 | 37.24 | C |
| ATOM | 6 | O | LEU | 1046 | −22.669 | −1.886 | −37.029 | 36.06 | O |
| ATOM | 7 | N | LEU | 1046 | −20.8 | −2.523 | −39.117 | 37.83 | N |
| ATOM | 8 | CA | LEU | 1046 | −20.858 | −3.287 | −37.783 | 38.05 | C |
| ATOM | 9 | N | LEU | 1047 | −22.803 | −4.188 | −36.833 | 37.34 | N |
| ATOM | 10 | CA | LEU | 1047 | −24.322 | −4.334 | −36.88 | 37.41 | C |
| ATOM | 11 | CB | LEU | 1047 | −24.559 | −5.846 | −36.963 | 38.63 | C |
| ATOM | 12 | CG | LEU | 1047 | −24.045 | −6.619 | −38.197 | 39.63 | C |
| ATOM | 13 | CD1 | LEU | 1047 | −23.493 | −7.978 | −37.765 | 40.91 | C |
| ATOM | 14 | CD2 | LEU | 1047 | −25.172 | −6.793 | −39.21 | 40.19 | C |
| ATOM | 15 | C | LEU | 1047 | −25.1 | −3.582 | −35.917 | 36.45 | C |
| ATOM | 16 | O | LEU | 1047 | −25.898 | −2.729 | −36.286 | 36.58 | O |
| ATOM | 17 | N | GLN | 1048 | −24.943 | −4.046 | −34.699 | 36.14 | N |
| ATOM | 18 | CA | GLN | 1048 | −25.308 | −3.208 | −33.552 | 37.2 | C |
| ATOM | 19 | CB | GLN | 1048 | −24.1 | −3.359 | −32.547 | 38.59 | C |
| ATOM | 20 | CG | GLN | 1048 | −22.726 | −3.016 | −33.094 | 41.49 | C |
| ATOM | 21 | CD | GLN | 1048 | −21.59 | −3.712 | −32.361 | 43.83 | C |
| ATOM | 22 | OE1 | GLN | 1048 | −21.408 | −3.52 | −31.158 | 44.72 | O |
| ATOM | 23 | NE2 | GLN | 1048 | −20.825 | −4.534 | −33.079 | 42.9 | N |
| ATOM | 24 | C | GLN | 1048 | −25.331 | −1.753 | −33.995 | 35.99 | C |
| ATOM | 25 | O | GLN | 1048 | −26.367 | −1.101 | −33.978 | 35.9 | O |
| ATOM | 26 | N | ASN | 1049 | −24.192 | −1.292 | −34.49 | 34.21 | N |
| ATOM | 27 | CA | ASN | 1049 | −24.188 | 0.042 | −34.802 | 33.13 | C |
| ATOM | 28 | CB | ASN | 1049 | −22.763 | 0.474 | −35.102 | 34.55 | C |
| ATOM | 29 | CG | ASN | 1049 | −22.03 | 0.787 | −33.852 | 36.88 | C |
| ATOM | 30 | OD1 | ASN | 1049 | −22.593 | 1.274 | −32.899 | 38.35 | O |
| ATOM | 31 | ND2 | ASN | 1049 | −20.756 | 0.562 | −33.862 | 36.72 | N |
| ATOM | 32 | C | ASN | 1049 | −25.042 | 0.484 | −35.87 | 31.5 | C |
| ATOM | 33 | O | ASN | 1049 | −24.714 | 1.503 | −36.268 | 33.07 | O |
| ATOM | 34 | N | THR | 1050 | −26.135 | −0.177 | −36.286 | 29.28 | N |
| ATOM | 35 | CA | THR | 1050 | −27.071 | 0.242 | −37.372 | 27.57 | C |
| ATOM | 36 | CB | THR | 1050 | −26.772 | −0.569 | −38.656 | 27.93 | C |
| ATOM | 37 | OG1 | THR | 1050 | −26.853 | −1.982 | −38.404 | 28.31 | O |
| ATOM | 38 | CG2 | THR | 1050 | −25.354 | −0.265 | −39.069 | 28.62 | C |
| ATOM | 39 | C | THR | 1050 | −28.501 | −0.015 | −36.874 | 26.39 | C |
| ATOM | 40 | O | THR | 1050 | −29.511 | 0.174 | −37.56 | 26.33 | O |
| ATOM | 41 | N | VAL | 1051 | −28.568 | −0.357 | −35.614 | 23.92 | N |
| ATOM | 42 | CA | VAL | 1051 | −29.836 | −0.634 | −35.034 | 22.71 | C |
| ATOM | 43 | CB | VAL | 1051 | −29.705 | −1.748 | −34.014 | 22.99 | C |
| ATOM | 44 | CG1 | VAL | 1051 | −31.041 | −2.037 | −33.406 | 21.99 | C |
| ATOM | 45 | CG2 | VAL | 1051 | −29.082 | −2.987 | −34.659 | 23.78 | C |
| ATOM | 46 | C | VAL | 1051 | −30.375 | 0.589 | −34.295 | 22.22 | C |
| ATOM | 47 | O | VAL | 1051 | −29.95 | 0.831 | −33.199 | 20.21 | O |
| ATOM | 48 | N | HIS | 1052 | −31.251 | 1.366 | −34.82 | 22.87 | N |
| ATOM | 49 | CA | HIS | 1052 | −31.674 | 2.419 | −33.928 | 24 | C |
| ATOM | 50 | CB | HIS | 1052 | −31.576 | 3.704 | −34.653 | 24.15 | C |
| ATOM | 51 | CG | HIS | 1052 | −32.273 | 4.827 | −33.985 | 23.62 | C |
| ATOM | 52 | CD2 | HIS | 1052 | −33.461 | 5.416 | −34.247 | 24.61 | C |
| ATOM | 53 | ND1 | HIS | 1052 | −31.722 | 5.51 | −32.926 | 25.74 | N |
| ATOM | 54 | CE1 | HIS | 1052 | −32.534 | 6.488 | −32.571 | 25.69 | C |
| ATOM | 55 | NE2 | HIS | 1052 | −33.596 | 6.453 | −33.358 | 27.01 | N |
| ATOM | 56 | C | HIS | 1052 | −33.129 | 2.083 | −33.65 | 24.08 | C |
| ATOM | 57 | O | HIS | 1052 | −33.725 | 1.402 | −34.453 | 25.06 | O |
| ATOM | 58 | N | ILE | 1053 | −33.727 | 2.592 | −32.609 | 25.32 | N |
| ATOM | 59 | CA | ILE | 1053 | −35.131 | 2.237 | −32.376 | 26.95 | C |
| ATOM | 60 | CB | ILE | 1053 | −35.181 | 1.212 | −31.221 | 27.35 | C |
| ATOM | 61 | CG2 | ILE | 1053 | −36.585 | 1.044 | −30.766 | 26.5 | C |
| ATOM | 62 | CG1 | ILE | 1053 | −34.506 | 0.12 | −31.596 | 27.84 | C |
| ATOM | 63 | CD | ILE | 1053 | −32.991 | 0.116 | −31.455 | 30.41 | C |
| ATOM | 64 | C | ILE | 1053 | −35.828 | 3.54 | −31.879 | 27.08 | C |
| ATOM | 65 | O | ILE | 1053 | −35.243 | 4.138 | −31.014 | 27.08 | O |
| ATOM | 66 | N | ASP | 1054 | −36.982 | 3.996 | −32.351 | 27.49 | N |
| ATOM | 67 | CA | ASP | 1054 | −37.546 | 5.236 | −31.77 | 27.84 | C |
| ATOM | 68 | CB | ASP | 1054 | −38.199 | 6.114 | −32.815 | 28.33 | C |
| ATOM | 69 | CG | ASP | 1054 | −38.818 | 7.383 | −32.249 | 28.99 | C |

TABLE 1B-continued

| | | | | | | | | | |
|---|---|---|---|---|---|---|---|---|---|
| ATOM | 70  | OD1 | ASP | 1054 | −38.773 | 7.627  | −31.021 | 28.77 | O |
| ATOM | 71  | OD2 | ASP | 1054 | −39.366 | 8.145  | −33.064 | 30.36 | O |
| ATOM | 72  | C   | ASP | 1054 | −38.537 | 4.749  | −30.768 | 27.75 | C |
| ATOM | 73  | O   | ASP | 1054 | −39.568 | 4.12   | −31.051 | 28.21 | O |
| ATOM | 74  | N   | LEU | 1055 | −38.158 | 4.976  | −29.561 | 28.32 | N |
| ATOM | 75  | CA  | LEU | 1055 | −38.975 | 4.494  | −28.544 | 29.2  | C |
| ATOM | 76  | CB  | LEU | 1055 | −38.127 | 4.545  | −27.289 | 28.05 | C |
| ATOM | 77  | CG  | LEU | 1055 | −36.86  | 3.674  | −27.342 | 27.28 | C |
| ATOM | 78  | CD1 | LEU | 1055 | −36.032 | 3.941  | −26.098 | 27.69 | C |
| ATOM | 79  | CD2 | LEU | 1055 | −37.238 | 2.199  | −27.412 | 26.67 | C |
| ATOM | 80  | C   | LEU | 1055 | −40.331 | 5.239  | −28.441 | 30.11 | C |
| ATOM | 81  | O   | LEU | 1055 | −41.3   | 4.617  | −28.07  | 30.04 | O |
| ATOM | 82  | N   | SER | 1056 | −40.451 | 6.507  | −28.822 | 30.85 | N |
| ATOM | 83  | CA  | SER | 1056 | −41.728 | 7.269  | −28.615 | 33.07 | C |
| ATOM | 84  | CB  | SER | 1056 | −41.442 | 8.729  | −28.747 | 32.67 | C |
| ATOM | 85  | OG  | SER | 1056 | −41.007 | 8.96   | −30.076 | 31.6  | O |
| ATOM | 86  | C   | SER | 1056 | −42.712 | 6.925  | −29.718 | 34.59 | C |
| ATOM | 87  | O   | SER | 1056 | −43.94  | 7.153  | −29.689 | 35.04 | O |
| ATOM | 88  | N   | ALA | 1057 | −42.081 | 6.42   | −30.703 | 36.25 | N |
| ATOM | 89  | CA  | ALA | 1057 | −42.822 | 6.002  | −31.859 | 38.14 | C |
| ATOM | 90  | CB  | ALA | 1057 | −41.819 | 5.716  | −32.996 | 36.82 | C |
| ATOM | 91  | C   | ALA | 1057 | −43.573 | 4.697  | −31.555 | 39.49 | C |
| ATOM | 92  | O   | ALA | 1057 | −44.274 | 4.161  | −32.415 | 40.68 | O |
| ATOM | 93  | N   | ILE | 1058 | −43.475 | 4.255  | −30.311 | 40.19 | N |
| ATOM | 94  | CA  | ILE | 1058 | −43.995 | 2.962  | −29.948 | 41.59 | C |
| ATOM | 95  | CB  | ILE | 1058 | −42.872 | 2.192  | −29.127 | 42.24 | C |
| ATOM | 96  | CG2 | ILE | 1058 | −42.904 | 2.642  | −27.671 | 45.17 | C |
| ATOM | 97  | CG1 | ILE | 1058 | −43.068 | 0.676  | −29.213 | 43.34 | C |
| ATOM | 98  | CD  | ILE | 1058 | −42.673 | 0.062  | −30.552 | 43.01 | C |
| ATOM | 99  | C   | ILE | 1058 | −45.257 | 2.918  | −29.14  | 41.13 | C |
| ATOM | 100 | O   | ILE | 1058 | −45.292 | 3.407  | −28.015 | 41.55 | O |
| ATOM | 101 | N   | ASP | 1059 | −46.315 | 2.389  | −29.753 | 41.15 | N |
| ATOM | 102 | CA  | ASP | 1059 | −47.605 | 2.129  | −29.055 | 41.81 | C |
| ATOM | 103 | CB  | ASP | 1059 | −48.138 | 0.801  | −29.462 | 42.5  | C |
| ATOM | 104 | CG  | ASP | 1059 | −49.4   | 0.451  | −28.71  | 42.86 | C |
| ATOM | 105 | OD1 | ASP | 1059 | −49.464 | 0.728  | −27.494 | 43.52 | O |
| ATOM | 106 | OD2 | ASP | 1059 | −50.325 | −0.113 | −29.323 | 44.01 | O |
| ATOM | 107 | C   | ASP | 1059 | −47.288 | 2.221  | −27.554 | 41.59 | C |
| ATOM | 108 | O   | ASP | 1059 | −46.381 | 1.613  | −27.024 | 42.14 | O |
| ATOM | 109 | N   | PRO | 1060 | −48.13  | 2.869  | −26.869 | 41.04 | N |
| ATOM | 110 | CD  | PRO | 1060 | −48.701 | 3.943  | −27.675 | 41.33 | C |
| ATOM | 111 | CA  | PRO | 1060 | −48.061 | 3.174  | −25.457 | 41.53 | C |
| ATOM | 112 | CB  | PRO | 1060 | −48.349 | 4.654  | −25.458 | 40.32 | C |
| ATOM | 113 | CG  | PRO | 1060 | −49.253 | 4.76   | −26.709 | 40.85 | C |
| ATOM | 114 | C   | PRO | 1060 | −48.658 | 2.397  | −24.392 | 41.35 | C |
| ATOM | 115 | O   | PRO | 1060 | −48.591 | 2.565  | −23.203 | 42.29 | O |
| ATOM | 116 | N   | GLU | 1061 | −49.145 | 1.297  | −24.822 | 41.69 | N |
| ATOM | 117 | CA  | GLU | 1061 | −49.723 | 0.813  | −23.678 | 41.96 | C |
| ATOM | 118 | CB  | GLU | 1061 | −51.163 | 0.879  | −23.965 | 43.79 | C |
| ATOM | 119 | CG  | GLU | 1061 | −51.39  | 0.487  | −25.385 | 47.3  | C |
| ATOM | 120 | CD  | GLU | 1061 | −52.836 | 0.513  | −25.748 | 49.83 | C |
| ATOM | 121 | OE1 | GLU | 1061 | −53.643 | 0.923  | −24.889 | 50.97 | O |
| ATOM | 122 | OE2 | GLU | 1061 | −53.172 | 0.124  | −26.887 | 51.87 | O |
| ATOM | 123 | C   | GLU | 1061 | −49.023 | −0.456 | −23.755 | 40.72 | C |
| ATOM | 124 | O   | GLU | 1061 | −48.908 | −1.181 | −22.797 | 40    | O |
| ATOM | 125 | N   | LEU | 1062 | −48.49  | −0.721 | −24.936 | 39.26 | N |
| ATOM | 126 | CA  | LEU | 1062 | −47.736 | −1.936 | −25.047 | 37.05 | C |
| ATOM | 127 | CB  | LEU | 1062 | −47.144 | −2.067 | −26.447 | 36.62 | C |
| ATOM | 128 | CG  | LEU | 1062 | −46.166 | −3.232 | −26.606 | 36.37 | C |
| ATOM | 129 | CD1 | LEU | 1062 | −46.871 | −4.543 | −26.286 | 37.04 | C |
| ATOM | 130 | CD2 | LEU | 1062 | −45.613 | −3.252 | −28.022 | 35.34 | C |
| ATOM | 131 | C   | LEU | 1062 | −46.61  | −1.713 | −24.034 | 36.08 | C |
| ATOM | 132 | O   | LEU | 1062 | −46.172 | −2.59  | −23.284 | 35    | O |
| ATOM | 133 | N   | VAL | 1063 | −46.211 | −0.472 | −23.986 | 35.17 | N |
| ATOM | 134 | CA  | VAL | 1063 | −45.136 | −0.06  | −23.15  | 35.46 | C |
| ATOM | 135 | CB  | VAL | 1063 | −44.642 | 1.236  | −23.725 | 35.44 | C |
| ATOM | 136 | CG1 | VAL | 1063 | −43.706 | 1.89   | −22.788 | 35.6  | C |
| ATOM | 137 | CG2 | VAL | 1063 | −43.997 | 0.967  | −25.086 | 35.93 | C |
| ATOM | 138 | C   | VAL | 1063 | −45.523 | 0.057  | −21.678 | 35.67 | C |
| ATOM | 139 | O   | VAL | 1063 | −44.712 | −0.239 | −20.794 | 35.29 | O |
| ATOM | 140 | N   | GLN | 1064 | −46.754 | 0.5    | −21.423 | 35.76 | N |
| ATOM | 141 | CA  | GLN | 1064 | −47.262 | 0.647  | −20.053 | 36.63 | C |
| ATOM | 142 | CB  | GLN | 1064 | −48.699 | 1.158  | −20.085 | 38.64 | C |
| ATOM | 143 | CG  | GLN | 1064 | −49.181 | 1.631  | −18.737 | 44.03 | C |
| ATOM | 144 | CD  | GLN | 1064 | −50.665 | 1.931  | −18.728 | 47.48 | C |
| ATOM | 145 | OE1 | GLN | 1064 | −51.319 | 1.924  | −19.775 | 49.46 | O |
| ATOM | 146 | NE2 | GLN | 1064 | −51.208 | 2.201  | −17.544 | 48.03 | N |
| ATOM | 147 | C   | GLN | 1064 | −47.177 | −0.761 | −19.454 | 35.07 | C |
| ATOM | 148 | O   | GLN | 1064 | −46.523 | −0.982 | −18.435 | 34.95 | O |
| ATOM | 149 | N   | ALA | 1065 | −47.864 | −1.693 | −20.097 | 32.4  | N |

TABLE 1B-continued

| | | | | | | | | |
|---|---|---|---|---|---|---|---|---|
| ATOM | 150 | CA | ALA | 1065 | −47.798 | −3.114 | −19.773 | 30.99 | C |
| ATOM | 151 | CB | ALA | 1065 | −48.238 | −3.895 | −21.008 | 29.54 | C |
| ATOM | 152 | C | ALA | 1065 | −46.37 | −3.59 | −19.366 | 29.66 | C |
| ATOM | 153 | O | ALA | 1065 | −46.137 | −4 | −18.23 | 31.42 | O |
| ATOM | 154 | N | VAL | 1066 | −45.417 | −3.545 | −20.298 | 26.55 | N |
| ATOM | 155 | CA | VAL | 1066 | −44.063 | −4.031 | −20.015 | 24.46 | C |
| ATOM | 156 | CB | VAL | 1066 | −43.31 | −4.334 | −21.353 | 23.5 | C |
| ATOM | 157 | CG1 | VAL | 1066 | −44.296 | −4.837 | −22.408 | 23.77 | C |
| ATOM | 158 | CG2 | VAL | 1066 | −42.598 | −3.102 | −21.852 | 22.22 | C |
| ATOM | 159 | C | VAL | 1066 | −43.16 | −3.163 | −19.111 | 23.52 | C |
| ATOM | 160 | O | VAL | 1066 | −42.126 | −3.645 | −18.638 | 24.4 | O |
| ATOM | 161 | N | GLN | 1067 | −43.544 | −1.911 | −18.848 | 22.41 | N |
| ATOM | 162 | CA | GLN | 1067 | −42.703 | −1.021 | −18.038 | 21.71 | C |
| ATOM | 163 | CB | GLN | 1067 | −43.417 | 0.277 | −17.642 | 23.75 | C |
| ATOM | 164 | CG | GLN | 1067 | −42.446 | 1.315 | −17.06 | 27.36 | C |
| ATOM | 165 | CD | GLN | 1067 | −41.496 | 1.888 | −18.115 | 28.42 | C |
| ATOM | 166 | OE1 | GLN | 1067 | −40.309 | 2.121 | −17.854 | 30.71 | O |
| ATOM | 167 | NE2 | GLN | 1067 | −42.022 | 2.126 | −19.308 | 28.25 | N |
| ATOM | 168 | C | GLN | 1067 | −42.169 | −1.645 | −16.773 | 20.39 | C |
| ATOM | 169 | O | GLN | 1067 | −41.027 | −1.394 | −16.392 | 17.45 | O |
| ATOM | 170 | N | HIS | 1068 | −42.972 | −2.464 | −16.108 | 18.61 | N |
| ATOM | 171 | CA | HIS | 1068 | −42.458 | −3.041 | −14.886 | 17.47 | C |
| ATOM | 172 | CB | HIS | 1068 | −43.563 | −3.74 | −14.101 | 16.08 | C |
| ATOM | 173 | CG | HIS | 1068 | −44.015 | −5.023 | −14.704 | 16.78 | C |
| ATOM | 174 | CD2 | HIS | 1068 | −43.866 | −6.3 | −14.282 | 16.5 | C |
| ATOM | 175 | ND1 | HIS | 1068 | −44.741 | −5.082 | −15.874 | 16.21 | N |
| ATOM | 176 | CE1 | HIS | 1068 | −45.024 | −6.344 | −16.145 | 15.79 | C |
| ATOM | 177 | NE2 | HIS | 1068 | −44.504 | −7.102 | −15.194 | 17.99 | N |
| ATOM | 178 | C | HIS | 1068 | −41.251 | −3.967 | −15.081 | 17.41 | C |
| ATOM | 179 | O | HIS | 1068 | −40.582 | −4.28 | −14.101 | 15.49 | O |
| ATOM | 180 | N | VAL | 1069 | −40.949 | −4.402 | −16.31 | 15.97 | N |
| ATOM | 181 | CA | VAL | 1069 | −39.75 | −5.237 | −16.509 | 15.14 | C |
| ATOM | 182 | CB | VAL | 1069 | −39.978 | −6.463 | −17.444 | 14.83 | C |
| ATOM | 183 | CG1 | VAL | 1069 | −40.968 | −7.409 | −16.839 | 16.23 | C |
| ATOM | 184 | CG2 | VAL | 1069 | −40.429 | −6.01 | −18.813 | 17.27 | C |
| ATOM | 185 | C | VAL | 1069 | −38.579 | −4.455 | −17.106 | 16.95 | C |
| ATOM | 186 | O | VAL | 1069 | −37.484 | −5.005 | −17.258 | 13.59 | O |
| ATOM | 187 | N | VAL | 1070 | −38.802 | −3.19 | −17.461 | 17.23 | N |
| ATOM | 188 | CA | VAL | 1070 | −37.741 | −2.37 | −18.048 | 19.93 | C |
| ATOM | 189 | CB | VAL | 1070 | −38.294 | −1.133 | −18.74 | 20.65 | C |
| ATOM | 190 | CG1 | VAL | 1070 | −37.135 | −0.251 | −19.247 | 22.41 | C |
| ATOM | 191 | CG2 | VAL | 1070 | −39.181 | −1.565 | −19.885 | 22.99 | C |
| ATOM | 192 | C | VAL | 1070 | −36.783 | −1.934 | −16.969 | 20.17 | C |
| ATOM | 193 | O | VAL | 1070 | −37.19 | −1.383 | −15.954 | 19.99 | O |
| ATOM | 194 | N | ILE | 1071 | −35.497 | −2.152 | −17.202 | 21.73 | N |
| ATOM | 195 | CA | ILE | 1071 | −34.52 | −1.843 | −16.175 | 24.48 | C |
| ATOM | 196 | CB | ILE | 1071 | −33.326 | −2.83 | −16.285 | 24.86 | C |
| ATOM | 197 | CG2 | ILE | 1071 | −32.302 | −2.542 | −15.218 | 25.75 | C |
| ATOM | 198 | CG1 | ILE | 1071 | −33.828 | −4.283 | −16.134 | 27.22 | C |
| ATOM | 199 | CD | ILE | 1071 | −34.561 | −4.632 | −14.81 | 30.1 | C |
| ATOM | 200 | C | ILE | 1071 | −34.02 | −0.401 | −15.981 | 26.09 | C |
| ATOM | 201 | O | ILE | 1071 | −33.915 | 0.054 | −14.842 | 29.19 | O |
| ATOM | 202 | N | GLY | 1072 | −33.74 | 0.345 | −17.04 | 25.89 | N |
| ATOM | 203 | CA | GLY | 1072 | −33.245 | 1.696 | −16.813 | 24.16 | C |
| ATOM | 204 | C | GLY | 1072 | −31.743 | 1.564 | −16.874 | 24.08 | C |
| ATOM | 205 | O | GLY | 1072 | −31.158 | 0.805 | −16.098 | 23.13 | O |
| ATOM | 206 | N | PRO | 1073 | −31.075 | 2.312 | −17.755 | 24.22 | N |
| ATOM | 207 | CD | PRO | 1073 | −31.504 | 3.335 | −18.725 | 23.18 | C |
| ATOM | 208 | CA | PRO | 1073 | −29.626 | 2.111 | −17.78 | 24.27 | C |
| ATOM | 209 | CB | PRO | 1073 | −29.194 | 2.872 | −19.033 | 24.61 | C |
| ATOM | 210 | CG | PRO | 1073 | −30.194 | 3.967 | −19.142 | 24.35 | C |
| ATOM | 211 | C | PRO | 1073 | −28.769 | 2.398 | −16.555 | 24.59 | C |
| ATOM | 212 | O | PRO | 1073 | −27.782 | 1.708 | −16.346 | 24.13 | O |
| ATOM | 213 | N | SER | 1074 | −29.118 | 3.376 | −15.734 | 24.35 | N |
| ATOM | 214 | CA | SER | 1074 | −28.298 | 3.626 | −14.555 | 24.76 | C |
| ATOM | 215 | CB | SER | 1074 | −28.922 | 4.721 | −13.681 | 27.55 | C |
| ATOM | 216 | OG | SER | 1074 | −30.159 | 4.284 | −13.126 | 32.15 | O |
| ATOM | 217 | C | SER | 1074 | −28.218 | 2.348 | −13.723 | 22.97 | C |
| ATOM | 218 | O | SER | 1074 | −27.185 | 2.03 | −13.139 | 24.56 | O |
| ATOM | 219 | N | SER | 1075 | −29.324 | 1.613 | −13.705 | 21.28 | N |
| ATOM | 220 | CA | SER | 1075 | −29.494 | 0.399 | −12.907 | 19.44 | C |
| ATOM | 221 | CB | SER | 1075 | −30.977 | 0.062 | −12.849 | 18.46 | C |
| ATOM | 222 | OG | SER | 1075 | −31.684 | 1.089 | −12.195 | 14.27 | O |
| ATOM | 223 | C | SER | 1075 | −28.732 | −0.873 | −13.249 | 20.54 | C |
| ATOM | 224 | O | SER | 1075 | −28.633 | −1.795 | −12.429 | 21.36 | O |
| ATOM | 225 | N | LEU | 1076 | −28.183 | −0.923 | −14.446 | 20.1 | N |
| ATOM | 226 | CA | LEU | 1076 | −27.483 | −2.104 | −14.875 | 19.87 | C |
| ATOM | 227 | CB | LEU | 1076 | −28.224 | −2.699 | −16.063 | 19.21 | C |
| ATOM | 228 | CG | LEU | 1076 | −27.534 | −3.89 | −16.707 | 19.12 | C |
| ATOM | 229 | CD1 | LEU | 1076 | −27.461 | −5.021 | −15.696 | 17.77 | C |

TABLE 1B-continued

| | | | | | | | | |
|---|---|---|---|---|---|---|---|---|
| ATOM | 230 | CD2 | LEU | 1076 | −28.302 | −4.319 | −17.948 | 19.82 | C |
| ATOM | 231 | C | LEU | 1076 | −26.041 | −1.87 | −15.285 | 20.54 | C |
| ATOM | 232 | O | LEU | 1076 | −25.769 | −0.986 | −16.091 | 22.3 | O |
| ATOM | 233 | N | ILE | 1077 | −25.105 | −2.632 | −14.731 | 19.46 | N |
| ATOM | 234 | CA | ILE | 1077 | −23.738 | −2.495 | −15.208 | 18.87 | C |
| ATOM | 235 | CB | ILE | 1077 | −22.653 | −2.504 | −14.094 | 19.56 | C |
| ATOM | 236 | CG2 | ILE | 1077 | −21.285 | −2.271 | −14.737 | 19.59 | C |
| ATOM | 237 | CG1 | ILE | 1077 | −22.892 | −1.405 | −13.059 | 21.62 | C |
| ATOM | 238 | CD | ILE | 1077 | −24.062 | −1.664 | −12.118 | 28.65 | C |
| ATOM | 239 | C | ILE | 1077 | −23.51 | −3.766 | −16.037 | 17.95 | C |
| ATOM | 240 | O | ILE | 1077 | −23.793 | −4.863 | −15.563 | 15.66 | O |
| ATOM | 241 | N | VAL | 1078 | −23.053 | −3.637 | −17.28 | 17.31 | N |
| ATOM | 242 | CA | VAL | 1078 | −22.745 | −4.842 | −18.052 | 17.78 | C |
| ATOM | 243 | CB | VAL | 1078 | −23.077 | −4.777 | −19.553 | 18.44 | C |
| ATOM | 244 | CG1 | VAL | 1078 | −22.56 | −6.065 | −20.228 | 18.64 | C |
| ATOM | 245 | CG2 | VAL | 1078 | −24.569 | −4.616 | −19.782 | 17.46 | C |
| ATOM | 246 | C | VAL | 1078 | −21.243 | −4.876 | −17.998 | 19.43 | C |
| ATOM | 247 | O | VAL | 1078 | −20.587 | −3.934 | −18.433 | 19.77 | O |
| ATOM | 248 | N | HIS | 1079 | −20.68 | −5.943 | −17.467 | 20.51 | N |
| ATOM | 249 | CA | HIS | 1079 | −19.24 | −6.009 | −17.402 | 21.34 | C |
| ATOM | 250 | CB | HIS | 1079 | −18.849 | −6.917 | −16.23 | 19.83 | C |
| ATOM | 251 | CG | HIS | 1079 | −19.417 | −6.458 | −14.919 | 19.74 | C |
| ATOM | 252 | CD2 | HIS | 1079 | −20.228 | −7.077 | −14.027 | 19.88 | C |
| ATOM | 253 | ND1 | HIS | 1079 | −19.212 | −5.185 | −14.427 | 20.23 | N |
| ATOM | 254 | CE1 | HIS | 1079 | −19.876 | −5.038 | −13.293 | 18.18 | C |
| ATOM | 255 | NE2 | HIS | 1079 | −20.5 | −6.172 | −13.028 | 19.41 | N |
| ATOM | 256 | C | HIS | 1079 | −18.73 | −6.499 | −18.768 | 22.35 | C |
| ATOM | 257 | O | HIS | 1079 | −18.699 | −7.702 | −19.04 | 21.87 | O |
| ATOM | 258 | N | PHE | 1080 | −18.366 | −5.555 | −19.639 | 23.27 | N |
| ATOM | 259 | CA | PHE | 1080 | −17.898 | −5.913 | −20.977 | 25.46 | C |
| ATOM | 260 | CB | PHE | 1080 | −17.882 | −4.686 | −21.918 | 27.46 | C |
| ATOM | 261 | CG | PHE | 1080 | −19.259 | −4.25 | −22.39 | 29.48 | C |
| ATOM | 262 | CD1 | PHE | 1080 | −20.027 | −5.062 | −23.223 | 30.23 | C |
| ATOM | 263 | CD2 | PHE | 1080 | −19.798 | −3.04 | −21.968 | 30 | C |
| ATOM | 264 | CE1 | PHE | 1080 | −21.318 | −4.669 | −23.622 | 31.49 | C |
| ATOM | 265 | CE2 | PHE | 1080 | −21.078 | −2.644 | −22.36 | 30.98 | C |
| ATOM | 266 | CZ | PHE | 1080 | −21.838 | −3.459 | −23.187 | 30.57 | C |
| ATOM | 267 | C | PHE | 1080 | −16.536 | −6.6 | −20.987 | 26.31 | C |
| ATOM | 268 | O | PHE | 1080 | −16.179 | −7.225 | −21.975 | 26.79 | O |
| ATOM | 269 | N | ASN | 1081 | −15.765 | −6.508 | −19.907 | 27.81 | N |
| ATOM | 270 | CA | ASN | 1081 | −14.479 | −7.194 | −19.918 | 29.51 | C |
| ATOM | 271 | CB | ASN | 1081 | −13.346 | −6.286 | −19.398 | 32.42 | C |
| ATOM | 272 | CG | ASN | 1081 | −12.313 | −5.938 | −20.504 | 36.54 | C |
| ATOM | 273 | OD1 | ASN | 1081 | −12.536 | −5.047 | −21.34 | 36.01 | O |
| ATOM | 274 | ND2 | ASN | 1081 | −11.193 | −6.663 | −20.514 | 36.11 | N |
| ATOM | 275 | C | ASN | 1081 | −14.538 | −8.517 | −19.146 | 28.92 | C |
| ATOM | 276 | O | ASN | 1081 | −13.544 | −8.976 | −18.587 | 29.73 | O |
| ATOM | 277 | N | GLU | 1082 | −15.714 | −9.14 | −19.149 | 27.42 | N |
| ATOM | 278 | CA | GLU | 1082 | −15.91 | −10.408 | −18.464 | 27.47 | C |
| ATOM | 279 | CB | GLU | 1082 | −16.04 | −10.16 | −16.981 | 28.91 | C |
| ATOM | 280 | CG | GLU | 1082 | −14.864 | −10.669 | −16.224 | 31.39 | C |
| ATOM | 281 | CD | GLU | 1082 | −15.313 | −11.523 | −15.08 | 33.01 | C |
| ATOM | 282 | OE1 | GLU | 1082 | −15.894 | −10.968 | −14.122 | 30.29 | O |
| ATOM | 283 | OE2 | GLU | 1082 | −15.11 | −12.751 | −15.15 | 33.33 | O |
| ATOM | 284 | C | GLU | 1082 | −17.11 | −11.203 | −18.964 | 26.21 | C |
| ATOM | 285 | O | GLU | 1082 | −18.227 | −11.076 | −18.471 | 27.02 | O |
| ATOM | 286 | N | VAL | 1083 | −16.846 | −12.06 | −19.93 | 24.63 | N |
| ATOM | 287 | CA | VAL | 1083 | −17.86 | −12.87 | −20.574 | 23.96 | C |
| ATOM | 288 | CB | VAL | 1083 | −17.298 | −13.188 | −22 | 23.43 | C |
| ATOM | 289 | CG1 | VAL | 1083 | −18.161 | −14.146 | −22.766 | 23.66 | C |
| ATOM | 290 | CG2 | VAL | 1083 | −17.164 | −11.872 | −22.762 | 24.22 | C |
| ATOM | 291 | C | VAL | 1083 | −18.239 | −14.119 | −19.748 | 22.62 | C |
| ATOM | 292 | O | VAL | 1083 | −17.357 | −14.809 | −19.245 | 22.61 | O |
| ATOM | 293 | N | ILE | 1084 | −19.539 | −14.371 | −19.543 | 21.85 | N |
| ATOM | 294 | CA | ILE | 1084 | −19.95 | −15.584 | −18.81 | 22.19 | C |
| ATOM | 295 | CB | ILE | 1084 | −21.503 | −15.625 | −18.472 | 23.79 | C |
| ATOM | 296 | CG2 | ILE | 1084 | −21.863 | −16.953 | −17.767 | 24.46 | C |
| ATOM | 297 | CG1 | ILE | 1084 | −21.889 | −14.48 | −17.523 | 24.21 | C |
| ATOM | 298 | CD | ILE | 1084 | −23.311 | −14.031 | −17.657 | 27.1 | C |
| ATOM | 299 | C | ILE | 1084 | −19.588 | −16.697 | −19.82 | 21.17 | C |
| ATOM | 300 | O | ILE | 1084 | −18.999 | −17.715 | −19.466 | 22 | O |
| ATOM | 301 | N | GLY | 1085 | −19.905 | −16.471 | −21.091 | 20.77 | N |
| ATOM | 302 | CA | GLY | 1085 | −19.577 | −17.449 | −22.115 | 21.09 | C |
| ATOM | 303 | C | GLY | 1085 | −20.052 | −17.055 | −23.5 | 22.33 | C |
| ATOM | 304 | O | GLY | 1085 | −20.901 | −16.179 | −23.636 | 21.38 | O |
| ATOM | 305 | N | ARG | 1086 | −19.501 | −17.678 | −24.536 | 24.79 | N |
| ATOM | 306 | CA | ARG | 1086 | −19.944 | −17.371 | −25.886 | 27.33 | C |
| ATOM | 307 | CB | ARG | 1086 | −19.034 | −16.315 | −26.53 | 30.23 | C |
| ATOM | 308 | CG | ARG | 1086 | −17.68 | −16.806 | −26.973 | 34.24 | C |
| ATOM | 309 | CD | ARG | 1086 | −16.572 | −15.889 | −26.484 | 36.27 | C |

TABLE 1B-continued

| | | | | | | | | |
|---|---|---|---|---|---|---|---|---|
| ATOM | 310 | NE | ARG | 1086 | −16.649 | −14.513 | −26.972 | 38.68 | N |
| ATOM | 311 | CZ | ARG | 1086 | −15.93 | −13.53 | −26.443 | 40.82 | C |
| ATOM | 312 | NH1 | ARG | 1086 | −15.116 | −13.806 | −25.431 | 42.74 | N |
| ATOM | 313 | NH2 | ARG | 1086 | −16.009 | −12.29 | −26.908 | 40.02 | N |
| ATOM | 314 | C | ARG | 1086 | −20.039 | −18.618 | −26.755 | 26.1 | C |
| ATOM | 315 | O | ARG | 1086 | −19.714 | −19.722 | −26.323 | 26.61 | O |
| ATOM | 316 | N | GLY | 1087 | −20.526 | −18.421 | −27.97 | 25.65 | N |
| ATOM | 317 | CA | GLY | 1087 | −20.693 | −19.502 | −28.918 | 24.38 | C |
| ATOM | 318 | C | GLY | 1087 | −21.688 | −19 | −29.939 | 24.55 | C |
| ATOM | 319 | O | GLY | 1087 | −21.875 | −17.796 | −30.112 | 23.97 | O |
| ATOM | 320 | N | HIS | 1088 | −22.325 | −19.946 | −30.604 | 25.2 | N |
| ATOM | 321 | CA | HIS | 1088 | −23.333 | −19.7 | −31.616 | 25.57 | C |
| ATOM | 322 | CB | HIS | 1088 | −23.894 | −21.035 | −32.012 | 28.7 | C |
| ATOM | 323 | CG | HIS | 1088 | −22.846 | −21.938 | −32.566 | 32.77 | C |
| ATOM | 324 | CD2 | HIS | 1088 | −22.251 | −21.968 | −33.785 | 32.79 | C |
| ATOM | 325 | ND1 | HIS | 1088 | −22.396 | −23.074 | −31.911 | 34.14 | N |
| ATOM | 326 | CE1 | HIS | 1088 | −21.605 | −23.783 | −32.719 | 35.12 | C |
| ATOM | 327 | NE2 | HIS | 1088 | −21.517 | −23.138 | −33.868 | 34.26 | N |
| ATOM | 328 | C | HIS | 1088 | −24.476 | −18.786 | −31.172 | 25.12 | C |
| ATOM | 329 | O | HIS | 1088 | −25.102 | −18.116 | −31.997 | 24.17 | O |
| ATOM | 330 | N | PHE | 1089 | −24.776 | −18.797 | −29.875 | 23.19 | N |
| ATOM | 331 | CA | PHE | 1089 | −25.859 | −17.976 | −29.332 | 22.94 | C |
| ATOM | 332 | CB | PHE | 1089 | −26.286 | −18.457 | −27.929 | 22.43 | C |
| ATOM | 333 | CG | PHE | 1089 | −25.143 | −18.641 | −26.966 | 22.92 | C |
| ATOM | 334 | CD1 | PHE | 1089 | −24.626 | −19.908 | −26.724 | 22.34 | C |
| ATOM | 335 | CD2 | PHE | 1089 | −24.553 | −17.545 | −26.334 | 24.58 | C |
| ATOM | 336 | CE1 | PHE | 1089 | −23.54 | −20.084 | −25.877 | 23.16 | C |
| ATOM | 337 | CE2 | PHE | 1089 | −23.462 | −17.715 | −25.482 | 22.08 | C |
| ATOM | 338 | CZ | PHE | 1089 | −22.955 | −18.985 | −25.257 | 21.68 | C |
| ATOM | 339 | C | PHE | 1089 | −25.351 | −16.561 | −29.248 | 22.27 | C |
| ATOM | 340 | O | PHE | 1089 | −26.116 | −15.601 | −29.243 | 20.96 | O |
| ATOM | 341 | N | GLY | 1090 | −24.035 | −16.452 | −29.167 | 23.56 | N |
| ATOM | 342 | CA | GLY | 1090 | −23.423 | −15.151 | −29.11 | 23.31 | C |
| ATOM | 343 | C | GLY | 1090 | −22.48 | −14.936 | −27.958 | 23.5 | C |
| ATOM | 344 | O | GLY | 1090 | −21.532 | −15.694 | −27.727 | 24.61 | O |
| ATOM | 345 | N | CYS | 1091 | −22.778 | −13.877 | −27.225 | 21.88 | N |
| ATOM | 346 | CA | CYS | 1091 | −21.968 | −13.472 | −26.116 | 21.85 | C |
| ATOM | 347 | CB | CYS | 1091 | −21.026 | −12.375 | −26.578 | 22.79 | C |
| ATOM | 348 | SG | CYS | 1091 | −19.78 | −12.017 | −25.368 | 29.92 | S |
| ATOM | 349 | C | CYS | 1091 | −22.807 | −12.981 | −24.951 | 21.01 | C |
| ATOM | 350 | O | CYS | 1091 | −23.561 | −12.013 | −25.071 | 20.39 | O |
| ATOM | 351 | N | VAL | 1092 | −22.66 | −13.683 | −23.83 | 20.12 | N |
| ATOM | 352 | CA | VAL | 1092 | −23.357 | −13.391 | −22.586 | 17.5 | C |
| ATOM | 353 | CB | VAL | 1092 | −23.984 | −14.676 | −22.018 | 16.22 | C |
| ATOM | 354 | CG1 | VAL | 1092 | −24.836 | −14.367 | −20.794 | 14.54 | C |
| ATOM | 355 | CG2 | VAL | 1092 | −24.828 | −15.333 | −23.087 | 15.2 | C |
| ATOM | 356 | C | VAL | 1092 | −22.325 | −12.833 | −21.61 | 16.82 | C |
| ATOM | 357 | O | VAL | 1092 | −21.296 | −13.464 | −21.335 | 16.7 | O |
| ATOM | 358 | N | TYR | 1093 | −22.593 | −11.633 | −21.109 | 15.42 | N |
| ATOM | 359 | CA | TYR | 1093 | −21.682 | −10.994 | −20.185 | 17.23 | C |
| ATOM | 360 | CB | TYR | 1093 | −21.427 | −9.531 | −20.566 | 17.62 | C |
| ATOM | 361 | CG | TYR | 1093 | −20.851 | −9.299 | −21.945 | 20.58 | C |
| ATOM | 362 | CD1 | TYR | 1093 | −21.686 | −9.105 | −23.037 | 21.94 | C |
| ATOM | 363 | CE1 | TYR | 1093 | −21.165 | −8.829 | −24.305 | 24.31 | C |
| ATOM | 364 | CD2 | TYR | 1093 | −19.466 | −9.224 | −22.147 | 21.64 | C |
| ATOM | 365 | CE2 | TYR | 1093 | −18.932 | −8.951 | −23.409 | 23.55 | C |
| ATOM | 366 | CZ | TYR | 1093 | −19.79 | −8.751 | −24.484 | 25.26 | C |
| ATOM | 367 | OH | TYR | 1093 | −19.291 | −8.455 | −25.738 | 26.62 | O |
| ATOM | 368 | C | TYR | 1093 | −22.211 | −11.008 | −18.773 | 18.22 | C |
| ATOM | 369 | O | TYR | 1093 | −23.396 | −11.209 | −18.521 | 19.61 | O |
| ATOM | 370 | N | HIS | 1094 | −21.289 | −10.793 | −17.853 | 18.6 | N |
| ATOM | 371 | CA | HIS | 1094 | −21.604 | −10.698 | −16.452 | 18.83 | C |
| ATOM | 372 | CB | HIS | 1094 | −20.316 | −10.789 | −15.638 | 19.99 | C |
| ATOM | 373 | CG | HIS | 1094 | −19.836 | −12.185 | −15.394 | 21.1 | C |
| ATOM | 374 | CD2 | HIS | 1094 | −18.704 | −12.818 | −15.783 | 22.5 | C |
| ATOM | 375 | ND1 | HIS | 1094 | −20.491 | −13.057 | −14.551 | 21.79 | N |
| ATOM | 376 | CE1 | HIS | 1094 | −19.777 | −14.161 | −14.421 | 21.06 | C |
| ATOM | 377 | NE2 | HIS | 1094 | −18.687 | −14.04 | −15.157 | 21.09 | N |
| ATOM | 378 | C | HIS | 1094 | −22.177 | −9.281 | −16.328 | 18.78 | C |
| ATOM | 379 | O | HIS | 1094 | −21.78 | −8.382 | −17.073 | 18.3 | O |
| ATOM | 380 | N | GLY | 1095 | −23.116 | −9.099 | −15.41 | 19.1 | N |
| ATOM | 381 | CA | GLY | 1095 | −23.7 | −7.791 | −15.188 | 19.67 | C |
| ATOM | 382 | C | GLY | 1095 | −24.024 | −7.631 | −13.713 | 21.24 | C |
| ATOM | 383 | O | GLY | 1095 | −24.131 | −8.621 | −12.986 | 19.08 | O |
| ATOM | 384 | N | THR | 1096 | −24.141 | −6.388 | −13.259 | 23.02 | N |
| ATOM | 385 | CA | THR | 1096 | −24.501 | −6.095 | −11.874 | 22.84 | C |
| ATOM | 386 | CB | THR | 1096 | −23.404 | −5.275 | −11.14 | 23.36 | C |
| ATOM | 387 | OG1 | THR | 1096 | −22.428 | −6.166 | −10.589 | 26.41 | O |
| ATOM | 388 | CG2 | THR | 1096 | −24.01 | −4.451 | −10.016 | 24.26 | C |
| ATOM | 389 | C | THR | 1096 | −25.793 | −5.281 | −11.94 | 21.4 | C |

TABLE 1B-continued

| ATOM | 390 | O | THR | 1096 | −25.842 | −4.216 | −12.559 | 20.93 | O |
|---|---|---|---|---|---|---|---|---|---|
| ATOM | 391 | N | LEU | 1097 | −26.841 | −5.798 | −11.314 | 21.53 | N |
| ATOM | 392 | CA | LEU | 1097 | −28.141 | −5.141 | −11.326 | 21.82 | C |
| ATOM | 393 | CB | LEU | 1097 | −29.209 | −6.159 | −11.758 | 20.06 | C |
| ATOM | 394 | CG | LEU | 1097 | −30.646 | −5.76 | −12.111 | 19.25 | C |
| ATOM | 395 | CD1 | LEU | 1097 | −30.665 | −4.708 | −13.216 | 18.42 | C |
| ATOM | 396 | CD2 | LEU | 1097 | −31.385 | −7.007 | −12.565 | 16.83 | C |
| ATOM | 397 | C | LEU | 1097 | −28.519 | −4.53 | −9.981 | 21.19 | C |
| ATOM | 398 | O | LEU | 1097 | −28.367 | −5.164 | −8.938 | 19.7 | O |
| ATOM | 399 | N | LEU | 1098 | −28.996 | −3.286 | −10.021 | 23.17 | N |
| ATOM | 400 | CA | LEU | 1098 | −29.46 | −2.583 | −8.822 | 24.41 | C |
| ATOM | 401 | CB | LEU | 1098 | −29.613 | −1.09 | −9.083 | 26.16 | C |
| ATOM | 402 | CG | LEU | 1098 | −28.496 | −0.161 | −8.629 | 29.18 | C |
| ATOM | 403 | CD1 | LEU | 1098 | −29.114 | 1.203 | −8.341 | 28.63 | C |
| ATOM | 404 | CD2 | LEU | 1098 | −27.822 | −0.709 | −7.365 | 29.03 | C |
| ATOM | 405 | C | LEU | 1098 | −30.837 | −3.144 | −8.541 | 24.65 | C |
| ATOM | 406 | O | LEU | 1098 | −31.779 | −2.833 | −9.276 | 23.31 | O |
| ATOM | 407 | N | ASP | 1099 | −30.973 | −3.96 | −7.497 | 24.68 | N |
| ATOM | 408 | CA | ASP | 1099 | −32.283 | −4.545 | −7.224 | 26.36 | C |
| ATOM | 409 | CB | ASP | 1099 | −32.18 | −5.778 | −6.306 | 27.06 | C |
| ATOM | 410 | CG | ASP | 1099 | −32.004 | −5.446 | −4.831 | 29.17 | C |
| ATOM | 411 | OD1 | ASP | 1099 | −31.643 | −6.4 | −4.128 | 31.65 | O |
| ATOM | 412 | OD2 | ASP | 1099 | −32.229 | −4.305 | −4.365 | 28.08 | O |
| ATOM | 413 | C | ASP | 1099 | −33.244 | −3.518 | −6.686 | 27.55 | C |
| ATOM | 414 | O | ASP | 1099 | −32.875 | −2.344 | −6.562 | 26.26 | O |
| ATOM | 415 | N | ASN | 1100 | −34.477 | −3.923 | −6.374 | 29.32 | N |
| ATOM | 416 | CA | ASN | 1100 | −35.391 | −2.909 | −5.913 | 30.82 | C |
| ATOM | 417 | CB | ASN | 1100 | −36.817 | −3.375 | −5.712 | 28.63 | C |
| ATOM | 418 | CG | ASN | 1100 | −37.784 | −2.203 | −5.776 | 27.15 | C |
| ATOM | 419 | OD1 | ASN | 1100 | −37.902 | −1.518 | −6.802 | 25.47 | O |
| ATOM | 420 | ND2 | ASN | 1100 | −38.459 | −1.946 | −4.667 | 25.33 | N |
| ATOM | 421 | C | ASN | 1100 | −34.817 | −2.17 | −4.731 | 34.06 | C |
| ATOM | 422 | O | ASN | 1100 | −34.99 | −0.959 | −4.698 | 33.4 | O |
| ATOM | 423 | N | ASP | 1101 | −34.244 | −2.749 | −3.684 | 36.87 | N |
| ATOM | 424 | CA | ASP | 1101 | −33.561 | −1.645 | −3.071 | 40.16 | C |
| ATOM | 425 | CB | ASP | 1101 | −33.957 | −1.09 | −1.753 | 42.43 | C |
| ATOM | 426 | CG | ASP | 1101 | −33.365 | 0.343 | −1.643 | 44.17 | C |
| ATOM | 427 | OD1 | ASP | 1101 | −33.676 | 1.142 | −2.566 | 43.29 | O |
| ATOM | 428 | OD2 | ASP | 1101 | −32.573 | 0.673 | −0.723 | 44.41 | O |
| ATOM | 429 | C | ASP | 1101 | −32.097 | −1.555 | −3.027 | 40.36 | C |
| ATOM | 430 | O | ASP | 1101 | −31.468 | −1.272 | −4.032 | 40.01 | O |
| ATOM | 431 | N | GLY | 1102 | −31.538 | −1.723 | −1.849 | 40.9 | N |
| ATOM | 432 | CA | GLY | 1102 | −30.121 | −1.537 | −1.771 | 40.87 | C |
| ATOM | 433 | C | GLY | 1102 | −29.265 | −2.35 | −2.702 | 39.17 | C |
| ATOM | 434 | O | GLY | 1102 | −28.437 | −1.801 | −3.436 | 38.81 | O |
| ATOM | 435 | N | LYS | 1103 | −29.541 | −3.645 | −2.757 | 37.87 | N |
| ATOM | 436 | CA | LYS | 1103 | −28.614 | −4.503 | −3.44 | 35.83 | C |
| ATOM | 437 | CB | LYS | 1103 | −28.57 | −5.866 | −2.672 | 37.7 | C |
| ATOM | 438 | CG | LYS | 1103 | −29.817 | −6.811 | −2.577 | 41.49 | C |
| ATOM | 439 | CD | LYS | 1103 | −30.76 | −6.723 | −1.312 | 43.33 | C |
| ATOM | 440 | CE | LYS | 1103 | −32.272 | −6.806 | −1.734 | 43.17 | C |
| ATOM | 441 | NZ | LYS | 1103 | −33.348 | −7.174 | −0.746 | 44.65 | N |
| ATOM | 442 | C | LYS | 1103 | −28.306 | −4.733 | −4.911 | 32.44 | C |
| ATOM | 443 | O | LYS | 1103 | −29.144 | −4.908 | −5.808 | 32.36 | O |
| ATOM | 444 | N | LYS | 1104 | −26.985 | −4.671 | −5.06 | 29.44 | N |
| ATOM | 445 | CA | LYS | 1104 | −26.201 | −4.881 | −6.257 | 29.31 | C |
| ATOM | 446 | CB | LYS | 1104 | −24.733 | −4.422 | −5.988 | 31.35 | C |
| ATOM | 447 | CG | LYS | 1104 | −24.465 | −2.898 | −5.603 | 33.76 | C |
| ATOM | 448 | CD | LYS | 1104 | −23.118 | −2.693 | −4.801 | 37.44 | C |
| ATOM | 449 | CE | LYS | 1104 | −22.131 | −1.588 | −5.33 | 39.69 | C |
| ATOM | 450 | NZ | LYS | 1104 | −22.349 | −0.137 | −4.967 | 39.76 | N |
| ATOM | 451 | C | LYS | 1104 | −26.285 | −6.422 | −6.37 | 28.22 | C |
| ATOM | 452 | O | LYS | 1104 | −25.698 | −7.139 | −5.554 | 26.29 | O |
| ATOM | 453 | N | ILE | 1105 | −27.052 | −6.91 | −7.349 | 26.65 | N |
| ATOM | 454 | CA | ILE | 1105 | −27.265 | −8.348 | −7.598 | 26.94 | C |
| ATOM | 455 | CB | ILE | 1105 | −28.789 | −8.661 | −7.72 | 27.99 | C |
| ATOM | 456 | CG2 | ILE | 1105 | −29.026 | −9.839 | −8.673 | 30.38 | C |
| ATOM | 457 | CG1 | ILE | 1105 | −29.391 | −8.883 | −6.322 | 30.76 | C |
| ATOM | 458 | CD | ILE | 1105 | −28.852 | −10.101 | −5.536 | 35.19 | C |
| ATOM | 459 | C | ILE | 1105 | −26.558 | −8.837 | −8.877 | 25.68 | C |
| ATOM | 460 | O | ILE | 1105 | −26.505 | −8.118 | −9.874 | 24.13 | O |
| ATOM | 461 | N | HIS | 1106 | −26.034 | −10.06 | −8.854 | 23.56 | N |
| ATOM | 462 | CA | HIS | 1106 | −25.334 | −10.602 | −10.023 | 22.94 | C |
| ATOM | 463 | CB | HIS | 1106 | −24.409 | −11.758 | −9.615 | 24.08 | C |
| ATOM | 464 | CG | HIS | 1106 | −23.469 | −12.194 | −10.699 | 27.15 | C |
| ATOM | 465 | CD2 | HIS | 1106 | −23.422 | −11.885 | −12.018 | 28.42 | C |
| ATOM | 466 | ND1 | HIS | 1106 | −22.378 | −13.001 | −10.458 | 27.68 | N |
| ATOM | 467 | CE1 | HIS | 1106 | −21.695 | −13.161 | −11.578 | 29.8 | C |
| ATOM | 468 | NE2 | HIS | 1106 | −22.307 | −12.493 | −12.54 | 29.95 | N |
| ATOM | 469 | C | HIS | 1106 | −26.296 | −11.099 | −11.09 | 20.67 | C |

TABLE 1B-continued

| | | | | | | | | |
|---|---|---|---|---|---|---|---|---|
| ATOM | 470 | O | HIS | 1106 | −27.245 | −11.815 | −10.798 | 21.19 | O |
| ATOM | 471 | N | CYS | 1107 | −26.062 | −10.724 | −12.335 | 17.6 | N |
| ATOM | 472 | CA | CYS | 1107 | −26.938 | −11.208 | −13.385 | 17.33 | C |
| ATOM | 473 | CB | CYS | 1107 | −28.014 | −10.171 | −13.699 | 18.03 | C |
| ATOM | 474 | SG | CYS | 1107 | −27.321 | −8.564 | −14.194 | 19.36 | S |
| ATOM | 475 | C | CYS | 1107 | −26.13 | −11.512 | −14.638 | 17.39 | C |
| ATOM | 476 | O | CYS | 1107 | −24.931 | −11.213 | −14.715 | 17.99 | O |
| ATOM | 477 | N | ALA | 1108 | −26.793 | −12.125 | −15.608 | 14.48 | N |
| ATOM | 478 | CA | ALA | 1108 | −26.172 | −12.458 | −16.878 | 15.95 | C |
| ATOM | 479 | CB | ALA | 1108 | −26.418 | −13.93 | −17.204 | 15.75 | C |
| ATOM | 480 | C | ALA | 1108 | −26.89 | −11.56 | −17.883 | 15.24 | C |
| ATOM | 481 | O | ALA | 1108 | −28.107 | −11.399 | −17.798 | 12.68 | O |
| ATOM | 482 | N | VAL | 1109 | −26.177 | −10.958 | −18.827 | 15.61 | N |
| ATOM | 483 | CA | VAL | 1109 | −26.885 | −10.087 | −19.76 | 16.53 | C |
| ATOM | 484 | CB | VAL | 1109 | −26.732 | −8.557 | −19.371 | 18.81 | C |
| ATOM | 485 | CG1 | VAL | 1109 | −26.215 | −8.404 | −17.944 | 20.45 | C |
| ATOM | 486 | CG2 | VAL | 1109 | −25.815 | −7.839 | −20.346 | 19.51 | C |
| ATOM | 487 | C | VAL | 1109 | −26.504 | −10.231 | −21.227 | 17.08 | C |
| ATOM | 488 | O | VAL | 1109 | −25.378 | −10.611 | −21.561 | 17.04 | O |
| ATOM | 489 | N | LYS | 1110 | −27.461 | −9.952 | −22.107 | 17.38 | N |
| ATOM | 490 | CA | LYS | 1110 | −27.158 | −9.965 | −23.534 | 17.22 | C |
| ATOM | 491 | CB | LYS | 1110 | −26.814 | −11.372 | −24.044 | 19.64 | C |
| ATOM | 492 | CG | LYS | 1110 | −27.959 | −12.334 | −24.212 | 18.31 | C |
| ATOM | 493 | CD | LYS | 1110 | −28.051 | −12.821 | −25.655 | 19.3 | C |
| ATOM | 494 | CE | LYS | 1110 | −26.738 | −13.341 | −26.235 | 20.56 | C |
| ATOM | 495 | NZ | LYS | 1110 | −26.86 | −13.284 | −27.731 | 20.37 | N |
| ATOM | 496 | C | LYS | 1110 | −28.156 | −9.305 | −24.468 | 15.54 | C |
| ATOM | 497 | O | LYS | 1110 | −29.348 | −9.176 | −24.183 | 14.09 | O |
| ATOM | 498 | N | SER | 1111 | −27.58 | −8.874 | −25.586 | 15.93 | N |
| ATOM | 499 | CA | SER | 1111 | −28.193 | −8.161 | −26.691 | 16.27 | C |
| ATOM | 500 | CB | SER | 1111 | −27.094 | −7.361 | −27.375 | 15.21 | C |
| ATOM | 501 | OG | SER | 1111 | −27.529 | −6.71 | −28.544 | 18.36 | O |
| ATOM | 502 | C | SER | 1111 | −28.889 | −9.092 | −27.599 | 15.76 | C |
| ATOM | 503 | O | SER | 1111 | −28.454 | −10.211 | −27.947 | 12.53 | O |
| ATOM | 504 | N | LEU | 1112 | −30.098 | −8.685 | −27.952 | 17.34 | N |
| ATOM | 505 | CA | LEU | 1112 | −30.711 | −9.683 | −28.742 | 20.62 | C |
| ATOM | 506 | CB | LEU | 1112 | −32.234 | −9.458 | −28.562 | 20.06 | C |
| ATOM | 507 | CG | LEU | 1112 | −32.642 | −9.744 | −27.101 | 21.55 | C |
| ATOM | 508 | CD1 | LEU | 1112 | −33.953 | −9.403 | −26.868 | 19.7 | C |
| ATOM | 509 | CD2 | LEU | 1112 | −32.411 | −11.154 | −26.774 | 19.53 | C |
| ATOM | 510 | C | LEU | 1112 | −30.167 | −9.375 | −30.102 | 21.91 | C |
| ATOM | 511 | O | LEU | 1112 | −30.723 | −8.688 | −30.799 | 23.49 | O |
| ATOM | 512 | N | ASN | 1113 | −29.063 | −10.052 | −30.556 | 22.86 | N |
| ATOM | 513 | CA | ASN | 1113 | −28.909 | −9.404 | −31.85 | 23.45 | C |
| ATOM | 514 | CB | ASN | 1113 | −27.43 | −9.495 | −32.245 | 23.43 | C |
| ATOM | 515 | CG | ASN | 1113 | −26.585 | −9.117 | −31.09 | 25.58 | C |
| ATOM | 516 | OD1 | ASN | 1113 | −26.541 | −8.023 | −30.63 | 25.22 | O |
| ATOM | 517 | ND2 | ASN | 1113 | −25.914 | −10.072 | −30.585 | 22.74 | N |
| ATOM | 518 | C | ASN | 1113 | −29.885 | −9.566 | −33 | 22.92 | C |
| ATOM | 519 | O | ASN | 1113 | −29.831 | −8.839 | −33.944 | 23.28 | O |
| ATOM | 520 | N | ARG | 1114 | −30.958 | −10.381 | −32.816 | 21.82 | N |
| ATOM | 521 | CA | ARG | 1114 | −31.849 | −10.5 | −33.937 | 22.01 | C |
| ATOM | 522 | CB | ARG | 1114 | −32.4 | −11.948 | −33.913 | 22.1 | C |
| ATOM | 523 | CG | ARG | 1114 | −31.25 | −12.857 | −34.102 | 25.83 | C |
| ATOM | 524 | CD | ARG | 1114 | −31.459 | −14.259 | −33.982 | 28.53 | C |
| ATOM | 525 | NE | ARG | 1114 | −32.736 | −14.557 | −34.514 | 30.33 | N |
| ATOM | 526 | CZ | ARG | 1114 | −33.501 | −15.502 | −34.01 | 32.37 | C |
| ATOM | 527 | NH1 | ARG | 1114 | −33.154 | −16.204 | −32.927 | 30.58 | N |
| ATOM | 528 | NH2 | ARG | 1114 | −34.661 | −15.652 | −34.574 | 33.1 | N |
| ATOM | 529 | C | ARG | 1114 | −32.938 | −9.462 | −33.984 | 21.79 | C |
| ATOM | 530 | O | ARG | 1114 | −33.683 | −9.45 | −34.91 | 22.34 | O |
| ATOM | 531 | N | ILE | 1115 | −33.051 | −8.545 | −33.03 | 22.68 | N |
| ATOM | 532 | CA | ILE | 1115 | −34.107 | −7.541 | −33.104 | 21.2 | C |
| ATOM | 533 | CB | ILE | 1115 | −34.741 | −7.354 | −31.703 | 24.03 | C |
| ATOM | 534 | CG2 | ILE | 1115 | −35.642 | −6.144 | −31.668 | 23.21 | C |
| ATOM | 535 | CG1 | ILE | 1115 | −35.589 | −8.58 | −31.351 | 24.72 | C |
| ATOM | 536 | CD | ILE | 1115 | −35.868 | −8.729 | −29.851 | 26.57 | C |
| ATOM | 537 | C | ILE | 1115 | −33.318 | −6.335 | −33.548 | 21.28 | C |
| ATOM | 538 | O | ILE | 1115 | −32.489 | −5.821 | −32.809 | 20.76 | O |
| ATOM | 539 | N | THR | 1116 | −33.595 | −5.909 | −34.77 | 22.08 | N |
| ATOM | 540 | CA | THR | 1116 | −32.856 | −4.857 | −35.452 | 23.07 | C |
| ATOM | 541 | CB | THR | 1116 | −32.421 | −5.438 | −36.786 | 23.06 | C |
| ATOM | 542 | OG1 | THR | 1116 | −33.597 | −5.795 | −37.535 | 23.74 | O |
| ATOM | 543 | CG2 | THR | 1116 | −31.615 | −6.729 | −36.558 | 24.03 | C |
| ATOM | 544 | C | THR | 1116 | −33.622 | −3.572 | −35.704 | 23.05 | C |
| ATOM | 545 | O | THR | 1116 | −33.056 | −2.585 | −36.174 | 23.27 | O |
| ATOM | 546 | N | ASP | 1117 | −34.92 | −3.61 | −35.44 | 22.99 | N |
| ATOM | 547 | CA | ASP | 1117 | −35.759 | −2.447 | −35.643 | 24.43 | C |
| ATOM | 548 | CB | ASP | 1117 | −36.122 | −2.292 | −37.121 | 26.12 | C |
| ATOM | 549 | CG | ASP | 1117 | −37.083 | −3.345 | −37.6 | 28.5 | C |

TABLE 1B-continued

| | | | | | | | | |
|---|---|---|---|---|---|---|---|---|
| ATOM | 550 | OD1 | ASP | 1117 | −37.787 | −3.933 | −36.756 | 30.79 | O |
| ATOM | 551 | OD2 | ASP | 1117 | −37.151 | −3.569 | −38.826 | 30.95 | O |
| ATOM | 552 | C | ASP | 1117 | −37.002 | −2.491 | −34.764 | 23.72 | C |
| ATOM | 553 | O | ASP | 1117 | −37.291 | −3.5 | −34.122 | 23.98 | O |
| ATOM | 554 | N | ILE | 1118 | −37.743 | −1.388 | −34.77 | 24.56 | N |
| ATOM | 555 | CA | ILE | 1118 | −38.888 | −1.211 | −33.891 | 25.74 | C |
| ATOM | 556 | CB | ILE | 1118 | −39.278 | 0.274 | −33.878 | 25.32 | C |
| ATOM | 557 | CG2 | ILE | 1118 | −39.571 | 0.743 | −35.276 | 26.13 | C |
| ATOM | 558 | CG1 | ILE | 1118 | −40.435 | 0.497 | −32.915 | 24.98 | C |
| ATOM | 559 | CD | ILE | 1118 | −40.733 | 1.964 | −32.613 | 28.73 | C |
| ATOM | 560 | C | ILE | 1118 | −40.092 | −2.113 | −34.069 | 25.74 | C |
| ATOM | 561 | O | ILE | 1118 | −40.779 | −2.448 | −33.099 | 25.12 | O |
| ATOM | 562 | N | GLY | 1119 | −40.346 | −2.504 | −35.307 | 25.89 | N |
| ATOM | 563 | CA | GLY | 1119 | −41.422 | −3.437 | −35.543 | 25.68 | C |
| ATOM | 564 | C | GLY | 1119 | −41.012 | −4.734 | −34.844 | 25.67 | C |
| ATOM | 565 | O | GLY | 1119 | −41.864 | −5.425 | −34.288 | 25.14 | O |
| ATOM | 566 | N | GLU | 1120 | −39.715 | −5.066 | −34.85 | 23.75 | N |
| ATOM | 567 | CA | GLU | 1120 | −39.226 | −6.295 | −34.212 | 23.95 | C |
| ATOM | 568 | CB | GLU | 1120 | −37.817 | −6.627 | −34.706 | 24.69 | C |
| ATOM | 569 | CG | GLU | 1120 | −37.823 | −7.463 | −35.977 | 25.41 | C |
| ATOM | 570 | CD | GLU | 1120 | −36.543 | −7.319 | −36.777 | 27.56 | C |
| ATOM | 571 | OE1 | GLU | 1120 | −35.575 | −6.731 | −36.247 | 26.97 | O |
| ATOM | 572 | OE2 | GLU | 1120 | −36.499 | −7.797 | −37.934 | 28.81 | O |
| ATOM | 573 | C | GLU | 1120 | −39.262 | −6.176 | −32.692 | 23.53 | C |
| ATOM | 574 | O | GLU | 1120 | −39.737 | −7.076 | −31.996 | 20.73 | O |
| ATOM | 575 | N | VAL | 1121 | −38.759 | −5.057 | −32.192 | 22.95 | N |
| ATOM | 576 | CA | VAL | 1121 | −38.797 | −4.775 | −30.769 | 24.45 | C |
| ATOM | 577 | CB | VAL | 1121 | −38.396 | −3.315 | −30.51 | 24.85 | C |
| ATOM | 578 | CG1 | VAL | 1121 | −38.695 | −2.929 | −29.063 | 21.7 | C |
| ATOM | 579 | CG2 | VAL | 1121 | −36.933 | −3.111 | −30.857 | 23.7 | C |
| ATOM | 580 | C | VAL | 1121 | −40.259 | −4.934 | −30.333 | 26.12 | C |
| ATOM | 581 | O | VAL | 1121 | −40.567 | −5.618 | −29.349 | 26.27 | O |
| ATOM | 582 | N | SER | 1122 | −41.16 | −4.303 | −31.084 | 26.23 | N |
| ATOM | 583 | CA | SER | 1122 | −42.583 | −4.322 | −30.75 | 27.11 | C |
| ATOM | 584 | CB | SER | 1122 | −43.374 | −3.492 | −31.766 | 28.38 | C |
| ATOM | 585 | OG | SER | 1122 | −44.763 | −3.526 | −31.482 | 32.31 | O |
| ATOM | 586 | C | SER | 1122 | −43.171 | −5.722 | −30.644 | 26.65 | C |
| ATOM | 587 | O | SER | 1122 | −43.865 | −6.045 | −29.677 | 25.95 | O |
| ATOM | 588 | N | GLN | 1123 | −42.893 | −6.553 | −31.641 | 26.43 | N |
| ATOM | 589 | CA | GLN | 1123 | −43.39 | −7.919 | −31.636 | 26.5 | C |
| ATOM | 590 | CB | GLN | 1123 | −43.046 | −8.607 | −32.955 | 29.41 | C |
| ATOM | 591 | CG | GLN | 1123 | −43.203 | −10.123 | −32.919 | 33.88 | C |
| ATOM | 592 | CD | GLN | 1123 | −43.393 | −10.721 | −34.301 | 36.39 | C |
| ATOM | 593 | OE1 | GLN | 1123 | −42.587 | −10.498 | −35.203 | 36.5 | O |
| ATOM | 594 | NE2 | GLN | 1123 | −44.467 | −11.489 | −34.472 | 38.02 | N |
| ATOM | 595 | C | GLN | 1123 | −42.801 | −8.714 | −30.47 | 25.95 | C |
| ATOM | 596 | O | GLN | 1123 | −43.454 | −9.597 | −29.918 | 24.87 | O |
| ATOM | 597 | N | PHE | 1124 | −41.557 | −8.402 | −30.114 | 24.65 | N |
| ATOM | 598 | CA | PHE | 1124 | −40.871 | −9.079 | −29.023 | 23.66 | C |
| ATOM | 599 | CB | PHE | 1124 | −39.414 | −8.629 | −28.955 | 23.72 | C |
| ATOM | 600 | CG | PHE | 1124 | −38.77 | −8.86 | −27.618 | 23.58 | C |
| ATOM | 601 | CD1 | PHE | 1124 | −38.694 | −10.14 | −27.076 | 25.18 | C |
| ATOM | 602 | CD2 | PHE | 1124 | −38.24 | −7.798 | −26.902 | 24 | C |
| ATOM | 603 | CE1 | PHE | 1124 | −38.097 | −10.354 | −25.834 | 25.88 | C |
| ATOM | 604 | CE2 | PHE | 1124 | −37.642 | −8 | −25.662 | 25.31 | C |
| ATOM | 605 | CZ | PHE | 1124 | −37.568 | −9.276 | −25.128 | 25.33 | C |
| ATOM | 606 | C | PHE | 1124 | −41.544 | −8.749 | −27.715 | 24.78 | C |
| ATOM | 607 | O | PHE | 1124 | −41.873 | −9.621 | −26.92 | 26.5 | O |
| ATOM | 608 | N | LEU | 1125 | −41.723 | −7.466 | −27.479 | 23.2 | N |
| ATOM | 609 | CA | LEU | 1125 | −42.356 | −7.073 | −26.261 | 22.77 | C |
| ATOM | 610 | CB | LEU | 1125 | −42.567 | −5.598 | −26.229 | 21.09 | C |
| ATOM | 611 | CG | LEU | 1125 | −41.236 | −4.899 | −26.129 | 17.73 | C |
| ATOM | 612 | CD1 | LEU | 1125 | −41.631 | −3.496 | −26.146 | 19.09 | C |
| ATOM | 613 | CD2 | LEU | 1125 | −40.427 | −5.218 | −24.871 | 16.2 | C |
| ATOM | 614 | C | LEU | 1125 | −43.682 | −7.72 | −26.132 | 25.71 | C |
| ATOM | 615 | O | LEU | 1125 | −44.116 | −8.03 | −25.032 | 23.93 | O |
| ATOM | 616 | N | THR | 1126 | −44.368 | −7.944 | −27.228 | 26.97 | N |
| ATOM | 617 | CA | THR | 1126 | −45.639 | −8.549 | −26.998 | 30.56 | C |
| ATOM | 618 | CB | THR | 1126 | −46.474 | −8.47 | −28.349 | 30.39 | C |
| ATOM | 619 | OG1 | THR | 1126 | −47.089 | −7.172 | −28.448 | 31.21 | O |
| ATOM | 620 | CG2 | THR | 1126 | −47.536 | −9.509 | −28.425 | 32.25 | C |
| ATOM | 621 | C | THR | 1126 | −45.308 | −9.955 | −26.367 | 32.6 | C |
| ATOM | 622 | O | THR | 1126 | −46.214 | −10.759 | −26.142 | 30.99 | O |
| ATOM | 623 | N | GLU | 1127 | −44.006 | −10.139 | −25.994 | 35.71 | N |
| ATOM | 624 | CA | GLU | 1127 | −43.324 | −11.363 | −25.421 | 37.11 | C |
| ATOM | 625 | CB | GLU | 1127 | −42.663 | −12.118 | −26.553 | 36.36 | C |
| ATOM | 626 | CG | GLU | 1127 | −43.597 | −12.481 | −27.631 | 39.29 | C |
| ATOM | 627 | CD | GLU | 1127 | −44.476 | −13.585 | −27.184 | 41.29 | C |
| ATOM | 628 | OE1 | GLU | 1127 | −44.087 | −14.213 | −26.181 | 41.62 | O |
| ATOM | 629 | OE2 | GLU | 1127 | −45.523 | −13.843 | −27.816 | 43.61 | O |

TABLE 1B-continued

| | | | | | | | | |
|---|---|---|---|---|---|---|---|---|
| ATOM | 630 | C | GLU | 1127 | −42.227 | −11.228 | −24.313 | 36.65 | C |
| ATOM | 631 | O | GLU | 1127 | −41.449 | −12.168 | −24.042 | 36.3 | O |
| ATOM | 632 | N | GLY | 1128 | −42.13 | −10.02 | −23.774 | 37.88 | N |
| ATOM | 633 | CA | GLY | 1128 | −41.248 | −9.679 | −22.675 | 36.79 | C |
| ATOM | 634 | C | GLY | 1128 | −42.463 | −9.503 | −21.803 | 36.28 | C |
| ATOM | 635 | O | GLY | 1128 | −42.531 | −8.689 | −20.88 | 34.64 | O |
| ATOM | 636 | N | ILE | 1129 | −43.485 | −10.238 | −22.251 | 36.52 | N |
| ATOM | 637 | CA | ILE | 1129 | −44.786 | −10.362 | −21.617 | 37.06 | C |
| ATOM | 638 | CB | ILE | 1129 | −45.997 | −10.386 | −22.653 | 35.43 | C |
| ATOM | 639 | CG2 | ILE | 1129 | −47.188 | −11.204 | −22.111 | 33.75 | C |
| ATOM | 640 | CG1 | ILE | 1129 | −46.554 | −8.978 | −22.897 | 35.19 | C |
| ATOM | 641 | CD | ILE | 1129 | −46.993 | −8.179 | −21.639 | 36.58 | C |
| ATOM | 642 | C | ILE | 1129 | −44.562 | −11.78 | −21.112 | 38.14 | C |
| ATOM | 643 | O | ILE | 1129 | −43.906 | −12.012 | −20.096 | 40.02 | O |
| ATOM | 644 | N | ILE | 1130 | −45.05 | −12.697 | −21.936 | 39.77 | N |
| ATOM | 645 | CA | ILE | 1130 | −45.059 | −14.15 | −21.818 | 39.09 | C |
| ATOM | 646 | CB | ILE | 1130 | −45.827 | −14.638 | −23.165 | 37.23 | C |
| ATOM | 647 | CG2 | ILE | 1130 | −46.725 | −15.832 | −22.942 | 35.01 | C |
| ATOM | 648 | CG1 | ILE | 1130 | −46.834 | −13.555 | −23.613 | 36.25 | C |
| ATOM | 649 | CD | ILE | 1130 | −47.219 | −13.572 | −25.099 | 35.76 | C |
| ATOM | 650 | C | ILE | 1130 | −43.655 | −14.881 | −21.549 | 41.51 | C |
| ATOM | 651 | O | ILE | 1130 | −43.156 | −15.56 | −22.452 | 39.43 | O |
| ATOM | 652 | N | MET | 1131 | −43.035 | −14.698 | −20.346 | 42.91 | N |
| ATOM | 653 | CA | MET | 1131 | −41.742 | −15.349 | −19.835 | 44.95 | C |
| ATOM | 654 | CB | MET | 1131 | −40.472 | −15.204 | −20.764 | 46.01 | C |
| ATOM | 655 | CG | MET | 1131 | −39.274 | −16.281 | −20.43 | 45.5 | C |
| ATOM | 656 | SD | MET | 1131 | −37.426 | −16.086 | −20.877 | 48.89 | S |
| ATOM | 657 | CE | MET | 1131 | −36.526 | −17.834 | −20.399 | 44.9 | C |
| ATOM | 658 | C | MET | 1131 | −41.305 | −14.898 | −18.397 | 45.24 | C |
| ATOM | 659 | O | MET | 1131 | −40.606 | −15.644 | −17.7 | 46.07 | O |
| ATOM | 660 | N | LYS | 1132 | −41.711 | −13.684 | −17.992 | 45.8 | N |
| ATOM | 661 | CA | LYS | 1132 | −41.448 | −13.047 | −16.667 | 44.47 | C |
| ATOM | 662 | CB | LYS | 1132 | −41.153 | −11.536 | −16.863 | 44.62 | C |
| ATOM | 663 | CG | LYS | 1132 | −41.633 | −10.562 | −15.744 | 45.98 | C |
| ATOM | 664 | CD | LYS | 1132 | −40.704 | −10.607 | −14.528 | 47.24 | C |
| ATOM | 665 | CE | LYS | 1132 | −41.097 | −9.681 | −13.372 | 48.16 | C |
| ATOM | 666 | NZ | LYS | 1132 | −39.906 | −9.52 | −12.48 | 50.03 | N |
| ATOM | 667 | C | LYS | 1132 | −42.766 | −13.202 | −15.908 | 43.38 | C |
| ATOM | 668 | O | LYS | 1132 | −42.822 | −13.535 | −14.706 | 44.16 | O |
| ATOM | 669 | N | ASP | 1133 | −43.81 | −12.924 | −16.69 | 40.97 | N |
| ATOM | 670 | CA | ASP | 1133 | −45.216 | −12.985 | −16.338 | 37.24 | C |
| ATOM | 671 | CB | ASP | 1133 | −45.968 | −11.948 | −17.229 | 39.7 | C |
| ATOM | 672 | CG | ASP | 1133 | −45.378 | −10.475 | −17.104 | 44.34 | C |
| ATOM | 673 | OD1 | ASP | 1133 | −45.471 | −9.672 | −18.073 | 46.2 | O |
| ATOM | 674 | OD2 | ASP | 1133 | −44.832 | −10.103 | −16.036 | 45.51 | O |
| ATOM | 675 | C | ASP | 1133 | −45.599 | −14.51 | −16.559 | 32.78 | C |
| ATOM | 676 | O | ASP | 1133 | −46.634 | −14.894 | −17.119 | 29.59 | O |
| ATOM | 677 | N | PHE | 1134 | −44.642 | −15.327 | −16.103 | 27.86 | N |
| ATOM | 678 | CA | PHE | 1134 | −44.601 | −16.796 | −16.002 | 22.57 | C |
| ATOM | 679 | CB | PHE | 1134 | −43.753 | −17.483 | −17.107 | 22.44 | C |
| ATOM | 680 | CG | PHE | 1134 | −44.565 | −18.066 | −18.259 | 19.89 | C |
| ATOM | 681 | CD1 | PHE | 1134 | −43.967 | −18.296 | −19.503 | 16.65 | C |
| ATOM | 682 | CD2 | PHE | 1134 | −45.934 | −18.311 | −18.126 | 18.05 | C |
| ATOM | 683 | CE1 | PHE | 1134 | −44.725 | −18.745 | −20.598 | 15.13 | C |
| ATOM | 684 | CE2 | PHE | 1134 | −46.697 | −18.762 | −19.214 | 16.83 | C |
| ATOM | 685 | CZ | PHE | 1134 | −46.092 | −18.973 | −20.449 | 16.75 | C |
| ATOM | 686 | C | PHE | 1134 | −43.795 | −16.804 | −14.689 | 19.23 | C |
| ATOM | 687 | O | PHE | 1134 | −42.732 | −16.175 | −14.607 | 15.87 | O |
| ATOM | 688 | N | SER | 1135 | −44.293 | −17.468 | −13.656 | 15.8 | N |
| ATOM | 689 | CA | SER | 1135 | −43.575 | −17.473 | −12.397 | 13.93 | C |
| ATOM | 690 | CB | SER | 1135 | −44.165 | −16.454 | −11.426 | 12.94 | C |
| ATOM | 691 | OG | SER | 1135 | −43.254 | −16.177 | −10.383 | 15.88 | O |
| ATOM | 692 | C | SER | 1135 | −43.654 | −18.829 | −11.775 | 12.54 | C |
| ATOM | 693 | O | SER | 1135 | −44.695 | −19.221 | −11.262 | 11.79 | O |
| ATOM | 694 | N | HIS | 1136 | −42.548 | −19.547 | −11.831 | 11.97 | N |
| ATOM | 695 | CA | HIS | 1136 | −42.491 | −20.859 | −11.253 | 12.4 | C |
| ATOM | 696 | CB | HIS | 1136 | −43.068 | −21.88 | −12.226 | 10.91 | C |
| ATOM | 697 | CG | HIS | 1136 | −43.199 | −23.24 | −11.633 | 12.1 | C |
| ATOM | 698 | CD2 | HIS | 1136 | −44.246 | −23.858 | −11.036 | 10.8 | C |
| ATOM | 699 | ND1 | HIS | 1136 | −42.127 | −24.097 | −11.518 | 10.52 | N |
| ATOM | 700 | CE1 | HIS | 1136 | −42.506 | −25.185 | −10.872 | 11.14 | C |
| ATOM | 701 | NE2 | HIS | 1136 | −43.786 | −25.065 | −10.569 | 11.88 | N |
| ATOM | 702 | C | HIS | 1136 | −41.034 | −21.143 | −10.917 | 13.17 | C |
| ATOM | 703 | O | HIS | 1136 | −40.127 | −20.784 | −11.67 | 12.81 | O |
| ATOM | 704 | N | PRO | 1137 | −40.79 | −21.774 | −9.763 | 14.54 | N |
| ATOM | 705 | CD | PRO | 1137 | −41.762 | −22.325 | −8.797 | 13.56 | C |
| ATOM | 706 | CA | PRO | 1137 | −39.414 | −22.076 | −9.36 | 15.38 | C |
| ATOM | 707 | CB | PRO | 1137 | −39.597 | −22.831 | −8.035 | 13.45 | C |
| ATOM | 708 | CG | PRO | 1137 | −40.974 | −23.438 | −8.155 | 17.2 | C |
| ATOM | 709 | C | PRO | 1137 | −38.568 | −22.842 | −10.386 | 15.05 | C |

TABLE 1B-continued

| | | | | | | | | |
|---|---|---|---|---|---|---|---|---|
| ATOM | 710 | O | PRO | 1137 | −37.334 | −22.756 | −10.366 | 14.8 | O |
| ATOM | 711 | N | ASN | 1138 | −39.23 | −23.571 | −11.286 | 14.53 | N |
| ATOM | 712 | CA | ASN | 1138 | −38.546 | −24.338 | −12.328 | 13.54 | C |
| ATOM | 713 | CB | ASN | 1138 | −38.979 | −25.801 | −12.281 | 11.91 | C |
| ATOM | 714 | CG | ASN | 1138 | −38.491 | −26.491 | −11.042 | 15.12 | C |
| ATOM | 715 | OD1 | ASN | 1138 | −39.279 | −26.876 | −10.183 | 14.55 | O |
| ATOM | 716 | ND2 | ASN | 1138 | −37.176 | −26.639 | −10.928 | 15.25 | N |
| ATOM | 717 | C | ASN | 1138 | −38.752 | −23.804 | −13.736 | 12.76 | C |
| ATOM | 718 | O | ASN | 1138 | −38.733 | −24.573 | −14.699 | 13.13 | O |
| ATOM | 719 | N | VAL | 1139 | −38.967 | −22.493 | −13.836 | 14.58 | N |
| ATOM | 720 | CA | VAL | 1139 | −39.148 | −21.797 | −15.115 | 14.5 | C |
| ATOM | 721 | CB | VAL | 1139 | −40.634 | −21.332 | −15.343 | 16.08 | C |
| ATOM | 722 | CG1 | VAL | 1139 | −40.715 | −20.404 | −16.561 | 14.73 | C |
| ATOM | 723 | CG2 | VAL | 1139 | −41.543 | −22.544 | −15.556 | 14.08 | C |
| ATOM | 724 | C | VAL | 1139 | −38.246 | −20.56 | −15.074 | 15.17 | C |
| ATOM | 725 | O | VAL | 1139 | −38.351 | −19.736 | −14.157 | 13.04 | O |
| ATOM | 726 | N | LEU | 1140 | −37.358 | −20.427 | −16.059 | 14.62 | N |
| ATOM | 727 | CA | LEU | 1140 | −36.445 | −19.281 | −16.098 | 13.44 | C |
| ATOM | 728 | CB | LEU | 1140 | −35.213 | −19.59 | −16.962 | 12.31 | C |
| ATOM | 729 | CG | LEU | 1140 | −34.085 | −18.546 | −16.992 | 10.46 | C |
| ATOM | 730 | CD1 | LEU | 1140 | −33.328 | −18.594 | −15.684 | 13.12 | C |
| ATOM | 731 | CD2 | LEU | 1140 | −33.128 | −18.82 | −18.148 | 9.58 | C |
| ATOM | 732 | C | LEU | 1140 | −37.118 | −18.024 | −16.634 | 14.11 | C |
| ATOM | 733 | O | LEU | 1140 | −37.551 | −17.962 | −17.786 | 14.02 | O |
| ATOM | 734 | N | SER | 1141 | −37.201 | −17.012 | −15.791 | 15.03 | N |
| ATOM | 735 | CA | SER | 1141 | −37.794 | −15.759 | −16.214 | 17.47 | C |
| ATOM | 736 | CB | SER | 1141 | −38.961 | −15.397 | −15.302 | 17.42 | C |
| ATOM | 737 | OG | SER | 1141 | −39.908 | −16.448 | −15.288 | 16.21 | O |
| ATOM | 738 | C | SER | 1141 | −36.75 | −14.654 | −16.178 | 18.33 | C |
| ATOM | 739 | O | SER | 1141 | −35.783 | −14.702 | −15.405 | 19.08 | O |
| ATOM | 740 | N | LEU | 1142 | −36.949 | −13.664 | −17.031 | 18.51 | N |
| ATOM | 741 | CA | LEU | 1142 | −36.046 | −12.537 | −17.079 | 20.96 | C |
| ATOM | 742 | CB | LEU | 1142 | −36.333 | −11.641 | −18.288 | 24.4 | C |
| ATOM | 743 | CG | LEU | 1142 | −37.635 | −11.494 | −19.093 | 26.67 | C |
| ATOM | 744 | CD1 | LEU | 1142 | −37.157 | −11.596 | −20.531 | 28.07 | C |
| ATOM | 745 | CD2 | LEU | 1142 | −38.723 | −12.554 | −18.83 | 30.08 | C |
| ATOM | 746 | C | LEU | 1142 | −36.199 | −11.719 | −15.831 | 20.09 | C |
| ATOM | 747 | O | LEU | 1142 | −37.276 | −11.671 | −15.243 | 18.69 | O |
| ATOM | 748 | N | LEU | 1143 | −35.102 | −11.099 | −15.418 | 19.75 | N |
| ATOM | 749 | CA | LEU | 1143 | −35.129 | −10.217 | −14.275 | 18.51 | C |
| ATOM | 750 | CB | LEU | 1143 | −33.714 | −10.014 | −13.7 | 20.09 | C |
| ATOM | 751 | CG | LEU | 1143 | −33.069 | −11.105 | −12.816 | 20.67 | C |
| ATOM | 752 | CD1 | LEU | 1143 | −31.795 | −10.548 | −12.2 | 19.71 | C |
| ATOM | 753 | CD2 | LEU | 1143 | −34.021 | −11.539 | −11.693 | 20.92 | C |
| ATOM | 754 | C | LEU | 1143 | −35.662 | −8.929 | −14.905 | 18.23 | C |
| ATOM | 755 | O | LEU | 1143 | −36.354 | −8.141 | −14.258 | 18.44 | O |
| ATOM | 756 | N | GLY | 1144 | −35.359 | −8.731 | −16.191 | 16.4 | N |
| ATOM | 757 | CA | GLY | 1144 | −35.837 | −7.543 | −16.874 | 14.04 | C |
| ATOM | 758 | C | GLY | 1144 | −35.224 | −7.371 | −18.245 | 15.5 | C |
| ATOM | 759 | O | GLY | 1144 | −34.485 | −8.226 | −18.713 | 15.81 | O |
| ATOM | 760 | N | ILE | 1145 | −35.539 | −6.274 | −18.911 | 16.87 | N |
| ATOM | 761 | CA | ILE | 1145 | −34.972 | −6.031 | −20.225 | 18.26 | C |
| ATOM | 762 | CB | ILE | 1145 | −35.981 | −6.403 | −21.409 | 19.17 | C |
| ATOM | 763 | CG2 | ILE | 1145 | −36.919 | −7.552 | −21.014 | 19.39 | C |
| ATOM | 764 | CG1 | ILE | 1145 | −36.829 | −5.188 | −21.848 | 21.36 | C |
| ATOM | 765 | CD | ILE | 1145 | −37.787 | −4.592 | −20.8 | 25.83 | C |
| ATOM | 766 | C | ILE | 1145 | −34.699 | −4.549 | −20.34 | 18.79 | C |
| ATOM | 767 | O | ILE | 1145 | −35.295 | −3.764 | −19.609 | 19.26 | O |
| ATOM | 768 | N | CYS | 1146 | −33.713 | −4.129 | −21.11 | 21.57 | N |
| ATOM | 769 | CA | CYS | 1146 | −33.808 | −2.713 | −21.347 | 24.57 | C |
| ATOM | 770 | CB | CYS | 1146 | −32.932 | −1.749 | −20.568 | 27.61 | C |
| ATOM | 771 | SG | CYS | 1146 | −33.831 | −0.088 | −20.586 | 32.88 | S |
| ATOM | 772 | C | CYS | 1146 | −33.743 | −2.422 | −22.789 | 23.95 | C |
| ATOM | 773 | O | CYS | 1146 | −33.051 | −3.059 | −23.594 | 24.57 | O |
| ATOM | 774 | N | LEU | 1147 | −34.617 | −1.474 | −23.069 | 23.64 | N |
| ATOM | 775 | CA | LEU | 1147 | −34.914 | −0.935 | −24.363 | 23.73 | C |
| ATOM | 776 | CB | LEU | 1147 | −36.373 | −0.494 | −24.408 | 23.23 | C |
| ATOM | 777 | CG | LEU | 1147 | −37.678 | −1.312 | −24.387 | 24.45 | C |
| ATOM | 778 | CD1 | LEU | 1147 | −37.461 | −2.649 | −25.062 | 23.58 | C |
| ATOM | 779 | CD2 | LEU | 1147 | −38.205 | −1.491 | −22.981 | 24.44 | C |
| ATOM | 780 | C | LEU | 1147 | −34.067 | 0.269 | −24.673 | 23.59 | C |
| ATOM | 781 | O | LEU | 1147 | −34.394 | 1.389 | −24.275 | 23.87 | O |
| ATOM | 782 | N | ARG | 1148 | −33.001 | 0.038 | −25.412 | 23.12 | N |
| ATOM | 783 | CA | ARG | 1148 | −32.106 | 1.095 | −25.808 | 22.97 | C |
| ATOM | 784 | CB | ARG | 1148 | −30.734 | 0.495 | −25.988 | 23.4 | C |
| ATOM | 785 | CG | ARG | 1148 | −30.35 | −0.366 | −24.817 | 24.2 | C |
| ATOM | 786 | CD | ARG | 1148 | −28.914 | −0.697 | −24.921 | 21.72 | C |
| ATOM | 787 | NE | ARG | 1148 | −28.681 | −1.755 | −25.884 | 20.32 | N |
| ATOM | 788 | CZ | ARG | 1148 | −27.484 | −2.001 | −26.385 | 20.41 | C |
| ATOM | 789 | NH1 | ARG | 1148 | −26.471 | −1.248 | −25.996 | 19.37 | N |

TABLE 1B-continued

| | | | | | | | | |
|---|---|---|---|---|---|---|---|---|
| ATOM | 790 | NH2 | ARG | 1148 | −27.284 | −2.999 | −27.237 | 19.66 | N |
| ATOM | 791 | C | ARG | 1148 | −32.534 | 1.748 | −27.12 | 22.97 | C |
| ATOM | 792 | O | ARG | 1148 | −33.294 | 1.182 | −27.908 | 21.03 | O |
| ATOM | 793 | N | SER | 1149 | −32.069 | 2.956 | −27.361 | 23.25 | N |
| ATOM | 794 | CA | SER | 1149 | −32.407 | 3.517 | −28.637 | 23.55 | C |
| ATOM | 795 | CB | SER | 1149 | −32.661 | 4.995 | −28.55 | 24.41 | C |
| ATOM | 796 | OG | SER | 1149 | −31.484 | 5.636 | −28.145 | 25.43 | O |
| ATOM | 797 | C | SER | 1149 | −31.292 | 3.142 | −29.624 | 23.14 | C |
| ATOM | 798 | O | SER | 1149 | −31.555 | 3.159 | −30.796 | 23.95 | O |
| ATOM | 799 | N | GLU | 1150 | −30.052 | 2.888 | −29.203 | 23.72 | N |
| ATOM | 800 | CA | GLU | 1150 | −29.119 | 2.289 | −30.16 | 25.39 | C |
| ATOM | 801 | CB | GLU | 1150 | −27.729 | 2.816 | −30.061 | 27.71 | C |
| ATOM | 802 | CG | GLU | 1150 | −27.793 | 4.064 | −29.446 | 32.33 | C |
| ATOM | 803 | CD | GLU | 1150 | −27.698 | 5.005 | −30.524 | 35.64 | C |
| ATOM | 804 | OE1 | GLU | 1150 | −26.732 | 5.794 | −30.561 | 34.51 | O |
| ATOM | 805 | OE2 | GLU | 1150 | −28.587 | 4.89 | −31.384 | 37 | O |
| ATOM | 806 | C | GLU | 1150 | −28.961 | 0.921 | −29.518 | 23.45 | C |
| ATOM | 807 | O | GLU | 1150 | −28.64 | 0.859 | −28.325 | 21.36 | O |
| ATOM | 808 | N | GLY | 1151 | −28.982 | −0.078 | −30.413 | 22.51 | N |
| ATOM | 809 | CA | GLY | 1151 | −28.828 | −1.495 | −30.147 | 21.13 | C |
| ATOM | 810 | C | GLY | 1151 | −30.042 | −2.16 | −29.833 | 20.26 | C |
| ATOM | 811 | O | GLY | 1151 | −30.916 | −1.448 | −29.502 | 20.28 | O |
| ATOM | 812 | N | SER | 1152 | −30.155 | −3.445 | −30.24 | 20.15 | N |
| ATOM | 813 | CA | SER | 1152 | −31.201 | −4.317 | −29.94 | 19.17 | C |
| ATOM | 814 | CB | SER | 1152 | −30.704 | −5.674 | −30.274 | 20.12 | C |
| ATOM | 815 | OG | SER | 1152 | −29.814 | −5.608 | −31.375 | 20.17 | O |
| ATOM | 816 | C | SER | 1152 | −31.474 | −4.253 | −28.464 | 18.39 | C |
| ATOM | 817 | O | SER | 1152 | −30.637 | −3.799 | −27.66 | 15.67 | O |
| ATOM | 818 | N | PRO | 1153 | −32.619 | −4.743 | −28.024 | 18.17 | N |
| ATOM | 819 | CD | PRO | 1153 | −33.834 | −4.874 | −28.851 | 15.64 | C |
| ATOM | 820 | CA | PRO | 1153 | −32.914 | −4.755 | −26.603 | 16.33 | C |
| ATOM | 821 | CB | PRO | 1153 | −34.306 | −5.346 | −26.545 | 18.14 | C |
| ATOM | 822 | CG | PRO | 1153 | −34.939 | −4.917 | −27.824 | 17.45 | C |
| ATOM | 823 | C | PRO | 1153 | −31.918 | −5.665 | −25.921 | 17.54 | C |
| ATOM | 824 | O | PRO | 1153 | −31.433 | −6.614 | −26.549 | 17.31 | O |
| ATOM | 825 | N | LEU | 1154 | −31.624 | −5.412 | −24.651 | 16.29 | N |
| ATOM | 826 | CA | LEU | 1154 | −30.743 | −6.284 | −23.875 | 16.17 | C |
| ATOM | 827 | CB | LEU | 1154 | −29.845 | −5.47 | −22.952 | 16.61 | C |
| ATOM | 828 | CG | LEU | 1154 | −28.429 | −5.058 | −23.319 | 16.57 | C |
| ATOM | 829 | CD1 | LEU | 1154 | −28.235 | −4.914 | −24.811 | 15.54 | C |
| ATOM | 830 | CD2 | LEU | 1154 | −28.161 | −3.773 | −22.572 | 15.34 | C |
| ATOM | 831 | C | LEU | 1154 | −31.663 | −7.095 | −22.962 | 15.58 | C |
| ATOM | 832 | O | LEU | 1154 | −32.679 | −6.569 | −22.521 | 15.77 | O |
| ATOM | 833 | N | VAL | 1155 | −31.348 | −8.362 | −22.703 | 14.14 | N |
| ATOM | 834 | CA | VAL | 1155 | −32.147 | −9.128 | −21.742 | 14.36 | C |
| ATOM | 835 | CB | VAL | 1155 | −32.666 | −10.516 | −22.236 | 16.13 | C |
| ATOM | 836 | CG1 | VAL | 1155 | −34.096 | −10.383 | −22.707 | 17.55 | C |
| ATOM | 837 | CG2 | VAL | 1155 | −31.778 | −11.09 | −23.31 | 14.8 | C |
| ATOM | 838 | C | VAL | 1155 | −31.24 | −9.405 | −20.56 | 13.32 | C |
| ATOM | 839 | O | VAL | 1155 | −30.046 | −9.654 | −20.728 | 12.82 | O |
| ATOM | 840 | N | VAL | 1156 | −31.817 | −9.344 | −19.366 | 13.23 | N |
| ATOM | 841 | CA | VAL | 1156 | −31.095 | −9.583 | −18.123 | 13.25 | C |
| ATOM | 842 | CB | VAL | 1156 | −31.197 | −8.352 | −17.18 | 11.59 | C |
| ATOM | 843 | CG1 | VAL | 1156 | −30.163 | −8.455 | −16.064 | 9.84 | C |
| ATOM | 844 | CG2 | VAL | 1156 | −31.001 | −7.072 | −17.976 | 10.35 | C |
| ATOM | 845 | C | VAL | 1156 | −31.713 | −10.806 | −17.432 | 13.41 | C |
| ATOM | 846 | O | VAL | 1156 | −32.897 | −10.813 | −17.102 | 12.45 | O |
| ATOM | 847 | N | LEU | 1157 | −30.904 | −11.839 | −17.228 | 14.42 | N |
| ATOM | 848 | CA | LEU | 1157 | −31.358 | −13.065 | −16.587 | 14.54 | C |
| ATOM | 849 | CB | LEU | 1157 | −31.107 | −14.235 | −17.529 | 17.37 | C |
| ATOM | 850 | CG | LEU | 1157 | −32.159 | −14.084 | −18.616 | 17.45 | C |
| ATOM | 851 | CD1 | LEU | 1157 | −31.523 | −13.964 | −19.97 | 15.68 | C |
| ATOM | 852 | CD2 | LEU | 1157 | −33.12 | −15.235 | −18.51 | 14.04 | C |
| ATOM | 853 | C | LEU | 1157 | −30.666 | −13.312 | −15.263 | 15.03 | C |
| ATOM | 854 | O | LEU | 1157 | −29.591 | −12.768 | −15.021 | 14.87 | O |
| ATOM | 855 | N | PRO | 1158 | −31.29 | −14.11 | −14.369 | 15.01 | N |
| ATOM | 856 | CD | PRO | 1158 | −32.657 | −14.659 | −14.452 | 14.36 | C |
| ATOM | 857 | CA | PRO | 1158 | −30.676 | −14.411 | −13.067 | 14.63 | C |
| ATOM | 858 | CB | PRO | 1158 | −31.664 | −15.38 | −12.424 | 12.4 | C |
| ATOM | 859 | CG | PRO | 1158 | −32.975 | −14.977 | −13.006 | 16.67 | C |
| ATOM | 860 | C | PRO | 1158 | −29.354 | −15.117 | −13.36 | 14.38 | C |
| ATOM | 861 | O | PRO | 1158 | −29.27 | −15.852 | −14.346 | 14.05 | O |
| ATOM | 862 | N | TYR | 1159 | −28.328 | −14.908 | −12.544 | 14.53 | N |
| ATOM | 863 | CA | TYR | 1159 | −27.079 | −15.618 | −12.797 | 16.89 | C |
| ATOM | 864 | CB | TYR | 1159 | −25.916 | −15.097 | −11.927 | 17.44 | C |
| ATOM | 865 | CG | TYR | 1159 | −24.597 | −15.847 | −12.146 | 20.62 | C |
| ATOM | 866 | CD1 | TYR | 1159 | −24.05 | −15.994 | −13.426 | 19.72 | C |
| ATOM | 867 | CE1 | TYR | 1159 | −22.843 | −16.704 | −13.627 | 21.21 | C |
| ATOM | 868 | CD2 | TYR | 1159 | −23.906 | −16.42 | −11.072 | 20.45 | C |
| ATOM | 869 | CE2 | TYR | 1159 | −22.705 | −17.124 | −11.266 | 19.01 | C |

TABLE 1B-continued

| | | | | | | | | |
|---|---|---|---|---|---|---|---|---|
| ATOM | 870 | CZ | TYR | 1159 | −22.18 | −17.266 | −12.539 | 20.38 | C |
| ATOM | 871 | OH | TYR | 1159 | −21.009 | −17.988 | −12.714 | 18.95 | O |
| ATOM | 872 | C | TYR | 1159 | −27.345 | −17.084 | −12.475 | 16.92 | C |
| ATOM | 873 | O | TYR | 1159 | −27.794 | −17.419 | −11.377 | 17.08 | O |
| ATOM | 874 | N | MET | 1160 | −27.097 | −17.939 | −13.463 | 17.77 | N |
| ATOM | 875 | CA | MET | 1160 | −27.272 | −19.382 | −13.334 | 19.63 | C |
| ATOM | 876 | CB | MET | 1160 | −28.094 | −19.903 | −14.538 | 20.87 | C |
| ATOM | 877 | CG | MET | 1160 | −29.59 | −19.473 | −14.517 | 23.25 | C |
| ATOM | 878 | SD | MET | 1160 | −30.392 | −20 | −12.946 | 26.21 | S |
| ATOM | 879 | CE | MET | 1160 | −31.976 | −19.029 | −12.819 | 25.57 | C |
| ATOM | 880 | C | MET | 1160 | −25.838 | −19.959 | −13.289 | 19.44 | C |
| ATOM | 881 | O | MET | 1160 | −25.262 | −20.285 | −14.323 | 19.44 | O |
| ATOM | 882 | N | LYS | 1161 | −25.283 | −20.054 | −12.07 | 20.74 | N |
| ATOM | 883 | CA | LYS | 1161 | −23.897 | −20.517 | −11.782 | 21.83 | C |
| ATOM | 884 | CB | LYS | 1161 | −23.718 | −20.814 | −10.255 | 23.08 | C |
| ATOM | 885 | CG | LYS | 1161 | −22.277 | −21.256 | −9.7 | 26.14 | C |
| ATOM | 886 | CD | LYS | 1161 | −22.276 | −21.43 | −8.113 | 29.21 | C |
| ATOM | 887 | CE | LYS | 1161 | −21.135 | −22.295 | −7.464 | 30.75 | C |
| ATOM | 888 | NZ | LYS | 1161 | −21.405 | −22.621 | −5.992 | 32.69 | N |
| ATOM | 889 | C | LYS | 1161 | −23.378 | −21.704 | −12.581 | 21.45 | C |
| ATOM | 890 | O | LYS | 1161 | −22.233 | −21.692 | −13.029 | 22.38 | O |
| ATOM | 891 | N | HIS | 1162 | −24.209 | −22.721 | −12.768 | 21.1 | N |
| ATOM | 892 | CA | HIS | 1162 | −23.77 | −23.916 | −13.475 | 21.05 | C |
| ATOM | 893 | CB | HIS | 1162 | −24.271 | −25.147 | −12.729 | 21.67 | C |
| ATOM | 894 | CG | HIS | 1162 | −23.95 | −25.13 | −11.267 | 23.58 | C |
| ATOM | 895 | CD2 | HIS | 1162 | −24.75 | −24.981 | −10.184 | 25.8 | C |
| ATOM | 896 | ND1 | HIS | 1162 | −22.664 | −25.242 | −10.782 | 22.88 | N |
| ATOM | 897 | CE1 | HIS | 1162 | −22.686 | −25.164 | −9.461 | 24.94 | C |
| ATOM | 898 | NE2 | HIS | 1162 | −23.94 | −25.005 | −9.074 | 27.06 | N |
| ATOM | 899 | C | HIS | 1162 | −24.145 | −24.003 | −14.948 | 20.46 | C |
| ATOM | 900 | O | HIS | 1162 | −23.893 | −25.021 | −15.601 | 20.52 | O |
| ATOM | 901 | N | GLY | 1163 | −24.748 | −22.944 | −15.473 | 16.19 | N |
| ATOM | 902 | CA | GLY | 1163 | −25.101 | −22.941 | −16.879 | 15.75 | C |
| ATOM | 903 | C | GLY | 1163 | −26.153 | −23.945 | −17.287 | 14.03 | C |
| ATOM | 904 | O | GLY | 1163 | −27.039 | −24.295 | −16.505 | 14.31 | O |
| ATOM | 905 | N | ASP | 1164 | −26.054 | −24.402 | −18.529 | 13.99 | N |
| ATOM | 906 | CA | ASP | 1164 | −27.003 | −25.356 | −19.055 | 15.09 | C |
| ATOM | 907 | CB | ASP | 1164 | −26.891 | −25.453 | −20.586 | 17.44 | C |
| ATOM | 908 | CG | ASP | 1164 | −25.468 | −25.264 | −21.092 | 20.23 | C |
| ATOM | 909 | OD1 | ASP | 1164 | −24.817 | −24.255 | −20.729 | 26.07 | O |
| ATOM | 910 | OD2 | ASP | 1164 | −25.007 | −26.121 | −21.872 | 21.73 | O |
| ATOM | 911 | C | ASP | 1164 | −26.853 | −26.719 | −18.399 | 15.19 | C |
| ATOM | 912 | O | ASP | 1164 | −25.765 | −27.128 | −17.969 | 11.3 | O |
| ATOM | 913 | N | LEU | 1165 | −27.979 | −27.399 | −18.29 | 15.65 | N |
| ATOM | 914 | CA | LEU | 1165 | −28.022 | −28.704 | −17.674 | 17.38 | C |
| ATOM | 915 | CB | LEU | 1165 | −29.472 | −29.172 | −17.594 | 19.29 | C |
| ATOM | 916 | CG | LEU | 1165 | −29.893 | −30.157 | −16.507 | 23.06 | C |
| ATOM | 917 | CD1 | LEU | 1165 | −29.794 | −29.502 | −15.132 | 24.16 | C |
| ATOM | 918 | CD2 | LEU | 1165 | −31.336 | −30.597 | −16.783 | 22.91 | C |
| ATOM | 919 | C | LEU | 1165 | −27.191 | −29.661 | −18.523 | 18.34 | C |
| ATOM | 920 | O | LEU | 1165 | −26.598 | −30.599 | −17.999 | 16.81 | O |
| ATOM | 921 | N | ARG | 1166 | −27.115 | −29.426 | −19.828 | 16.61 | N |
| ATOM | 922 | CA | ARG | 1166 | −26.328 | −30.347 | −20.631 | 20.77 | C |
| ATOM | 923 | CB | ARG | 1166 | −26.59 | −30.209 | −22.129 | 21.19 | C |
| ATOM | 924 | CG | ARG | 1166 | −25.748 | −31.255 | −22.956 | 29.35 | C |
| ATOM | 925 | CD | ARG | 1166 | −24.754 | −30.446 | −23.364 | 33.96 | C |
| ATOM | 926 | NE | ARG | 1166 | −23.929 | −30.501 | −24.55 | 41.69 | N |
| ATOM | 927 | CZ | ARG | 1166 | −23.013 | −31.595 | −24.116 | 43.95 | C |
| ATOM | 928 | NH1 | ARG | 1166 | −22.272 | −31.74 | −25.146 | 44.72 | N |
| ATOM | 929 | NH2 | ARG | 1166 | −23.215 | −32.382 | −23.404 | 44.74 | N |
| ATOM | 930 | C | ARG | 1166 | −24.826 | −30.272 | −20.398 | 19.99 | C |
| ATOM | 931 | O | ARG | 1166 | −24.174 | −31.312 | −20.34 | 19.94 | O |
| ATOM | 932 | N | ASN | 1167 | −24.262 | −29.069 | −20.302 | 20.09 | N |
| ATOM | 933 | CA | ASN | 1167 | −22.826 | −28.947 | −20.049 | 19.35 | C |
| ATOM | 934 | CB | ASN | 1167 | −22.35 | −27.498 | −20.026 | 21.75 | C |
| ATOM | 935 | CG | ASN | 1167 | −22.323 | −26.86 | −21.38 | 26.57 | C |
| ATOM | 936 | OD1 | ASN | 1167 | −22.67 | −25.69 | −21.512 | 29.34 | O |
| ATOM | 937 | ND2 | ASN | 1167 | −21.89 | −27.601 | −22.393 | 26.01 | N |
| ATOM | 938 | C | ASN | 1167 | −22.595 | −29.437 | −18.655 | 19.05 | C |
| ATOM | 939 | O | ASN | 1167 | −21.566 | −30.028 | −18.345 | 20.21 | O |
| ATOM | 940 | N | PHE | 1168 | −23.551 | −29.154 | −17.788 | 17 | N |
| ATOM | 941 | CA | PHE | 1168 | −23.364 | −29.544 | −16.419 | 16.81 | C |
| ATOM | 942 | CB | PHE | 1168 | −24.575 | −29.188 | −15.577 | 16.11 | C |
| ATOM | 943 | CG | PHE | 1168 | −24.368 | −29.47 | −14.139 | 17.57 | C |
| ATOM | 944 | CD1 | PHE | 1168 | −23.567 | −28.633 | −13.361 | 17.68 | C |
| ATOM | 945 | CD2 | PHE | 1168 | −24.888 | −30.625 | −13.572 | 17.09 | C |
| ATOM | 946 | CE1 | PHE | 1168 | −23.286 | −28.954 | −12.042 | 16.42 | C |
| ATOM | 947 | CE2 | PHE | 1168 | −24.613 | −30.953 | −12.258 | 16.65 | C |
| ATOM | 948 | CZ | PHE | 1168 | −23.809 | −30.118 | −11.49 | 16.79 | C |
| ATOM | 949 | C | PHE | 1168 | −23.054 | −31.024 | −16.257 | 17.57 | C |

TABLE 1B-continued

| | | | | | | | | |
|---|---|---|---|---|---|---|---|---|
| ATOM | 950 | O | PHE | 1168 | −22.004 | −31.379 | −15.725 | 17.47 | O |
| ATOM | 951 | N | ILE | 1169 | −23.967 | −31.872 | −16.733 | 18.48 | N |
| ATOM | 952 | CA | ILE | 1169 | −23.849 | −33.323 | −16.618 | 19.22 | C |
| ATOM | 953 | CB | ILE | 1169 | −25.221 | −33.994 | −16.911 | 18.85 | C |
| ATOM | 954 | CG2 | ILE | 1169 | −26.323 | −33.291 | −16.107 | 20.15 | C |
| ATOM | 955 | CG1 | ILE | 1169 | −25.562 | −33.883 | −18.398 | 19.02 | C |
| ATOM | 956 | CD | ILE | 1169 | −26.743 | −34.735 | −18.851 | 21.26 | C |
| ATOM | 957 | C | ILE | 1169 | −22.742 | −33.938 | −17.49 | 20.6 | C |
| ATOM | 958 | O | ILE | 1169 | −22.254 | −35.022 | −17.203 | 21.94 | O |
| ATOM | 959 | N | ARG | 1170 | −22.346 | −33.234 | −18.547 | 24.45 | N |
| ATOM | 960 | CA | ARG | 1170 | −21.269 | −33.682 | −19.438 | 27.69 | C |
| ATOM | 961 | CB | ARG | 1170 | −21.419 | −32.978 | −20.852 | 28.31 | C |
| ATOM | 962 | CG | ARG | 1170 | −22.013 | −33.766 | −22.12 | 33.76 | C |
| ATOM | 963 | CD | ARG | 1170 | −21.062 | −33.577 | −23.383 | 38.78 | C |
| ATOM | 964 | NE | ARG | 1170 | −21.589 | −33.737 | −24.767 | 44.17 | N |
| ATOM | 965 | CZ | ARG | 1170 | −21.776 | −34.883 | −25.421 | 45.25 | C |
| ATOM | 966 | NH1 | ARG | 1170 | −21.509 | −36.042 | −24.837 | 45.69 | N |
| ATOM | 967 | NH2 | ARG | 1170 | −22.158 | −34.868 | −26.699 | 46.99 | N |
| ATOM | 968 | C | ARG | 1170 | −19.801 | −33.42 | −18.85 | 28.11 | C |
| ATOM | 969 | O | ARG | 1170 | −18.863 | −33.886 | −19.461 | 28.96 | O |
| ATOM | 970 | N | ASN | 1171 | −19.616 | −32.761 | −17.676 | 31.77 | N |
| ATOM | 971 | CA | ASN | 1171 | −18.278 | −32.351 | −17.071 | 35.84 | C |
| ATOM | 972 | CB | ASN | 1171 | −18.34 | −30.837 | −16.751 | 35.9 | C |
| ATOM | 973 | CG | ASN | 1171 | −17.124 | −30.291 | −15.963 | 36.69 | C |
| ATOM | 974 | OD1 | ASN | 1171 | −15.967 | −30.5 | −16.337 | 38.54 | O |
| ATOM | 975 | ND2 | ASN | 1171 | −17.402 | −29.552 | −14.892 | 38.57 | N |
| ATOM | 976 | C | ASN | 1171 | −17.734 | −33.05 | −15.837 | 38.26 | C |
| ATOM | 977 | O | ASN | 1171 | −18.335 | −33.996 | −15.33 | 37.47 | O |
| ATOM | 978 | N | GLU | 1172 | −16.634 | −32.526 | −15.299 | 42.42 | N |
| ATOM | 979 | CA | GLU | 1172 | −16.084 | −33.21 | −14.185 | 44.62 | C |
| ATOM | 980 | CB | GLU | 1172 | −14.662 | −33.533 | −14.33 | 47.34 | C |
| ATOM | 981 | CG | GLU | 1172 | −14.476 | −34.899 | −14.945 | 51.52 | C |
| ATOM | 982 | CD | GLU | 1172 | −13 | −35.209 | −15.021 | 54.32 | C |
| ATOM | 983 | OE1 | GLU | 1172 | −12.209 | −34.331 | −14.607 | 56.07 | O |
| ATOM | 984 | OE2 | GLU | 1172 | −12.619 | −36.306 | −15.481 | 55.09 | O |
| ATOM | 985 | C | GLU | 1172 | −16.394 | −32.813 | −12.868 | 45.4 | C |
| ATOM | 986 | O | GLU | 1172 | −15.676 | −32.606 | −11.9 | 45.64 | O |
| ATOM | 987 | N | THR | 1173 | −17.5 | −33.46 | −12.882 | 45.94 | N |
| ATOM | 988 | CA | THR | 1173 | −18.303 | −33.412 | −11.801 | 45.89 | C |
| ATOM | 989 | CB | THR | 1173 | −18.9 | −31.986 | −11.806 | 48.24 | C |
| ATOM | 990 | OG1 | THR | 1173 | −19.351 | −31.627 | −13.121 | 51.69 | O |
| ATOM | 991 | CG2 | THR | 1173 | −17.814 | −30.958 | −11.388 | 49.83 | C |
| ATOM | 992 | C | THR | 1173 | −19.225 | −34.615 | −12.011 | 44.29 | C |
| ATOM | 993 | O | THR | 1173 | −19.564 | −34.981 | −13.109 | 44.1 | O |
| ATOM | 994 | N | HIS | 1174 | −19.669 | −35.201 | −10.93 | 42.7 | N |
| ATOM | 995 | CA | HIS | 1174 | −20.433 | −36.472 | −10.943 | 41.89 | C |
| ATOM | 996 | CB | HIS | 1174 | −19.872 | −37.118 | −9.842 | 39.55 | C |
| ATOM | 997 | CG | HIS | 1174 | −18.497 | −37.364 | −10.145 | 37.93 | C |
| ATOM | 998 | CD2 | HIS | 1174 | −18.032 | −38.092 | −11.169 | 36.9 | C |
| ATOM | 999 | ND1 | HIS | 1174 | −17.45 | −36.607 | −9.675 | 37.27 | N |
| ATOM | 1000 | CE1 | HIS | 1174 | −16.388 | −36.875 | −10.408 | 37.46 | C |
| ATOM | 1001 | NE2 | HIS | 1174 | −16.72 | −37.767 | −11.321 | 38.87 | N |
| ATOM | 1002 | C | HIS | 1174 | −21.626 | −36.098 | −10.522 | 43.19 | C |
| ATOM | 1003 | O | HIS | 1174 | −22.216 | −36.764 | −9.624 | 40.83 | O |
| ATOM | 1004 | N | ASN | 1175 | −22.132 | −35.21 | −11.301 | 45 | N |
| ATOM | 1005 | CA | ASN | 1175 | −22.901 | −34.607 | −10.372 | 46.48 | C |
| ATOM | 1006 | CB | ASN | 1175 | −22.07 | −33.389 | −10.053 | 48.49 | C |
| ATOM | 1007 | CG | ASN | 1175 | −21.478 | −33.586 | −8.735 | 50.32 | C |
| ATOM | 1008 | OD1 | ASN | 1175 | −22.172 | −33.645 | −7.717 | 50.43 | O |
| ATOM | 1009 | ND2 | ASN | 1175 | −20.165 | −33.807 | −8.744 | 52.85 | N |
| ATOM | 1010 | C | ASN | 1175 | −24.337 | −34.512 | −10.263 | 45.16 | C |
| ATOM | 1011 | O | ASN | 1175 | −24.947 | −33.607 | −9.572 | 45.76 | O |
| ATOM | 1012 | N | PRO | 1176 | −24.862 | −35.721 | −10.584 | 42.63 | N |
| ATOM | 1013 | CD | PRO | 1176 | −25.399 | −35.28 | −11.89 | 42.59 | C |
| ATOM | 1014 | CA | PRO | 1176 | −24.501 | −37.027 | −11.106 | 39.43 | C |
| ATOM | 1015 | CB | PRO | 1176 | −23.589 | −36.804 | −12.308 | 40.33 | C |
| ATOM | 1016 | CG | PRO | 1176 | −24.229 | −35.822 | −12.818 | 41.13 | C |
| ATOM | 1017 | C | PRO | 1176 | −24.454 | −38.352 | −10.571 | 35.88 | C |
| ATOM | 1018 | O | PRO | 1176 | −24.315 | −39.218 | −11.379 | 36.9 | O |
| ATOM | 1019 | N | THR | 1177 | −24.742 | −38.551 | −9.294 | 31.21 | N |
| ATOM | 1020 | CA | THR | 1177 | −25.219 | −39.893 | −8.976 | 27.86 | C |
| ATOM | 1021 | CB | THR | 1177 | −25.691 | −39.919 | −7.539 | 28.3 | C |
| ATOM | 1022 | OG1 | THR | 1177 | −26.718 | −38.926 | −7.34 | 28.69 | O |
| ATOM | 1023 | CG2 | THR | 1177 | −24.519 | −39.58 | −6.658 | 29.42 | C |
| ATOM | 1024 | C | THR | 1177 | −26.551 | −39.987 | −9.875 | 25.62 | C |
| ATOM | 1025 | O | THR | 1177 | −27.064 | −38.967 | −10.392 | 24.15 | O |
| ATOM | 1026 | N | VAL | 1178 | −27.117 | −41.19 | −10.018 | 23.06 | N |
| ATOM | 1027 | CA | VAL | 1178 | −28.349 | −41.394 | −10.787 | 20 | C |
| ATOM | 1028 | CB | VAL | 1178 | −28.65 | −42.913 | −10.982 | 21.95 | C |
| ATOM | 1029 | CG1 | VAL | 1178 | −30.109 | −43.124 | −11.338 | 22.35 | C |

TABLE 1B-continued

| | | | | | | | |
|---|---|---|---|---|---|---|---|
| ATOM | 1030 | CG2 | VAL | 1178 | −27.774 | −43.49 | −12.098 | 21.65 | C |
| ATOM | 1031 | C | VAL | 1178 | −29.551 | −40.708 | −10.115 | 19.06 | C |
| ATOM | 1032 | O | VAL | 1178 | −30.457 | −40.256 | −10.801 | 14.69 | O |
| ATOM | 1033 | N | LYS | 1179 | −29.555 | −40.61 | −8.784 | 17.59 | N |
| ATOM | 1034 | CA | LYS | 1179 | −30.674 | −39.95 | −8.098 | 17.37 | C |
| ATOM | 1035 | CB | LYS | 1179 | −30.595 | −40.091 | −6.573 | 15.86 | C |
| ATOM | 1036 | CG | LYS | 1179 | −31.893 | −39.607 | −5.945 | 17.43 | C |
| ATOM | 1037 | CD | LYS | 1179 | −31.973 | −39.615 | −4.431 | 18.96 | C |
| ATOM | 1038 | CE | LYS | 1179 | −33.444 | −39.433 | −4.033 | 19.52 | C |
| ATOM | 1039 | NZ | LYS | 1179 | −33.713 | −39.473 | −2.586 | 23.06 | N |
| ATOM | 1040 | C | LYS | 1179 | −30.722 | −38.466 | −8.432 | 16.18 | C |
| ATOM | 1041 | O | LYS | 1179 | −31.795 | −37.904 | −8.696 | 16 | O |
| ATOM | 1042 | N | ASP | 1180 | −29.545 | −37.85 | −8.368 | 16.29 | N |
| ATOM | 1043 | CA | ASP | 1180 | −29.319 | −36.44 | −8.672 | 16.7 | C |
| ATOM | 1044 | CB | ASP | 1180 | −27.8 | −36.166 | −8.754 | 21.3 | C |
| ATOM | 1045 | CG | ASP | 1180 | −27.093 | −36.177 | −7.382 | 24.33 | C |
| ATOM | 1046 | OD1 | ASP | 1180 | −25.843 | −36.324 | −7.358 | 24.63 | O |
| ATOM | 1047 | OD2 | ASP | 1180 | −27.766 | −36.02 | −6.34 | 25.45 | O |
| ATOM | 1048 | C | ASP | 1180 | −29.941 | −36.166 | −10.046 | 16.85 | C |
| ATOM | 1049 | O | ASP | 1180 | −30.788 | −35.284 | −10.204 | 17.45 | O |
| ATOM | 1050 | N | LEU | 1181 | −29.495 | −36.942 | −11.031 | 14.01 | N |
| ATOM | 1051 | CA | LEU | 1181 | −29.948 | −36.844 | −12.417 | 15.35 | C |
| ATOM | 1052 | CB | LEU | 1181 | −29.241 | −37.908 | −13.252 | 12.86 | C |
| ATOM | 1053 | CG | LEU | 1181 | −28.102 | −37.644 | −14.236 | 16.66 | C |
| ATOM | 1054 | CD1 | LEU | 1181 | −27.429 | −36.281 | −14.107 | 14.78 | C |
| ATOM | 1055 | CD2 | LEU | 1181 | −27.138 | −38.797 | −14.016 | 16.96 | C |
| ATOM | 1056 | C | LEU | 1181 | −31.465 | −36.989 | −12.604 | 15.84 | C |
| ATOM | 1057 | O | LEU | 1181 | −32.057 | −36.288 | −13.425 | 13.36 | O |
| ATOM | 1058 | N | ILE | 1182 | −32.083 | −37.924 | −11.884 | 16.57 | N |
| ATOM | 1059 | CA | ILE | 1182 | −33.535 | −38.106 | −11.971 | 18.12 | C |
| ATOM | 1060 | CB | ILE | 1182 | −34.009 | −39.375 | −11.205 | 19.44 | C |
| ATOM | 1061 | CG2 | ILE | 1182 | −35.549 | −39.429 | −11.179 | 18.44 | C |
| ATOM | 1062 | CG1 | ILE | 1182 | −33.477 | −40.659 | −11.866 | 22.47 | C |
| ATOM | 1063 | CD | ILE | 1182 | −32.11 | −40.629 | −12.516 | 26.66 | C |
| ATOM | 1064 | C | ILE | 1182 | −34.088 | −36.87 | −11.276 | 17.03 | C |
| ATOM | 1065 | O | ILE | 1182 | −35.165 | −36.364 | −11.611 | 15.91 | O |
| ATOM | 1066 | N | GLY | 1183 | −33.315 | −36.388 | −10.307 | 15.99 | N |
| ATOM | 1067 | CA | GLY | 1183 | −33.702 | −35.204 | −9.562 | 17.43 | C |
| ATOM | 1068 | C | GLY | 1183 | −33.873 | −34.015 | −10.488 | 17.32 | C |
| ATOM | 1069 | O | GLY | 1183 | −34.833 | −33.258 | −10.36 | 16.44 | O |
| ATOM | 1070 | N | PHE | 1184 | −32.95 | −33.843 | −11.427 | 17.05 | N |
| ATOM | 1071 | CA | PHE | 1184 | −33.052 | −32.724 | −12.357 | 17.09 | C |
| ATOM | 1072 | CB | PHE | 1184 | −31.749 | −32.522 | −13.141 | 18.5 | C |
| ATOM | 1073 | CG | PHE | 1184 | −30.522 | −32.379 | −12.283 | 19.66 | C |
| ATOM | 1074 | CD1 | PHE | 1184 | −30.502 | −31.544 | −11.167 | 20.39 | C |
| ATOM | 1075 | CD2 | PHE | 1184 | −29.367 | −33.075 | −12.616 | 22.04 | C |
| ATOM | 1076 | CE1 | PHE | 1184 | −29.335 | −31.414 | −10.398 | 22.54 | C |
| ATOM | 1077 | CE2 | PHE | 1184 | −28.208 | −32.956 | −11.865 | 23.06 | C |
| ATOM | 1078 | CZ | PHE | 1184 | −28.186 | −32.127 | −10.754 | 23.72 | C |
| ATOM | 1079 | C | PHE | 1184 | −34.199 | −32.938 | −13.338 | 15.91 | C |
| ATOM | 1080 | O | PHE | 1184 | −34.91 | −31.994 | −13.682 | 15.75 | O |
| ATOM | 1081 | N | GLY | 1185 | −34.377 | −34.172 | −13.794 | 14.93 | N |
| ATOM | 1082 | CA | GLY | 1185 | −35.457 | −34.458 | −14.723 | 15.28 | C |
| ATOM | 1083 | C | GLY | 1185 | −36.789 | −34.122 | −14.088 | 15.23 | C |
| ATOM | 1084 | O | GLY | 1185 | −37.713 | −33.646 | −14.75 | 12.8 | O |
| ATOM | 1085 | N | LEU | 1186 | −36.864 | −34.366 | −12.783 | 14.32 | N |
| ATOM | 1086 | CA | LEU | 1186 | −38.056 | −34.098 | −12.006 | 14.34 | C |
| ATOM | 1087 | CB | LEU | 1186 | −37.88 | −34.62 | −10.572 | 13.65 | C |
| ATOM | 1088 | CG | LEU | 1186 | −39.029 | −34.398 | −9.581 | 16.71 | C |
| ATOM | 1089 | CD1 | LEU | 1186 | −40.35 | −34.885 | −10.173 | 12.78 | C |
| ATOM | 1090 | CD2 | LEU | 1186 | −38.722 | −35.145 | −8.28 | 14.5 | C |
| ATOM | 1091 | C | LEU | 1186 | −38.351 | −32.601 | −11.996 | 14.32 | C |
| ATOM | 1092 | O | LEU | 1186 | −39.479 | −32.196 | −12.256 | 14.05 | O |
| ATOM | 1093 | N | GLN | 1187 | −37.351 | −31.77 | −11.71 | 13.6 | N |
| ATOM | 1094 | CA | GLN | 1187 | −37.605 | −30.34 | −11.698 | 13.35 | C |
| ATOM | 1095 | CB | GLN | 1187 | −36.387 | −29.575 | −11.206 | 14.52 | C |
| ATOM | 1096 | CG | GLN | 1187 | −35.823 | −30.07 | −9.902 | 16.14 | C |
| ATOM | 1097 | CD | GLN | 1187 | −34.745 | −29.136 | −9.4 | 18.91 | C |
| ATOM | 1098 | OE1 | GLN | 1187 | −35.02 | −27.993 | −9.054 | 23.4 | O |
| ATOM | 1099 | NE2 | GLN | 1187 | −33.51 | −29.609 | −9.375 | 19 | N |
| ATOM | 1100 | C | GLN | 1187 | −38.004 | −29.829 | −13.081 | 11.58 | C |
| ATOM | 1101 | O | GLN | 1187 | −38.696 | −28.821 | −13.194 | 13.07 | O |
| ATOM | 1102 | N | VAL | 1188 | −37.576 | −30.506 | −14.138 | 11.09 | N |
| ATOM | 1103 | CA | VAL | 1188 | −37.949 | −30.071 | −15.492 | 11.72 | C |
| ATOM | 1104 | CB | VAL | 1188 | −37.075 | −30.744 | −16.577 | 9.94 | C |
| ATOM | 1105 | CG1 | VAL | 1188 | −37.652 | −30.471 | −17.966 | 11.58 | C |
| ATOM | 1106 | CG2 | VAL | 1188 | −35.659 | −30.193 | −16.495 | 9.54 | C |
| ATOM | 1107 | C | VAL | 1188 | −39.418 | −30.373 | −15.781 | 11.54 | C |
| ATOM | 1108 | O | VAL | 1188 | −40.106 | −29.587 | −16.419 | 12.41 | O |
| ATOM | 1109 | N | ALA | 1189 | −39.894 | −31.519 | −15.304 | 14.27 | N |

TABLE 1B-continued

| ATOM | 1110 | CA | ALA | 1189 | −41.281 | −31.913 | −15.513 | 13.61 | C |
|---|---|---|---|---|---|---|---|---|---|
| ATOM | 1111 | CB | ALA | 1189 | −41.481 | −33.359 | −15.09 | 13.82 | C |
| ATOM | 1112 | C | ALA | 1189 | −42.195 | −31.007 | −14.706 | 13.97 | C |
| ATOM | 1113 | O | ALA | 1189 | −43.352 | −30.79 | −15.072 | 16.38 | O |
| ATOM | 1114 | N | LYS | 1190 | −41.674 | −30.504 | −13.593 | 12.74 | N |
| ATOM | 1115 | CA | LYS | 1190 | −42.434 | −29.617 | −12.722 | 15.29 | C |
| ATOM | 1116 | CB | LYS | 1190 | −41.708 | −29.434 | −11.399 | 14.89 | C |
| ATOM | 1117 | CG | LYS | 1190 | −42.14 | −30.477 | −10.409 | 18.23 | C |
| ATOM | 1118 | CD | LYS | 1190 | −41.278 | −30.504 | −9.175 | 18.47 | C |
| ATOM | 1119 | CE | LYS | 1190 | −41.793 | −31.579 | −8.246 | 18.95 | C |
| ATOM | 1120 | NZ | LYS | 1190 | −41.279 | −31.37 | −6.871 | 20.27 | N |
| ATOM | 1121 | C | LYS | 1190 | −42.637 | −28.279 | −13.398 | 14.43 | C |
| ATOM | 1122 | O | LYS | 1190 | −43.721 | −27.703 | −13.373 | 15.22 | O |
| ATOM | 1123 | N | GLY | 1191 | −41.573 | −27.782 | −14.001 | 13.21 | N |
| ATOM | 1124 | CA | GLY | 1191 | −41.666 | −26.523 | −14.706 | 12.63 | C |
| ATOM | 1125 | C | GLY | 1191 | −42.579 | −26.713 | −15.895 | 12.4 | C |
| ATOM | 1126 | O | GLY | 1191 | −43.406 | −25.849 | −16.174 | 12.86 | O |
| ATOM | 1127 | N | MET | 1192 | −42.442 | −27.85 | −16.582 | 12.14 | N |
| ATOM | 1128 | CA | MET | 1192 | −43.271 | −28.144 | −17.741 | 11.6 | C |
| ATOM | 1129 | CB | MET | 1192 | −42.701 | −29.326 | −18.541 | 10.64 | C |
| ATOM | 1130 | CG | MET | 1192 | −41.421 | −29.006 | −19.336 | 13.7 | C |
| ATOM | 1131 | SD | MET | 1192 | −41.513 | −27.621 | −20.534 | 17.92 | S |
| ATOM | 1132 | CE | MET | 1192 | −42.921 | −28.121 | −21.647 | 20.8 | C |
| ATOM | 1133 | C | MET | 1192 | −44.736 | −28.383 | −17.363 | 12.32 | C |
| ATOM | 1134 | O | MET | 1192 | −45.624 | −28.038 | −18.147 | 13.61 | O |
| ATOM | 1135 | N | LYS | 1193 | −44.993 | −28.955 | −16.181 | 11.86 | N |
| ATOM | 1136 | CA | LYS | 1193 | −46.373 | −29.158 | −15.712 | 12.84 | C |
| ATOM | 1137 | CB | LYS | 1193 | −46.395 | −29.822 | −14.301 | 13.93 | C |
| ATOM | 1138 | CG | LYS | 1193 | −47.766 | −29.826 | −13.567 | 17.85 | C |
| ATOM | 1139 | CD | LYS | 1193 | −47.72 | −30.237 | −12.045 | 23.67 | C |
| ATOM | 1140 | CE | LYS | 1193 | −46.391 | −29.929 | −11.3 | 26.38 | C |
| ATOM | 1141 | NZ | LYS | 1193 | −45.901 | −28.542 | −10.955 | 30.9 | N |
| ATOM | 1142 | C | LYS | 1193 | −46.955 | −27.734 | −15.649 | 12.03 | C |
| ATOM | 1143 | O | LYS | 1193 | −48.068 | −27.479 | −16.108 | 12.04 | O |
| ATOM | 1144 | N | TYR | 1194 | −46.18 | −26.795 | −15.112 | 12.64 | N |
| ATOM | 1145 | CA | TYR | 1194 | −46.647 | −25.407 | −14.997 | 12.34 | C |
| ATOM | 1146 | CB | TYR | 1194 | −45.668 | −24.591 | −14.147 | 11.64 | C |
| ATOM | 1147 | CG | TYR | 1194 | −45.962 | −23.1 | −14.065 | 11.89 | C |
| ATOM | 1148 | CD1 | TYR | 1194 | −46.907 | −22.58 | −13.167 | 12.34 | C |
| ATOM | 1149 | CE1 | TYR | 1194 | −47.178 | −21.199 | −13.125 | 13.81 | C |
| ATOM | 1150 | CD2 | TYR | 1194 | −45.304 | −22.208 | −14.911 | 12.87 | C |
| ATOM | 1151 | CE2 | TYR | 1194 | −45.572 | −20.84 | −14.879 | 12.27 | C |
| ATOM | 1152 | CZ | TYR | 1194 | −46.502 | −20.34 | −13.994 | 12.63 | C |
| ATOM | 1153 | OH | TYR | 1194 | −46.763 | −18.991 | −14.015 | 13.8 | O |
| ATOM | 1154 | C | TYR | 1194 | −46.863 | −24.747 | −16.369 | 14.72 | C |
| ATOM | 1155 | O | TYR | 1194 | −47.966 | −24.29 | −16.668 | 13.67 | O |
| ATOM | 1156 | N | LEU | 1195 | −45.829 | −24.707 | −17.205 | 14.63 | N |
| ATOM | 1157 | CA | LEU | 1195 | −45.961 | −24.114 | −18.53 | 14.48 | C |
| ATOM | 1158 | CB | LEU | 1195 | −44.659 | −24.313 | −19.327 | 11.22 | C |
| ATOM | 1159 | CG | LEU | 1195 | −43.558 | −23.232 | −19.419 | 12.32 | C |
| ATOM | 1160 | CD1 | LEU | 1195 | −43.924 | −22.016 | −18.591 | 11.57 | C |
| ATOM | 1161 | CD2 | LEU | 1195 | −42.204 | −23.817 | −19 | 9.97 | C |
| ATOM | 1162 | C | LEU | 1195 | −47.153 | −24.75 | −19.26 | 14.78 | C |
| ATOM | 1163 | O | LEU | 1195 | −48.011 | −24.048 | −19.799 | 15.68 | O |
| ATOM | 1164 | N | ALA | 1196 | −47.226 | −26.077 | −19.255 | 15.59 | N |
| ATOM | 1165 | CA | ALA | 1196 | −48.323 | −26.76 | −19.931 | 17.53 | C |
| ATOM | 1166 | CB | ALA | 1196 | −48.122 | −28.286 | −19.882 | 17.48 | C |
| ATOM | 1167 | C | ALA | 1196 | −49.71 | −26.397 | −19.395 | 17.02 | C |
| ATOM | 1168 | O | ALA | 1196 | −50.7 | −26.616 | −20.083 | 18.22 | O |
| ATOM | 1169 | N | SER | 1197 | −49.799 | −25.859 | −18.181 | 18.14 | N |
| ATOM | 1170 | CA | SER | 1197 | −51.109 | −25.484 | −17.646 | 18.76 | C |
| ATOM | 1171 | CB | SER | 1197 | −51.115 | −25.544 | −16.114 | 19.04 | C |
| ATOM | 1172 | OG | SER | 1197 | −50.19 | −24.624 | −15.551 | 20.46 | O |
| ATOM | 1173 | C | SER | 1197 | −51.49 | −24.081 | −18.123 | 18.11 | C |
| ATOM | 1174 | O | SER | 1197 | −52.665 | −23.732 | −18.177 | 20.7 | O |
| ATOM | 1175 | N | LYS | 1198 | −50.487 | −23.29 | −18.48 | 18.69 | N |
| ATOM | 1176 | CA | LYS | 1198 | −50.698 | −21.937 | −18.988 | 19.35 | C |
| ATOM | 1177 | CB | LYS | 1198 | −49.478 | −21.06 | −18.689 | 20.72 | C |
| ATOM | 1178 | CG | LYS | 1198 | −49.059 | −21.106 | −17.24 | 19.87 | C |
| ATOM | 1179 | CD | LYS | 1198 | −50.309 | −21.238 | −16.407 | 21.44 | C |
| ATOM | 1180 | CE | LYS | 1198 | −50.069 | −21.004 | −14.947 | 22.31 | C |
| ATOM | 1181 | NZ | LYS | 1198 | −51.33 | −20.451 | −14.393 | 23.65 | N |
| ATOM | 1182 | C | LYS | 1198 | −50.86 | −22.094 | −20.488 | 19.76 | C |
| ATOM | 1183 | O | LYS | 1198 | −50.899 | −21.117 | −21.234 | 20.25 | O |
| ATOM | 1184 | N | LYS | 1199 | −50.943 | −23.356 | −20.901 | 19.44 | N |
| ATOM | 1185 | CA | LYS | 1199 | −51.079 | −23.747 | −22.302 | 21.24 | C |
| ATOM | 1186 | CB | LYS | 1199 | −52.326 | −23.134 | −22.952 | 23.73 | C |
| ATOM | 1187 | CG | LYS | 1199 | −53.683 | −23.601 | −22.468 | 27.68 | C |
| ATOM | 1188 | CD | LYS | 1199 | −54.769 | −22.601 | −22.926 | 32.24 | C |
| ATOM | 1189 | CE | LYS | 1199 | −55.458 | −22.948 | −24.274 | 35.47 | C |

TABLE 1B-continued

| | | | | | | | | |
|---|---|---|---|---|---|---|---|---|
| ATOM | 1190 | NZ | LYS | 1199 | −54.653 | −22.791 | −25.529 | 34.96 | N |
| ATOM | 1191 | C | LYS | 1199 | −49.88 | −23.276 | −23.119 | 21.02 | C |
| ATOM | 1192 | O | LYS | 1199 | −50.037 | −22.907 | −24.277 | 20.05 | O |
| ATOM | 1193 | N | PHE | 1200 | −48.687 | −23.274 | −22.546 | 18.53 | N |
| ATOM | 1194 | CA | PHE | 1200 | −47.542 | −22.814 | −23.312 | 18.34 | C |
| ATOM | 1195 | CB | PHE | 1200 | −46.658 | −21.964 | −22.404 | 19.51 | C |
| ATOM | 1196 | CG | PHE | 1200 | −45.328 | −21.61 | −22.982 | 18.89 | C |
| ATOM | 1197 | CD1 | PHE | 1200 | −44.242 | −22.452 | −22.793 | 19.96 | C |
| ATOM | 1198 | CD2 | PHE | 1200 | −45.133 | −20.398 | −23.634 | 20.92 | C |
| ATOM | 1199 | CE1 | PHE | 1200 | −42.977 | −22.092 | −23.23 | 21.7 | C |
| ATOM | 1200 | CE2 | PHE | 1200 | −43.865 | −20.025 | −24.08 | 20.16 | C |
| ATOM | 1201 | CZ | PHE | 1200 | −42.786 | −20.872 | −23.876 | 20.78 | C |
| ATOM | 1202 | C | PHE | 1200 | −46.778 | −23.969 | −23.946 | 17.03 | C |
| ATOM | 1203 | O | PHE | 1200 | −46.409 | −24.92 | −23.282 | 16.04 | O |
| ATOM | 1204 | N | VAL | 1201 | −46.575 | −23.887 | −25.253 | 17.46 | N |
| ATOM | 1205 | CA | VAL | 1201 | −45.868 | −24.933 | −25.977 | 18.28 | C |
| ATOM | 1206 | CB | VAL | 1201 | −46.586 | −25.227 | −27.312 | 17.97 | C |
| ATOM | 1207 | CG1 | VAL | 1201 | −45.917 | −26.389 | −28.045 | 16.62 | C |
| ATOM | 1208 | CG2 | VAL | 1201 | −48.053 | −25.553 | −27.018 | 19.79 | C |
| ATOM | 1209 | C | VAL | 1201 | −44.427 | −24.474 | −26.19 | 17.03 | C |
| ATOM | 1210 | O | VAL | 1201 | −44.146 | −23.552 | −26.951 | 16.94 | O |
| ATOM | 1211 | N | HIS | 1202 | −43.516 | −25.127 | −25.484 | 18.22 | N |
| ATOM | 1212 | CA | HIS | 1202 | −42.117 | −24.766 | −25.55 | 19.44 | C |
| ATOM | 1213 | CB | HIS | 1202 | −41.352 | −25.573 | −24.503 | 20.61 | C |
| ATOM | 1214 | CG | HIS | 1202 | −39.987 | −25.039 | −24.218 | 23.13 | C |
| ATOM | 1215 | CD2 | HIS | 1202 | −39.507 | −24.329 | −23.17 | 22.29 | C |
| ATOM | 1216 | ND1 | HIS | 1202 | −38.938 | −25.18 | −25.101 | 25.25 | N |
| ATOM | 1217 | CE1 | HIS | 1202 | −37.87 | −24.579 | −24.608 | 23.7 | C |
| ATOM | 1218 | NE2 | HIS | 1202 | −38.189 | −24.055 | −23.438 | 24.81 | N |
| ATOM | 1219 | C | HIS | 1202 | −41.5 | −24.923 | −26.946 | 19.79 | C |
| ATOM | 1220 | O | HIS | 1202 | −41.037 | −23.946 | −27.514 | 19.21 | O |
| ATOM | 1221 | N | ARG | 1203 | −41.491 | −26.145 | −27.484 | 21.16 | N |
| ATOM | 1222 | CA | ARG | 1203 | −40.951 | −26.456 | −28.821 | 20.86 | C |
| ATOM | 1223 | CB | ARG | 1203 | −41.293 | −25.36 | −29.847 | 22.37 | C |
| ATOM | 1224 | CG | ARG | 1203 | −42.756 | −24.976 | −29.983 | 27.08 | C |
| ATOM | 1225 | CD | ARG | 1203 | −42.888 | −23.623 | −30.689 | 30.84 | C |
| ATOM | 1226 | NE | ARG | 1203 | −42.868 | −23.673 | −32.153 | 36.66 | N |
| ATOM | 1227 | CZ | ARG | 1203 | −43.94 | −23.521 | −32.934 | 38.15 | C |
| ATOM | 1228 | NH1 | ARG | 1203 | −45.139 | −23.308 | −32.399 | 37.56 | N |
| ATOM | 1229 | NH2 | ARG | 1203 | −43.811 | −23.569 | −34.258 | 38.08 | N |
| ATOM | 1230 | C | ARG | 1203 | −39.442 | −26.705 | −28.93 | 20.03 | C |
| ATOM | 1231 | O | ARG | 1203 | −38.962 | −27.062 | −30.001 | 20.19 | O |
| ATOM | 1232 | N | ASP | 1204 | −38.68 | −26.498 | −27.866 | 18.22 | N |
| ATOM | 1233 | CA | ASP | 1204 | −37.242 | −26.727 | −27.961 | 17.39 | C |
| ATOM | 1234 | CB | ASP | 1204 | −36.519 | −25.454 | −28.397 | 18.69 | C |
| ATOM | 1235 | CG | ASP | 1204 | −35.059 | −25.705 | −28.756 | 20.08 | C |
| ATOM | 1236 | OD1 | ASP | 1204 | −34.278 | −24.736 | −28.736 | 20.95 | O |
| ATOM | 1237 | OD2 | ASP | 1204 | −34.697 | −26.864 | −29.063 | 20.4 | O |
| ATOM | 1238 | C | ASP | 1204 | −36.713 | −27.183 | −26.617 | 16.06 | C |
| ATOM | 1239 | O | ASP | 1204 | −35.627 | −26.811 | −26.194 | 14.59 | O |
| ATOM | 1240 | N | LEU | 1205 | −37.524 | −27.984 | −25.947 | 15.88 | N |
| ATOM | 1241 | CA | LEU | 1205 | −37.178 | −28.529 | −24.656 | 15.06 | C |
| ATOM | 1242 | CB | LEU | 1205 | −38.41 | −29.214 | −24.078 | 15.7 | C |
| ATOM | 1243 | CG | LEU | 1205 | −38.336 | −29.828 | −22.689 | 16.1 | C |
| ATOM | 1244 | CD1 | LEU | 1205 | −38.054 | −28.738 | −21.67 | 17.91 | C |
| ATOM | 1245 | CD2 | LEU | 1205 | −39.655 | −30.512 | −22.377 | 18.02 | C |
| ATOM | 1246 | C | LEU | 1205 | −36.067 | −29.543 | −24.93 | 15.1 | C |
| ATOM | 1247 | O | LEU | 1205 | −36.226 | −30.41 | −25.777 | 13.35 | O |
| ATOM | 1248 | N | ALA | 1206 | −34.944 | −29.396 | −24.234 | 13.57 | N |
| ATOM | 1249 | CA | ALA | 1206 | −33.775 | −30.261 | −24.359 | 12.02 | C |
| ATOM | 1250 | CB | ALA | 1206 | −33.038 | −29.999 | −25.683 | 12.69 | C |
| ATOM | 1251 | C | ALA | 1206 | −32.917 | −29.824 | −23.184 | 11.59 | C |
| ATOM | 1252 | O | ALA | 1206 | −33.116 | −28.719 | −22.665 | 11.21 | O |
| ATOM | 1253 | N | ALA | 1207 | −31.968 | −30.648 | −22.754 | 11.55 | N |
| ATOM | 1254 | CA | ALA | 1207 | −31.153 | −30.25 | −21.606 | 13.24 | C |
| ATOM | 1255 | CB | ALA | 1207 | −30.255 | −31.394 | −21.164 | 12.55 | C |
| ATOM | 1256 | C | ALA | 1207 | −30.324 | −28.984 | −21.838 | 13.57 | C |
| ATOM | 1257 | O | ALA | 1207 | −29.973 | −28.29 | −20.884 | 12.7 | O |
| ATOM | 1258 | N | ARG | 1208 | −30.008 | −28.66 | −23.087 | 14.61 | N |
| ATOM | 1259 | CA | ARG | 1208 | −29.226 | −27.451 | −23.316 | 15.15 | C |
| ATOM | 1260 | CB | ARG | 1208 | −28.74 | −27.384 | −24.759 | 15.13 | C |
| ATOM | 1261 | CG | ARG | 1208 | −29.829 | −27.618 | −25.745 | 15.45 | C |
| ATOM | 1262 | CD | ARG | 1208 | −29.409 | −27.3 | −27.17 | 14.22 | C |
| ATOM | 1263 | NE | ARG | 1208 | −30.574 | −27.433 | −28.039 | 16.17 | N |
| ATOM | 1264 | CZ | ARG | 1208 | −31.128 | −28.598 | −28.368 | 17.5 | C |
| ATOM | 1265 | NH1 | ARG | 1208 | −30.616 | −29.734 | −27.913 | 15.22 | N |
| ATOM | 1266 | NH2 | ARG | 1208 | −32.211 | −28.63 | −29.132 | 17.23 | N |
| ATOM | 1267 | C | ARG | 1208 | −30.094 | −26.238 | −23.004 | 15.44 | C |
| ATOM | 1268 | O | ARG | 1208 | −29.59 | −25.126 | −22.823 | 14.4 | O |
| ATOM | 1269 | N | ASN | 1209 | −31.402 | −26.452 | −22.915 | 15.58 | N |

TABLE 1B-continued

| | | | | | | | | |
|---|---|---|---|---|---|---|---|---|
| ATOM | 1270 | CA | ASN | 1209 | −32.323 | −25.351 | −22.64 | 15.77 | C |
| ATOM | 1271 | CB | ASN | 1209 | −33.479 | −25.394 | −23.644 | 18.91 | C |
| ATOM | 1272 | CG | ASN | 1209 | −33.06 | −24.919 | −25.021 | 18.29 | C |
| ATOM | 1273 | OD1 | ASN | 1209 | −32.54 | −23.817 | −25.167 | 22.07 | O |
| ATOM | 1274 | ND2 | ASN | 1209 | −33.282 | −25.741 | −26.03 | 20.52 | N |
| ATOM | 1275 | C | ASN | 1209 | −32.869 | −25.211 | −21.218 | 15.85 | C |
| ATOM | 1276 | O | ASN | 1209 | −33.85 | −24.493 | −20.997 | 14.98 | O |
| ATOM | 1277 | N | CYS | 1210 | −32.235 | −25.897 | −20.265 | 14.98 | N |
| ATOM | 1278 | CA | CYS | 1210 | −32.605 | −25.834 | −18.848 | 13.93 | C |
| ATOM | 1279 | CB | CYS | 1210 | −32.902 | −27.23 | −18.301 | 14.01 | C |
| ATOM | 1280 | SG | CYS | 1210 | −34.181 | −28.128 | −19.141 | 18.21 | S |
| ATOM | 1281 | C | CYS | 1210 | −31.381 | −25.299 | −18.117 | 13.47 | C |
| ATOM | 1282 | O | CYS | 1210 | −30.281 | −25.796 | −18.337 | 14.75 | O |
| ATOM | 1283 | N | MET | 1211 | −31.542 | −24.306 | −17.251 | 11.84 | N |
| ATOM | 1284 | CA | MET | 1211 | −30.389 | −23.777 | −16.526 | 12.37 | C |
| ATOM | 1285 | CB | MET | 1211 | −30.373 | −22.25 | −16.618 | 12.33 | C |
| ATOM | 1286 | CG | MET | 1211 | −30.417 | −21.723 | −18.04 | 15.48 | C |
| ATOM | 1287 | SD | MET | 1211 | −28.921 | −22.155 | −18.986 | 16.79 | S |
| ATOM | 1288 | CE | MET | 1211 | −29.629 | −22.57 | −20.593 | 17.49 | C |
| ATOM | 1289 | C | MET | 1211 | −30.355 | −24.221 | −15.051 | 13.11 | C |
| ATOM | 1290 | O | MET | 1211 | −31.405 | −24.444 | −14.433 | 12.82 | O |
| ATOM | 1291 | N | LEU | 1212 | −29.138 | −24.339 | −14.515 | 14.5 | N |
| ATOM | 1292 | CA | LEU | 1212 | −28.858 | −24.757 | −13.126 | 18.15 | C |
| ATOM | 1293 | CB | LEU | 1212 | −27.783 | −25.854 | −13.117 | 18.33 | C |
| ATOM | 1294 | CG | LEU | 1212 | −28.063 | −27.342 | −12.907 | 23.14 | C |
| ATOM | 1295 | CD1 | LEU | 1212 | −26.759 | −28.114 | −12.725 | 22.22 | C |
| ATOM | 1296 | CD2 | LEU | 1212 | −28.895 | −27.512 | −11.67 | 22.5 | C |
| ATOM | 1297 | C | LEU | 1212 | −28.318 | −23.607 | −12.264 | 18.5 | C |
| ATOM | 1298 | O | LEU | 1212 | −27.306 | −23.003 | −12.624 | 17.66 | O |
| ATOM | 1299 | N | ASP | 1213 | −28.945 | −23.3 | −11.131 | 19.27 | N |
| ATOM | 1300 | CA | ASP | 1213 | −28.396 | −22.225 | −10.308 | 21.32 | C |
| ATOM | 1301 | CB | ASP | 1213 | −29.477 | −21.318 | −9.693 | 21.56 | C |
| ATOM | 1302 | CG | ASP | 1213 | −30.303 | −22.006 | −8.609 | 23.87 | C |
| ATOM | 1303 | OD1 | ASP | 1213 | −29.909 | −23.083 | −8.098 | 22.69 | O |
| ATOM | 1304 | OD2 | ASP | 1213 | −31.359 | −21.435 | −8.26 | 23.31 | O |
| ATOM | 1305 | C | ASP | 1213 | −27.537 | −22.792 | −9.199 | 22.81 | C |
| ATOM | 1306 | O | ASP | 1213 | −27.369 | −24.013 | −9.088 | 21.8 | O |
| ATOM | 1307 | N | GLU | 1214 | −27.015 | −21.875 | −8.387 | 23.36 | N |
| ATOM | 1308 | CA | GLU | 1214 | −26.15 | −22.172 | −7.263 | 25.25 | C |
| ATOM | 1309 | CB | GLU | 1214 | −25.713 | −20.823 | −6.591 | 27.38 | C |
| ATOM | 1310 | CG | GLU | 1214 | −26.765 | −19.881 | −5.826 | 31.52 | C |
| ATOM | 1311 | CD | GLU | 1214 | −27.635 | −18.892 | −6.678 | 36.11 | C |
| ATOM | 1312 | OE1 | GLU | 1214 | −28.537 | −19.36 | −7.408 | 37.3 | O |
| ATOM | 1313 | OE2 | GLU | 1214 | −27.447 | −17.642 | −6.592 | 38.7 | O |
| ATOM | 1314 | C | GLU | 1214 | −26.736 | −23.199 | −6.26 | 25.42 | C |
| ATOM | 1315 | O | GLU | 1214 | −25.992 | −23.936 | −5.608 | 25.26 | O |
| ATOM | 1316 | N | LYS | 1215 | −28.062 | −23.282 | −6.172 | 25.13 | N |
| ATOM | 1317 | CA | LYS | 1215 | −28.709 | −24.231 | −5.258 | 25.77 | C |
| ATOM | 1318 | CB | LYS | 1215 | −29.843 | −23.524 | −4.475 | 28.21 | C |
| ATOM | 1319 | CG | LYS | 1215 | −29.356 | −22.414 | −3.48 | 33.22 | C |
| ATOM | 1320 | CD | LYS | 1215 | −30.496 | −21.715 | −2.665 | 36.61 | C |
| ATOM | 1321 | CE | LYS | 1215 | −29.956 | −20.614 | −1.691 | 39.24 | C |
| ATOM | 1322 | NZ | LYS | 1215 | −30.983 | −19.842 | −0.882 | 40.6 | N |
| ATOM | 1323 | C | LYS | 1215 | −29.23 | −25.491 | −5.998 | 25.36 | C |
| ATOM | 1324 | O | LYS | 1215 | −30.031 | −26.261 | −5.464 | 24.65 | O |
| ATOM | 1325 | N | PHE | 1216 | −28.739 | −25.682 | −7.225 | 23.22 | N |
| ATOM | 1326 | CA | PHE | 1216 | −29.075 | −26.811 | −8.091 | 21.85 | C |
| ATOM | 1327 | CB | PHE | 1216 | −28.465 | −28.108 | −7.517 | 23.16 | C |
| ATOM | 1328 | CG | PHE | 1216 | −26.958 | −28.012 | −7.263 | 24.21 | C |
| ATOM | 1329 | CD1 | PHE | 1216 | −26.463 | −27.77 | −5.975 | 26.27 | C |
| ATOM | 1330 | CD2 | PHE | 1216 | −26.043 | −28.113 | −8.314 | 23.83 | C |
| ATOM | 1331 | CE1 | PHE | 1216 | −25.081 | −27.629 | −5.741 | 24.88 | C |
| ATOM | 1332 | CE2 | PHE | 1216 | −24.659 | −27.972 | −8.088 | 25.08 | C |
| ATOM | 1333 | CZ | PHE | 1216 | −24.183 | −27.73 | −6.803 | 25.51 | C |
| ATOM | 1334 | C | PHE | 1216 | −30.569 | −26.93 | −8.396 | 20.58 | C |
| ATOM | 1335 | O | PHE | 1216 | −31.144 | −28.015 | −8.54 | 17.6 | O |
| ATOM | 1336 | N | THR | 1217 | −31.179 | −25.759 | −8.521 | 19.63 | N |
| ATOM | 1337 | CA | THR | 1217 | −32.576 | −25.635 | −8.871 | 17.9 | C |
| ATOM | 1338 | CB | THR | 1217 | −33.199 | −24.4 | −8.134 | 18.25 | C |
| ATOM | 1339 | OG1 | THR | 1217 | −33.309 | −24.708 | −6.736 | 22.27 | O |
| ATOM | 1340 | CG2 | THR | 1217 | −34.587 | −24.057 | −8.663 | 18.17 | C |
| ATOM | 1341 | C | THR | 1217 | −32.473 | −25.47 | −10.396 | 16.93 | C |
| ATOM | 1342 | O | THR | 1217 | −31.649 | −24.686 | −10.886 | 16.95 | O |
| ATOM | 1343 | N | VAL | 1218 | −33.243 | −26.282 | −11.127 | 14.5 | N |
| ATOM | 1344 | CA | VAL | 1218 | −33.271 | −26.27 | −12.593 | 12.8 | C |
| ATOM | 1345 | CB | VAL | 1218 | −33.428 | −27.71 | −13.207 | 13.21 | C |
| ATOM | 1346 | CG1 | VAL | 1218 | −33.421 | −27.636 | −14.734 | 9.72 | C |
| ATOM | 1347 | CG2 | VAL | 1218 | −32.297 | −28.638 | −12.73 | 11.3 | C |
| ATOM | 1348 | C | VAL | 1218 | −34.455 | −25.437 | −13.066 | 12.06 | C |
| ATOM | 1349 | O | VAL | 1218 | −35.546 | −25.515 | −12.503 | 10.84 | O |

TABLE 1B-continued

| | | | | | | | | |
|---|---|---|---|---|---|---|---|---|
| ATOM | 1350 | N | LYS | 1219 | −34.229 | −24.646 | −14.107 | 12.68 | N |
| ATOM | 1351 | CA | LYS | 1219 | −35.268 | −23.8 | −14.659 | 13.73 | C |
| ATOM | 1352 | CB | LYS | 1219 | −35.033 | −22.337 | −14.228 | 13.19 | C |
| ATOM | 1353 | CG | LYS | 1219 | −34.861 | −22.121 | −12.692 | 17.83 | C |
| ATOM | 1354 | CD | LYS | 1219 | −35.229 | −20.688 | −12.283 | 21.91 | C |
| ATOM | 1355 | CE | LYS | 1219 | −35.232 | −20.482 | −10.768 | 22.55 | C |
| ATOM | 1356 | NZ | LYS | 1219 | −33.871 | −20.066 | −10.367 | 26.09 | N |
| ATOM | 1357 | C | LYS | 1219 | −35.258 | −23.95 | −16.187 | 13.7 | C |
| ATOM | 1358 | O | LYS | 1219 | −34.202 | −23.854 | −16.83 | 14.06 | O |
| ATOM | 1359 | N | VAL | 1220 | −36.437 | −24.224 | −16.746 | 12.71 | N |
| ATOM | 1360 | CA | VAL | 1220 | −36.641 | −24.392 | −18.188 | 13.54 | C |
| ATOM | 1361 | CB | VAL | 1220 | −38.027 | −25.056 | −18.466 | 10.73 | C |
| ATOM | 1362 | CG1 | VAL | 1220 | −38.189 | −25.371 | −19.946 | 12.56 | C |
| ATOM | 1363 | CG2 | VAL | 1220 | −38.177 | −26.319 | −17.619 | 13.35 | C |
| ATOM | 1364 | C | VAL | 1220 | −36.617 | −22.987 | −18.794 | 13.96 | C |
| ATOM | 1365 | O | VAL | 1220 | −37.273 | −22.079 | −18.28 | 13.77 | O |
| ATOM | 1366 | N | ALA | 1221 | −35.866 | −22.814 | −19.874 | 15.44 | N |
| ATOM | 1367 | CA | ALA | 1221 | −35.742 | −21.521 | −20.529 | 17.32 | C |
| ATOM | 1368 | CB | ALA | 1221 | −34.291 | −21.059 | −20.472 | 19.47 | C |
| ATOM | 1369 | C | ALA | 1221 | −36.193 | −21.558 | −21.967 | 18.52 | C |
| ATOM | 1370 | O | ALA | 1221 | −36.144 | −22.607 | −22.622 | 17.22 | O |
| ATOM | 1371 | N | ASP | 1222 | −36.655 | −20.409 | −22.44 | 19.34 | N |
| ATOM | 1372 | CA | ASP | 1222 | −37.05 | −20.259 | −23.823 | 20.45 | C |
| ATOM | 1373 | C | ASP | 1222 | −36.096 | −19.138 | −24.197 | 21.22 | C |
| ATOM | 1374 | O | ASP | 1222 | −36.346 | −17.986 | −23.881 | 20.31 | O |
| ATOM | 1375 | CB | ASP | 1222 | −38.513 | −19.79 | −23.946 | 0 | C |
| ATOM | 1376 | CG | ASP | 1222 | −38.938 | −19.5 | −25.394 | 0 | C |
| ATOM | 1377 | OD1 | ASP | 1222 | −38.028 | −19.47 | −26.254 | 0 | O |
| ATOM | 1378 | OD2 | ASP | 1222 | −40.162 | −19.394 | −25.634 | 0 | O1− |
| ATOM | 1379 | N | PHE | 1223 | −34.946 | −19.467 | −24.764 | 22.78 | N |
| ATOM | 1380 | CA | PHE | 1223 | −34.068 | −18.376 | −25.174 | 24.51 | C |
| ATOM | 1381 | CB | PHE | 1223 | −32.649 | −18.78 | −25.064 | 23.52 | C |
| ATOM | 1382 | CG | PHE | 1223 | −32.181 | −18.589 | −23.73 | 22.43 | C |
| ATOM | 1383 | CD1 | PHE | 1223 | −32.106 | −17.305 | −23.205 | 22.25 | C |
| ATOM | 1384 | CD2 | PHE | 1223 | −31.915 | −19.675 | −22.943 | 22.04 | C |
| ATOM | 1385 | CE1 | PHE | 1223 | −31.767 | −17.121 | −21.898 | 23.44 | C |
| ATOM | 1386 | CE2 | PHE | 1223 | −31.579 | −19.511 | −21.655 | 23.35 | C |
| ATOM | 1387 | CZ | PHE | 1223 | −31.497 | −18.23 | −21.115 | 21.72 | C |
| ATOM | 1388 | C | PHE | 1223 | −34.508 | −18.133 | −26.543 | 26.06 | C |
| ATOM | 1389 | O | PHE | 1223 | −35.441 | −17.365 | −26.738 | 27.77 | O |
| ATOM | 1390 | N | GLY | 1224 | −33.816 | −18.621 | −27.533 | 25.8 | N |
| ATOM | 1391 | CA | GLY | 1224 | −34.608 | −18.551 | −28.715 | 26.02 | C |
| ATOM | 1392 | C | GLY | 1224 | −34.467 | −17.321 | −29.46 | 24.52 | C |
| ATOM | 1393 | O | GLY | 1224 | −33.784 | −17.447 | −30.43 | 26.4 | O |
| ATOM | 1394 | N | LEU | 1225 | −35.099 | −16.199 | −29.133 | 23.41 | N |
| ATOM | 1395 | CA | LEU | 1225 | −34.742 | −15.069 | −29.965 | 22.22 | C |
| ATOM | 1396 | CB | LEU | 1225 | −35.724 | −13.898 | −29.921 | 24.33 | C |
| ATOM | 1397 | CG | LEU | 1225 | −35.597 | −13.386 | −31.376 | 24.95 | C |
| ATOM | 1398 | CD1 | LEU | 1225 | −36.22 | −14.383 | −32.359 | 27.59 | C |
| ATOM | 1399 | CD2 | LEU | 1225 | −36.271 | −12.083 | −31.549 | 27.1 | C |
| ATOM | 1400 | C | LEU | 1225 | −33.399 | −14.576 | −29.482 | 21.21 | C |
| ATOM | 1401 | O | LEU | 1225 | −32.701 | −13.862 | −30.192 | 23.15 | O |
| ATOM | 1402 | N | ALA | 1226 | −33.014 | −14.967 | −28.279 | 18.87 | N |
| ATOM | 1403 | CA | ALA | 1226 | −31.743 | −14.53 | −27.759 | 18.09 | C |
| ATOM | 1404 | CB | ALA | 1226 | −31.729 | −14.712 | −26.281 | 17.96 | C |
| ATOM | 1405 | C | ALA | 1226 | −30.563 | −15.254 | −28.404 | 19.16 | C |
| ATOM | 1406 | O | ALA | 1226 | −29.424 | −14.798 | −28.296 | 19.43 | O |
| ATOM | 1407 | N | ARG | 1227 | −30.825 | −16.383 | −29.063 | 19.46 | N |
| ATOM | 1408 | CA | ARG | 1227 | −29.762 | −17.127 | −29.734 | 19.73 | C |
| ATOM | 1409 | CB | ARG | 1227 | −30.173 | −18.589 | −29.955 | 21.4 | C |
| ATOM | 1410 | CG | ARG | 1227 | −29.913 | −19.468 | −28.749 | 21.1 | C |
| ATOM | 1411 | CD | ARG | 1227 | −30.775 | −20.709 | −28.773 | 24.1 | C |
| ATOM | 1412 | NE | ARG | 1227 | −30.764 | −21.366 | −27.479 | 24.33 | N |
| ATOM | 1413 | CZ | ARG | 1227 | −29.659 | −21.795 | −26.901 | 25.32 | C |
| ATOM | 1414 | NH1 | ARG | 1227 | −28.485 | −21.653 | −27.513 | 23.64 | N |
| ATOM | 1415 | NH2 | ARG | 1227 | −29.722 | −22.259 | −25.669 | 22.87 | N |
| ATOM | 1416 | C | ARG | 1227 | −29.502 | −16.471 | −31.081 | 19.24 | C |
| ATOM | 1417 | O | ARG | 1227 | −30.343 | −16.548 | −31.967 | 19.55 | O |
| ATOM | 1418 | N | ASP | 1228 | −28.353 | −15.814 | −31.225 | 18.7 | N |
| ATOM | 1419 | CA | ASP | 1228 | −27.993 | −15.164 | −32.476 | 20.06 | C |
| ATOM | 1420 | CB | ASP | 1228 | −26.596 | −14.543 | −32.363 | 22.84 | C |
| ATOM | 1421 | CG | ASP | 1228 | −26.564 | −13.326 | −31.44 | 25.1 | C |
| ATOM | 1422 | OD1 | ASP | 1228 | −27.649 | −12.775 | −31.148 | 28.18 | O |
| ATOM | 1423 | OD2 | ASP | 1228 | −25.463 | −12.912 | −31.015 | 24.23 | O |
| ATOM | 1424 | C | ASP | 1228 | −28.032 | −16.191 | −33.614 | 21.09 | C |
| ATOM | 1425 | O | ASP | 1228 | −28.69 | −15.971 | −34.635 | 20.36 | O |
| ATOM | 1426 | N | MET | 1229 | −27.319 | −17.303 | −33.401 | 22.55 | N |
| ATOM | 1427 | CA | MET | 1229 | −27.226 | −18.451 | −34.317 | 25.14 | C |
| ATOM | 1428 | CB | MET | 1229 | −25.849 | −18.58 | −34.936 | 26.88 | C |
| ATOM | 1429 | CG | MET | 1229 | −25.515 | −17.46 | −35.798 | 31.32 | C |

TABLE 1B-continued

| ATOM | 1430 | SD | MET | 1229 | −24.024 | −17.65 | −36.705 | 35.03 | S |
|---|---|---|---|---|---|---|---|---|---|
| ATOM | 1431 | CE | MET | 1229 | −23.377 | −16.183 | −36.259 | 34.46 | C |
| ATOM | 1432 | C | MET | 1229 | −27.431 | −19.769 | −33.598 | 26.07 | C |
| ATOM | 1433 | O | MET | 1229 | −27.166 | −19.877 | −32.409 | 24.93 | O |
| ATOM | 1434 | N | TYR | 1230 | −27.867 | −20.747 | −34.392 | 28.36 | N |
| ATOM | 1435 | CA | TYR | 1230 | −28.082 | −22.125 | −33.992 | 31.64 | C |
| ATOM | 1436 | CB | TYR | 1230 | −29.453 | −22.541 | −34.464 | 32.55 | C |
| ATOM | 1437 | CG | TYR | 1230 | −30.516 | −21.962 | −33.652 | 35.13 | C |
| ATOM | 1438 | CD1 | TYR | 1230 | −30.798 | −20.603 | −33.714 | 36.14 | C |
| ATOM | 1439 | CE1 | TYR | 1230 | −31.725 | −20.077 | −32.932 | 36.69 | C |
| ATOM | 1440 | CD2 | TYR | 1230 | −31.171 | −22.761 | −32.768 | 36.34 | C |
| ATOM | 1441 | CE2 | TYR | 1230 | −32.087 | −22.251 | −31.994 | 37.04 | C |
| ATOM | 1442 | CZ | TYR | 1230 | −32.365 | −20.915 | −32.096 | 38.54 | C |
| ATOM | 1443 | OH | TYR | 1230 | −33.288 | −20.428 | −31.255 | 40.67 | O |
| ATOM | 1444 | C | TYR | 1230 | −27.115 | −23.13 | −34.593 | 33.96 | C |
| ATOM | 1445 | O | TYR | 1230 | −26.726 | −22.999 | −35.739 | 31.96 | O |
| ATOM | 1446 | N | ASP | 1231 | −26.708 | −24.121 | −33.842 | 37.48 | N |
| ATOM | 1447 | CA | ASP | 1231 | −25.919 | −25.139 | −34.375 | 40.93 | C |
| ATOM | 1448 | CB | ASP | 1231 | −24.61 | −25.288 | −33.497 | 44.37 | C |
| ATOM | 1449 | CG | ASP | 1231 | −23.925 | −24.048 | −33.276 | 48.97 | C |
| ATOM | 1450 | OD1 | ASP | 1231 | −24.038 | −23.129 | −34.127 | 52.21 | O |
| ATOM | 1451 | OD2 | ASP | 1231 | −23.288 | −23.979 | −32.223 | 52.03 | O |
| ATOM | 1452 | C | ASP | 1231 | −26.456 | −26.616 | −34.314 | 40.83 | C |
| ATOM | 1453 | O | ASP | 1231 | −27.297 | −26.882 | −33.463 | 42.4 | O |
| ATOM | 1454 | N | LYS | 1232 | −26.267 | −27.085 | −35.575 | 42.17 | N |
| ATOM | 1455 | CA | LYS | 1232 | −25.533 | −28.505 | −35.598 | 41.36 | C |
| ATOM | 1456 | CB | LYS | 1232 | −24.062 | −27.847 | −35.332 | 43.03 | C |
| ATOM | 1457 | CG | LYS | 1232 | −23.742 | −27.489 | −33.868 | 42.47 | C |
| ATOM | 1458 | CD | LYS | 1232 | −22.298 | −27.062 | −33.676 | 44.85 | C |
| ATOM | 1459 | CE | LYS | 1232 | −22.066 | −26.5 | −32.281 | 45.67 | C |
| ATOM | 1460 | NZ | LYS | 1232 | −22.63 | −27.363 | −31.219 | 45.92 | N |
| ATOM | 1461 | C | LYS | 1232 | −25.864 | −29.353 | −34.331 | 42.16 | C |
| ATOM | 1462 | O | LYS | 1232 | −24.92 | −29.911 | −33.817 | 42.14 | O |
| ATOM | 1463 | N | GLU | 1233 | −27.06 | −29.753 | −34.739 | 41.02 | N |
| ATOM | 1464 | CA | GLU | 1233 | −28.195 | −29.943 | −33.706 | 38.27 | C |
| ATOM | 1465 | CB | GLU | 1233 | −27.97 | −29.831 | −32.326 | 38.85 | C |
| ATOM | 1466 | CG | GLU | 1233 | −28.074 | −28.876 | −31.65 | 39.43 | C |
| ATOM | 1467 | CD | GLU | 1233 | −27.167 | −29.213 | −30.633 | 40.62 | C |
| ATOM | 1468 | OE1 | GLU | 1233 | −27.027 | −30.394 | −30.339 | 41.43 | O |
| ATOM | 1469 | OE2 | GLU | 1233 | −26.558 | −28.342 | −30.077 | 40.48 | O |
| ATOM | 1470 | C | GLU | 1233 | −29.459 | −29.134 | −34.191 | 36.4 | C |
| ATOM | 1471 | O | GLU | 1233 | −30.524 | −29.669 | −33.898 | 34.53 | O |
| ATOM | 1472 | N | TYR | 1234 | −29.475 | −28.188 | −35.121 | 36.25 | N |
| ATOM | 1473 | CA | TYR | 1234 | −30.734 | −27.685 | −35.527 | 36.56 | C |
| ATOM | 1474 | CB | TYR | 1234 | −30.911 | −26.216 | −35.002 | 33.99 | C |
| ATOM | 1475 | CG | TYR | 1234 | −31.224 | −25.972 | −33.511 | 31.79 | C |
| ATOM | 1476 | CD1 | TYR | 1234 | −30.212 | −25.93 | −32.539 | 31.24 | C |
| ATOM | 1477 | CE1 | TYR | 1234 | −30.517 | −25.712 | −31.174 | 30.51 | C |
| ATOM | 1478 | CD2 | TYR | 1234 | −32.541 | −25.784 | −33.081 | 30.83 | C |
| ATOM | 1479 | CE2 | TYR | 1234 | −32.85 | −25.571 | −31.73 | 31.34 | C |
| ATOM | 1480 | CZ | TYR | 1234 | −31.84 | −25.539 | −30.786 | 30.26 | C |
| ATOM | 1481 | OH | TYR | 1234 | −32.168 | −25.366 | −29.461 | 30.54 | O |
| ATOM | 1482 | C | TYR | 1234 | −30.732 | −27.612 | −37.001 | 38.61 | C |
| ATOM | 1483 | O | TYR | 1234 | −29.768 | −27.222 | −37.647 | 38.99 | O |
| ATOM | 1484 | N | TYR | 1235 | −31.838 | −28.06 | −37.605 | 40.77 | N |
| ATOM | 1485 | CA | TYR | 1235 | −31.738 | −27.772 | −38.957 | 42.64 | C |
| ATOM | 1486 | CB | TYR | 1235 | −31.678 | −29.069 | −39.669 | 46.84 | C |
| ATOM | 1487 | CG | TYR | 1235 | −32.849 | −29.778 | −39.865 | 50.38 | C |
| ATOM | 1488 | CD1 | TYR | 1235 | −34.004 | −29.171 | −39.769 | 53.12 | C |
| ATOM | 1489 | CE1 | TYR | 1235 | −35.198 | −29.749 | −40.213 | 55.79 | C |
| ATOM | 1490 | CD2 | TYR | 1235 | −32.817 | −31.021 | −40.357 | 53.24 | C |
| ATOM | 1491 | CE2 | TYR | 1235 | −34.04 | −31.664 | −40.801 | 55.03 | C |
| ATOM | 1492 | CZ | TYR | 1235 | −35.279 | −30.998 | −40.743 | 55.74 | C |
| ATOM | 1493 | OH | TYR | 1235 | −36.599 | −31.478 | −41.034 | 56.64 | O |
| ATOM | 1494 | C | TYR | 1235 | −32.684 | −26.594 | −39.33 | 42.38 | C |
| ATOM | 1495 | O | TYR | 1235 | −33.349 | −26.096 | −38.446 | 40.51 | O |
| ATOM | 1496 | N | SER | 1236 | −32.562 | −26.056 | −40.555 | 43.09 | N |
| ATOM | 1497 | CA | SER | 1236 | −33.212 | −24.801 | −41.007 | 45.87 | C |
| ATOM | 1498 | CB | SER | 1236 | −32.195 | −23.721 | −41.381 | 45.81 | C |
| ATOM | 1499 | OG | SER | 1236 | −32.456 | −22.403 | −40.912 | 46.19 | O |
| ATOM | 1500 | C | SER | 1236 | −33.855 | −25.128 | −42.242 | 46.98 | C |
| ATOM | 1501 | O | SER | 1236 | −33.2 | −25.525 | −43.229 | 46.05 | O |
| ATOM | 1502 | N | VAL | 1237 | −35.127 | −24.83 | −42.112 | 49.49 | N |
| ATOM | 1503 | CA | VAL | 1237 | −36.152 | −25.135 | −42.976 | 53.03 | C |
| ATOM | 1504 | CB | VAL | 1237 | −36.004 | −26.282 | −43.795 | 54.51 | C |
| ATOM | 1505 | CG1 | VAL | 1237 | −37.535 | −26.564 | −44.634 | 55.14 | C |
| ATOM | 1506 | CG2 | VAL | 1237 | −34.579 | −26.099 | −44.653 | 55.8 | C |
| ATOM | 1507 | C | VAL | 1237 | −37.635 | −25.216 | −42.705 | 53.76 | C |
| ATOM | 1508 | O | VAL | 1237 | −38.019 | −25.752 | −41.647 | 56 | O |
| ATOM | 1509 | N | HIS | 1238 | −37.758 | −23.997 | −43.136 | 52.4 | N |

TABLE 1B-continued

| | | | | | | | | |
|---|---|---|---|---|---|---|---|---|
| ATOM | 1510 | CA | HIS | 1238 | −37.717 | −23.906 | −44.535 | 51.91 | C |
| ATOM | 1511 | CB | HIS | 1238 | −38.465 | −22.886 | −45.254 | 54.35 | C |
| ATOM | 1512 | CG | HIS | 1238 | −39.616 | −23.437 | −45.974 | 57.6 | C |
| ATOM | 1513 | CD2 | HIS | 1238 | −40.346 | −22.958 | −47.004 | 58.86 | C |
| ATOM | 1514 | ND1 | HIS | 1238 | −40.192 | −24.626 | −45.598 | 58.65 | N |
| ATOM | 1515 | CE1 | HIS | 1238 | −41.237 | −24.859 | −46.368 | 60.01 | C |
| ATOM | 1516 | NE2 | HIS | 1238 | −41.353 | −23.862 | −47.23 | 59.82 | N |
| ATOM | 1517 | C | HIS | 1238 | −36.249 | −23.225 | −44.582 | 48.89 | C |
| ATOM | 1518 | O | HIS | 1238 | −35.761 | −22.506 | −43.669 | 48.04 | O |
| ATOM | 1519 | N | ASN | 1239 | −35.594 | −23.733 | −45.588 | 45.16 | N |
| ATOM | 1520 | CA | ASN | 1239 | −34.522 | −23.154 | −46.263 | 42.36 | C |
| ATOM | 1521 | CB | ASN | 1239 | −34.461 | −23.909 | −47.567 | 39.19 | C |
| ATOM | 1522 | CG | ASN | 1239 | −33.336 | −24.794 | −47.582 | 36.67 | C |
| ATOM | 1523 | OD1 | ASN | 1239 | −32.361 | −24.421 | −47.049 | 32.64 | O |
| ATOM | 1524 | ND2 | ASN | 1239 | −33.421 | −25.953 | −48.131 | 35.18 | N |
| ATOM | 1525 | C | ASN | 1239 | −35.228 | −21.819 | −46.602 | 41.96 | C |
| ATOM | 1526 | O | ASN | 1239 | −34.606 | −20.882 | −47.041 | 40.93 | O |
| ATOM | 1527 | N | LYS | 1240 | −36.529 | −21.728 | −46.411 | 42.34 | N |
| ATOM | 1528 | CA | LYS | 1240 | −37.182 | −20.524 | −46.813 | 43.5 | C |
| ATOM | 1529 | CB | LYS | 1240 | −38.236 | −20.938 | −47.786 | 45.68 | C |
| ATOM | 1530 | CG | LYS | 1240 | −38.978 | −19.876 | −48.424 | 49.63 | C |
| ATOM | 1531 | CD | LYS | 1240 | −39.862 | −20.598 | −49.314 | 52.15 | C |
| ATOM | 1532 | CE | LYS | 1240 | −40.698 | −19.81 | −50.23 | 53.54 | C |
| ATOM | 1533 | NZ | LYS | 1240 | −41.324 | −20.804 | −51.138 | 53.01 | N |
| ATOM | 1534 | C | LYS | 1240 | −37.69 | −19.72 | −45.646 | 42.44 | C |
| ATOM | 1535 | O | LYS | 1240 | −37.456 | −18.534 | −45.622 | 43.49 | O |
| ATOM | 1536 | N | THR | 1241 | −38.354 | −20.336 | −44.673 | 40.41 | N |
| ATOM | 1537 | CA | THR | 1241 | −38.785 | −19.59 | −43.49 | 38.28 | C |
| ATOM | 1538 | CB | THR | 1241 | −39.811 | −20.311 | −42.655 | 37.86 | C |
| ATOM | 1539 | OG1 | THR | 1241 | −39.215 | −21.421 | −41.969 | 35.48 | O |
| ATOM | 1540 | CG2 | THR | 1241 | −40.791 | −20.851 | −43.504 | 37.56 | C |
| ATOM | 1541 | C | THR | 1241 | −37.666 | −19.407 | −42.501 | 37.63 | C |
| ATOM | 1542 | O | THR | 1241 | −37.766 | −18.558 | −41.64 | 38.27 | O |
| ATOM | 1543 | N | GLY | 1242 | −36.621 | −20.22 | −42.576 | 36.14 | N |
| ATOM | 1544 | CA | GLY | 1242 | −35.569 | −20.096 | −41.584 | 33.51 | C |
| ATOM | 1545 | C | GLY | 1242 | −35.945 | −20.657 | −40.222 | 32.78 | C |
| ATOM | 1546 | O | GLY | 1242 | −35.296 | −20.446 | −39.216 | 32.4 | O |
| ATOM | 1547 | N | ALA | 1243 | −36.965 | −21.453 | −40.154 | 30.86 | N |
| ATOM | 1548 | CA | ALA | 1243 | −37.285 | −21.872 | −38.837 | 30.24 | C |
| ATOM | 1549 | CB | ALA | 1243 | −38.591 | −22.411 | −38.953 | 31.17 | C |
| ATOM | 1550 | C | ALA | 1243 | −36.196 | −22.869 | −38.28 | 29.29 | C |
| ATOM | 1551 | O | ALA | 1243 | −35.507 | −23.504 | −39.074 | 28.68 | O |
| ATOM | 1552 | N | LYS | 1244 | −35.951 | −22.972 | −36.968 | 27.71 | N |
| ATOM | 1553 | CA | LYS | 1244 | −34.908 | −23.918 | −36.53 | 27.48 | C |
| ATOM | 1554 | CB | LYS | 1244 | −33.923 | −23.33 | −35.522 | 28.19 | C |
| ATOM | 1555 | CG | LYS | 1244 | −33.554 | −21.899 | −35.836 | 29.18 | C |
| ATOM | 1556 | CD | LYS | 1244 | −32.685 | −21.772 | −37.068 | 30.21 | C |
| ATOM | 1557 | CE | LYS | 1244 | −32.757 | −20.362 | −37.658 | 34.05 | C |
| ATOM | 1558 | NZ | LYS | 1244 | −33.43 | −19.381 | −36.754 | 35.34 | N |
| ATOM | 1559 | C | LYS | 1244 | −35.595 | −25.092 | −35.941 | 27.46 | C |
| ATOM | 1560 | O | LYS | 1244 | −36.579 | −24.986 | −35.212 | 27.05 | O |
| ATOM | 1561 | N | LEU | 1245 | −35.016 | −26.227 | −36.213 | 26.57 | N |
| ATOM | 1562 | CA | LEU | 1245 | −35.698 | −27.39 | −35.828 | 25.63 | C |
| ATOM | 1563 | CB | LEU | 1245 | −36.319 | −27.817 | −37.122 | 26.81 | C |
| ATOM | 1564 | CG | LEU | 1245 | −37.185 | −26.893 | −37.928 | 27.54 | C |
| ATOM | 1565 | CD1 | LEU | 1245 | −36.824 | −27.236 | −39.225 | 29.71 | C |
| ATOM | 1566 | CD2 | LEU | 1245 | −38.559 | −27.221 | −37.86 | 29.25 | C |
| ATOM | 1567 | C | LEU | 1245 | −34.862 | −28.475 | −35.12 | 23.78 | C |
| ATOM | 1568 | O | LEU | 1245 | −33.954 | −29.072 | −35.711 | 24.46 | O |
| ATOM | 1569 | N | PRO | 1246 | −35.134 | −28.688 | −33.814 | 21.49 | N |
| ATOM | 1570 | CD | PRO | 1246 | −36.076 | −27.899 | −32.992 | 22.41 | C |
| ATOM | 1571 | CA | PRO | 1246 | −34.45 | −29.686 | −32.982 | 20.52 | C |
| ATOM | 1572 | CB | PRO | 1246 | −34.893 | −29.326 | −31.563 | 20.74 | C |
| ATOM | 1573 | CG | PRO | 1246 | −36.27 | −28.784 | −31.769 | 22.45 | C |
| ATOM | 1574 | C | PRO | 1246 | −34.929 | −31.054 | −33.419 | 18.08 | C |
| ATOM | 1575 | O | PRO | 1246 | −35.579 | −31.778 | −32.663 | 17.77 | O |
| ATOM | 1576 | N | VAL | 1247 | −34.609 | −31.386 | −34.664 | 17.04 | N |
| ATOM | 1577 | CA | VAL | 1247 | −35.005 | −32.65 | −35.261 | 16.91 | C |
| ATOM | 1578 | CB | VAL | 1247 | −34.141 | −33.039 | −36.451 | 18.82 | C |
| ATOM | 1579 | CG1 | VAL | 1247 | −34.435 | −32.219 | −37.548 | 17.47 | C |
| ATOM | 1580 | CG2 | VAL | 1247 | −32.717 | −32.843 | −36.16 | 22.1 | C |
| ATOM | 1581 | C | VAL | 1247 | −34.917 | −33.816 | −34.315 | 16.17 | C |
| ATOM | 1582 | O | VAL | 1247 | −35.866 | −34.571 | −34.161 | 15.61 | O |
| ATOM | 1583 | N | LYS | 1248 | −33.768 | −33.966 | −33.677 | 15.85 | N |
| ATOM | 1584 | CA | LYS | 1248 | −33.576 | −35.092 | −32.784 | 14.63 | C |
| ATOM | 1585 | CB | LYS | 1248 | −32.092 | −35.337 | −32.625 | 17.18 | C |
| ATOM | 1586 | CG | LYS | 1248 | −31.533 | −35.883 | −33.913 | 19.71 | C |
| ATOM | 1587 | CD | LYS | 1248 | −30.083 | −36.145 | −33.764 | 22.1 | C |
| ATOM | 1588 | CE | LYS | 1248 | −29.479 | −36.741 | −34.994 | 23.2 | C |
| ATOM | 1589 | NZ | LYS | 1248 | −28.029 | −36.572 | −34.748 | 29.5 | N |

TABLE 1B-continued

| | | | | | | | | |
|---|---|---|---|---|---|---|---|---|
| ATOM | 1590 | C | LYS | 1248 | −34.291 | −35.113 | −31.44 | 15.45 | C |
| ATOM | 1591 | O | LYS | 1248 | −34.255 | −36.141 | −30.745 | 13.52 | O |
| ATOM | 1592 | N | TRP | 1249 | −34.935 | −33.999 | −31.079 | 12.34 | N |
| ATOM | 1593 | CA | TRP | 1249 | −35.734 | −33.909 | −29.855 | 12.07 | C |
| ATOM | 1594 | CB | TRP | 1249 | −35.377 | −32.678 | −29.002 | 11.94 | C |
| ATOM | 1595 | CG | TRP | 1249 | −34.121 | −32.803 | −28.185 | 11.75 | C |
| ATOM | 1596 | CD2 | TRP | 1249 | −32.786 | −32.749 | −28.683 | 9.74 | C |
| ATOM | 1597 | CE2 | TRP | 1249 | −31.921 | −32.988 | −27.594 | 11.73 | C |
| ATOM | 1598 | CE3 | TRP | 1249 | −32.235 | −32.534 | −29.955 | 11.43 | C |
| ATOM | 1599 | CD1 | TRP | 1249 | −34.021 | −33.056 | −26.836 | 10.88 | C |
| ATOM | 1600 | NE1 | TRP | 1249 | −32.699 | −33.171 | −26.48 | 10.21 | N |
| ATOM | 1601 | CZ2 | TRP | 1249 | −30.528 | −33.017 | −27.737 | 12.35 | C |
| ATOM | 1602 | CZ3 | TRP | 1249 | −30.85 | −32.564 | −30.102 | 9.5 | C |
| ATOM | 1603 | CH2 | TRP | 1249 | −30.013 | −32.804 | −28.995 | 11.36 | C |
| ATOM | 1604 | C | TRP | 1249 | −37.187 | −33.763 | −30.288 | 13.69 | C |
| ATOM | 1605 | O | TRP | 1249 | −38.075 | −33.743 | −29.447 | 14.98 | O |
| ATOM | 1606 | N | MET | 1250 | −37.435 | −33.665 | −31.595 | 13.34 | N |
| ATOM | 1607 | CA | MET | 1250 | −38.799 | −33.485 | −32.102 | 13.11 | C |
| ATOM | 1608 | CB | MET | 1250 | −38.806 | −32.79 | −33.475 | 11.56 | C |
| ATOM | 1609 | CG | MET | 1250 | −38.605 | −31.283 | −33.468 | 15.9 | C |
| ATOM | 1610 | SD | MET | 1250 | −38.179 | −30.668 | −35.141 | 17.57 | S |
| ATOM | 1611 | CE | MET | 1250 | −39.682 | −31.196 | −36.142 | 17.78 | C |
| ATOM | 1612 | C | MET | 1250 | −39.579 | −34.772 | −32.239 | 12.68 | C |
| ATOM | 1613 | O | MET | 1250 | −39.028 | −35.823 | −32.568 | 13.57 | O |
| ATOM | 1614 | N | ALA | 1251 | −40.884 | −34.68 | −32.026 | 12.09 | N |
| ATOM | 1615 | CA | ALA | 1251 | −41.718 | −35.859 | −32.137 | 13.59 | C |
| ATOM | 1616 | CB | ALA | 1251 | −42.981 | −35.663 | −31.356 | 13.36 | C |
| ATOM | 1617 | C | ALA | 1251 | −42.044 | −36.246 | −33.58 | 16.39 | C |
| ATOM | 1618 | O | ALA | 1251 | −42.113 | −35.397 | −34.48 | 14.98 | O |
| ATOM | 1619 | N | LEU | 1252 | −42.254 | −37.548 | −33.773 | 17.37 | N |
| ATOM | 1620 | CA | LEU | 1252 | −42.573 | −38.11 | −35.074 | 17.41 | C |
| ATOM | 1621 | CB | LEU | 1252 | −43.224 | −39.505 | −34.909 | 17.7 | C |
| ATOM | 1622 | CG | LEU | 1252 | −43.415 | −40.392 | −36.149 | 15.74 | C |
| ATOM | 1623 | CD1 | LEU | 1252 | −42.258 | −40.179 | −37.122 | 14.12 | C |
| ATOM | 1624 | CD2 | LEU | 1252 | −43.491 | −41.858 | −35.733 | 16.89 | C |
| ATOM | 1625 | C | LEU | 1252 | −43.49 | −37.2 | −35.88 | 17.33 | C |
| ATOM | 1626 | O | LEU | 1252 | −43.167 | −36.85 | −37.008 | 16.45 | O |
| ATOM | 1627 | N | GLU | 1253 | −44.609 | −36.78 | −35.293 | 18.42 | N |
| ATOM | 1628 | CA | GLU | 1253 | −45.558 | −35.955 | −36.034 | 20.38 | C |
| ATOM | 1629 | CB | GLU | 1253 | −46.936 | −35.976 | −35.347 | 22.08 | C |
| ATOM | 1630 | CG | GLU | 1253 | −47.116 | −35.11 | −34.102 | 23.88 | C |
| ATOM | 1631 | CD | GLU | 1253 | −46.628 | −35.757 | −32.814 | 27.39 | C |
| ATOM | 1632 | OE1 | GLU | 1253 | −46.309 | −36.965 | −32.809 | 28.41 | O |
| ATOM | 1633 | OE2 | GLU | 1253 | −46.575 | −35.044 | −31.791 | 29.51 | O |
| ATOM | 1634 | C | GLU | 1253 | −45.127 | −34.518 | −36.358 | 21.17 | C |
| ATOM | 1635 | O | GLU | 1253 | −45.629 | −33.92 | −37.32 | 20.27 | O |
| ATOM | 1636 | N | SER | 1254 | −44.198 | −33.972 | −35.574 | 19.04 | N |
| ATOM | 1637 | CA | SER | 1254 | −43.695 | −32.62 | −35.817 | 20.94 | C |
| ATOM | 1638 | CB | SER | 1254 | −42.98 | −32.078 | −34.573 | 17.59 | C |
| ATOM | 1639 | OG | SER | 1254 | −43.826 | −32.137 | −33.439 | 17.95 | O |
| ATOM | 1640 | C | SER | 1254 | −42.705 | −32.72 | −36.971 | 20.79 | C |
| ATOM | 1641 | O | SER | 1254 | −42.545 | −31.793 | −37.757 | 21.89 | O |
| ATOM | 1642 | N | LEU | 1255 | −42.033 | −33.858 | −37.066 | 21.85 | N |
| ATOM | 1643 | CA | LEU | 1255 | −41.078 | −34.054 | −38.149 | 23.75 | C |
| ATOM | 1644 | CB | LEU | 1255 | −40.31 | −35.356 | −37.971 | 22.37 | C |
| ATOM | 1645 | CG | LEU | 1255 | −39.313 | −35.423 | −36.82 | 21.95 | C |
| ATOM | 1646 | CD1 | LEU | 1255 | −38.573 | −36.757 | −36.904 | 22.01 | C |
| ATOM | 1647 | CD2 | LEU | 1255 | −38.337 | −34.255 | −36.903 | 20.85 | C |
| ATOM | 1648 | C | LEU | 1255 | −41.833 | −34.1 | −39.466 | 25.17 | C |
| ATOM | 1649 | O | LEU | 1255 | −41.315 | −33.701 | −40.51 | 25.31 | O |
| ATOM | 1650 | N | GLN | 1256 | −43.06 | −34.601 | −39.397 | 26.07 | N |
| ATOM | 1651 | CA | GLN | 1256 | −43.92 | −34.717 | −40.555 | 27.58 | C |
| ATOM | 1652 | CB | GLN | 1256 | −44.909 | −35.877 | −40.345 | 27.79 | C |
| ATOM | 1653 | CG | GLN | 1256 | −44.289 | −37.284 | −40.403 | 30.43 | C |
| ATOM | 1654 | CD | GLN | 1256 | −45.281 | −38.364 | −39.99 | 33.67 | C |
| ATOM | 1655 | OE1 | GLN | 1256 | −45.421 | −39.39 | −40.654 | 35.61 | O |
| ATOM | 1656 | NE2 | GLN | 1256 | −45.972 | −38.132 | −38.88 | 34.01 | N |
| ATOM | 1657 | C | GLN | 1256 | −44.657 | −33.395 | −40.834 | 27.62 | C |
| ATOM | 1658 | O | GLN | 1256 | −44.562 | −32.87 | −41.937 | 29.77 | O |
| ATOM | 1659 | N | THR | 1257 | −45.358 | −32.837 | −39.845 | 27.72 | N |
| ATOM | 1660 | CA | THR | 1257 | −46.1 | −31.578 | −40.036 | 27.3 | C |
| ATOM | 1661 | CB | THR | 1257 | −47.357 | −31.499 | −39.114 | 26.41 | C |
| ATOM | 1662 | OG1 | THR | 1257 | −46.963 | −31.701 | −37.75 | 26.82 | O |
| ATOM | 1663 | CG2 | THR | 1257 | −48.414 | −32.514 | −39.521 | 25.55 | C |
| ATOM | 1664 | C | THR | 1257 | −45.381 | −30.216 | −39.847 | 27.61 | C |
| ATOM | 1665 | O | THR | 1257 | −45.77 | −29.234 | −40.466 | 27.07 | O |
| ATOM | 1666 | N | GLN | 1258 | −44.355 | −30.167 | −39 | 28.64 | N |
| ATOM | 1667 | CA | GLN | 1258 | −43.603 | −28.941 | −38.626 | 29.71 | C |
| ATOM | 1668 | CB | GLN | 1258 | −43.165 | −28.034 | −39.826 | 30.88 | C |
| ATOM | 1669 | CG | GLN | 1258 | −41.693 | −27.435 | −39.662 | 34.29 | C |

TABLE 1B-continued

| | | | | | | | | |
|---|---|---|---|---|---|---|---|---|
| ATOM | 1670 | CD | GLN | 1258 | −41.388 | −26.084 | −40.38 | 35.42 | C |
| ATOM | 1671 | OE1 | GLN | 1258 | −41.11 | −25.07 | −39.724 | 37.02 | O |
| ATOM | 1672 | NE2 | GLN | 1258 | −41.413 | −26.085 | −41.712 | 35.8 | N |
| ATOM | 1673 | C | GLN | 1258 | −44.51 | −28.144 | −37.677 | 28.89 | C |
| ATOM | 1674 | O | GLN | 1258 | −44.27 | −26.967 | −37.414 | 29.27 | O |
| ATOM | 1675 | N | LYS | 1259 | −45.553 | −28.805 | −37.168 | 28.49 | N |
| ATOM | 1676 | CA | LYS | 1259 | −46.496 | −28.196 | −36.221 | 28.29 | C |
| ATOM | 1677 | CB | LYS | 1259 | −47.963 | −28.4 | −36.727 | 28.96 | C |
| ATOM | 1678 | CG | LYS | 1259 | −48.203 | −28.05 | −38.258 | 31 | C |
| ATOM | 1679 | CD | LYS | 1259 | −49.257 | −26.931 | −38.585 | 32.59 | C |
| ATOM | 1680 | CE | LYS | 1259 | −50.617 | −27.453 | −39.126 | 33.31 | C |
| ATOM | 1681 | NZ | LYS | 1259 | −51.559 | −27.921 | −38.065 | 36.13 | N |
| ATOM | 1682 | C | LYS | 1259 | −46.215 | −28.858 | −34.828 | 26.44 | C |
| ATOM | 1683 | O | LYS | 1259 | −46.07 | −30.079 | −34.741 | 26.47 | O |
| ATOM | 1684 | N | PHE | 1260 | −46.088 | −28.045 | −33.767 | 25.21 | N |
| ATOM | 1685 | CA | PHE | 1260 | −45.781 | −28.507 | −32.388 | 24.1 | C |
| ATOM | 1686 | CB | PHE | 1260 | −44.607 | −27.704 | −31.792 | 23.41 | C |
| ATOM | 1687 | CG | PHE | 1260 | −43.308 | −27.831 | −32.547 | 25.91 | C |
| ATOM | 1688 | CD1 | PHE | 1260 | −43.116 | −27.165 | −33.758 | 27.41 | C |
| ATOM | 1689 | CD2 | PHE | 1260 | −42.265 | −28.605 | −32.036 | 27.23 | C |
| ATOM | 1690 | CE1 | PHE | 1260 | −41.902 | −27.269 | −34.449 | 26.54 | C |
| ATOM | 1691 | CE2 | PHE | 1260 | −41.049 | −28.714 | −32.721 | 27.29 | C |
| ATOM | 1692 | CZ | PHE | 1260 | −40.871 | −28.045 | −33.927 | 26.57 | C |
| ATOM | 1693 | C | PHE | 1260 | −46.937 | −28.426 | −31.368 | 22.89 | C |
| ATOM | 1694 | O | PHE | 1260 | −47.811 | −27.568 | −31.478 | 22.69 | O |
| ATOM | 1695 | N | THR | 1261 | −46.919 | −29.294 | −30.354 | 21.28 | N |
| ATOM | 1696 | CA | THR | 1261 | −47.968 | −29.297 | −29.325 | 21.08 | C |
| ATOM | 1697 | CB | THR | 1261 | −49.112 | −30.269 | −29.709 | 21.01 | C |
| ATOM | 1698 | OG1 | THR | 1261 | −48.76 | −31.601 | −29.316 | 21.47 | O |
| ATOM | 1699 | CG2 | THR | 1261 | −49.338 | −30.256 | −31.227 | 21.65 | C |
| ATOM | 1700 | C | THR | 1261 | −47.389 | −29.708 | −27.957 | 20.48 | C |
| ATOM | 1701 | O | THR | 1261 | −46.199 | −30.017 | −27.857 | 17.26 | O |
| ATOM | 1702 | N | THR | 1262 | −48.204 | −29.707 | −26.902 | 20.44 | N |
| ATOM | 1703 | CA | THR | 1262 | −47.678 | −30.099 | −25.592 | 19.37 | C |
| ATOM | 1704 | CB | THR | 1262 | −48.688 | −29.783 | −24.445 | 18.52 | C |
| ATOM | 1705 | OG1 | THR | 1262 | −48.865 | −28.364 | −24.364 | 22.58 | O |
| ATOM | 1706 | CG2 | THR | 1262 | −48.153 | −30.24 | −23.091 | 17.69 | C |
| ATOM | 1707 | C | THR | 1262 | −47.24 | −31.571 | −25.597 | 17.47 | C |
| ATOM | 1708 | O | THR | 1262 | −46.342 | −31.946 | −24.851 | 18.79 | O |
| ATOM | 1709 | N | LYS | 1263 | −47.834 | −32.392 | −26.47 | 19.24 | N |
| ATOM | 1710 | CA | LYS | 1263 | −47.446 | −33.809 | −26.592 | 18.23 | C |
| ATOM | 1711 | CB | LYS | 1263 | −48.518 | −34.637 | −27.304 | 16.94 | C |
| ATOM | 1712 | CG | LYS | 1263 | −49.874 | −34.561 | −26.667 | 19.51 | C |
| ATOM | 1713 | CD | LYS | 1263 | −49.769 | −34.879 | −25.188 | 23.06 | C |
| ATOM | 1714 | CE | LYS | 1263 | −51.108 | −35.281 | −24.587 | 22.44 | C |
| ATOM | 1715 | NZ | LYS | 1263 | −50.893 | −35.855 | −23.223 | 24.48 | N |
| ATOM | 1716 | C | LYS | 1263 | −46.14 | −33.96 | −27.367 | 17.16 | C |
| ATOM | 1717 | O | LYS | 1263 | −45.417 | −34.929 | −27.17 | 18.48 | O |
| ATOM | 1718 | N | SER | 1264 | −45.838 | −33.039 | −28.271 | 16.85 | N |
| ATOM | 1719 | CA | SER | 1264 | −44.569 | −33.169 | −28.971 | 17.48 | C |
| ATOM | 1720 | CB | SER | 1264 | −44.558 | −32.344 | −30.259 | 17.7 | C |
| ATOM | 1721 | OG | SER | 1264 | −44.882 | −30.994 | −30.001 | 18.83 | O |
| ATOM | 1722 | C | SER | 1264 | −43.496 | −32.696 | −27.968 | 17.45 | C |
| ATOM | 1723 | O | SER | 1264 | −42.329 | −33.071 | −28.077 | 17.64 | O |
| ATOM | 1724 | N | ASP | 1265 | −43.928 | −31.889 | −26.988 | 14.49 | N |
| ATOM | 1725 | CA | ASP | 1265 | −43.089 | −31.368 | −25.888 | 14.77 | C |
| ATOM | 1726 | CB | ASP | 1265 | −43.831 | −30.278 | −25.093 | 16.44 | C |
| ATOM | 1727 | CG | ASP | 1265 | −43.451 | −28.85 | −25.492 | 17.46 | C |
| ATOM | 1728 | OD1 | ASP | 1265 | −42.537 | −28.634 | −26.318 | 17.88 | O |
| ATOM | 1729 | OD2 | ASP | 1265 | −44.092 | −27.925 | −24.949 | 18.78 | O |
| ATOM | 1730 | C | ASP | 1265 | −42.801 | −32.522 | −24.911 | 12.9 | C |
| ATOM | 1731 | O | ASP | 1265 | −41.713 | −32.626 | −24.349 | 13.55 | O |
| ATOM | 1732 | N | VAL | 1266 | −43.818 | −33.35 | −24.681 | 11.93 | N |
| ATOM | 1733 | CA | VAL | 1266 | −43.692 | −34.515 | −23.816 | 13.82 | C |
| ATOM | 1734 | CB | VAL | 1266 | −45.068 | −35.254 | −23.686 | 14.9 | C |
| ATOM | 1735 | CG1 | VAL | 1266 | −44.876 | −36.7 | −23.246 | 10.56 | C |
| ATOM | 1736 | CG2 | VAL | 1266 | −45.966 | −34.507 | −22.686 | 12.47 | C |
| ATOM | 1737 | C | VAL | 1266 | −42.65 | −35.397 | −24.52 | 14.39 | C |
| ATOM | 1738 | O | VAL | 1266 | −41.717 | −35.906 | −23.892 | 14.25 | O |
| ATOM | 1739 | N | TRP | 1267 | −42.788 | −35.55 | −25.835 | 14.88 | N |
| ATOM | 1740 | CA | TRP | 1267 | −41.816 | −36.352 | −26.578 | 15.69 | C |
| ATOM | 1741 | CB | TRP | 1267 | −42.062 | −36.328 | −28.087 | 16.09 | C |
| ATOM | 1742 | CG | TRP | 1267 | −41.057 | −37.186 | −28.883 | 17.05 | C |
| ATOM | 1743 | CD2 | TRP | 1267 | −41.368 | −38.331 | −29.682 | 17.26 | C |
| ATOM | 1744 | CE2 | TRP | 1267 | −40.157 | −38.801 | −30.243 | 17.57 | C |
| ATOM | 1745 | CE3 | TRP | 1267 | −42.556 | −39.004 | −29.981 | 17.76 | C |
| ATOM | 1746 | CD1 | TRP | 1267 | −39.694 | −37.01 | −28.986 | 17.69 | C |
| ATOM | 1747 | NE1 | TRP | 1267 | −39.151 | −37.98 | −29.804 | 18.08 | N |
| ATOM | 1748 | CZ2 | TRP | 1267 | −40.107 | −39.916 | −31.087 | 19.89 | C |
| ATOM | 1749 | CZ3 | TRP | 1267 | −42.505 | −40.112 | −30.822 | 18.54 | C |

TABLE 1B-continued

| ATOM | 1750 | CH2 | TRP | 1267 | −41.289 | −40.556 | −31.362 | 19.43 | C |
|---|---|---|---|---|---|---|---|---|---|
| ATOM | 1751 | C | TRP | 1267 | −40.411 | −35.813 | −26.332 | 16.62 | C |
| ATOM | 1752 | O | TRP | 1267 | −39.511 | −36.586 | −26.023 | 17.18 | O |
| ATOM | 1753 | N | SER | 1268 | −40.217 | −34.501 | −26.488 | 14.99 | N |
| ATOM | 1754 | CA | SER | 1268 | −38.891 | −33.91 | −26.286 | 14.28 | C |
| ATOM | 1755 | CB | SER | 1268 | −38.876 | −32.398 | −26.566 | 14.67 | C |
| ATOM | 1756 | OG | SER | 1268 | −39.424 | −32.051 | −27.825 | 19.01 | O |
| ATOM | 1757 | C | SER | 1268 | −38.408 | −34.098 | −24.858 | 12.79 | C |
| ATOM | 1758 | O | SER | 1268 | −37.216 | −34.252 | −24.62 | 12.21 | O |
| ATOM | 1759 | N | PHE | 1269 | −39.327 | −34.039 | −23.9 | 10.34 | N |
| ATOM | 1760 | CA | PHE | 1269 | −38.932 | −34.194 | −22.512 | 12.36 | C |
| ATOM | 1761 | CB | PHE | 1269 | −40.12 | −33.897 | −21.59 | 12.12 | C |
| ATOM | 1762 | CG | PHE | 1269 | −39.85 | −34.2 | −20.149 | 15.09 | C |
| ATOM | 1763 | CD1 | PHE | 1269 | −39.046 | −33.365 | −19.372 | 14.94 | C |
| ATOM | 1764 | CD2 | PHE | 1269 | −40.355 | −35.363 | −19.582 | 14.21 | C |
| ATOM | 1765 | CE1 | PHE | 1269 | −38.751 | −33.695 | −18.053 | 15.06 | C |
| ATOM | 1766 | CE2 | PHE | 1269 | −40.063 | −35.699 | −18.267 | 15.58 | C |
| ATOM | 1767 | CZ | PHE | 1269 | −39.26 | −34.863 | −17.503 | 14.09 | C |
| ATOM | 1768 | C | PHE | 1269 | −38.371 | −35.603 | −22.286 | 11.45 | C |
| ATOM | 1769 | O | PHE | 1269 | −37.429 | −35.791 | −21.522 | 14.03 | O |
| ATOM | 1770 | N | GLY | 1270 | −38.945 | −36.591 | −22.965 | 12.93 | N |
| ATOM | 1771 | CA | GLY | 1270 | −38.442 | −37.947 | −22.849 | 13.38 | C |
| ATOM | 1772 | C | GLY | 1270 | −37.016 | −38.029 | −23.388 | 12.82 | C |
| ATOM | 1773 | O | GLY | 1270 | −36.209 | −38.804 | −22.873 | 13.02 | O |
| ATOM | 1774 | N | VAL | 1271 | −36.702 | −37.248 | −24.428 | 12.51 | N |
| ATOM | 1775 | CA | VAL | 1271 | −35.34 | −37.23 | −24.987 | 12.39 | C |
| ATOM | 1776 | CB | VAL | 1271 | −35.256 | −36.469 | −26.371 | 12.83 | C |
| ATOM | 1777 | CG1 | VAL | 1271 | −33.818 | −36.39 | −26.846 | 14.09 | C |
| ATOM | 1778 | CG2 | VAL | 1271 | −36.044 | −37.203 | −27.429 | 12.97 | C |
| ATOM | 1779 | C | VAL | 1271 | −34.414 | −36.555 | −23.96 | 11.86 | C |
| ATOM | 1780 | O | VAL | 1271 | −33.262 | −36.961 | −23.81 | 13.66 | O |
| ATOM | 1781 | N | LEU | 1272 | −34.927 | −35.537 | −23.254 | 12.4 | N |
| ATOM | 1782 | CA | LEU | 1272 | −34.163 | −34.832 | −22.21 | 11.28 | C |
| ATOM | 1783 | CB | LEU | 1272 | −34.961 | −33.628 | −21.648 | 12.83 | C |
| ATOM | 1784 | CG | LEU | 1272 | −34.465 | −32.674 | −20.527 | 12.7 | C |
| ATOM | 1785 | CD1 | LEU | 1272 | −35.271 | −31.379 | −20.589 | 11.58 | C |
| ATOM | 1786 | CD2 | LEU | 1272 | −34.622 | −33.302 | −19.134 | 16.29 | C |
| ATOM | 1787 | C | LEU | 1272 | −33.857 | −35.824 | −21.083 | 10.67 | C |
| ATOM | 1788 | O | LEU | 1272 | −32.73 | −35.884 | −20.59 | 9.63 | O |
| ATOM | 1789 | N | LEU | 1273 | −34.853 | −36.612 | −20.682 | 10.3 | N |
| ATOM | 1790 | CA | LEU | 1273 | −34.622 | −37.59 | −19.62 | 12.31 | C |
| ATOM | 1791 | CB | LEU | 1273 | −35.879 | −38.415 | −19.343 | 13.07 | C |
| ATOM | 1792 | CG | LEU | 1273 | −37.038 | −37.707 | −18.634 | 15.53 | C |
| ATOM | 1793 | CD1 | LEU | 1273 | −38.259 | −38.639 | −18.597 | 13.92 | C |
| ATOM | 1794 | CD2 | LEU | 1273 | −36.605 | −37.302 | −17.236 | 12.41 | C |
| ATOM | 1795 | C | LEU | 1273 | −33.494 | −38.518 | −20.061 | 11.72 | C |
| ATOM | 1796 | O | LEU | 1273 | −32.638 | −38.887 | −19.265 | 10.87 | O |
| ATOM | 1797 | N | TRP | 1274 | −33.508 | −38.888 | −21.34 | 10.2 | N |
| ATOM | 1798 | CA | TRP | 1274 | −32.487 | −39.765 | −21.891 | 11.44 | C |
| ATOM | 1799 | CB | TRP | 1274 | −32.866 | −40.2 | −23.321 | 10.95 | C |
| ATOM | 1800 | CG | TRP | 1274 | −31.903 | −41.19 | −23.98 | 10.98 | C |
| ATOM | 1801 | CD2 | TRP | 1274 | −30.712 | −40.861 | −24.698 | 9.72 | C |
| ATOM | 1802 | CE2 | TRP | 1274 | −30.124 | −42.072 | −25.12 | 11.07 | C |
| ATOM | 1803 | CE3 | TRP | 1274 | −30.083 | −39.652 | −25.024 | 13.5 | C |
| ATOM | 1804 | CD1 | TRP | 1274 | −31.989 | −42.562 | −23.993 | 10.52 | C |
| ATOM | 1805 | NE1 | TRP | 1274 | −30.921 | −43.096 | −24.679 | 9.57 | N |
| ATOM | 1806 | CZ2 | TRP | 1274 | −28.93 | −42.109 | −25.858 | 13.29 | C |
| ATOM | 1807 | CZ3 | TRP | 1274 | −28.897 | −39.688 | −25.756 | 13.28 | C |
| ATOM | 1808 | CH2 | TRP | 1274 | −28.335 | −40.91 | −26.166 | 12.43 | C |
| ATOM | 1809 | C | TRP | 1274 | −31.104 | −39.087 | −21.867 | 11.05 | C |
| ATOM | 1810 | O | TRP | 1274 | −30.12 | −39.746 | −21.551 | 10.69 | O |
| ATOM | 1811 | N | GLU | 1275 | −31.015 | −37.79 | −22.184 | 11.93 | N |
| ATOM | 1812 | CA | GLU | 1275 | −29.706 | −37.111 | −22.147 | 12.13 | C |
| ATOM | 1813 | CB | GLU | 1275 | −29.778 | −35.657 | −22.624 | 14.74 | C |
| ATOM | 1814 | CG | GLU | 1275 | −30.309 | −35.362 | −24.01 | 18.02 | C |
| ATOM | 1815 | CD | GLU | 1275 | −30.436 | −33.856 | −24.191 | 20.57 | C |
| ATOM | 1816 | OE1 | GLU | 1275 | −31.573 | −33.324 | −24.15 | 19.95 | O |
| ATOM | 1817 | OE2 | GLU | 1275 | −29.385 | −33.197 | −24.333 | 21.55 | O |
| ATOM | 1818 | C | GLU | 1275 | −29.203 | −37.059 | −20.694 | 12.79 | C |
| ATOM | 1819 | O | GLU | 1275 | −27.999 | −37.121 | −20.435 | 9.21 | O |
| ATOM | 1820 | N | LEU | 1276 | −30.139 | −36.898 | −19.759 | 11.64 | N |
| ATOM | 1821 | CA | LEU | 1276 | −29.83 | −36.83 | −18.333 | 13.52 | C |
| ATOM | 1822 | CB | LEU | 1276 | −31.128 | −36.608 | −17.524 | 13.33 | C |
| ATOM | 1823 | CG | LEU | 1276 | −31.604 | −35.226 | −17.028 | 12.41 | C |
| ATOM | 1824 | CD1 | LEU | 1276 | −31.498 | −34.247 | −18.143 | 17.11 | C |
| ATOM | 1825 | CD2 | LEU | 1276 | −33.046 | −35.271 | −16.511 | 11.26 | C |
| ATOM | 1826 | C | LEU | 1276 | −29.15 | −38.125 | −17.882 | 15.4 | C |
| ATOM | 1827 | O | LEU | 1276 | −28.046 | −38.11 | −17.327 | 16.84 | O |
| ATOM | 1828 | N | MET | 1277 | −29.804 | −39.249 | −18.154 | 14.23 | N |
| ATOM | 1829 | CA | MET | 1277 | −29.288 | −40.553 | −17.76 | 16.99 | C |

TABLE 1B-continued

| | | | | | | | | |
|---|---|---|---|---|---|---|---|---|
| ATOM | 1830 | CB | MET | 1277 | −30.375 | −41.605 | −17.97 | 17.95 | C |
| ATOM | 1831 | CG | MET | 1277 | −31.64 | −41.311 | −17.168 | 21.05 | C |
| ATOM | 1832 | SD | MET | 1277 | −31.277 | −41.118 | −15.408 | 28.97 | S |
| ATOM | 1833 | CE | MET | 1277 | −30.177 | −42.52 | −15.198 | 24.12 | C |
| ATOM | 1834 | C | MET | 1277 | −27.986 | −40.976 | −18.442 | 16.88 | C |
| ATOM | 1835 | O | MET | 1277 | −27.249 | −41.794 | −17.902 | 17.63 | O |
| ATOM | 1836 | N | THR | 1278 | −27.703 | −40.425 | −19.62 | 16.09 | N |
| ATOM | 1837 | CA | THR | 1278 | −26.466 | −40.753 | −20.339 | 16.44 | C |
| ATOM | 1838 | CB | THR | 1278 | −26.677 | −40.824 | −21.869 | 15.75 | C |
| ATOM | 1839 | OG1 | THR | 1278 | −27.275 | −39.605 | −22.322 | 14.11 | O |
| ATOM | 1840 | CG2 | THR | 1278 | −27.55 | −42.021 | −22.261 | 16.13 | C |
| ATOM | 1841 | C | THR | 1278 | −25.412 | −39.675 | −20.096 | 16.13 | C |
| ATOM | 1842 | O | THR | 1278 | −24.332 | −39.707 | −20.682 | 16.66 | O |
| ATOM | 1843 | N | ARG | 1279 | −25.745 | −38.744 | −19.212 | 16.79 | N |
| ATOM | 1844 | CA | ARG | 1279 | −24.908 | −37.593 | −18.881 | 17.42 | C |
| ATOM | 1845 | CB | ARG | 1279 | −23.641 | −37.996 | −18.127 | 17.17 | C |
| ATOM | 1846 | CG | ARG | 1279 | −23.982 | −38.325 | −16.685 | 19.24 | C |
| ATOM | 1847 | CD | ARG | 1279 | −22.78 | −38.507 | −15.793 | 20.29 | C |
| ATOM | 1848 | NE | ARG | 1279 | −22.028 | −37.264 | −15.776 | 22.44 | N |
| ATOM | 1849 | CZ | ARG | 1279 | −20.833 | −37.071 | −15.228 | 24.32 | C |
| ATOM | 1850 | NH1 | ARG | 1279 | −20.181 | −38.022 | −14.565 | 25.1 | N |
| ATOM | 1851 | NH2 | ARG | 1279 | −20.267 | −35.895 | −15.386 | 23.97 | N |
| ATOM | 1852 | C | ARG | 1279 | −24.534 | −36.77 | −20.082 | 17.7 | C |
| ATOM | 1853 | O | ARG | 1279 | −23.371 | −36.456 | −20.262 | 21.43 | O |
| ATOM | 1854 | N | GLY | 1280 | −25.503 | −36.432 | −20.924 | 15.97 | N |
| ATOM | 1855 | CA | GLY | 1280 | −25.186 | −35.597 | −22.068 | 16.82 | C |
| ATOM | 1856 | C | GLY | 1280 | −24.787 | −36.224 | −23.392 | 17.54 | C |
| ATOM | 1857 | O | GLY | 1280 | −24.189 | −35.542 | −24.221 | 16.85 | O |
| ATOM | 1858 | N | ALA | 1281 | −25.111 | −37.498 | −23.6 | 17.75 | N |
| ATOM | 1859 | CA | ALA | 1281 | −24.802 | −38.185 | −24.853 | 17.82 | C |
| ATOM | 1860 | CB | ALA | 1281 | −25.111 | −39.671 | −24.708 | 16.36 | C |
| ATOM | 1861 | C | ALA | 1281 | −25.662 | −37.587 | −25.972 | 18.54 | C |
| ATOM | 1862 | O | ALA | 1281 | −26.8 | −37.201 | −25.727 | 18.61 | O |
| ATOM | 1863 | N | PRO | 1282 | −25.133 | −37.482 | −27.207 | 18.63 | N |
| ATOM | 1864 | CD | PRO | 1282 | −23.748 | −37.732 | −27.652 | 19.37 | C |
| ATOM | 1865 | CA | PRO | 1282 | −25.969 | −36.916 | −28.279 | 19.93 | C |
| ATOM | 1866 | CB | PRO | 1282 | −24.942 | −36.503 | −29.346 | 20.38 | C |
| ATOM | 1867 | CG | PRO | 1282 | −23.812 | −37.491 | −29.157 | 19.28 | C |
| ATOM | 1868 | C | PRO | 1282 | −26.983 | −37.973 | −28.768 | 20.28 | C |
| ATOM | 1869 | O | PRO | 1282 | −26.594 | −39.101 | −29.08 | 20.76 | O |
| ATOM | 1870 | N | PRO | 1283 | −28.29 | −37.634 | −28.852 | 20.54 | N |
| ATOM | 1871 | CD | PRO | 1283 | −28.977 | −36.338 | −28.822 | 20.35 | C |
| ATOM | 1872 | CA | PRO | 1283 | −29.214 | −38.685 | −29.314 | 21.42 | C |
| ATOM | 1873 | CB | PRO | 1283 | −30.604 | −38.102 | −29.052 | 20.81 | C |
| ATOM | 1874 | CG | PRO | 1283 | −30.371 | −36.751 | −28.434 | 21.83 | C |
| ATOM | 1875 | C | PRO | 1283 | −29.054 | −39.061 | −30.783 | 21.78 | C |
| ATOM | 1876 | O | PRO | 1283 | −28.764 | −38.205 | −31.615 | 22.56 | O |
| ATOM | 1877 | N | TYR | 1284 | −29.274 | −40.337 | −31.092 | 20.5 | N |
| ATOM | 1878 | CA | TYR | 1284 | −29.159 | −40.848 | −32.46 | 21.94 | C |
| ATOM | 1879 | CB | TYR | 1284 | −30.292 | −40.303 | −33.317 | 22.25 | C |
| ATOM | 1880 | CG | TYR | 1284 | −31.641 | −40.352 | −32.651 | 21.17 | C |
| ATOM | 1881 | CD1 | TYR | 1284 | −32.432 | −41.504 | −32.706 | 20.04 | C |
| ATOM | 1882 | CE1 | TYR | 1284 | −33.676 | −41.545 | −32.084 | 18.05 | C |
| ATOM | 1883 | CD2 | TYR | 1284 | −32.122 | −39.247 | −31.955 | 19.85 | C |
| ATOM | 1884 | CE2 | TYR | 1284 | −33.348 | −39.277 | −31.331 | 19.2 | C |
| ATOM | 1885 | CZ | TYR | 1284 | −34.125 | −40.42 | −31.396 | 18.12 | C |
| ATOM | 1886 | OH | TYR | 1284 | −35.343 | −40.403 | −30.772 | 15.51 | O |
| ATOM | 1887 | C | TYR | 1284 | −27.85 | −40.349 | −33.034 | 22.78 | C |
| ATOM | 1888 | O | TYR | 1284 | −27.828 | −39.743 | −34.1 | 20.74 | O |
| ATOM | 1889 | N | PRO | 1285 | −26.729 | −40.632 | −32.372 | 24.32 | N |
| ATOM | 1890 | CD | PRO | 1285 | −26.367 | −41.515 | −31.248 | 25.4 | C |
| ATOM | 1891 | CA | PRO | 1285 | −25.535 | −40.079 | −33.002 | 26.46 | C |
| ATOM | 1892 | CB | PRO | 1285 | −24.43 | −40.483 | −32.031 | 25.47 | C |
| ATOM | 1893 | CG | PRO | 1285 | −24.901 | −41.795 | −31.53 | 25.65 | C |
| ATOM | 1894 | C | PRO | 1285 | −25.149 | −40.395 | −34.446 | 28.83 | C |
| ATOM | 1895 | O | PRO | 1285 | −24.72 | −39.505 | −35.186 | 28.91 | O |
| ATOM | 1896 | N | ASP | 1286 | −25.312 | −41.639 | −34.859 | 30.51 | N |
| ATOM | 1897 | CA | ASP | 1286 | −24.845 | −42.035 | −36.171 | 34.63 | C |
| ATOM | 1898 | CB | ASP | 1286 | −24.278 | −43.468 | −35.991 | 37.19 | C |
| ATOM | 1899 | CG | ASP | 1286 | −22.867 | −43.46 | −35.32 | 40.75 | C |
| ATOM | 1900 | OD1 | ASP | 1286 | −22.625 | −44.11 | −34.265 | 42.38 | O |
| ATOM | 1901 | OD2 | ASP | 1286 | −21.982 | −42.776 | −35.881 | 42.78 | O |
| ATOM | 1902 | C | ASP | 1286 | −25.778 | −41.846 | −37.407 | 35.2 | C |
| ATOM | 1903 | O | ASP | 1286 | −25.432 | −42.243 | −38.535 | 35.64 | O |
| ATOM | 1904 | N | VAL | 1287 | −26.884 | −41.115 | −37.173 | 33.72 | N |
| ATOM | 1905 | CA | VAL | 1287 | −27.987 | −40.815 | −38.126 | 33.27 | C |
| ATOM | 1906 | CB | VAL | 1287 | −29.318 | −41.221 | −37.487 | 32.97 | C |
| ATOM | 1907 | CG1 | VAL | 1287 | −29.1 | −42.389 | −36.558 | 32.75 | C |
| ATOM | 1908 | CG2 | VAL | 1287 | −29.893 | −40.035 | −36.693 | 34.84 | C |
| ATOM | 1909 | C | VAL | 1287 | −28.233 | −39.357 | −38.616 | 32.3 | C |

TABLE 1B-continued

| | | | | | | | | |
|---|---|---|---|---|---|---|---|---|
| ATOM | 1910 | O | VAL | 1287 | −28.04 | −38.4 | −37.861 | 31.13 | O |
| ATOM | 1911 | N | ASN | 1288 | −28.724 | −39.201 | −39.852 | 30 | N |
| ATOM | 1912 | CA | ASN | 1288 | −29.047 | −37.87 | −40.387 | 27.35 | C |
| ATOM | 1913 | CB | ASN | 1288 | −28.569 | −37.722 | −41.843 | 25.1 | C |
| ATOM | 1914 | CG | ASN | 1288 | −29.298 | −38.651 | −42.807 | 23.58 | C |
| ATOM | 1915 | OD1 | ASN | 1288 | −30.486 | −38.905 | −42.657 | 20.67 | O |
| ATOM | 1916 | ND2 | ASN | 1288 | −28.586 | −39.14 | −43.814 | 21.64 | N |
| ATOM | 1917 | C | ASN | 1288 | −30.575 | −37.662 | −40.279 | 26.78 | C |
| ATOM | 1918 | O | ASN | 1288 | −31.322 | −38.629 | −40.141 | 25.63 | O |
| ATOM | 1919 | N | THR | 1289 | −31.033 | −36.412 | −40.355 | 27.2 | N |
| ATOM | 1920 | CA | THR | 1289 | −32.457 | −36.08 | −40.193 | 28.7 | C |
| ATOM | 1921 | CB | THR | 1289 | −32.638 | −34.569 | −40.092 | 29.7 | C |
| ATOM | 1922 | OG1 | THR | 1289 | −32.974 | −34.004 | −41.359 | 32.14 | O |
| ATOM | 1923 | CG2 | THR | 1289 | −31.363 | −33.978 | −39.679 | 30.98 | C |
| ATOM | 1924 | C | THR | 1289 | −33.422 | −36.64 | −41.205 | 28.93 | C |
| ATOM | 1925 | O | THR | 1289 | −34.637 | −36.448 | −41.092 | 29.84 | O |
| ATOM | 1926 | N | PHE | 1290 | −32.885 | −37.331 | −42.202 | 28.3 | N |
| ATOM | 1927 | CA | PHE | 1290 | −33.758 | −37.948 | −43.159 | 28.01 | C |
| ATOM | 1928 | CB | PHE | 1290 | −33.15 | −38.156 | −44.519 | 28.4 | C |
| ATOM | 1929 | CG | PHE | 1290 | −34.013 | −39.008 | −45.375 | 30.93 | C |
| ATOM | 1930 | CD1 | PHE | 1290 | −35.181 | −38.489 | −45.906 | 30.67 | C |
| ATOM | 1931 | CD2 | PHE | 1290 | −33.737 | −40.355 | −45.547 | 29.81 | C |
| ATOM | 1932 | CE1 | PHE | 1290 | −36.058 | −39.292 | −46.589 | 32.06 | C |
| ATOM | 1933 | CE2 | PHE | 1290 | −34.615 | −41.167 | −46.231 | 32.26 | C |
| ATOM | 1934 | CZ | PHE | 1290 | −35.777 | −40.635 | −46.752 | 31.34 | C |
| ATOM | 1935 | C | PHE | 1290 | −34.152 | −39.321 | −42.675 | 27.78 | C |
| ATOM | 1936 | O | PHE | 1290 | −35.296 | −39.718 | −42.827 | 27.15 | O |
| ATOM | 1937 | N | ASP | 1291 | −33.237 | −40.09 | −42.117 | 26.53 | N |
| ATOM | 1938 | CA | ASP | 1291 | −33.727 | −41.38 | −41.705 | 28.3 | C |
| ATOM | 1939 | CB | ASP | 1291 | −32.878 | −42.484 | −42.312 | 31.72 | C |
| ATOM | 1940 | CG | ASP | 1291 | −31.43 | −42.208 | −42.173 | 34.91 | C |
| ATOM | 1941 | OD1 | ASP | 1291 | −31.077 | −41.644 | −41.112 | 36.01 | O |
| ATOM | 1942 | OD2 | ASP | 1291 | −30.662 | −42.549 | −43.101 | 32.69 | O |
| ATOM | 1943 | C | ASP | 1291 | −33.923 | −41.575 | −40.212 | 26.5 | C |
| ATOM | 1944 | O | ASP | 1291 | −34.187 | −42.688 | −39.761 | 25.11 | O |
| ATOM | 1945 | N | ILE | 1292 | −33.793 | −40.505 | −39.436 | 24.99 | N |
| ATOM | 1946 | CA | ILE | 1292 | −34.075 | −40.621 | −38.016 | 24.84 | C |
| ATOM | 1947 | CB | ILE | 1292 | −33.607 | −39.358 | −37.223 | 25.08 | C |
| ATOM | 1948 | CG2 | ILE | 1292 | −34.193 | −38.124 | −37.85 | 24.46 | C |
| ATOM | 1949 | CG1 | ILE | 1292 | −34.071 | −39.404 | −35.759 | 23.22 | C |
| ATOM | 1950 | CD | ILE | 1292 | −34.253 | −40.785 | −35.155 | 25.97 | C |
| ATOM | 1951 | C | ILE | 1292 | −35.61 | −40.707 | −38.075 | 24.13 | C |
| ATOM | 1952 | O | ILE | 1292 | −36.254 | −41.303 | −37.217 | 23.5 | O |
| ATOM | 1953 | N | THR | 1293 | −36.179 | −40.143 | −39.14 | 23.68 | N |
| ATOM | 1954 | CA | THR | 1293 | −37.624 | −40.139 | −39.33 | 24.12 | C |
| ATOM | 1955 | CB | THR | 1293 | −38.036 | −39.061 | −40.377 | 26.66 | C |
| ATOM | 1956 | OG1 | THR | 1293 | −37.503 | −37.787 | −39.975 | 28.33 | O |
| ATOM | 1957 | CG2 | THR | 1293 | −39.558 | −38.934 | −40.463 | 27.13 | C |
| ATOM | 1958 | C | THR | 1293 | −38.115 | −41.527 | −39.741 | 24.12 | C |
| ATOM | 1959 | O | THR | 1293 | −39.176 | −41.98 | −39.316 | 23.92 | O |
| ATOM | 1960 | N | VAL | 1294 | −37.323 | −42.201 | −40.559 | 22.73 | N |
| ATOM | 1961 | CA | VAL | 1294 | −37.638 | −43.542 | −40.998 | 22.69 | C |
| ATOM | 1962 | CB | VAL | 1294 | −36.657 | −43.948 | −42.108 | 23.12 | C |
| ATOM | 1963 | CG1 | VAL | 1294 | −36.576 | −45.413 | −42.18 | 23.01 | C |
| ATOM | 1964 | CG2 | VAL | 1294 | −37.084 | −43.339 | −43.438 | 23.05 | C |
| ATOM | 1965 | C | VAL | 1294 | −37.51 | −44.466 | −39.76 | 22.25 | C |
| ATOM | 1966 | O | VAL | 1294 | −38.398 | −45.284 | −39.49 | 22.56 | O |
| ATOM | 1967 | N | TYR | 1295 | −36.405 | −44.297 | −39.017 | 20.41 | N |
| ATOM | 1968 | CA | TYR | 1295 | −36.074 | −45.036 | −37.775 | 19.13 | C |
| ATOM | 1969 | CB | TYR | 1295 | −34.786 | −44.436 | −37.133 | 20.43 | C |
| ATOM | 1970 | CG | TYR | 1295 | −34.263 | −45.004 | −35.773 | 22.2 | C |
| ATOM | 1971 | CD1 | TYR | 1295 | −33.174 | −45.889 | −35.729 | 22.09 | C |
| ATOM | 1972 | CE1 | TYR | 1295 | −32.652 | −46.373 | −34.502 | 22.58 | C |
| ATOM | 1973 | CD2 | TYR | 1295 | −34.823 | −44.609 | −34.54 | 21.45 | C |
| ATOM | 1974 | CE2 | TYR | 1295 | −34.299 | −45.093 | −33.299 | 22.41 | C |
| ATOM | 1975 | CZ | TYR | 1295 | −33.216 | −45.979 | −33.302 | 22.9 | C |
| ATOM | 1976 | OH | TYR | 1295 | −32.719 | −46.521 | −32.132 | 23.86 | O |
| ATOM | 1977 | C | TYR | 1295 | −37.238 | −44.967 | −36.781 | 17.02 | C |
| ATOM | 1978 | O | TYR | 1295 | −37.635 | −45.987 | −36.217 | 17.06 | O |
| ATOM | 1979 | N | LEU | 1296 | −37.768 | −43.764 | −36.557 | 15.78 | N |
| ATOM | 1980 | CA | LEU | 1296 | −38.892 | −43.564 | −35.636 | 15.62 | C |
| ATOM | 1981 | CB | LEU | 1296 | −39.19 | −42.069 | −35.44 | 13.27 | C |
| ATOM | 1982 | CG | LEU | 1296 | −38.167 | −41.253 | −34.648 | 14.85 | C |
| ATOM | 1983 | CD1 | LEU | 1296 | −38.665 | −39.812 | −34.44 | 13.49 | C |
| ATOM | 1984 | CD2 | LEU | 1296 | −37.931 | −41.928 | −33.301 | 12.69 | C |
| ATOM | 1985 | C | LEU | 1296 | −40.107 | −44.233 | −36.242 | 17.24 | C |
| ATOM | 1986 | O | LEU | 1296 | −40.917 | −44.859 | −35.547 | 17.7 | O |
| ATOM | 1987 | N | LEU | 1297 | −40.224 | −44.085 | −37.555 | 18.13 | N |
| ATOM | 1988 | CA | LEU | 1297 | −41.313 | −44.68 | −38.292 | 20.85 | C |
| ATOM | 1989 | CB | LEU | 1297 | −41.21 | −44.288 | −39.778 | 22.8 | C |

TABLE 1B-continued

| | | | | | | | | |
|---|---|---|---|---|---|---|---|---|
| ATOM | 1990 | CG | LEU | 1297 | −42.437 | −43.505 | −40.283 | 24.14 | C |
| ATOM | 1991 | CD1 | LEU | 1297 | −43.187 | −42.928 | −39.098 | 26.68 | C |
| ATOM | 1992 | CD2 | LEU | 1297 | −42.036 | −42.403 | −41.242 | 24.5 | C |
| ATOM | 1993 | C | LEU | 1297 | −41.316 | −46.203 | −38.086 | 21.11 | C |
| ATOM | 1994 | O | LEU | 1297 | −42.353 | −46.759 | −37.735 | 21.79 | O |
| ATOM | 1995 | N | GLN | 1298 | −40.167 | −46.864 | −38.265 | 21.59 | N |
| ATOM | 1996 | CA | GLN | 1298 | −40.059 | −48.32 | −38.058 | 21.53 | C |
| ATOM | 1997 | CB | GLN | 1298 | −38.663 | −48.825 | −38.468 | 22.02 | C |
| ATOM | 1998 | CG | GLN | 1298 | −38.339 | −48.635 | −39.955 | 22.67 | C |
| ATOM | 1999 | CD | GLN | 1298 | −36.856 | −48.747 | −40.277 | 25.11 | C |
| ATOM | 2000 | OE1 | GLN | 1298 | −36.02 | −48.914 | −39.385 | 25.42 | O |
| ATOM | 2001 | NE2 | GLN | 1298 | −36.522 | −48.646 | −41.566 | 27.23 | N |
| ATOM | 2002 | C | GLN | 1298 | −40.305 | −48.629 | −36.58 | 21.21 | C |
| ATOM | 2003 | O | GLN | 1298 | −40.241 | −49.785 | −36.143 | 23.95 | O |
| ATOM | 2004 | N | GLY | 1299 | −40.571 | −47.578 | −35.81 | 19.63 | N |
| ATOM | 2005 | CA | GLY | 1299 | −40.842 | −47.739 | −34.395 | 16.55 | C |
| ATOM | 2006 | C | GLY | 1299 | −39.635 | −47.944 | −33.491 | 16.17 | C |
| ATOM | 2007 | O | GLY | 1299 | −39.782 | −48.481 | −32.394 | 15.64 | O |
| ATOM | 2008 | N | ARG | 1300 | −38.453 | −47.536 | −33.944 | 15.6 | N |
| ATOM | 2009 | CA | ARG | 1300 | −37.23 | −47.663 | −33.15 | 14.57 | C |
| ATOM | 2010 | CB | ARG | 1300 | −35.987 | −47.624 | −34.061 | 13.21 | C |
| ATOM | 2011 | CG | ARG | 1300 | −35.606 | −48.953 | −34.696 | 12.55 | C |
| ATOM | 2012 | CD | ARG | 1300 | −34.87 | −48.794 | −36.041 | 12.57 | C |
| ATOM | 2013 | NE | ARG | 1300 | −35.26 | −49.892 | −36.918 | 14.36 | N |
| ATOM | 2014 | CZ | ARG | 1300 | −34.748 | −51.118 | −36.859 | 15.98 | C |
| ATOM | 2015 | NH1 | ARG | 1300 | −33.792 | −51.41 | −35.981 | 17.16 | N |
| ATOM | 2016 | NH2 | ARG | 1300 | −35.251 | −52.073 | −37.624 | 12.34 | N |
| ATOM | 2017 | C | ARG | 1300 | −37.171 | −46.474 | −32.196 | 14.89 | C |
| ATOM | 2018 | O | ARG | 1300 | −37.633 | −45.389 | −32.536 | 14.23 | O |
| ATOM | 2019 | N | ARG | 1301 | −36.615 | −46.663 | −31.006 | 14.09 | N |
| ATOM | 2020 | CA | ARG | 1301 | −36.504 | −45.548 | −30.085 | 14.82 | C |
| ATOM | 2021 | CB | ARG | 1301 | −37.522 | −45.684 | −28.96 | 15.03 | C |
| ATOM | 2022 | CG | ARG | 1301 | −38.961 | −45.614 | −29.449 | 16.03 | C |
| ATOM | 2023 | CD | ARG | 1301 | −39.267 | −44.225 | −30.023 | 16.85 | C |
| ATOM | 2024 | NE | ARG | 1301 | −40.663 | −44.068 | −30.429 | 17.41 | N |
| ATOM | 2025 | CZ | ARG | 1301 | −41.145 | −44.345 | −31.635 | 17.22 | C |
| ATOM | 2026 | NH1 | ARG | 1301 | −40.354 | −44.8 | −32.598 | 15.84 | N |
| ATOM | 2027 | NH2 | ARG | 1301 | −42.435 | −44.167 | −31.876 | 21.38 | N |
| ATOM | 2028 | C | ARG | 1301 | −35.097 | −45.495 | −29.524 | 15.64 | C |
| ATOM | 2029 | O | ARG | 1301 | −34.282 | −46.375 | −29.805 | 15.79 | O |
| ATOM | 2030 | N | LEU | 1302 | −34.804 | −44.455 | −28.757 | 12.85 | N |
| ATOM | 2031 | CA | LEU | 1302 | −33.493 | −44.32 | −28.141 | 15.61 | C |
| ATOM | 2032 | CB | LEU | 1302 | −33.38 | −42.956 | −27.437 | 15.94 | C |
| ATOM | 2033 | CG | LEU | 1302 | −33.299 | −41.659 | −28.26 | 12.87 | C |
| ATOM | 2034 | CD1 | LEU | 1302 | −33.581 | −40.444 | −27.379 | 14 | C |
| ATOM | 2035 | CD2 | LEU | 1302 | −31.927 | −41.543 | −28.882 | 15.39 | C |
| ATOM | 2036 | C | LEU | 1302 | −33.409 | −45.472 | −27.131 | 16.47 | C |
| ATOM | 2037 | O | LEU | 1302 | −34.375 | −45.735 | −26.408 | 16.43 | O |
| ATOM | 2038 | N | LEU | 1303 | −32.276 | −46.168 | −27.086 | 16.41 | N |
| ATOM | 2039 | CA | LEU | 1303 | −32.143 | −47.309 | −26.187 | 18.6 | C |
| ATOM | 2040 | CB | LEU | 1303 | −31.037 | −48.239 | −26.727 | 19.3 | C |
| ATOM | 2041 | CG | LEU | 1303 | −31.469 | −48.766 | −28.121 | 22.94 | C |
| ATOM | 2042 | CD1 | LEU | 1303 | −30.288 | −49.341 | −28.91 | 22.68 | C |
| ATOM | 2043 | CD2 | LEU | 1303 | −32.563 | −49.818 | −27.95 | 19.49 | C |
| ATOM | 2044 | C | LEU | 1303 | −31.953 | −46.931 | −24.703 | 18.49 | C |
| ATOM | 2045 | O | LEU | 1303 | −31.622 | −45.788 | −24.38 | 17.75 | O |
| ATOM | 2046 | N | GLN | 1304 | −32.218 | −47.876 | −23.804 | 16.43 | N |
| ATOM | 2047 | CA | GLN | 1304 | −32.094 | −47.608 | −22.376 | 17.47 | C |
| ATOM | 2048 | CB | GLN | 1304 | −32.686 | −48.76 | −21.556 | 16.36 | C |
| ATOM | 2049 | CG | GLN | 1304 | −32.738 | −48.413 | −20.069 | 20 | C |
| ATOM | 2050 | CD | GLN | 1304 | −33.444 | −49.453 | −19.219 | 19.17 | C |
| ATOM | 2051 | OE1 | GLN | 1304 | −33.769 | −49.195 | −18.06 | 23.21 | O |
| ATOM | 2052 | NE2 | GLN | 1304 | −33.674 | −50.632 | −19.78 | 20.05 | N |
| ATOM | 2053 | C | GLN | 1304 | −30.64 | −47.385 | −21.956 | 17.45 | C |
| ATOM | 2054 | O | GLN | 1304 | −29.788 | −48.223 | −22.207 | 18.13 | O |
| ATOM | 2055 | N | PRO | 1305 | −30.335 | −46.245 | −21.318 | 17.11 | N |
| ATOM | 2056 | CD | PRO | 1305 | −31.109 | −44.993 | −21.246 | 17.67 | C |
| ATOM | 2057 | CA | PRO | 1305 | −28.943 | −46.017 | −20.906 | 18.76 | C |
| ATOM | 2058 | CB | PRO | 1305 | −28.948 | −44.557 | −20.464 | 17.33 | C |
| ATOM | 2059 | CG | PRO | 1305 | −30.016 | −43.951 | −21.316 | 20.16 | C |
| ATOM | 2060 | C | PRO | 1305 | −28.493 | −46.925 | −19.762 | 19.88 | C |
| ATOM | 2061 | O | PRO | 1305 | −29.317 | −47.39 | −18.987 | 17.37 | O |
| ATOM | 2062 | N | GLU | 1306 | −27.188 | −47.169 | −19.668 | 23.66 | N |
| ATOM | 2063 | CA | GLU | 1306 | −26.634 | −47.978 | −18.586 | 28.01 | C |
| ATOM | 2064 | CB | GLU | 1306 | −25.106 | −48.108 | −18.749 | 29.98 | C |
| ATOM | 2065 | CG | GLU | 1306 | −24.401 | −48.854 | −17.605 | 34.82 | C |
| ATOM | 2066 | CD | GLU | 1306 | −22.979 | −49.299 | −17.948 | 36.96 | C |
| ATOM | 2067 | OE1 | GLU | 1306 | −22.688 | −50.51 | −17.812 | 38.32 | O |
| ATOM | 2068 | OE2 | GLU | 1306 | −22.154 | −48.447 | −18.346 | 37.25 | O |
| ATOM | 2069 | C | GLU | 1306 | −26.971 | −47.185 | −17.315 | 29.78 | C |

TABLE 1B-continued

| | | | | | | | | | |
|---|---|---|---|---|---|---|---|---|---|
| ATOM | 2070 | O | GLU | 1306 | −26.886 | −45.961 | −17.323 | 32.55 | O |
| ATOM | 2071 | N | TYR | 1307 | −27.381 | −47.857 | −16.243 | 30.97 | N |
| ATOM | 2072 | CA | TYR | 1307 | −27.716 | −47.179 | −14.971 | 30.01 | C |
| ATOM | 2073 | CB | TYR | 1307 | −26.643 | −46.14 | −14.567 | 31.8 | C |
| ATOM | 2074 | CG | TYR | 1307 | −25.18 | −46.581 | −14.564 | 33.12 | C |
| ATOM | 2075 | CD1 | TYR | 1307 | −24.21 | −45.814 | −15.214 | 33.66 | C |
| ATOM | 2076 | CE1 | TYR | 1307 | −22.866 | −46.218 | −15.262 | 34.33 | C |
| ATOM | 2077 | CD2 | TYR | 1307 | −24.771 | −47.765 | −13.946 | 33.66 | C |
| ATOM | 2078 | CE2 | TYR | 1307 | −23.429 | −48.179 | −13.986 | 34.02 | C |
| ATOM | 2079 | CZ | TYR | 1307 | −22.484 | −47.406 | −14.654 | 35.13 | C |
| ATOM | 2080 | OH | TYR | 1307 | −21.185 | −47.867 | −14.776 | 34.55 | O |
| ATOM | 2081 | C | TYR | 1307 | −29.076 | −46.452 | −14.918 | 28.96 | C |
| ATOM | 2082 | O | TYR | 1307 | −29.432 | −45.895 | −13.881 | 27.44 | O |
| ATOM | 2083 | N | CYS | 1308 | −29.82 | −46.405 | −16.019 | 27.77 | N |
| ATOM | 2084 | CA | CYS | 1308 | −31.126 | −45.744 | −15.988 | 25.91 | C |
| ATOM | 2085 | CB | CYS | 1308 | −31.56 | −45.362 | −17.409 | 25.12 | C |
| ATOM | 2086 | SG | CYS | 1308 | −33.321 | −44.917 | −17.596 | 24 | S |
| ATOM | 2087 | C | CYS | 1308 | −32.055 | −46.804 | −15.414 | 25.06 | C |
| ATOM | 2088 | O | CYS | 1308 | −31.968 | −47.96 | −15.812 | 23.71 | O |
| ATOM | 2089 | N | PRO | 1309 | −32.952 | −46.442 | −14.477 | 24.93 | N |
| ATOM | 2090 | CD | PRO | 1309 | −33.195 | −45.18 | −13.761 | 25.38 | C |
| ATOM | 2091 | CA | PRO | 1309 | −33.817 | −47.503 | −13.954 | 23.94 | C |
| ATOM | 2092 | CB | PRO | 1309 | −34.344 | −46.928 | −12.635 | 25.11 | C |
| ATOM | 2093 | CG | PRO | 1309 | −33.496 | −45.682 | −12.386 | 26.23 | C |
| ATOM | 2094 | C | PRO | 1309 | −34.961 | −47.871 | −14.891 | 23.92 | C |
| ATOM | 2095 | O | PRO | 1309 | −35.53 | −47.017 | −15.567 | 24.15 | O |
| ATOM | 2096 | N | ASP | 1310 | −35.291 | −49.155 | −14.902 | 22.35 | N |
| ATOM | 2097 | CA | ASP | 1310 | −36.365 | −49.695 | −15.72 | 22.11 | C |
| ATOM | 2098 | CB | ASP | 1310 | −36.698 | −51.109 | −15.24 | 25.28 | C |
| ATOM | 2099 | CG | ASP | 1310 | −35.592 | −52.102 | −15.553 | 27.4 | C |
| ATOM | 2100 | OD1 | ASP | 1310 | −34.505 | −51.668 | −15.992 | 28.7 | O |
| ATOM | 2101 | OD2 | ASP | 1310 | −35.806 | −53.317 | −15.357 | 28.25 | O |
| ATOM | 2102 | C | ASP | 1310 | −37.632 | −48.84 | −15.739 | 20.06 | C |
| ATOM | 2103 | O | ASP | 1310 | −38.174 | −48.544 | −16.8 | 18.79 | O |
| ATOM | 2104 | N | PRO | 1311 | −38.142 | −48.451 | −14.562 | 19.74 | N |
| ATOM | 2105 | CD | PRO | 1311 | −37.807 | −48.805 | −13.174 | 18.73 | C |
| ATOM | 2106 | CA | PRO | 1311 | −39.351 | −47.629 | −14.602 | 18.41 | C |
| ATOM | 2107 | CB | PRO | 1311 | −39.741 | −47.517 | −13.128 | 17.9 | C |
| ATOM | 2108 | CG | PRO | 1311 | −38.441 | −47.673 | −12.42 | 18.48 | C |
| ATOM | 2109 | C | PRO | 1311 | −39.143 | −46.265 | −15.261 | 16.43 | C |
| ATOM | 2110 | O | PRO | 1311 | −40.071 | −45.71 | −15.842 | 14.98 | O |
| ATOM | 2111 | N | LEU | 1312 | −37.935 | −45.716 | −15.191 | 14.58 | N |
| ATOM | 2112 | CA | LEU | 1312 | −37.73 | −44.428 | −15.824 | 13.14 | C |
| ATOM | 2113 | CB | LEU | 1312 | −36.413 | −43.778 | −15.407 | 13.51 | C |
| ATOM | 2114 | CG | LEU | 1312 | −36.337 | −42.287 | −15.754 | 11.5 | C |
| ATOM | 2115 | CD1 | LEU | 1312 | −37.488 | −41.494 | −15.114 | 13.78 | C |
| ATOM | 2116 | CD2 | LEU | 1312 | −35.01 | −41.77 | −15.254 | 13.81 | C |
| ATOM | 2117 | C | LEU | 1312 | −37.74 | −44.62 | −17.316 | 13.15 | C |
| ATOM | 2118 | O | LEU | 1312 | −38.261 | −43.785 | −18.051 | 11.21 | O |
| ATOM | 2119 | N | TYR | 1313 | −37.162 | −45.722 | −17.777 | 14.68 | N |
| ATOM | 2120 | CA | TYR | 1313 | −37.159 | −45.972 | −19.208 | 14.13 | C |
| ATOM | 2121 | CB | TYR | 1313 | −36.325 | −47.198 | −19.573 | 15.38 | C |
| ATOM | 2122 | CG | TYR | 1313 | −36.105 | −47.341 | −21.075 | 15.55 | C |
| ATOM | 2123 | CD1 | TYR | 1313 | −35.638 | −46.265 | −21.841 | 17.29 | C |
| ATOM | 2124 | CE1 | TYR | 1313 | −35.407 | −46.393 | −23.216 | 16.45 | C |
| ATOM | 2125 | CD2 | TYR | 1313 | −36.338 | −48.552 | −21.721 | 14.65 | C |
| ATOM | 2126 | CE2 | TYR | 1313 | −36.111 | −48.694 | −23.088 | 17.53 | C |
| ATOM | 2127 | CZ | TYR | 1313 | −35.644 | −47.608 | −23.832 | 16.76 | C |
| ATOM | 2128 | OH | TYR | 1313 | −35.418 | −47.749 | −25.18 | 17.88 | O |
| ATOM | 2129 | C | TYR | 1313 | −38.591 | −46.156 | −19.687 | 14.31 | C |
| ATOM | 2130 | O | TYR | 1313 | −38.936 | −45.653 | −20.751 | 14.78 | O |
| ATOM | 2131 | N | GLU | 1314 | −39.421 | −46.863 | −18.913 | 15.45 | N |
| ATOM | 2132 | CA | GLU | 1314 | −40.832 | −47.065 | −19.287 | 19.13 | C |
| ATOM | 2133 | CB | GLU | 1314 | −41.636 | −47.741 | −18.155 | 21.74 | C |
| ATOM | 2134 | CG | GLU | 1314 | −42.374 | −49.072 | −18.498 | 30.22 | C |
| ATOM | 2135 | CD | GLU | 1314 | −43.763 | −48.91 | −19.15 | 35.3 | C |
| ATOM | 2136 | OE1 | GLU | 1314 | −43.865 | −48.965 | −20.4 | 38.8 | O |
| ATOM | 2137 | OE2 | GLU | 1314 | −44.76 | −48.739 | −18.411 | 38.41 | O |
| ATOM | 2138 | C | GLU | 1314 | −41.414 | −45.674 | −19.54 | 17.22 | C |
| ATOM | 2139 | O | GLU | 1314 | −42.127 | −45.461 | −20.52 | 17.96 | O |
| ATOM | 2140 | N | VAL | 1315 | −41.111 | −44.742 | −18.635 | 15.21 | N |
| ATOM | 2141 | CA | VAL | 1315 | −41.578 | −43.359 | −18.745 | 13.46 | C |
| ATOM | 2142 | CB | VAL | 1315 | −40.957 | −42.44 | −17.656 | 14.51 | C |
| ATOM | 2143 | CG1 | VAL | 1315 | −41.324 | −40.976 | −17.926 | 13.39 | C |
| ATOM | 2144 | CG2 | VAL | 1315 | −41.438 | −42.857 | −16.274 | 12.16 | C |
| ATOM | 2145 | C | VAL | 1315 | −41.138 | −42.819 | −20.092 | 14.52 | C |
| ATOM | 2146 | O | VAL | 1315 | −41.951 | −42.333 | −20.887 | 10.37 | O |
| ATOM | 2147 | N | MET | 1316 | −39.834 | −42.921 | −20.333 | 14.75 | N |
| ATOM | 2148 | CA | MET | 1316 | −39.252 | −42.436 | −21.57 | 17.75 | C |
| ATOM | 2149 | CB | MET | 1316 | −37.763 | −42.803 | −21.663 | 20.34 | C |

TABLE 1B-continued

| | | | | | | | | |
|---|---|---|---|---|---|---|---|---|
| ATOM | 2150 | CG | MET | 1316 | −36.819 | −42.276 | −20.559 | 19.79 | C |
| ATOM | 2151 | SD | MET | 1316 | −35.114 | −42.567 | −21.17 | 21.6 | S |
| ATOM | 2152 | CE | MET | 1316 | −34.136 | −42.746 | −19.658 | 23.16 | C |
| ATOM | 2153 | C | MET | 1316 | −39.987 | −43.02 | −22.77 | 18.51 | C |
| ATOM | 2154 | O | MET | 1316 | −40.42 | −42.274 | −23.651 | 19.69 | O |
| ATOM | 2155 | N | LEU | 1317 | −40.142 | −44.345 | −22.815 | 17.78 | N |
| ATOM | 2156 | CA | LEU | 1317 | −40.829 | −44.956 | −23.945 | 17.94 | C |
| ATOM | 2157 | CB | LEU | 1317 | −40.888 | −46.473 | −23.795 | 17.54 | C |
| ATOM | 2158 | CG | LEU | 1317 | −39.502 | −47.099 | −23.888 | 18.27 | C |
| ATOM | 2159 | CD1 | LEU | 1317 | −39.58 | −48.542 | −23.434 | 19.06 | C |
| ATOM | 2160 | CD2 | LEU | 1317 | −38.961 | −46.976 | −25.315 | 18.11 | C |
| ATOM | 2161 | C | LEU | 1317 | −42.226 | −44.399 | −24.094 | 19.36 | C |
| ATOM | 2162 | O | LEU | 1317 | −42.676 | −44.125 | −25.206 | 19.4 | O |
| ATOM | 2163 | N | LYS | 1318 | −42.917 | −44.22 | −22.976 | 18.7 | N |
| ATOM | 2164 | CA | LYS | 1318 | −44.268 | −43.685 | −23.029 | 20.42 | C |
| ATOM | 2165 | CB | LYS | 1318 | −44.879 | −43.663 | −21.625 | 21.8 | C |
| ATOM | 2166 | CG | LYS | 1318 | −45.9 | −44.794 | −21.389 | 26.1 | C |
| ATOM | 2167 | CD | LYS | 1318 | −46.046 | −45.138 | −19.905 | 26.99 | C |
| ATOM | 2168 | CE | LYS | 1318 | −47.177 | −46.138 | −19.636 | 30.43 | C |
| ATOM | 2169 | NZ | LYS | 1318 | −48.042 | −45.717 | −18.483 | 32.95 | N |
| ATOM | 2170 | C | LYS | 1318 | −44.284 | −42.288 | −23.657 | 20.66 | C |
| ATOM | 2171 | O | LYS | 1318 | −45.195 | −41.942 | −24.417 | 21.24 | O |
| ATOM | 2172 | N | CYS | 1319 | −43.268 | −41.49 | −23.353 | 18.11 | N |
| ATOM | 2173 | CA | CYS | 1319 | −43.188 | −40.152 | −23.918 | 16.47 | C |
| ATOM | 2174 | CB | CYS | 1319 | −41.964 | −39.408 | −23.386 | 15.37 | C |
| ATOM | 2175 | SG | CYS | 1319 | −42.114 | −38.898 | −21.672 | 12.54 | S |
| ATOM | 2176 | C | CYS | 1319 | −43.074 | −40.248 | −25.422 | 18 | C |
| ATOM | 2177 | O | CYS | 1319 | −43.512 | −39.35 | −26.139 | 15.45 | O |
| ATOM | 2178 | N | TRP | 1320 | −42.489 | −41.338 | −25.911 | 18.62 | N |
| ATOM | 2179 | CA | TRP | 1320 | −42.323 | −41.463 | −27.348 | 19.38 | C |
| ATOM | 2180 | CB | TRP | 1320 | −40.935 | −41.999 | −27.689 | 17.86 | C |
| ATOM | 2181 | CG | TRP | 1320 | −39.797 | −41.256 | −27.06 | 16.31 | C |
| ATOM | 2182 | CD2 | TRP | 1320 | −38.626 | −41.84 | −26.488 | 16.1 | C |
| ATOM | 2183 | CE2 | TRP | 1320 | −37.816 | −40.782 | −26.019 | 15.34 | C |
| ATOM | 2184 | CE3 | TRP | 1320 | −38.182 | −43.162 | −26.327 | 14.66 | C |
| ATOM | 2185 | CD1 | TRP | 1320 | −39.659 | −39.902 | −26.926 | 13.95 | C |
| ATOM | 2186 | NE1 | TRP | 1320 | −38.471 | −39.609 | −26.299 | 14.46 | N |
| ATOM | 2187 | CZ2 | TRP | 1320 | −36.587 | −41.004 | −25.396 | 16.01 | C |
| ATOM | 2188 | CZ3 | TRP | 1320 | −36.967 | −43.385 | −25.714 | 13.39 | C |
| ATOM | 2189 | CH2 | TRP | 1320 | −36.179 | −42.311 | −25.252 | 14.92 | C |
| ATOM | 2190 | C | TRP | 1320 | −43.361 | −42.293 | −28.093 | 21.79 | C |
| ATOM | 2191 | O | TRP | 1320 | −43.098 | −42.741 | −29.207 | 21.52 | O |
| ATOM | 2192 | N | HIS | 1321 | −44.534 | −42.501 | −27.508 | 21.94 | N |
| ATOM | 2193 | CA | HIS | 1321 | −45.57 | −43.266 | −28.198 | 22.23 | C |
| ATOM | 2194 | CB | HIS | 1321 | −46.832 | −43.3 | −27.343 | 23.03 | C |
| ATOM | 2195 | CG | HIS | 1321 | −47.853 | −44.286 | −27.811 | 24.08 | C |
| ATOM | 2196 | CD2 | HIS | 1321 | −48.285 | −45.442 | −27.259 | 24.79 | C |
| ATOM | 2197 | ND1 | HIS | 1321 | −48.555 | −44.135 | −28.986 | 25.03 | N |
| ATOM | 2198 | CE1 | HIS | 1321 | −49.378 | −45.157 | −29.137 | 24.27 | C |
| ATOM | 2199 | NE2 | HIS | 1321 | −49.233 | −45.964 | −28.103 | 26.25 | N |
| ATOM | 2200 | C | HIS | 1321 | −45.87 | −42.58 | −29.538 | 22 | C |
| ATOM | 2201 | O | HIS | 1321 | −45.966 | −41.351 | −29.602 | 19.88 | O |
| ATOM | 2202 | N | PRO | 1322 | −46.016 | −43.358 | −30.63 | 21.9 | N |
| ATOM | 2203 | CD | PRO | 1322 | −45.801 | −44.808 | −30.784 | 22.07 | C |
| ATOM | 2204 | CA | PRO | 1322 | −46.3 | −42.721 | −31.926 | 22.49 | C |
| ATOM | 2205 | CB | PRO | 1322 | −46.304 | −43.905 | −32.904 | 20.78 | C |
| ATOM | 2206 | CG | PRO | 1322 | −46.567 | −45.108 | −32.037 | 20.57 | C |
| ATOM | 2207 | C | PRO | 1322 | −47.579 | −41.918 | −31.963 | 23.4 | C |
| ATOM | 2208 | O | PRO | 1322 | −47.778 | −41.017 | −32.789 | 22.39 | O |
| ATOM | 2209 | N | LYS | 1323 | −48.405 | −42.188 | −30.98 | 24.92 | N |
| ATOM | 2210 | CA | LYS | 1323 | −49.697 | −41.569 | −30.918 | 25.96 | C |
| ATOM | 2211 | CB | LYS | 1323 | −50.574 | −42.739 | −30.573 | 28.31 | C |
| ATOM | 2212 | CG | LYS | 1323 | −51.827 | −42.832 | −31.242 | 30.59 | C |
| ATOM | 2213 | CD | LYS | 1323 | −51.727 | −43.515 | −32.566 | 32.35 | C |
| ATOM | 2214 | CE | LYS | 1323 | −52.933 | −44.485 | −32.88 | 34.1 | C |
| ATOM | 2215 | NZ | LYS | 1323 | −52.65 | −45.312 | −34.124 | 34.56 | N |
| ATOM | 2216 | C | LYS | 1323 | −49.758 | −40.444 | −29.909 | 26.46 | C |
| ATOM | 2217 | O | LYS | 1323 | −50.007 | −40.667 | −28.758 | 25.08 | O |
| ATOM | 2218 | N | ALA | 1324 | −49.634 | −39.187 | −30.295 | 26.66 | N |
| ATOM | 2219 | CA | ALA | 1324 | −49.62 | −38.088 | −29.304 | 27.92 | C |
| ATOM | 2220 | CB | ALA | 1324 | −49.95 | −36.785 | −29.987 | 25.6 | C |
| ATOM | 2221 | C | ALA | 1324 | −50.446 | −38.245 | −28.055 | 28.17 | C |
| ATOM | 2222 | O | ALA | 1324 | −50.036 | −37.905 | −26.931 | 27.6 | O |
| ATOM | 2223 | N | GLU | 1325 | −51.686 | −38.71 | −28.301 | 29.23 | N |
| ATOM | 2224 | CA | GLU | 1325 | −52.504 | −38.853 | −27.162 | 29.6 | C |
| ATOM | 2225 | CB | GLU | 1325 | −53.952 | −38.627 | −27.542 | 31.15 | C |
| ATOM | 2226 | CG | GLU | 1325 | −54.643 | −39.516 | −28.214 | 34.14 | C |
| ATOM | 2227 | CD | GLU | 1325 | −54.089 | −39.858 | −29.564 | 37.11 | C |
| ATOM | 2228 | OE1 | GLU | 1325 | −53.647 | −39.081 | −30.455 | 37.72 | O |
| ATOM | 2229 | OE2 | GLU | 1325 | −54.189 | −41.064 | −29.758 | 38.5 | O |

TABLE 1B-continued

| | | | | | | | | |
|---|---|---|---|---|---|---|---|---|
| ATOM | 2230 | C | GLU | 1325 | −52.362 | −40.01 | −26.213 | 28.69 | C |
| ATOM | 2231 | O | GLU | 1325 | −52.972 | −39.871 | −25.213 | 28.59 | O |
| ATOM | 2232 | N | MET | 1326 | −51.468 | −40.993 | −26.388 | 28.82 | N |
| ATOM | 2233 | CA | MET | 1326 | −51.245 | −42.047 | −25.396 | 29.26 | C |
| ATOM | 2234 | CB | MET | 1326 | −50.955 | −43.396 | −26.095 | 32.22 | C |
| ATOM | 2235 | CG | MET | 1326 | −52.066 | −44.064 | −26.984 | 38.68 | C |
| ATOM | 2236 | SD | MET | 1326 | −53.888 | −43.928 | −26.71 | 45.38 | S |
| ATOM | 2237 | CE | MET | 1326 | −54.572 | −45.537 | −27.685 | 43.56 | C |
| ATOM | 2238 | C | MET | 1326 | −50.005 | −41.619 | −24.608 | 28 | C |
| ATOM | 2239 | O | MET | 1326 | −49.463 | −42.377 | −23.802 | 28.97 | O |
| ATOM | 2240 | N | ARG | 1327 | −49.56 | −40.394 | −24.86 | 25.84 | N |
| ATOM | 2241 | CA | ARG | 1327 | −48.4 | −39.855 | −24.179 | 23.95 | C |
| ATOM | 2242 | CB | ARG | 1327 | −47.76 | −38.751 | −25.018 | 22.84 | C |
| ATOM | 2243 | CG | ARG | 1327 | −47.176 | −39.309 | −26.287 | 22.89 | C |
| ATOM. | 2244 | CD | ARG | 1327 | −46.312 | −38.32 | −27.012 | 21.37 | C |
| ATOM | 2245 | NE | ARG | 1327 | −46.201 | −38.754 | −28.39 | 19.79 | N |
| ATOM | 2246 | CZ | ARG | 1327 | −46.045 | −37.934 | −29.417 | 19 | C |
| ATOM | 2247 | NH1 | ARG | 1327 | −45.971 | −36.629 | −29.214 | 17.36 | N |
| ATOM | 2248 | NH2 | ARG | 1327 | −45.993 | −38.425 | −30.647 | 17.81 | N |
| ATOM | 2249 | C | ARG | 1327 | −48.784 | −39.293 | −22.835 | 22.04 | C |
| ATOM | 2250 | O | ARG | 1327 | −49.876 | −38.761 | −22.666 | 21.25 | O |
| ATOM | 2251 | N | PRO | 1328 | −47.899 | −39.441 | −21.854 | 21.95 | N |
| ATOM | 2252 | CD | PRO | 1328 | −46.644 | −40.199 | −21.724 | 22.8 | C |
| ATOM | 2253 | CA | PRO | 1328 | −48.266 | −38.874 | −20.605 | 21.34 | C |
| ATOM | 2254 | CB | PRO | 1328 | −47.249 | −39.534 | −19.606 | 21.48 | C |
| ATOM | 2255 | CG | PRO | 1328 | −46.083 | −39.682 | −20.415 | 23.57 | C |
| ATOM | 2256 | C | PRO | 1328 | −48.31 | −37.37 | −20.508 | 20.97 | C |
| ATOM | 2257 | O | PRO | 1328 | −47.608 | −36.705 | −21.26 | 21.32 | O |
| ATOM | 2258 | N | SER | 1329 | −49.152 | −36.854 | −19.61 | 20.09 | N |
| ATOM | 2259 | CA | SER | 1329 | −49.285 | −35.419 | −19.361 | 19.4 | C |
| ATOM | 2260 | CB | SER | 1329 | −50.552 | −35.135 | −18.548 | 19.48 | C |
| ATOM | 2261 | OG | SER | 1329 | −50.436 | −35.663 | −17.232 | 21.56 | O |
| ATOM | 2262 | C | SER | 1329 | −48.066 | −35.09 | −18.518 | 19.12 | C |
| ATOM | 2263 | O | SER | 1329 | −47.354 | −35.999 | −18.093 | 18.4 | O |
| ATOM | 2264 | N | PHE | 1330 | −47.8 | −33.816 | −18.259 | 19.43 | N |
| ATOM | 2265 | CA | PHE | 1330 | −46.627 | −33.511 | −17.447 | 19.52 | C |
| ATOM | 2266 | CB | PHE | 1330 | −46.166 | −32.066 | −17.716 | 17.45 | C |
| ATOM | 2267 | CG | PHE | 1330 | −45.31 | −31.927 | −18.971 | 16.35 | C |
| ATOM | 2268 | CD1 | PHE | 1330 | −44.005 | −32.427 | −18.999 | 16.41 | C |
| ATOM | 2269 | CD2 | PHE | 1330 | −45.809 | −31.319 | −20.124 | 16.49 | C |
| ATOM | 2270 | CE1 | PHE | 1330 | −43.212 | −32.32 | −20.152 | 15.43 | C |
| ATOM | 2271 | CE2 | PHE | 1330 | −45.025 | −31.21 | −21.28 | 15.83 | C |
| ATOM | 2272 | CZ | PHE | 1330 | −43.724 | −31.711 | −21.292 | 16.39 | C |
| ATOM | 2273 | C | PHE | 1330 | −46.951 | −33.816 | −15.978 | 18.21 | C |
| ATOM | 2274 | O | PHE | 1330 | −46.066 | −34.112 | −15.172 | 17.21 | O |
| ATOM | 2275 | N | SER | 1331 | −48.247 | −33.808 | −15.67 | 21.81 | N |
| ATOM | 2276 | CA | SER | 1331 | −48.763 | −34.137 | −14.341 | 22.73 | C |
| ATOM | 2277 | CB | SER | 1331 | −50.291 | −34.012 | −14.318 | 25.32 | C |
| ATOM | 2278 | OG | SER | 1331 | −50.7 | −32.663 | −14.454 | 25.24 | O |
| ATOM | 2279 | C | SER | 1331 | −48.379 | −35.581 | −14.001 | 21.79 | C |
| ATOM | 2280 | O | SER | 1331 | −47.698 | −35.816 | −12.999 | 21 | O |
| ATOM | 2281 | N | GLU | 1332 | −48.824 | −36.533 | −14.831 | 23.52 | N |
| ATOM | 2282 | CA | GLU | 1332 | −48.512 | −37.95 | −14.628 | 24.89 | C |
| ATOM | 2283 | CB | GLU | 1332 | −49.171 | −38.856 | −15.729 | 29.5 | C |
| ATOM | 2284 | CG | GLU | 1332 | −48.682 | −38.665 | −17.21 | 37.98 | C |
| ATOM | 2285 | CD | GLU | 1332 | −49.432 | −39.536 | −18.28 | 43.96 | C |
| ATOM | 2286 | OE1 | GLU | 1332 | −50.339 | −40.303 | −17.982 | 45.97 | O |
| ATOM | 2287 | OE2 | GLU | 1332 | −49.132 | −39.46 | −19.444 | 47.85 | O |
| ATOM | 2288 | C | GLU | 1332 | −46.981 | −38.047 | −14.635 | 22.38 | C |
| ATOM | 2289 | O | GLU | 1332 | −46.393 | −38.787 | −13.855 | 23.87 | O |
| ATOM | 2290 | N | LEU | 1333 | −46.327 | −37.261 | −15.481 | 20.18 | N |
| ATOM | 2291 | CA | LEU | 1333 | −44.875 | −37.295 | −15.507 | 18.89 | C |
| ATOM | 2292 | CB | LEU | 1333 | −44.318 | −36.39 | −16.622 | 20.31 | C |
| ATOM | 2293 | CG | LEU | 1333 | −43.658 | −37.081 | −17.836 | 19.84 | C |
| ATOM | 2294 | CD1 | LEU | 1333 | −44.137 | −38.513 | −17.983 | 21.18 | C |
| ATOM | 2295 | CD2 | LEU | 1333 | −43.963 | −36.29 | −19.091 | 19.76 | C |
| ATOM | 2296 | C | LEU | 1333 | −44.292 | −36.926 | −14.138 | 18.06 | C |
| ATOM | 2297 | O | LEU | 1333 | −43.457 | −37.67 | −13.629 | 17.4 | O |
| ATOM | 2298 | N | VAL | 1334 | −44.712 | −35.829 | −13.5 | 16.42 | N |
| ATOM | 2299 | CA | VAL | 1334 | −44.101 | −35.581 | −12.195 | 14.44 | C |
| ATOM | 2300 | CB | VAL | 1334 | −44.155 | −34.045 | −11.723 | 14.47 | C |
| ATOM | 2301 | CG1 | VAL | 1334 | −44.851 | −33.176 | −12.744 | 12.5 | C |
| ATOM | 2302 | CG2 | VAL | 1334 | −44.749 | −33.899 | −10.336 | 13.35 | C |
| ATOM | 2303 | C | VAL | 1334 | −44.503 | −36.562 | −11.069 | 15.52 | C |
| ATOM | 2304 | O | VAL | 1334 | −43.676 | −36.818 | −10.2 | 15.12 | O |
| ATOM | 2305 | N | SER | 1335 | −45.698 | −37.161 | −11.059 | 15.65 | N |
| ATOM | 2306 | CA | SER | 1335 | −45.927 | −38.104 | −9.947 | 17.61 | C |
| ATOM | 2307 | CB | SER | 1335 | −47.396 | −38.541 | −9.762 | 19.13 | C |
| ATOM | 2308 | OG | SER | 1335 | −48.28 | −37.995 | −10.714 | 21.27 | O |
| ATOM | 2309 | C | SER | 1335 | −45.104 | −39.319 | −10.16 | 16.26 | C |

TABLE 1B-continued

| ATOM | 2310 | O | SER | 1335 | −44.45 | −39.844 | −9.265 | 15.18 | O |
|---|---|---|---|---|---|---|---|---|---|
| ATOM | 2311 | N | ARG | 1336 | −45.057 | −39.739 | −11.396 | 16.43 | N |
| ATOM | 2312 | CA | ARG | 1336 | −44.326 | −40.942 | −11.638 | 19.04 | C |
| ATOM | 2313 | CB | ARG | 1336 | −44.461 | −41.125 | −13.056 | 23.11 | C |
| ATOM | 2314 | CG | ARG | 1336 | −44.507 | −42.397 | −13.484 | 26.63 | C |
| ATOM | 2315 | CD | ARG | 1336 | −45.813 | −42.346 | −14.321 | 29.99 | C |
| ATOM | 2316 | NE | ARG | 1336 | −45.664 | −41.73 | −15.664 | 32.06 | N |
| ATOM | 2317 | CZ | ARG | 1336 | −45.635 | −42.334 | −16.856 | 31.45 | C |
| ATOM | 2318 | NH1 | ARG | 1336 | −45.722 | −43.613 | −17.103 | 33.52 | N |
| ATOM | 2319 | NH2 | ARG | 1336 | −45.423 | −41.616 | −17.91 | 31.66 | N |
| ATOM | 2320 | C | ARG | 1336 | −42.905 | −40.758 | −11.309 | 20.68 | C |
| ATOM | 2321 | O | ARG | 1336 | −42.324 | −41.569 | −10.577 | 20.06 | O |
| ATOM | 2322 | N | ILE | 1337 | −42.301 | −39.726 | −11.874 | 19.97 | N |
| ATOM | 2323 | CA | ILE | 1337 | −40.913 | −39.442 | −11.613 | 19.1 | C |
| ATOM | 2324 | CB | ILE | 1337 | −40.414 | −38.268 | −12.509 | 19.3 | C |
| ATOM | 2325 | CG2 | ILE | 1337 | −38.941 | −37.989 | −12.218 | 16.69 | C |
| ATOM | 2326 | CG1 | ILE | 1337 | −40.561 | −38.655 | −13.993 | 18.86 | C |
| ATOM | 2327 | CD | ILE | 1337 | −40.445 | −37.496 | −14.979 | 19.36 | C |
| ATOM | 2328 | C | ILE | 1337 | −40.602 | −39.176 | −10.112 | 18.87 | C |
| ATOM | 2329 | O | ILE | 1337 | −39.518 | −39.543 | −9.663 | 18.78 | O |
| ATOM | 2330 | N | SER | 1338 | −41.51 | −38.572 | −9.332 | 19.34 | N |
| ATOM | 2331 | CA | SER | 1338 | −41.229 | −38.346 | −7.892 | 20.11 | C |
| ATOM | 2332 | CB | SER | 1338 | −42.325 | −37.541 | −7.183 | 20.76 | C |
| ATOM | 2333 | OG | SER | 1338 | −42.75 | −36.416 | −7.912 | 24.23 | O |
| ATOM | 2334 | C | SER | 1338 | −41.226 | −39.708 | −7.224 | 18.9 | C |
| ATOM | 2335 | O | SER | 1338 | −40.459 | −39.975 | −6.294 | 18.76 | O |
| ATOM | 2336 | N | ALA | 1339 | −42.151 | −40.536 | −7.701 | 18.39 | N |
| ATOM | 2337 | CA | ALA | 1339 | −42.345 | −41.896 | −7.23 | 18.01 | C |
| ATOM | 2338 | CB | ALA | 1339 | −43.48 | −42.548 | −8.012 | 17.08 | C |
| ATOM | 2339 | C | ALA | 1339 | −41.057 | −42.677 | −7.427 | 19.89 | C |
| ATOM | 2340 | O | ALA | 1339 | −40.581 | −43.341 | −6.509 | 22.03 | O |
| ATOM | 2341 | N | ILE | 1340 | −40.492 | −42.583 | −8.63 | 20.82 | N |
| ATOM | 2342 | CA | ILE | 1340 | −39.253 | −43.275 | −8.976 | 21.34 | C |
| ATOM | 2343 | CB | ILE | 1340 | −39.016 | −43.206 | −10.523 | 22.55 | C |
| ATOM | 2344 | CG2 | ILE | 1340 | −37.663 | −43.825 | −10.888 | 23.59 | C |
| ATOM | 2345 | CG1 | ILE | 1340 | −40.11 | −43.985 | −11.294 | 25.81 | C |
| ATOM | 2346 | CD | ILE | 1340 | −41.497 | −44.205 | −10.626 | 29.71 | C |
| ATOM | 2347 | C | ILE | 1340 | −38.07 | −42.658 | −8.21 | 21.59 | C |
| ATOM | 2348 | O | ILE | 1340 | −37.153 | −43.365 | −7.79 | 18.89 | O |
| ATOM | 2349 | N | PHE | 1341 | −38.127 | −41.339 | −8.007 | 22.51 | N |
| ATOM | 2350 | CA | PHE | 1341 | −37.084 | −40.571 | −7.312 | 23.12 | C |
| ATOM | 2351 | CB | PHE | 1341 | −37.366 | −39.076 | −7.448 | 21.04 | C |
| ATOM | 2352 | CG | PHE | 1341 | −36.369 | −38.216 | −6.741 | 18.35 | C |
| ATOM | 2353 | CD1 | PHE | 1341 | −35.128 | −37.965 | −7.31 | 17.9 | C |
| ATOM | 2354 | CD2 | PHE | 1341 | −36.658 | −37.671 | −5.494 | 18.97 | C |
| ATOM | 2355 | CE1 | PHE | 1341 | −34.186 | −37.181 | −6.652 | 18.18 | C |
| ATOM | 2356 | CE2 | PHE | 1341 | −35.723 | −36.886 | −4.825 | 18.68 | C |
| ATOM | 2357 | CZ | PHE | 1341 | −34.479 | −36.64 | −5.411 | 17.63 | C |
| ATOM | 2358 | C | PHE | 1341 | −36.941 | −40.905 | −5.837 | 25.96 | C |
| ATOM | 2359 | O | PHE | 1341 | −35.867 | −41.019 | −5.279 | 24.76 | O |
| ATOM | 2360 | N | SER | 1342 | −38.107 | −41.03 | −5.204 | 28.8 | N |
| ATOM | 2361 | CA | SER | 1342 | −38.188 | −41.346 | −3.8 | 33.62 | C |
| ATOM | 2362 | CB | SER | 1342 | −39.589 | −41.431 | −3.385 | 34.36 | C |
| ATOM | 2363 | OG | SER | 1342 | −39.895 | −40.25 | −2.726 | 37.13 | O |
| ATOM | 2364 | C | SER | 1342 | −37.681 | −42.675 | −3.572 | 36.29 | C |
| ATOM | 2365 | O | SER | 1342 | −36.913 | −42.931 | −2.739 | 36.94 | O |
| ATOM | 2366 | N | THR | 1343 | −38.255 | −43.619 | −4.223 | 38.79 | N |
| ATOM | 2367 | CA | THR | 1343 | −38.007 | −45.046 | −4.101 | 42.78 | C |
| ATOM | 2368 | CB | THR | 1343 | −38.082 | −45.62 | −5.347 | 43.14 | C |
| ATOM | 2369 | OG1 | THR | 1343 | −37.499 | −44.974 | −6.327 | 45.03 | O |
| ATOM | 2370 | CG2 | THR | 1343 | −39.089 | −46.338 | −5.894 | 42.28 | C |
| ATOM | 2371 | C | THR | 1343 | −36.447 | −45.187 | −4.538 | 44.77 | C |
| ATOM | 2372 | O | THR | 1343 | −36.291 | −46.076 | −5.408 | 45.85 | O |
| ATOM | 2373 | N | PHE | 1344 | −35.516 | −44.538 | −3.915 | 46.03 | N |
| ATOM | 2374 | CA | PHE | 1344 | −34.193 | −44.422 | −4.598 | 47.65 | C |
| ATOM | 2375 | CB | PHE | 1344 | −34.478 | −43.644 | −5.88 | 48.08 | C |
| ATOM | 2376 | CG | PHE | 1344 | −33.55 | −44.017 | −6.982 | 46.41 | C |
| ATOM | 2377 | CD1 | PHE | 1344 | −34.002 | −44.165 | −8.282 | 45.61 | C |
| ATOM | 2378 | CD2 | PHE | 1344 | −32.205 | −44.245 | −6.71 | 45.61 | C |
| ATOM | 2379 | CE1 | PHE | 1344 | −33.134 | −44.529 | −9.297 | 45.07 | C |
| ATOM | 2380 | CE2 | PHE | 1344 | −31.332 | −44.609 | −7.721 | 44.04 | C |
| ATOM | 2381 | CZ | PHE | 1344 | −31.798 | −44.75 | −9.016 | 44.55 | C |
| ATOM | 2382 | C | PHE | 1344 | −33.357 | −43.599 | −3.602 | 49.92 | C |
| ATOM | 2383 | O | PHE | 1344 | −33.488 | −42.376 | −3.477 | 51.55 | O |
| ATOM | 2384 | N | ILE | 1345 | −32.396 | −44.351 | −3.076 | 51.14 | N |
| ATOM | 2385 | CA | ILE | 1345 | −31.802 | −43.901 | −1.816 | 51.51 | C |
| ATOM | 2386 | CB | ILE | 1345 | −30.772 | −44.991 | −1.309 | 51.18 | C |
| ATOM | 2387 | CG2 | ILE | 1345 | −29.756 | −44.342 | −0.398 | 49.1 | C |
| ATOM | 2388 | CG1 | ILE | 1345 | −31.473 | −46.176 | −0.598 | 51.89 | C |
| ATOM | 2389 | CD | ILE | 1345 | −32.276 | −45.84 | 0.682 | 51.67 | C |

TABLE 1B-continued

| | | | | | | | | | |
|---|---|---|---|---|---|---|---|---|---|
| ATOM | 2390 | C | ILE | 1345 | −31.323 | −42.476 | −1.708 | 52.76 | C |
| ATOM | 2391 | O | ILE | 1345 | −30.098 | −42.321 | −2.071 | 51.79 | O |
| ATOM | 2392 | N | GLY | 1346 | −32.172 | −41.554 | −1.404 | 52.64 | N |
| ATOM | 2393 | CA | GLY | 1346 | −31.848 | −40.112 | −1.194 | 53.2 | C |
| ATOM | 2394 | C | GLY | 1346 | −30.478 | −40.01 | −0.552 | 53.8 | C |
| ATOM | 2395 | OT1 | GLY | 1346 | −30.041 | −41.005 | 0.076 | 53.54 | O |
| ATOM | 2396 | OXT | GLY | 1346 | −29.834 | −38.946 | −0.669 | 53.44 | O |
| TER | 2397 | | GLY | 346 | | | | | |
| HETATM | 2398 | C18 | M97 | 1 | −28.421 | −19.33 | −23.501 | 20.4 | C |
| HETATM | 2399 | C17 | M97 | 1 | −28.05 | −18.355 | −24.625 | 22.33 | C |
| HETATM | 2400 | C16 | M97 | 1 | −28.763 | −17.001 | −24.516 | 20.81 | C |
| HETATM | 2401 | C15 | M97 | 1 | −28.583 | −16.465 | −23.104 | 21.33 | C |
| HETATM | 2402 | C23 | M97 | 1 | −28.693 | −15.112 | −22.776 | 21.71 | C |
| HETATM | 2403 | C22 | M97 | 1 | −28.525 | −14.706 | −21.456 | 23.83 | C |
| HETATM | 2404 | C21 | M97 | 1 | −28.245 | −15.591 | −20.427 | 21.68 | C |
| HETATM | 2405 | C20 | M97 | 1 | −28.13 | −16.961 | −20.742 | 19.42 | C |
| HETATM | 2406 | C19 | M97 | 1 | −28.303 | −17.326 | −22.047 | 20.56 | C |
| HETATM | 2407 | N3 | M97 | 1 | −28.175 | −18.712 | −22.175 | 21.67 | N |
| HETATM | 2408 | C3 | M97 | 1 | −27.916 | −19.167 | −20.955 | 17.66 | C |
| HETATM | 2409 | C2 | M97 | 1 | −27.883 | −18.147 | −20.082 | 18.09 | C |
| HETATM | 2410 | C6 | M97 | 1 | −27.568 | −18.343 | −18.599 | 16.61 | C |
| HETATM | 2411 | C8 | M97 | 1 | −28.539 | −17.7 | −17.605 | 18.67 | C |
| HETATM | 2412 | O2 | M97 | 1 | −29.767 | −17.736 | −17.726 | 19.12 | O |
| HETATM | 2413 | N2 | M97 | 1 | −27.899 | −17.101 | −16.607 | 17.51 | N |
| HETATM | 2414 | C7 | M97 | 1 | −26.579 | −17.132 | −16.804 | 17.32 | C |
| HETATM | 2415 | O1 | M97 | 1 | −25.745 | −16.754 | −15.985 | 18.84 | O |
| HETATM | 2416 | C1 | M97 | 1 | −26.241 | −17.726 | −18.172 | 16.61 | C |
| HETATM | 2417 | C4 | M97 | 1 | −25.08 | −18.719 | −18.217 | 18.4 | C |
| HETATM | 2418 | C10 | M97 | 1 | −24.374 | −18.961 | −19.389 | 16.93 | C |
| HETATM | 2419 | C11 | M97 | 1 | −24.497 | −18.49 | −20.685 | 19.11 | C |
| HETATM | 2420 | C12 | M97 | 1 | −23.573 | −18.885 | −21.641 | 19.55 | C |
| HETATM | 2421 | C13 | M97 | 1 | −22.536 | −19.749 | −21.281 | 19.99 | C |
| HETATM | 2422 | C14 | M97 | 1 | −22.425 | −20.218 | −19.981 | 18.84 | C |
| HETATM | 2423 | C9 | M97 | 1 | −23.349 | −19.826 | −19.016 | 18.71 | C |
| HETATM | 2424 | N1 | M97 | 1 | −23.479 | −20.067 | −17.715 | 17.96 | N |
| HETATM | 2425 | C5 | M97 | 1 | −24.523 | −19.402 | −17.22 | 18.43 | C |
| HETATM | 2426 | O | HOH | 1 | −29.733 | −45.042 | −32.394 | 23.71 | O |
| HETATM | 2427 | O | HOH | 11 | −41.978 | −18.659 | −8.604 | 33.69 | O |
| HETATM | 2428 | O | HOH | 19 | −14.344 | −9.842 | −22.4 | 23.99 | O |
| HETATM | 2429 | O | HOH | 21 | −43.049 | −29.657 | −28.643 | 33.17 | O |
| HETATM | 2430 | O | HOH | 22 | −27.163 | −0.128 | −19.346 | 37.35 | O |
| HETATM | 2431 | O | HOH | 23 | −11.942 | −12.723 | −13.277 | 40.63 | O |
| HETATM | 2432 | O | HOH | 25 | −33.037 | −32.588 | −8.01 | 24.8 | O |
| HETATM | 2433 | O | HOH | 26 | −25.627 | −43.198 | −8.776 | 24.3 | O |
| HETATM | 2434 | O | HOH | 29 | −46.913 | −39.523 | −36.653 | 28 | O |
| HETATM | 2435 | O | HOH | 30 | −30.849 | −12.281 | −30.69 | 21.24 | O |
| HETATM | 2436 | O | HOH | 31 | −34.444 | −22.254 | −29.224 | 14.19 | O |
| HETATM | 2437 | O | HOH | 33 | −50.753 | −27.924 | −27.093 | 26.45 | O |
| HETATM | 2438 | O | HOH | 34 | −27.308 | −38.76 | −4.252 | 35.8 | O |
| HETATM | 2439 | O | HOH | 38 | −16.629 | −37.696 | −14.044 | 24.11 | O |
| HETATM | 2440 | O | HOH | 43 | −37.896 | −19.153 | −11.112 | 20.78 | O |
| HETATM | 2441 | O | HOH | 45 | −40.294 | 3.592 | −21.002 | 46.87 | O |
| HETATM | 2442 | O | HOH | 47 | −19.865 | −18.501 | −9.486 | 42.76 | O |
| HETATM | 2443 | O | HOH | 49 | −36.45 | −37.969 | −30.939 | 15.37 | O |
| HETATM | 2444 | O | HOH | 50 | −29.817 | −27.464 | −2.853 | 38.04 | O |
| HETATM | 2445 | O | HOH | 51 | −35.913 | −29.539 | −28.732 | 15.99 | O |
| HETATM | 2446 | O | HOH | 55 | −35.063 | −49.437 | −29.855 | 33.2 | O |
| HETATM | 2447 | O | HOH | 63 | −17.108 | −3.162 | −15.949 | 31.66 | O |
| HETATM | 2448 | O | HOH | 65 | −36.185 | −14.548 | −12.6 | 24.69 | O |
| HETATM | 2449 | O | HOH | 66 | −37.492 | −51.897 | −39.152 | 22.65 | O |
| HETATM | 2450 | O | HOH | 74 | −21.385 | −26.942 | −16.186 | 40.62 | O |
| HETATM | 2451 | O | HOH | 77 | −32.568 | −48.216 | −6.703 | 47.5 | O |
| HETATM | 2452 | O | HOH | 78 | −40.231 | −18.222 | −13.28 | 21.62 | O |
| HETATM | 2453 | O | HOH | 80 | −49.359 | −48.928 | −27.562 | 28.98 | O |
| HETATM | 2454 | O | HOH | 81 | −50.28 | −38.693 | −33.409 | 34.22 | O |
| HETATM | 2455 | O | HOH | 89 | −48.667 | −5.949 | −17.295 | 35.77 | O |
| HETATM | 2456 | O | HOH | 90 | −43.326 | −45.18 | −33.961 | 31.65 | O |
| HETATM | 2457 | O | HOH | 93 | −29.409 | −47.043 | −11.708 | 31.44 | O |
| HETATM | 2458 | O | HOH | 95 | −10.204 | −6.223 | −17.26 | 18.06 | O |
| HETATM | 2459 | O | HOH | 96 | −31.221 | −3.393 | −19.944 | 22.32 | O |
| HETATM | 2460 | O | HOH | 98 | −36.257 | −17.223 | −13.142 | 20.12 | O |
| HETATM | 2461 | O | HOH | 99 | −33.234 | −50.471 | −24.546 | 20.45 | O |
| HETATM | 2462 | O | HOH | 107 | −46.234 | −2.234 | −15.955 | 20.16 | O |
| HETATM | 2463 | O | HOH | 113 | −27.073 | −24.228 | −30.542 | 26.4 | O |
| HETATM | 2464 | O | HOH | 119 | −40.31 | −29.4 | −26.968 | 12.91 | O |
| HETATM | 2465 | O | HOH | 122 | −27.616 | −41.457 | −42.019 | 25.56 | O |
| HETATM | 2466 | O | HOH | 123 | −37.721 | −50.822 | −18.769 | 37.76 | O |
| HETATM | 2467 | O | HOH | 128 | −36.977 | −26.973 | −6.723 | 47.18 | O |
| HETATM | 2468 | O | HOH | 132 | −46.704 | −25.042 | −34.234 | 25.99 | O |
| HETATM | 2469 | O | HOH | 135 | −27.544 | −24.241 | −23.965 | 30.92 | O |

TABLE 1B-continued

| | | | | | | | | | |
|---|---|---|---|---|---|---|---|---|---|
| HETATM | 2470 | O | HOH | 140 | −37.425 | 3.24 | −35.007 | 18.34 | O |
| HETATM | 2471 | O | HOH | 143 | −20.008 | −12.815 | −30.386 | 40.51 | O |
| HETATM | 2472 | O | HOH | 147 | −14.407 | −15.827 | −13.914 | 30.48 | O |
| HETATM | 2473 | O | HOH | 151 | −49.199 | −31.854 | −19.993 | 33.45 | O |
| HETATM | 2474 | O | HOH | 152 | −33.758 | −21.539 | −26.003 | 45.57 | O |
| HETATM | 2475 | O | HOH | 156 | −21.439 | −40.205 | −36.699 | 50.64 | O |
| HETATM | 2476 | O | HOH | 160 | −27.226 | −43.392 | −33.693 | 25.08 | O |
| HETATM | 2477 | O | HOH | 164 | −25.061 | −26.966 | −24.102 | 22.64 | O |
| HETATM | 2478 | O | HOH | 167 | −39.626 | −16.67 | −10.802 | 34.02 | O |
| HETATM | 2479 | O | HOH | 171 | −19.142 | −1.168 | −17.551 | 32.21 | O |
| HETATM | 2480 | O | HOH | 172 | −30.803 | −0.387 | −20.702 | 32.83 | O |
| HETATM | 2481 | O | HOH | 176 | −54.115 | −25.794 | −25.837 | 53.46 | O |
| HETATM | 2482 | O | HOH | 181 | −23.869 | −36.686 | −5.557 | 40.21 | O |
| HETATM | 2483 | O | HOH | 184 | −29.269 | −30.565 | −24.802 | 22.28 | O |
| HETATM | 2484 | O | HOH | 189 | −50.2 | −45.277 | −19.345 | 38.58 | O |
| HETATM | 2485 | O | HOH | 191 | −21.65 | −29.789 | −23.813 | 31.45 | O |
| HETATM | 2486 | O | HOH | 192 | −23.062 | −24.401 | −6.237 | 35.26 | O |
| HETATM | 2487 | O | HOH | 194 | −25.27 | 1.306 | −15.454 | 29.8 | O |
| HETATM | 2488 | O | HOH | 195 | −28.159 | −42.387 | −7.202 | 22.48 | O |
| HETATM | 2489 | O | HOH | 199 | −13.955 | −14.842 | −16.709 | 32.78 | O |
| HETATM | 2490 | O | HOH | 200 | −36.82 | −41.718 | 0.531 | 50.12 | O |
| HETATM | 2491 | O | HOH | 201 | −28.644 | −20.12 | −36.964 | 18.87 | O |
| HETATM | 2492 | O | HOH | 203 | −50.477 | −32.049 | −17.177 | 24.64 | O |
| HETATM | 2493 | O | HOH | 216 | −39.142 | −22.788 | −29.507 | 33.97 | O |
| HETATM | 2494 | O | HOH | 219 | −47.47 | −15.035 | −20.201 | 35.71 | O |
| HETATM | 2495 | O | HOH | 224 | −46.506 | −27.482 | −23.402 | 21.71 | O |
| HETATM | 2496 | O | HOH | 234 | −41.895 | −31.848 | −31.831 | 20.74 | O |
| HETATM | 2497 | O | HOH | 235 | −26.441 | −19.233 | −9.527 | 33.45 | O |
| HETATM | 2498 | O | HOH | 239 | −37.357 | −36.383 | −42.714 | 31.76 | O |
| HETATM | 2499 | O | HOH | 240 | −31.471 | −4.986 | 0.652 | 22.91 | O |
| HETATM | 2500 | O | HOH | 243 | −28.65 | −42.512 | −29.641 | 22.84 | O |
| HETATM | 2501 | O | HOH | 244 | −36.603 | −42.277 | −29.106 | 19.94 | O |
| HETATM | 2502 | O | HOH | 248 | −29.027 | −13.664 | −10.124 | 31.23 | O |
| HETATM | 2503 | O | HOH | 249 | −40.094 | −50.827 | −15.065 | 43.7 | O |
| HETATM | 2504 | O | HOH | 251 | −23.436 | −42.81 | −11.982 | 46.35 | O |
| HETATM | 2505 | O | HOH | 252 | −31.443 | −12.916 | −9.468 | 43.08 | O |
| HETATM | 2506 | O | HOH | 253 | −45.124 | −10.841 | −28.548 | 57.83 | O |
| HETATM | 2507 | O | HOH | 256 | −47.989 | −21.853 | −27.175 | 28.06 | O |
| HETATM | 2508 | O | HOH | 257 | −44.346 | −21.809 | −29.799 | 45.06 | O |
| HETATM | 2509 | O | HOH | 258 | −48.882 | −41.587 | −10.969 | 52.61 | O |
| HETATM | 2510 | O | HOH | 259 | −29.049 | −34.816 | −39.703 | 52.2 | O |
| HETATM | 2511 | O | HOH | 267 | −36.421 | 1.247 | −12.805 | 36 | O |
| HETATM | 2512 | O | HOH | 279 | −29.355 | −45.223 | −28.378 | 33.41 | O |
| HETATM | 2513 | O | HOH | 282 | −42.248 | −20.932 | −28.066 | 29.16 | O |
| HETATM | 2514 | O | HOH | 283 | −33.773 | −4.7 | 2.104 | 49.74 | O |
| HETATM | 2515 | O | HOH | 285 | −21.851 | −38.325 | −6.435 | 31.66 | O |
| HETATM | 2516 | O | HOH | 287 | −26.26 | −43.568 | −28.371 | 25.76 | O |
| HETATM | 2517 | O | HOH | 291 | −22.18 | −11.552 | −29.799 | 43.2 | O |
| HETATM | 2518 | O | HOH | 293 | −48.423 | −37.306 | −38.97 | 42.54 | O |
| HETATM | 2519 | O | HOH | 298 | −24.451 | −45.031 | −29.768 | 43.48 | O |
| HETATM | 2520 | O | HOH | 340 | −24.526 | −9.586 | −25.61 | 15.08 | O |
| HETATM | 2521 | O | HOH | 342 | −27.622 | −21.226 | −29.674 | 29.04 | O |
| HETATM | 2522 | O | HOH | 348 | −40.859 | −30.744 | −29.704 | 25.01 | O |
| HETATM | 2523 | O | HOH | 352 | −32.508 | −49.493 | −33.945 | 34.9 | O |
| HETATM | 2524 | O | HOH | 356 | −18.731 | −15.159 | −30.315 | 33.75 | O |
| HETATM | 2525 | O | HOH | 358 | −34.046 | −54.592 | −37.088 | 20.7 | O |
| HETATM | 2526 | O | HOH | 360 | −31.208 | −32.444 | −33.609 | 20.04 | O |
| HETATM | 2527 | O | HOH | 363 | −30.618 | −33.523 | −8.002 | 25.2 | O |
| HETATM | 2528 | O | HOH | 365 | −14.406 | −16.156 | −24.124 | 39.38 | O |
| HETATM | 2529 | O | HOH | 373 | −38.591 | −25.485 | −32.288 | 30.06 | O |
| HETATM | 2530 | O | HOH | 377 | −48.553 | −17.92 | −12.222 | 37.86 | O |
| HETATM | 2531 | O | HOH | 380 | −36.774 | −36.981 | −33.348 | 22.77 | O |
| HETATM | 2532 | O | HOH | 381 | −24.808 | −41.352 | −28.041 | 28 | O |
| HETATM | 2533 | O | HOH | 388 | −24.856 | −17.892 | −7.816 | 27.87 | O |
| HETATM | 2534 | O | HOH | 389 | −26.781 | −11.754 | −6.859 | 37.48 | O |
| HETATM | 2535 | O | HOH | 390 | −26.698 | −26.085 | −28.658 | 43.43 | O |
| HETATM | 2536 | O | HOH | 396 | −39.993 | −0.244 | −8.176 | 44.09 | O |
| HETATM | 2537 | O | HOH | 399 | −22.572 | −23.838 | −19.334 | 35.76 | O |
| HETATM | 2538 | O | HOH | 408 | −39.893 | −27.132 | −7.517 | 28.65 | O |
| HETATM | 2539 | O | HOH | 410 | −51.294 | −26.589 | −30.152 | 36.54 | O |
| HETATM | 2540 | O | HOH | 416 | −27.033 | −4.323 | −31.352 | 40.18 | O |
| HETATM | 2541 | O | HOH | 418 | −32.288 | −20.615 | −47.531 | 46.09 | O |
| HETATM | 2542 | O | HOH | 420 | −21.59 | −20.992 | −15.896 | 47.82 | O |
| HETATM | 2543 | O | HOH | 421 | −33.255 | −1.487 | −28.193 | 15.19 | O |
| HETATM | 2544 | O | HOH | 422 | −33.862 | −14.639 | −36.562 | 39.85 | O |
| HETATM | 2545 | O | HOH | 423 | −24.055 | −22.398 | −28.638 | 38.93 | O |
| HETATM | 2546 | O | HOH | 424 | −23.254 | −24.538 | −37.285 | 41.97 | O |
| HETATM | 2547 | O | HOH | 425 | −27.795 | −30.29 | −26.912 | 29.38 | O |

TABLE 1B-continued

| HETATM | 2548 | O | HOH | 426 | −24.824 | −29.707 | −29.385 | 39.8 | O |
| HETATM | 2549 | O | HOH | 427 | −42.553 | −46.3 | −15.041 | 21.97 | O |

The electronic representation of the c-Met structure was then displayed on a computer screen for visual inspection and analysis. All important motifs involved in c-Met ligand recognition and binding were identified, including those described above.

A three dimensional graphical representation of the c-Met binding pocket was then generated as part of an electronic representation of the ligand bound binding site. In an embodiment, the electronic representation of the binding pocket contains the coordinates of c-Met residues up to 6 Å from every atom of the ligand. This model contains twenty three amino acid residues (Table 4).

The structure coordinates of amino acid residues that constitute the binding pocket define the chemical environment of the ligand binding site, and thereby are useful in designing compounds that may interact with those residues.

The binding site amino acid residues are key residues for ligand binding. Alternatively, the binding site amino acid residues may be residues that are spatially related in the definition of the three-dimensional shape of the binding pocket. The amino acid residues may be contiguous or non-contiguous in the primary sequence.

The c-Met inhibition model is formed by three-dimensional coordinates of amino acid residues selected from the X-ray crystallographic structure of the complex of c-Met bound to the selective c-Met inhibitor as explained above. This model is mostly hydrophobic in nature. The only exception is c-Met hinge binding motif, which corresponds to the backbone amide of M1160 and the backbone carbonyl of P115.

Computer programs are also employed to estimate the attraction, repulsion, and steric hindrance of the ligand to the kinase inhibition model. Generally the tighter the fit between the inhibitor and c-Met at the molecular level and atomic level (e.g., the lower the steric hindrance, and/or the greater the attractive force), the more potent the potential drug will be because these properties are consistent with a tighter-binding constant.

To increase the likelihood of finding a suitable ligand, a set of seed molecules has been compiled. This set contains fragments that are modified to result in a molecule that tightly binds the model.

Alternatively, a potential ligand is obtained by screening a random chemical library. A ligand selected in this manner is then systematically modified by computer-modeling programs until one or more promising potential ligands are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1: 109-128 (1993). Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus, through the use of the structure coordinates disclosed herein and computer modeling, a large number of these compounds are rapidly screened on the computer monitor screen, and a few likely candidates are determined or identified without the laborious synthesis of untold numbers of compounds.

Once a potential ligand (agonist or antagonist) is identified, it is either selected from commercial libraries of compounds or synthesized de novo. As mentioned above, the de novo synthesis of one or even a relatively small group of specific compounds is reasonable in the art of drug design.

For all of the drug design strategies described herein further refinements to the structure of the drug are generally necessary and are made by the successive iterations of any and/or all of the steps provided by the aforementioned strategies.

Another aspect of the invention involves using the structure coordinates generated from the c-Met/inhibitor complex to generate a three-dimensional shape. This is achieved through the use of commercially available software that is capable of generating three-dimensional graphical representations of molecules or portions thereof from a set of structure coordinates.

The variations in coordinates discussed above may be generated because of mathematical manipulations of the c-Met/inhibitor complex structure coordinates. For example, the structure coordinates set forth in Table 1A or Table 1B could be manipulated by crystallographic permutations of the structure coordinates, fractionalization of the structure coordinates, integer additions or subtractions to sets of the structure coordinates, or combinations thereof.

Alternatively, modifications in the crystal structure due to mutations, additions, substitutions, and/or deletions of amino acids, or other changes in any of the components that make up the crystal also account for variations in structure coordinates. If such variations are within an acceptable standard error, as compared to the original coordinates, the resulting three-dimensional shape is considered to be the same. Thus, for example, a ligand that bound to the binding pocket of the c-Met kinase domain is also expected to bind to another binding pocket whose structure coordinates, when compared to those described, have a root mean square difference of equal to or less than about 1.5 Å, more preferably less than about 1.0 Å, and even more preferably, less than about 0.5 Å, from the backbone atoms.

Various computational analyses can be performed to analyze c-Met or other kinases or the kinase domains thereof. Such analyses may be carried out through the use of known software applications, such as ProMod, SWISS-MODEL (Swiss Institute of Bioinformatics), and the Molecular Similarity application of QUANTA (Accelrys, Inc., San Diego, Calif.). Programs, such as QUANTA permit comparisons between different structures, different conformations of the same structure, and different parts of the same structure. Comparison of structures using such computer software may involve the following steps: 1) loading the structures to be compared; 2) defining the atom equivalencies in the structures; 3) performing a fitting operation; and 4) analyzing the results. Each structure is identified by a name. One structure is identified as the target (i.e., the fixed structure) and all remaining structures are working structures (i.e., moving structures). Since atom equivalency with QUANTA is defined by user input, for the purpose of this invention, applicants define equivalent atoms as protein backbone atoms (N, Cα, C, and O) for all conserved residues between the two structures being compared. Only rigid fitting operations are also considered. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms (Å), is reported by software applications, such as QUANTA.

For the purpose of this invention, any c-Met molecule or molecular complex or kinase domain thereof that has a root mean square deviation of conserved residue backbone atoms (N, Cα, C, O) of less than about 1.5 Å, more preferably less than about 1.0 Å, and even more preferably less than about 0.5 Å, when superimposed on the relevant backbone atoms described by structure coordinates listed in Table 1A or Table 1B are considered equivalent.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of the c-Met or other kinases of the invention or the kinase domain portion thereof, as defined by the structure coordinates described herein.

3. Use of the c-Met Inhibition Model to Derive an Inhibition Model for Another Kinase The c-Met inhibition model can be modified to construct a model for the inhibition of another kinase. This method is known as homology modeling. The model for the new kinase can be generated by replacing electronic representations of particular residues of the c-Met inhibition model with electronic representations of corresponding residues of the new kinase.

The new kinase is a kinase with a difference of at least one amino acid residue from the wild-type human c-Met. The another kinase can be a mutant c-Met protein, a paralog of c-Met protein, a family member or a related sequence (homologous) of c-Met, a kinase with at least 10% amino acid sequence identity or homology to c-Met, or a kinase with at least 30% nucleotide or amino acid sequence similarity to wild type c-Met.

There are several applications for this methodology.

3.1. Methodology to Derive an Inhibition Model for Another Kinase from the c-Met Inhibition Model Typically, construction of such an inhibition model involves: performing sequence alignment between the amino acid sequence of other kinase against the amino acid sequence of c-Met, identifying conserved amino acid residues between c-Met and the kinase of interest, generating atomic coordinates of all conserved amino acids in the other kinase from the electronic representation of c-Met residues; generating conformations for the structurally variable residues in the other kinase; replacing the non-conserved residues of c-Met with residues from the other kinase structure; building side chain conformations; and refining and/or evaluating the structure.

This method is known as homology modeling. The method is accomplished using commercially available software. Non-limiting examples of such programs are MOE (CCG, Montreal, Canada), ICM (Molsoft, La Jolla, Calif.), and Insight II/Discover (Accelrys, Inc., San Diego, Calif.).

The success of homology models depends on the sequence alignment. Four motifs were selected to guide such an alignment: P-loop, salt-bridge, DFG-motif and the A-loop.

The geometry of the residues forming the kinase hinge is very important and differs from one kinase to the other. The hinge also assumes different conformations depending on the bound ligand. To optimize the shape and geometry of the model's binding pocket, fragments from known inhibitors were used. Those fragments were modified by attaching atomic groups suitable to complement the pocket.

Once the inhibition model is built, a three dimensional graphical representation of the binding pockets of c-Met paralogs, significant c-Met homologs, and/or other kinases is generated. The new kinase inhibition model is defined as an electronic representation of residues corresponding to the c-Met inhibition model.

The resulting pair-wise comparison of binding pocket residues provides a basis for evaluating similarities and differences in polarity and hydrophobicity, and therefore differences in the chemical environment, of the binding pockets of various kinases by using the inhibition model. This inhibitor model is important for drug design, e.g. designing inhibitors of c-Met paralogs, significant c-Met homologs, and/or other kinases. The kinase, for which an inhibitor is designed using the inhibitor model, can be any known kinase.

3.2. Similarity Assessment Method for Comparing Inhibition Models Derived for a Series of New Kinase Proteins.

To assess the similarity of inhibition models, a weighting system is applied. In one embodiment of the invention, residues are assigned the following weights:

2 critical for ligand binding residues
1 residue side chain lining the inhibition model
0.5 backbone atoms part of the inhibition model
additions, deletions and changes in backbone flexibility, lack of residue
−1 alignment
dramatic changes in size and/or polarity inside the inhibition model, lack of
−2 alignment of critical residues The following illustrative examples demonstrate that the highest similarity assessment value of 25 is obtained when the system is applied to the c-Met protein. All other proteins are expected to score below the maximum of 25.

TABLE 2

(SEQ ID NOs. 11, 3, 4, 5, 6, 7, 8, and 9, respectively)

| PROTEIN | C-MET (SEQ ID NO: 11) | weight | AXL (SEQ ID NO: 3) | weight | FLT-3 (SEQ ID NO: 4) | weight | cKIT (SEQ ID NO: 5) | weight |
|---|---|---|---|---|---|---|---|---|
| | I_1084 | 2 | L_542 | 1 | L_616 | 1 | L_595 | 1 |
| | G_1085 | 2 | G_543 | 2 | G_617 | 2 | G_596 | 2 |
| | F_1089 | 2 | F_547 | 2 | F_621 | 2 | F_600 | 2 |
| | V_1092 | 2 | V_550 | 2 | V_624 | 2 | V_603 | 2 |
| | A_1108 | 1 | A_565 | 1 | A_642 | 1 | A_621 | 1 |
| | V_1109b | 0.5 | V_566 | 0.5 | V_643 | 0.5 | V_1109 | 0.5 |
| | K_1110b | 0.5 | K_567 | 0.5 | K_644 | 0.5 | K_623 | 0.5 |

TABLE 2-continued (SEQ ID NOs. 11, 3, 4, 5, 6, 7, 8, and 9, respectively)

|  | | | | | | | | |
|---|---|---|---|---|---|---|---|---|
| | L_1140 | 1 | M_598 | 0.5 | V_675 | 0.5 | V_654 | 0.5 |
| | V_1155 | 1 | V_618 | 1 | L_689 | 0.5 | I_669 | 0.5 |
| | L_1157 | 1 | L_620 | 1 | F_691 | 0.5 | T_670 | −2 |
| | P_1158 | 1 | P_621 | 1 | E_692 | −1 | E_671 | −1 |
| | Y_1159b | 0.5 | F_622 | 0.5 | Y_693 | 0.5 | Y_672 | 0.5 |
| | M_1160 | 1 | M_623 | 1 | C_694 | 0.5 | C_673 | 0.5 |
| | K_1161b | 0.5 | K_624 | 0.5 | C_695 | 0.5 | C_674 | 0.5 |
| | H_1162b | 0.5 | H_625 | 0.5 | Y_696 | 0.5 | Y_675 | 0.5 |
| | G_1163 | 0.5 | G_626 | 0.5 | G_697 | 0.5 | G_676 | 0.5 |
| | D_1164 | 1 | D_627 | 1 | D_698 | 1 | D_677 | 1 |
| | M_1211 | 1 | M_679 | 1 | L_818 | 0.5 | L_799 | 0.5 |
| | A_1221 | 1 | A_689 | 1 | C_828 | 0.5 | C_809 | 0.5 |
| | D_1222 | 1 | D_690 | 1 | D_629 | 1 | D_810 | 1 |
| | F_1223 | 1 | F_691 | 1 | F_630 | 1 | F_811 | 1 |
| | A_1226 | 1 | S_694 | −1 | A_833 | 1 | A_814 | 1 |
| | R_1227 | 2 | K_695 | 1 | R_834 | 2 | R_815 | 2 |
| Similarity assessment value | | 25 | | 20.5 | | 19 | | 17 |

| PROTEIN | IRK (SEQ ID NO: 6) | weight | cFMS (SEQ ID NO: 7) | weight | cABL (SEQ ID NO: 8) | weight | PIM1 (SEQ ID NO: 9) | weight |
|---|---|---|---|---|---|---|---|---|
| | L_1002 | 1 | L_588 | 1 | L_266 | 1 | L_44 | 1 |
| | G_1003 | 1 | G_589 | 2 | G_267 | 2 | G_45 | 2 |
| | F_1007 | 2 | F_593 | 2 | Y_271 | 1 | F_49 | 2 |
| | V_1010 | 2 | V_596 | 2 | V_274 | 2 | V_52 | 2 |
| | A_1028 | 1 | A_614 | 1 | A_287 | 1 | A_65 | 1 |
| | V_1029 | 0.5 | V_615 | 0.5 | V_288 | 0.5 | I_66 | 0.5 |
| | K_1030 | 0.5 | K_616 | 0.5 | K_289 | 0.5 | K_67 | 0.5 |
| | V_1060 | 0.5 | V_647 | 0.5 | V_317 | 0.5 | V_103 | 1 |
| | V_1075 | 1 | V_661 | 1 | I_331 | 0.5 | L_118 | 1 |
| | M_1076 | 0.5 | T_663 | −2 | T_333 | −2 | L_120 | 1 |
| | E_1077 | −1 | E_664 | −1 | E_334 | −1 | E_121 | −1 |
| | L_1078 | 0.5 | Y_665 | 0.5 | F_335 | 0.5 | R_122 | 0.5 |
| | M_1079 | 1 | C_666 | 1 | M_336 | 1 | P_123 | −1 |
| | | | | | | | E_124 | −1 |
| | A_1080 | 0.5 | C_667 | 0.5 | T_337 | 0.5 | P_125 | −1 |
| | H_1081 | 0.5 | Y_668 | 0.5 | Y_338 | 0.5 | V_126 | 0.5 |
| | G_1082 | 0.5 | G_669 | 0.5 | G_339 | 0.5 | Q_127 | −1 |
| | D_1083 | 1 | D_670 | 1 | N_340 | −2 | D_128 | 1 |
| | M_1139 | 1 | L_785 | 0.5 | L_388 | 0.5 | L_174 | 0.5 |
| | G_1149 | −1 | G_795 | −1 | A_398 | 1 | I_185 | 1 |
| | D_1150 | 1 | D_796 | 1 | D_399 | 1 | D_186 | 1 |
| | F_1151 | 1 | F_797 | 1 | F_400 | 1 | F_187 | 1 |
| | T_1154 | −1 | A_800 | 1 | S_403 | −1 | A_191 | 1 |
| | R_1155 | 2 | R_801 | 2 | R_404 | 2 | L_192 | −2 |
| Similarity assessment value | | 16 | | 15.5 | | 11.5 | | 11.5 |

Residues which constitute a unique hydrophobic interaction critical for binding c-Met to the selective c-Met inhibitor are allocated a maximum weight of 2. Those residues include I1084, G1085, F1089, V1092 and R1227.

Conserved residue substitutions, are assigned half of this maximum value (1) to take into account size changes. Residues such as alanine, valine, leucine and isoleucine are exchanged by conserved substitutions. Similarly, the following residue pairs constitute conservative substitutions: serine and threonine, asparagine and glutamic acid, phenylalanine and tyrosine, and asparagine and glutamine.

When residues contribute only their backbone atoms to the creation of the inhibition model a weight of 0.5 is assigned.

Two penalty levels have been assigned (one severe (−2), one moderate (−1)) to residues which are considered to contribute negatively to the similarity assessment relative to c-Met.

Determination of the similarity assessment provides a critical analysis of the target inhibition model for a kinase relative to the one described in this application for the selective c-Met inhibitor and c-Met.

The results of the similarity assessments indicate the expected selectivity of novel ligands identified with the inhibition model. In one embodiment of the invention, similarity assessment values above 90% of that of the selective c-Met inhibitor and c-Met (25) indicate the lowest level of compound selectivity; similarity assessment values between 90% and 50% are expected at the next level; and similarity assessment values below 50% indicate the highest level of selectivity.

These similarity assessments of various inhibition models are also critical in order to identify regions within the inhibition models that can be employed to ensure adequate complementarity between the inhibition model and ligand to overcome these differences, and therefore, lead to increased likelihood of success in the electronic screening or design process.

For instance, in the design process, the presence of a polar residue in place of a hydrophobic one may significantly alter the inhibitor's chemical environment. Modifications of the inhibitor to include a polar complementary atomic group within the inhibitory model will provide maximum electrostatic interactions with the inhibition model.

4. Use of the Inhibition Model for Ligand Screening (Enrichment), Fitting and Selection The kinase inhibition model is used for ligand screening (enrichment), fitting, and selection.

The electronic representation of compounds and/or fragments is generated as described above. In one embodiment of the invention, electronic representations of compounds and/or fragments are assembled into electronic databases. In another embodiment of the invention, these databases include chemical entities' coordinates in any SMILES, mol, sdf, or mol2 formats.

Selected chemical entities or fragments may be positioned in a variety of orientations inside the inhibition model. Chemical entities come from different sources including, but not limited to, proprietary compound repositories, commercial data bases, or virtual data bases. Non-limiting exemplary sources of fragments include reagent data bases, de-novo design, etc.

The selected chemical entities or fragments are used to perform a fitting of the electronic representation of compounds and/or fragments and the inhibition model. The fitting is done manually or is computer assisted (docking). In one embodiment, docking programs used in the present invention are ICM (Molsoft, La Jolla, Calif.), FelxiDock (Tripos, St. Louis, Mo.), GRAM (Medical Univ. Of South Carolina), DOCK3.5 and 4.0 (Univ. Calif. San Francisco), Glide (Schrödinger, Portland, Oreg.), Gold (Cambridge Crystallographic Data Centre, UK), FLEX-X (Bi-oSolveIT GmbH, Germany); or AUTODOCK (Scripps Research Institute).

The results of the fitting operation are then analyzed to quantify the association between the chemical entity and the binding pocket. The quality of fitting of these entities to the inhibition model is evaluated either by using a scoring function, shape complementarity, or estimating the interaction energy.

Methods for evaluating the association of a chemical entity with the target include energy minimization and molecular dynamics with standard molecular mechanics force fields, such as CHARMM and AMBER.

Additional data is obtained using Free Energy Perturbations (FEP), to account for other energetic effects such as desolvation penalties. Information about the chemical interactions with the target are then used to elucidate chemical modifications that can enhance selectivity of binding of the compound.

Potential binding compounds are identified based on favorable geometric fit and energetically favorable complementary interactions. Energetically favorable electrostatic interactions include attractive charge-charge, dipole-dipole and charge-dipole interactions between the target enzyme, and the small molecule.

The association with the binding pocket is further assessed by means of visual inspection followed by energy minimization and molecular dynamics. Examples of such programs include: MOE (CCG, Montreal, Canada), QUANTA/CHARMM (Accelrys, Inc., San Diego, Calif.); Gaussian (M. J. Frisch, Gaussian, Inc., Carnegie, Pa.); AMBER (P. A. Kollman, University of California at San Francisco); Jaguar (Schrödinger, Portland, Oreg.); SPARTAN (Wavefunction, Inc., Irvine, Calif.); Impact (Schrödinger, Portland, Oreg.); Insight II/Discover (Accelrys, Inc., San Diego, Calif.); MacroModel (Schrödinger, Portland, Oreg.); Maestro (Schrödinger, Portland, Oreg.); and DelPhi (Accelrys, Inc., San Diego, Calif.).

Once suitable fragments have been identified, they are connected into a single compound or complex on the three-dimensional image displayed on a computer screen in relation to all or a portion of the inhibition model.

5. Use of the Inhibition Model for Ligand Design

The design of compounds using the inhibition model includes calculation of non-covalent molecular interactions important in the compound's binding association including hydrogen bonding, van der Waals interactions, hydrophobic interactions and electrostatic interactions.

The compound's binding affinity to the inhibition model is further optimized by computational evaluation of the deformation energy of binding, i.e. the energy difference between bound and free states of the chemical entity.

Computer calculations may suggest more than one conformation similar in overall binding energy for a chemical entity. In these cases the deformation energy of binding is defined as the difference between the energy of the free entity and the average energy of the conformations observed when the inhibitor binds to the protein.

EXAMPLES

Examples are provided below to further illustrate different features of the present invention. The examples also illustrate useful methodology for practicing the invention. These examples do not limit the claimed invention.

Material and Methods

Expression and Purification of the cMet1 Kinase Domain cDNA of full-length cMet purchased from Origen Technologies was used as template for PCR amplification. The DNA fragment encoding the kinase domain (1038-1346) was inserted into a Novagen vector pet28a between Nco1 and Sal1 sites. The primers were designed to contain a six-histidine tag to the N-terminus. In order to express dephosphorylated cMet kinase protein, a tyrosine phosphatase PTP1B (1-283) was sequentially ligated into the construct between SalI and NotI sites. A second ribosome binding site was incorporated in the PTP1B primer after the SalI site.

c-Met1 Protein Expression

The N-terminal His-tagged proteins were expressed in Circlegrow broth (Q-Biogen). The transformed *E. Coli* cell line BL21(DE3)RIL (Stratagene) was cultured to OD=0.8 at 37° C. and induced with 0.3 mM of IPTG for overnight at 12° C. The co-expressed protein was purified by metal-chelation chromatography followed by anion and cation columns. In a typical preparation 4 liters of cells were lysed by sonication in 140 ml buffer containing 20 mM MOPS pH 6.5, 200 mM NaCl, 7.5% glycerol, 0.1% Igepal, supplied with 1 mM PMSF. The supernatant was obtained by centrifugation at 50,000 g for 30 minutes and followed by incubation with 8 mL of Ni-NTA His Bind resin (Novagen) at 4° C. for one hour. A second step 50 ml wash buffer (with 100 mM NaCl and 5 mM imidazole) was applied after initial wash with the lysis buffer. Protein was eluted by 200 mM imidazole pH8.5, 100 mM NaCl and 7.5% glycerol and directly cleared by passing 10 ml QFF column. The salt concentration and the pH value of the protein flow through were adjusted to 50 mM and 7.5 by dilution, and then loaded to 1 ml SP FF column. The protein was further gel-filtered in an equilibrium buffer of 20 mM TrisHCl pH8.5, 150 mM NaCl, 7.5% glycerol and 2 mM DTT. The monomeric cMet protein was concentrated to 30 mg/ml for storage at −80° C.

c-Met1 Protein Purification was Performed as Follows:

BL21(DE3)RIL cells were chilled on ice before being induced at 12° C. overnight at a density of OD600=1.

4-6 L cell pellets were then resuspended in 150 ml of 50 mM $K_2HPO_4$ pH 8.0, 200 mM NaCl, 7% Glycerol, 0.1% Igepal.=buffer A, +1.5 mM PMSF.

Cell suspensions were subsequently sonicated at 60% for 10 min, in cycles of 5 s on and 8 s off, and kept in ice.

Sonicated suspensions were centrifuged at 50,000×g for 30 min at 4° C. The resulting supernatants were transferred to 8 ml fresh nickle beads. This solution was rotated for 40 min at 4° C.

Supernatant liquid was allowed to drain off.

The nickel beads (which bound cMet1 protein) were resuspended twice with 50 ml of buffer A.

Nickel beads were then resuspended twice with 25 ml 50 mM $K_2HPO_4$, 100 mM NaCl, 7.5% Glycerol, 10 mM Imidazole (pH 8.5).

cMet1 protein was eluted from the nickel beads with 30 ml 200 mM Imidazole (pH8.5), 100 mM NaCl, 7.5% Glycerol.

The eluted flow-through directly drains to 10 ml QFF (in 100 mM NaCl).

(a) The first 2 ml of the flow through is not collected, but sent to waste.

(b) All remaining fractions are collected and concentrated down to ~500 ul for Gelfiltration in 20 mM TrisHCl pH 8.5, 150 mM NaCl, 7.5% Glycerol, 1 mM DTT. Peak elutes around 16 ml from a 24 ml superdex 200.

c-Met1 Crystallization, Data Collection and Structure Determination

The c-Met protein was diluted to 10 mg/ml by a buffer of 20 mM TrisHCl 8.5, 100 mM NCl and 5% glycerol. The selective c-Met inhibitor was added to 1 mM from a 10 mM (50% DMSO) stock solution. 20 mM $Li_2SO_4$ was also included in the protein solution. Thin needle crystals were obtained at 4° C. by hanging drop methodology using 15% ethanol, 12% ethylene glycol, 100 mM imidazole pH8.5 as precipitant. Typically, 250 nL protein solution was mixed with an equal volume of reservoir solution and streak-seeding method was employed to reduce the crystal nucleus. The crystals were harvested after adding ethylene glycol to 30%. The triclinic crystal has unit cell dimension of a=53.22 Å, b=57.97 Å, c=64.93 Å, α=88.11°, β=67.97°, γ=85.58°. There are two copies of c-Met polypeptide chain per asymmetric unit and the solvent content is 45%.

Diffraction images were collected at Cornell High Energy Synchrotron Source beamline A1 at 100 K with CCD detector. Raw data were reduced with DENZO and scaled and merged by using SCALEPACK on CHESS site. The complex structure was solved by molecular replacement using the program MOLREP implemented in CCP4. The Initial mode was ligand free c-Met kinase crystal structure (PDB code 2G15) from 1060-1346, excluding 1222-1239 (activation loop). With data up to 3 Å, a unique solution was found with correlation coefficient 0.34 versus 0.19 for the next highest peak. Structure refinement consisted of iterative cycles of modeling building in Coot, following by simulated annealing, minimization, and restrained B-factor refinement in CNX. The N-terminal and the A-loop amino acids were revealed during the refinement and built back to the electron density with different conformation from the initial model. Water molecules were added based on Fo-Fc maps (3σ) with density recapitulated in 2Fo-Fc maps (1σ). All waters satisfy the hydrogen-bonding criteria as implemented in the CNX programs Waterpick and Waterdelete. Non-crystallographic symmetry was not employed for the refinement though the two subunits are almost identical. In both subunits, the inhibitor conformation was unambiguously defined in the electron density and included for the refinement at late stage. Final rounds of improvement were performed in REFAC5 with TLS protocols to 2 Å and no σ cutoff. The finished model has continuous electron density from 1047 to 1346 but missing 1038-1046, and also contains 500 water molecules with a crystallographic R-value of 20.9% ($R_{free}$=25.3%). The x-ray data and refinement statistics are summarized in Table 3.

TABLE 3

| Data collection | |
|---|---|
| Space group | P1 |
| Cell dimensions a, b, c (Å) | 53.22, 57.97, 64.93 |
| Cell angles α, β, γ (deg) | 88.11, 67.97, 85.58 |
| Resolution (Å) | 30.0-2.0 |
| Unique reflections | 38978 |
| Completeness (2.07-2.00 Å) | 84.8% (51.4%) |
| $R_{sym}$ (2.07-2.00 Å) | 11.0% (26%) |
| Mean I/σ (I) | 6.9 |
| Redundancy | 1.8 |
| Refinement | |
| Intensity cutoff | 0.0 |
| $R_{cryst}{}^a$ | 22.3% |
| $R_{free}{}^a$ | 24.6% |
| rmsd in bond length (Å) | 0.009 |
| rmsd in bond angle (°) | 1.77 |
| Average B factor (Å$^2$) | 23.00 |

$^a R_{cys}$ and $R_{free}$ = (Σ|Fobs − Fcalc|)/(Σ|Fobs|). $R_{free}$ was calculated over a randomly selected 5% of the reflections not used in refinement. Parentheses indicate the outer resolution shell.

Example 1

The Structure of the c-Met1/Inhibitor Complex

The unphosphorylated c-Met kinase domain bound to the selective c-Met inhibitor follows the bi-lobal architecture with N-terminal domain mainly β-sheet connected through a hinge segment to the mainly α-helical C-terminal lobe. All of the residues of the kinase domain are well defined in the structure, including those from the activation loop and the nucleotide binding loop (P-loop). Residues of those loops have an average B-values less than 35 Å.

The selective c-Met inhibitor binds the interdomain cleft between the N- and C-lobes. The carbonyl group from the succinamide ring forms hydrogen bond with the backbone amide of M1160 and the N—H group forms hydrogen bonds with the backbone carbonyl of P1158. The indole ring is close to the ATP binding site opening while the tricyclic ring is bound deep inside the hydrophobic pocket. While the selective c-Met inhibitor binding mode is similar to the binding of many ATP competitive inhibitors, the kinase domain of c-Met bound to the selective c-Met inhibitor assumes an inactive conformation resembling that found in some receptor tyrosine kinases.

The activation loop is in the canonical, autoinhibitory conformation with a short anti-parallel strand observed in many inactive RTKs present in the structure. Two tyrosine residues Y1234 and Y1235 located in the A-loop of the kinase domain are responsible for c-Met catalytic activity. While Y1234 is exposed, Y1235 is sequestered into the active site occupying the site of the substrate tyrosine (FIG. 1). FIG. 1 shows the activation loop of the unphosphorylated c-Met bound to selective inhibitor AQ197 is shown in dark gray. The peptide substrate, as seen in the structure of the phosphorylated insulin receptor IRK in complex with ATP and a peptide (PDB entry 1IR3), is shown in lighter grey. FIG. 1 was generated by superimposing the catalytic segments of those two kinases. Similar orientation has been found for Y1162 in the inactive IRK (1IRK), Y842 of FLT3 (1RJB), Y823 in c-Kit (1T45), Y412 of c-Abl (2HYY) as well as Y823 of c-Kit (1T46) bound to Gleevec, and Y809 of cFMS bound to arylamides (2IOY) and quinolone (2IOV) series of inhibitors.

Y1235 of unphosphorylated c-Met bound to the selective c-Met inhibitor is held by a hydrogen bond network formed by catalytic loop (C-loop) N1204 and R1208, strictly conserved residues across the type III RTKs. Their hydrogen bond interactions correlate well with observed substrate preferences in active RTKs like IRK and c-Kit, where the corresponding Asp residue interacts with the attacking hydroxyl side chain of the substrate, while the arginine residue engages in hydrogen bonding interactions that orient asparagine (FIG. 2). FIG. 2 is a cartoon image of c-Met kinase domain. The activation loop is in the canonical, autoinhibitory conformation forming a typical short anti-parallel strand. This particular conformation has been observed in other inactive RTKs. While Y1235 is mimicking the substrate tyrosine residue Y1234 is exposed. Residues shown in sticks are labeled. Y1235 of c-Met bound to the selective c-Met inhibitor is sequestered by the hydrogen bond network formed by N1204 and R1208. These two residues are part of the catalytic loop (C-loop) and strictly conserved across the type III RTKs. The aromatic side chain of F1089 (sticks) stabilize the downfold of the loop by van de Waals contacts with the selective c-Met inhibitor. Similar specific conformations induced by small molecule fitting are present in the crystal structures of Abl bound to Gleevec and FGFR-1 bound to SU-5402 (PDB entry 1FGK). In the structure of the selective c-Met inhibitor bound to c-Met the conformation of the A-loop dramatically differs from those reported previously for the c-Met receptor kinase domain (Wang, W. et al. 2006. Proc. Natl. Acad. Sci. USA 103:3563-3568 (2006); Schiering, N. et al. 2003. Proc. Natl. Acad. Sci. USA 100:112654-12659). The wild type apo-c-Met reported by Wang et al. shows the activation loop in an open conformation, unsuitable for substrate binding, but does not block the ATP binding site. Y1234 is pulled closer to the N-terminal domain, making hydrogen bonds with E1127 an important catalytic residue as we explained above. The structure of mutant c-Met resolved by Schiering et al. was obtained from baculovirus cultures where the Y1194, Y1234 and Y1235 were mutated to prevent their phosphorylation during production. In this case the activation loop resembles the activated conformation.

Two different conformations of the DFG motif are known. In the activated kinases the DFG motif is in so-called 'DFG-in' conformation. This conformation permits $Mg^{2+}$ ion ligation by asparagine residue and phenylalanine makes room for the ATP tucking itself away under the αC helix. In this case the kinase has the ability to bind the ATP productively. In the 'DFG-out' conformation which is exhibited by our structure the aspartic acid and the phenylalanine switched sides, with aspartic acid point away from where the ATP would bind and phenylalanine is situated in the approximated position of the ATP adenine moiety. Stabilization of this portion of the A-loop is provided in part by the tricyclic group of the selective c-Met inhibitor, which is making van der Waals interactions with phenylalanine residue from the DFG motif. This is why, although the hydroxyl group of the Y1235 is in position for phosphor-transfer, the DFG-out motif occludes the ATP binding site interfering with a possibility of cis-transfer.

The nucleotide binding loop, the P-loop is well ordered in the structure of c-Met bound to the selective c-Met inhibitor, where residues I1084 to G1087 form part of the β1 strand. In contrast, in the publicly available unbound c-Met these four residues are disordered. F1089 stabilizes the downfold of the loop by van de Waals contacts with the selective c-Met inhibitor (FIG. 2). Crystal structures of Abl and FGFR complexed with inhibitors STI-571 (2HYY) and SU-5402 (1FGI), respectively, adopt similar conformations induced by inhibitor fitting.

While there are common features shared by Gleevec bound to c-Abl and c-Met bound to the selective c-Met inhibitor, there is an important difference in the alignment of the lysine-glutamic acid pair. In phosphorylated kinases corresponding glutamic acid residue stabilizes the orientation of lysine residue after kinase activation. When Gleevec binds c-Abl the salt bridge is well preserved and forms part of the hydrogen bond network with the inhibitor. When the selective c-Met inhibitor binds c-Met, the ion pair is disrupted, residues K1110 and E1127 are 16 Å apart, accentuating the inactive nature of the c-Met kinase conformation in the presence of the selective c-Met inhibitor With respect to FIG. 4, strictly conserved Lys (β3) and Glu (αC) in active kinases form an ion pair necessary for stabilizing the phosphate group transfer. Unphosphorylated c-Met bound to AQ197 shows this salt bridge disrupted as a result of the conformational changes of the A-loop and the helix αC (magenta). In yellow, the αC structure of the active form of insulin receptor kinase. Catalytic important Glutamic acid residues are shown in sticks.

A similar situation to c-Abl is present in c-Kit bound to Gleevec, lysine-glutamic acid maintain salt bridge distance. c-Kit structure is remarkable in another way. The unphosphorylated apo-structure appears very similar to the structure in complex with Gleevec. This fact may confirm the overall belief that Gleevec recognizes and binds the canonical, auto-inhibited kinase conformation.

Another receptor kinase cFMS bound to small molecule inhibitors is also in the canonical inactive conformation (Schubert, C. et al. 2007. J. Biol. Chem. 282:4094-4101). These inhibitors resemble the binding mode of Gleevec, but being small they do not reach the back pocket.

It is reasonable to suggest based on this description of the binding mode of the selective c-Met inhibitor bound to the non-phosphorylated form of c-Met, that the selective c-Met inhibitor binds a pre-existing pocket formed in the unphosphorylated c-Met, with the tricyclic moiety fitting perfectly between two phenylalanine residues F1089 from the P-loop and F1223 from the DFG motif. Both residues have their aromatic rings in van der Waals, hydrophobic contact with the selective c-Met inhibitor.

Example 1A

The Construction of the c-Met2 Inhibition Model

The three dimensional electronic representation of the ligand bound to c-Met was used. Twenty three residues of c-Met at distances up to 6 Å from every atom of the ligand were selected. The coordinates of these twenty three residues constitute the inhibition model of c-Met.

The amino acids of the inhibition model of c-Met derived from the structure of c-Met2 kinase domain are described herein and are defined by a set of structure coordinates set forth in Table 4.

TABLE 4

| (SEQ ID NO: 11) | | | | | | | | | |
|---|---|---|---|---|---|---|---|---|---|
| ATOM | 1 | N | ILE | 1084 | −19.676 | −14.451 | −19.716 | 15.47 | N |
| ATOM | 2 | CA | ILE | 1084 | −20.082 | −15.696 | −19.067 | 15.31 | C |
| ATOM | 3 | CB | ILE | 1084 | −21.542 | −15.681 | −18.586 | 14.71 | C |
| ATOM | 4 | CG1 | ILE | 1084 | −21.729 | −14.619 | −17.505 | 14.37 | C |
| ATOM | 5 | CD1 | ILE | 1084 | −23.127 | −14.461 | −17.033 | 6.51 | C |
| ATOM | 6 | CG2 | ILE | 1084 | −21.928 | −17.056 | −18.067 | 14.52 | C |
| ATOM | 7 | C | ILE | 1084 | −19.802 | −16.886 | −19.998 | 14.64 | C |
| ATOM | 8 | O | ILE | 1084 | −19.178 | −17.865 | −19.589 | 14.54 | O |
| ATOM | 9 | N | GLY | 1085 | −20.235 | −16.777 | −21.247 | 14.55 | N |
| ATOM | 10 | CA | GLY | 1085 | −19.946 | −17.782 | −22.243 | 13.94 | C |
| ATOM | 11 | C | GLY | 1085 | −20.087 | −17.158 | −23.592 | 14.69 | C |
| ATOM | 12 | O | GLY | 1085 | −20.694 | −16.104 | −23.725 | 13.22 | O |
| ATOM | 13 | N | PHE | 1089 | −24.836 | −18.883 | −30.097 | 15.3 | N |
| ATOM | 14 | CA | PHE | 1089 | −25.9 | −18.001 | −29.571 | 13.53 | C |
| ATOM | 15 | CB | PHE | 1089 | −26.393 | −18.453 | −28.156 | 12.25 | C |
| ATOM | 16 | CG | PHE | 1089 | −25.281 | −18.681 | −27.155 | 12.52 | C |
| ATOM | 17 | CD1 | PHE | 1089 | −24.789 | −19.972 | −26.93 | 10.55 | C |
| ATOM | 18 | CE1 | PHE | 1089 | −23.728 | −20.182 | −26.026 | 10.53 | C |
| ATOM | 19 | CZ | PHE | 1089 | −23.173 | −19.124 | −25.36 | 10.12 | C |
| ATOM | 20 | CE2 | PHE | 1089 | −23.625 | −17.83 | −25.583 | 9.89 | C |
| ATOM | 21 | CD2 | PHE | 1089 | −24.694 | −17.613 | −26.476 | 12.9 | C |
| ATOM | 22 | C | PHE | 1089 | −25.449 | −16.545 | −29.503 | 13.39 | C |
| ATOM | 23 | O | PHE | 1089 | −26.284 | −15.658 | −29.406 | 14.08 | O |
| ATOM | 24 | N | VAL | 1092 | −22.639 | −13.849 | −23.919 | 12.22 | N |
| ATOM | 25 | CA | VAL | 1092 | −23.38 | −13.53 | −22.701 | 10.83 | C |
| ATOM | 26 | CB | VAL | 1092 | −24.097 | −14.78 | −22.141 | 10.23 | C |
| ATOM | 27 | CG1 | VAL | 1092 | −24.877 | −14.441 | −20.91 | 8.74 | C |
| ATOM | 28 | CG2 | VAL | 1092 | −24.998 | −15.332 | −23.184 | 11.17 | C |
| ATOM | 29 | C | VAL | 1092 | −22.393 | −12.944 | −21.691 | 10.92 | C |
| ATOM | 30 | O | VAL | 1092 | −21.402 | −13.605 | −21.364 | 9.96 | O |
| ATOM | 31 | N | ALA | 1108 | −26.911 | −12.095 | −15.851 | 8.12 | N |
| ATOM | 32 | CA | ALA | 1108 | −26.39 | −12.461 | −17.121 | 8.23 | C |
| ATOM | 33 | CB | ALA | 1108 | −26.701 | −13.958 | −17.42 | 7.36 | C |
| ATOM | 34 | C | ALA | 1108 | −27.054 | −11.581 | −18.146 | 7.48 | C |
| ATOM | 35 | O | ALA | 1108 | −28.294 | −11.377 | −18.103 | 6.23 | O |
| ATOM | 36 | N | VAL | 1109 | −26.262 | −11.022 | −19.053 | 6.4 | N |
| ATOM | 37 | CA | VAL | 1109 | −26.871 | −10.086 | −19.974 | 7.09 | C |
| ATOM | 38 | CB | VAL | 1109 | −26.761 | −8.561 | −19.567 | 7.99 | C |
| ATOM | 39 | CG1 | VAL | 1109 | −25.877 | −8.259 | −18.375 | 9.38 | C |
| ATOM | 40 | CG2 | VAL | 1109 | −26.627 | −7.612 | −20.741 | 7.64 | C |
| ATOM | 41 | C | VAL | 1109 | −26.574 | −10.363 | −21.435 | 8.01 | C |
| ATOM | 42 | O | VAL | 1109 | −25.47 | −10.729 | −21.79 | 5.65 | O |
| ATOM | 43 | N | LYS | 1110 | −27.587 | −10.221 | −22.269 | 7.51 | N |
| ATOM | 44 | CA | LYS | 1110 | −27.256 | −10.294 | −23.664 | 9.65 | C |
| ATOM | 45 | CB | LYS | 1110 | −27.073 | −11.731 | −24.086 | 10.89 | C |
| ATOM | 46 | CG | LYS | 1110 | −28.259 | −12.478 | −24.304 | 12.06 | C |
| ATOM | 47 | CD | LYS | 1110 | −28.291 | −12.786 | −25.777 | 14.94 | C |
| ATOM | 48 | CE | LYS | 1110 | −26.923 | −13.196 | −26.354 | 15.05 | C |
| ATOM | 49 | NZ | LYS | 1110 | −27.04 | −13.161 | −27.915 | 11.9 | N |
| ATOM | 50 | C | LYS | 1110 | −28.105 | −9.473 | −24.577 | 9.23 | C |
| ATOM | 51 | O | LYS | 1110 | −29.287 | −9.193 | −24.318 | 8.86 | O |
| ATOM | 52 | N | LEU | 1140 | −37.463 | −20.519 | −16.111 | 8.72 | N |
| ATOM | 53 | CA | LEU | 1140 | −36.55 | −19.367 | −16.142 | 11.04 | C |
| ATOM | 54 | CB | LEU | 1140 | −35.314 | −19.688 | −17 | 10.97 | C |
| ATOM | 55 | CG | LEU | 1140 | −34.23 | −18.646 | −17.065 | 9.46 | C |
| ATOM | 56 | CD1 | LEU | 1140 | −33.609 | −18.426 | −15.69 | 8.34 | C |
| ATOM | 57 | CD2 | LEU | 1140 | −33.188 | −19.076 | −18.042 | 11.77 | C |
| ATOM | 58 | C | LEU | 1140 | −37.252 | −18.13 | −16.69 | 12.97 | C |
| ATOM | 59 | O | LEU | 1140 | −37.803 | −18.148 | −17.804 | 12.64 | O |
| ATOM | 60 | N | VAL | 1155 | −31.611 | −8.495 | −22.98 | 8.16 | N |
| ATOM | 61 | CA | VAL | 1155 | −32.323 | −9.277 | −21.923 | 8.76 | C |
| ATOM | 62 | CB | VAL | 1155 | −32.814 | −10.693 | −22.353 | 9.39 | C |
| ATOM | 63 | CG1 | VAL | 1155 | −34.033 | −10.582 | −23.316 | 10.94 | C |
| ATOM | 64 | CG2 | VAL | 1155 | −31.728 | −11.492 | −22.993 | 8.74 | C |
| ATOM | 65 | C | VAL | 1155 | −31.427 | −9.427 | −20.73 | 8.02 | C |
| ATOM | 66 | O | VAL | 1155 | −30.209 | −9.527 | −20.889 | 7.13 | O |
| ATOM | 67 | N | LEU | 1157 | −30.843 | −11.847 | −17.422 | 7.79 | N |
| ATOM | 68 | CA | LEU | 1157 | −31.27 | −13.118 | −16.786 | 7.81 | C |
| ATOM | 69 | CB | LEU | 1157 | −30.902 | −14.33 | −17.682 | 9.69 | C |
| ATOM | 70 | CG | LEU | 1157 | −32.066 | −14.227 | −18.65 | 11.62 | C |
| ATOM | 71 | CD1 | LEU | 1157 | −31.674 | −13.539 | −19.933 | 11.32 | C |
| ATOM | 72 | CD2 | LEU | 1157 | −32.851 | −15.474 | −18.797 | 10.57 | C |
| ATOM | 73 | C | LEU | 1157 | −30.661 | −13.291 | −15.419 | 8.75 | C |
| ATOM | 74 | O | LEU | 1157 | −29.588 | −12.733 | −15.162 | 7.63 | O |
| ATOM | 75 | N | PRO | 1158 | −31.285 | −14.129 | −14.552 | 9.58 | N |
| ATOM | 76 | CA | PRO | 1158 | −30.573 | −14.427 | −13.309 | 10.72 | C |
| ATOM | 77 | CB | PRO | 1158 | −31.566 | −15.292 | −12.497 | 10.18 | C |
| ATOM | 78 | CG | PRO | 1158 | −32.788 | −15.258 | −13.187 | 11.04 | C |

TABLE 4-continued (SEQ ID NO: 11)

| ATOM | 79 | CD | PRO | 1158 | −32.545 | −14.873 | −14.637 | 9.45 | C |
|---|---|---|---|---|---|---|---|---|---|
| ATOM | 80 | C | PRO | 1158 | −29.342 | −15.228 | −13.655 | 11.46 | C |
| ATOM | 81 | O | PRO | 1158 | −29.302 | −15.934 | −14.683 | 11.52 | O |
| ATOM | 82 | N | TYR | 1159 | −28.326 | −15.091 | −12.828 | 12.18 | N |
| ATOM | 83 | CA | TYR | 1159 | −27.094 | −15.799 | −13.05 | 13.78 | C |
| ATOM | 84 | CB | TYR | 1159 | −25.976 | −15.173 | −12.234 | 13.95 | C |
| ATOM | 85 | CG | TYR | 1159 | −24.668 | −15.894 | −12.374 | 15.44 | C |
| ATOM | 86 | CD1 | TYR | 1159 | −23.973 | −15.906 | −13.604 | 15.19 | C |
| ATOM | 87 | CE1 | TYR | 1159 | −22.762 | −16.583 | −13.73 | 15.55 | C |
| ATOM | 88 | CZ | TYR | 1159 | −22.229 | −17.235 | −12.622 | 15.73 | C |
| ATOM | 89 | OH | TYR | 1159 | −21.025 | −17.924 | −12.718 | 18.54 | O |
| ATOM | 90 | CE2 | TYR | 1159 | −22.889 | −17.225 | −11.399 | 16.11 | C |
| ATOM | 91 | CD2 | TYR | 1159 | −24.099 | −16.548 | −11.276 | 14.98 | C |
| ATOM | 92 | C | TYR | 1159 | −27.328 | −17.25 | −12.659 | 14.12 | C |
| ATOM | 93 | O | TYR | 1159 | −27.868 | −17.544 | −11.573 | 13.85 | O |
| ATOM | 94 | N | MET | 1160 | −26.977 | −18.141 | −13.575 | 13.76 | N |
| ATOM | 95 | CA | MET | 1160 | −27.199 | −19.572 | −13.403 | 14.48 | C |
| ATOM | 96 | CB | MET | 1160 | −28.079 | −20.159 | −14.542 | 14.71 | C |
| ATOM | 97 | CG | MET | 1160 | −29.48 | −19.592 | −14.597 | 15.91 | C |
| ATOM | 98 | SD | MET | 1160 | −30.533 | −20.154 | −13.195 | 20.68 | S |
| ATOM | 99 | CE | MET | 1160 | −31.401 | −18.698 | −12.74 | 20.48 | C |
| ATOM | 100 | C | MET | 1160 | −25.816 | −20.14 | −13.382 | 14.64 | C |
| ATOM | 101 | O | MET | 1160 | −25.182 | −20.283 | −14.417 | 15.02 | O |
| ATOM | 102 | N | LYS | 1161 | −25.314 | −20.346 | −12.167 | 15.21 | N |
| ATOM | 103 | CA | LYS | 1161 | −23.952 | −20.771 | −11.91 | 14.1 | C |
| ATOM | 104 | CB | LYS | 1161 | −23.758 | −21.08 | −10.427 | 15.12 | C |
| ATOM | 105 | CG | LYS | 1161 | −22.333 | −21.497 | −10.095 | 17.53 | C |
| ATOM | 106 | CD | LYS | 1161 | −22.188 | −21.839 | −8.613 | 24.97 | C |
| ATOM | 107 | CE | LYS | 1161 | −20.714 | −21.982 | −8.207 | 26.67 | C |
| ATOM | 108 | NZ | LYS | 1161 | −20.549 | −21.583 | −6.789 | 32.02 | N |
| ATOM | 109 | C | LYS | 1161 | −23.518 | −21.98 | −12.746 | 13.45 | C |
| ATOM | 110 | O | LYS | 1161 | −22.404 | −22.006 | −13.258 | 12.16 | O |
| ATOM | 111 | N | HIS | 1162 | −24.38 | −22.987 | −12.865 | 12.66 | N |
| ATOM | 112 | CA | HIS | 1162 | −23.979 | −24.201 | −13.569 | 12.84 | C |
| ATOM | 113 | CB | HIS | 1162 | −24.427 | −25.452 | −12.815 | 11.85 | C |
| ATOM | 114 | CG | HIS | 1162 | −23.908 | −25.504 | −11.426 | 13.4 | C |
| ATOM | 115 | ND1 | HIS | 1162 | −22.554 | −25.561 | −11.145 | 15.28 | N |
| ATOM | 116 | CE1 | HIS | 1162 | −22.385 | −25.595 | −9.838 | 16.31 | C |
| ATOM | 117 | NE2 | HIS | 1162 | −23.575 | −25.537 | −9.261 | 17.98 | N |
| ATOM | 118 | CD2 | HIS | 1162 | −24.542 | −25.471 | −10.232 | 14.71 | C |
| ATOM | 119 | C | HIS | 1162 | −24.36 | −24.282 | −15.038 | 13.45 | C |
| ATOM | 120 | O | HIS | 1162 | −24.234 | −25.367 | −15.634 | 14.09 | O |
| ATOM | 121 | N | GLY | 1163 | −24.807 | −23.162 | −15.62 | 12.39 | N |
| ATOM | 122 | CA | GLY | 1163 | −25.108 | −23.113 | −17.056 | 11.81 | C |
| ATOM | 123 | C | GLY | 1163 | −26.195 | −24.111 | −17.397 | 11.37 | C |
| ATOM | 124 | O | GLY | 1163 | −27.052 | −24.405 | −16.541 | 12.27 | O |
| ATOM | 125 | N | ASP | 1164 | −26.16 | −24.657 | −18.612 | 10.58 | N |
| ATOM | 126 | CA | ASP | 1164 | −27.202 | −25.57 | −19.037 | 11.05 | C |
| ATOM | 127 | CB | ASP | 1164 | −27.395 | −25.576 | −20.566 | 10.73 | C |
| ATOM | 128 | CG | ASP | 1164 | −26.214 | −26.22 | −21.317 | 14.82 | C |
| ATOM | 129 | OD1 | ASP | 1164 | −26.203 | −27.447 | −21.509 | 16.5 | O |
| ATOM | 130 | OD2 | ASP | 1164 | −25.324 | −25.485 | −21.76 | 16.71 | O |
| ATOM | 131 | C | ASP | 1164 | −26.958 | −26.97 | −18.481 | 10.14 | C |
| ATOM | 132 | O | ASP | 1164 | −25.836 | −27.355 | −18.139 | 9.32 | O |
| ATOM | 133 | N | ASP | 1211 | −31.568 | −24.508 | −17.398 | 11.25 | N |
| ATOM | 134 | CA | ASP | 1211 | −30.407 | −23.962 | −16.703 | 12.07 | C |
| ATOM | 135 | CB | ASP | 1211 | −30.29 | −22.425 | −16.878 | 13.35 | C |
| ATOM | 136 | CG | ASP | 1211 | −29.946 | −21.986 | −18.38 | 15.72 | C |
| ATOM | 137 | OD1 | ASP | 1211 | −28.869 | −22.268 | −19.063 | 3.34 | O |
| ATOM | 138 | OD2 | ASP | 1211 | −30.838 | −21.298 | −18.869 | 22.8 | O |
| ATOM | 139 | C | ASP | 1211 | −30.314 | −24.43 | −15.238 | 11.76 | C |
| ATOM | 140 | O | ASP | 1211 | −31.303 | −24.781 | −14.626 | 11.98 | O |
| ATOM | 141 | N | ALA | 1221 | −35.874 | −22.995 | −19.798 | 9.64 | N |
| ATOM | 142 | CA | ALA | 1221 | −35.638 | −21.759 | −20.538 | 11.43 | C |
| ATOM | 143 | CB | ALA | 1221 | −34.165 | −21.475 | −20.605 | 12.72 | C |
| ATOM | 144 | C | ALA | 1221 | −36.215 | −21.756 | −21.953 | 12.59 | C |
| ATOM | 145 | O | ALA | 1221 | −36.317 | −22.801 | −22.617 | 11.05 | O |
| ATOM | 146 | O | ASP | 1222 | −36.499 | −18.098 | −24.227 | 17.5 | O |
| ATOM | 147 | N | ASP | 1222 | −36.5 | −20.634 | −22.356 | 20 | N |
| ATOM | 148 | CA | ASP | 1222 | −36.941 | −20.406 | −23.727 | 20 | C |
| ATOM | 149 | C | ASP | 1222 | −36.151 | −19.273 | −24.377 | 20 | C |
| ATOM | 150 | CB | ASP | 1222 | −38.437 | −20.091 | −23.763 | 20 | C |
| ATOM | 151 | CG | ASP | 1222 | −38.824 | −18.99 | −22.796 | 20 | C |
| ATOM | 152 | OD1 | ASP | 1222 | −37.994 | −18.638 | −21.932 | 20 | O |
| ATOM | 153 | OD2 | ASP | 1222 | −39.935 | −18.418 | −22.824 | 20 | O |
| ATOM | 154 | N | PHE | 1223 | −35.113 | −19.54 | −24.88 | 16.19 | N |
| ATOM | 155 | CA | PHE | 1223 | −34.306 | −18.466 | −25.34 | 17.32 | C |
| ATOM | 156 | CB | PHE | 1223 | −32.818 | −18.714 | −25.181 | 16 | C |

TABLE 4-continued (SEQ ID NO: 11)

| ATOM | 157 | CG  | PHE | 1223 | −32.355 | −18.541 | −23.754 | 11.65 | C |
| ---- | --- | --- | --- | ---- | ------- | ------- | ------- | ----- | - |
| ATOM | 158 | CD1 | PHE | 1223 | −32.357 | −17.286 | −23.16  | 11.27 | C |
| ATOM | 159 | CE1 | PHE | 1223 | −31.94  | −17.128 | −21.826 | 15.53 | C |
| ATOM | 160 | CZ  | PHE | 1223 | −31.549 | −18.252 | −21.091 | 14.31 | C |
| ATOM | 161 | CE2 | PHE | 1223 | −31.558 | −19.492 | −21.689 | 14.38 | C |
| ATOM | 162 | CD2 | PHE | 1223 | −31.98  | −19.622 | −23.01  | 14.35 | C |
| ATOM | 163 | C   | PHE | 1223 | −34.816 | −18.009 | −26.7   | 20.29 | C |
| ATOM | 164 | O   | PHE | 1223 | −35.386 | −16.886 | −26.787 | 22.15 | O |
| ATOM | 165 | N   | ALA | 1226 | −32.985 | −15.014 | −28.359 | 16.83 | N |
| ATOM | 166 | CA  | ALA | 1226 | −31.681 | −14.627 | −27.816 | 15.78 | C |
| ATOM | 167 | CB  | ALA | 1226 | −31.656 | −14.803 | −26.309 | 15.05 | C |
| ATOM | 168 | C   | ALA | 1226 | −30.512 | −15.38  | −28.432 | 15.33 | C |
| ATOM | 169 | O   | ALA | 1226 | −29.385 | −14.922 | −28.31  | 14.85 | O |
| ATOM | 170 | N   | ARG | 1227 | −30.768 | −16.534 | −29.062 | 14.69 | N |
| ATOM | 171 | CA  | ARG | 1227 | −29.719 | −17.245 | −29.776 | 13.62 | C |
| ATOM | 172 | CB  | ARG | 1227 | −30.066 | −18.729 | −29.985 | 14.18 | C |
| ATOM | 173 | CG  | ARG | 1227 | −30.303 | −19.5   | −28.711 | 12.15 | C |
| ATOM | 174 | CD  | ARG | 1227 | −30.765 | −20.926 | −28.952 | 14.86 | C |
| ATOM | 175 | NE  | ARG | 1227 | −30.801 | −21.623 | −27.669 | 17.43 | N |
| ATOM | 176 | CZ  | ARG | 1227 | −29.719 | −22.054 | −27.024 | 18.53 | C |
| ATOM | 177 | NH1 | ARG | 1227 | −28.513 | −21.933 | −27.574 | 20.01 | N |
| ATOM | 178 | NH2 | ARG | 1227 | −29.843 | −22.65  | −25.851 | 19.76 | N |
| ATOM | 179 | C   | ARG | 1227 | −29.535 | −16.57  | −31.118 | 13.93 | C |
| ATOM | 180 | O   | ARG | 1227 | −30.445 | −16.603 | −31.947 | 14.89 | O |

Example 2

The Construction of the c-Abl Inhibition Model

A 3-dimensional model for the inhibition of c-Abl was created using the process described below.

The sequence alignment of c-Abl kinase and the amino acid sequence of c-Met was performed using MOE alignment tools. Care was taken to make sure that known kinase motifs: DFG motif, the hinge residues and the salt bridge residues were superposed.

The identification of conserved amino acid residues between c-Met and c-Abl, generation of atomic coordinates of all conserved amino acids in c-Abl from the electronic representation of c-Met residues; rotamer search of the structurally variable and replacement of non-conserved residues of c-Met with residues from c-Abl sequence; building of side chain conformations; and final refinement and evaluation of the c-Abl structure were carried out in an automated fashion using MOE homology tools.

Example 3

The Similarity Assessment of c-Abl Inhibition Model

From Table 2, it can be determined that the similarity assessment value is less than 50% for c-Abl. Three residues show negative weights: T333 (L1157), N340 (D1164), and S403 (A1226). The inhibition model will have a significant change in polarity factor.

L1157 is located deep into the c-Met inhibition model. This residue is one of several which confers c-Met its mainly hydrophobic nature. In this position, c-Abl model shows a T333, a highly polar residue. Therefore, the chemical environment of an inhibitor has changed dramatically. The selective c-Met inhibitor does not have any atomic group to make favorable electrostatic interactions with T333. N340 and S403 also lack favorable electrostatic interactions with the selective c-Met inhibitor. Thus, the selective c-Met inhibitor is not predicted to inhibit c-Abl.

The amino acids of the inhibition model of c-Abl derived from the c-Met inhibition model are described herein and are defined by a set of structure coordinates set forth in Table 5.

TABLE 5

(SEQ ID NO: 8)

| ATOM | N   | LEU | 266 | −19.916 | −14.441 | −18.273 | N |
| ---- | --- | --- | --- | ------- | ------- | ------- | - |
| ATOM | CA  | LEU | 266 | −20.814 | −15.367 | −18.929 | C |
| ATOM | CB  | LEU | 266 | −22.191 | −14.827 | −19.221 | C |
| ATOM | C   | LEU | 266 | −20.09  | −16.157 | −20.018 | C |
| ATOM | O   | LEU | 266 | −19.184 | −16.942 | −19.745 | O |
| ATOM | CG  | LEU | 266 | −23.209 | −15.308 | −18.209 | C |
| ATOM | CD1 | LEU | 266 | −22.892 | −14.842 | −16.81  | C |
| ATOM | CD2 | LEU | 266 | −24.581 | −14.82  | −18.593 | C |
| ATOM | N   | GLY | 267 | −20.417 | −15.864 | −21.327 | N |
| ATOM | CA  | GLY | 267 | −19.615 | −16.503 | −22.345 | C |
| ATOM | C   | GLY | 267 | −20.218 | −16.526 | −23.733 | C |
| ATOM | O   | GLY | 267 | −21.424 | −16.638 | −23.949 | O |
| ATOM | N   | TYR | 271 | −24.397 | −19.744 | −29.694 | N |
| ATOM | CA  | TYR | 271 | −25.559 | −18.884 | −29.522 | C |
| ATOM | CB  | TYR | 271 | −26.283 | −19.182 | −28.204 | C |
| ATOM | C   | TYR | 271 | −25.27  | −17.375 | −29.625 | C |
| ATOM | O   | TYR | 271 | −26.133 | −16.521 | −29.392 | O |
| ATOM | CG  | TYR | 271 | −25.398 | −19.096 | −26.995 | C |
| ATOM | CD1 | TYR | 271 | −24.792 | −17.887 | −26.648 | C |
| ATOM | CD2 | TYR | 271 | −25.102 | −20.248 | −26.264 | C |
| ATOM | CE1 | TYR | 271 | −23.869 | −17.829 | −25.616 | C |
| ATOM | CE2 | TYR | 271 | −24.179 | −20.197 | −25.219 | C |
| ATOM | CZ  | TYR | 271 | −23.557 | −18.989 | −24.92  | C |
| ATOM | OH  | TYR | 271 | −22.608 | −18.958 | −23.929 | O |
| ATOM | N   | VAL | 274 | −23.294 | −14.153 | −24.61  | N |
| ATOM | CA  | VAL | 274 | −24.16  | −13.806 | −23.491 | C |
| ATOM | CB  | VAL | 274 | −25.02  | −14.966 | −23.017 | C |
| ATOM | C   | VAL | 274 | −23.242 | −13.359 | −22.365 | C |
| ATOM | O   | VAL | 274 | −22.23  | −13.983 | −22.045 | O |
| ATOM | CG1 | VAL | 274 | −26.029 | −14.498 | −21.991 | C |
| ATOM | CG2 | VAL | 274 | −25.781 | −15.575 | −24.163 | C |
| ATOM | N   | ALA | 287 | −27.677 | −12.533 | −15.683 | N |
| ATOM | CA  | ALA | 287 | −27.163 | −12.605 | −17.031 | C |
| ATOM | CB  | ALA | 287 | −27.621 | −13.873 | −17.711 | C |
| ATOM | C   | ALA | 287 | −27.733 | −11.415 | −17.791 | C |
| ATOM | O   | ALA | 287 | −28.826 | −10.907 | −17.535 | O |
| ATOM | N   | VAL | 288 | −26.977 | −11.03  | −18.871 | N |
| ATOM | CA  | VAL | 288 | −27.516 | −10.069 | −19.803 | C |
| ATOM | CB  | VAL | 288 | −26.987 | −8.657  | −19.576 | C |
| ATOM | C   | VAL | 288 | −27.201 | −10.557 | −21.208 | C |
| ATOM | O   | VAL | 288 | −26.124 | −11.023 | −21.58  | O |
| ATOM | CG1 | VAL | 288 | −27.658 | −7.659  | −20.495 | C |

TABLE 5-continued (SEQ ID NO: 8)

| ATOM | | | | | | | |
|------|------|-----|-----|---------|---------|---------|-----|
| ATOM | CG2 | VAL | 288 | −27.21 | −8.185 | −18.157 | C |
| ATOM | N | LYS | 289 | −28.252 | −10.312 | −22.064 | N |
| ATOM | CA | LYS | 289 | −28.041 | −10.491 | −23.48 | C |
| ATOM | CB | LYS | 289 | −28.329 | −11.881 | −24.014 | C |
| ATOM | C | LYS | 289 | −28.817 | −9.471 | −24.288 | C |
| ATOM | O | LYS | 289 | −29.858 | −8.937 | −23.914 | O |
| ATOM | CG | LYS | 289 | −27.284 | −12.24 | −25.052 | C |
| ATOM | CD | LYS | 289 | −27.779 | −13.297 | −26.008 | C |
| ATOM | CE | LYS | 289 | −26.677 | −13.676 | −26.976 | C |
| ATOM | NZ | LYS | 289 | −27.262 | −14.535 | −28.044 | N1+ |
| ATOM | N | VAL | 317 | −36.3 | −20.382 | −15.116 | N |
| ATOM | CA | VAL | 317 | −35.436 | −19.216 | −15.287 | C |
| ATOM | CB | VAL | 317 | −34.28 | −19.474 | −16.244 | C |
| ATOM | C | VAL | 317 | −36.337 | −18.127 | −15.852 | C |
| ATOM | O | VAL | 317 | −37.128 | −18.313 | −16.773 | O |
| ATOM | CG1 | VAL | 317 | −33.439 | −20.65 | −15.809 | C |
| ATOM | CG2 | VAL | 317 | −33.373 | −18.267 | −16.334 | C |
| ATOM | N | ILE | 331 | −32.2 | −7.875 | −22.796 | N |
| ATOM | CA | ILE | 331 | −32.865 | −8.817 | −21.914 | C |
| ATOM | CB | ILE | 331 | −33.299 | −10.061 | −22.683 | C |
| ATOM | C | ILE | 331 | −31.906 | −9.163 | −20.783 | C |
| ATOM | O | ILE | 331 | −30.744 | −9.528 | −20.955 | O |
| ATOM | CG1 | ILE | 331 | −34.398 | −9.745 | −23.684 | C |
| ATOM | CG2 | ILE | 331 | −33.763 | −11.172 | −21.764 | C |
| ATOM | CD1 | ILE | 331 | −35.654 | −9.209 | −23.03 | C |
| ATOM | N | THR | 333 | −31.711 | −11.403 | −17.09 | N |
| ATOM | CA | THR | 333 | −32.291 | −12.558 | −16.398 | C |
| ATOM | CB | THR | 333 | −32.376 | −13.8 | −17.293 | C |
| ATOM | C | THR | 333 | −31.371 | −12.885 | −15.243 | C |
| ATOM | O | THR | 333 | −30.16 | −12.687 | −15.306 | O |
| ATOM | OG1 | THR | 333 | −31.099 | −14.206 | −17.797 | O |
| ATOM | CG2 | THR | 333 | −33.289 | −13.577 | −18.477 | C |
| ATOM | N | GLU | 334 | −31.929 | −13.562 | −14.194 | N |
| ATOM | CA | GLU | 334 | −31.049 | −14.086 | −13.162 | C |
| ATOM | CB | GLU | 334 | −31.793 | −14.548 | −11.918 | C |
| ATOM | C | GLU | 334 | −30.016 | −15.113 | −13.667 | C |
| ATOM | O | GLU | 334 | −30.153 | −15.806 | −14.674 | O |
| ATOM | CG | GLU | 334 | −32.718 | −15.726 | −12.155 | C |
| ATOM | CD | GLU | 334 | −33.907 | −15.472 | −13.064 | C |
| ATOM | OE1 | GLU | 334 | −34.471 | −16.519 | −13.499 | O1− |
| ATOM | OE2 | GLU | 334 | −34.185 | −14.264 | −13.348 | O |
| ATOM | N | PHE | 335 | −28.897 | −15.174 | −12.855 | N |
| ATOM | CA | PHE | 335 | −27.724 | −15.967 | −13.224 | C |
| ATOM | CB | PHE | 335 | −26.472 | −15.304 | −12.651 | C |
| ATOM | C | PHE | 335 | −27.822 | −17.389 | −12.673 | C |
| ATOM | O | PHE | 335 | −27.992 | −17.648 | −11.486 | O |
| ATOM | CG | PHE | 335 | −25.147 | −15.936 | −12.949 | C |
| ATOM | CD1 | PHE | 335 | −24.88 | −16.583 | −14.156 | C |
| ATOM | CD2 | PHE | 335 | −24.145 | −15.864 | −11.983 | C |
| ATOM | CE1 | PHE | 335 | −23.637 | −17.166 | −14.389 | C |
| ATOM | CE2 | PHE | 335 | −22.898 | −16.44 | −12.214 | C |
| ATOM | CZ | PHE | 335 | −22.645 | −17.095 | −13.416 | C |
| ATOM | N | MET | 336 | −27.676 | −18.363 | −13.637 | N |
| ATOM | CA | MET | 336 | −27.674 | −19.773 | −13.292 | C |
| ATOM | CB | MET | 336 | −28.489 | −20.582 | −14.273 | C |
| ATOM | C | MET | 336 | −26.24 | −20.281 | −13.223 | C |
| ATOM | O | MET | 336 | −25.533 | −20.558 | −14.187 | O |
| ATOM | CG | MET | 336 | −29.927 | −20.877 | −13.875 | C |
| ATOM | SD | MET | 336 | −30.643 | −20.004 | −12.452 | S |
| ATOM | CE | MET | 336 | −31.071 | −18.464 | −13.296 | C |
| ATOM | N | THR | 337 | −25.767 | −20.22 | −11.937 | N |
| ATOM | CA | THR | 337 | −24.346 | −20.219 | −11.611 | C |
| ATOM | CB | THR | 337 | −24.222 | −20.086 | −10.094 | C |
| ATOM | C | THR | 337 | −23.595 | −21.487 | −12.019 | C |
| ATOM | O | THR | 337 | −22.386 | −21.482 | −12.227 | O |
| ATOM | OG1 | THR | 337 | −25.449 | −19.587 | −9.527 | O |
| ATOM | CG2 | THR | 337 | −23.079 | −19.169 | −9.723 | C |
| ATOM | N | TYR | 338 | −24.343 | −22.643 | −11.985 | N |
| ATOM | CA | TYR | 338 | −23.729 | −23.934 | −12.217 | C |
| ATOM | CB | TYR | 338 | −24.416 | −24.993 | −11.379 | C |
| ATOM | C | TYR | 338 | −23.762 | −24.378 | −13.682 | C |
| ATOM | O | TYR | 338 | −23.383 | −25.493 | −14.026 | O |
| ATOM | CG | TYR | 338 | −23.568 | −25.565 | −10.292 | C |
| ATOM | CD1 | TYR | 338 | −22.236 | −25.927 | −10.513 | C |
| ATOM | CD2 | TYR | 338 | −24.147 | −25.802 | −9.046 | C |
| ATOM | CE1 | TYR | 338 | −21.497 | −26.545 | −9.507 | C |
| ATOM | CE2 | TYR | 338 | −23.411 | −26.411 | −8.034 | C |
| ATOM | CZ | TYR | 338 | −22.098 | −26.795 | −8.277 | C |
| ATOM | OH | TYR | 338 | −21.418 | −27.465 | −7.287 | O |
| ATOM | N | GLY | 339 | −24.173 | −23.424 | −14.591 | N |
| ATOM | CA | GLY | 339 | −24.111 | −23.721 | −16.01 | C |
| ATOM | C | GLY | 339 | −25.334 | −24.505 | −16.464 | C |
| ATOM | O | GLY | 339 | −26.443 | −24.373 | −15.942 | O |
| ATOM | N | ASN | 340 | −25.101 | −25.257 | −17.604 | N |
| ATOM | CA | ASN | 340 | −26.191 | −26.036 | −18.17 | C |
| ATOM | CB | ASN | 340 | −26.524 | −25.799 | −19.634 | C |
| ATOM | C | ASN | 340 | −26.198 | −27.515 | −17.8 | C |
| ATOM | O | ASN | 340 | −25.188 | −28.131 | −17.466 | O |
| ATOM | CG | ASN | 340 | −25.47 | −26.41 | −20.502 | C |
| ATOM | OD1 | ASN | 340 | −25.344 | −27.622 | −20.648 | O |
| ATOM | ND2 | ASN | 340 | −24.639 | −25.481 | −21.052 | N |
| ATOM | N | LEU | 388 | −30.765 | −24.965 | −17.173 | N |
| ATOM | CA | LEU | 388 | −29.637 | −24.46 | −16.404 | C |
| ATOM | CB | LEU | 388 | −29.54 | −22.942 | −16.453 | C |
| ATOM | C | LEU | 388 | −29.728 | −24.852 | −14.933 | C |
| ATOM | O | LEU | 388 | −30.785 | −25.113 | −14.356 | O |
| ATOM | CG | LEU | 388 | −29.205 | −22.298 | −17.782 | C |
| ATOM | CD1 | LEU | 388 | −28.098 | −23.005 | −18.523 | C |
| ATOM | CD2 | LEU | 388 | −30.424 | −22.172 | −18.658 | C |
| ATOM | N | ALA | 398 | −35.889 | −22.88 | −19.129 | N |
| ATOM | CA | ALA | 398 | −36.044 | −21.552 | −19.7 | C |
| ATOM | CB | ALA | 398 | −34.943 | −20.618 | −19.251 | C |
| ATOM | C | ALA | 398 | −36.046 | −21.615 | −21.211 | C |
| ATOM | O | ALA | 398 | −35.39 | −22.427 | −21.854 | O |
| ATOM | N | ASP | 399 | −36.893 | −20.694 | −21.784 | N |
| ATOM | CA | ASP | 399 | −36.858 | −20.444 | −23.21 | C |
| ATOM | CB | ASP | 399 | −38.239 | −20.251 | −23.829 | C |
| ATOM | C | ASP | 399 | −35.954 | −19.212 | −23.354 | C |
| ATOM | O | ASP | 399 | −35.733 | −18.392 | −22.468 | O |
| ATOM | CG | ASP | 399 | −38.247 | −20.184 | −25.363 | C |
| ATOM | OD1 | ASP | 399 | −37.116 | −20.365 | −25.93 | O |
| ATOM | OD2 | ASP | 399 | −39.369 | −19.86 | −25.882 | O1− |
| ATOM | N | PHE | 400 | −35.483 | −19.083 | −24.627 | N |
| ATOM | CA | PHE | 400 | −34.56 | −18.038 | −24.992 | C |
| ATOM | CB | PHE | 400 | −33.141 | −18.571 | −25.139 | C |
| ATOM | C | PHE | 400 | −34.97 | −17.332 | −26.27 | C |
| ATOM | O | PHE | 400 | −34.492 | −16.233 | −26.549 | O |
| ATOM | CG | PHE | 400 | −32.584 | −19.079 | −23.847 | C |
| ATOM | CD1 | PHE | 400 | −32.179 | −20.407 | −23.749 | C |
| ATOM | CE1 | PHE | 400 | −31.711 | −20.913 | −22.54 | C |
| ATOM | CZ | PHE | 400 | −31.651 | −20.091 | −21.42 | C |
| ATOM | CE2 | PHE | 400 | −32.052 | −18.762 | −21.512 | C |
| ATOM | CD2 | PHE | 400 | −32.512 | −18.255 | −22.723 | C |
| ATOM | N | GLY | 401 | −35.767 | −18.029 | −27.165 | N |
| ATOM | CA | GLY | 401 | −36.219 | −17.353 | −28.371 | C |
| ATOM | C | GLY | 401 | −35.078 | −16.919 | −29.288 | C |
| ATOM | O | GLY | 401 | −34.093 | −17.609 | −29.541 | O |
| ATOM | N | SER | 403 | −32.943 | −14.891 | −28.539 | N |
| ATOM | CA | SER | 403 | −31.691 | −14.692 | −27.847 | C |
| ATOM | CB | SER | 403 | −31.925 | −14.71 | −26.353 | C |
| ATOM | C | SER | 403 | −30.655 | −15.749 | −28.247 | C |
| ATOM | O | SER | 403 | −29.448 | −15.589 | −28.049 | O |
| ATOM | OG | SER | 403 | −31.052 | −13.781 | −25.724 | O |
| ATOM | N | ARG | 404 | −31.161 | −16.939 | −28.747 | N |
| ATOM | CA | ARG | 404 | −30.26 | −17.923 | −29.325 | C |
| ATOM | C | ARG | 404 | −30.241 | −17.654 | −30.824 | C |
| ATOM | O | ARG | 404 | −31.151 | −17.963 | −31.589 | O |
| ATOM | CB | ARG | 404 | −30.647 | −19.349 | −28.982 | C |
| ATOM | CG | ARG | 404 | −30.039 | −19.673 | −27.637 | C |
| ATOM | CD | ARG | 404 | −30.267 | −21.085 | −27.152 | C |
| ATOM | NE | ARG | 404 | −29.692 | −21.2 | −25.81 | N1+ |
| ATOM | CZ | ARG | 404 | −28.984 | −22.31 | −25.348 | C |
| ATOM | NH1 | ARG | 404 | −28.74 | −23.394 | −26.179 | N |
| ATOM | NH2 | ARG | 404 | −28.465 | −22.29 | −24.064 | N |

Example 4

The Use of c-Abl Inhibition Model in the Fitting and Optimization of a Small Molecular Template N-(4-methyl-3-(4-(pyridin-3-yl)pyrimidin-2-ylamino) phenyl)nicotinamide, which is known as a c-Abl inhibitor (Schindler et al, 2000) was placed inside the c-Abl inhibition model.

Docking and optimization against the c-Abl inhibition model was performed. The docking procedure was carried out using ICM software. A conformation in which the pyridine ring and the hinge residues were in close proximity was selected. Further optimization was carried out using MOE energy minimization tools.

Hydrogen bonds between the pyridine and the critical amino group of the hinge from M336 and the compound's amino group and T333 were identified. The presence of these hydrogen bonds is in agreement with experimental X-ray crystallographic data for the complex c-Abl kinase/Gleevec.

The overall protein-ligand interaction energy was negative (−68 kcal/mol), as it is calculated using MOE energy calculation tools, indicating a high probability of interaction.

(−)-trans-3-(5,6-dihydro-4H-pyrrolo[3,2,1-ij]quinolin-1-yl)-4(1H-indol-3-yl)pyrrolidine-2,5-dione, the selective c-Met inhibitor, was also docked in the c-Abl inhibition model where the pyrrolidine carbonyl ring makes a hydrogen bonds with the amino group of M336.

Further energy optimization using MOE tools was carried out. Two hydrogen bonds where observed between the pyrrolidine ring and hinge residues M336 and E334. Although the overall interaction energy is negative (−50 kcal/mol), a lack of feature complementarity between the selective c-Met inhibitor and c-Abl inhibitor model is clearly observed.

The hydrophobic tricyclic ring is placed in a polar region of the c-Abl inhibition model. Additionally no interactions between the selective c-Met inhibitor and a critical residue in c-Abl T333 are observed. N340 and S403 will also lack favorable electrostatic interactions with the selective c-Met inhibitor. Taken together, it is expected that the selective c-Met inhibitor does not bind to the inactive form of c-Abl kinase. This conclusion is consistent with the observation that the selective c-Met inhibitor does not inhibit the activity of c-Abl effectively, while it inhibits the activity of c-Met effectively (WO 2006/086484 A1).

Example 5

The Construction of FGFR-2 Inhibition Model

A 3-dimensional inhibition model of FGFR-2 was created using the process.

The sequence alignment of FGFR-2 kinase and the amino acid sequence of c-Met were performed using MOE alignment tools. Known kinase motifs: the P-loop F492, the DFG motif (644-646), the hinge residue A567, the salt bridge K517-E534, and tyrosine residues Y656 and Y657 in the A-loop, residues which are phosphorylated upon activation, were superposed.

The identification of conserved amino acid residues between c-Met and FGFR-2; generation of atomic coordinates of all conserved amino acids in FGFR-2 from the electronic representation of c-Met residues; rotamer search of the structurally variable and replacement of non-conserved residues of c-Met with residues from FGFR-2 sequence; building of side chain conformations; and final refinement and evaluation of the FGFR-2 structure was carried out in an automated fashion using MOE homology tools.

Example 6

The Similarity Assessment of FGFR2 Inhibition Model

The FGFR-2 model is 78% similar to c-Met1 (Table 6). One residue shows negative weights: E565 (P1158). The inhibition model has no significant changes in polarity factor. The only differences are in size: I548 (L1140), gate keeper V564 (L1157), hinge residue A567 (M1160), and L633 (M1211).

Although, the FGFR-2 binding pocket is 78% similar, the presence of a smaller gate keeper residue V564, hinge residue (A567) and L633, results in a larger binding site.

TABLE 6

| (SEQ ID NOs. 11 and 13, respectively) | | | |
|---|---|---|---|
| PROTEIN | CMET (SEQ ID NO: 11) | weight | FGFR-2 (SEQ ID NO: 13) | weight |
| | I_1084 | 2 | L_487 | 1 |
| | G_1085 | 2 | G_488 | 2 |
| | F_1089 | 2 | F_492 | 2 |
| | V_1092 | 2 | V_495 | 2 |
| | A_1108 | 1 | A_515 | 1 |

The amino acids of the inhibition model of FGFR-2 derived from the c-Met inhibition model are described herein and are defined by a set of structure coordinates set forth in Table 7.

TABLE 7

| (SEQ ID NO. 14) | | | | | | | | |
|---|---|---|---|---|---|---|---|---|
| ATOM | 1 | N | LEU | 487 | −15.283 | −12.748 | −21.3 | N |
| ATOM | 2 | CA | LEU | 487 | −15.06 | −13.48 | −22.53 | C |
| ATOM | 3 | CB | LEU | 487 | −13.576 | −13.545 | −22.839 | C |
| ATOM | 4 | C | LEU | 487 | −15.629 | −14.889 | −22.364 | C |
| ATOM | 5 | O | LEU | 487 | −15.735 | −15.456 | −21.281 | O |
| ATOM | 6 | CG | LEU | 487 | −13.279 | −13.768 | −24.307 | C |
| ATOM | 7 | CD1 | LEU | 487 | −13.885 | −12.686 | −25.169 | C |
| ATOM | 8 | CD2 | LEU | 487 | −11.787 | −13.812 | −24.52 | C |
| ATOM | 9 | N | GLY | 488 | −15.929 | −15.472 | −23.57 | N |
| ATOM | 10 | CA | GLY | 488 | −16.524 | −16.79 | −23.653 | C |
| ATOM | 11 | C | GLY | 488 | −16.466 | −17.181 | −25.116 | C |
| ATOM | 12 | O | GLY | 488 | −15.582 | −16.783 | −25.867 | O |
| ATOM | 13 | N | PHE | 492 | −23.749 | −19.863 | −29.63 | N |
| ATOM | 14 | CA | PHE | 492 | −25.002 | −19.22 | −29.231 | C |
| ATOM | 15 | CB | PHE | 492 | −25.587 | −19.86 | −27.979 | C |
| ATOM | 16 | C | PHE | 492 | −25.001 | −17.689 | −29.085 | C |
| ATOM | 17 | O | PHE | 492 | −26.019 | −17.067 | −28.781 | O |
| ATOM | 18 | CG | PHE | 492 | −24.719 | −19.956 | −26.759 | C |
| ATOM | 19 | CD1 | PHE | 492 | −24.804 | −21.1 | −25.968 | C |
| ATOM | 20 | CD2 | PHE | 492 | −23.836 | −18.942 | −26.382 | C |
| ATOM | 21 | CE1 | PHE | 492 | −24.02 | −21.234 | −24.825 | C |

TABLE 7-continued

| (SEQ ID NO. 14) | | | | | | | | |
|---|---|---|---|---|---|---|---|---|
| ATOM | 22 | CE2 | PHE | 492 | −23.048 | −19.07 | −25.241 | C |
| ATOM | 23 | CZ | PHE | 492 | −23.141 | −20.219 | −24.461 | C |
| ATOM | 24 | N | GLY | 493 | −23.77 | −17.113 | −29.309 | N |
| ATOM | 25 | CA | GLY | 493 | −23.455 | −15.731 | −29.017 | C |
| ATOM | 26 | C | GLY | 493 | −22.503 | −15.689 | −27.832 | C |
| ATOM | 27 | O | GLY | 493 | −21.708 | −16.582 | −27.563 | O |
| ATOM | 28 | N | GLN | 494 | −22.526 | −14.481 | −27.17 | N |
| ATOM | 29 | CA | GLN | 494 | −21.732 | −14.296 | −25.963 | C |
| ATOM | 30 | CB | GLN | 494 | −21.048 | −12.945 | −26.027 | C |
| ATOM | 31 | C | GLN | 494 | −22.718 | −14.31 | −24.793 | C |
| ATOM | 32 | O | GLN | 494 | −23.886 | −13.945 | −24.911 | O |
| ATOM | 33 | CG | GLN | 494 | −20.061 | −12.71 | −24.903 | C |
| ATOM | 34 | CD | GLN | 494 | −19.703 | −11.252 | −24.848 | C |
| ATOM | 35 | OE1 | GLN | 494 | −20.153 | −10.395 | −25.598 | O |
| ATOM | 36 | NE2 | GLN | 494 | −18.807 | −10.945 | −23.868 | N |
| ATOM | 37 | N | VAL | 495 | −22.162 | −14.629 | −23.575 | N |
| ATOM | 38 | CA | VAL | 495 | −22.939 | −14.409 | −22.373 | C |
| ATOM | 39 | CB | VAL | 495 | −22.86 | −15.58 | −21.402 | C |
| ATOM | 40 | C | VAL | 495 | −22.459 | −13.103 | −21.75 | C |
| ATOM | 41 | O | VAL | 495 | −21.278 | −12.855 | −21.519 | O |
| ATOM | 42 | CG1 | VAL | 495 | −21.452 | −15.945 | −20.985 | C |
| ATOM | 43 | CG2 | VAL | 495 | −23.702 | −15.34 | −20.173 | C |
| ATOM | 44 | N | VAL | 496 | −23.484 | −12.248 | −21.413 | N |
| ATOM | 45 | CA | VAL | 496 | −23.179 | −11.07 | −20.645 | C |
| ATOM | 46 | CB | VAL | 496 | −22.851 | −9.761 | −21.324 | C |
| ATOM | 47 | C | VAL | 496 | −23.249 | −11.167 | −19.14 | C |
| ATOM | 48 | O | VAL | 496 | −24.216 | −11.678 | −18.581 | O |
| ATOM | 49 | CG1 | VAL | 496 | −23.894 | −9.375 | −22.346 | C |
| ATOM | 50 | CG2 | VAL | 496 | −21.48 | −9.77 | −21.952 | C |
| ATOM | 51 | N | VAL | 514 | −25.883 | −11.411 | −12.079 | N |
| ATOM | 52 | CA | VAL | 514 | −26.859 | −11.989 | −12.989 | C |
| ATOM | 53 | CB | VAL | 514 | −28.229 | −11.335 | −12.845 | C |
| ATOM | 54 | C | VAL | 514 | −26.37 | −11.928 | −14.442 | C |
| ATOM | 55 | O | VAL | 514 | −25.251 | −11.529 | −14.762 | O |
| ATOM | 56 | CG1 | VAL | 514 | −28.19 | −9.827 | −12.937 | C |
| ATOM | 57 | CG2 | VAL | 514 | −28.95 | −11.778 | −11.595 | C |
| ATOM | 58 | N | ALA | 515 | −27.267 | −12.383 | −15.386 | N |
| ATOM | 59 | CA | ALA | 515 | −26.791 | −12.451 | −16.749 | C |
| ATOM | 60 | CB | ALA | 515 | −26.728 | −13.861 | −17.274 | C |
| ATOM | 61 | C | ALA | 515 | −27.514 | −11.523 | −17.703 | C |
| ATOM | 62 | O | ALA | 515 | −28.703 | −11.235 | −17.586 | O |
| ATOM | 63 | N | VAL | 516 | −26.711 | −11.107 | −18.744 | N |
| ATOM | 64 | CA | VAL | 516 | −27.23 | −10.248 | −19.791 | C |
| ATOM | 65 | CB | VAL | 516 | −26.383 | −8.987 | −19.971 | C |
| ATOM | 66 | C | VAL | 516 | −27.215 | −10.994 | −21.123 | C |
| ATOM | 67 | O | VAL | 516 | −26.31 | −11.744 | −21.483 | O |
| ATOM | 68 | CG1 | VAL | 516 | −27.079 | −7.964 | −20.836 | C |
| ATOM | 69 | CG2 | VAL | 516 | −26.019 | −8.316 | −18.674 | C |
| ATOM | 70 | N | LYS | 517 | −28.253 | −10.572 | −21.928 | N |
| ATOM | 71 | CA | LYS | 517 | −28.249 | −10.726 | −23.368 | C |
| ATOM | 72 | CB | LYS | 517 | −27.776 | −11.986 | −24.071 | C |
| ATOM | 73 | C | LYS | 517 | −28.797 | −9.577 | −24.194 | C |
| ATOM | 74 | O | LYS | 517 | −29.796 | −8.954 | −23.846 | O |
| ATOM | 75 | CG | LYS | 517 | −28.92 | −12.668 | −24.793 | C |
| ATOM | 76 | CD | LYS | 517 | −28.518 | −13.807 | −25.713 | C |
| ATOM | 77 | CE | LYS | 517 | −27.58 | −13.411 | −26.843 | C |
| ATOM | 78 | NZ | LYS | 517 | −27.474 | −14.567 | −27.763 | N1+ |
| ATOM | 79 | N | ILE | 548 | −36.281 | −20.184 | −15.458 | N |
| ATOM | 80 | CA | ILE | 548 | −35.436 | −19.031 | −15.752 | C |
| ATOM | 81 | CB | ILE | 548 | −34.664 | −19.219 | −17.06 | C |
| ATOM | 82 | C | ILE | 548 | −36.408 | −17.853 | −15.822 | C |
| ATOM | 83 | O | ILE | 548 | −37.458 | −17.886 | −16.452 | O |
| ATOM | 84 | CG1 | ILE | 548 | −33.392 | −20.028 | −16.883 | C |
| ATOM | 85 | CG2 | ILE | 548 | −34.252 | −17.907 | −17.69 | C |
| ATOM | 86 | CD1 | ILE | 548 | −33.627 | −21.413 | −16.336 | C |
| ATOM | 87 | N | VAL | 562 | −31.795 | −7.739 | −22.294 | N |
| ATOM | 88 | CA | VAL | 562 | −32.342 | −8.134 | −21.014 | C |
| ATOM | 89 | CB | VAL | 562 | −33.499 | −9.124 | −21.117 | C |
| ATOM | 90 | C | VAL | 562 | −31.274 | −8.662 | −20.068 | C |
| ATOM | 91 | O | VAL | 562 | −30.216 | −9.164 | −20.451 | O |
| ATOM | 92 | CG1 | VAL | 562 | −34.749 | −8.496 | −21.679 | C |
| ATOM | 93 | CG2 | VAL | 562 | −33.149 | −10.372 | −21.896 | C |
| ATOM | 94 | N | VAL | 564 | −31.237 | −11.518 | −16.699 | N |
| ATOM | 95 | CA | VAL | 564 | −31.896 | −12.694 | −16.127 | C |
| ATOM | 96 | CB | VAL | 564 | −32.086 | −13.727 | −17.235 | C |
| ATOM | 97 | C | VAL | 564 | −31.098 | −13.219 | −14.919 | C |
| ATOM | 98 | O | VAL | 564 | −29.92 | −12.905 | −14.743 | O |
| ATOM | 99 | CG1 | VAL | 564 | −32.973 | −14.887 | −16.875 | C |

TABLE 7-continued (SEQ ID NO. 14)

| ATOM | 100 | CG2 | VAL | 564 | −30.789 | −14.232 | −17.825 | C |
|---|---|---|---|---|---|---|---|---|
| ATOM | 101 | N | GLU | 565 | −31.782 | −14.111 | −14.099 | N |
| ATOM | 102 | CA | GLU | 565 | −31.085 | −14.734 | −12.973 | C |
| ATOM | 103 | CB | GLU | 565 | −31.992 | −15.005 | −11.782 | C |
| ATOM | 104 | C | GLU | 565 | −29.941 | −15.717 | −13.297 | C |
| ATOM | 105 | O | GLU | 565 | −29.737 | −16.147 | −14.431 | O |
| ATOM | 106 | CG | GLU | 565 | −32.392 | −16.452 | −11.541 | C |
| ATOM | 107 | CD | GLU | 565 | −31.43 | −17.186 | −10.607 | C |
| ATOM | 108 | OE1 | GLU | 565 | −31.684 | −18.423 | −10.464 | O1− |
| ATOM | 109 | OE2 | GLU | 565 | −30.465 | −16.501 | −10.16 | O |
| ATOM | 110 | N | TYR | 566 | −29.152 | −16.054 | −12.215 | N |
| ATOM | 111 | CA | TYR | 566 | −27.823 | −16.588 | −12.406 | C |
| ATOM | 112 | CB | TYR | 566 | −26.781 | −15.718 | −11.724 | C |
| ATOM | 113 | C | TYR | 566 | −27.641 | −18.044 | −11.99 | C |
| ATOM | 114 | O | TYR | 566 | −28.024 | −18.531 | −10.93 | O |
| ATOM | 115 | CG | TYR | 566 | −25.444 | −15.789 | −12.391 | C |
| ATOM | 116 | CD1 | TYR | 566 | −25.275 | −15.305 | −13.689 | C |
| ATOM | 117 | CE1 | TYR | 566 | −24.024 | −15.355 | −14.299 | C |
| ATOM | 118 | CD2 | TYR | 566 | −24.353 | −16.321 | −11.703 | C |
| ATOM | 119 | CE2 | TYR | 566 | −23.098 | −16.379 | −12.308 | C |
| ATOM | 120 | CZ | TYR | 566 | −22.945 | −15.891 | −13.6 | C |
| ATOM | 121 | OH | TYR | 566 | −21.693 | −15.924 | −14.174 | O |
| ATOM | 122 | N | ALA | 567 | −26.891 | −18.744 | −12.906 | N |
| ATOM | 123 | CA | ALA | 567 | −26.494 | −20.101 | −12.647 | C |
| ATOM | 124 | CB | ALA | 567 | −26.697 | −20.945 | −13.884 | C |
| ATOM | 125 | C | ALA | 567 | −25.023 | −20.106 | −12.297 | C |
| ATOM | 126 | O | ALA | 567 | −24.142 | −19.656 | −13.025 | O |
| ATOM | 127 | N | SER | 568 | −24.777 | −20.692 | −11.076 | N |
| ATOM | 128 | CA | SER | 568 | −23.392 | −20.872 | −10.669 | C |
| ATOM | 129 | CB | SER | 568 | −23.287 | −21.156 | −9.18 | C |
| ATOM | 130 | C | SER | 568 | −22.779 | −22.049 | −11.436 | C |
| ATOM | 131 | O | SER | 568 | −21.589 | −22.069 | −11.739 | O |
| ATOM | 132 | OG | SER | 568 | −23.589 | −19.986 | −8.424 | O |
| ATOM | 133 | N | LYS | 569 | −23.612 | −23.14 | −11.637 | N |
| ATOM | 134 | CA | LYS | 569 | −23.125 | −24.243 | −12.446 | C |
| ATOM | 135 | CB | LYS | 569 | −23.916 | −25.503 | −12.162 | C |
| ATOM | 136 | C | LYS | 569 | −23.157 | −23.937 | −13.939 | C |
| ATOM | 137 | O | LYS | 569 | −22.249 | −24.312 | −14.674 | O |
| ATOM | 138 | CG | LYS | 569 | −23.179 | −26.423 | −11.212 | C |
| ATOM | 139 | CD | LYS | 569 | −21.753 | −26.645 | −11.661 | C |
| ATOM | 140 | CE | LYS | 569 | −21.016 | −27.517 | −10.675 | C |
| ATOM | 141 | NZ | LYS | 569 | −19.648 | −27.708 | −11.215 | N1+ |
| ATOM | 142 | N | GLY | 570 | −24.319 | −23.373 | −14.413 | N |
| ATOM | 143 | CA | GLY | 570 | −24.453 | −23.038 | −15.812 | C |
| ATOM | 144 | C | GLY | 570 | −25.524 | −23.921 | −16.407 | C |
| ATOM | 145 | O | GLY | 570 | −26.559 | −24.245 | −15.824 | O |
| ATOM | 146 | N | ASN | 571 | −25.286 | −24.249 | −17.721 | N |
| ATOM | 147 | CA | ASN | 571 | −26.274 | −25.077 | −18.386 | C |
| ATOM | 148 | CB | ASN | 571 | −26.321 | −24.743 | −19.86 | C |
| ATOM | 149 | C | ASN | 571 | −26.109 | −26.524 | −17.918 | C |
| ATOM | 150 | O | ASN | 571 | −25.024 | −27.043 | −17.664 | O |
| ATOM | 151 | CG | ASN | 571 | −25.797 | −25.724 | −20.862 | C |
| ATOM | 152 | OD1 | ASN | 571 | −25.578 | −26.912 | −20.665 | O |
| ATOM | 153 | ND2 | ASN | 571 | −25.585 | −25.128 | −22.072 | N |
| ATOM | 154 | N | LEU | 633 | −31.139 | −24.989 | −17.022 | N |
| ATOM | 155 | CA | LEU | 633 | −30.144 | −24.369 | −16.179 | C |
| ATOM | 156 | CB | LEU | 633 | −30.509 | −22.921 | −15.923 | C |
| ATOM | 157 | C | LEU | 633 | −29.959 | −25.091 | −14.857 | C |
| ATOM | 158 | O | LEU | 633 | −30.903 | −25.516 | −14.191 | O |
| ATOM | 159 | CG | LEU | 633 | −29.311 | −21.997 | −15.935 | C |
| ATOM | 160 | CD1 | LEU | 633 | −28.592 | −22.042 | −17.263 | C |
| ATOM | 161 | CD2 | LEU | 633 | −29.768 | −20.585 | −15.665 | C |
| ATOM | 162 | N | ALA | 643 | −36.35 | −23.324 | −19.23 | N |
| ATOM | 163 | CA | ALA | 643 | −36.544 | −22.152 | −20.052 | C |
| ATOM | 164 | CB | ALA | 643 | −35.423 | −21.153 | −19.88 | C |
| ATOM | 165 | C | ALA | 643 | −36.674 | −22.565 | −21.505 | C |
| ATOM | 166 | O | ALA | 643 | −36.305 | −23.66 | −21.933 | O |
| ATOM | 167 | N | ASP | 644 | −37.2 | −21.581 | −22.31 | N |
| ATOM | 168 | CA | ASP | 644 | −37.014 | −21.613 | −23.75 | C |
| ATOM | 169 | C | ASP | 644 | −35.623 | −20.964 | −23.979 | C |
| ATOM | 170 | O | ASP | 644 | −34.857 | −20.648 | −23.073 | O |
| ATOM | 171 | CB | ASP | 644 | −38.16 | −20.848 | −24.389 | C |
| ATOM | 172 | CG | ASP | 644 | −38.22 | −20.841 | −25.905 | C |
| ATOM | 173 | OD1 | ASP | 644 | −37.259 | −21.446 | −26.484 | O |
| ATOM | 174 | OD2 | ASP | 644 | −39.176 | −20.165 | −26.375 | O1− |
| ATOM | 175 | N | PHE | 645 | −35.297 | −20.757 | −25.29 | N |
| ATOM | 176 | CA | PHE | 645 | −34.1 | −20.044 | −25.673 | C |
| ATOM | 177 | CB | PHE | 645 | −32.96 | −21.008 | −25.921 | C |

TABLE 7-continued (SEQ ID NO. 14)

| ATOM | 178 | C   | PHE | 645 | −34.416 | −19.213 | −26.908 | C   |
|------|-----|-----|-----|-----|---------|---------|---------|-----|
| ATOM | 179 | O   | PHE | 645 | −34.014 | −18.058 | −27.023 | O   |
| ATOM | 180 | CG  | PHE | 645 | −31.717 | −20.552 | −25.231 | C   |
| ATOM | 181 | CD1 | PHE | 645 | −31.097 | −19.35  | −25.573 | C   |
| ATOM | 182 | CD2 | PHE | 645 | −31.156 | −21.354 | −24.239 | C   |
| ATOM | 183 | CE1 | PHE | 645 | −29.924 | −18.956 | −24.935 | C   |
| ATOM | 184 | CE2 | PHE | 645 | −29.98  | −20.965 | −23.603 | C   |
| ATOM | 185 | CZ  | PHE | 645 | −29.366 | −19.766 | −23.952 | C   |
| ATOM | 186 | N   | GLY | 646 | −35.072 | −19.861 | −27.936 | N   |
| ATOM | 187 | CA  | GLY | 646 | −35.65  | −19.091 | −29.017 | C   |
| ATOM | 188 | C   | GLY | 646 | −34.659 | −18.179 | −29.727 | C   |
| ATOM | 189 | O   | GLY | 646 | −33.522 | −18.494 | −30.065 | O   |
| ATOM | 190 | N   | ALA | 648 | −33.161 | −15.84  | −28.383 | N   |
| ATOM | 191 | CA  | ALA | 648 | −32.005 | −15.478 | −27.595 | C   |
| ATOM | 192 | CB  | ALA | 648 | −32.175 | −15.893 | −26.152 | C   |
| ATOM | 193 | C   | ALA | 648 | −30.73  | −16.122 | −28.147 | C   |
| ATOM | 194 | O   | ALA | 648 | −29.621 | −15.677 | −27.855 | O   |
| ATOM | 195 | N   | ARG | 649 | −30.876 | −17.281 | −28.889 | N   |
| ATOM | 196 | CA  | ARG | 649 | −29.696 | −17.894 | −29.479 | C   |
| ATOM | 197 | CB  | ARG | 649 | −29.859 | −19.371 | −29.767 | C   |
| ATOM | 198 | C   | ARG | 649 | −29.344 | −17.17  | −30.777 | C   |
| ATOM | 199 | O   | ARG | 649 | −30.151 | −16.969 | −31.678 | O   |
| ATOM | 200 | CG  | ARG | 649 | −29.749 | −20.201 | −28.508 | C   |
| ATOM | 201 | CD  | ARG | 649 | −29.878 | −21.666 | −28.861 | C   |
| ATOM | 202 | NE  | ARG | 649 | −30.114 | −22.502 | −27.687 | N1+ |
| ATOM | 203 | CZ  | ARG | 649 | −29.201 | −22.79  | −26.717 | C   |
| ATOM | 204 | NH1 | ARG | 649 | −27.944 | −22.278 | −26.724 | N   |
| ATOM | 205 | NH2 | ARG | 649 | −29.564 | −23.67  | −25.761 | N   |

Example 7

The Use of FGFR-2 Inhibition Model in the Fitting and Optimization of a Small Molecular Template Virtual screening of ArQule's collection of kinase inhibitors was carried out using the described FGFR-2 inhibition model. Additional filters were applied for compound selection: molecular weight between 250 and 350, number of hetero atoms less or equal 5, number of hydrogen bonds donors less or equal 3, AlogP less than 5.

Docking and optimization against the FGFR-2 inhibition model was performed. The docking procedure was carried out using ICM software. Further optimization was carried out using MOE energy minimization tools.

ARQ13194808, a racemic mixture of two enantiomers, was identified from this virtual screening (MW 342, logP 4.17). Individual enantiomers were optimized in the model binding site. A single enantiomer was determined to have a preferential binding interaction.

Hydrogen bonds between the pyridine and the critical amino and carbonyl groups of the hinge residue A567 were identified. The fused benzene ring makes aromatic interactions with the F492 from the P-loop.

The overall protein-ligand interaction energy was negative (−40 kcal/mol) and the compounds energy was low (37 kcal/mol) just 3 kcal/mol above the energy minimum in the absence of the protein, as it is calculated using MOE energy calculation tools, indicating a high probability of interaction.

Based on the analysis of these results, ARQ13194808 could be selected as a starting point for designing a FGFR-2 kinase inhibitor.

(−)-trans-3-(5,6-dihydro-4H-pyrrolo[3,2,1-ij]quinolin-1-yl)-4(1H-indol-3-yl)pyrrolidine-2,5-dione, the selective c-Met inhibitor, was also docked in the FGFR-2 inhibition model. A docking pose, where the pyrrolidine carbonyl ring was making hydrogen bonds with the amino group of A567, was selected.

Further energy optimization using MOE tools was carried out. Two hydrogen bonds where observed between the pyrrolidine ring and hinge residue A567. The overall interaction energy is negative (−37 kcal/mol) and the compound's energy is equal to 51 kcal/mol, which is 5 kcal/mol above the energy minimum in the absence of the protein.

Example 8

Cloning, Expression and Purification of c-Met2

As used herein, the c-Met protein of Table 1A is related to the cMet1 protein. cMet1 contains a mutation at residue position 1166, a substitution of glutamine for arginine. Wild type cMet, which has the same sequence as cMet2 of the present application, contains an arginine residue at position 1166. cMet1 contains a glutamine residue at position 1166. Tables 1B and 4, relate to the cMet2 protein. Table 1B provides the complete sequence and atomic structure of the cMet2/the selective cMet inhibitor complex.

The DNA fragment encoding the kinase domain (1038-1346) of cMet was PCR amplified using full length human cDNA with primers designed to contain a non-cleavable N-terminus 6xHis tag. The resulting DNA fragment was inserted into pET28a vector between NcoI and SalI sites. A bicistronic form of this vector was designed for co-expression with phosphatase by sequentially inserting the PTP1B gene (1-283) between SalI and NotI sites. A second ribosome binding site was incorporated into the PTP1B primer after the SalI site. The construct generated initially contained a random mutation in cMet gene at position 1166 (Arginine to Glutamine), which was corrected to the wild-type form using site-directed mutagenesis kit (Stratagene). All constructs and mutants were verified by sequencing the entire coding region from both 5' and 3' directions.

Plasmids were transformed into E. Coli strain BL21 (DE3)-RILP cells. The culture was grown at 25° C. in 2xYT medium up to an $A_{600}$ of 0.6 when overexpression of cMet protein was induced with 0.25 mM IPTG at 12° C. The incubation continued at 12° C. for 16 h before harvesting. Frozen cell pastes suspended in lysis buffer (50 mM Tris pH 8.5, 150 mM NaCl, 0.01% 2-mercapto ethanol, 30 mM imidazole, 1 mM PMSF, 100 µg/ml lysozyme, 10 µg/ml DNAase-1) were lysed by using Branson 450D sonifier on ice at 60% power. The lysate was clarified by centrifugation at 30,000×g at 4° C. for 45 min, and the supernatant loaded onto a 10 ml Ni-Chelating Sepharose column (GE Healthcare). The column washed with 25 mM Tris pH 8.5, 100 mM NaCl, 0.01% 2-mercapto ethanol, 30 mM imidazole, pH 8.5 and the unphosphorylated cMet was eluted with 500 mM imidazole in the same buffer. cMet protein was further purified with an anion exchange column, Fast Trap QFF 5 ml column (GE Healthcare), after dialysis with 25 mM Tris pH 8.5 and 10% glycerol. Eluted protein was concentrated to 20 mg/ml and stored at −80° C. in buffer composed of 25 mM Tris pH 8.5, 100 mM NaCl, 0.1% 2-mercaptoethanol and 10% glycerol.

Crystallization of cMet2 in Complex with the Selective c-Met Inhibitor

Co-crystals of unphosphorylated cMet kinase domain and the selective c-Met inhibitor were grown by the hanging drop vapor diffusion method at 4° C. using a drop size of 1 µl from 12% ethanol, 14% ethylene glycol and 0.1M imidazole buffer, pH 8.5. For cMet/the selective c-Met inhibitor complex preparation, 10 mM the selective c-Met inhibitor solution was prepared in 50% DMSO/water, diluted to 1.2 mM with buffer solution (25 mM Tris pH 8.5, 100 mM NaCl), and immediately mixed in equal volumes with cMet (20 mg/ml). The complex was incubated on ice for 30 min and centrifuged at 13,000×g prior to crystallization. Large single crystals suitable for data collection were obtained after microseeding from thin needle-like clusters generated from initial screening. Crystals were harvested into a cryoprotected solution of 12% ethanol, 20% ethylene glycol, 10% glycerol and 0.1M imidazole buffer, pH 8.5, and flash-frozen in liquid nitrogen. X-ray diffraction data were collected at beamline X29 of the National Synchrotron Light Source (Brookhaven, N.Y.) on a CCD detector under cryogenic temperature. The diffraction data was integrated, processed and scaled using HKL2000 at NSLS site. The crystals belong to P1 space group with unit cell dimension of a=53.47 Å, b=58.67 Å, c=64.96 Å, α=88.41, β=68.10, γ=85.52, and contain two molecules of cMet in the asymmetric unit with solvent content of 46%.

The structure was determined by molecular replacement utilizing MOLREP as implemented in CCP4 package. The atomic coordinates of the published cMet structure 2G15 was used as search model and the activation and p-loop residues were deleted from the model. The initial electron density map for the selective c-Met inhibitor, P-loop and activation loop regions were well resolved, leaving no ambiguities for the binding mode of the inhibitor. Structure refinement consisted of iterative cycles of model building in Coot, followed by simulated annealing, B-factor minimization, and restrained B-factor refinement in CNX. The residues for activation loop, P-loop and the N-terminal regions different from the initial model were built during the refinement process. The selective c-Met inhibitor conformation was identical in both copies of cMet and was built during the final stages of refinement. Water molecules were added based on Fo-Fc maps (3σ) with density recapitulated in 2Fo-Fc maps (1σ). All waters satisfy the hydrogen-bonding criteria as implemented in the CNX programs Waterpick and Waterdelete. Final rounds of refinement were performed using REFMAC5 restrained refinement protocol. The final model consists of two copies of cMet with residues from 1046 to 1346, two selective c-Met inhibitor molecules and 600 hundred water molecules with crystallographic R value of 19.8% ($R_{free}$=25.9%). The data collection and refinement statistics are summarized in Table 8.

TABLE 8

Diffraction data and refinement statistics

| Data collection | |
|---|---|
| Space group | P1 |
| Cell dimensions a, b, c (Å) | 53.47, 58.67, 64.96 |
| Cell angles α, β, γ (deg) | 88.41, 68.10, 85.52 |
| Resolution (Å) | 50.0-1.93 |
| Unique reflections | 47320 |
| Completeness | 93% (96%) |
| $R_{sym}$ | 0.102 (0.28) |
| Mean I/σ (I) | 6.9 |
| Redundancy | 2 |
| Refinement | |
| $R^a$ | 0.198 |
| $R_{free}$ | 0.259 |
| RMSD Bond distance (Å) | 0.018 |
| RMSD Bond angle (deg) | 1.951 |

$^a$R and $R_{free}$ = (Σ|Fobs − Fcalc|)/(Σ|Fobs|). $R_{free}$ was calculated over a randomly chosen 5% of the reflections not used in refinement. Parentheses indicate the outer resolution shell.

Other embodiments are within the following claims. While several embodiments have been shown and described, various modifications may be made without departing from the spirit and scope of the present invention.

What is claimed is:

1. A process for screening or designing wild type c-Met inhibitors comprising:
   a) crystallizing the wild type c-Met kinase domain of SEQ ID NO:2 bound to (−)-trans-3-(5,6-dihydro-4H-pyrrolo[3,2,1-ij]quinolin-1-yl)-4(1H-indol-3-yl)pyrrolidine-2,5-dione, wherein the resultant crystal is in space group P1 and having unit cell dimensions of a=53.47 Å, b=58.67 Å, c=64.96 Å, α=88.41°, β=68.10° and γ=85.52°,
   b) obtaining the three dimensional atomic coordinates and constructing a three-dimensional model for the c-Met kinase domain,
   c) utilizing the model to identify inhibitor of cMet activity.

2. The process of claim 1 further comprising obtaining the inhibitor and determining its inhibition of the wild type c-Met which has an amino acid sequence of SEQ ID NO: 12.

* * * * *

UNITED STATES PATENT AND TRADEMARK OFFICE
CERTIFICATE OF CORRECTION

PATENT NO.         : 7,960,134 B1
APPLICATION NO.    : 12/221440
DATED              : June 14, 2011
INVENTOR(S)        : Mark A. Ashwell Page 1 of 1

It is certified that error appears in the above-identified patent and that said Letters Patent is hereby corrected as shown below:

At col. 235, SEQ ID NO 2, the 35th residue "Pro" should be corrected to "Phe".

At col. 235, SEQ ID NO 2, the 48th residue "Trp" should be corrected to "Tyr".

Signed and Sealed this
Sixteenth Day of August, 2011

David J. Kappos
*Director of the United States Patent and Trademark Office*